(12) United States Patent
Thess

(10) Patent No.: US 10,738,306 B2
(45) Date of Patent: *Aug. 11, 2020

(54) ARTIFICIAL NUCLEIC ACID MOLECULES FOR IMPROVED PROTEIN OR PEPTIDE EXPRESSION

(71) Applicant: CureVac AG, Tübingen (DE)

(72) Inventor: Andreas Thess, Kusterdingen (DE)

(73) Assignee: CureVac AG, Tübingen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/590,370

(22) Filed: May 9, 2017

(65) Prior Publication Data

US 2017/0247699 A1 Aug. 31, 2017

Related U.S. Application Data

(63) Continuation of application No. 14/388,226, filed as application No. PCT/EP2013/000937 on Mar. 27, 2013, now Pat. No. 9,683,233.

(30) Foreign Application Priority Data

Mar. 27, 2012 (WO) ................ PCT/EP2012/001336
Jun. 8, 2012 (WO) ................ PCT/EP2012/002447

(51) Int. Cl.
*C12N 15/113* (2010.01)
*C12N 15/67* (2006.01)
*C12N 15/85* (2006.01)
*A61K 39/00* (2006.01)
*A61K 48/00* (2006.01)

(52) U.S. Cl.
CPC ............ *C12N 15/113* (2013.01); *A61K 39/00* (2013.01); *A61K 48/0008* (2013.01); *C12N 15/67* (2013.01); *C12N 15/85* (2013.01); *A61K 48/00* (2013.01); *A61K 2039/5156* (2013.01); *A61K 2039/5256* (2013.01); *A61K 2039/53* (2013.01); *C12N 2310/531* (2013.01); *C12N 2320/52* (2013.01); *C12N 2840/105* (2013.01)

(58) Field of Classification Search
None
See application file for complete search history.

(56) References Cited

U.S. PATENT DOCUMENTS

| 5,908,779 | A | 6/1999 | Carmichael et al. |
| 6,783,961 | B1 * | 8/2004 | Edwards ............... C07K 14/47 435/91.1 |
| 6,822,072 | B1 * | 11/2004 | Edwards ............. C12N 15/1096 435/320.1 |
| 7,432,049 | B2 * | 10/2008 | Liew ...................... A61P 19/00 435/6.18 |
| 7,700,359 | B2 * | 4/2010 | Chan ................... C12Q 1/6886 436/6 |
| 8,217,016 | B2 | 7/2012 | Hoerr et al. |
| 8,383,340 | B2 | 2/2013 | Ketterer et al. |
| 8,703,906 | B2 | 4/2014 | Baumhof et al. |
| 8,968,746 | B2 | 3/2015 | Baumhof et al. |
| 9,155,788 | B2 | 10/2015 | Hoerr et al. |
| 9,234,013 | B2 | 1/2016 | Thess et al. |
| 9,447,431 | B2 | 9/2016 | Thess et al. |
| 9,669,089 | B2 | 6/2017 | Thess et al. |
| 9,683,233 | B2 * | 6/2017 | Thess ..................... C12N 15/67 |
| 9,839,697 | B2 | 12/2017 | Thess et al. |
| 10,047,375 | B2 * | 8/2018 | Thess ..................... C12N 15/67 |
| 2005/0009028 | A1 | 1/2005 | Heintz et al. |
| 2005/0032730 | A1 | 2/2005 | Von Der Mulbe et al. |
| 2005/0048549 | A1 | 3/2005 | Cao et al. |
| 2005/0059624 | A1 | 3/2005 | Hoerr et al. |
| 2005/0250723 | A1 | 11/2005 | Hoerr et al. |
| 2006/0188490 | A1 | 8/2006 | Hoerr et al. |
| 2007/0111203 | A1 | 5/2007 | Cao et al. |
| 2007/0172949 | A9 | 7/2007 | Liu et al. |
| 2008/0025944 | A1 | 1/2008 | Hoerr |
| 2008/0267873 | A1 | 10/2008 | Hoerr |
| 2009/0324584 | A1 | 12/2009 | Hoerr et al. |
| 2010/0048883 | A1 | 2/2010 | Ketterer et al. |
| 2010/0120152 | A1 | 5/2010 | Wooddell et al. |
| 2010/0129392 | A1 | 5/2010 | Shi et al. |
| 2010/0189729 | A1 | 7/2010 | Hoerr et al. |
| 2010/0203076 | A1 | 8/2010 | Fotin-Mleczek et al. |

(Continued)

FOREIGN PATENT DOCUMENTS

| WO | WO 1995/015394 | 6/1995 |
| WO | WO 1998/042856 | 10/1998 |

(Continued)

OTHER PUBLICATIONS

Sequence Alignment of SEQ ID No. 1453 with SEQ ID No. 55428 of U.S. Pat. No. 7,432,049, Sequence Search conducted on Aug. 18, 2019, 1 page. (Year: 2019).*
Sequence Alignment of SEQ ID No. 1455 with SEQ ID No. 1476 of U.S. Pat. No. 6,783,961, Sequence Search conducted on Aug. 18, 2019, 1 page. (Year: 2019).*
Sequence Alignment of SEQ ID No. 1456 with SEQ ID No. 787 of U.S. Pat. No. 6,822,072, Sequence Search conducted on Aug. 18, 2019, 1 page. (Year: 2019).*
Sequence Alignment of SEQ ID No. 1457 with SEQ ID No. 55594 of U.S. Pat. No. 7,432,049, Sequence Search conducted on Aug. 18, 2019, 1 page. (Year: 2019).*

(Continued)

*Primary Examiner* — Channing S Mahatan
(74) *Attorney, Agent, or Firm* — Parker Highlander PLLC

(57) ABSTRACT

The invention relates to an artificial nucleic acid molecule comprising at least one 5'UTR element which is derived from a TOP gene, at least one open reading frame, and preferably at least one histone stem-loop. Optionally the artificial nucleic acid molecule may further comprise, e.g. a poly(A)sequence, a poyladenylation signal, and/or a 3'UTR. The invention further relates to the use of such an artificial nucleic acid molecule in gene therapy and/or genetic vaccination.

Figure 5:
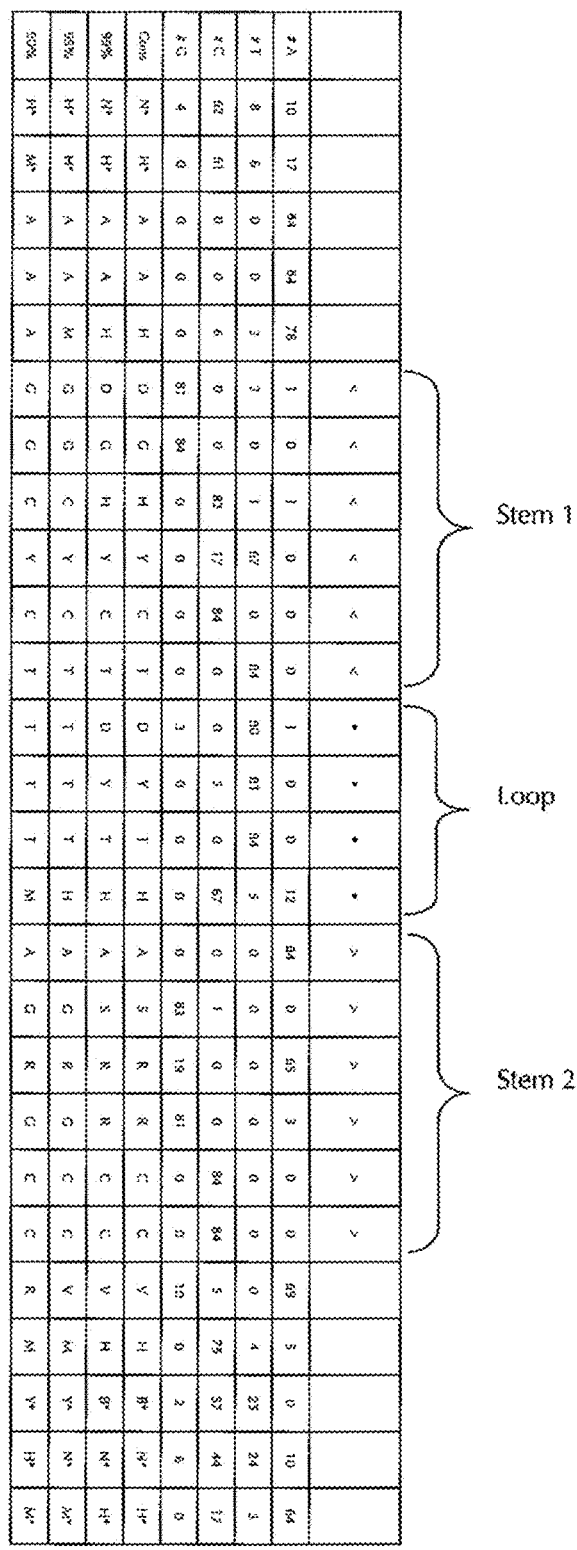

20 Claims, 39 Drawing Sheets
Specification includes a Sequence Listing.

(56) References Cited

U.S. PATENT DOCUMENTS

| | | |
|---|---|---|
| 2010/0239608 A1 | 9/2010 | Von Der Millbe et al. |
| 2010/0291156 A1 | 11/2010 | Barner et al. |
| 2010/0303851 A1 | 12/2010 | Hoerr et al. |
| 2010/0305196 A1 | 12/2010 | Probst et al. |
| 2011/0053829 A1 | 3/2011 | Baumhof |
| 2011/0077287 A1 | 3/2011 | Von Der Mülbe et al. |
| 2011/0250225 A1 | 10/2011 | Fotin-Mleczek |
| 2011/0269950 A1 | 11/2011 | Von Der Mülbe et al. |
| 2011/0311472 A1 | 12/2011 | Hoerr et al. |
| 2012/0009221 A1 | 1/2012 | Hoerr et al. |
| 2012/0021043 A1 | 1/2012 | Kramps et al. |
| 2012/0213818 A1 | 8/2012 | Hoerr et al. |
| 2012/0258046 A1 | 10/2012 | Mutzke |
| 2013/0121988 A1 | 5/2013 | Hoerr et al. |
| 2013/0129754 A1 | 5/2013 | Thess et al. |
| 2013/0195867 A1 | 8/2013 | Hoerr et al. |
| 2013/0202645 A1 | 8/2013 | Banner et al. |
| 2013/0251742 A1 | 9/2013 | Probst et al. |
| 2013/0259879 A1 | 10/2013 | Baumhof et al. |
| 2013/0273001 A1 | 10/2013 | Hoerr et al. |
| 2013/0280283 A1 | 10/2013 | Lorenz et al. |
| 2013/0295043 A1 | 11/2013 | Kallen et al. |
| 2013/0336998 A1 | 12/2013 | Kallen et al. |
| 2014/0037660 A1 | 2/2014 | Fotin-Mleczek et al. |
| 2014/0147454 A1 | 5/2014 | Chakraborty et al. |
| 2014/0294877 A1 | 10/2014 | Baumhof et al. |
| 2015/0050302 A1 | 2/2015 | Thess |
| 2015/0057340 A1 | 2/2015 | Thess et al. |
| 2015/0093413 A1 | 4/2015 | Thess |
| 2015/0104476 A1 | 4/2015 | Von Der Mülbe et al. |
| 2015/0118183 A1 | 4/2015 | Baumhof |
| 2015/0118264 A1 | 4/2015 | Baumhof et al. |
| 2015/0141498 A1 | 5/2015 | Mutzke |
| 2015/0165006 A1 | 6/2015 | Thess et al. |
| 2015/0184195 A1 | 7/2015 | Thess et al. |
| 2015/0218554 A1 | 8/2015 | Thess |
| 2015/0258214 A1 | 9/2015 | Baumhof et al. |
| 2015/0306249 A1 | 10/2015 | Baumhof et al. |
| 2015/0320847 A1 | 11/2015 | Thess et al. |

FOREIGN PATENT DOCUMENTS

| | | |
|---|---|---|
| WO | WO 2001/012824 | 2/2001 |
| WO | WO 2002/098443 | 12/2002 |
| WO | WO 2005/035771 | 4/2005 |
| WO | WO 2005/040377 | 5/2005 |
| WO | WO 2006/008154 | 1/2006 |
| WO | WO 2006/024518 | 3/2006 |
| WO | WO 2007/024708 | 3/2007 |
| WO | WO 2009/030481 | 3/2009 |
| WO | WO 2009/095226 | 8/2009 |
| WO | WO 2010/023260 | 3/2010 |
| WO | WO 2010/132867 | 11/2010 |
| WO | WO 2011/069529 | 6/2011 |
| WO | WO 2012/013326 | 2/2012 |
| WO | WO 2012/019630 | 2/2012 |
| WO | WO 2012/019780 | 2/2012 |
| WO | WO 2012/116714 | 9/2012 |
| WO | WO 2013/120626 | 8/2013 |
| WO | WO 2013/120627 | 8/2013 |
| WO | WO 2013/120628 | 8/2013 |
| WO | WO 2013/120629 | 8/2013 |
| WO | WO 2015/024665 | 2/2015 |
| WO | WO 2015/024668 | 2/2015 |

OTHER PUBLICATIONS

Sequence Alignment of SEQ ID No. 1458 with SEQ ID No. 8351 of U.S. Pat. No. 6,783,961, Sequence Search conducted on Aug. 18, 2019, 1 page. (Year: 2019).*
Sequence Alignment of Seq ID No. 1368 with Seq ID No. 12385 of U.S. Pat. No. 7,700,359, Sequence Search conducted on Aug. 18, 2019; 2 pages (Year: 2019).*
Sequence Alignment of Seq ID No. 1452 with Seq ID No. 12350 of U.S. Pat. No. 7,432,049, Sequence Search conducted on Aug. 18, 2019, 2 pages. (Year: 2019).*
Sequence Alignment of Seq ID No. 1453 with Seq ID No. 55428 of U.S. Pat. No. 7,432,049, Sequence Search conducted Aug. 18, 2019, 1 page. (Year: 2019).*
Sequence Alignment of Seq ID No. 1454 with Seq ID No. 184 of U.S. Pat. No. 6,783,961, Sequence Search conducted on Aug. 18, 2019, 1 page. (Year: 2019).*
Dhamija et al., "IL-1-induced Post-transcriptional Mechanisms Target Overlapping Translational Silencing and Destabilizing Elements in IKBC mRNA," J. Biol. Chem., 285(38):29165-29178, 2010.
Dugaiczyk et al., "Nucleotide sequence and the encoded amino acids of human serum albumin mRNA," *Proc. Natl. Acad. Sci. USA*, 79:71-75, 1982.
Kübler et al.,"Self-adjuvanted mRNA vaccination in advanced prostate cancer patients: a first-in-man phase I/IIa study," *Journal of ImmunoTherapy of Cancer*, 3:26, 2015.
Office Action issued in U.S. Appl. No. 14/378,572, dated Sep. 21, 2017.
Office Action issued in U.S. Appl. No. 14/378,591, dated Apr. 9, 2018.
Office Action issued in U.S. Appl. No. 14/378,591, dated Aug. 23, 2017.
Office Action issued in U.S. Appl. No. 14/388,224, dated Jul. 28, 2017.
Office Action issued in U.S. Appl. No. 15/233,933, dated Apr. 6, 2018.
Office Action issued in U.S. Appl. No. 15/233,933, dated Dec. 7, 2017.
Office Action issued in U.S. Appl. No. 15/233,933, dated Jul. 28, 2017.
Office Action issued in U.S. Appl. No. 15/465,322, dated Apr. 2, 2018.
Office Action issued in U.S. Appl. No. 15/465,322, dated Nov. 20, 2017.
Office Action issued in U.S. Appl. No. 15/590,370, dated Apr. 30, 2018.
Office Action issued in U.S. Appl. No. 15/899,326, dated May 23, 2018.
Shen and Higgins, "The 5' untranslated region-mediated enhancement of intracellular listeriolysin O production is required for *Listeria monocytogenes* pathogenicity," *Molecular Microbiology*, 57(5):1460-1473, 2005.
Shuptrine et al., "Monoclonal antibodies for the treatment of cancer," *Seminars in Cancer Biology*, 22:3-13, 2012.
Van Dijk et al., "Identification of RNA sequences and structures involved in site-specific cleavage of IGF-II mRNAs," *RNA*, 1623-1635, 1998.
Attwood, "The babel of bioinformatics," *Science*, 290(5491):471-473, 2000.
Avni et al., "The 5' terminal oligopyrimidine tract confers translational control on TOP mRNAs in a cell type-and sequence context-dependent manner," *Nucleic Acids Research*, 25(5):995-1001, 1997.
Avni et al., "Vertebrate mRNAs with a 5'-terminal pyrimidine tract are candidates for translational repression in quiescent cells: characterization of the translational cis-regulatory element," *Mol. Cell. Biol.*, 14(6):3822-3833, 1994.
Battle and Doudna, "The stem-loop binding protein forms a highly stable and specific complex with the stem-loop of histone mRNAs", *RNA*, 7:123-132, 2001.
Blumenthal et al., "Definition of an allergen (immunobiology)," *Allergens and Allergen Immunotherapy*, Ed R. Lockey, S. Bukantz and J. Bousquet, pp. 37-50, 2004.
Caldarola et al., "Translational regulation of terminal oligopyrimidine mRNAs induced by serum and amino acids involves distinct signaling events," *The Journal of Biological Chemistry*, 279(14):13522-135531, 2004.
Cameron et al., "Recent advances in transgenic technology," *Molecular Biotechnology*, 7:253-265, 1997.
Chakrabarti et al., "The mammalian target of rapamycin complex 1 regulates leptin biosynthesis in adipocytes at the level of translation:

(56) References Cited

OTHER PUBLICATIONS the role of the 5'-untranslated region in the expression of leptin messenger ribonucleic acid," *Molecular Endocrinology*, 22(10):2260-2267, 2008.
Cheung et al., "Specific interaction of HeLa cell proteins with coxsackievirus B3 3'UTR: La autoantigen binds the 3' and 5' UTR independently of the poly(A) tail," *Cell Microbiol*, 9(7):1705-1715, 2007.
Collart et al., "A human histone H2B.1 variant gene, located on chromosome 1, utilizes alternative 3' end processing", *Journal of Cellular Biochemistry*, 50:374-385, 1992.
Damgaard and Lykke-Andersen, "Translational coregulation of 5'TOP mRNAs by TIA-1 and TIAR," *Genes Dev.*, 25:2057-2068, 2011.
Database EMBL Accession No. EM_STD:AB063609, "*Homo sapiens* RPL36AL mRNA for ribosomal protein L36a-like, complete cds," 2002.
Database Geneseq Accession No. ATN08647, "Human transcriptional regulatory element SEQ ID No. 6587," 2008.
Davuluri et al., "CART classification of human 5' UTR sequences," *Genome Research*, 10(11):1807-1816, 2000.
Deml et al., "Multiple effects of codon usage optimization on expression and immunogenicity of DNA candidate vaccines encoding the human immunodeficiency virus type 1 Gag protein," Journal of Virology, 75(22):10991-11001, 2001.
Dollé et al., "Nerve growth factor overexpression and autocrine loop in breast cancer cells," *Oncogene*, 22(36):5592-5601, 2003.
Dominski et al., "Stem-loop binding protein facilitates 3'-end formation by stabilizing U7 snRNP binding to histone pre-mRNA," *Mol Cell Biol.*, 19(5):3561-3570, 1999.
Eckner et al., "Mature mRNA 3' end formation stimulates RNA export from the nucleus," *The EMBO Journal*, 10(11):3513-3522, 1991.
Gallie et al., "The histone 3'-terminal stem-loop is necessary for translation in Chinese hamster ovary cells", *Nucleic Acids Res*, 24(10):1954-62, 1996.
Gerwitz et al., "Nucleic acid therapeutics: state of the art and future prospects," *Blood*, 92(3):712-736, 1998.
Ginn et al., "Gene therapy clinical trails worldwide to 2012—an update," *Journal of Gene Medicine*, 15:65-77, 2013.
Gorgoni et al., "The stem-loop binding protein stimulates histone translation at an early step in the initiation pathway," *RNA*, 11:1030-1042, 2005.
Haines et al., "CL22—a novel cationic peptide for efficient transfection of mammalian cells," *Gene Ther.*, 8:99-110, 2001.
Henke et al., "Coxsackievirus B3 vaccines: use as an expression vector for prevention of myocarditis," *Expert Rev. Vaccines*, 7(10):1557-1567, 2008.
Holtkamp et al., "Modification of antigen-encoding RNA increases stability, translational efficacy, and T-cell stimulatory capacity of dendritic cells", *Blood*, 108(13):4009-17, 2006.
Iadevaia et al., "All translation elongation factors and the e, f, and h subunits of translation initiation factor 3 are encoded by 5'-terminal oligopyrimidine (TOP) mRNAs," *RNA*, 14:1730-1736, 2008.
Kato et al., "Histone H2B as an antigen recognized by lung cancer-specific human monoclonal antibody HB4C5", *Human Antibodies and Hybridomas*, 2(2):94-101, 1991.
Kim et al., "Coxsackievirus B3 used as a gene therapy vector to express functional FGF2," *Gene Ther.*, 19(12):1159-1165, 2012.
Kim et al., "Systematic analysis of attenuated *Coxsackievirus* expressing a foreign gene as a viral vaccine vector," *Vaccine*, 28(5):1234-1240, 2010.
Knapinska et al., "Molecular mechanisms regulation mRNA stability: physiological and pathological significance," *Current Genomics*, 6(6):1-16, 2005.
Kramarova et al., "A sequence predicted to form a stem-loop is proposed to be required for formation of an RNA-protein complex involving the 3'UTR of β-subunit $F_0F_1$-ATPase mRNA," *Biochim. Biophys. Acta.*, 1777(7-8):747-757, 2008.
Kudla et al., "High guanine and cytosine content increases mRNA levels in mammalian cells," *PLoS Biology*, 4:0933-0942, 2006.
Ledda et al., "Effect of 3' UTR length on the translational regulation of 5'-terminal oligopyrimidine mRNAs," *Gene*, 344:213-220, 2005.
Levy et al., "Oligopyrimidine tract at the 5' end of mammalian ribosomal protein mRNAs is required for their translational control," *Proc. Natl. Acad. Sci. USA*, 88:3319-3323, 1991.
Levy et al., "Sequence and functional characterization of the terminal exon of the human insulin receptor gene", *Biochim Biophys Acta.*, 1263(3):253-7, 1995.
Ling et al, "The histone 3'-terminal stem-loop-binding protein enhances translation through a functional and physical interaction with eukaryotic initiation factor 4G (eIF4G) and eIF3", *Mol Cell Biol.*, 22(22):7853-67, 2002.
Lopez and Samuelsson, "Early evolution of histone mRNA 3' end processing", *Bioinformatics*, 14(1):1-10, 2008.
Lorenzi et al., "Intranasal vaccination with messenger RNA as a new approach in gene therapy: use against tuberculosis," *BMC Biotechnology*, 10:77, 2010.
Meier et al., "Fibroblast growth factor-2 but not Mel-CAM and/or β3 integrin promotes progression of melanocytes to melanoma," *Exp. Dermatol.*, 12(3):296-306, 2003.
Meyuhas, "Synthesis of the translational apparatus is regulated at the translational level," *Eur. J. Biochem.*, 267:6321-6330, 2000.
Montoliu, "Gene transfer strategies in animal transgenesis," *Cloning and Stem Cells*, 4(1):39-46, 2002.
Narita et al., "NELF interacts with CDC and participates in 3' end processing of replication-dependent histone mRNAs", *Molecular Cell*, 26(3):349-365, 2007.
Ngo et al., "Computational complexity, protein structure prediction, and the levinthal paradox," *The Protein Folding Problem and Tertiary Structure Prediction*, Ed. K. Merz and S. Le Grand, pp. 491-495, 1994.
Niemann, "Transgenic farm animals get off the ground," *Transgenic Research*, 7:73-75, 1998.
Office Action issued in U.S. Appl. No. 13/321,474, dated Apr. 6, 2015.
Office Action issued in U.S. Appl. No. 13/321,474, dated May 20, 2014.
Office Action issued in U.S. Appl. No. 14/378,538, dated Jun. 21, 2016.
Office Action issued in U.S. Appl. No. 14/378,538, dated Nov. 12, 2015.
Office Action issued in U.S. Appl. No. 14/378,538, dated Oct. 11, 2016.
Office Action issued in U.S. Appl. No. 14/378,572, dated Aug. 12, 2016.
Office Action issued in U.S. Appl. No. 14/378,572, dated Mar. 14, 2017.
Office Action issued in U.S. Appl. No. 14/378,572, dated Mar. 3, 2016.
Office Action issued in U.S. Appl. No. 14/378,591, dated Aug. 22, 2016.
Office Action issued in U.S. Appl. No. 14/378,591, dated Jan. 27, 2017.
Office Action issued in U.S. Appl. No. 14/378,606, dated May 27, 2015.
Office Action issued in U.S. Appl. No. 14/378,606, dated Nov. 3, 2015.
Office Action issued in U.S. Appl. No. 14/388,224, dated Apr. 21, 2016.
Office Action issued in U.S. Appl. No. 14/388,224, dated Oct. 17, 2016.
Office Action issued in U.S. Appl. No. 14/388,226, dated Jun. 21, 2016.
Office Action issued in U.S. Appl. No. 14/945,349, dated Feb. 6, 2017.
Oliveira et al., "Inhibition of translational initiation in *Saccharomyces cerevisiae* by secondary structure: the roles of the stability and position of stem-loops in the mRNA leader," *Mol. Microbiol.*, 9(3):521-532, 1993.

(56) References Cited

OTHER PUBLICATIONS

Orom et al., "MicroRNA-10a binds the 5'UTR of ribosomal protein mRNAs and enhances their translation," *Molecular Cell*, 30:460-471, 2008.
Palmowski et al., "Intravenous injection of a lentiviral vector encoding NY-ESO-1 induces an effective CTL response," *J. Immunol.*, 172(3):1582-1587, 2004.
Pandey et al., "Introns in histone genes alter the distribution of 3' ends", *Nucleic Acids Res.*, 18(11):3161-70, 1990.
PCT International Search Report and Written Opinion issued in International Application No. PCT/EP2013/000938, dated Nov. 13, 2013.
PCT International Search Report and Written Opinion issued in International Application No. PCT/EP2013/000937, dated Aug. 30, 2013.
PCT International Search Report and Written Opinion issued in International Application No. PCT/EP2013/000461, dated Apr. 16, 2013.
PCT International Search Report and Written Opinion issued in International Application No. PCT/EP2013/000458, dated Apr. 24, 2013.
PCT International Search Report and Written Opinion issued in International Application No. PCT/EP2013/000459, dated Apr. 23, 2013.
PCT International Search Report and Written Opinion issued in International Application No. PCT/EP2013/000460, dated Apr. 22, 2013.
PCT International Search Report and Written Opinion issued in International Application No. PCT/EP2011/004077, dated Nov. 10, 2011.
Prelle et al., "Establishment of pluripotent cell lines from vertebrate species—present status and future prospects," *Cells Tissues Organs*, 165:220-236, 1999.
Ristevski, "Making better transgenic models," *Molecular Biotechnology*, 29:153-163, 2005.
Roesler et al., "Immunize and disappear—safety-optimized mRNA vaccination with a panel of 29 allergens", *Journal of Allergy and Clinical Immunology*, 124(5):1070-1077, 2009.
Russell et al., "The stability of human beta-globin mRNA is dependent on structural determinants positioned within its 3' untranslated region", Blood, 87:5314-5323, 1996.
Sanchez et al., "Increased levels of polyadenylated histone H2B mRNA accumulate during *Entamoeba invadens* cyst formation", *Molecular and Biochemical Parasitology*, 67(1):137-146, 1994.
Sánchez et al., "The oligo(A) tail on histone mRNA plays an active role in translational silencing of histone mRNA during Xenopus oogenesis", *Mol Cell Biol.*, 24(6):2513-25, 2004.
Sharma et al., "Functional role of the 5' terminal cloverleaf in Coxsackievirus RNA replication," *Virology*, 393(2):238-249, 2009.
Shen et al., "Structures required for poly(A) tail-independent translation overlap with, but ar distinct from, cap-independent translation and RNA replication signals at the 3' end of *Tobacco necrosis virus* RNA," *Virology*, 358:448-458, 2007.
Sigmund, "Viewpoint: are studies in genetically altered mice out of control?" *Arteriosclerosis, Thrombosis, and Vascular Biology*, 20:1425-1429, 2000.
Skolnick et al., "From genes to protein structure and function: novel applications of computational approaches in the genomic era," *Trends in Biotech.*, 18:34-39, 2000.
Smith, "Gene transfer in higher animals: theoretical considerations and key concepts," *Journal of Biotechnology*, 99:1-22, 2002.
Stauber et al., "A signal regulating mouse histone H4 mRNA levels in a mammalian cell cycle mutant and sequences controlling RNA 3' processing are both contained within the same 80-bp fragment", EMBO J., 5(12):3297-303, 1986.
Svoboda et al., "Hairpin RNA: a secondary structure of primary importance", Cell Mol Life Sci, 63(7-8):901-8, 2006.
Thess et al., "Sequence-engineered mRNA without chemical nucleoside modifications enables an effective protein therapy in large animals," *Molecular Therapy*, pp. 1-9 and Supplementary Material, 2015.
Van Ooij et al., "Polyadenylation of genomic RNA and initiation of antigenomic RNA in a positive-strand RNA virus are controlled by the same cis-element," *Nucleic Acids Res.*, 34(10):2953-2965, 2006.
Wagner et al., "A genome-wide RNA interference screen reveals that variant histones are necessary for replication-dependent histone pre-mRNA processing", *Molecular Cell*, 28(4):692-699, 2007.
Weiss et al., "Prophylactic mRNA vaccination against allergy", Current Opinion in Allergy and Clinical Immunology, 10(6):567-574, 2010.
Williams et al., "A simple, highly efficient method for heterologous expression in mammalian primary neurons using cationic lipid-mediated mRNA transfection", *Frontiers in Neuroscience*, 4:1-20, 2010.
Wooddell et al., "Sustained liver-specific trans gene expression from the albumin promoter in mice following hydrodynamic plasmid DNA delivery," *The Journal of Gene Medicine*, 10:551-563, 2008.
Yamashita et al., "Comprehensive detection of human terminal oligo-pyrimidine (TOP) genes and analysis of their characteristics," *Nucleic Acids Res*, 36(11):3707-3715 and Supplementary Data (six pages), 2008.
Zhong et al., "A double-stranded RNA binding protein required for activation of repressed messages in mammalian germ cells", *Nat Genet.*, 22(2):171-4, 1999.
Zhu et al., "Binding of the La autoantigen to the 5' untranslated region of a chimeric human translation elongation factor 1A reporter mRNA inhibits translation in vitro," *Biochimica et Biophysica Acta*, 1521:19-29, 2001.
Database GenBank, [online], Accession No. AK222475, Nov. 17, 2007, <https://www.ncbi.nlm.nih.gov/nuccore/62896508?sat=46&satkey=15856460>.
Database GenBank, [online], Accession No. AK222780, Nov. 17, 2007, <https://www.ncbi.nlm.nih.gov/nuccore/62897118?sat=46&satkey=15856751>.
Database GenBank, [online], Accession No. D28385, Mar. 10, 2009, <https://www.ncbi.nlm.nih.gov/nuccore/461233?sat=46&satkey=15629526>.
Database GenBank, [online], Accession No. D28406, Jan. 22, 2005, <https://www.ncbi.nlm.nih.gov/nuccore/461241?sat=46&satkey=15629534>.
Database GenBank, [online], Accession No. D28448, Jan. 22, 2005, <https://www.ncbi.nlm.nih.gov/nuccore/461226?sat=46&satkey=15629520>.
Database GenBank, [online], Accession No. NM_001199291, Mar. 5, 2012, <https://www.ncbi.nlm.nih.gov/nuccore/313482809?sat=15&satkey=6403420>.
Database GenBank, [online], Accession No. NM_004046, Mar. 24, 2012, <https://www.ncbi.nlm.nih.gov/nuccore/50345980?sat=15&satkey=6379190>.
Database GenBank, [online], Accession No. NM_004374, Jan. 23, 2012, <https://www.ncbi.nlm.nih.gov/nuccore/301069354?sat=15&satkey=6401626>.
Hoeksema et al., "Placing the RPL32 Promoter Upstream of a Second Promoter Results in a Strongly Increased Number of Stably Transfected Mammalian Cell Lines That Display High Protein Expression Levels," *Biotechnol. Res. Int.*, 2011(492875):1-11, 2011.
Kato et al., "Construction of a human full-length cDNA bank," *Gene*, 150:243-250, 1994.

* cited by examiner

Figure 1

| | #A | #T | #G | #C | Cons | 99% | 95% | 90% |
|---|---|---|---|---|---|---|---|---|
| | 52 | 20 | 45 | 14 | N+ | N+ | N+ | N+ |
| | 32 | 32 | 59 | 8 | N+ | N+ | N+ | H+ |
| | 71 | 37 | 20 | 3 | N | N | H | H |
| | 82 | 27 | 25 | 3 | N | N | H | H |
| | 76 | 8 | 38 | 9 | N | N | N | A |
| | 13 | 5 | 0 | 115 | C | C | R | R | ⎫
| | 0 | 0 | 0 | 131 | C | C | C | C | ⎪
| | 12 | 21 | 86 | 12 | N | N | N | N | ⎪
| | 12 | 65 | 8 | 26 | N | N | N | G | ⎬ Stem 1
| | 9 | 58 | 54 | 10 | N | N | N | B | ⎪
| | 1 | 86 | 42 | 2 | N | N | B | Y | ⎪
| | 46 | 70 | 13 | 2 | N | N | H | H | ⎫
| | 3 | 65 | 58 | 5 | N | N | B | Y | ⎬ Loop
| | 0 | 131 | 0 | 0 | T | T | T | T | ⎪
| | 75 | 28 | 27 | 1 | N | H | H | H | ⎭
| | 82 | 1 | 2 | 46 | N | Y | R | R | ⎫
| | 53 | 17 | 6 | 55 | N | N | S | S | ⎪
| | 79 | 13 | 31 | 8 | N | N | N | H | ⎬ Stem 2
| | 30 | 10 | 91 | N | N | N | N | | 
| | 0 | 131 | 0 | 0 | C | C | C | C | ⎪
| | 4 | 113 | 0 | 0 | H | H | Y | Y | ⎭
| | 94 | 5 | 25 | N | N | N | D | R | 
| | 17 | 31 | 1 | N | N | H | H | H | 
| | 35 | 32 | 58 | 6 | N+ | N+ | H+ | H+ | 
| | 74 | 30 | 30 | 7 | N+ | N+ | N+ | H+ | 
| | 56 | 28 | 40 | 7 | N+ | N+ | N+ | H+ |

Figure 2

Figure 3

Figure 4 nucleotide sequence of PpLuc(GC) – ag – A64

GGGAGAAAGCTTGAGGATGGAGGACGCCAAGAACATCAAGAAGGGCCCGGCGCCCTTCTA
CCCGCTGGAGGACGGGACCGCCGGCGAGCAGCTCCACAAGGCCATGAAGCGGTACGCCCT
GGTGCCGGGCACGATCGCCTTCACCGACGCCCACATCGAGGTCGACATCACCTACGCGGA
GTACTTCGAGATGAGCGTGCGCCTGGCCGAGGCCATGAAGCGGTACGGCCTGAACACCAA
CCACCGGATCGTGGTGTGCTCGGAGAACAGCCTGCAGTTCTTCATGCCGGTGCTGGGCGC
CCTCTTCATCGGCGTGGCCGTCGCCCCGGCGAACGACATCTACAACGAGCGGGAGCTGCT
GAACAGCATGGGGATCAGCCAGCCGACCGTGGTGTTCGTGAGCAAGAAGGGCCTGCAGAA
GATCCTGAACGTGCAGAAGAAGCTGCCCATCATCCAGAAGATCATCATCATGGACAGCAA
GACCGACTACCAGGGCTTCCAGTCGATGTACACGTTCGTGACCAGCCACCTCCCGCCGGG
CTTCAACGAGTACGACTTCGTCCCGGAGAGCTTCGACCGGGACAAGACCATCGCCCTGAT
CATGAACAGCAGCGGCAGCACCGGCCTGCCGAAGGGGGTGGCCCTGCCGCACCGGACCGC
CTGCGTGCGCTTCTCGCACGCCCGGGACCCCATCTTCGGCAACCAGATCATCCCGGACAC
CGCCATCCTGAGCGTGGTGCCGTTCCACCACGGCTTCGGCATGTTCACGACCCTGGGCTA
CCTCATCTGCGGCTTCCGGGTGGTCCTGATGTACCGGTTCGAGGAGGAGCTGTTCCTGCG
GAGCCTGCAGGACTACAAGATCCAGAGCGCGCTGCTCGTGCCGACCCTGTTCAGCTTCTT
CGCCAAGAGCACCCTGATCGACAAGTACGACCTGTCGAACCTGCACGAGATCGCCAGCGG
GGGCGCCCCGCTGAGCAAGGAGGTGGGCGAGGCCGTGGCCAAGCGGTTCCACCTCCCGGG
CATCCGCCAGGGCTACGGCCTGACCGAGACCACGAGCGCGATCCTGATCACCCCCGAGGG
GGACGACAAGCCGGGCGCCGTGGGCAAGGTGGTCCCGTTCTTCGAGGCCAAGGTGGTGGA
CCTGGACACCGGCAAGACCCTGGGCGTGAACCAGCGGGGCGAGCTGTGCGTGCGGGGGCC
GATGATCATGAGCGGCTACGTGAACAACCCGGAGGCCACCAACGCCCTCATCGACAAGGA
CGGCTGGCTGCACAGCGGCGACATCGCCTACTGGGACGAGGACGAGCACTTCTTCATCGT
CGACCGGCTGAAGTCGCTGATCAAGTACAAGGGCTACCAGGTGGCGCCGGCCGAGCTGGA
GAGCATCCTGCTCCAGCACCCCAACATCTTCGACGCCGGCGTGGCCGGGCTGCCGGACGA
CGACGCCGGCGAGCTGCCGGCCGCGGTGGTGGTGCTGGAGCACGGCAAGACCATGACGGA
GAAGGAGATCGTCGACTACGTGGCCAGCCAGGTGACCACCGCCAAGAAGCTGCGGGGCGG
CGTGGTGTTCGTGGACGAGGTCCCGAAGGGCCTGACCGGGAAGCTCGACGCCCGGAAGAT
CCGCGAGATCCTGATCAAGGCCAAGAAGGGCGGCAAGATCGCCGTGTAAGACTAGTTATA
AGACTGACTAGCCCGATGGGCCTCCCAACGGGCCCTCCTCCCCTCCTTGCACCGAGATTA
ATAGATCTAAAAAAAAAAAAAAAAAAAAAAAAAAAAAAAAAAAAAAAAAAAAAAAAAAAA
AAAAAAAAAAAA

Figure 6 nucleotide sequence of RPL32 – PpLuc(GC) – ag – A64 – C30 – histoneSL

```
GGGGCGCTGCCTACGGAGGTGGCAGCCATCTCCTTCTCGGCATCAAGCTTGAGGATGGAG
GACGCCAAGAACATCAAGAAGGGCCCGGCGCCCTTCTACCCGCTGGAGGACGGGACCGCC
GGCGAGCAGCTCCACAAGGCCATGAAGCGGTACGCCCTGGTGCCGGGCACGATCGCCTTC
ACCGACGCCCACATCGAGGTCGACATCACCTACGCGGAGTACTTCGAGATGAGCGTGCGC
CTGGCCGAGGCCATGAAGCGGTACGGCCTGAACACCAACCACCGGATCGTGGTGTGCTCG
GAGAACAGCCTGCAGTTCTTCATGCCGGTGCTGGGCGCCCTCTTCATCGGCGTGGCCGTC
GCCCCGGCGAACGACATCTACAACGAGCGGGAGCTGCTGAACAGCATGGGGATCAGCCAG
CCGACCGTGGTGTTCGTGAGCAAGAAGGGCCTGCAGAAGATCCTGAACGTGCAGAAGAAG
CTGCCCATCATCCAGAAGATCATCATCATGGACAGCAAGACCGACTACCAGGGCTTCCAG
TCGATGTACACGTTCGTGACCAGCCACCTCCCGCCGGGCTTCAACGAGTACGACTTCGTC
CCGGAGAGCTTCGACCGGGACAAGACCATCGCCCTGATCATGAACAGCAGCGGCAGCACC
GGCCTGCCGAAGGGGGTGGCCCTGCCGCACCGGACCGCCTGCGTGCGCTTCTCGCACGCC
CGGGACCCCATCTTCGGCAACCAGATCATCCCGGACACCGCCATCCTGAGCGTGGTGCCG
TTCCACCACGGCTTCGGCATGTTCACGACCCTGGGCTACCTCATCTGCGGCTTCCGGGTG
GTCCTGATGTACCGGTTCGAGGAGGAGCTGTTCCTGCGGAGCCTGCAGGACTACAAGATC
CAGAGCGCGCTGCTCGTGCCGACCCTGTTCAGCTTCTTCGCCAAGAGCACCCTGATCGAC
AAGTACGACCTGTCGAACCTGCACGAGATCGCCAGCGGGGCGCCCCGCTGAGCAAGGAG
GTGGGCGAGGCCGTGGCCAAGCGGTTCCACCTCCCGGGCATCCGCCAGGGCTACGGCCTG
ACCGAGACCACGAGCGCGATCCTGATCACCCCGAGGGGACGACAAGCCGGGCGCCGTG
GGCAAGGTGGTCCCGTTCTTCGAGGCCAAGGTGGTGGACCTGGACACCGGCAAGACCCTG
GGCGTGAACCAGCGGGGCGAGCTGTGCGTGCGGGGCCGATGATCATGAGCGGCTACGTG
AACAACCCGGAGGCCACCAACGCCCTCATCGACAAGGACGGCTGGCTGCACAGCGGCGAC
ATCGCCTACTGGGACGAGGACGAGCACTTCTTCATCGTCGACCGGCTGAAGTCGCTGATC
AAGTACAAGGGCTACCAGGTGGCGCCGGCCGAGCTGGAGAGCATCCTGCTCCAGCACCCC
AACATCTTCGACGCCGGCGTGGCCGGGCTGCCGGACGACGACGCCGGCGAGCTGCCGGCC
GCGGTGGTGGTGCTGGAGCACGGCAAGACCATGACGGAGAAGGAGATCGTCGACTACGTG
GCCAGCCAGGTGACCACCGCCAAGAAGCTGCGGGGCGGCGTGGTGTTCGTGGACGAGGTC
CCGAAGGGCCTGACCGGGAAGCTCGACGCCCGGAAGATCCGCGAGATCCTGATCAAGGCC
AAGAAGGGCGGCAAGATCGCCGTGTAAGACTAGTTATAAGACTGACTAGCCCGATGGGCC
TCCCAACGGGCCCTCCTCCCCTCCTTGCACCGAGATTAATAGATCTAAAAAAAAAAAAAA
AAAAAAAAAAAAAAAAAAAAAAAAAAAAAAAAAAAAAAAAAAAAAAAAAATGCATCCCCC
CCCCCCCCCCCCCCCCCCCCCCCCAAAGGCTCTTTTCAGAGCCACCAGAATT
```

Figure 7 nucleotide sequence of PpLuc(GC) – ag – A64 – histoneSL

GGGAGAAAGCTTGAGGATGGAGGACGCCAAGAACATCAAGAAGGGCCCGGCGCCCTTCTA
CCCGCTGGAGGACGGGACCGCCGGCGAGCAGCTCCACAAGGCCATGAAGCGGTACGCCCT
GGTGCCGGGCACGATCGCCTTCACCGACGCCCACATCGAGGTCGACATCACCTACGCGGA
GTACTTCGAGATGAGCGTGCGCCTGGCCGAGGCCATGAAGCGGTACGGCCTGAACACCAA
CCACCGGATCGTGGTGTGCTCGGAGAACAGCCTGCAGTTCTTCATGCCGGTGCTGGGCGC
CCTCTTCATCGGCGTGGCCGTCGCCCCGGCGAACGACATCTACAACGAGCGGGAGCTGCT
GAACAGCATGGGGATCAGCCAGCCGACCGTGGTGTTCGTGAGCAAGAAGGGCCTGCAGAA
GATCCTGAACGTGCAGAAGAAGCTGCCCATCATCCAGAAGATCATCATCATGGACAGCAA
GACCGACTACCAGGGCTTCCAGTCGATGTACACGTTCGTGACCAGCCACCTCCCGCCGGG
CTTCAACGAGTACGACTTCGTCCCGGAGAGCTTCGACCGGGACAAGACCATCGCCCTGAT
CATGAACAGCAGCGGCAGCACCGGCCTGCCGAAGGGGGTGGCCCTGCCGCACCGGACCGC
CTGCGTGCGCTTCTCGCACGCCCGGGACCCCATCTTCGGCAACCAGATCATCCCGGACAC
CGCCATCCTGAGCGTGGTGCCGTTCCACCACGGCTTCGGCATGTTCACGACCCTGGGCTA
CCTCATCTGCGGCTTCCGGGTGGTCCTGATGTACCGGTTCGAGGAGGAGCTGTTCCTGCG
GAGCCTGCAGGACTACAAGATCCAGAGCGCGCTGCTCGTGCCGACCCTGTTCAGCTTCTT
CGCCAAGAGCACCCTGATCGACAAGTACGACCTGTCGAACCTGCACGAGATCGCCAGCGG
GGGCGCCCCGCTGAGCAAGGAGGTGGGCGAGGCCGTGGCCAAGCGGTTCCACCTCCCGGG
CATCCGCCAGGGCTACGGCCTGACCGAGACCACGAGCGCGATCCTGATCACCCCCGAGGG
GGACGACAAGCCGGGCGCCGTGGGCAAGGTGGTCCCGTTCTTCGAGGCCAAGGTGGTGGA
CCTGGACACCGGCAAGACCCTGGGCGTGAACCAGCGGGGCGAGCTGTGCGTGCGGGGGCC
GATGATCATGAGCGGCTACGTGAACAACCCGGAGGCCACCAACGCCCTCATCGACAAGGA
CGGCTGGCTGCACAGCGGCGACATCGCCTACTGGGACGAGGACGAGCACTTCTTCATCGT
CGACCGGCTGAAGTCGCTGATCAAGTACAAGGGCTACCAGGTGGCGCCGGCCGAGCTGGA
GAGCATCCTGCTCCAGCACCCCAACATCTTCGACGCCGGCGTGGCCGGGCTGCCGGACGA
CGACGCCGGCGAGCTGCCGGCCGCGGTGGTGGTGCTGGAGCACGGCAAGACCATGACGGA
GAAGGAGATCGTCGACTACGTGGCCAGCCAGGTGACCACCGCCAAGAAGCTGCGGGGCGG
CGTGGTGTTCGTGGACGAGGTCCCGAAGGGCCTGACCGGGAAGCTCGACGCCCGGAAGAT
CCGCGAGATCCTGATCAAGGCCAAGAAGGGCGGCAAGATCGCCGTGTAAGACTAGTTATA
AGACTGACTAGCCCGATGGGCCTCCCAACGGGCCCTCCTCCCCTCCTTGCACCGAGATTA
ATAAAAAAAAAAAAAAAAAAAAAAAAAAAAAAAAAAAAAAAAAAAAAAAAAAAAAAAAAA
AAAAAATGCATCAAAGGCTCTTTTCAGAGCCACCA

Figure 9 nucleotide sequence of RPL32 – PpLuc(GC) – ag – A64

```
GGGGCGCTGCCTACGGAGGTGGCAGCCATCTCCTTCTCGGCATCAAGCTTGAGGATGGAG
GACGCCAAGAACATCAAGAAGGGCCCGGCGCCCTTCTACCCGCTGGAGGACGGGACCGCC
GGCGAGCAGCTCCACAAGGCCATGAAGCGGTACGCCCTGGTGCCGGGCACGATCGCCTTC
ACCGACGCCCACATCGAGGTCGACATCACCTACGCGGAGTACTTCGAGATGAGCGTGCGC
CTGGCCGAGGCCATGAAGCGGTACGGCCTGAACACCAACCACCGGATCGTGGTGTGCTCG
GAGAACAGCCTGCAGTTCTTCATGCCGGTGCTGGGCGCCCTCTTCATCGGCGTGGCCGTC
GCCCCGGCGAACGACATCTACAACGAGCGGGAGCTGCTGAACAGCATGGGGATCAGCCAG
CCGACCGTGGTGTTCGTGAGCAAGAAGGGCCTGCAGAAGATCCTGAACGTGCAGAAGAAG
CTGCCCATCATCCAGAAGATCATCATCATGGACAGCAAGACCGACTACCAGGGCTTCCAG
TCGATGTACACGTTCGTGACCAGCCACCTCCCGCCGGGCTTCAACGAGTACGACTTCGTC
CCGGAGAGCTTCGACCGGGACAAGACCATCGCCCTGATCATGAACAGCAGCGGCAGCACC
GGCCTGCCGAAGGGGGTGGCCCTGCCGCACCGGACCGCCTGCGTGCGCTTCTCGCACGCC
CGGGACCCCATCTTCGGCAACCAGATCATCCCGGACACCGCCATCCTGAGCGTGGTGCCG
TTCCACCACGGCTTCGGCATGTTCACGACCCTGGGCTACCTCATCTGCGGCTTCCGGGTG
GTCCTGATGTACCGGTTCGAGGAGGAGCTGTTCCTGCGGAGCCTGCAGGACTACAAGATC
CAGAGCGCGCTGCTCGTGCCGACCCTGTTCAGCTTCTTCGCCAAGAGCACCCTGATCGAC
AAGTACGACCTGTCGAACCTGCACGAGATCGCCAGCGGGGCGCCCCGCTGAGCAAGGAG
GTGGGCGAGGCCGTGGCCAAGCGGTTCCACCTCCCGGGCATCCGCCAGGGCTACGGCCTG
ACCGAGACCACGAGCGCGATCCTGATCACCCCGAGGGGGACGACAAGCCGGGCGCCGTG
GGCAAGGTGGTCCCGTTCTTCGAGGCCAAGGTGGTGGACCTGGACACCGGCAAGACCCTG
GGCGTGAACCAGCGGGGCGAGCTGTGCGTGCGGGGCCGATGATCATGAGCGGCTACGTG
AACAACCCGGAGGCCACCAACGCCCTCATCGACAAGGACGGCTGGCTGCACAGCGGCGAC
ATCGCCTACTGGGACGAGGACGAGCACTTCTTCATCGTCGACCGGCTGAAGTCGCTGATC
AAGTACAAGGGCTACCAGGTGGCGCCGGCCGAGCTGGAGAGCATCCTGCTCCAGCACCCC
AACATCTTCGACGCCGGCGTGGCCGGGCTGCCGGACGACGACGCCGGCGAGCTGCCGGCC
GCGGTGGTGGTGCTGGAGCACGGCAAGACCATGACGGAGAAGGAGATCGTCGACTACGTG
GCCAGCCAGGTGACCACCGCCAAGAAGCTGCGGGGCGGCGTGGTGTTCGTGGACGAGGTC
CCGAAGGGCCTGACCGGGAAGCTCGACGCCCGGAAGATCCGCGAGATCCTGATCAAGGCC
AAGAAGGGCGGCAAGATCGCCGTGTAAGACTAGTTATAAGACTGACTAGCCCGATGGGCC
TCCCAACGGGCCCTCCTCCCCTCCTTGCACCGAGATTAATAGATCTAAAAAAAAAAAAAA
AAAAAAAAAAAAAAAAAAAAAAAAAAAAAAAAAAAAAAAAAAAAAAAAAA
```

Figure 10 nucleotide sequence of RPL32 – PpLuc(GC) – ag – A64 – histoneSL

GGGGCGCTGCCTACGGAGGTGGCAGCCATCTCCTTCTCGGCATCAAGCTTGAGGATGGAG
GACGCCAAGAACATCAAGAAGGGCCCGGCGCCCTTCTACCCGCTGGAGGACGGGACCGCC
GGCGAGCAGCTCCACAAGGCCATGAAGCGGTACGCCCTGGTGCCGGGCACGATCGCCTTC
ACCGACGCCCACATCGAGGTCGACATCACCTACGCGGAGTACTTCGAGATGAGCGTGCGC
CTGGCCGAGGCCATGAAGCGGTACGGCCTGAACACCAACCACCGGATCGTGGTGTGCTCG
GAGAACAGCCTGCAGTTCTTCATGCCGGTGCTGGGCGCCCTCTTCATCGGCGTGGCCGTC
GCCCCGGCGAACGACATCTACAACGAGCGGGAGCTGCTGAACAGCATGGGGATCAGCCAG
CCGACCGTGGTGTTCGTGAGCAAGAAGGGCCTGCAGAAGATCCTGAACGTGCAGAAGAAG
CTGCCCATCATCCAGAAGATCATCATCATGGACAGCAAGACCGACTACCAGGGCTTCCAG
TCGATGTACACGTTCGTGACCAGCCACCTCCCGCCGGGCTTCAACGAGTACGACTTCGTC
CCGGAGAGCTTCGACCGGGACAAGACCATCGCCCTGATCATGAACAGCAGCGGCAGCACC
GGCCTGCCGAAGGGGGTGGCCCTGCCGCACCGGACCGCCTGCGTGCGCTTCTCGCACGCC
CGGGACCCCATCTTCGGCAACCAGATCATCCCGGACACCGCCATCCTGAGCGTGGTGCCG
TTCCACCACGGCTTCGGCATGTTCACGACCCTGGGCTACCTCATCTGCGGCTTCCGGGTG
GTCCTGATGTACCGGTTCGAGGAGGAGCTGTTCCTGCGGAGCCTGCAGGACTACAAGATC
CAGAGCGCGCTGCTCGTGCCGACCCTGTTCAGCTTCTTCGCCAAGAGCACCCTGATCGAC
AAGTACGACCTGTCGAACCTGCACGAGATCGCCAGCGGGGCGCCCCGCTGAGCAAGGAG
GTGGGCGAGGCCGTGGCCAAGCGGTTCCACCTCCCGGGCATCCGCCAGGGCTACGGCCTG
ACCGAGACCACGAGCGCGATCCTGATCACCCCCGAGGGGGACGACAAGCCGGGCGCCGTG
GGCAAGGTGGTCCCGTTCTTCGAGGCCAAGGTGGTGGACCTGGACACCGGCAAGACCCTG
GGCGTGAACCAGCGGGGCGAGCTGTGCGTGCGGGGCCGATGATCATGAGCGGCTACGTG
AACAACCCGGAGGCCACCAACGCCCTCATCGACAAGGACGGCTGGCTGCACAGCGGCGAC
ATCGCCTACTGGGACGAGGACGAGCACTTCTTCATCGTCGACCGGCTGAAGTCGCTGATC
AAGTACAAGGGCTACCAGGTGGCGCCGGCCGAGCTGGAGAGCATCCTGCTCCAGCACCCC
AACATCTTCGACGCCGGCGTGGCCGGGCTGCCGGACGACGACGCCGGCGAGCTGCCGGCC
GCGGTGGTGGTGCTGGAGCACGGCAAGACCATGACGGAGAAGGAGATCGTCGACTACGTG
GCCAGCCAGGTGACCACCGCCAAGAAGCTGCGGGGCGGCGTGGTGTTCGTGGACGAGGTC
CCGAAGGGCCTGACCGGGAAGCTCGACGCCCGGAAGATCCGCGAGATCCTGATCAAGGCC
AAGAAGGGCGGCAAGATCGCCGTGTAAGACTAGTTATAAGACTGACTAGCCCGATGGGCC
TCCCAACGGGCCCTCCTCCCCTCCTTGCACCGAGATTAATAAAAAAAAAAAAAAAAAAAA
AAAAAAAAAAAAAAAAAAAAAAAAAAAAAAAAAAAAAAAAAAATGCATCAAAGGCTCTT
TTCAGAGCCACCA

Figure 11 nucleotide sequence of RPL32 – PpLuc(GC) – albumin7 – A64 – C30 – histoneSL

GGGGCGCTGCCTACGGAGGTGGCAGCCATCTCCTTCTCGGCATCAAGCTTGAGG*ATGGAG*
*GACGCCAAGAACATCAAGAAGGGCCCGGCGCCCTTCTACCCGCTGGAGGACGGGACCGCC*
*GGCGAGCAGCTCCACAAGGCCATGAAGCGGTACGCCCTGGTGCCGGGCACGATCGCCTTC*
*ACCGACGCCCACATCGAGGTCGACATCACCTACGCGGAGTACTTCGAGATGAGCGTGCGC*
*CTGGCCGAGGCCATGAAGCGGTACGGCCTGAACACCAACCACCGGATCGTGGTGTGCTCG*
*GAGAACAGCCTGCAGTTCTTCATGCCGGTGCTGGGCGCCCTCTTCATCGGCGTGGCCGTC*
*GCCCCGGCGAACGACATCTACAACGAGCGGGAGCTGCTGAACAGCATGGGGATCAGCCAG*
*CCGACCGTGGTGTTCGTGAGCAAGAAGGGCCTGCAGAAGATCCTGAACGTGCAGAAGAAG*
*CTGCCCATCATCCAGAAGATCATCATCATGGACAGCAAGACCGACTACCAGGGCTTCCAG*
*TCGATGTACACGTTCGTGACCAGCCACCTCCCGCCGGGCTTCAACGAGTACGACTTCGTC*
*CCGGAGAGCTTCGACCGGGACAAGACCATCGCCCTGATCATGAACAGCAGCGGCAGCACC*
*GGCCTGCCGAAGGGGGTGGCCCTGCCGCACCGGACCGCCTGCGTGCGCTTCTCGCACGCC*
*CGGGACCCCATCTTCGGCAACCAGATCATCCCGGACACCGCCATCCTGAGCGTGGTGCCG*
*TTCCACCACGGCTTCGGCATGTTCACGACCCTGGGCTACCTCATCTGCGGCTTCCGGGTG*
*GTCCTGATGTACCGGTTCGAGGAGGAGCTGTTCCTGCGGAGCCTGCAGGACTACAAGATC*
*CAGAGCGCGCTGCTCGTGCCGACCCTGTTCAGCTTCTTCGCCAAGAGCACCCTGATCGAC*
*AAGTACGACCTGTCGAACCTGCACGAGATCGCCAGCGGGGCGCCCCGCTGAGCAAGGAG*
*GTGGGCGAGGCCGTGGCCAAGCGGTTCCACCTCCCGGGCATCCGCCAGGGCTACGGCCTG*
*ACCGAGACCACGAGCGCGATCCTGATCACCCCGAGGGGGACGACAAGCCGGGCGCCGTG*
*GGCAAGGTGGTCCCGTTCTTCGAGGCCAAGGTGGTGGACCTGGACACCGGCAAGACCCTG*
*GGCGTGAACCAGCGGGGCGAGCTGTGCGTGCGGGGGCCGATGATCATGAGCGGCTACGTG*
*AACAACCCGGAGGCCACCAACGCCCTCATCGACAAGGACGGCTGGCTGCACAGCGGCGAC*
*ATCGCCTACTGGGACGAGGACGAGCACTTCTTCATCGTCGACCGGCTGAAGTCGCTGATC*
*AAGTACAAGGGCTACCAGGTGGCGCCGGCCGAGCTGGAGAGCATCCTGCTCCAGCACCCC*
*AACATCTTCGACGCCGGCGTGGCCGGGCTGCCGGACGACGACGCCGGCGAGCTGCCGGCC*
*GCGGTGGTGGTGCTGGAGCACGGCAAGACCATGACGGAGAAGGAGATCGTCGACTACGTG*
*GCCAGCCAGGTGACCACCGCCAAGAAGCTGCGGGGCGGCGTGGTGTTCGTGGACGAGGTC*
*CCGAAGGGCCTGACCGGGAAGCTCGACGCCCGGAAGATCCGCGAGATCCTGATCAAGGCC*
*AAGAAGGGCGGCAAGATCGCCGTGTAAGACTAGT*GCATCACATTTAAAAGCATCTCAGCC
TACCATGAGAATAAGAGAAAGAAAATGAAGATCAATAGCTTATTCATCTCTTTTTCTTTT
TCGTTGGTGTAAAGCCAACACCCTGTCTAAAAAACATAAATTTCTTTAATCATTTTGCCT
CTTTTCTCTGTGCTTCAATTAATAAAAAATGGAAAGAACCTAGATCTAAAAAAAAAAAA
AAAAAAAAAAAAAAAAAAAAAAAAAAAAAAAAAAAAAAAAAAAAAAAATGCATCCCC
CCCCCCCCCCCCCCCCCCCCCCCCCAAAGGCTCTTTTCAGAGCCACCAGAATT

Figure 13 nucleotide sequence of RPL35 – PpLuc(GC) – albumin7 – A64 – C30 – histoneSL

GGGGAGCGGGCGGCGGCGTTGGCGGCTTGTGCAGCAAAGCTTGAGGATGGAGGACGCCAA
GAACATCAAGAAGGGCCCGGCGCCCTTCTACCCGCTGGAGGACGGGACCGCCGGCGAGCA
GCTCCACAAGGCCATGAAGCGGTACGCCCTGGTGCCGGGCACGATCGCCTTCACCGACGC
CCACATCGAGGTCGACATCACCTACGCGGAGTACTTCGAGATGAGCGTGCGCCTGGCCGA
GGCCATGAAGCGGTACGGCCTGAACACCAACCACCGGATCGTGGTGTGCTCGGAGAACAG
CCTGCAGTTCTTCATGCCGGTGCTGGGCGCCCTCTTCATCGGCGTGGCCGTCGCCCCGGC
GAACGACATCTACAACGAGCGGGAGCTGCTGAACAGCATGGGGATCAGCCAGCCGACCGT
GGTGTTCGTGAGCAAGAAGGGCCTGCAGAAGATCCTGAACGTGCAGAAGAAGCTGCCCAT
CATCCAGAAGATCATCATCATGGACAGCAAGACCGACTACCAGGGCTTCCAGTCGATGTA
CACGTTCGTGACCAGCCACCTCCCGCCGGGCTTCAACGAGTACGACTTCGTCCCGGAGAG
CTTCGACCGGGACAAGACCATCGCCCTGATCATGAACAGCAGCGGCAGCACCGGCCTGCC
GAAGGGGGTGGCCCTGCCGCACCGGACCGCCTGCGTGCGCTTCTCGCACGCCCGGGACCC
CATCTTCGGCAACCAGATCATCCCGGACACCGCCATCCTGAGCGTGGTGCCGTTCCACCA
CGGCTTCGGCATGTTCACGACCCTGGGCTACCTCATCTGCGGCTTCCGGGTGGTCCTGAT
GTACCGGTTCGAGGAGGAGCTGTTCCTGCGGAGCCTGCAGGACTACAAGATCCAGAGCGC
GCTGCTCGTGCCGACCCTGTTCAGCTTCTTCGCCAAGAGCACCCTGATCGACAAGTACGA
CCTGTCGAACCTGCACGAGATCGCCAGCGGGGCGCCCCGCTGAGCAAGGAGGTGGGCGA
GGCCGTGGCCAAGCGGTTCCACCTCCCGGGCATCCGCCAGGGCTACGGCCTGACCGAGAC
CACGAGCGCGATCCTGATCACCCCGAGGGGACGACAAGCCGGGCGCCGTGGGCAAGGT
GGTCCCGTTCTTCGAGGCCAAGGTGGTGGACCTGGACACCGGCAAGACCCTGGGCGTGAA
CCAGCGGGGCGAGCTGTGCGTGCGGGGCCGATGATCATGAGCGGCTACGTGAACAACCC
GGAGGCCACCAACGCCCTCATCGACAAGGACGGCTGGCTGCACAGCGGCGACATCGCCTA
CTGGGACGAGGACGAGCACTTCTTCATCGTCGACCGGCTGAAGTCGCTGATCAAGTACAA
GGGCTACCAGGTGGCGCCGGCCGAGCTGGAGAGCATCCTGCTCCAGCACCCCAACATCTT
CGACGCCGGCGTGGCCGGGCTGCCGGACGACGACGCCGGCGAGCTGCCGGCCGCGGTGGT
GGTGCTGGAGCACGGCAAGACCATGACGGAGAAGGAGATCGTCGACTACGTGGCCAGCCA
GGTGACCACCGCCAAGAAGCTGCGGGGCGGCGTGGTGTTCGTGGACGAGGTCCCGAAGGG
CCTGACCGGGAAGCTCGACGCCCGGAAGATCCGCGAGATCCTGATCAAGGCCAAGAAGGG
CGGCAAGATCGCCGTGTAAGACTAGTGCATCACATTTAAAAGCATCTCAGCCTACCATGA
GAATAAGAGAAAGAAAATGAAGATCAATAGCTTATTCATCTCTTTTTCTTTTTCGTTGGT
GTAAAGCCAACACCCTGTCTAAAAAACATAAATTTCTTTAATCATTTTGCCTCTTTTCTC
TGTGCTTCAATTAATAAAAAATGGAAAGAACCTAGATCTAAAAAAAAAAAAAAAAAAAA
AAAAAAAAAAAAAAAAAAAAAAAAAAAAAAAAAAAAAAAAAATGCATCCCCCCCCCCC
CCCCCCCCCCCCCCCCCAAAGGCTCTTTTCAGAGCCACCAGAATT

Figure 14 nucleotide sequence of RPL21 – PpLuc(GC) – albumin7 – A64 – C30 – histoneSL

```
GGGGCCGGAACCGCCATCTTCCAGTAATTCGCCAAAAAGCTTGAGGATGGAGGACGCCAA
GAACATCAAGAAGGGCCCGGCGCCCTTCTACCCGCTGGAGGACGGGACCGCCGGCGAGCA
GCTCCACAAGGCCATGAAGCGGTACGCCCTGGTGCCGGGCACGATCGCCTTCACCGACGC
CCACATCGAGGTCGACATCACCTACGCGGAGTACTTCGAGATGAGCGTGCGCCTGGCCGA
GGCCATGAAGCGGTACGGCCTGAACACCAACCACCGGATCGTGGTGTGCTCGGAGAACAG
CCTGCAGTTCTTCATGCCGGTGCTGGGCGCCCTCTTCATCGGCGTGGCCGTCGCCCCGGC
GAACGACATCTACAACGAGCGGGAGCTGCTGAACAGCATGGGGATCAGCCAGCCGACCGT
GGTGTTCGTGAGCAAGAAGGGCCTGCAGAAGATCCTGAACGTGCAGAAGAAGCTGCCCAT
CATCCAGAAGATCATCATCATGGACAGCAAGACCGACTACCAGGGCTTCCAGTCGATGTA
CACGTTCGTGACCAGCCACCTCCCGCCGGGCTTCAACGAGTACGACTTCGTCCCGGAGAG
CTTCGACCGGGACAAGACCATCGCCCTGATCATGAACAGCAGCGGCAGCACCGGCCTGCC
GAAGGGGGTGGCCCTGCCGCACCGGACCGCCTGCGTGCGCTTCTCGCACGCCCGGGACCC
CATCTTCGGCAACCAGATCATCCCGGACACCGCCATCCTGAGCGTGGTGCCGTTCCACCA
CGGCTTCGGCATGTTCACGACCCTGGGCTACCTCATCTGCGGCTTCCGGGTGGTCCTGAT
GTACCGGTTCGAGGAGGAGCTGTTCCTGCGGAGCCTGCAGGACTACAAGATCCAGAGCGC
GCTGCTCGTGCCGACCCTGTTCAGCTTCTTCGCCAAGAGCACCCTGATCGACAAGTACGA
CCTGTCGAACCTGCACGAGATCGCCAGCGGGGGCGCCCCGCTGAGCAAGGAGGTGGGCGA
GGCCGTGGCCAAGCGGTTCCACCTCCCGGGCATCCGCCAGGGCTACGGCCTGACCGAGAC
CACGAGCGCGATCCTGATCACCCCCGAGGGGGACGACAAGCCGGGCGCCGTGGGCAAGGT
GGTCCCGTTCTTCGAGGCCAAGGTGGTGGACCTGGACACCGGCAAGACCCTGGGCGTGAA
CCAGCGGGGCGAGCTGTGCGTGCGGGGCCGATGATCATGAGCGGCTACGTGAACAACCC
GGAGGCCACCAACGCCCTCATCGACAAGGACGGCTGGCTGCACAGCGGCGACATCGCCTA
CTGGGACGAGGACGAGCACTTCTTCATCGTCGACCGGCTGAAGTCGCTGATCAAGTACAA
GGGCTACCAGGTGGCGCCGGCCGAGCTGGAGAGCATCCTGCTCCAGCACCCCAACATCTT
CGACGCCGGCGTGGCCGGGCTGCCGGACGACGACGCCGGCGAGCTGCCGGCCGCGGTGGT
GGTGCTGGAGCACGGCAAGACCATGACGGAGAAGGAGATCGTCGACTACGTGGCCAGCCA
GGTGACCACCGCCAAGAAGCTGCGGGGCGGCGTGGTGTTCGTGGACGAGGTCCCGAAGGG
CCTGACCGGGAAGCTCGACGCCCGGAAGATCCGCGAGATCCTGATCAAGGCCAAGAAGGG
CGGCAAGATCGCCGTGTAAGACTAGTGCATCACATTTAAAAGCATCTCAGCCTACCATGA
GAATAAGAGAAAGAAAATGAAGATCAATAGCTTATTCATCTCTTTTTCTTTTTCGTTGGT
GTAAAGCCAACACCCTGTCTAAAAAACATAAATTTCTTTAATCATTTTGCCTCTTTTCTC
TGTGCTTCAATTAATAAAAAATGGAAAGAACCTAGATCTAAAAAAAAAAAAAAAAAAAAA
AAAAAAAAAAAAAAAAAAAAAAAAAAAAAAAAAAAAAAAAAAAATGCATCCCCCCCCCCC
CCCCCCCCCCCCCCCCCAAAGGCTCTTTTCAGAGCCACCAGAATT
```

Figure 15 nucleotide sequence of atp5a1 – PpLuc(GC) – albumin7 – A64 – C30 – histoneSL

```
GGGCGGCTCGGCCATTTTGTCCCAGTCAGTCCGGAGGCTGCGGCTGCAGAAGTACCGCCT
GCGGAGTAACTGCAAAGAAGCTTGAGGATGGAGGACGCCAAGAACATCAAGAAGGGCCCG
GCGCCCTTCTACCCGCTGGAGGACGGGACCGCCGGCGAGCAGCTCCACAAGGCCATGAAG
CGGTACGCCCTGGTGCCGGGCACGATCGCCTTCACCGACGCCCACATCGAGGTCGACATC
ACCTACGCGGAGTACTTCGAGATGAGCGTGCGCCTGGCCGAGGCCATGAAGCGGTACGGC
CTGAACACCAACCACCGGATCGTGGTGTGCTCGGAGAACAGCCTGCAGTTCTTCATGCCG
GTGCTGGGCGCCCTCTTCATCGGCGTGGCCGTCGCCCCGGCAACGACATCTACAACGAG
CGGGAGCTGCTGAACAGCATGGGGATCAGCCAGCCGACCGTGGTGTTCGTGAGCAAGAAG
GGCCTGCAGAAGATCCTGAACGTGCAGAAGAAGCTGCCCATCATCCAGAAGATCATCATC
ATGGACAGCAAGACCGACTACCAGGGCTTCCAGTCGATGTACACGTTCGTGACCAGCCAC
CTCCCGCCGGGCTTCAACGAGTACGACTTCGTCCCGGAGAGCTTCGACCGGGACAAGACC
ATCGCCCTGATCATGAACAGCAGCGGCAGCACCGGCCTGCCGAAGGGGGTGGCCCTGCCG
CACCGGACCGCCTGCGTGCGCTTCTCGCACGCCCGGACCCCATCTTCGGCAACCAGATC
ATCCCGGACACCGCCATCCTGAGCGTGGTGCCGTTCCACCACGGCTTCGGCATGTTCACG
ACCCTGGGCTACCTCATCTGCGGCTTCCGGGTGGTCCTGATGTACCGGTTCGAGGAGGAG
CTGTTCCTGCGGAGCCTGCAGGACTACAAGATCCAGAGCGCGCTGCTCGTGCCGACCCTG
TTCAGCTTCTTCGCCAAGAGCACCCTGATCGACAAGTACGACCTGTCGAACCTGCACGAG
ATCGCCAGCGGGGGCGCCCCGCTGAGCAAGGAGGTGGGCGAGGCCGTGGCCAAGCGGTTC
CACCTCCCGGGCATCCGCCAGGGCTACGGCCTGACCGAGACCACGAGCGCGATCCTGATC
ACCCCCGAGGGGGACGACAAGCCGGGCGCCGTGGGCAAGGTGGTCCCGTTCTTCGAGGCC
AAGGTGGTGGACCTGGACACCGGCAAGACCCTGGGCGTGAACCAGCGGGGCGAGCTGTGC
GTGCGGGGCCCGATGATCATGAGCGGCTACGTGAACAACCCGGAGGCCACCAACGCCCTC
ATCGACAAGGACGGCTGGCTGCACAGCGGCGACATCGCCTACTGGGACGAGGACGAGCAC
TTCTTCATCGTCGACCGGCTGAAGTCGCTGATCAAGTACAAGGGCTACCAGGTGGCGCCG
GCCGAGCTGGAGAGCATCCTGCTCCAGCACCCCAACATCTTCGACGCCGGCGTGGCCGGG
CTGCCGGACGACGACGCCGGCGAGCTGCCGGCCGCGGTGGTGGTGCTGGAGCACGGCAAG
ACCATGACGGAGAAGGAGATCGTCGACTACGTGGCCAGCCAGGTGACCACCGCCAAGAAG
CTGCGGGGCGGCGTGGTGTTCGTGGACGAGGTCCCGAAGGGCCTGACCGGGAAGCTCGAC
GCCCGGAAGATCCGCGAGATCCTGATCAAGGCCAAGAAGGGCGGCAAGATCGCCGTGTAA
GACTAGTGCATCACATTTAAAAGCATCTCAGCCTACCATGAGAATAAGAGAAAGAAAATG
AAGATCAATAGCTTATTCATCTCTTTTTCTTTTTCGTTGGTGTAAAGCCAACACCCTGTC
TAAAAAACATAAATTTCTTTAATCATTTTGCCTCTTTTCTCTGTGCTTCAATTAATAAAA
AATGGAAAGAACCTAGATCTAAAAAAAAAAAAAAAAAAAAAAAAAAAAAAAAAAAAAAAA
AAAAAAAAAAAAAAAAAAAAAAAATGCATCCCCCCCCCCCCCCCCCCCCCCCCCCCCCC
AAAGGCTCTTTTCAGAGCCACCAGAATT
```

Figure 16 nucleotide sequence of HSD17B4 – PpLuc(GC) – albumin7 – A64 – C30 – histoneSL

GGGTCCCGCAGTCGGCGTCCAGCGGCTCTGCTTGTTCGTGTGTGTGTCGTTGCAGGCCTT
ATTCAAGCTTGAGGATGGAGGACGCCAAGAACATCAAGAAGGGCCCGGCGCCCTTCTACC
CGCTGGAGGACGGGACCGCCGGCGAGCAGCTCCACAAGGCCATGAAGCGGTACGCCCTGG
TGCCGGGCACGATCGCCTTCACCGACGCCCACATCGAGGTCGACATCACCTACGCGGAGT
ACTTCGAGATGAGCGTGCGCCTGGCCGAGGCCATGAAGCGGTACGGCCTGAACACCAACC
ACCGGATCGTGGTGTGCTCGGAGAACAGCCTGCAGTTCTTCATGCCGGTGCTGGGCGCCC
TCTTCATCGGCGTGGCCGTCGCCCCGGCGAACGACATCTACAACGAGCGGGAGCTGCTGA
ACAGCATGGGGATCAGCCAGCCGACCGTGGTGTTCGTGAGCAAGAAGGGCCTGCAGAAGA
TCCTGAACGTGCAGAAGAAGCTGCCCATCATCCAGAAGATCATCATCATGGACAGCAAGA
CCGACTACCAGGGCTTCCAGTCGATGTACACGTTCGTGACCAGCCACCTCCCGCCGGGCT
TCAACGAGTACGACTTCGTCCCGGAGAGCTTCGACCGGGACAAGACCATCGCCCTGATCA
TGAACAGCAGCGGCAGCACCGGCCTGCCGAAGGGGGTGGCCCTGCCGCACCGGACCGCCT
GCGTGCGCTTCTCGCACGCCCGGGACCCCATCTTCGGCAACCAGATCATCCCGGACACCG
CCATCCTGAGCGTGGTGCCGTTCCACCACGGCTTCGGCATGTTCACGACCCTGGGCTACC
TCATCTGCGGCTTCCGGGTGGTCCTGATGTACCGGTTCGAGGAGGAGCTGTTCCTGCGGA
GCCTGCAGGACTACAAGATCCAGAGCGCGCTGCTCGTGCCGACCCTGTTCAGCTTCTTCG
CCAAGAGCACCCTGATCGACAAGTACGACCTGTCGAACCTGCACGAGATCGCCAGCGGGG
GCGCCCCGCTGAGCAAGGAGGTGGGCGAGGCCGTGGCCAAGCGGTTCCACCTCCCGGGCA
TCCGCCAGGGCTACGGCCTGACCGAGACCACGAGCGCGATCCTGATCACCCCCGAGGGGG
ACGACAAGCCGGGCGCCGTGGGCAAGGTGGTCCCGTTCTTCGAGGCCAAGGTGGTGGACC
TGGACACCGGCAAGACCCTGGGCGTGAACCAGCGGGGCGAGCTGTGCGTGCGGGGGCCGA
TGATCATGAGCGGCTACGTGAACAACCCGGAGGCCACCAACGCCCTCATCGACAAGGACG
GCTGGCTGCACAGCGGCGACATCGCCTACTGGGACGAGGACGAGCACTTCTTCATCGTCG
ACCGGCTGAAGTCGCTGATCAAGTACAAGGGCTACCAGGTGGCGCCGGCCGAGCTGGAGA
GCATCCTGCTCCAGCACCCCAACATCTTCGACGCCGGCGTGGCCGGGCTGCCGGACGACG
ACGCCGGCGAGCTGCCGGCCGCGGTGGTGGTGCTGGAGCACGGCAAGACCATGACGGAGA
AGGAGATCGTCGACTACGTGGCCAGCCAGGTGACCACCGCCAAGAAGCTGCGGGGCGGCG
TGGTGTTCGTGGACGAGGTCCCGAAGGGCCTGACCGGGAAGCTCGACGCCCGGAAGATCC
GCGAGATCCTGATCAAGGCCAAGAAGGGCGGCAAGATCGCCGTGTAAGACTAGTGCATCA
CATTTAAAAGCATCTCAGCCTACCATGAGAATAAGAGAAAGAAAATGAAGATCAATAGCT
TATTCATCTCTTTTTCTTTTTCGTTGGTGTAAAGCCAACACCCTGTCTAAAAACATAAA
TTTCTTTAATCATTTTGCCTCTTTTCTCTGTGCTTCAATTAATAAAAAATGGAAAGAACC
TAGATCTAAAAAAAAAAAAAAAAAAAAAAAAAAAAAAAAAAAAAAAAAAAAAAAAAAAAA
AAAAAAAAAAATGCATCCCCCCCCCCCCCCCCCCCCCCCCCCCCAAAGGCTCTTTTC
AGAGCCACCAGAATT

Figure 17 nucleotide sequence of AIG1 – PpLuc(GC) – albumin7 – A64 – C30 – histoneSL

GGGCCGCCCAGCCGGTCCAGGCCTCTGGCGAACAAGCTTGAGGATGGAGGACGCCAAGAA
CATCAAGAAGGGCCCGGCGCCCTTCTACCCGCTGGAGGACGGGACCGCCGGCGAGCAGCT
CCACAAGGCCATGAAGCGGTACGCCCTGGTGCCGGGCACGATCGCCTTCACCGACGCCCA
CATCGAGGTCGACATCACCTACGCGGAGTACTTCGAGATGAGCGTGCGCCTGGCCGAGGC
CATGAAGCGGTACGGCCTGAACACCAACCACCGGATCGTGGTGTGCTCGGAGAACAGCCT
GCAGTTCTTCATGCCGGTGCTGGGCGCCCTCTTCATCGGCGTGGCCGTCGCCCCGGCGAA
CGACATCTACAACGAGCGGGAGCTGCTGAACAGCATGGGGATCAGCCAGCCGACCGTGGT
GTTCGTGAGCAAGAAGGGCCTGCAGAAGATCCTGAACGTGCAGAAGAAGCTGCCCATCAT
CCAGAAGATCATCATCATGGACAGCAAGACCGACTACCAGGGCTTCCAGTCGATGTACAC
GTTCGTGACCAGCCACCTCCCGCCGGGCTTCAACGAGTACGACTTCGTCCCGGAGAGCTT
CGACCGGGACAAGACCATCGCCCTGATCATGAACAGCAGCGGCAGCACCGGCCTGCCGAA
GGGGGTGGCCCTGCCGCACCGGACCGCCTGCGTGCGCTTCTCGCACGCCCGGGACCCCAT
CTTCGGCAACCAGATCATCCCGGACACCGCCATCCTGAGCGTGGTGCCGTTCCACCACGG
CTTCGGCATGTTCACGACCCTGGGCTACCTCATCTGCGGCTTCCGGGTGGTCCTGATGTA
CCGGTTCGAGGAGGAGCTGTTCCTGCGGAGCCTGCAGGACTACAAGATCCAGAGCGCGCT
GCTCGTGCCGACCCTGTTCAGCTTCTTCGCCAAGAGCACCCTGATCGACAAGTACGACCT
GTCGAACCTGCACGAGATCGCCAGCGGGGCGCCCCGCTGAGCAAGGAGGTGGGCGAGGC
CGTGGCCAAGCGGTTCCACCTCCCGGGCATCCGCCAGGGCTACGGCCTGACCGAGACCAC
GAGCGCGATCCTGATCACCCCCGAGGGGGACGACAAGCCGGGCGCCGTGGGCAAGGTGGT
CCCGTTCTTCGAGGCCAAGGTGGTGGACCTGGACACCGGCAAGACCCTGGGCGTGAACCA
GCGGGGCGAGCTGTGCGTGCGGGGCCGATGATCATGAGCGGCTACGTGAACAACCCGGA
GGCCACCAACGCCCTCATCGACAAGGACGGCTGGCTGCACAGCGGCGACATCGCCTACTG
GGACGAGGACGAGCACTTCTTCATCGTCGACCGGCTGAAGTCGCTGATCAAGTACAAGGG
CTACCAGGTGGCGCCGGCCGAGCTGGAGAGCATCCTGCTCCAGCACCCCAACATCTTCGA
CGCCGGCGTGGCCGGGCTGCCGGACGACGACGCCGGCGAGCTGCCGGCCGCGGTGGTGGT
GCTGGAGCACGGCAAGACCATGACGGAGAAGGAGATCGTCGACTACGTGGCCAGCCAGGT
GACCACCGCCAAGAAGCTGCGGGGCGGCGTGGTGTTCGTGGACGAGGTCCCGAAGGGCCT
GACCGGGAAGCTCGACGCCCGGAAGATCCGCGAGATCCTGATCAAGGCCAAGAAGGGCGG
CAAGATCGCCGTGTAAGACTAGTGCATCACATTTAAAAGCATCTCAGCCTACCATGAGAA
TAAGAGAAAGAAAATGAAGATCAATAGCTTATTCATCTCTTTTTCTTTTTCGTTGGTGTA
AAGCCAACACCCTGTCTAAAAAACATAAATTTCTTTAATCATTTTGCCTCTTTTCTCTGT
GCTTCAATTAATAAAAAATGGAAAGAACCTAGATCTAAAAAAAAAAAAAAAAAAAAAAAA
AAAAAAAAAAAAAAAAAAAAAAAAAAAAAAAAAAAAAAAATGCATCCCCCCCCCCCCCCC
CCCCCCCCCCCCCCCAAAGGCTCTTTTCAGAGCCACCAGAATT

Figure 18 nucleotide sequence of COX6C – PpLuc(GC) – albumin7 – A64 – C30 – histoneSL

```
GGAGTCAGGAAGGACGTTGGTGTTGAGGTTAGCATACGTATCAAGGACAGTAACTACCAA
GCTTGAGGATGGAGGACGCCAAGAACATCAAGAAGGGCCCGGCGCCCTTCTACCCGCTGG
AGGACGGGACCGCCGGCGAGCAGCTCCACAAGGCCATGAAGCGGTACGCCCTGGTGCCGG
GCACGATCGCCTTCACCGACGCCCACATCGAGGTCGACATCACCTACGCGGAGTACTTCG
AGATGAGCGTGCGCCTGGCCGAGGCCATGAAGCGGTACGGCCTGAACACCAACCACCGGA
TCGTGGTGTGCTCGGAGAACAGCCTGCAGTTCTTCATGCCGGTGCTGGGCGCCCTCTTCA
TCGGCGTGGCCGTCGCCCCGGCGAACGACATCTACAACGAGCGGGAGCTGCTGAACAGCA
TGGGGATCAGCCAGCCGACCGTGGTGTTCGTGAGCAAGAAGGGCCTGCAGAAGATCCTGA
ACGTGCAGAAGAAGCTGCCCATCATCCAGAAGATCATCATCATGGACAGCAAGACCGACT
ACCAGGGCTTCCAGTCGATGTACACGTTCGTGACCAGCCACCTCCCGCCGGGCTTCAACG
AGTACGACTTCGTCCCGGAGAGCTTCGACCGGGACAAGACCATCGCCCTGATCATGAACA
GCAGCGGCAGCACCGGCCTGCCGAAGGGGGTGGCCCTGCCGCACCGGACCGCCTGCGTGC
GCTTCTCGCACGCCCGGGACCCCATCTTCGGCAACCAGATCATCCCGGACACCGCCATCC
TGAGCGTGGTGCCGTTCCACCACGGCTTCGGCATGTTCACGACCCTGGGCTACCTCATCT
GCGGCTTCCGGGTGGTCCTGATGTACCGGTTCGAGGAGGAGCTGTTCCTGCGGAGCCTGC
AGGACTACAAGATCCAGAGCGCGCTGCTCGTGCCGACCCTGTTCAGCTTCTTCGCCAAGA
GCACCCTGATCGACAAGTACGACCTGTCGAACCTGCACGAGATCGCCAGCGGGGGCGCCC
CGCTGAGCAAGGAGGTGGGCGAGGCCGTGGCCAAGCGGTTCCACCTCCCGGGCATCCGCC
AGGGCTACGGCCTGACCGAGACCACGAGCGCGATCCTGATCACCCCCGAGGGGGACGACA
AGCCGGGCGCCGTGGGCAAGGTGGTCCCGTTCTTCGAGGCCAAGGTGGTGGACCTGGACA
CCGGCAAGACCCTGGGCGTGAACCAGCGGGGCGAGCTGTGCGTGCGGGGGCCGATGATCA
TGAGCGGCTACGTGAACAACCCGGAGGCCACCAACGCCCTCATCGACAAGGACGGCTGGC
TGCACAGCGGCGACATCGCCTACTGGGACGAGGACGAGCACTTCTTCATCGTCGACCGGC
TGAAGTCGCTGATCAAGTACAAGGGCTACCAGGTGGCGCCGGCCGAGCTGGAGAGCATCC
TGCTCCAGCACCCCAACATCTTCGACGCCGGCGTGGCCGGGCTGCCGGACGACGACGCCG
GCGAGCTGCCGGCCGCGGTGGTGGTGCTGGAGCACGGCAAGACCATGACGGAGAAGGAGA
TCGTCGACTACGTGGCCAGCCAGGTGACCACCGCCAAGAAGCTGCGGGGCGGCGTGGTGT
TCGTGGACGAGGTCCCGAAGGGCCTGACCGGGAAGCTCGACGCCCGGAAGATCCGCGAGA
TCCTGATCAAGGCCAAGAAGGGCGGCAAGATCGCCGTGTAAGACTAGTGCATCACATTTA
AAAGCATCTCAGCCTACCATGAGAATAAGAGAAAGAAAATGAAGATCAATAGCTTATTCA
TCTCTTTTTCTTTTCGTTGGTGTAAAGCCAACACCCTGTCTAAAAAACATAAATTTCTT
TAATCATTTTGCCTCTTTTCTCTGTGCTTCAATTAATAAAAAATGGAAAGAACCTAGATC
TAAAAAAAAAAAAAAAAAAAAAAAAAAAAAAAAAAAAAAAAAAAAAAAAAAAAAAAAAAA
AAAAATGCATCCCCCCCCCCCCCCCCCCCCCCCCCCCCCAAAGGCTCTTTTCAGAGCC
ACCAGAATT
```

Figure 19 nucleotide sequence of ASAH1 – PpLuc(GC) – albumin7 – A64 – C30 – histoneSL

```
GGGCCTCTGCTGGAGTCCGGGGAGTGGCGTTGGCTGCTAGAGCGAAGCTTGAGGATGGAG
GACGCCAAGAACATCAAGAAGGGCCCGGCGCCCTTCTACCCGCTGGAGGACGGGACCGCC
GGCGAGCAGCTCCACAAGGCCATGAAGCGGTACGCCCTGGTGCCGGGCACGATCGCCTTC
ACCGACGCCCACATCGAGGTCGACATCACCTACGCGGAGTACTTCGAGATGAGCGTGCGC
CTGGCCGAGGCCATGAAGCGGTACGGCCTGAACACCAACCACCGGATCGTGGTGTGCTCG
GAGAACAGCCTGCAGTTCTTCATGCCGGTGCTGGGCGCCCTCTTCATCGGCGTGGCCGTC
GCCCCGGCGAACGACATCTACAACGAGCGGGAGCTGCTGAACAGCATGGGGATCAGCCAG
CCGACCGTGGTGTTCGTGAGCAAGAAGGCCTGCAGAAGATCCTGAACGTGCAGAAGAAG
CTGCCCATCATCCAGAAGATCATCATCATGGACAGCAAGACCGACTACCAGGGCTTCCAG
TCGATGTACACGTTCGTGACCAGCCACCTCCCGCCGGGCTTCAACGAGTACGACTTCGTC
CCGGAGAGCTTCGACCGGGACAAGACCATCGCCCTGATCATGAACAGCAGCGGCAGCACC
GGCCTGCCGAAGGGGGTGGCCCTGCCGCACCGGACCGCCTGCGTGCGCTTCTCGCACGCC
CGGGACCCCATCTTCGGCAACCAGATCATCCCGGACACCGCCATCCTGAGCGTGGTGCCG
TTCCACCACGGCTTCGGCATGTTCACGACCCTGGGCTACCTCATCTGCGGCTTCCGGGTG
GTCCTGATGTACCGGTTCGAGGAGGAGCTGTTCCTGCGGAGCCTGCAGGACTACAAGATC
CAGAGCGCGCTGCTCGTGCCGACCCTGTTCAGCTTCTTCGCCAAGAGCACCCTGATCGAC
AAGTACGACCTGTCGAACCTGCACGAGATCGCCAGCGGGGCGCCCCGCTGAGCAAGGAG
GTGGGCGAGGCCGTGGCCAAGCGGTTCCACCTCCCGGGCATCCGCCAGGGCTACGGCCTG
ACCGAGACCACGAGCGCGATCCTGATCACCCCCGAGGGGGACGACAAGCCGGGCGCCGTG
GGCAAGGTGGTCCCGTTCTTCGAGGCAAGGTGGTGGACCTGGACACCGGCAAGACCCTG
GGCGTGAACCAGCGGGGCGAGCTGTGCGTGCGGGGCCGATGATCATGAGCGGCTACGTG
AACAACCCGGAGGCCACCAACGCCCTCATCGACAAGGACGGCTGGCTGCACAGCGGCGAC
ATCGCCTACTGGGACGAGGACGAGCACTTCTTCATCGTCGACCGGCTGAAGTCGCTGATC
AAGTACAAGGGCTACCAGGTGGCGCCGGCCGAGCTGGAGAGCATCCTGCTCCAGCACCCC
AACATCTTCGACGCCGGCGTGGCCGGGCTGCCGGACGACGACGCCGGCGAGCTGCCGGCC
GCGGTGGTGGTGCTGGAGCACGGCAAGACCATGACGGAGAAGGAGATCGTCGACTACGTG
GCCAGCCAGGTGACCACCGCCAAGAAGCTGCGGGGCGGCGTGGTGTTCGTGGACGAGGTC
CCGAAGGGCCTGACCGGGAAGCTCGACGCCCGGAAGATCCGCGAGATCCTGATCAAGGCC
AAGAAGGGCGGCAAGATCGCCGTGTAAGACTAGTGCATCACATTTAAAAGCATCTCAGCC
TACCATGAGAATAAGAGAAAGAAAATGAAGATCAATAGCTTATTCATCTCTTTTTCTTTT
TCGTTGGTGTAAAGCCAACACCCTGTCTAAAAAACATAAATTTCTTTAATCATTTTGCCT
CTTTTCTCTGTGCTTCAATTAATAAAAAATGGAAAGAACCTAGATCTAAAAAAAAAAAA
AAAAAAAAAAAAAAAAAAAAAAAAAAAAAAAAAAAAAAAAAAAAAAAAATGCATCCCC
CCCCCCCCCCCCCCCCCCCCCCCCCAAAGGCTCTTTTCAGAGCCACCAGAATT
```

Figure 20 nucleotide sequence of RPL35 – PpLuc(GC) – ag – A64

GGGGAGCGGGCGGCGGCGTTGGCGGCTTGTGCAGCAAAGCTTGAGGATGGAGGACGCCAA
GAACATCAAGAAGGGCCCGGCGCCCTTCTACCCGCTGGAGGACGGGACCGCCGGCGAGCA
GCTCCACAAGGCCATGAAGCGGTACGCCCTGGTGCCGGGCACGATCGCCTTCACCGACGC
CCACATCGAGGTCGACATCACCTACGCGGAGTACTTCGAGATGAGCGTGCGCCTGGCCGA
GGCCATGAAGCGGTACGGCCTGAACACCAACCACCGGATCGTGGTGTGCTCGGAGAACAG
CCTGCAGTTCTTCATGCCGGTGCTGGGCGCCCTCTTCATCGGCGTGGCCGTCGCCCCGGC
GAACGACATCTACAACGAGCGGGAGCTGCTGAACAGCATGGGGATCAGCCAGCCGACCGT
GGTGTTCGTGAGCAAGAAGGGCCTGCAGAAGATCCTGAACGTGCAGAAGAAGCTGCCCAT
CATCCAGAAGATCATCATCATGGACAGCAAGACCGACTACCAGGGCTTCCAGTCGATGTA
CACGTTCGTGACCAGCCACCTCCCGCCGGGCTTCAACGAGTACGACTTCGTCCCGGAGAG
CTTCGACCGGGACAAGACCATCGCCCTGATCATGAACAGCAGCGGCAGCACCGGCCTGCC
GAAGGGGGTGGCCCTGCCGCACCGGACCGCCTGCGTGCGCTTCTCGCACGCCCGGGACCC
CATCTTCGGCAACCAGATCATCCCGGACACCGCCATCCTGAGCGTGGTGCCGTTCCACCA
CGGCTTCGGCATGTTCACGACCCTGGGCTACCTCATCTGCGGCTTCCGGGTGGTCCTGAT
GTACCGGTTCGAGGAGGAGCTGTTCCTGCGGAGCCTGCAGGACTACAAGATCCAGAGCGC
GCTGCTCGTGCCGACCCTGTTCAGCTTCTTCGCCAAGAGCACCCTGATCGACAAGTACGA
CCTGTCGAACCTGCACGAGATCGCCAGCGGGGCGCCCCGCTGAGCAAGGAGGTGGGCGA
GGCCGTGGCCAAGCGGTTCCACCTCCCGGGCATCCGCCAGGGCTACGGCCTGACCGAGAC
CACGAGCGCGATCCTGATCACCCCCGAGGGGGACGACAAGCCGGGCGCCGTGGGCAAGGT
GGTCCCGTTCTTCGAGGCCAAGGTGGTGGACCTGGACACCGGCAAGACCCTGGGCGTGAA
CCAGCGGGGCGAGCTGTGCGTGCGGGGGCCGATGATCATGAGCGGCTACGTGAACAACCC
GGAGGCCACCAACGCCCTCATCGACAAGGACGGCTGGCTGCACAGCGGCGACATCGCCTA
CTGGGACGAGGACGAGCACTTCTTCATCGTCGACCGGCTGAAGTCGCTGATCAAGTACAA
GGGCTACCAGGTGGCGCCGGCCGAGCTGGAGAGCATCCTGCTCCAGCACCCCAACATCTT
CGACGCCGGCGTGGCCGGGCTGCCGGACGACGACGCCGGCGAGCTGCCGGCCGCGGTGGT
GGTGCTGGAGCACGGCAAGACCATGACGGAGAAGGAGATCGTCGACTACGTGGCCAGCCA
GGTGACCACCGCCAAGAAGCTGCGGGGCGGCGTGGTGTTCGTGGACGAGGTCCCGAAGGG
CCTGACCGGGAAGCTCGACGCCCGGAAGATCCGCGAGATCCTGATCAAGGCCAAGAAGGG
CGGCAAGATCGCCGTGTAAGACTAGTTATAAGACTGACTAGCCCGATGGGCCTCCCAACG
GGCCCTCCTCCCCTCCTTGCACCGAGATTAATAAAAAAAAAAAAAAAAAAAAAAAAAAAA
AAAAAAAAAAAAAAAAAAAAAAAAAAAAAAAAAA

Figure 22 nucleotide sequence of rpl21 – PpLuc(GC) – ag – A64

```
GGGGCCGGAACCGCCATCTTCCAGTAATTCGCCAAAAAGCTTGAGGATGGAGGACGCCAA
GAACATCAAGAAGGGCCCGGCGCCCTTCTACCCGCTGGAGGACGGGACCGCCGGCGAGCA
GCTCCACAAGGCCATGAAGCGGTACGCCCTGGTGCCGGGCACGATCGCCTTCACCGACGC
CCACATCGAGGTCGACATCACCTACGCGGAGTACTTCGAGATGAGCGTGCGCCTGGCCGA
GGCCATGAAGCGGTACGGCCTGAACACCAACCACCGGATCGTGGTGTGCTCGGAGAACAG
CCTGCAGTTCTTCATGCCGGTGCTGGGCGCCCTCTTCATCGGCGTGGCCGTCGCCCCGGC
GAACGACATCTACAACGAGCGGGAGCTGCTGAACAGCATGGGGATCAGCCAGCCGACCGT
GGTGTTCGTGAGCAAGAAGGGCCTGCAGAAGATCCTGAACGTGCAGAAGAAGCTGCCCAT
CATCCAGAAGATCATCATCATGGACAGCAAGACCGACTACCAGGGCTTCCAGTCGATGTA
CACGTTCGTGACCAGCCACCTCCCGCCGGGCTTCAACGAGTACGACTTCGTCCCGGAGAG
CTTCGACCGGGACAAGACCATCGCCCTGATCATGAACAGCAGCGGCAGCACCGGCCTGCC
GAAGGGGGTGGCCCTGCCGCACCGGACCGCCTGCGTGCGCTTCTCGCACGCCCGGGACCC
CATCTTCGGCAACCAGATCATCCCGGACACCGCCATCCTGAGCGTGGTGCCGTTCCACCA
CGGCTTCGGCATGTTCACGACCCTGGGCTACCTCATCTGCGGCTTCCGGGTGGTCCTGAT
GTACCGGTTCGAGGAGGAGCTGTTCCTGCGGAGCCTGCAGGACTACAAGATCCAGAGCGC
GCTGCTCGTGCCGACCCTGTTCAGCTTCTTCGCCAAGAGCACCCTGATCGACAAGTACGA
CCTGTCGAACCTGCACGAGATCGCCAGCGGGGCGCCCCGCTGAGCAAGGAGGTGGGCGA
GGCCGTGGCCAAGCGGTTCCACCTCCCGGGCATCCGCCAGGGCTACGGCCTGACCGAGAC
CACGAGCGCGATCCTGATCACCCCCGAGGGGACGACAAGCCGGGCGCCGTGGGCAAGGT
GGTCCCGTTCTTCGAGGCCAAGGTGGTGGACCTGGACACCGGCAAGACCCTGGGCGTGAA
CCAGCGGGGCGAGCTGTGCGTGCGGGGCCGATGATCATGAGCGGCTACGTGAACAACCC
GGAGGCCACCAACGCCCTCATCGACAAGGACGGCTGGCTGCACAGCGGCGACATCGCCTA
CTGGGACGAGGACGAGCACTTCTTCATCGTCGACCGGCTGAAGTCGCTGATCAAGTACAA
GGGCTACCAGGTGGCGCCGGCCGAGCTGGAGAGCATCCTGCTCCAGCACCCCAACATCTT
CGACGCCGGCGTGGCCGGGCTGCCGGACGACGACGCCGGCGAGCTGCCGGCCGCGGTGGT
GGTGCTGGAGCACGGCAAGACCATGACGGAGAAGGAGATCGTCGACTACGTGGCCAGCCA
GGTGACCACCGCCAAGAAGCTGCGGGGCGGCGTGGTGTTCGTGGACGAGGTCCCGAAGGG
CCTGACCGGGAAGCTCGACGCCCGGAAGATCCGCGAGATCCTGATCAAGGCCAAGAAGGG
CGGCAAGATCGCCGTGTAAGACTAGTTATAAGACTGACTAGCCCGATGGGCCTCCCAACG
GGCCCTCCTCCCCTCCTTGCACCGAGATTAATAAAAAAAAAAAAAAAAAAAAAAAAAAAA
AAAAAAAAAAAAAAAAAAAAAAAAAAAAAAAA
```

Figure 23 nucleotide sequence of atp5a1 – PpLuc(GC) – ag – A64

GGGCGGCTCGGCCATTTTGTCCCAGTCAGTCCGGAGGCTGCGGCTGCAGAAGTACCGCCT
GCGGAGTAACTGCAAAGAAGCTTGAGGATGGAGGACGCCAAGAACATCAAGAAGGGCCCG
GCGCCCTTCTACCCGCTGGAGGACGGGACCGCCGGCGAGCAGCTCCACAAGGCCATGAAG
CGGTACGCCCTGGTGCCGGGCACGATCGCCTTCACCGACGCCCACATCGAGGTCGACATC
ACCTACGCGGAGTACTTCGAGATGAGCGTGCGCCTGGCCGAGGCCATGAAGCGGTACGGC
CTGAACACCAACCACCGGATCGTGGTGTGCTCGGAGAACAGCCTGCAGTTCTTCATGCCG
GTGCTGGGCGCCCTCTTCATCGGCGTGGCCGTCGCCCCGGCGAACGACATCTACAACGAG
CGGGAGCTGCTGAACAGCATGGGGATCAGCCAGCCGACCGTGGTGTTCGTGAGCAAGAAG
GGCCTGCAGAAGATCCTGAACGTGCAGAAGAAGCTGCCCATCATCCAGAAGATCATCATC
ATGGACAGCAAGACCGACTACCAGGGCTTCCAGTCGATGTACACGTTCGTGACCAGCCAC
CTCCCGCCGGGCTTCAACGAGTACGACTTCGTCCCGGAGAGCTTCGACCGGGACAAGACC
ATCGCCCTGATCATGAACAGCAGCGGCAGCACCGGCCTGCCGAAGGGGGTGGCCCTGCCG
CACCGGACCGCCTGCGTGCGCTTCTCGCACGCCCGGGACCCCATCTTCGGCAACCAGATC
ATCCCGGACACCGCCATCCTGAGCGTGGTGCCGTTCCACCACGGCTTCGGCATGTTCACG
ACCCTGGGCTACCTCATCTGCGGCTTCCGGGTGGTCCTGATGTACCGGTTCGAGGAGGAG
CTGTTCCTGCGGAGCCTGCAGGACTACAAGATCCAGAGCGCGCTGCTCGTGCCGACCCTG
TTCAGCTTCTTCGCCAAGAGCACCCTGATCGACAAGTACGACCTGTCGAACCTGCACGAG
ATCGCCAGCGGGGCGCCCCGCTGAGCAAGGAGGTGGGCGAGGCCGTGGCCAAGCGGTTC
CACCTCCCGGGCATCCGCCAGGGCTACGGCCTGACCGAGACCACGAGCGCGATCCTGATC
ACCCCCGAGGGGACGACAAGCCGGGCGCCGTGGGCAAGGTGGTCCCGTTCTTCGAGGCC
AAGGTGGTGGACCTGGACACCGGCAAGACCCTGGGCGTGAACCAGCGGGGCGAGCTGTGC
GTGCGGGGGCCGATGATCATGAGCGGCTACGTGAACAACCCGGAGGCCACCAACGCCCTC
ATCGACAAGGACGGCTGGCTGCACAGCGGCGACATCGCCTACTGGGACGAGGACGAGCAC
TTCTTCATCGTCGACCGGCTGAAGTCGCTGATCAAGTACAAGGGCTACCAGGTGGCGCCG
GCCGAGCTGGAGAGCATCCTGCTCCAGCACCCCAACATCTTCGACGCCGGCGTGGCCGGG
CTGCCGGACGACGACGCCGGCGAGCTGCCGGCCGCGGTGGTGGTGCTGGAGCACGGCAAG
ACCATGACGGAGAAGGAGATCGTCGACTACGTGGCCAGCCAGGTGACCACCGCCAAGAAG
CTGCGGGGCGGCGTGGTGTTCGTGGACGAGGTCCCGAAGGGCCTGACCGGGAAGCTCGAC
GCCCGGAAGATCCGCGAGATCCTGATCAAGGCCAAGAAGGGCGGCAAGATCGCCGTGTAA
GACTAGTTATAAGACTGACTAGCCCGATGGGCCTCCCAACGGGCCCTCCTCCCCTCCTTG
CACCGAGATTAATAAAAAAAAAAAAAAAAAAAAAAAAAAAAAAAAAAAAAAAAAAAAAAA
AAAAAAAAAAAAAAAAA

Figure 24 nucleotide sequence of HSD17B4 – PpLuc(GC) – ag – A64

```
GGGTCCCGCAGTCGGCGTCCAGCGGCTCTGCTTGTTCGTGTGTGTGTCGTTGCAGGCCTT
ATTCAAGCTTGAGGATGGAGGACGCCAAGAACATCAAGAAGGGCCCGGCGCCCTTCTACC
CGCTGGAGGACGGGACCGCCGGCGAGCAGCTCCACAAGGCCATGAAGCGGTACGCCCTGG
TGCCGGGCACGATCGCCTTCACCGACGCCCACATCGAGGTCGACATCACCTACGCGGAGT
ACTTCGAGATGAGCGTGCGCCTGGCCGAGGCCATGAAGCGGTACGGCCTGAACACCAACC
ACCGGATCGTGGTGTGCTCGGAGAACAGCCTGCAGTTCTTCATGCCGGTGCTGGGCGCCC
TCTTCATCGGCGTGGCCGTCGCCCCGGCGAACGACATCTACAACGAGCGGGAGCTGCTGA
ACAGCATGGGGATCAGCCAGCCGACCGTGGTGTTCGTGAGCAAGAAGGGCCTGCAGAAGA
TCCTGAACGTGCAGAAGAAGCTGCCCATCATCCAGAAGATCATCATCATGGACAGCAAGA
CCGACTACCAGGGCTTCCAGTCGATGTACACGTTCGTGACCAGCCACCTCCCGCCGGGCT
TCAACGAGTACGACTTCGTCCCGGAGAGCTTCGACCGGGACAAGACCATCGCCCTGATCA
TGAACAGCAGCGGCAGCACCGGCCTGCCGAAGGGGGTGGCCCTGCCGCACCGGACCGCCT
GCGTGCGCTTCTCGCACGCCCGGGACCCCATCTTCGGCAACCAGATCATCCCGGACACCG
CCATCCTGAGCGTGGTGCCGTTCCACCACGGCTTCGGCATGTTCACGACCCTGGGCTACC
TCATCTGCGGCTTCCGGGTGGTCCTGATGTACCGGTTCGAGGAGGAGCTGTTCCTGCGGA
GCCTGCAGGACTACAAGATCCAGAGCGCGCTGCTCGTGCCGACCCTGTTCAGCTTCTTCG
CCAAGAGCACCCTGATCGACAAGTACGACCTGTCGAACCTGCACGAGATCGCCAGCGGGG
GCGCCCCGCTGAGCAAGGAGGTGGGCGAGGCCGTGGCCAAGCGGTTCCACCTCCCGGGCA
TCCGCCAGGGCTACGGCCTGACCGAGACCACGAGCGCGATCCTGATCACCCCCGAGGGGG
ACGACAAGCCGGGCGCCGTGGGCAAGGTGGTCCCGTTCTTCGAGGCCAAGGTGGTGGACC
TGGACACCGGCAAGACCCTGGGCGTGAACCAGCGGGGCGAGCTGTGCGTGCGGGGGCCGA
TGATCATGAGCGGCTACGTGAACAACCCGGAGGCCACCAACGCCCTCATCGACAAGGACG
GCTGGCTGCACAGCGGCGACATCGCCTACTGGGACGAGGACGAGCACTTCTTCATCGTCG
ACCGGCTGAAGTCGCTGATCAAGTACAAGGGCTACCAGGTGGCGCCGGCCGAGCTGGAGA
GCATCCTGCTCCAGCACCCCAACATCTTCGACGCCGGCGTGGCCGGGCTGCCGGACGACG
ACGCCGGCGAGCTGCCGGCCGCGGTGGTGGTGCTGGAGCACGGCAAGACCATGACGGAGA
AGGAGATCGTCGACTACGTGGCCAGCCAGGTGACCACCGCCAAGAAGCTGCGGGGCGGCG
TGGTGTTCGTGGACGAGGTCCCGAAGGGCCTGACCGGGAAGCTCGACGCCCGGAAGATCC
GCGAGATCCTGATCAAGGCCAAGAAGGGCGGCAAGATCGCCGTGTAAGACTAGTTATAAG
ACTGACTAGCCCGATGGGCCTCCCAACGGGCCCTCCTCCCCTCCTTGCACCGAGATTAAT
AAAAAAAAAAAAAAAAAAAAAAAAAAAAAAAAAAAAAAAAAAAAAAAAAAAAAAAAAAAA
AAAA
```

Figure 25 nucleotide sequence of AIG1 – PpLuc(GC) – ag – A64

GGGCCGCCCAGCCGGTCCAGGCCTCTGGCGAACAAGCTTGAGGATGGAGGACGCCAAGAA
CATCAAGAAGGGCCCGGCGCCCTTCTACCCGCTGGAGGACGGGACCGCCGGCGAGCAGCT
CCACAAGGCCATGAAGCGGTACGCCCTGGTGCCGGGCACGATCGCCTTCACCGACGCCCA
CATCGAGGTCGACATCACCTACGCGGAGTACTTCGAGATGAGCGTGCGCCTGGCCGAGGC
CATGAAGCGGTACGGCCTGAACACCAACCACCGGATCGTGGTGTGCTCGGAGAACAGCCT
GCAGTTCTTCATGCCGGTGCTGGGCGCCCTCTTCATCGGCGTGGCCGTCGCCCCGGCGAA
CGACATCTACAACGAGCGGGAGCTGCTGAACAGCATGGGGATCAGCCAGCCGACCGTGGT
GTTCGTGAGCAAGAAGGGCCTGCAGAAGATCCTGAACGTGCAGAAGAAGCTGCCCATCAT
CCAGAAGATCATCATCATGGACAGCAAGACCGACTACCAGGGCTTCCAGTCGATGTACAC
GTTCGTGACCAGCCACCTCCCGCCGGGCTTCAACGAGTACGACTTCGTCCCGGAGAGCTT
CGACCGGGACAAGACCATCGCCCTGATCATGAACAGCAGCGGCAGCACCGGCCTGCCGAA
GGGGGTGGCCCTGCCGCACCGGACCGCCTGCGTGCGCTTCTCGCACGCCCGGGACCCCAT
CTTCGGCAACCAGATCATCCCGGACACCGCCATCCTGAGCGTGGTGCCGTTCCACCACGG
CTTCGGCATGTTCACGACCCTGGGCTACCTCATCTGCGGCTTCCGGGTGGTCCTGATGTA
CCGGTTCGAGGAGGAGCTGTTCCTGCGGAGCCTGCAGGACTACAAGATCCAGAGCGCGCT
GCTCGTGCCGACCCTGTTCAGCTTCTTCGCCAAGAGCACCCTGATCGACAAGTACGACCT
GTCGAACCTGCACGAGATCGCCAGCGGGGCGCCCCGCTGAGCAAGGAGGTGGGCGAGGC
CGTGGCCAAGCGGTTCCACCTCCCGGGCATCCGCCAGGGCTACGGCCTGACCGAGACCAC
GAGCGCGATCCTGATCACCCCCGAGGGGACGACAAGCCGGGCGCCGTGGGCAAGGTGGT
CCCGTTCTTCGAGGCCAAGGTGGTGGACCTGGACACCGGCAAGACCCTGGGCGTGAACCA
GCGGGGCGAGCTGTGCGTGCGGGGCCGATGATCATGAGCGGCTACGTGAACAACCCGGA
GGCCACCAACGCCCTCATCGACAAGGACGGCTGGCTGCACAGCGGCGACATCGCCTACTG
GGACGAGGACGAGCACTTCTTCATCGTCGACCGGCTGAAGTCGCTGATCAAGTACAAGGG
CTACCAGGTGGCGCCGGCCGAGCTGGAGAGCATCCTGCTCCAGCACCCCAACATCTTCGA
CGCCGGCGTGGCCGGGCTGCCGGACGACGACGCCGGCGAGCTGCCGGCCGCGGTGGTGGT
GCTGGAGCACGGCAAGACCATGACGGAGAAGGAGATCGTCGACTACGTGGCCAGCCAGGT
GACCACCGCCAAGAAGCTGCGGGGCGGCGTGGTGTTCGTGGACGAGGTCCCGAAGGGCCT
GACCGGGAAGCTCGACGCCCGGAAGATCCGCGAGATCCTGATCAAGGCCAAGAAGGGCGG
CAAGATCGCCGTGTAAGACTAGTTATAAGACTGACTAGCCCGATGGGCCTCCCAACGGGC
CCTCCTCCCTCCTTGCACCGAGATTAATAAAAAAAAAAAAAAAAAAAAAAAAAAAAAAAA
AAAAAAAAAAAAAAAAAAAAAAAAAAAAAAAA

Figure 26 nucleotide sequence of COX6C – PpLuc(GC) – ag – A64

GGAGTCAGGAAGGACGTTGGTGTTGAGGTTAGCATACGTATCAAGGACAGTAACTACCAA
GCTTGAGGATGGAGGACGCCAAGAACATCAAGAAGGGCCCGGCGCCCTTCTACCCGCTGG
AGGACGGGACCGCCGGCGAGCAGCTCCACAAGGCCATGAAGCGGTACGCCCTGGTGCCGG
GCACGATCGCCTTCACCGACGCCCACATCGAGGTCGACATCACCTACGCGGAGTACTTCG
AGATGAGCGTGCGCCTGGCCGAGGCCATGAAGCGGTACGGCCTGAACACCAACCACCGGA
TCGTGGTGTGCTCGGAGAACAGCCTGCAGTTCTTCATGCCGGTGCTGGGCGCCCTCTTCA
TCGGCGTGGCCGTCGCCCCGGCGAACGACATCTACAACGAGCGGGAGCTGCTGAACAGCA
TGGGGATCAGCCAGCCGACCGTGGTGTTCGTGAGCAAGAAGGGCCTGCAGAAGATCCTGA
ACGTGCAGAAGAAGCTGCCCATCATCCAGAAGATCATCATCATGGACAGCAAGACCGACT
ACCAGGGCTTCCAGTCGATGTACACGTTCGTGACCAGCCACCTCCCGCCGGGCTTCAACG
AGTACGACTTCGTCCCGGAGAGCTTCGACCGGGACAAGACCATCGCCCTGATCATGAACA
GCAGCGGCAGCACCGGCCTGCCGAAGGGGGTGGCCCTGCCGCACCGGACCGCCTGCGTGC
GCTTCTCGCACGCCCGGGACCCCATCTTCGGCAACCAGATCATCCCGGACACCGCCATCC
TGAGCGTGGTGCCGTTCCACCACGGCTTCGGCATGTTCACGACCCTGGGCTACCTCATCT
GCGGCTTCCGGGTGGTCCTGATGTACCGGTTCGAGGAGGAGCTGTTCCTGCGGAGCCTGC
AGGACTACAAGATCCAGAGCGCGCTGCTCGTGCCGACCCTGTTCAGCTTCTTCGCCAAGA
GCACCCTGATCGACAAGTACGACCTGTCGAACCTGCACGAGATCGCCAGCGGGGCGCCC
CGCTGAGCAAGGAGGTGGGCGAGGCCGTGGCCAAGCGGTTCCACCTCCCGGGCATCCGCC
AGGGCTACGGCCTGACCGAGACCACGAGCGCGATCCTGATCACCCCCGAGGGGACGACA
AGCCGGGCGCCGTGGGCAAGGTGGTCCCGTTCTTCGAGGCCAAGGTGGTGGACCTGGACA
CCGGCAAGACCCTGGGCGTGAACCAGCGGGGCGAGCTGTGCGTGCGGGGCCGATGATCA
TGAGCGGCTACGTGAACAACCCGGAGGCCACCAACGCCCTCATCGACAAGGACGGCTGGC
TGCACAGCGGCGACATCGCCTACTGGGACGAGGACGAGCACTTCTTCATCGTCGACCGGC
TGAAGTCGCTGATCAAGTACAAGGGCTACCAGGTGGCGCCGGCCGAGCTGGAGAGCATCC
TGCTCCAGCACCCCAACATCTTCGACGCCGGCGTGGCCGGGCTGCCGGACGACGACGCCG
GCGAGCTGCCGGCCGCGGTGGTGGTGCTGGAGCACGGCAAGACCATGACGGAGAAGGAGA
TCGTCGACTACGTGGCCAGCCAGGTGACCACCGCCAAGAAGCTGCGGGGCGGCGTGGTGT
TCGTGGACGAGGTCCCGAAGGGCCTGACCGGGAAGCTCGACGCCCGGAAGATCCGCGAGA
TCCTGATCAAGGCCAAGAAGGGCGGCAAGATCGCCGTGTAAGACTAGTTATAAGACTGAC
TAGCCCGATGGGCCTCCCAACGGGCCCTCCTCCCCTCCTTGCACCGAGATTAATAAAAAA
AAAAAAAAAAAAAAAAAAAAAAAAAAAAAAAAAAAAAAAAAAAAAAAAAAAAAAAAAAAA

Figure 27 nucleotide sequence of ASAH1 – PpLuc(GC) – ag – A64

GGGCCTCTGCTGGAGTCCGGGGAGTGGCGTTGGCTGCTAGAGCGAAGCTTGAGGATGGAG
GACGCCAAGAACATCAAGAAGGGCCCGGCGCCCTTCTACCCGCTGGAGGACGGGACCGCC
GGCGAGCAGCTCCACAAGGCCATGAAGCGGTACGCCCTGGTGCCGGGCACGATCGCCTTC
ACCGACGCCCACATCGAGGTCGACATCACCTACGCGGAGTACTTCGAGATGAGCGTGCGC
CTGGCCGAGGCCATGAAGCGGTACGGCCTGAACACCAACCACCGGATCGTGGTGTGCTCG
GAGAACAGCCTGCAGTTCTTCATGCCGGTGCTGGGCGCCCTCTTCATCGGCGTGGCCGTC
GCCCCGGCGAACGACATCTACAACGAGCGGGAGCTGCTGAACAGCATGGGGATCAGCCAG
CCGACCGTGGTGTTCGTGAGCAAGAAGGGCCTGCAGAAGATCCTGAACGTGCAGAAGAAG
CTGCCCATCATCCAGAAGATCATCATCATGGACAGCAAGACCGACTACCAGGGCTTCCAG
TCGATGTACACGTTCGTGACCAGCCACCTCCCGCCGGGCTTCAACGAGTACGACTTCGTC
CCGGAGAGCTTCGACGGGACAAGACCATCGCCCTGATCATGAACAGCAGCGGCAGCACC
GGCCTGCCGAAGGGGGTGGCCCTGCCGCACCGGACCGCCTGCGTGCGCTTCTCGCACGCC
CGGGACCCCATCTTCGGCAACCAGATCATCCCGGACACCGCCATCCTGAGCGTGGTGCCG
TTCCACCACGGCTTCGGCATGTTCACGACCCTGGGCTACCTCATCTGCGGCTTCCGGGTG
GTCCTGATGTACCGGTTCGAGGAGGAGCTGTTCCTGCGGAGCCTGCAGGACTACAAGATC
CAGAGCGCGCTGCTCGTGCCGACCCTGTTCAGCTTCTTCGCCAAGAGCACCCTGATCGAC
AAGTACGACCTGTCGAACCTGCACGAGATCGCCAGCGGGGCGCCCCGCTGAGCAAGGAG
GTGGGCGAGGCCGTGGCCAAGCGGTTCCACCTCCCGGGCATCCGCCAGGGCTACGGCCTG
ACCGAGACCACGAGCGCGATCCTGATCACCCCCGAGGGGGACGACAAGCCGGGCGCCGTG
GGCAAGGTGGTCCCGTTCTTCGAGGCCAAGGTGGTGGACCTGGACACCGGCAAGACCCTG
GGCGTGAACCAGCGGGGCGAGCTGTGCGTGCGGGGCCGATGATCATGAGCGGCTACGTG
AACAACCCGGAGGCCACCAACGCCCTCATCGACAAGGACGGCTGGCTGCACAGCGGCGAC
ATCGCCTACTGGGACGAGGACGAGCACTTCTTCATCGTCGACCGGCTGAAGTCGCTGATC
AAGTACAAGGGCTACCAGGTGGCGCCGGCCGAGCTGGAGAGCATCCTGCTCCAGCACCCC
AACATCTTCGACGCCGGCGTGGCCGGGCTGCCGGACGACGACGCCGGCGAGCTGCCGGCC
GCGGTGGTGGTGCTGGAGCACGGCAAGACCATGACGGAGAAGGAGATCGTCGACTACGTG
GCCAGCCAGGTGACCACCGCCAAGAAGCTGCGGGGCGGCGTGGTGTTCGTGGACGAGGTC
CCGAAGGGCCTGACCGGGAAGCTCGACGCCCGGAAGATCCGCGAGATCCTGATCAAGGCC
AAGAAGGGCGGCAAGATCGCCGTGTAAGACTAGTTATAAGACTGACTAGCCCGATGGGCC
TCCCAACGGGCCCTCCTCCCCTCCTTGCACCGAGATTAATAAAAAAAAAAAAAAAAAAAA
AAAAAAAAAAAAAAAAAAAAAAAAAAAAAAAAAAAAAAAA

Figure 28 nucleotide sequence of RPL35 – PpLuc(GC) – ag – A64 – histoneSL

```
GGGGAGCGGGCGGCGGCGTTGGCGGCTTGTGCAGCAAAGCTTGAGGATGGAGGACGCCAA
GAACATCAAGAAGGGCCCGGCGCCCTTCTACCCGCTGGAGGACGGGACCGCCGGCGAGCA
GCTCCACAAGGCCATGAAGCGGTACGCCCTGGTGCCGGGCACGATCGCCTTCACCGACGC
CCACATCGAGGTCGACATCACCTACGCGGAGTACTTCGAGATGAGCGTGCGCCTGGCCGA
GGCCATGAAGCGGTACGGCCTGAACACCAACCACGGATCGTGGTGTGCTCGGAGAACAG
CCTGCAGTTCTTCATGCCGGTGCTGGGCGCCCTCTTCATCGGCGTGGCCGTCGCCCCGGC
GAACGACATCTACAACGAGCGGGAGCTGCTGAACAGCATGGGGATCAGCCAGCCGACCGT
GGTGTTCGTGAGCAAGAAGGGCCTGCAGAAGATCCTGAACGTGCAGAAGAAGCTGCCCAT
CATCCAGAAGATCATCATCATGGACAGCAAGACCGACTACCAGGGCTTCCAGTCGATGTA
CACGTTCGTGACCAGCCACCTCCCGCCGGGCTTCAACGAGTACGACTTCGTCCCGGAGAG
CTTCGACCGGGACAAGACCATCGCCCTGATCATGAACAGCAGCGGCAGCACCGGCCTGCC
GAAGGGGGTGGCCCTGCCGCACCGGACCGCCTGCGTGCGCTTCTCGCACGCCCGGGACCC
CATCTTCGGCAACCAGATCATCCCGGACACCGCCATCCTGAGCGTGGTGCCGTTCCACCA
CGGCTTCGGCATGTTCACGACCCTGGGCTACCTCATCTGCGGCTTCCGGGTGGTCCTGAT
GTACCGGTTCGAGGAGGAGCTGTTCCTGCGGAGCCTGCAGGACTACAAGATCCAGAGCGC
GCTGCTCGTGCCGACCCTGTTCAGCTTCTTCGCCAAGAGCACCCTGATCGACAAGTACGA
CCTGTCGAACCTGCACGAGATCGCCAGCGGGGGCGCCCCGCTGAGCAAGGAGGTGGGCGA
GGCCGTGGCCAAGCGGTTCCACCTCCCGGGCATCCGCCAGGGCTACGGCCTGACCGAGAC
CACGAGCGCGATCCTGATCACCCCGAGGGGGACGACAAGCCGGGCGCCGTGGGCAAGGT
GGTCCCGTTCTTCGAGGCCAAGGTGGTGGACCTGGACACCGGCAAGACCCTGGGCGTGAA
CCAGCGGGGCGAGCTGTGCGTGCGGGGGCCGATGATCATGAGCGGCTACGTGAACAACCC
GGAGGCCACCAACGCCCTCATCGACAAGGACGGCTGGCTGCACAGCGGCGACATCGCCTA
CTGGGACGAGGACGAGCACTTCTTCATCGTCGACCGGCTGAAGTCGCTGATCAAGTACAA
GGGCTACCAGGTGGCGCCGGCCGAGCTGGAGAGCATCCTGCTCCAGCACCCCAACATCTT
CGACGCCGGCGTGGCCGGGCTGCCGGACGACGACGCCGGCGAGCTGCCGGCCGCGGTGGT
GGTGCTGGAGCACGGCAAGACCATGACGGAGAAGGAGATCGTCGACTACGTGGCCAGCCA
GGTGACCACCGCCAAGAAGCTGCGGGGCGGCGTGGTGTTCGTGGACGAGGTCCCGAAGGG
CCTGACCGGGAAGCTCGACGCCCGGAAGATCCGCGAGATCCTGATCAAGGCAAGAAGGG
CGGCAAGATCGCCGTGTAAGACTAGTTATAAGACTGACTAGCCCGATGGGCCTCCCAACG
GGCCCTCCTCCCCTCCTTGCACCGAGATTAATAAAAAAAAAAAAAAAAAAAAAAAAAAAA
AAAAAAAAAAAAAAAAAAAAAAAAAAAAAAAAAAATGCATCAAAGGCTCTTTTCAGAGC
CACCA
```

Figure 29 nucleotide sequence of rpl21 – PpLuc(GC) – ag – A64 – histoneSL

```
GGGGCCGGAACCGCCATCTTCCAGTAATTCGCCAAAAAGCTTGAGGATGGAGGACGCCAA
GAACATCAAGAAGGGCCCGGCGCCCTTCTACCCGCTGGAGGACGGGACCGCCGGCGAGCA
GCTCCACAAGGCCATGAAGCGGTACGCCCTGGTGCCGGGCACGATCGCCTTCACCGACGC
CCACATCGAGGTCGACATCACCTACGCGGAGTACTTCGAGATGAGCGTGCGCCTGGCCGA
GGCCATGAAGCGGTACGGCCTGAACACCAACCACCGGATCGTGGTGTGCTCGGAGAACAG
CCTGCAGTTCTTCATGCCGGTGCTGGGCGCCCTCTTCATCGGCGTGGCCGTCGCCCCGGC
GAACGACATCTACAACGAGCGGGAGCTGCTGAACAGCATGGGGATCAGCCAGCCGACCGT
GGTGTTCGTGAGCAAGAAGGGCCTGCAGAAGATCCTGAACGTGCAGAAGAAGCTGCCCAT
CATCCAGAAGATCATCATCATGGACAGCAAGACCGACTACCAGGGCTTCCAGTCGATGTA
CACGTTCGTGACCAGCCACCTCCCGCCGGGCTTCAACGAGTACGACTTCGTCCCGGAGAG
CTTCGACCGGGACAAGACCATCGCCCTGATCATGAACAGCAGCGGCAGCACCGGCCTGCC
GAAGGGGGTGGCCCTGCCGCACCGGACCGCCTGCGTGCGCTTCTCGCACGCCCGGGACCC
CATCTTCGGCAACCAGATCATCCCGGACACCGCCATCCTGAGCGTGGTGCCGTTCCACCA
CGGCTTCGGCATGTTCACGACCCTGGGCTACCTCATCTGCGGCTTCCGGGTGGTCCTGAT
GTACCGGTTCGAGGAGGAGCTGTTCCTGCGGAGCCTGCAGGACTACAAGATCCAGAGCGC
GCTGCTCGTGCCGACCCTGTTCAGCTTCTTCGCCAAGAGCACCCTGATCGACAAGTACGA
CCTGTCGAACCTGCACGAGATCGCCAGCGGGGCGCCCCGCTGAGCAAGGAGGTGGGCGA
GGCCGTGGCCAAGCGGTTCCACCTCCCGGGCATCCGCCAGGGCTACGGCCTGACCGAGAC
CACGAGCGCGATCCTGATCACCCCGAGGGGACGACAAGCCGGGCGCCGTGGGCAAGGT
GGTCCCGTTCTTCGAGGCCAAGGTGGTGGACCTGGACACCGGCAAGACCCTGGGCGTGAA
CCAGCGGGGCGAGCTGTGCGTGCGGGGCCGATGATCATGAGCGGCTACGTGAACAACCC
GGAGGCCACCAACGCCCTCATCGACAAGGACGGCTGGCTGCACAGCGGCGACATCGCCTA
CTGGGACGAGGACGAGCACTTCTTCATCGTCGACCGGCTGAAGTCGCTGATCAAGTACAA
GGGCTACCAGGTGGCGCCGGCCGAGCTGGAGAGCATCCTGCTCCAGCACCCCAACATCTT
CGACGCCGGCGTGGCCGGGCTGCCGGACGACGACGCCGGCGAGCTGCCGGCCGCGGTGGT
GGTGCTGGAGCACGGCAAGACCATGACGGAGAAGGAGATCGTCGACTACGTGGCCAGCCA
GGTGACCACCGCCAAGAAGCTGCGGGGCGGCGTGGTGTTCGTGGACGAGGTCCCGAAGGG
CCTGACCGGGAAGCTCGACGCCCGGAAGATCCGCGAGATCCTGATCAAGGCAAGAAGGG
CGGCAAGATCGCCGTGTAAGACTAGTTATAAGACTGACTAGCCCGATGGGCCTCCCAACG
GGCCCTCCTCCCCTCCTTGCACCGAGATTAATAAAAAAAAAAAAAAAAAAAAAAAAAAAA
AAAAAAAAAAAAAAAAAAAAAAAAAAAAAAAAAAAATGCATCAAAGGCTCTTTTCAGAGC
CACCA
```

Figure 30 nucleotide sequence of atp5a1 – PpLuc(GC) – ag – A64 – histoneSL

```
GGGCGGCTCGGCCATTTTGTCCCAGTCAGTCCGGAGGCTGCGGCTGCAGAAGTACCGCCT
GCGGAGTAACTGCAAAGAAGCTTGAGGATGGAGGACGCCAAGAACATCAAGAAGGGCCCG
GCGCCCTTCTACCCGCTGGAGGACGGGACCGCCGGCGAGCAGCTCCACAAGGCCATGAAG
CGGTACGCCCTGGTGCCGGGCACGATCGCCTTCACCGACGCCCACATCGAGGTCGACATC
ACCTACGCGGAGTACTTCGAGATGAGCGTGCGCCTGGCCGAGGCCATGAAGCGGTACGGC
CTGAACACCAACCACCGGATCGTGGTGTGCTCGGAGAACAGCCTGCAGTTCTTCATGCCG
GTGCTGGGCGCCCTCTTCATCGGCGTGGCCGTCGCCCCGGCGAACGACATCTACAACGAG
CGGGAGCTGCTGAACAGCATGGGGATCAGCCAGCCGACCGTGGTGTTCGTGAGCAAGAAG
GGCCTGCAGAAGATCCTGAACGTGCAGAAGAAGCTGCCCATCATCCAGAAGATCATCATC
ATGGACAGCAAGACCGACTACCAGGGCTTCCAGTCGATGTACACGTTCGTGACCAGCCAC
CTCCCGCCGGGCTTCAACGAGTACGACTTCGTCCCGGAGAGCTTCGACCGGGACAAGACC
ATCGCCCTGATCATGAACAGCAGCGGCAGCACCGGCCTGCCGAAGGGGGTGGCCCTGCCG
CACCGGACCGCCTGCGTGCGCTTCTCGCACGCCCGGGACCCCATCTTCGGCAACCAGATC
ATCCCGGACACCGCCATCCTGAGCGTGGTGCCGTTCCACCACGGCTTCGGCATGTTCACG
ACCCTGGGCTACCTCATCTGCGGCTTCCGGGTGGTCCTGATGTACCGGTTCGAGGAGGAG
CTGTTCCTGCGGAGCCTGCAGGACTACAAGATCCAGAGCGCGCTGCTCGTGCCGACCCTG
TTCAGCTTCTTCGCCAAGAGCACCCTGATCGACAAGTACGACCTGTCGAACCTGCACGAG
ATCGCCAGCGGGGCGCCCCGCTGAGCAAGGAGGTGGGCGAGGCCGTGGCCAAGCGGTTC
CACCTCCCGGGCATCCGCCAGGGCTACGGCCTGACCGAGACCACGAGCGCGATCCTGATC
ACCCCCGAGGGGACGACAAGCCGGGCGCCGTGGGCAAGGTGGTCCCGTTCTTCGAGGCC
AAGGTGGTGGACCTGGACACCGGCAAGACCCTGGGCGTGAACCAGCGGGGCGAGCTGTGC
GTGCGGGGCCGATGATCATGAGCGGCTACGTGAACAACCCGGAGGCCACCAACGCCCTC
ATCGACAAGGACGGCTGGCTGCACAGCGGCGACATCGCCTACTGGGACGAGGACGAGCAC
TTCTTCATCGTCGACCGGCTGAAGTCGCTGATCAAGTACAAGGGCTACCAGGTGGCGCCG
GCCGAGCTGGAGAGCATCCTGCTCCAGCACCCCAACATCTTCGACGCCGGCGTGGCCGGG
CTGCCGGACGACGACGCCGGCGAGCTGCCGGCCGCGGTGGTGGTGCTGGAGCACGGCAAG
ACCATGACGGAGAAGGAGATCGTCGACTACGTGGCCAGCCAGGTGACCACCGCCAAGAAG
CTGCGGGGCGGCGTGGTGTTCGTGGACGAGGTCCCGAAGGGCCTGACCGGGAAGCTCGAC
GCCCGGAAGATCCGCGAGATCCTGATCAAGGCCAAGAAGGGCGGCAAGATCGCCGTGTAA
GACTAGTTATAAGACTGACTAGCCCGATGGGCCTCCCAACGGGCCCTCCTCCCCTCCTTG
CACCGAGATTAATAAAAAAAAAAAAAAAAAAAAAAAAAAAAAAAAAAAAAAAAAAAAAAA
AAAAAAAAAAAAAAAAATGCATCAAAGGCTCTTTTCAGAGCCACCA
```

Figure 31 nucleotide sequence of HSD17B4 – PpLuc(GC) – ag – A64 – histoneSL

```
GGGTCCCGCAGTCGGCGTCCAGCGGCTCTGCTTGTTCGTGTGTGTGTCGTTGCAGGCCTT
ATTCAAGCTTGAGGATGGAGGACGCCAAGAACATCAAGAAGGGCCCGGCGCCCTTCTACC
CGCTGGAGGACGGGACCGCCGGCGAGCAGCTCCACAAGGCCATGAAGCGGTACGCCCTGG
TGCCGGGCACGATCGCCTTCACCGACGCCCACATCGAGGTCGACATCACCTACGCGGAGT
ACTTCGAGATGAGCGTGCGCCTGGCCGAGGCCATGAAGCGGTACGGCCTGAACACCAACC
ACCGGATCGTGGTGTGCTCGGAGAACAGCCTGCAGTTCTTCATGCCGGTGCTGGGCGCCC
TCTTCATCGGCGTGGCCGTCGCCCCGGCGAACGACATCTACAACGAGCGGGAGCTGCTGA
ACAGCATGGGGATCAGCCAGCCGACCGTGGTGTTCGTGAGCAAGAAGGGCCTGCAGAAGA
TCCTGAACGTGCAGAAGAAGCTGCCCATCATCCAGAAGATCATCATCATGGACAGCAAGA
CCGACTACCAGGGCTTCCAGTCGATGTACACGTTCGTGACCAGCCACCTCCCGCCGGGCT
TCAACGAGTACGACTTCGTCCCGGAGAGCTTCGACCGGGACAAGACCATCGCCCTGATCA
TGAACAGCAGCGGCAGCACCGGCCTGCCGAAGGGGGTGGCCCTGCCGCACCGGACCGCCT
GCGTGCGCTTCTCGCACGCCCGGGACCCCATCTTCGGCAACCAGATCATCCCGGACACCG
CCATCCTGAGCGTGGTGCCGTTCCACCACGGCTTCGGCATGTTCACGACCCTGGGCTACC
TCATCTGCGGCTTCCGGGTGGTCCTGATGTACCGGTTCGAGGAGGAGCTGTTCCTGCGGA
GCCTGCAGGACTACAAGATCCAGAGCGCGCTGCTCGTGCCGACCCTGTTCAGCTTCTTCG
CCAAGAGCACCCTGATCGACAAGTACGACCTGTCGAACCTGCACGAGATCGCCAGCGGGG
GCGCCCCGCTGAGCAAGGAGGTGGGCGAGGCCGTGGCCAAGCGGTTCCACCTCCCGGGCA
TCCGCCAGGGCTACGGCCTGACCGAGACCACGAGCGCGATCCTGATCACCCCCGAGGGGG
ACGACAAGCCGGGCGCCGTGGGCAAGGTGGTCCCGTTCTTCGAGGCCAAGGTGGTGGACC
TGGACACCGGCAAGACCCTGGGCGTGAACCAGCGGGGCGAGCTGTGCGTGCGGGGGCCGA
TGATCATGAGCGGCTACGTGAACAACCCGGAGGCCACCAACGCCCTCATCGACAAGGACG
GCTGGCTGCACAGCGGCGACATCGCCTACTGGGACGAGGACGAGCACTTCTTCATCGTCG
ACCGGCTGAAGTCGCTGATCAAGTACAAGGGCTACCAGGTGGCGCCGGCCGAGCTGGAGA
GCATCCTGCTCCAGCACCCCAACATCTTCGACGCCGGCGTGGCCGGGCTGCCGGACGACG
ACGCCGGCGAGCTGCCGGCCGCGGTGGTGGTGCTGGAGCACGGCAAGACCATGACGGAGA
AGGAGATCGTCGACTACGTGGCCAGCCAGGTGACCACCGCCAAGAAGCTGCGGGGCGGCG
TGGTGTTCGTGGACGAGGTCCCGAAGGGCCTGACCGGGAAGCTCGACGCCCGGAAGATCC
GCGAGATCCTGATCAAGGCCAAGAAGGGCGGCAAGATCGCCGTGTAAGACTAGTTATAAG
ACTGACTAGCCCGATGGGCCTCCCAACGGGCCCTCCTCCCCTCCTTGCACCGAGATTAAT
AAAAAAAAAAAAAAAAAAAAAAAAAAAAAAAAAAAAAAAAAAAAAAAAAAAAAAAAAAAA
AAAATGCATCAAAGGCTCTTTTCAGAGCCACCA
```

Figure 32 nucleotide sequence of AIG1 – PpLuc(GC) – ag – A64 – histoneSL

GGGCCGCCCAGCCGGTCCAGGCCTCTGGCGAACAAGCTTGAGGATGGAGGACGCCAAGAA
CATCAAGAAGGGCCCGGCGCCCTTCTACCCGCTGGAGGACGGGACCGCCGGCGAGCAGCT
CCACAAGGCCATGAAGCGGTACGCCCTGGTGCCGGGCACGATCGCCTTCACCGACGCCCA
CATCGAGGTCGACATCACCTACGCGGAGTACTTCGAGATGAGCGTGCGCCTGGCCGAGGC
CATGAAGCGGTACGGCCTGAACACCAACCACCGGATCGTGGTGTGCTCGGAGAACAGCCT
GCAGTTCTTCATGCCGGTGCTGGGCGCCCTCTTCATCGGCGTGGCCGTCGCCCCGGCGAA
CGACATCTACAACGAGCGGGAGCTGCTGAACAGCATGGGGATCAGCCAGCCGACCGTGGT
GTTCGTGAGCAAGAAGGGCCTGCAGAAGATCCTGAACGTGCAGAAGAAGCTGCCCATCAT
CCAGAAGATCATCATCATGGACAGCAAGACCGACTACCAGGGCTTCCAGTCGATGTACAC
GTTCGTGACCAGCCACCTCCCGCCGGGCTTCAACGAGTACGACTTCGTCCCGGAGAGCTT
CGACCGGGACAAGACCATCGCCCTGATCATGAACAGCAGCGGCAGCACCGGCCTGCCGAA
GGGGGTGGCCCTGCCGCACCGGACCGCCTGCGTGCGCTTCTCGCACGCCCGGGACCCCAT
CTTCGGCAACCAGATCATCCCGGACACCGCCATCCTGAGCGTGGTGCCGTTCCACCACGG
CTTCGGCATGTTCACGACCCTGGGCTACCTCATCTGCGGCTTCCGGGTGGTCCTGATGTA
CCGGTTCGAGGAGGAGCTGTTCCTGCGGAGCCTGCAGGACTACAAGATCCAGAGCGCGCT
GCTCGTGCCGACCCTGTTCAGCTTCTTCGCCAAGAGCACCCTGATCGACAAGTACGACCT
GTCGAACCTGCACGAGATCGCCAGCGGGGCGCCCCGCTGAGCAAGGAGGTGGGCGAGGC
CGTGGCCAAGCGGTTCCACCTCCCGGGCATCCGCCAGGGCTACGGCCTGACCGAGACCAC
GAGCGCGATCCTGATCACCCCCGAGGGGGACGACAAGCCGGGCGCCGTGGGCAAGGTGGT
CCCGTTCTTCGAGGCCAAGGTGGTGGACCTGGACACCGGCAAGACCCTGGGCGTGAACCA
GCGGGGCGAGCTGTGCGTGCGGGGCCGATGATCATGAGCGGCTACGTGAACAACCCGGA
GGCCACCAACGCCCTCATCGACAAGGACGGCTGGCTGCACAGCGGCGACATCGCCTACTG
GGACGAGGACGAGCACTTCTTCATCGTCGACCGGCTGAAGTCGCTGATCAAGTACAAGGG
CTACCAGGTGGCGCCGGCCGAGCTGGAGAGCATCCTGCTCCAGCACCCCAACATCTTCGA
CGCCGGCGTGGCCGGGCTGCCGGACGACGACGCCGGCGAGCTGCCGGCCGCGGTGGTGGT
GCTGGAGCACGGCAAGACCATGACGGAGAAGGAGATCGTCGACTACGTGGCCAGCCAGGT
GACCACCGCCAAGAAGCTGCGGGGCGGCGTGGTGTTCGTGGACGAGGTCCCGAAGGGCCT
GACCGGGAAGCTCGACGCCCGGAAGATCCGCGAGATCCTGATCAAGGCCAAGAAGGGCGG
CAAGATCGCCGTGTAAGACTAGTTATAAGACTGACTAGCCCGATGGGCCTCCCAACGGGC
CCTCCTCCCCTCCTTGCACCGAGATTAATAAAAAAAAAAAAAAAAAAAAAAAAAAAAAAA
AAAAAAAAAAAAAAAAAAAAAAAAAAAAAAAAATGCATCAAAGGCTCTTTTCAGAGCCAC
CA

Figure 33 nucleotide sequence of COX6C – PpLuc(GC) – ag – A64 – histoneSL

```
GGAGTCAGGAAGGACGTTGGTGTTGAGGTTAGCATACGTATCAAGGACAGTAACTACCAA
GCTTGAGGATGGAGGACGCCAAGAACATCAAGAAGGGCCCGGCGCCCTTCTACCCGCTGG
AGGACGGGACCGCCGGCGAGCAGCTCCACAAGGCCATGAAGCGGTACGCCCTGGTGCCGG
GCACGATCGCCTTCACCGACGCCCACATCGAGGTCGACATCACCTACGCGGAGTACTTCG
AGATGAGCGTGCGCCTGGCCGAGGCCATGAAGCGGTACGGCCTGAACACCAACCACCGGA
TCGTGGTGTGCTCGGAGAACAGCCTGCAGTTCTTCATGCCGGTGCTGGGCGCCCTCTTCA
TCGGCGTGGCCGTCGCCCCGGCAACGACATCTACAACGAGCGGGAGCTGCTGAACAGCA
TGGGGATCAGCCAGCCGACCGTGGTGTTCGTGAGCAAGAAGGGCCTGCAGAAGATCCTGA
ACGTGCAGAAGAAGCTGCCCATCATCCAGAAGATCATCATCATGGACAGCAAGACCGACT
ACCAGGGCTTCCAGTCGATGTACACGTTCGTGACCAGCCACCTCCCGCCGGGCTTCAACG
AGTACGACTTCGTCCCGGAGAGCTTCGACCGGGACAAGACCATCGCCCTGATCATGAACA
GCAGCGGCAGCACCGGCCTGCCGAAGGGGGTGGCCCTGCCGCACCGGACCGCCTGCGTGC
GCTTCTCGCACGCCCGGGACCCCATCTTCGGCAACCAGATCATCCCGGACACCGCCATCC
TGAGCGTGGTGCCGTTCCACCACGGCTTCGGCATGTTCACGACCCTGGGCTACCTCATCT
GCGGCTTCCGGGTGGTCCTGATGTACCGGTTCGAGGAGGAGCTGTTCCTGCGGAGCCTGC
AGGACTACAAGATCCAGAGCGCGCTGCTCGTGCCGACCCTGTTCAGCTTCTTCGCCAAGA
GCACCCTGATCGACAAGTACGACCTGTCGAACCTGCACGAGATCGCCAGCGGGGCGCCC
CGCTGAGCAAGGAGGTGGGCGAGGCCGTGGCCAAGCGGTTCCACCTCCCGGGCATCCGCC
AGGGCTACGGCCTGACCGAGACCACGAGCGCGATCCTGATCACCCCCGAGGGGGACGACA
AGCCGGGCGCCGTGGGCAAGGTGGTCCCGTTCTTCGAGGCCAAGGTGGTGGACCTGGACA
CCGGCAAGACCCTGGGCGTGAACCAGCGGGGCGAGCTGTGCGTGCGGGGCCGATGATCA
TGAGCGGCTACGTGAACAACCCGGAGGCCACCAACGCCCTCATCGACAAGGACGGCTGGC
TGCACAGCGGCGACATCGCCTACTGGGACGAGGACGAGCACTTCTTCATCGTCGACCGGC
TGAAGTCGCTGATCAAGTACAAGGGCTACCAGGTGGCGCCGGCCGAGCTGGAGAGCATCC
TGCTCCAGCACCCCAACATCTTCGACGCCGGCGTGGCCGGGCTGCCGGACGACGACGCCG
GCGAGCTGCCGGCCGCGGTGGTGGTGCTGGAGCACGGCAAGACCATGACGGAGAAGGAGA
TCGTCGACTACGTGGCCAGCCAGGTGACCACCGCCAAGAAGCTGCGGGGCGGCGTGGTGT
TCGTGGACGAGGTCCCGAAGGGCCTGACCGGGAAGCTCGACGCCCGGAAGATCCGCGAGA
TCCTGATCAAGGCCAAGAAGGGCGGCAAGATCGCCGTGTAAGACTAGTTATAAGACTGAC
TAGCCCGATGGGCCTCCCAACGGGCCCTCCTCCCCTCCTTGCACCGAGATTAATAAAAA
AAAAAAAAAAAAAAAAAAAAAAAAAAAAAAAAAAAAAAAAAAAAAAAAAAAAAAAAAAA
TGCATCAAAGGCTCTTTTCAGAGCCACCA
```

Figure 34 nucleotide sequence of ASAH1 – PpLuc(GC) – ag – A64 – histoneSL

```
GGGCCTCTGCTGGAGTCCGGGGAGTGGCGTTGGCTGCTAGAGCGAAGCTTGAGGATGGAG
GACGCCAAGAACATCAAGAAGGGCCCGGCGCCCTTCTACCCGCTGGAGGACGGGACCGCC
GGCGAGCAGCTCCACAAGGCCATGAAGCGGTACGCCCTGGTGCCGGGCACGATCGCCTTC
ACCGACGCCCACATCGAGGTCGACATCACCTACGCGGAGTACTTCGAGATGAGCGTGCGC
CTGGCCGAGGCCATGAAGCGGTACGGCCTGAACACCAACCACCGGATCGTGGTGTGCTCG
GAGAACAGCCTGCAGTTCTTCATGCCGGTGCTGGGCGCCCTCTTCATCGGCGTGGCCGTC
GCCCCGGCGAACGACATCTACAACGAGCGGGAGCTGCTGAACAGCATGGGGATCAGCCAG
CCGACCGTGGTGTTCGTGAGCAAGAAGGGCCTGCAGAAGATCCTGAACGTGCAGAAGAAG
CTGCCCATCATCCAGAAGATCATCATCATGGACAGCAAGACCGACTACCAGGGCTTCCAG
TCGATGTACACGTTCGTGACCAGCCACCTCCCGCCGGGCTTCAACGAGTACGACTTCGTC
CCGGAGAGCTTCGACCGGGACAAGACCATCGCCCTGATCATGAACAGCAGCGGCAGCACC
GGCCTGCCGAAGGGGGTGGCCCTGCCGCACCGGACCGCCTGCGTGCGCTTCTCGCACGCC
CGGGACCCCATCTTCGGCAACCAGATCATCCCGGACACCGCCATCCTGAGCGTGGTGCCG
TTCCACCACGGCTTCGGCATGTTCACGACCCTGGGCTACCTCATCTGCGGCTTCCGGGTG
GTCCTGATGTACCGGTTCGAGGAGGAGCTGTTCCTGCGGAGCCTGCAGGACTACAAGATC
CAGAGCGCGCTGCTCGTGCCGACCCTGTTCAGCTTCTTCGCCAAGAGCACCCTGATCGAC
AAGTACGACCTGTCGAACCTGCACGAGATCGCCAGCGGGGCGCCCCGCTGAGCAAGGAG
GTGGGCGAGGCCGTGGCCAAGCGGTTCCACCTCCCGGGCATCCGCCAGGGCTACGGCCTG
ACCGAGACCACGAGCGCGATCCTGATCACCCCCGAGGGGACGACAAGCCGGGCGCCGTG
GGCAAGGTGGTCCCGTTCTTCGAGGCCAAGGTGGTGGACCTGGACACCGGCAAGACCCTG
GGCGTGAACCAGCGGGGCGAGCTGTGCGTGCGGGGCCGATGATCATGAGCGGCTACGTG
AACAACCCGGAGGCCACCAACGCCCTCATCGACAAGGACGGCTGGCTGCACAGCGGCGAC
ATCGCCTACTGGGACGAGGACGAGCACTTCTTCATCGTCGACCGGCTGAAGTCGCTGATC
AAGTACAAGGGCTACCAGGTGGCGCCGGCCGAGCTGGAGAGCATCCTGCTCCAGCACCCC
AACATCTTCGACGCCGGCGTGGCCGGGCTGCCGGACGACGACGCCGGCGAGCTGCCGGCC
GCGGTGGTGGTGCTGGAGCACGGCAAGACCATGACGGAGAAGGAGATCGTCGACTACGTG
GCCAGCCAGGTGACCACCGCCAAGAAGCTGCGGGGCGGCGTGGTGTTCGTGGACGAGGTC
CCGAAGGGCCTGACCGGGAAGCTCGACGCCCGGAAGATCCGCGAGATCCTGATCAAGGCC
AAGAAGGGCGGCAAGATCGCCGTGTAAGACTAGTTATAAGACTGACTAGCCCGATGGGCC
TCCCAACGGGCCCTCCTCCCCTCCTTGCACCGAGATTAATAAAAAAAAAAAAAAAAAAAA
AAAAAAAAAAAAAAAAAAAAAAAAAAAAAAAAAAAAAAAAAAAATGCATCAAAGGCTCTT
TTCAGAGCCACCA
```

Figure 35 nucleotide sequence of mRPL21 − PpLuc(GC) − albumin7 − A64 − C30 − histoneSL

GGGGCCGCCGCAGCCATCTTCCAGTAACTCGCCAAAAAGCTTGAGGATGGAGGACGCCAA
GAACATCAAGAAGGGCCCGGCGCCCTTCTACCCGCTGGAGGACGGGACCGCCGGCGAGCA
GCTCCACAAGGCCATGAAGCGGTACGCCCTGGTGCCGGGCACGATCGCCTTCACCGACGC
CCACATCGAGGTCGACATCACCTACGCGGAGTACTTCGAGATGAGCGTGCGCCTGGCCGA
GGCCATGAAGCGGTACGGCCTGAACACCAACCACCGGATCGTGGTGTGCTCGGAGAACAG
CCTGCAGTTCTTCATGCCGGTGCTGGGCGCCCTCTTCATCGGCGTGGCCGTCGCCCCGGC
GAACGACATCTACAACGAGCGGGAGCTGCTGAACAGCATGGGGATCAGCCAGCCGACCGT
GGTGTTCGTGAGCAAGAAGGGCCTGCAGAAGATCCTGAACGTGCAGAAGAAGCTGCCCAT
CATCCAGAAGATCATCATCATGGACAGCAAGACCGACTACCAGGGCTTCCAGTCGATGTA
CACGTTCGTGACCAGCCACCTCCCGCCGGGCTTCAACGAGTACGACTTCGTCCCGGAGAG
CTTCGACCGGGACAAGACCATCGCCCTGATCATGAACAGCAGCGGCAGCACCGGCCTGCC
GAAGGGGGTGGCCCTGCCGCACCGGACCGCCTGCGTGCGCTTCTCGCACGCCCGGGACCC
CATCTTCGGCAACCAGATCATCCCGGACACCGCCATCCTGAGCGTGGTGCCGTTCCACCA
CGGCTTCGGCATGTTCACGACCCTGGGCTACCTCATCTGCGGCTTCCGGGTGGTCCTGAT
GTACCGGTTCGAGGAGGAGCTGTTCCTGCGGAGCCTGCAGGACTACAAGATCCAGAGCGC
GCTGCTCGTGCCGACCCTGTTCAGCTTCTTCGCCAAGAGCACCCTGATCGACAAGTACGA
CCTGTCGAACCTGCACGAGATCGCCAGCGGGGCGCCCCGCTGAGCAAGGAGGTGGGCGA
GGCCGTGGCCAAGCGGTTCCACCTCCCGGGCATCCGCCAGGGCTACGGCCTGACCGAGAC
CACGAGCGCGATCCTGATCACCCCCGAGGGGACGACAAGCCGGGCGCCGTGGGCAAGGT
GGTCCCGTTCTTCGAGGCCAAGGTGGTGGACCTGGACACCGGCAAGACCCTGGGCGTGAA
CCAGCGGGGCGAGCTGTGCGTGCGGGGCCGATGATCATGAGCGGCTACGTGAACAACCC
GGAGGCCACCAACGCCCTCATCGACAAGGACGGCTGGCTGCACAGCGGCGACATCGCCTA
CTGGGACGAGGACGAGCACTTCTTCATCGTCGACCGGCTGAAGTCGCTGATCAAGTACAA
GGGCTACCAGGTGGCGCCGGCCGAGCTGGAGAGCATCCTGCTCCAGCACCCCAACATCTT
CGACGCCGGCGTGGCCGGGCTGCCGGACGACGACGCCGGCGAGCTGCCGGCCGCGGTGGT
GGTGCTGGAGCACGGCAAGACCATGACGGAGAAGGAGATCGTCGACTACGTGGCCAGCCA
GGTGACCACCGCCAAGAAGCTGCGGGGCGGCGTGGTGTTCGTGGACGAGGTCCCGAAGGG
CCTGACCGGGAAGCTCGACGCCCGGAAGATCCGCGAGATCCTGATCAAGGCCAAGAAGGG
CGGCAAGATCGCCGTGTAAGACTAGTGCATCACATTTAAAAGCATCTCAGCCTACCATGA
GAATAAGAGAAAGAAAATGAAGATCAATAGCTTATTCATCTCTTTTTCTTTTTCGTTGGT
GTAAAGCCAACACCCTGTCTAAAAAACATAAATTTCTTTAATCATTTTGCCTCTTTTCTC
TGTGCTTCAATTAATAAAAAATGGAAAGAACCTAGATCTAAAAAAAAAAAAAAAAAAAAA
AAAAAAAAAAAAAAAAAAAAAAAAAAAAAAAAAAAAAAAAAAATGCATCCCCCCCCCCC
CCCCCCCCCCCCCCCCCAAAGGCTCTTTTCAGAGCCACCAGAATT

Figure 37 nucleotide sequence of mRPL35A – PpLuc(GC) – albumin7 – A64 – C30 – histoneSL

GGGCCATCTTGGCGCCTGTGGAGGCCTGCTGGGAACAGGACTTCTAACAGCAAGTAAGCT
TGAGGATGGAGGACGCCAAGAACATCAAGAAGGGCCCGGCGCCCTTCTACCCGCTGGAGG
ACGGGACCGCCGGCGAGCAGCTCCACAAGGCCATGAAGCGGTACGCCCTGGTGCCGGGCA
CGATCGCCTTCACCGACGCCCACATCGAGGTCGACATCACCTACGCGGAGTACTTCGAGA
TGAGCGTGCGCCTGGCCGAGGCCATGAAGCGGTACGGCCTGAACACCAACCACCGGATCG
TGGTGTGCTCGGAGAACAGCCTGCAGTTCTTCATGCCGGTGCTGGGCGCCCTCTTCATCG
GCGTGGCCGTCGCCCCGGCGAACGACATCTACAACGAGCGGGAGCTGCTGAACAGCATGG
GGATCAGCCAGCCGACCGTGGTGTTCGTGAGCAAGAAGGGCCTGCAGAAGATCCTGAACG
TGCAGAAGAAGCTGCCCATCATCCAGAAGATCATCATCATGGACAGCAAGACCGACTACC
AGGGCTTCCAGTCGATGTACACGTTCGTGACCAGCCACCTCCCGCCGGGCTTCAACGAGT
ACGACTTCGTCCCGGAGAGCTTCGACCGGGACAAGACCATCGCCCTGATCATGAACAGCA
GCGGCAGCACCGGCCTGCCGAAGGGGGTGGCCCTGCCGCACCGGACCGCCTGCGTGCGCT
TCTCGCACGCCCGGGACCCCATCTTCGGCAACCAGATCATCCCGGACACCGCCATCCTGA
GCGTGGTGCCGTTCCACCACGGCTTCGGCATGTTCACGACCCTGGGCTACCTCATCTGCG
GCTTCCGGGTGGTCCTGATGTACCGGTTCGAGGAGGAGCTGTTCCTGCGGAGCCTGCAGG
ACTACAAGATCCAGAGCGCGCTGCTCGTGCCGACCCTGTTCAGCTTCTTCGCCAAGAGCA
CCCTGATCGACAAGTACGACCTGTCGAACCTGCACGAGATCGCCAGCGGGGGCGCCCCGC
TGAGCAAGGAGGTGGGCGAGGCCGTGGCCAAGCGGTTCCACCTCCCGGGCATCCGCCAGG
GCTACGGCCTGACCGAGACCACGAGCGCGATCCTGATCACCCCCGAGGGGACGACAAGC
CGGGCGCCGTGGGCAAGGTGGTCCCGTTCTTCGAGGCCAAGGTGGTGGACCTGGACACCG
GCAAGACCCTGGGCGTGAACCAGCGGGGCGAGCTGTGCGTGCGGGGCCGATGATCATGA
GCGGCTACGTGAACAACCCGGAGGCCACCAACGCCCTCATCGACAAGGACGGCTGGCTGC
ACAGCGGCGACATCGCCTACTGGGACGAGGACGAGCACTTCTTCATCGTCGACCGGCTGA
AGTCGCTGATCAAGTACAAGGGCTACCAGGTGGCGCCGGCCGAGCTGGAGAGCATCCTGC
TCCAGCACCCCAACATCTTCGACGCCGGCGTGGCCGGGCTGCCGGACGACGACGCCGGCG
AGCTGCCGGCCGCGGTGGTGGTGCTGGAGCACGGCAAGACCATGACGGAGAAGGAGATCG
TCGACTACGTGGCCAGCCAGGTGACCACCGCCAAGAAGCTGCGGGGCGGCGTGGTGTTCG
TGGACGAGGTCCCGAAGGGCCTGACCGGGAAGCTCGACGCCCGGAAGATCCGCGAGATCC
TGATCAAGGCCAAGAAGGGCGGCAAGATCGCCGTGTAAGACTAGTGCATCACATTTAAAA
GCATCTCAGCCTACCATGAGAATAAGAGAAAGAAAATGAAGATCAATAGCTTATTCATCT
CTTTTTCTTTTTCGTTGGTGTAAAGCCAACACCCTGTCTAAAAAACATAAATTTCTTTAA
TCATTTTGCCTCTTTTCTCTGTGCTTCAATTAATAAAAAATGGAAAGAACCTAGATCTAA
AAAAAAAAAAAAAAAAAAAAAAAAAAAAAAAAAAAAAAAAAAAAAAAAAAAAAAAAAAAA
AATGCATCCCCCCCCCCCCCCCCCCCCCCCCCCCCCCAAAGGCTCTTTTCAGAGCCACC
AGAATT

Figure 38

ARTIFICIAL NUCLEIC ACID MOLECULES FOR IMPROVED PROTEIN OR PEPTIDE EXPRESSION

This application is a continuation of U.S. application Ser. No. 14/388,226, filed Sep. 25, 2014, which is a national phase application under 35 U.S.C. § 371 of International Application No. PCT/EP2013/000937, filed Mar. 27, 2013, which claims priority to International Application No. PCT/EP2012/001336, filed Mar. 27, 2012, and International Application No. PCT/EP2012/002447, filed Jun. 8, 2012. The entire text of each of the above referenced disclosures is specifically incorporated herein by reference.

The invention relates to artificial nucleic acid molecules comprising a 5'UTR element derived from the 5'UTR of a TOP gene, an open reading frame, and optionally a histone stem-loop, a 3'UTR element, a poly(A) sequence and/or a polyadenylation signal. The invention relates further to a vector comprising a 5'UTR element derived from the 5'UTR of a TOP gene, to a pharmaceutical composition comprising the artificial nucleic acid molecule or the vector, and to a kit comprising the artificial nucleic acid molecule, the vector and/or the pharmaceutical composition, preferably for use in the field of gene therapy and/or genetic vaccination.

Gene therapy and genetic vaccination belong to the most promising and quickly developing methods of modern medicine. They may provide highly specific and individual options for therapy of a large variety of diseases. Particularly, inherited genetic diseases but also autoimmune diseases, cancerous or tumour-related diseases as well as inflammatory diseases may be the subject of such treatment approaches. Also, it is envisaged to prevent (early) onset of such diseases by these approaches.

The main conceptual rational behind gene therapy is appropriate modulation of impaired gene expression associated with pathological conditions of specific diseases. Pathologically altered gene expression may result in lack or overproduction of essential gene products, for example, signalling factors such as hormones, housekeeping factors, metabolic enzymes, structural proteins or the like. Altered gene expression may not only be due to mis-regulation of transcription and/or translation, but also due to mutations within the ORF coding for a particular protein. Pathological mutations may be caused by e.g. chromosomal aberration, or by more specific mutations, such as point or frame-shift-mutations, all of them resulting in limited functionality and, potentially, total loss of function of the gene product. However, misregulation of transcription or translation may also occur, if mutations affect genes encoding proteins which are involved in the transcriptional or translational machinery of the cell. Such mutations may lead to pathological up- or down-regulation of genes which are—as such—functional. Genes encoding gene products which exert such regulating functions, may be, e.g., transcription factors, signal receptors, messenger proteins or the like. However, loss of function of such genes encoding regulatory proteins may, under certain circumstances, be reversed by artificial introduction of other factors acting further downstream of the impaired gene product. Such gene defects may also be compensated by gene therapy via substitution of the affected gene itself.

Genetic vaccination allows to evoke a desired immune response to selected antigens, such as characteristic components of bacterial surfaces, viral particles, tumour antigens or the like. Generally, vaccination is one of the pivotal achievements of modern medicine. However, effective vaccines are currently available only for a smaller number of diseases. Accordingly, infections that are not preventable by vaccination still affect millions of people every year.

Commonly, vaccines may be subdivided into "first", "second" and "third" generation vaccines. "First generation" vaccines are, typically, whole-organism vaccines. They are based on either live and attenuated or killed pathogens, e.g. viruses, bacteria or the like. The major drawback of live and attenuated vaccines is the risk for a reversion to life-threatening variants. Thus, although attenuated, such pathogens may still intrinsically bear unpredictable risks. Killed pathogens may not be as effective as desired for generating a specific immune response. In order to minimize these risks, "second generation" vaccines were developed. These are, typically, subunit vaccines, consisting of defined antigens or recombinant protein components which are derived from pathogens.

Genetic vaccines, i.e. vaccines for genetic vaccination, are usually understood as "third generation" vaccines. They are typically composed of genetically engineered nucleic acid molecules which allow expression of peptide or protein (antigen) fragments characteristic for a pathogen or a tumor antigen in vivo. Genetic vaccines are expressed upon administration to a patient and uptake by competent cells. Expression of the administered nucleic acids results in production of the encoded proteins. In the event these proteins are recognized as foreign by the patient's immune system, an immune response is triggered.

As can be seen from the above, both methods, gene therapy and genetic vaccination, are essentially based on the administration of nucleic acid molecules to a patient and subsequent transcription and/or translation of the encoded genetic information. Alternatively, genetic vaccination or gene therapy may also comprise methods which include isolation of specific body cells from a patient to be treated, subsequent in vitro transfection of such cells, and re-administration of the treated cells to the patient.

DNA as well as RNA may be used as nucleic acid molecules for administration in the context of gene therapy or genetic vaccination. DNA is known to be relatively stable and easy to handle. However, the use of DNA bears the risk of undesired insertion of the administered DNA-fragments into the patient's genome potentially resulting in loss of function of the impaired genes. As a further risk, the undesired generation of anti-DNA antibodies has emerged. Another drawback is the limited expression level of the encoded peptide or protein that is achievable upon DNA administration and its transcription/translation. Among other reasons, the expression level of the administered DNA will be dependent on the presence of specific transcription factors which regulate DNA transcription. In the absence of such factors, DNA transcription will not yield satisfying amounts of RNA. As a result, the level of translated peptide or protein obtained is limited.

By using RNA instead of DNA for gene therapy or genetic vaccination, the risk of undesired genomic integration and generation of anti-DNA antibodies is minimized or avoided. However, RNA is considered to be a rather unstable molecular species which may readily be degraded by ubiquitous RNAses.

In vivo, RNA-degradation contributes to the regulation of the RNA half-life time. That effect was considered and proven to fine tune the regulation of eukaryotic gene expression (Friedel et al., Conserved principles of mammalian transcriptional regulation revealed by RNA half-life, Nucleic Acid Research, 2009, 1-12). Accordingly, each naturally occurring mRNA has its individual half-life depending on the gene from which the mRNA is derived. It contributes to the regulation of the expression level of this gene. Unstable RNAs are important to realize transient gene expression at distinct points in time. However, long-lived RNAs may be associated with accumulation of distinct proteins or continuous expression of genes. In vivo, the half life of mRNAs may also be dependent on environmental factors, such as hormonal treatment, as has been shown, e.g., for insulin-like growth factor I, actin, and albumin mRNA (Johnson et al., Newly synthesized RNA: Simultaneous measurement in intact cells of transcription rates and RNA stability of insulin-like growth factor I, actin, and albumin in growth hormone-stimulated hepatocytes, Proc. Natl. Acad. Sci., Vol. 88, pp. 5287-5291, 1991).

For gene therapy and genetic vaccination, usually stable RNA is desired. This is, on the one hand, due to the fact that the product encoded by the RNA-sequence shall accumulate in vivo. On the other hand, the RNA has to maintain its structural and functional integrity when prepared for a suitable dosage form, in the course of its storage, and when administered. Thus, considerable attention was dedicated to provide stable RNA molecules for gene therapy or genetic vaccination in order to prevent them from being subject to early degradation or decay.

It has been reported that the G/C-content of nucleic acid molecules may influence their stability. Thus, nucleic acids comprising an increased amount of guanine (G) and/or cytosine (C) residues may be functionally more stable than nucleic acids containing a large amount of adenine (A) and thymine (T) or uracil (U) nucleotides. In this context, WO02/098443 provides a pharmaceutical composition containing an mRNA that is stabilised by sequence modifications in the translated region. Such a sequence modification takes advantage of the degeneracy of the genetic code. Accordingly, codons which contain a less favourable combination of nucleotides (less favourable in terms of RNA stability) may be substituted by alternative codons without altering the encoded amino acid sequence. This method of RNA stabilization is limited by the provisions of the specific nucleotide sequence of each single RNA molecule which is not allowed to leave the space of the desired amino acid sequence. Also, that approach is restricted to coding regions of the RNA.

As an alternative option for mRNA stabilisation, it has been found that naturally occurring eukaryotic mRNA molecules contain characteristic stabilising elements. For example, they may comprise so-called untranslated regions (UTR) at their 5'-end (5'UTR) and/or at their 3'-end (3'UTR) as well as other structural features, such as a 5'-cap structure or a 3'-poly(A) tail. Both, 5'UTR and 3'UTR are typically transcribed from the genomic DNA and are, thus, an element of the premature mRNA. Characteristic structural features of mature mRNA, such as the 5'-cap and the 3'-poly(A) tail (also called poly(A) tail or poly(A) sequence) are usually added to the transcribed (premature) mRNA during mRNA processing.

A 3'-poly(A) tail is typically a monotonous sequence stretch of adenine nucleotides added to the 3'-end of the transcribed mRNA. It may comprise up to about 400 adenine nucleotides. It was found that the length of such a 3'-poly(A) tail is a potentially critical element for the stability of the individual mRNA.

Nearly all eukaryotic mRNAs end with such a poly(A) sequence that is added to their 3' end by the ubiquitous cleavage/polyadenylation machinery. The presence of a poly (A) sequence at the 3' end is one of the most recognizable features of eukaryotic mRNAs. After cleavage, most pre-mRNAs, with the exception of replication-dependent histone transcripts, acquire a polyadenylated tail. In this context, 3' end processing is a nuclear co-transcriptional process that promotes transport of mRNAs from the nucleus to the cytoplasm and affects the stability and the translation of mRNAs. Formation of this 3' end occurs in a two step reaction directed by the cleavage/polyadenylation machinery and depends on the presence of two sequence elements in mRNA precursors (pre-mRNAs); a highly conserved hexanucleotide AAUAAA (polyadenylation signal) and a downstream G/U-rich sequence. In a first step, pre-mRNAs are cleaved between these two elements. In a second step tightly coupled to the first step the newly formed 3' end is extended by addition of a poly(A) sequence consisting of 200-250 adenylates which affects subsequently all aspects of mRNA metabolism, including mRNA export, stability and translation (Dominski, Z. and W. F. Marzluff (2007), Gene 396(2): 373-90.).

The only known exception to this rule are the replication-dependent histone mRNAs which terminate with a histone stem-loop instead of a poly(A) sequence. Exemplary histone stem-loop sequences are described in López et al. (Dávila López, M., & Samuelsson, T. (2008), RNA (New York, N.Y.), 14(1), 1-10. doi:10.1261/rna.782308.).

The stem-loops in histone pre-mRNAs are typically followed by a purine-rich sequence known as the histone downstream element (HDE). These pre-mRNAs are processed in the nucleus by a single endonucleolytic cleavage approximately 5 nucleotides downstream of the stem-loop, catalyzed by the U7 snRNP through base pairing of the U7 snRNA with the HDE.

Due to the requirement to package newly synthesized DNA into chromatin, histone synthesis is regulated in concert with the cell cycle. Increased synthesis of histone proteins during S phase is achieved by transcriptional activation of histone genes as well as posttranscriptional regulation of histone mRNA levels. It could be shown that the histone stem-loop is essential for all posttranscriptional steps of histone expression regulation. It is necessary for efficient processing, export of the mRNA into the cytoplasm, loading onto polyribosomes, and regulation of mRNA stability.

In the above context, a 32 kDa protein was identified, which is associated with the histone stem-loop at the 3'-end of the histone messages in both the nucleus and the cytoplasm. The expression level of this stem-loop binding protein (SLBP) is cell-cycle regulated and is highest during S-phase when histone mRNA levels are increased. SLBP is necessary for efficient 3'-end processing of histone pre-mRNA by the U7 snRNP. After completion of processing, SLBP remains associated with the stem-loop at the end of mature histone mRNAs and stimulates their translation into histone proteins in the cytoplasm. (Dominski, Z. and W. F. Marzluff (2007), Gene 396(2): 373-90). Interestingly, the RNA binding domain of SLBP is conserved throughout metazoa and protozoa (Dávila López, M., & Samuelsson, T. (2008), RNA (New York, N.Y.), 14(1), 1-10. doi:10.1261/rna.782308) and it could be shown that its binding to the histone stem-loop sequence is dependent on the stem-loop structure and that the minimum binding site contains at least 3 nucleotides 5' and 2 nucleotides 3' of the stem-loop (Pandey, N. B., et al. (1994), *Molecular and Cellular Biology*, 14(3), 1709-1720 and Williams, A. S., & Marzluff, W. F., (1995), *Nucleic Acids Research*, 23(4), 654-662.).

Even though histone genes are generally classified as either "replication-dependent", giving rise to mRNA ending in a histone stem-loop, or "replacement-type", giving rise to mRNA bearing a poly(A)-tail instead, naturally occurring mRNAs containing both a histone stem-loop and poly(A) or oligo(A) 3' thereof have been identified in some very rare cases. Sanchez et al. examined the effect of naturally occurring oligo(A) tails appended 3' of the histone stem-loop of histone mRNA during Xenopus oogenesis using Luciferase as a reporter protein and found that the oligo(A) tail is an active part of the translation repression mechanism that silences histone mRNA during oogenesis and its removal is part of the mechanism that activates translation of histone mRNAs (Sanchez, R. and W. F. Marzluff (2004), Mol Cell Biol 24(6): 2513-25).

Furthermore, the requirements for regulation of replication dependent histones at the level of pre-mRNA processing and mRNA stability have been investigated using artificial constructs coding for the marker protein alpha globin, taking advantage of the fact that the globin gene contains introns as opposed to the intron-less histone genes. For this purpose constructs were generated in which the alpha globin coding sequence was followed by a histone stem-loop signal (histone stem-loop followed by the histone downstream element) and a polyadenylation signal (Whitelaw, E., et al. (1986). Nucleic Acids Research, 14(17), 7059-7070; Pandey, N. B., & Marzluff, W. F. (1987). Molecular and Cellular Biology, 7(12), 4557-4559; Pandey, N. B., et al. (1990). Nucleic Acids Research, 18(11), 3161-3170).

Also, it was shown that the 3'UTR of α-globin mRNA may be an important factor for the well-known stability of α-globin mRNA (Rodgers et al., Regulated α-globin mRNA decay is a cytoplasmic event proceeding through 3'-to-5' exosome-dependent decapping, RNA, 8, pp. 1526-1537, 2002). The 3'UTR of α-globin mRNA is obviously involved in the formation of a specific ribonucleoprotein-complex, the α-complex, whose presence correlates with mRNA stability in vitro (Wang et al., An mRNA stability complex functions with poly(A)-binding protein to stabilize mRNA in vitro, Molecular and Cellular biology, Vol 19, No. 7, July 1999, p. 4552-4560).

Irrespective of factors influencing mRNA stability, effective translation of the administered nucleic acid molecules by the target cells or tissue is crucial for any approach using nucleic acid molecules for gene therapy or genetic vaccination. Along with the regulation of stability, also translation of the majority of mRNAs is regulated by structural features like UTRs, 5'-cap and 3'-poly(A) tail. In this context, it has been reported that the length of the poly(A) tail may play an important role for translational efficiency as well. Stabilizing 3'-elements, however, may also have an attenuating effect on translation.

Further regulative elements, which may have an influence on expression levels, may be found in the 5'UTR. For example, it has been reported that synthesis of particular proteins, e.g. proteins belonging to the translational apparatus, may be regulated not only at the transcriptional but also at the translational level. For example, translation of proteins encoded by so called 'TOP-genes' may be down-regulated by translational repression. Therein, the term 'TOP-gene' relates to a gene corresponding to an mRNA that is characterized by the presence of a TOP sequence at the 5'end and in most cases by a growth-associated translation regulation (Iadevaia et al., All translation elongation factors and the e, f, and h subunits of translation initiation factor 3 are encoded by 5'-terminal oligopyrimidine (TOP) mRNAs; RNA, 2008, 14:1730-1736). In this context, a TOP sequence—also called the '5'-terminal oligopyrimidine tract'—typically consists of a C residue at the cap site, followed by an uninterrupted sequence of up to 13 or even more pyrimidines (Avni et al., Vertebrate mRNAs with a 5'-terminal pyrimidine tract are Candidates for translational repression in quiescent cells: characterization of the translational cis-regulatory element, Molecular and Cellular Biology, 1994, p. 3822-3833). These TOP sequences are reported to be present in many mRNAs encoding components of the translational machinery and to be responsible for selective repression of the translation of these TOP containing mRNAs due to growth arrest (Meyuhas, et al., Translational Control of Ribosomal Protein mRNAs in Eukaryotes, Translational Control. Cold Spring Harbor Monograph Archive. Cold Spring Harbor Laboratory Press, 1996, p. 363-388).

It is the object of the invention to provide nucleic acid molecules which may be suitable for application in gene therapy and/or genetic vaccination. Particularly, it is the object of the invention to provide artificial nucleic acid molecules, such as an mRNA species, which provide for increased protein production from said artificial nucleic acid molecules, preferably which exhibit increased translational efficiency. Another object of the present invention is to provide nucleic acid molecules coding for such a superior mRNA species which may be amenable for use in gene therapy and/or genetic vaccination. It is a further object of the present invention to provide a pharmaceutical composition for use in gene therapy and/or genetic vaccination. In summary, it is the object of the present invention to provide improved nucleic acid species which overcome the above discussed disadvantages of the prior art by a cost-effective and straight-forward approach.

The object underlying the present invention is solved by the claimed subject-matter.

For the sake of clarity and readability the following definitions are provided. Any technical feature mentioned for these definitions may be read on each and every embodiment of the invention. Additional definitions and explanations may be specifically provided in the context of these embodiments.

Adaptive immune response: The adaptive immune response is typically understood to be an antigen-specific response of the immune system. Antigen specificity allows for the generation of responses that are tailored to specific pathogens or pathogen-infected cells. The ability to mount these tailored responses is usually maintained in the body by "memory cells". Should a pathogen infect the body more than once, these specific memory cells are used to quickly eliminate it. In this context, the first step of an adaptive immune response is the activation of naïve antigen-specific T cells or different immune cells able to induce an antigen-specific immune response by antigen-presenting cells. This occurs in the lymphoid tissues and organs through which naïve T cells are constantly passing. The three cell types that may serve as antigen-presenting cells are dendritic cells, macrophages, and B cells. Each of these cells has a distinct function in eliciting immune responses. Dendritic cells may take up antigens by phagocytosis and macropinocytosis and may become stimulated by contact with e.g. a foreign antigen to migrate to the local lymphoid tissue, where they differentiate into mature dendritic cells. Macrophages ingest particulate antigens such as bacteria and are induced by infectious agents or other appropriate stimuli to express MHC molecules. The unique ability of B cells to bind and internalize soluble protein antigens via their receptors may also be important to induce T cells. MHC-molecules are, typically, responsible for presentation of an antigen to T-cells. Therein, presenting the antigen on MHC molecules leads to activation of T cells which induces their proliferation and differentiation into armed effector T cells. The most important function of effector T cells is the killing of infected cells by CD8+ cytotoxic T cells and the activation of macrophages by Th1 cells which together make up cell-mediated immunity, and the activation of B cells by both Th2 and Th1 cells to produce different classes of antibody, thus driving the humoral immune response. T cells recognize an antigen by their T cell receptors which do not recognize and bind the antigen directly, but instead recognize short peptide fragments e.g. of pathogen-derived protein antigens, e.g. so-called epitopes, which are bound to MHC molecules on the surfaces of other cells.

Adaptive immune system: The adaptive immune system is essentially dedicated to eliminate or prevent pathogenic growth. It typically regulates the adaptive immune response by providing the vertebrate immune system with the ability to recognize and remember specific pathogens (to generate immunity), and to mount stronger attacks each time the pathogen is encountered. The system is highly adaptable because of somatic hypermutation (a process of accelerated somatic mutations), and V(D)J recombination (an irreversible genetic recombination of antigen receptor gene segments). This mechanism allows a small number of genes to generate a vast number of different antigen receptors, which are then uniquely expressed on each individual lymphocyte. Because the gene rearrangement leads to an irreversible change in the DNA of each cell, all of the progeny (offspring) of such a cell will then inherit genes encoding the same receptor specificity, including the Memory B cells and Memory T cells that are the keys to long-lived specific immunity.

Adjuvant/adjuvant component: An adjuvant or an adjuvant component in the broadest sense is typically a pharmacological and/or immunological agent that may modify, e.g. enhance, the effect of other agents, such as a drug or vaccine. It is to be interpreted in a broad sense and refers to a broad spectrum of substances. Typically, these substances are able to increase the immunogenicity of antigens. For example, adjuvants may be recognized by the innate immune systems and, e.g., may elicit an innate immune response. "Adjuvants" typically do not elicit an adaptive immune response. Insofar, "adjuvants" do not qualify as antigens. Their mode of action is distinct from the effects triggered by antigens resulting in an adaptive immune response.

Antigen: In the context of the present invention "antigen" refers typically to a substance which may be recognized by the immune system, preferably by the adaptive immune system, and is capable of triggering an antigen-specific immune response, e.g. by formation of antibodies and/or antigen-specific T cells as part of an adaptive immune response. Typically, an antigen may be or may comprise a peptide or protein which may be presented by the MHC to T-cells.

Artificial nucleic acid molecule: An artificial nucleic acid molecule may typically be understood to be a nucleic acid molecule, e.g. a DNA or an RNA, that does not occur naturally. In other words, an artificial nucleic acid molecule may be understood as a non-natural nucleic acid molecule. Such nucleic acid molecule may be non-natural due to its individual sequence (which does not occur naturally) and/or due to other modifications, e.g. structural modifications of nucleotides which do not occur naturally. An artificial nucleic acid molecule may be a DNA molecule, an RNA molecule or a hybrid-molecule comprising DNA and RNA portions. Typically, artificial nucleic acid molecules may be designed and/or generated by genetic engineering methods to correspond to a desired artificial sequence of nucleotides (heterologous sequence). In this context an artificial sequence is usually a sequence that may not occur naturally, i.e. it differs from the wild type sequence by at least one nucleotide. The term 'wild type' may be understood as a sequence occurring in nature. Further, the term 'artificial nucleic acid molecule' is not restricted to mean 'one single molecule' but is, typically, understood to comprise an ensemble of identical molecules. Accordingly, it may relate to a plurality of identical molecules contained in an aliquot.

Bicistronic RNA, multicistronic RNA: A bicistronic or multicistronic RNA is typically an RNA, preferably an mRNA, that typically may have two (bicistronic) or more (multicistronic) open reading frames (ORF). An open reading frame in this context is a sequence of codons that is translatable into a peptide or protein.

Carrier/polymeric carrier: A carrier in the context of the invention may typically be a compound that facilitates transport and/or complexation of another compound (cargo). A polymeric carrier is typically a carrier that is formed of a polymer. A carrier may be associated to its cargo by covalent or non-covalent interaction. A carrier may transport nucleic acids, e.g. RNA or DNA, to the target cells. The carrier may—for some embodiments—be a cationic component.

Cationic component: The term "cationic component" typically refers to a charged molecule, which is positively charged (cation) at a pH value typically from 1 to 9, preferably at a pH value of or below 9 (e.g. from 5 to 9), of or below 8 (e.g. from 5 to 8), of or below 7 (e.g. from 5 to 7), most preferably at a physiological pH, e.g. from 7.3 to 7.4. Accordingly, a cationic component may be any positively charged compound or polymer, preferably a cationic peptide or protein which is positively charged under physiological conditions, particularly under physiological conditions in vivo. A 'cationic peptide or protein' may contain at least one positively charged amino acid, or more than one positively charged amino acid, e.g. selected from Arg, His, Lys or Orn. Accordingly, 'polycationic' components are also within the scope exhibiting more than one positive charge under the conditions given.

5'-cap: A 5'-cap is an entity, typically a modified nucleotide entity, which generally 'caps' the 5'-end of a mature mRNA. A 5'-cap may typically be formed by a modified nucleotide, particularly by a derivative of a guanine nucleotide. Preferably, the 5'-cap is linked to the 5'-terminus via a 5'-5'-triphosphate linkage. A 5'-cap may be methylated, e.g. m7GpppN, wherein N is the terminal 5' nucleotide of the nucleic acid carrying the 5'-cap, typically the 5'-end of an RNA. Further examples of 5'cap structures include glyceryl, inverted deoxy abasic residue (moiety), 4%5' methylene nucleotide, 1-(beta-D-erythrofuranosyl) nucleotide, 4'-thio nucleotide, carbocyclic nucleotide, 1,5-anhydrohexitol nucleotide, L-nucleotides, alpha-nucleotide, modified base nucleotide, threo-pentofuranosyl nucleotide, acyclic 3',4'-seco nucleotide, acyclic 3,4-dihydroxybutyl nucleotide, acyclic 3,5 dihydroxypentyl nucleotide, 3'-3'-inverted nucleotide moiety, 3'-3'-inverted abasic moiety, 3'-2'-inverted nucleotide moiety, 3'-2'-inverted abasic moiety, 1,4-butanediol phosphate, 3'-phosphoramidate, hexylphosphate, aminohexyl phosphate, 3'-phosphate, 3'phosphorothioate, phosphorodithioate, or bridging or non-bridging methylphosphonate moiety.

Cellular immunity/cellular immune response: Cellular immunity relates typically to the activation of macrophages, natural killer cells (NK), antigen-specific cytotoxic T-lymphocytes, and the release of various cytokines in response to an antigen. In more general terms, cellular immunity is not based on antibodies, but on the activation of cells of the immune system. Typically, a cellular immune response may be characterized e.g. by activating antigen-specific cytotoxic T-lymphocytes that are able to induce apoptosis in cells, e.g. specific immune cells like dendritic cells or other cells, displaying epitopes of foreign antigens on their surface. Such cells may be virus-infected or infected with intracellular bacteria, or cancer cells displaying tumor antigens. Further characteristics may be activation of macrophages and natural killer cells, enabling them to destroy pathogens and stimulation of cells to secrete a variety of cytokines that influence the function of other cells involved in adaptive immune responses and innate immune responses.

DNA: DNA is the usual abbreviation for deoxy-ribo-nucleic-acid. It is a nucleic acid molecule, i.e. a polymer consisting of nucleotides. These nucleotides are usually deoxy-adenosine-monophosphate, deoxy-thymidine-monophosphate, deoxy-guanosine-monophosphate and deoxycytidine-monophosphate monomers which are—by themselves—composed of a sugar moiety (deoxyribose), a base moiety and a phosphate moiety, and polymerise by a characteristic backbone structure. The backbone structure is, typically, formed by phosphodiester bonds between the sugar moiety of the nucleotide, i.e. deoxyribose, of a first and a phosphate moiety of a second, adjacent monomer. The specific order of the monomers, i.e. the order of the bases linked to the sugar/phosphate-backbone, is called the DNA-sequence. DNA may be single stranded or double stranded. In the double stranded form, the nucleotides of the first strand typically hybridize with the nucleotides of the second strand, e.g. by A/T-base-pairing and G/C-base-pairing.

Epitope: Epitopes (also called 'antigen determinant') can be distinguished in T cell epitopes and B cell epitopes. T cell epitopes or parts of the proteins in the context of the present invention may comprise fragments preferably having a length of about 6 to about 20 or even more amino acids, e.g. fragments as processed and presented by MHC class I molecules, preferably having a length of about 8 to about 10 amino acids, e.g. 8, 9, or 10, (or even 11, or 12 amino acids), or fragments as processed and presented by MHC class II molecules, preferably having a length of about 13 or more amino acids, e.g. 13, 14, 15, 16, 17, 18, 19, 20 or even more amino acids, wherein these fragments may be selected from any part of the amino acid sequence. These fragments are typically recognized by T cells in form of a complex consisting of the peptide fragment and an MHC molecule, i.e. the fragments are typically not recognized in their native form. B cell epitopes are typically fragments located on the outer surface of (native) protein or peptide antigens as defined herein, preferably having 5 to 15 amino acids, more preferably having 5 to 12 amino acids, even more preferably having 6 to 9 amino acids, which may be recognized by antibodies, i.e. in their native form.

Such epitopes of proteins or peptides may furthermore be selected from any of the herein mentioned variants of such proteins or peptides. In this context antigenic determinants can be conformational or discontinuous epitopes which are composed of segments of the proteins or peptides as defined herein that are discontinuous in the amino acid sequence of the proteins or peptides as defined herein but are brought together in the three-dimensional structure or continuous or linear epitopes which are composed of a single polypeptide chain.

Fragment of a sequence: A fragment of a sequence may typically be a shorter portion of a full-length sequence of e.g. a nucleic acid molecule or an amino acid sequence. Accordingly, a fragment, typically, consists of a sequence that is identical to the corresponding stretch within the full-length sequence. A preferred fragment of a sequence in the context of the present invention, consists of a continuous stretch of entities, such as nucleotides or amino acids corresponding to a continuous stretch of entities in the molecule the fragment is derived from, which represents at least 20%, preferably at least 30%, more preferably at least 40%, more preferably at least 50%, even more preferably at least 60%, even more preferably at least 70%, and most preferably at least 80% of the total (i.e. full-length) molecule from which the fragment is derived.

G/C modified: A G/C-modified nucleic acid may typically be a nucleic acid, preferably an artificial nucleic acid molecule as defined herein, based on a modified wild-type sequence comprising a preferably increased number of guanosine and/or cytosine nucleotides as compared to the wild-type sequence. Such an increased number may be generated by substitution of codons containing adenosine or thymidine nucleotides by codons containing guanosine or cytosine nucleotides. If the enriched G/C content occurs in a coding region of DNA or RNA, it makes use of the degeneracy of the genetic code. Accordingly, the codon substitutions preferably do not alter the encoded amino acid residues, but exclusively increase the G/C content of the nucleic acid molecule.

Gene therapy: Gene therapy may typically be understood to mean a treatment of a patient's body or isolated elements of a patient's body, for example isolated tissues/cells, by nucleic acids encoding a peptide or protein. It typically may comprise at least one of the steps of a) administration of a nucleic acid, preferably an artificial nucleic acid molecule as defined herein, directly to the patient—by whatever administration route—or in vitro to isolated cells/tissues of the patient, which results in transfection of the patient's cells either in vivo/ex vivo or in vitro; b) transcription and/or translation of the introduced nucleic acid molecule; and optionally c) re-administration of isolated, transfected cells to the patient, if the nucleic acid has not been administered directly to the patient.

Genetic vaccination: Genetic vaccination may typically be understood to be vaccination by administration of a nucleic acid molecule encoding an antigen or an immunogen or fragments thereof. The nucleic acid molecule may be administered to a subject's body or to isolated cells of a subject. Upon transfection of certain cells of the body or upon transfection of the isolated cells, the antigen or immunogen may be expressed by those cells and subsequently presented to the immune system, eliciting an adaptive, i.e. antigen-specific immune response. Accordingly, genetic vaccination typically comprises at least one of the steps of a) administration of a nucleic acid, preferably an artificial nucleic acid molecule as defined herein, to a subject, preferably a patient, or to isolated cells of a subject, preferably a patient, which usually results in transfection of the subject's cells either in vivo or in vitro; b) transcription and/or translation of the introduced nucleic acid molecule; and optionally c) re-administration of isolated, transfected cells to the subject, preferably the patient, if the nucleic acid has not been administered directly to the patient.

Heterologous sequence: Two sequences are typically understood to be 'heterologous' if they are not derivable from the same gene. I.e., although heterologous sequences may be derivable from the same organism, they naturally (in nature) do not occur in the same nucleic acid molecule, such as in the same mRNA.

Humoral immunity/humoral immune response: Humoral immunity refers typically to antibody production and optionally to accessory processes accompanying antibody production. A humoral immune response may be typically characterized, e.g., by Th2 activation and cytokine production, germinal center formation and isotype switching, affinity maturation and memory cell generation. Humoral immunity also typically may refer to the effector functions of antibodies, which include pathogen and toxin neutralization, classical complement activation, and opsonin promotion of phagocytosis and pathogen elimination.

Immunogen: In the context of the present invention an immunogen may be typically understood to be a compound that is able to stimulate an immune response. Preferably, an immunogen is a peptide, polypeptide, or protein. In a particularly preferred embodiment, an immunogen in the sense of the present invention is the product of translation of a provided nucleic acid molecule, preferably an artificial nucleic acid molecule as defined herein. Typically, an immunogen elicits at least an adaptive immune response.

Immunostimulatory composition: In the context of the invention, an immunostimulatory composition may be typically understood to be a composition containing at least one component which is able to induce an immune response or from which a component which is able to induce an immune response is derivable. Such immune response may be preferably an innate immune response or a combination of an adaptive and an innate immune response. Preferably, an immunostimulatory composition in the context of the invention contains at least one artificial nucleic acid molecule, more preferably an RNA, for example an mRNA molecule. The immunostimulatory component, such as the mRNA may be complexed with a suitable carrier. Thus, the immunostimulatory composition may comprise an mRNA/carrier-complex. Furthermore, the immunostimulatory composition may comprise an adjuvant and/or a suitable vehicle for the immunostimulatory component, such as the mRNA.

Immune response: An immune response may typically be a specific reaction of the adaptive immune system to a particular antigen (so called specific or adaptive immune response) or an unspecific reaction of the innate immune system (so called unspecific or innate immune response), or a combination thereof.

Immune system: The immune system may protect organisms from infection. If a pathogen succeeds in passing a physical barrier of an organism and enters this organism, the innate immune system provides an immediate, but non-specific response. If pathogens evade this innate response, vertebrates possess a second layer of protection, the adaptive immune system. Here, the immune system adapts its response during an infection to improve its recognition of the pathogen. This improved response is then retained after the pathogen has been eliminated, in the form of an immunological memory, and allows the adaptive immune system to mount faster and stronger attacks each time this pathogen is encountered. According to this, the immune system comprises the innate and the adaptive immune system. Each of these two parts typically contains so called humoral and cellular components.

Immunostimulatory RNA: An immunostimulatory RNA (isRNA) in the context of the invention may typically be an RNA that is able to induce an innate immune response. It usually does not have an open reading frame and thus does not provide a peptide-antigen or immunogen but elicits an immune response e.g. by binding to a specific kind of Toll-like-receptor (TLR) or other suitable receptors. However, of course also mRNAs having an open reading frame and coding for a peptide/protein may induce an innate immune response and, thus, may be immunostimulatory RNAs.

Innate immune system: The innate immune system, also known as non-specific (or unspecific) immune system, typically comprises the cells and mechanisms that defend the host from infection by other organisms in a non-specific manner. This means that the cells of the innate system may recognize and respond to pathogens in a generic way, but unlike the adaptive immune system, it does not confer long-lasting or protective immunity to the host. The innate immune system may be, e.g., activated by ligands of Toll-like receptors (TLRs) or other auxiliary substances such as lipopolysaccharides, TNF-alpha, CD40 ligand, or cytokines, monokines, lymphokines, interleukins or chemokines, IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, IFN-alpha, IFN-beta, IFN-gamma, GM-CSF, G-CSF, M-CSF, LT-beta, TNF-alpha, growth factors, and hGH, a ligand of human Toll-like receptor TLR1, TLR2, TLR3, TLR4, TLR5, TLR6, TLR7, TLR8, TLR9, TLR10, a ligand of murine Toll-like receptor TLR1, TLR2, TLR3, TLR4, TLR5, TLR6, TLR7, TLR8, TLR9, TLR10, TLR11, TLR12 or TLR13, a ligand of a NOD-like receptor, a ligand of a RIG-I like receptor, an immunostimulatory nucleic acid, an immunostimulatory RNA (isRNA), a CpG-DNA, an antibacterial agent, or an anti-viral agent. The pharmaceutical composition according to the present invention may comprise one or more such substances. Typically, a response of the innate immune system includes recruiting immune cells to sites of infection, through the production of chemical factors, including specialized chemical mediators, called cytokines; activation of the complement cascade; identification and removal of foreign substances present in organs, tissues, the blood and lymph, by specialized white blood cells; activation of the adaptive immune system; and/or acting as a physical and chemical barrier to infectious agents.

Cloning site: A cloning site is typically understood to be a segment of a nucleic acid molecule, which is suitable for insertion of a nucleic acid sequence, e.g., a nucleic acid sequence comprising an open reading frame. Insertion may be performed by any molecular biological method known to the one skilled in the art, e.g. by restriction and ligation. A cloning site typically comprises one or more restriction enzyme recognition sites (restriction sites). These one or more restrictions sites may be recognized by restriction enzymes which cleave the DNA at these sites. A cloning site which comprises more than one restriction site may also be termed a multiple cloning site (MCS) or a polylinker.

Nucleic acid molecule: A nucleic acid molecule is a molecule comprising, preferably consisting of nucleic acid components. The term nucleic acid molecule preferably refers to DNA or RNA molecules. It is preferably used synonymous with the term "polynucleotide". Preferably, a nucleic acid molecule is a polymer comprising or consisting of nucleotide monomers which are covalently linked to each other by phosphodiester-bonds of a sugar/phosphate-backbone. The term "nucleic acid molecule" also encompasses modified nucleic acid molecules, such as base-modified, sugar-modified or backbone-modified etc. DNA or RNA molecules.

Open reading frame: An open reading frame (ORF) in the context of the invention may typically be a sequence of several nucleotide triplets which may be translated into a peptide or protein. An open reading frame preferably contains a start codon, i.e. a combination of three subsequent nucleotides coding usually for the amino acid methionine (ATG or AUG), at its 5'-end and a subsequent region which usually exhibits a length which is a multiple of 3 nucleotides. An ORF is preferably terminated by a stop-codon (e.g., TAA, TAG, TGA). Typically, this is the only stop-codon of the open reading frame. Thus, an open reading frame in the context of the present invention is preferably a nucleotide sequence, consisting of a number of nucleotides that may be divided by three, which starts with a start codon (e.g. ATG or AUG) and which preferably terminates with a stop codon (e.g., TAA, TGA, or TAG or UAA, UAG, UGA, respectively). The open reading frame may be isolated or it may be incorporated in a longer nucleic acid sequence, for example in a vector or an mRNA. An open reading frame may also be termed 'protein coding region'.

Peptide: A peptide or polypeptide is typically a polymer of amino acid monomers, linked by peptide bonds. It typically contains less than 50 monomer units. Nevertheless, the term peptide is not a disclaimer for molecules having more than 50 monomer units. Long peptides are also called polypeptides, typically having between 50 and 600 monomeric units.

Pharmaceutically effective amount: A pharmaceutically effective amount in the context of the invention is typically understood to be an amount that is sufficient to induce a pharmaceutical effect, such as an immune response, altering a pathological level of an expressed peptide or protein, or substituting a lacking gene product, e.g., in case of a pathological situation.

Protein A protein typically comprises one or more peptides or polypeptides. A protein is typically folded into 3-dimensional form, which may be required for to protein to exert its biological function.

Poly(A) sequence: A poly(A) sequence, also called poly (A) tail or 3'-poly(A) tail, is typically understood to be a sequence of adenine nucleotides, e.g., of up to about 400 adenine nucleotides, e.g. from about 20 to about 400, preferably from about 50 to about 400, more preferably from about 50 to about 300, even more preferably from about 50 to about 250, most preferably from about 60 to about 250 adenine nucleotides. A poly(A) sequence is typically located at the 3'end of an mRNA. In the context of the present invention, a poly(A) sequence may be located within an mRNA or any other nucleic acid molecule, such as, e.g., in a vector, for example, in a vector serving as template for the generation of an RNA, preferably an mRNA, e.g., by transcription of the vector.

Polyadenylation: Polyadenylation is typically understood to be the addition of a poly(A) sequence to a nucleic acid molecule, such as an RNA molecule, e.g. to a premature mRNA. Polyadenylation may be induced by a so called polyadenylation signal. This signal is preferably located within a stretch of nucleotides at the 3'-end of a nucleic acid molecule, such as an RNA molecule, to be polyadenylated. A polyadenylation signal typically comprises a hexamer consisting of adenine and uracil/thymine nucleotides, preferably the hexamer sequence AAUAAA. Other sequences, preferably hexamer sequences, are also conceivable. Polyadenylation typically occurs during processing of a pre-mRNA (also called premature-mRNA). Typically, RNA maturation (from pre-mRNA to mature mRNA) comprises the step of polyadenylation.

Restriction site: A restriction site, also termed 'restriction enzyme recognition site', is a nucleotide sequence recognized by a restriction enzyme. A restriction site is typically a short, preferably palindromic nucleotide sequence, e.g. a sequence comprising 4 to 8 nucleotides. A restriction site is preferably specifically recognized by a restriction enzyme. The restriction enzyme typically cleaves a nucleotide sequence comprising a restriction site at this site. In a double-stranded nucleotide sequence, such as a double-stranded DNA sequence, the restriction enzyme typically cuts both strands of the nucleotide sequence.

RNA, mRNA: RNA is the usual abbreviation for ribo-nucleic-acid. It is a nucleic acid molecule, i.e. a polymer consisting of nucleotides. These nucleotides are usually adenosine-monophosphate, uridine-monophosphate, guanosine-monophosphate and cytidine-monophosphate monomers which are connected to each other along a so-called backbone. The backbone is formed by phosphodi-ester bonds between the sugar, i.e. ribose, of a first and a phosphate moiety of a second, adjacent monomer. The specific succession of the monomers is called the RNA-sequence. Usually RNA may be obtainable by transcription of a DNA-sequence, e.g., inside a cell. In eukaryotic cells, transcription is typically performed inside the nucleus or the mitochondria. In vivo, transcription of DNA usually results in the so-called premature RNA which has to be processed into so-called messenger-RNA, usually abbreviated as mRNA. Processing of the premature RNA, e.g. in eukaryotic organisms, comprises a variety of different posttranscriptional-modifications such as splicing, 5'-capping, polyadenylation, export from the nucleus or the mitochondria and the like. The sum of these processes is also called maturation of RNA. The mature messenger RNA usually provides the nucleotide sequence that may be translated into an amino acid sequence of a particular peptide or protein. Typically, a mature mRNA comprises a 5'-cap, a 5'UTR, an open reading frame, a 3'UTR and a poly(A) sequence. Aside from messenger RNA, several non-coding types of RNA exist which may be involved in regulation of transcription and/or translation.

Sequence of a nucleic acid molecule: The sequence of a nucleic acid molecule is typically understood to be the particular and individual order, i.e. the succession of its nucleotides. The sequence of a protein or peptide is typically understood to be the order, i.e. the succession of its amino acids.

Sequence identity: Two or more sequences are identical if they exhibit the same length and order of nucleotides or amino acids. The percentage of identity typically describes the extent to which two sequences are identical, i.e. it typically describes the percentage of nucleotides that correspond in their sequence position with identical nucleotides of a reference-sequence. For determination of the degree of identity, the sequences to be compared are considered to exhibit the same length, i.e. the length of the longest sequence of the sequences to be compared. This means that a first sequence consisting of 8 nucleotides is 80% identical to a second sequence consisting of 10 nucleotides comprising the first sequence. In other words, in the context of the present invention, identity of sequences preferably relates to the percentage of nucleotides of a sequence which have the same position in two or more sequences having the same length. Gaps are usually regarded as non-identical positions, irrespective of their actual position in an alignment.

Stabilized nucleic acid molecule: A stabilized nucleic acid molecule is a nucleic acid molecule, preferably a DNA or RNA molecule that is modified such, that it is more stable to disintegration or degradation, e.g., by environmental factors or enzymatic digest, such as by an exo- or endonuclease degradation, than the nucleic acid molecule without the modification. Preferably, a stabilized nucleic acid molecule in the context of the present invention is stabilized in a cell, such as a prokaryotic or eukaryotic cell, preferably in a mammalian cell, such as a human cell. The stabilization effect may also be exerted outside of cells, e.g. in a buffer solution etc., for example, in a manufacturing process for a pharmaceutical composition comprising the stabilized nucleic acid molecule.

Transfection: The term 'transfection' refers to the introduction of nucleic acid molecules, such as DNA or RNA (e.g. mRNA) molecules, into cells, preferably into eukaryotic cells. In the context of the present invention, the term 'transfection' encompasses any method known to the skilled person for introducing nucleic acid molecules into cells, preferably into eukaryotic cells, such as into mammalian cells. Such methods encompass, for example, electroporation, lipofection, e.g. based on cationic lipids and/or liposomes, calcium phosphate precipitation, nanoparticle based transfection, virus based transfection, or transfection based on cationic polymers, such as DEAE-dextran or polyethylenimine etc. Preferably, the introduction is non-viral.

Vaccine: A vaccine is typically understood to be a prophylactic or therapeutic material providing at least one antigen, preferably an immunogen. The antigen or immunogen may be derived from any material that is suitable for vaccination. For example, the antigen or immunogen may be derived from a pathogen, such as from bacteria or virus particles etc., or from a tumor or cancerous tissue. The antigen or immunogen stimulates the body's adaptive immune system to provide an adaptive immune response.

Vector: The term 'vector' refers to a nucleic acid molecule, preferably to an artificial nucleic acid molecule. A vector in the context of the present invention is suitable for incorporating or harboring a desired nucleic acid sequence, such as a nucleic acid sequence comprising an open reading frame. Such vectors may be storage vectors, expression vectors, cloning vectors, transfer vectors etc. A storage vector is a vector which allows the convenient storage of a nucleic acid molecule, for example, of an mRNA molecule. Thus, the vector may comprise a sequence corresponding, e.g., to a desired mRNA sequence or a part thereof, such as a sequence corresponding to the open reading frame and the 3'UTR of an mRNA. An expression vector may be used for production of expression products such as RNA, e.g. mRNA, or peptides, polypeptides or proteins. For example, an expression vector may comprise sequences needed for transcription of a sequence stretch of the vector, such as a promoter sequence, e.g. an RNA promoter sequence. A cloning vector is typically a vector that contains a cloning site, which may be used to incorporate nucleic acid sequences into the vector. A cloning vector may be, e.g., a plasmid vector or a bacteriophage vector. A transfer vector may be a vector which is suitable for transferring nucleic acid molecules into cells or organisms, for example, viral vectors. A vector in the context of the present invention may be, e.g., an RNA vector or a DNA vector. Preferably, a vector is a DNA molecule. Preferably, a vector in the sense of the present application comprises a cloning site, a selection marker, such as an antibiotic resistance factor, and a sequence suitable for multiplication of the vector, such as an origin of replication. Preferably, a vector in the context of the present application is a plasmid vector.

Vehicle: A vehicle is typically understood to be a material that is suitable for storing, transporting, and/or administering a compound, such as a pharmaceutically active compound. For example, it may be a physiologically acceptable liquid which is suitable for storing, transporting, and/or administering a pharmaceutically active compound.

3'-untranslated region (3'UTR): A 3'UTR is typically the part of an mRNA which is located between the protein coding region (i.e. the open reading frame) and the poly(A) sequence of the mRNA. A 3'UTR of the mRNA is not translated into an amino acid sequence. The 3'UTR sequence is generally encoded by the gene which is transcribed into the respective mRNA during the gene expression process. The genomic sequence is first transcribed into pre-mature mRNA, which comprises optional introns. The pre-mature mRNA is then further processed into mature mRNA in a maturation process. This maturation process comprises the steps of 5'capping, splicing the pre-mature mRNA to excise optional introns and modifications of the 3'-end, such as polyadenylation of the 3'-end of the pre-mature mRNA and optional endo- or exonuclease cleavages etc. In the context of the present invention, a 3'UTR corresponds to the sequence of a mature mRNA which is located 3' to the stop codon of the protein coding region, preferably immediately 3' to the stop codon of the protein coding region, and which extends to the 5'-side of the poly(A) sequence, preferably to the nucleotide immediately 5' to the poly(A) sequence. The term "corresponds to" means that the 3'UTR sequence may be an RNA sequence, such as in the mRNA sequence used for defining the 3'UTR sequence, or a DNA sequence which corresponds to such RNA sequence. In the context of the present invention, the term "a 3'UTR of a gene", such as "a 3'UTR of an albumin gene", is the sequence which corresponds to the 3'UTR of the mature mRNA derived from this gene, i.e. the mRNA obtained by transcription of the gene and maturation of the pre-mature mRNA. The term "3'UTR of a gene" encompasses the DNA sequence and the RNA sequence of the 3'UTR.

5'-untranslated region (5'UTR): A 5'UTR is typically understood to be a particular section of messenger RNA (mRNA). It is located 5' of the open reading frame of the mRNA. Typically, the 5'UTR starts with the transcriptional start site and ends one nucleotide before the start codon of the open reading frame. The 5'UTR may comprise elements for controlling gene expression, also called regulatory elements. Such regulatory elements may be, for example, ribosomal binding sites or a 5'-Terminal Oligopyrimidine Tract. The 5'UTR may be posttranscriptionally modified, for example by addition of a 5'-cap. In the context of the present invention, a 5'UTR corresponds to the sequence of a mature mRNA which is located between the 5'cap and the start codon. Preferably, the 5'UTR corresponds to the sequence which extends from a nucleotide located 3' to the 5'-cap, preferably from the nucleotide located immediately 3' to the 5'cap, to a nucleotide located 5' to the start codon of the protein coding region, preferably to the nucleotide located immediately 5' to the start codon of the protein coding region. The nucleotide located immediately 3' to the 5'cap of a mature mRNA typically corresponds to the transcriptional start site. The term "corresponds to" means that the 5'UTR sequence may be an RNA sequence, such as in the mRNA sequence used for defining the 5'UTR sequence, or a DNA sequence which corresponds to such RNA sequence. In the context of the present invention, the term "a 5'UTR of a gene", such as "a 5'UTR of a TOP gene", is the sequence which corresponds to the 5'UTR of the mature mRNA derived from this gene, i.e. the mRNA obtained by transcription of the gene and maturation of the pre-mature mRNA. The term "5'UTR of a gene" encompasses the DNA sequence and the RNA sequence of the 5'UTR.

5'Terminal Oligopyrimidine Tract (TOP): The 5'terminal oligopyrimidine tract (TOP) is typically a stretch of pyrimidine nucleotides located at the 5' terminal region of a nucleic acid molecule, such as the 5' terminal region of certain mRNA molecules or the 5' terminal region of a functional entity, e.g. the transcribed region, of certain genes. The sequence starts with a cytidine, which usually corresponds to the transcriptional start site, and is followed by a stretch of usually about 3 to 30 pyrimidine nucleotides. For example, the TOP may comprise 3, 4, 5, 6, 7, 8, 9, 10, 11, 12, 13, 14, 15, 16, 17, 18, 19, 20, 21, 22, 23, 24, 25, 26, 27, 28, 29, 30 or even more nucleotides. The pyrimidine stretch and thus the 5' TOP ends one nucleotide 5' to the first purine nucleotide located downstream of the TOP. Messenger RNA that contains a 5'terminal oligopyrimidine tract is often referred to as 5' TOP mRNA. Accordingly, genes that provide such messenger RNAs are referred to as TOP genes. TOP sequences have, for example, been found in genes and mRNAs encoding peptide elongation factors and ribosomal proteins.

TOP motif: In the context of the present invention, a TOP motif is a nucleic acid sequence which corresponds to a 5'TOP as defined above. Thus, a TOP motif in the context of the present invention is preferably a stretch of pyrimidine nucleotides having a length of 3-30 nucleotides. Preferably, the TOP-motif consists of at least 3 pyrimidine nucleotides, preferably at least 4 pyrimidine nucleotides, preferably at least 5 pyrimidine nucleotides, more preferably at least 6 nucleotides, more preferably at least 7 nucleotides, most preferably at least 8 pyrimidine nucleotides, wherein the stretch of pyrimidine nucleotides preferably starts at its 5'end with a cytosine nucleotide. In TOP genes and TOP mRNAs, the TOP-motif preferably starts at its 5'end with the transcriptional start site and ends one nucleotide 5' to the first purin residue in said gene or mRNA. A TOP motif in the sense of the present invention is preferably located at the 5'end of a sequence which represents a 5'UTR or at the 5'end of a sequence which codes for a 5'UTR. Thus, preferably, a stretch of 3 or more pyrimidine nucleotides is called "TOP motif" in the sense of the present invention if this stretch is located at the 5'end of a respective sequence, such as the artificial nucleic acid molecule according to the present invention, the 5'UTR element of the artificial nucleic acid molecule according to the present invention, or the nucleic acid sequence which is derived from the 5'UTR of a TOP gene as described herein. In other words, a stretch of 3 or more pyrimidine nucleotides which is not located at the 5'-end of a 5'UTR or a 5'UTR element but anywhere within a 5'UTR or a 5'UTR element is preferably not referred to as "TOP motif".

TOP gene: TOP genes are typically characterised by the presence of a 5' terminal oligopyrimidine tract. Furthermore, most TOP genes are characterized by a growth-associated translational regulation. However, also TOP genes with a tissue specific translational regulation are known. As defined above, the 5'UTR of a TOP gene corresponds to the sequence of a 5'UTR of a mature mRNA derived from a TOP gene, which preferably extends from the nucleotide located 3' to the 5'cap to the nucleotide located 5' to the start codon. A 5'UTR of a TOP gene typically does not comprise any start codons, preferably no upstream AUGs (uAUGs) or upstream open reading frames (uORFs). Therein, upstream AUGs and upstream open reading frames are typically understood to be AUGs and open reading frames that occur 5' of the start codon (AUG) of the open reading frame that should be translated. The 5'UTRs of TOP genes are generally rather short. The lengths of 5'UTRs of TOP genes may vary between 20 nucleotides up to 500 nucleotides, and are typically less than about 200 nucleotides, preferably less than about 150 nucleotides, more preferably less than about 100 nucleotides. Exemplary 5'UTRs of TOP genes in the sense of the present invention are the nucleic acid sequences extending from the nucleotide at position 5 to the nucleotide located immediately 5' to the start codon (e.g. the ATG) in the sequences according to SEQ ID NOs. 1-1363, 1435, 1461 and 1462.

In a first aspect, the present invention relates to an artificial nucleic acid molecule comprising:
a. at least one 5'-untranslated region element (5'UTR element) which comprises or consists of a nucleic acid sequence which is derived from the 5'UTR of a TOP gene or which is derived from a variant of the 5'UTR of a TOP gene; and
b. at least one open reading frame (ORF).

Preferably, the artificial nucleic acid molecule further comprises:
c. at least one histone stem-loop.

Such an artificial nucleic acid molecule may be DNA or RNA. In case the artificial nucleic acid molecule is DNA it may be used for providing RNA, preferably an mRNA with a corresponding sequence as is described further below. The inventive artificial nucleic acid molecule is particularly useful in gene therapy and genetic vaccination because it may provide increased and/or prolonged protein production of the protein encoded by the open reading frame.

In this context, the term '5'UTR element' preferably refers to a nucleic acid sequence which represents a 5'UTR of an artificial nucleic acid sequence, such as an artificial mRNA, or which codes for a 5'UTR of an artificial nucleic acid molecule. Thus, preferably, a 5'UTR element may be the 5'UTR of an mRNA, preferably of an artificial mRNA, or it may be the transcription template for a 5'UTR of an mRNA. Thus, a 5'UTR element preferably is a nucleic acid sequence which corresponds to the 5'UTR of an mRNA, preferably to the 5'UTR of an artificial mRNA, such as an mRNA obtained by transcription of a genetically engineered vector construct. Preferably, a 5'UTR element in the sense of the present invention functions as a 5'UTR or codes for a nucleotide sequence that fulfils the function of a 5'UTR. The term '5'UTR element' furthermore refers to a fragment or part of a 5'UTR of an artificial nucleic acid sequence, such as an artificial mRNA, or which codes for a part or fragment of a 5'UTR of an artificial nucleic acid molecule. This means that the 5'UTR element in the sense of the present invention may be comprised in the 5'UTR of an artificial nucleic acid sequence, such as an artificial mRNA, or which codes for a 5'UTR of an artificial nucleic acid molecule.

According to the invention, the 5'UTR element comprises or consists of a nucleic acid sequence that is derived from the 5'UTR of a TOP gene or from a variant of the 5'UTR of a TOP gene.

The term 'a nucleic acid sequence which is derived from the 5'UTR of a TOP gene' preferably refers to a nucleic acid sequence which is based on the 5'UTR sequence of a TOP gene or on a fragment thereof. This term includes sequences corresponding to the entire 5'UTR sequence, i.e. the full length 5'UTR sequence of a TOP gene, and sequences corresponding to a fragment of the 5'UTR sequence of a TOP gene. Preferably, a fragment of a 5'UTR of a TOP gene consists of a continuous stretch of nucleotides corresponding to a continuous stretch of nucleotides in the full-length 5'UTR of a TOP gene, which represents at least 20%, preferably at least 30%, more preferably at least 40%, more preferably at least 50%, even more preferably at least 60%, even more preferably at least 70%, even more preferably at least 80%, and most preferably at least 90% of the full-length 5'UTR of a TOP gene. Such a fragment, in the sense of the present invention, is preferably a functional fragment as described herein. A particularly preferred fragment of a 5'UTR of a TOP gene is a 5'UTR of a TOP gene lacking the 5'TOP motif. The term '5'UTR of a TOP gene' preferably refers to the 5'UTR of a naturally occurring TOP gene.

The terms 'variant of the 5'UTR of a TOP gene' and 'variant thereof' in the context of a 5'UTR of a TOP gene refers to a variant of the 5'UTR of a naturally occurring TOP gene, preferably to a variant of the 5'UTR of a vertebrate TOP gene, preferably to a variant of the 3'UTR of a mammalian TOP gene, more preferably to a variant of the 3'UTR of a human TOP gene. Such variant may be a modified 5'UTR of a TOP gene. For example, a variant 5'UTR may exhibit one or more nucleotide deletions, insertions, additions and/or substitutions compared to the naturally occurring 5'UTR from which the variant is derived. Preferably, a variant of a 5'UTR of a TOP gene is at least 40%, preferably at least 50%, more preferably at least 60%, more preferably at least 70%, even more preferably at least 80%, even more preferably at least 90%, most preferably at least 95% identical to the naturally occurring 5'UTR the variant is derived from. Preferably, the variant is a functional variant as described herein.

The term "a nucleic acid sequence that is derived from a variant of the 5'UTR of a TOP gene" preferably refers to a nucleic acid sequence which is based on a variant of a 5'UTR sequence of a TOP gene or on a fragment thereof. This term includes sequences corresponding to the entire variant 5'UTR sequence, i.e. the full length variant 5'UTR sequence of a TOP gene, and sequences corresponding to a fragment of the variant 5'UTR sequence of a TOP gene. Preferably, a fragment of a variant of the 5'UTR of a TOP gene consists of a continuous stretch of nucleotides corresponding to a continuous stretch of nucleotides in the full-length variant 5'UTR of a TOP gene, which represents at least 20%, preferably at least 30%, more preferably at least 40%, more preferably at least 50%, even more preferably at least 60%, even more preferably at least 70%, even more preferably at least 80%, and most preferably at least 90% of the full-length variant 5'UTR of a TOP gene. Such a fragment of a variant, in the sense of the present invention, is preferably a functional fragment as described herein.

Thus, the 5'UTR element of the artificial nucleic acid molecule may comprise or consist of a fragment of the 5'UTR of a TOP gene or of a fragment of a variant of the 5'UTR of a TOP gene or may comprise or consist of the entire 5'UTR of a TOP gene or may comprise or consist of a variant of the 5'UTR of a TOP gene.

The 5'UTR element is preferably suitable for increasing protein production from the artificial nucleic acid molecule.

Preferably, the at least one 5'UTR element is functionally linked to the ORF. This means preferably that the 5'UTR element is associated with the ORF such that it may exert a function, such as a protein production increasing function for the protein encoded by the ORF or a stabilizing function on the artificial nucleic acid molecule. Preferably, the 5'UTR element and the ORF are associated in 5'→3' direction. Thus, preferably, the artificial nucleic acid molecule comprises the structure 5'-5'UTR element-(optional)linker-ORF-3', wherein the linker may be present or absent. For example, the linker may be one or more nucleotides, such as a stretch of 1-50 or 1-20 nucleotides, e.g., comprising or consisting of one or more restriction enzyme recognition sites (restriction sites).

Preferably, the 5'UTR element and the at least one open reading frame are heterologous. The term 'heterologous' in this context means that the open reading frame and the 5'UTR element are not occurring naturally (in nature) in this combination. Preferably, the 5'UTR element is derived from a different gene than the open reading frame. For example, the ORF may be derived from a different gene than the 5'UTR element, e.g. encoding a different protein or the same protein but of a different species etc. For example, the ORF does not encode the protein which is encoded by the gene from which the 5'UTR element is derived.

In a preferred embodiment, the 5'UTR element, preferably the artificial nucleic acid molecule, does not comprise a complete TOP-motif or 5'TOP sequence. Thus, preferably, the 5'UTR element, preferably the artificial nucleic acid molecule, does not comprise the complete TOP-motif of the TOP gene from which the nucleic acid sequence of the 5'UTR element is derived. For example, the 5'UTR element or the artificial nucleic acid molecule according to the present invention may comprise 1, 2, 3, 4, 5, 6, 7, 8, 9, 10 or more pyrimidine residues of the TOP-motif or 5'TOP, preferably 1, 2, 3, 4, 5, 6, 7, 8, 9, 10 or more pyrimidine residues of the TOP-motif located at the 3'side of the TOP-motif or 5'TOP. For example, the 5'UTR element may comprise or consist of a nucleic acid sequence which starts at its 5'end with a pyrimidine residue that corresponds to residue 2, 3, 4, 5, 6, 7, 8, 9, 10 etc. of the TOP-motif or 5'TOP of the TOP gene from which the nucleic acid sequence of the 5'UTR element is derived.

It is particularly preferred that the 5'UTR element, preferably the artificial nucleic acid molecule according to the present invention, does not comprise a TOP-motif or 5'TOP. For example, the nucleic acid sequence of the 5'UTR element which is derived from a 5'UTR of a TOP gene starts at its 5'-end with a nucleotide located at position 1, 2, 3, 4, 5, 6, 7, 8, 9 or 10 downstream of the 5'terminal oligopyrimidine tract (TOP) of the 5'UTR of a TOP gene. Position 1 downstream of the 5'terminal oligopyrimidine tract (TOP) is the first purine based nucleotide 3' of the TOP-motif or the 5'TOP. Accordingly, position 1 downstream of the 5'terminal oligopyrimidine tract is the first nucleotide following the 3'-end of the 5'terminal oligopyrimidine tract in 5'-3'-direction. Likewise, position 2 downstream of the 5'TOP is the second nucleotide following the end of the 5'terminal oligopyrimidine tract, position 3 the third nucleotide and so on.

Therefore, the 5'UTR element preferably starts 5, 10, 15, 20, 25, 30, 40 or 50 nucleotides downstream of the transcriptional start site of the 5'UTR of a TOP gene.

In some embodiments, the nucleic acid sequence of the 5'UTR element which is derived from a 5'UTR of a TOP gene terminates at its 3'-end with a nucleotide located at position 1, 2, 3, 4, 5, 6, 7, 8, 9 or 10 upstream of the start codon (e.g. A(U/T)G) of the gene or mRNA it is derived from. Thus, the 5'UTR element does not comprise any part of the protein coding region. Thus, preferably, the only protein coding part of the inventive artificial nucleic acid molecule is provided by the open reading frame. However, the open reading frame is preferably derived—as said above—from a gene that is different to the gene the 5'UTR element is derived from.

It is particularly preferred that the 5'UTR element does not comprise a start codon, such as the nucleotide sequence A(U/T)G. Thus, preferably, the artificial nucleic acid molecule will not comprise any upstream AUGs (or upstream ATGs in case it is a DNA molecule). In other words, in some embodiments, it may be preferred that the AUG or ATG, respectively, of the open reading frame is the only start codon of the artificial nucleic acid molecule.

Additionally, it is preferred that the 5'UTR element does not comprise an open reading frame. Thus, preferably, the artificial nucleic acid molecule will not comprise any upstream open reading frames.

The nucleic acid sequence which is derived from the 5'UTR of a TOP gene is derived from a eukaryotic TOP gene, preferably a plant or animal TOP gene, more preferably a chordate TOP gene, even more preferably a vertebrate TOP gene, most preferably a mammalian TOP gene, such as a human or mouse TOP gene.

Preferably, the artificial nucleic acid molecule according to the present invention comprises a 5'UTR element which comprises or consists of a nucleic acid sequence which is derived from the 5'UTR of a TOP gene or which is derived from a variant of the 5'UTR of a TOP gene, wherein the TOP gene is a plant or animal TOP gene, more preferably a chordate TOP gene, even more preferably a vertebrate TOP gene, most preferably a mammalian TOP gene, such as a human or mouse TOP gene and which optionally does not comprise the nucleotide sequence A(U/T)G and optionally does not comprise an open reading frame; at least one open reading frame (ORF); and optionally at least one histone-stem loop; wherein optionally the 5'UTR element does not comprise a TOP motif and wherein optionally the 5'UTR element starts at its 5'-end with a nucleotide located at position 1, 2, 3, 4, 5, 6, 7, 8, 9 or 10 downstream of the 5'terminal oligopyrimidine tract (TOP) of the 5'UTR of a TOP gene and wherein further optionally the 5'UTR element which is derived from a 5'UTR of a TOP gene terminates at its 3'-end with a nucleotide located at position 1, 2, 3, 4, 5, 6, 7, 8, 9 or 10 upstream of the start codon (A(U/T)G) of the gene or mRNA it is derived from.

For example, the 5'UTR element comprises or consists of a nucleic acid sequence which is derived from a nucleic acid sequence selected from the group consisting of SEQ ID NOs. 1-1363, SEQ ID NO. 1435, SEQ ID NO. 1461 or SEQ ID NO. 1462, from the homologs of SEQ ID NOs. 1-1363, SEQ ID NO. 1435, SEQ ID NO. 1461 or SEQ ID NO. 1462, from a variant thereof, or a corresponding RNA sequence. The term "homologs of SEQ ID NOs. 1-1363, SEQ ID NO. 1435, SEQ ID NO. 1461 or SEQ ID NO. 1462," refers to sequences of other species than *Homo sapiens* (human) or *Mus musculus* (mouse), which are homologous to the sequences according to SEQ ID NOs. 1-1363, SEQ ID NO. 1435, SEQ ID NO. 1461 or SEQ ID NO. 1462. For example, SEQ ID NO. 1 relates to a sequence comprising the 5'UTR of *Homo sapiens* alpha 2 macroglobulin (A2M). A homolog of SEQ ID NO. 1 in the context of the present invention is any such sequence derived from an alpha 2 macroglobulin (A2M) gene or mRNA of another species than *Homo sapiens* (human), such as any vertebrate, preferably any mammalian alpha 2 macroglobulin (A2M) gene other than the human alpha 2 macroglobulin (A2M) gene, such as a mouse, rat, rabbit, monkey etc. alpha 2 macroglobulin (A2M) gene.

In a preferred embodiment, the 5'UTR element comprises or consists of a nucleic acid sequence which is derived from a nucleic acid sequence extending from nucleotide position 5 (i.e. the nucleotide that is located at position 5 in the sequence) to the nucleotide position immediately 5' to the start codon (located at the 3' end of the sequences), e.g. the nucleotide position immediately 5' to the ATG sequence, of a nucleic acid sequence selected from SEQ ID NOs. 1-1363, SEQ ID NO. 1435, SEQ ID NO. 1461 or SEQ ID NO. 1462, from the homologs of SEQ ID NOs. 1-1363, SEQ ID NO. 1435, SEQ ID NO. 1461 or SEQ ID NO. 1462, from a variant thereof, or a corresponding RNA sequence. It is particularly preferred that the 5' UTR element is derived from a nucleic acid sequence extending from the nucleotide position immediately 3' to the 5'-TOP to the nucleotide position immediately 5' to the start codon (located at the 3' end of the sequences), e.g. the nucleotide position immediately 5' to the ATG sequence, of a nucleic acid sequence selected from SEQ ID NOs. 1-1363, SEQ ID NO. 1435, SEQ ID NO. 1461 or SEQ ID NO. 1462, from the homologs of SEQ ID NOs. 1-1363, SEQ ID NO. 1435, SEQ ID NO. 1461 or SEQ ID NO. 1462, from a variant thereof, or a corresponding RNA sequence.

In a preferred embodiment, the 5'UTR element comprises or consists of a nucleic acid sequence which has an identity of at least about 40%, preferably of at least about 50%, preferably of at least about 60%, preferably of at least about 70%, more preferably of at least about 80%, more preferably of at least about 90%, even more preferably of at least about 95%, even more preferably of at least about 99% to a nucleic acid sequence extending from nucleotide position 5 to the nucleotide position immediately 5' to the start codon (located at the 3' end of the sequences), e.g. the nucleotide position immediately 5' to the ATG sequence of a nucleic acid sequence, selected from SEQ ID NOs. 1-1363, SEQ ID NO. 1435, SEQ ID NO. 1461 or SEQ ID NO. 1462, or a corresponding RNA sequence, or wherein the at least one 5'UTR element comprises or consists of a fragment of a nucleic acid sequence which has an identity of at least about 40%, preferably of at least about 50%, preferably of at least about 60%, preferably of at least about 70%, more preferably of at least about 80%, more preferably of at least about 90%, even more preferably of at least about 95%, even more preferably of at least about 99% to a nucleic acid sequence extending from nucleotide position 5 to the nucleotide position immediately 5' to the start codon (located at the 3' end of the sequences), e.g. the nucleotide position immediately 5' to the ATG sequence of a nucleic acid sequence, selected from SEQ ID NOs. 1-1363, SEQ ID NO. 1435, SEQ ID NO. 1461 or SEQ ID NO. 1462, or a corresponding RNA sequence, wherein, preferably, the fragment is as described above, i.e. being a continuous stretch of nucleotides representing at least 20% etc. of the full-length 5'UTR the fragment is derived from.

Preferably, the 5'UTR element comprises or consists of a nucleic acid sequence which has an identity of at least about 40%, preferably of at least about 50%, preferably of at least about 60%, preferably of at least about 70%, more preferably of at least about 80%, more preferably of at least about 90%, even more preferably of at least about 95%, even more preferably of at least about 99% to a nucleic acid sequence extending from the nucleotide position immediately 3' to the 5'TOP to the nucleotide position immediately 5' to the start codon (located at the 3' end of the sequences), e.g. the nucleotide position immediately 5' to the ATG sequence, of a nucleic acid sequence selected from SEQ ID NOs. 1-1363, SEQ ID NO. 1435, SEQ ID NO. 1461 or SEQ ID NO. 1462, or a corresponding RNA sequence, or wherein the at least one 5'UTR element comprises or consists of a fragment of a nucleic acid sequence which has an identity of at least about 40%, preferably of at least about 50%, preferably of at least about 60%, preferably of at least about 70%, more preferably of at least about 80%, more preferably of at least about 90%, even more preferably of at least about 95%, even more preferably of at least about 99% to a nucleic acid sequence extending from the nucleotide position immediately 3' to the 5'TOP to the nucleotide position immediately 5' to the start codon (located at the 3' end of the sequences), e.g. the nucleotide position immediately 5' to the ATG sequence, of a nucleic acid sequence selected from SEQ ID NOs. 1-1363, SEQ ID NO. 1435, SEQ ID NO. 1461 or SEQ ID NO. 1462, or a corresponding RNA sequence, wherein, preferably, the fragment is as described above, i.e. being a continuous stretch of nucleotides representing at least 20% etc. of the full-length 5'UTR the fragment is derived from.

Preferably, the above defined fragments and variants (e.g. exhibiting at least 40% identity) of the sequences according to SEQ ID NOs. 1-1363, SEQ ID NO. 1435, SEQ ID NO. 1461 or SEQ ID NO. 1462, are functional fragments and variants as described herein.

Furthermore, the artificial nucleic acid molecule according to the present invention may comprise more than one 5'UTR elements as described above. For example, the artificial nucleic acid molecule according to the present invention may comprise one, two, three, four or more 5'UTR elements, wherein the individual 5'UTR elements may be the same or they may be different. For example, the artificial nucleic acid molecule according to the present invention may comprise two essentially identical 5'UTR elements as described above, e.g. two 5'UTR elements comprising or consisting of a nucleic acid sequence which is derived from a nucleic acid sequence selected from the group consisting of SEQ ID NOs. 1-1363, SEQ ID NO. 1435, SEQ ID NO. 1461 or SEQ ID NO. 1462, from the homologs of SEQ ID NOs. 1-1363, SEQ ID NO. 1435, SEQ ID NO. 1461 or SEQ ID NO. 1462, from a variant thereof, or a corresponding RNA sequence or from functional variants thereof, functional fragments thereof, or functional variant fragments thereof as described above.

In a particularly preferred embodiment, the 5'UTR element comprises or consists of a nucleic acid sequence which is derived from a 5'UTR of a TOP gene encoding a ribosomal protein or from a variant of a 5'UTR of a TOP gene encoding a ribosomal protein. Particularly preferred 5'UTR elements comprise or consist of a nucleic acid sequence which are derived from a 5' UTR of a TOP gene coding for a ribosomal protein selected from RPSA, RPS2, RPS3, RPS3A, RPS4, RPS5, RPS6, RPS7, RPS8, RPS9, RPS10, RPS11, RPS12, RPS13, RPS14, RPS15, RPS15A, RPS16, RPS17, RPS18, RPS19, RPS20, RPS21, RPS23, RPS24, RPS25, RPS26, RPS27, RPS27A, RPS28, RPS29, RPS30, RPL3, RPL4, RPL5, RPL6, RPL7, RPL7A, RPL8, RPL9, RPL10, RPL10A, RPL11, RPL12, RPL13, RPL13A, RPL14, RPL15, RPL17, RPL18, RPL18A, RPL19, RPL21, RPL22, RPL23, RPL23A, RPL24, RPL26, RPL27, RPL27A, RPL28, RPL29, RPL30, RPL31, RPL32, RPL34, RPL35, RPL35A, RPL36, RPL36A, RPL37, RPL37A, RPL38, RPL39, RPL40, RPL41, RPLP0, RPLP1, RPLP2, RPLP3, UBA52. Particularly preferred are nucleic acid sequences which are derived from a 5' UTR of TOP genes vertebrate coding for ribosomal proteins, such as mammalian ribosomal proteins e.g. human or mouse ribosomal proteins.

For example, the 5'UTR element comprises or consists of a nucleic acid sequence which is derived from a 5'UTR of a nucleic acid sequence according to any of SEQ ID NOs: 170, 232, 244, 259, 1284, 1285, 1286, 1287, 1288, 1289, 1290, 1291, 1292, 1293, 1294, 1295, 1296, 1297, 1298, 1299, 1300, 1301, 1302, 1303, 1304, 1305, 1306, 1307, 1308, 1309, 1310, 1311, 1312, 1313, 1314, 1315, 1316, 1317, 1318, 1319, 1320, 1321, 1322, 1323, 1324, 1325, 1326, 1327, 1328, 1329, 1330, 1331, 1332, 1333, 1334, 1335, 1336, 1337, 1338, 1339, 1340, 1341, 1342, 1343, 1344, 1346, 1347, 1348, 1349, 1350, 1351, 1352, 1353, 1354, 1355, 1356, 1357, 1358, 1359, or 1360; a corresponding RNA sequence, a homolog thereof, or a variant thereof as described herein, preferably lacking the 5'TOP motif. As described above, the sequence extending from position 5 to the nucleotide immediately 5' to the ATG (which is located at the 3'end of the sequences) corresponds to the 5'UTR of said sequences.

Preferably, the 5'UTR element comprises or consists of a nucleic acid sequence which has an identity of at least about 40%, preferably of at least about 50%, preferably of at least about 60%, preferably of at least about 70%, more preferably of at least about 80%, more preferably of at least about 90%, even more preferably of at least about 95%, even more preferably of at least about 99% to the 5'UTR of a nucleic acid sequence according to any of SEQ ID NOs: 170, 232, 244, 259, 1284, 1285, 1286, 1287, 1288, 1289, 1290, 1291, 1292, 1293, 1294, 1295, 1296, 1297, 1298, 1299, 1300, 1301, 1302, 1303, 1304, 1305, 1306, 1307, 1308, 1309, 1310, 1311, 1312, 1313, 1314, 1315, 1316, 1317, 1318, 1319, 1320, 1321, 1322, 1323, 1324, 1325, 1326, 1327, 1328, 1329, 1330, 1331, 1332, 1333, 1334, 1335, 1336, 1337, 1338, 1339, 1340, 1341, 1342, 1343, 1344, 1346, 1347, 1348, 1349, 1350, 1351, 1352, 1353, 1354, 1355, 1356, 1357, 1358, 1359, or 1360; or a corresponding RNA sequence, preferably lacking the 5'TOP motif, or wherein the at least one 5'UTR element comprises or consists of a fragment of a nucleic acid sequence which has an identity of at least about 40%, preferably of at least about 50%, preferably of at least about 60%, preferably of at least about 70%, more preferably of at least about 80%, more preferably of at least about 90%, even more preferably of at least about 95%, even more preferably of at least about 99% to the 5'UTR of a nucleic acid sequence according to SEQ ID NOs: 170, 232, 244, 259, 1284, 1285, 1286, 1287, 1288, 1289, 1290, 1291, 1292, 1293, 1294, 1295, 1296, 1297, 1298, 1299, 1300, 1301, 1302, 1303, 1304, 1305, 1306, 1307, 1308, 1309, 1310, 1311, 1312, 1313, 1314, 1315, 1316, 1317, 1318, 1319, 1320, 1321, 1322, 1323, 1324, 1325, 1326, 1327, 1328, 1329, 1330, 1331, 1332, 1333, 1334, 1335, 1336, 1337, 1338, 1339, 1340, 1341, 1342, 1343, 1344, 1346, 1347, 1348, 1349, 1350, 1351, 1352, 1353, 1354, 1355, 1356, 1357, 1358, 1359, or 1360; or a corresponding RNA sequence, wherein, preferably, the fragment is as described above, i.e. being a continuous stretch of nucleotides representing at least 20% etc. of the full-length 5'UTR, preferably lacking the 5'TOP motif. Preferably, the fragment exhibits a length of at least about 20 nucleotides or more, preferably of at least about 30 nucleotides or more, more preferably of at least about 40 nucleotides or more. Preferably, the fragment is a functional fragment as described herein.

Preferably, the 5'UTR element comprises or consists of a nucleic acid sequence which is derived from a 5'UTR of a TOP gene encoding a ribosomal Large protein (RPL) or from a variant of a 5'UTR of a TOP gene encoding a ribosomal Large protein (RPL). For example, the 5'UTR element comprises or consists of a nucleic acid sequence which is derived from a 5'UTR of a nucleic acid sequence according to any of SEQ ID NOs: 67, 259, 1284-1318, 1344, 1346, 1348-1354, 1357, 1461 and 1462, a corresponding RNA sequence, a homolog thereof, or a variant thereof as described herein, preferably lacking the 5'TOP motif.

Preferably, the 5'UTR element comprises or consists of a nucleic acid sequence which has an identity of at least about 40%, preferably of at least about 50%, preferably of at least about 60%, preferably of at least about 70%, more preferably of at least about 80%, more preferably of at least about 90%, even more preferably of at least about 95%, even more preferably of at least about 99% to the 5'UTR of a nucleic acid sequence according to any of SEQ ID NOs. 67, 259, 1284-1318, 1344, 1346, 1348-1354, 1357, and 1358 or a corresponding RNA sequence, preferably lacking the 5'TOP motif, or wherein the at least one 5'UTR element comprises or consists of a fragment of a nucleic acid sequence which has an identity of at least about 40%, preferably of at least about 50%, preferably of at least about 60%, preferably of at least about 70%, more preferably of at least about 80%, more preferably of at least about 90%, even more preferably of at least about 95%, even more preferably of at least about 99% to the 5'UTR of a nucleic acid sequence according to SEQ ID NOs: 67, 259, 1284-1318, 1344, 1346, 1348-1354, 1357, 1461 and 1462 or a corresponding RNA sequence, wherein, preferably, the fragment is as described above, i.e. being a continuous stretch of nucleotides representing at least 20% etc. of the full-length 5'UTR, preferably lacking the 5'TOP motif. Preferably, the fragment exhibits a length of at least about 20 nucleotides or more, preferably of at least about 30 nucleotides or more, more preferably of at least about 40 nucleotides or more. Preferably, the fragment is a functional fragment as described herein.

In a particularly preferred embodiment, the 5'UTR element comprises or consists of a nucleic acid sequence which is derived from the 5'UTR of a ribosomal protein Large 32 gene (RPL32), a ribosomal protein Large 35 gene (RPL35), a ribosomal protein Large 21 gene (RPL21), an ATP synthase, H+ transporting, mitochondrial F1 complex, alpha subunit 1, cardiac muscle (ATP5A1) gene, an hydroxysteroid (17-beta) dehydrogenase 4 gene (HSD17B4), an androgeninduced 1 gene (AIG1), cytochrome c oxidase subunit VIc gene (COX6C), or a N-acylsphingosine amidohydrolase (acid ceramidase) 1 gene (ASAH1) or from a variant thereof, preferably from a vertebrate ribosomal protein Large 32 gene (RPL32), a vertebrate ribosomal protein Large 35 gene (RPL35), a vertebrate ribosomal protein Large 21 gene (RPL21), a vertebrate ATP synthase, H+ transporting, mitochondrial F1 complex, alpha subunit 1, cardiac muscle (ATP5A1) gene, a vertebrate hydroxysteroid (17-beta) dehydrogenase 4 gene (HSD17B4), a vertebrate androgen-induced 1 gene (AIG1), a vertebrate cytochrome c oxidase subunit VIc gene (COX6C), or a vertebrate N-acylsphingosine amidohydrolase (acid ceramidase) 1 gene (ASAH1) or from a variant thereof, more preferably from a mammalian ribosomal protein Large 32 gene (RPL32), a ribosomal protein Large 35 gene (RPL35), a ribosomal protein Large 21 gene (RPL21), a mammalian ATP synthase, H+ transporting, mitochondrial F1 complex, alpha subunit 1, cardiac muscle (ATP5A1) gene, a mammalian hydroxysteroid (17-beta) dehydrogenase 4 gene (HSD17B4), a mammalian androgen-induced 1 gene (AIG1), a mammalian cytochrome c oxidase subunit VIc gene (COX6C), or a mammalian N-acylsphingosine amidohydrolase (acid ceramidase) 1 gene (ASAH1) or from a variant thereof, most preferably from a human ribosomal protein Large 32 gene (RPL32), a human ribosomal protein Large 35 gene (RPL35), a human ribosomal protein Large 21 gene (RPL21), a human ATP synthase, H+ transporting, mitochondrial F1 complex, alpha subunit 1, cardiac muscle (ATP5A1) gene, a human hydroxysteroid (17-beta) dehydrogenase 4 gene (HSD17B4), a human androgen-induced 1 gene (AIG1), a human cytochrome c oxidase subunit VIc gene (COX6C), or a human N-acylsphingosine amidohydrolase (acid ceramidase) 1 gene (ASAH1) or from a variant thereof, wherein preferably the 5'UTR element does not comprise the 5'TOP of said gene.

Accordingly, in a particularly preferred embodiment, the 5'UTR element comprises or consists of a nucleic acid sequence which has an identity of at least about 40%, preferably of at least about 50%, preferably of at least about 60%, preferably of at least about 70%, more preferably of at least about 80%, more preferably of at least about 90%, even more preferably of at least about 95%, even more preferably of at least about 99% to the nucleic acid sequence according to SEQ ID No. 1368, or SEQ ID NOs 1452-1460 or a corresponding RNA sequence, or wherein the at least one 5'UTR element comprises or consists of a fragment of a nucleic acid sequence which has an identity of at least about 40%, preferably of at least about 50%, preferably of at least about 60%, preferably of at least about 70%, more preferably of at least about 80%, more preferably of at least about 90%, even more preferably of at least about 95%, even more preferably of at least about 99% to the nucleic acid sequence according to SEQ ID No. 1368, or SEQ ID NOs 1452-1460 wherein, preferably, the fragment is as described above, i.e. being a continuous stretch of nucleotides representing at least 20% etc. of the full-length 5'UTR. Preferably, the fragment exhibits a length of at least about 20 nucleotides or more, preferably of at least about 30 nucleotides or more, more preferably of at least about 40 nucleotides or more. Preferably, the fragment is a functional fragment as described herein.

Preferably, the at least one 5'UTR element exhibits a length of at least about 20 nucleotides or more, preferably of at least about 30 nucleotides or more, more preferably of at least about 40 nucleotides or more. However, it may be preferred if the 5'UTR element of the artificial nucleic acid molecule is rather short. Accordingly, it may have a length of less than about 200, preferably less than 150, more preferably less than 100 nucleotides. For example, the 5'UTR may have a length of less than about 25, 30, 35, 40, 45, 50, 55, 60, 65, 70, 80, 85, 90, 95, 100, 105, 110, 115, 120, 125, 130, 135, 140, 145, 150, 155, 160, 165, 170, 175, 180, 185, 190, 195, 200 nucleotides Preferably, the 5'UTR element may have a length of about 20-25, 26-30, 31-35, 36-40, 41-45, 46-50, 51-55, 56-60, 61-65, 66-70, 71-80, 81-85, 86-90, 91-95, 96-100, 101-105, 106-110, 111-115, 116-120, 121-125, 126-130, 131-135, 136-140, 141-145, 146-150, 151-155, 156-160, 161-165, 166-170, 171-175, 176-180, 181-185, 186-190, 191-195, 196-200 or more nucleotides. For example, the 5'UTR element may have a length of about 20, 26, 31, 36, 41, 46, 51, 56, 61, 66, 71, 81, 86, 91, 96, 101, 106, 111, 116, 121, 126, 131, 136, 141, 146, 151, 156, 161, 166, 171, 176, 181, 186, 191 or 196 nucleotides. Preferably, the 5'UTR element may have a length from about 20, 30, 40 or more to less than about 200 nucleotides, more preferably from about 20, 30, 40 or more to less than about 150 nucleotides, most preferably from about 20, 30, 40 or more to less than about 100 nucleotides.

Preferred 5'UTR elements are derived from a 5' UTR of a TOP gene selected from RPSA, RPS2, RPS3, RPS3A, RPS4, RPS5, RPS6, RPS7, RPS8, RPS9, RPS10, RPS11, RPS12, RPS13, RPS14, RPS15, RPS15A, RPS16, RPS17, RPS18, RPS19, RPS20, RPS21, RPS23, RPS24, RPS25, RPS26, RPS27, RPS27A, RPS28, RPS29, RPS30, RPL3, RPL4, RPL5, RPL6, RPL7, RPL7A, RPL8, RPL9, RPL10, RPL10A, RPL11, RPL12, RPL13, RPL13A, RPL14, RPL15, RPL17, RPL18, RPL18A, RPL19, RPL21, RPL22, RPL23, RPL23A, RPL24, RPL26, RPL27, RPL27A, RPL28, RPL29, RPL30, RPL31, RPL32, RPL34, RPL35, RPL35A, RPL36, RPL36A, RPL37, RPL37A, RPL38, RPL39, RPL40, RPL41, RPLP0, RPLP1, RPLP2, RPLP3, RPLP0, RPLP1, RPLP2, EEF1A1, EEF1B2, EEF1D, EEF1G, EEF2, EIF3E, EIF3F, EIF3H, EIF2S3, EIF3C, EIF3K, EIF3EIP, EIF4A2, PABPC1, HNRNPA1, TPT1, TUBB1, UBA52, NPM1, ATP5G2, GNB2L1, NME2, UQCRB or from a variant thereof.

In some embodiments, the artificial nucleic acid molecule comprises a 5'UTR element which comprises or consists of a nucleic acid sequence which is derived from the 5'UTR of a vertebrate TOP gene, such as a mammalian, e.g. a human TOP gene, selected from RPSA, RPS2, RPS3, RPS3A, RPS4, RPS5, RPS6, RPS7, RPS8, RPS9, RPS10, RPS11, RPS12, RPS13, RPS14, RPS15, RPS15A, RPS16, RPS17, RPS18, RPS19, RPS20, RPS21, RPS23, RPS24, RPS25, RPS26, RPS27, RPS27A, RPS28, RPS29, RPS30, RPL3, RPL4, RPL5, RPL6, RPL7, RPL7A, RPL8, RPL9, RPL10, RPL10A, RPL11, RPL12, RPL13, RPL13A, RPL14, RPL15, RPL17, RPL18, RPL18A, RPL19, RPL21, RPL22, RPL23, RPL23A, RPL24, RPL26, RPL27, RPL27A, RPL28, RPL29, RPL30, RPL31, RPL32, RPL34, RPL35, RPL35A, RPL36, RPL36A, RPL37, RPL37A, RPL38, RPL39, RPL40, RPL41, RPLP0, RPLP1, RPLP2, RPLP3, RPLP0, RPLP1, RPLP2, EEF1A1, EEF1B2, EEF1D, EEF1G, EEF2, EIF3E, EIF3F, EIF3H, EIF2S3, EIF3C, EIF3K, EIF3EIP, EIF4A2, PABPC1, HNRNPA1, TPT1, TUBB1, UBA52, NPM1, ATP5G2, GNB2L1, NME2, UQCRB or from a variant thereof, wherein preferably the 5'UTR element does not comprise a TOP motif or the 5'TOP of said genes, and wherein optionally the 5'UTR element starts at its 5'-end with a nucleotide located at position 1, 2, 3, 4, 5, 6, 7, 8, 9 or 10 downstream of the 5'terminal oligopyrimidine tract (TOP) and wherein further optionally the 5'UTR element which is derived from a 5'UTR of a TOP gene terminates at its 3'-end with a nucleotide located at position 1, 2, 3, 4, 5, 6, 7, 8, 9 or 10 upstream of the start codon (A(U/T)G) of the gene it is derived from.

In a particularly preferred embodiment, the artificial nucleic acid molecule further comprises a histone stem-loop.

Accordingly, it is particularly preferred that the artificial nucleic acid molecule according to the present invention comprises:

a. at least one 5'-untranslated region element (5'UTR element) which comprises or consists of a nucleic acid sequence which is derived from the 5'UTR of a TOP gene or which is derived from a variant of the 5'UTR of a TOP gene as described above;
b. at least one open reading frame (ORF); and
c. at least one histone stem-loop.

The combination of a 5'UTR element as described above with a histone stem-loop may have a particularly advantageous effect in providing prolonged and possibly also enhanced translation of an RNA molecule.

In the context of the present invention, such a histone stem-loop is typically derived from a histone gene and comprises an intramolecular base pairing of two neighbored entirely or partially reverse complementary sequences, thereby forming a stem-loop. A stem-loop can occur in single-stranded DNA or, more commonly, in RNA. The structure is also known as a hairpin or hairpin loop and usually consists of a stem and a (terminal) loop within a consecutive sequence, wherein the stem is formed by two neighbored entirely or partially reverse complementary sequences separated by a short sequence as sort of spacer, which builds the loop of the stem-loop structure. The two neighbored entirely or partially reverse complementary sequences may be defined as e.g. stem-loop elements stem1 and stem2. The stem loop is formed when these two neighbored entirely or partially reverse complementary sequences, e.g. stem-loop elements stem1 and stem2, form base-pairs with each other, leading to a double stranded nucleic acid sequence comprising an unpaired loop at its terminal ending formed by the short sequence located between stem-loop elements stem1 and stem2 on the consecutive sequence. The unpaired loop thereby typically represents a region of the nucleic acid which is not capable of base pairing with either of these stem-loop elements. The resulting lollipop-shaped structure is a key building block of many RNA secondary structures. The formation of a stem-loop structure is thus dependent on the stability of the resulting stem and loop regions, wherein the first prerequisite is typically the presence of a sequence that can fold back on itself to form a paired double strand. The stability of paired stem-loop elements is determined by the length, the number of mismatches or bulges it contains (a small number of mismatches is typically tolerable, especially in a long double strand), and the base composition of the paired region. In the context of the present invention, optimal loop length is 3-10 bases, more preferably 3 to 8, 3 to 7, 3 to 6 or even more preferably 4 to 5 bases, and most preferably 4 bases.

Preferably, the at least one histone stem-loop is functionally associated to the ORF. This means that the at least one histone stem-loop is preferably positioned within the artificial nucleic acid molecule such that it is able to exert its function, for example, its function of increasing protein production from the ORF or stabilizing the artificial nucleic acid molecule.

Preferably, the histone stem-loop is located 3' to the ORF. For example, the histone stem-loop may be connected to the 3'-end of the ORF directly or via a linker, for example via a stretch of nucleotides, such as 2, 4, 6, 8, 10 etc. nucleotides, e.g. comprising one or more restriction sites, or the histone stem-loop may be located within or between or downstream of other structures located 3' to the ORF, such as within a 3'UTR element, or between a poly(A) sequence and a poly(C) sequence, or down-stream of a poly(A) and/or a poly(C) sequence, or the histone stem-loop may be located at the 3'-end of the artificial nucleic acid molecule. The term "located at the 3'-end" also includes embodiments, wherein the histone stem-loop is followed in 3'-direction by few nucleotides which remain, e.g., after a restriction enzyme cleavage.

Preferably, the 5'UTR element and the histone stem-loop are chosen and positioned such that they exert at least an additive, preferably a synergistic function on protein production from the ORF of the artificial nucleic acid molecule. Preferably, protein production from the ORF is increased at least in an additive, preferably in a synergistic way by the 5'UTR element and the histone stem-loop. Thus, the protein amount of the protein encoded by the ORF, such as a reporter protein, e.g. luciferase, at a certain time point after initiation of expression of the ORF, e.g. after transfection of a test cell line, is at least the same, preferably higher than what would be expected if the protein production increasing effects of the 5'UTR element and the histone stem-loop were purely additive. The additive, preferably synergistic effect may, for example, be determined by the following assay. Four artificial nucleic acid molecules, e.g. mRNAs, comprising an ORF encoding, e.g. a reporter protein such as luciferase, are generated, i.e. (i) lacking a 5'UTR element and a histone stem-loop (E0), (ii) containing a 5'UTR element derived from a 5'UTR of a TOP gene or of a variant thereof (E1), (iii) containing a histone stem-loop (E2), and (iv) containing both the 5'UTR element and the histone stem-loop (E1E2). Expression of the ORF contained in the artificial nucleic acid molecules is initiated, for example, by transfecting a test cell line, such as a mammalian cell line, e.g. HELA cells, or primary cells, e.g. HDF cells. Samples are taken at specific time points after initiation of expression, for example, after 6 hours, 24 hours, 48 hours, and/or 72 hours and the amount of protein produced by expression of the ORF contained in the artificial nucleic acid molecules is measured, for example, by an ELISA assay or a luciferase test, depending on the type of protein encoded by the ORF. The predicted amount of protein at a certain time point after initiation of expression obtained by construct E1E2 if the effects of the 3'UTR element and the 5'UTR element were purely additive (PPA) may be calculated as follows:

$$PPA_x = (E1_x - E0_x) + (E2_x - E0_x) + E0_x,$$

E0 is the amount of protein obtained for the construct E0 (lacking a 5'UTR and a histone stem-loop), E1 is the amount of protein obtained for the construct E1, E2 is the protein amount obtained for the construct E2, and x is the time point after initiation of expression. The effect on increasing protein production is additive if $E1E2_x = PPA_x$, and synergistic in the sense of the present invention if $E1E2_x > PPA_x$, wherein $E1E2_x$ is the amount of protein obtained from construct E1E2 at time point x. Preferably, E1E2 is at least 1.0, more preferably at least 1.1, more preferably at least 1.3, more preferably at least 1.5, even more preferably at least 1.75 times PPA at a given time point post initiation of expression, such as 24 hours, 48 hours or 72 hours post initiation of expression.

Thus, in a preferred embodiment, the present invention provides an artificial nucleic acid molecule comprising (a.) at least one 5'UTR element which comprises or consists of a nucleic acid sequence which is derived from the 5'UTR of a TOP gene or which is derived from a variant of the 5'UTR of a TOP gene as described above; (b.) at least one open reading frame (ORF); and (c.) at least one histone stem-loop as described herein, wherein the histone stem-loop and the 5'UTR element act at least additively, preferably synergistically to increase protein production from the ORF, preferably wherein E1E2 PPA, preferably E1E2 is at least PPA, more preferably E1E2 is at least 1.1 times PPA, more preferably E1E2 is at least 1.3 times PPA, even more preferably wherein E1E2 is at least 1.5 times PPA at a given time point post initiation of expression of the ORF, for example 24 hours, preferably 48 hours post initiation of expression, wherein E1E2 and PPA are as described above.

Furthermore, it is preferred that the at least one histone stem-loop and the at least one 5'UTR element have an at least additive, preferably a synergistic effect on total protein production from the artificial nucleic acid molecule in a certain time span, such as within 24 hours, 48 hours, or 72 hours post initiation of expression. The additive, preferably the synergistic effect may be determined as described above, with the difference that the area under the curve (AUC) for the amount of protein over time predicted for E1E2 if the effects are additive is compared to the actual AUC measured for E1E2.

In a preferred embodiment of the present invention, the inventive artificial nucleic acid molecule comprises or codes for (a.) at least one 5'UTR element as described above, (b.) at least one open reading frame, and (c.) at least one histone stem-loop, preferably according to at least one of the following formulae (I) or (II):

formula (I) (stem-loop sequence without stem bordering elements):

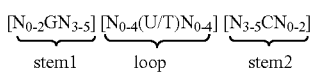

formula (II) (stem-loop sequence with stem bordering elements):

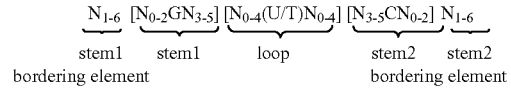

wherein:
stems or stem2 bordering element $N_{1-6}$ is a consecutive sequence of 1 to 6, preferably of 2 to 6, more preferably of 2 to 5, even more preferably of 3 to 5, most preferably of 4 to 5 or 5 N, wherein each N is independently from another selected from a nucleotide selected from A, U, T, G and C, or a nucleotide analogue thereof;

stem1 $[N_{0-2}GN_{3-5}]$ is reverse complementary or partially reverse complementary with element stem2, and is a consecutive sequence of between 5 to 7 nucleotides;

wherein $N_{0-2}$ is a consecutive sequence of 0 to 2, preferably of 0 to 1, more preferably of 1 N, wherein each N is independently from another selected from a nucleotide selected from A, U, T, G and C or a nucleotide analogue thereof;

wherein $N_{3-5}$ is a consecutive sequence of 3 to 5, preferably of 4 to 5, more preferably of 4 N, wherein each N is independently from another selected from a nucleotide selected from A, U, T, G and C or a nucleotide analogue thereof, and wherein G is guanosine or an analogue thereof, and may be optionally replaced by a cytidine or an analogue thereof, provided that its complementary nucleotide cytidine in stem2 is replaced by guanosine;

loop sequence $[N_{0-4}(U/T)N_{0-4}]$ is located between elements stem1 and stem2, and is a consecutive sequence of 3 to 5 nucleotides, more preferably of 4 nucleotides;

wherein each $N_{0-6}$ is independent from another a consecutive sequence of 0 to 4, preferably of 1 to 3, more preferably of 1 to 2 N, wherein each N is independently from another selected from a nucleotide selected from A, U, T, G and C or a nucleotide analogue thereof; and wherein U/T represents uridine, or optionally thymidine;

stem2 $[N_{3-5}CN_{0-2}]$ is reverse complementary or partially reverse complementary with element stem1, and is a consecutive sequence of between 5 to 7 nucleotides;

wherein $N_{3-5}$ is a consecutive sequence of 3 to 5, preferably of 4 to 5, more preferably of 4 N, wherein each N is independently from another selected from a nucleotide selected from A, U, T, G and C or a nucleotide analogue thereof;

wherein $N_{0-2}$ is a consecutive sequence of 0 to 2, preferably of 0 to 1, more preferably of 1 N, wherein each N is independently from another selected from a nucleotide selected from A, U, T, G or C or a nucleotide analogue thereof; and wherein C is cytidine or an analogue thereof, and may be optionally replaced by a guanosine or an analogue thereof provided that its complementary nucleotide guanosine in stem1 is replaced by cytidine;

wherein stem1 and stem2 are capable of base pairing with each other forming a reverse complementary sequence, wherein base pairing may occur between stem1 and stem2, e.g. by Watson-Crick base pairing of nucleotides A and U/T or G and C or by non-Watson-Crick base pairing e.g. wobble base pairing, reverse Watson-Crick base pairing, Hoogsteen base pairing, reverse Hoogsteen base pairing or are capable of base pairing with each other forming a partially reverse complementary sequence, wherein an incomplete base pairing may occur between stem1 and stem2, on the basis that one ore more bases in one stem do not have a complementary base in the reverse complementary sequence of the other stem.

In the above context, a wobble base pairing is typically a non-Watson-Crick base pairing between two nucleotides. The four main wobble base pairs in the present context, which may be used, are guanosine-uridine, inosine-uridine, inosine-adenosine, inosine-cytidine (G-U/T, I-U/T, I-A and I-C) and adenosine-cytidine (A-C).

Accordingly, in the context of the present invention, a wobble base is a base, which forms a wobble base pair with a further base as described above. Therefore, non-Watson-Crick base pairing, e.g. wobble base pairing, may occur in the stem of the histone stem-loop structure according to the present invention.

In the above context, a partially reverse complementary sequence comprises maximally two, preferably only one mismatch in the stem-structure of the stem-loop sequence formed by base pairing of stem1 and stem2. In other words, stem1 and stem2 are preferably capable of (full) base pairing with each other throughout the entire sequence of stem1 and stem2 (100% of possible correct Watson-Crick or non-Watson-Crick base pairings), thereby forming a reverse complementary sequence, wherein each base has its correct Watson-Crick or non-Watson-Crick base pendant as a complementary binding partner. Alternatively, stem1 and stem2 are preferably capable of partial base pairing with each other throughout the entire sequence of stem1 and stem2, wherein at least about 70%, 75%, 80%, 85%, 90%, or 95% of the 100% possible correct Watson-Crick or non-Watson-Crick base pairings are occupied with the correct Watson-Crick or non-Watson-Crick base pairings and at most about 30%, 25%, 20%, 15%, 10%, or 5% of the remaining bases are unpaired.

According to a preferred embodiment of the invention, the at least one histone stem-loop sequence (with stem bordering elements) of the inventive nucleic acid sequence as defined herein comprises a length of about 15 to about 45 nucleotides, preferably a length of about 15 to about 40 nucleotides, preferably a length of about 15 to about 35 nucleotides, preferably a length of about 15 to about 30 nucleotides and even more preferably a length of about 20 to about 30 and most preferably a length of about 24 to about 28 nucleotides.

Furthermore, the at least one histone stem-loop sequence (without stem bordering elements) of the inventive artificial nucleic acid molecule as defined herein may comprise a length of about 10 to about 30 nucleotides, preferably a length of about 10 to about 20 nucleotides, preferably a length of about 12 to about 20 nucleotides, preferably a length of about 14 to about 20 nucleotides and even more preferably a length of about 16 to about 17 and most preferably a length of about 16 nucleotides.

Preferably, the inventive artificial nucleic acid molecule may comprise or code for (a.) at least one 5'UTR element as described above; at least one open reading frame; and (c.) at least one histone stem-loop sequence according to at least one of the following specific formulae (Ia) or (IIa):
formula (Ia) (stem-loop sequence without stem bordering elements):

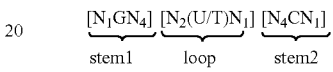

formula (IIa) (stem-loop sequence with stem bordering elements):

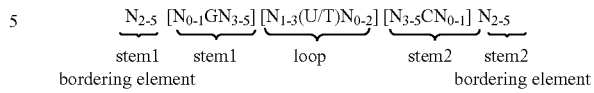

wherein N, C, G, T and U are as defined above.

Preferably, the inventive artificial nucleic acid molecule may comprise or code for (a.) at least one 5'UTR element as described above; at least one open reading frame; and (c.) at least one histone stem-loop sequence according to at least one of the following specific formulae (Ib) or (IIb):
formula (Ib) (stem-loop sequence without stem bordering elements):

[N$_1$GN$_4$] [N$_2$(U/T)N$_1$] [N$_4$CN$_1$]
  stem1        loop         stem2 formula (IIb) (stem-loop sequence with stem bordering elements):

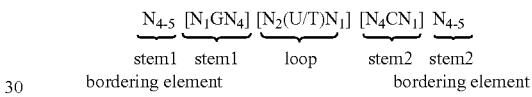

wherein N, C, G, T and U are as defined above.

Preferably, the inventive artificial nucleic acid molecule may comprise or code for (a.) at least one 5'UTR element as described above; at least one open reading frame; and (c.) at least one histone stem-loop sequence according to at least one of the following specific formulae (Ic) to (Ih) or (IIc) to (IIh), shown alternatively in its stem-loop structure and as a linear sequence representing histone stem-loop sequences as generated according to Example 1:
formula (Ic): (metazoan and protozoan histone stem-loop consensus sequence without stem bordering elements):

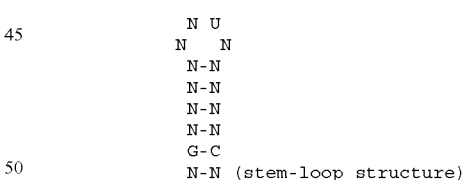

NGNNNNNNUNNNNNCN
(linear sequence)(SEQ ID NO: 1391)

formula (IIc): (metazoan and protozoan histone stem-loop consensus sequence with stem bordering elements):

N*N*NNNNGNNNNNNUNNNNNCNNNN*N*N*
(linear sequence)(SEQ ID NO: 1392)

formula (Id): (without stem bordering elements)

```
        N U
       N   N
       N-N
       N-N
       N-N
       N-N
       C-G
       N-N  (stem-loop structure)

NCNNNNNNNUNNNNNGN
    (linear sequence)(SEQ ID NO: 1393)
``` formula (IId): (with stem bordering elements)

```
        N U
       N   N
       N-N
       N-N
       N-N
       N-N
       C-G
    N*N*NNNN-NNNN*N*N*  (stem-loop structure)

N*N*NNNNCNNNNNNNUNNNNNGNNNN*N*N*
    (linear sequence)(SEQ ID NO: 1394)
``` formula (Ie): (protozoan histone stem-loop consensus sequence without stem bordering elements)

```
        N U
       N   N
       N-N
       N-N
       N-N
       N-N
       G-C
       D-H  (stem-loop structure)

DGNNNNNNNUNNNNNCH
    (linear sequence)(SEQ ID NO: 1395)
``` formula (IIe): (protozoan histone stem-loop consensus sequence with stem bordering elements)

```
        N U
       N   N
       N-N
       N-N
       N-N
       N-N
       G-C
    N*N*NNND-HNNN*N*N*  (stem-loop structure)

N*N*NNNDGNNNNNNNUNNNNNCHNNN*N*N*
    (linear sequence)(SEQ ID NO: 1396)
``` formula (If): (metazoan histone stem-loop consensus sequence without stem bordering elements)

```
        N U
       N   N
       Y-V
       Y-N
       B-D
       N-N
       G-C
       N-N  (stem-loop structure)

NGNBYYNNUNVNDNCN
    (linear sequence)(SEQ ID NO: 1397)
``` formula (IIf): (metazoan histone stem-loop consensus sequence with stem bordering elements)

```
        N U
       N   N
       Y-V
       Y-N
       B-D
       N-N
       G-C
    N*N*NNNN-NNNN*N*N*  (stem-loop structure)

N*N*NNNNGNBYYNNUNVNDNCNNNN*N*N*
    (linear sequence)(SEQ ID NO: 1398)
``` formula (Ig): (vertebrate histone stem-loop consensus sequence without stem bordering elements)

```
        N U
       D   H
       Y-A
       Y-B
       Y-R
       H-D
       G-C
       N-N  (stem-loop structure)

NGHYYYDNUHABRDCN
    (linear sequence)(SEQ ID NO: 1399)
``` formula (IIg): (vertebrate histone stem-loop consensus sequence with stem bordering elements)

```
        N U
       D   H
       Y-A
       Y-B
       Y-R
       H-D
       G-C
    N*N*HNNN-NNNN*N*H*  (stem-loop structure)

N*N*HNNNGHYYYDNUHABRDCNNNN*N*H*
    (linear sequence)(SEQ ID NO: 1400)
``` formula (Ih): (human histone stem-loop consensus sequence (*Homo sapiens*) without stem bordering elements)

```
        Y U
       D   H
       U-A
       C-S
       Y-R
       H-R
       G-C
       D-C  (stem-loop structure)

DGHYCUDYUHASRRCC
    (linear sequence)(SEQ ID NO: 1401)
``` formula (IIh): (human histone stem-loop consensus sequence (*Homo sapiens*) with stem bordering elements)

```
        Y U
       D   H
       U-A
       C-S
       Y-R
       H-R
       G-C
    N*H*AAHD-CVHB*N*H*  (stem loop structure)

N*H*AAHDGHYCUDYUHASRRCCVHB*N*H*
    (linear sequence)(SEQ ID NO: 1402)
``` wherein in each of above formulae (Ic) to (Ih) or (IIc) to (IIh):
N, C, G, A, T and U are as defined above;
each U may be replaced by T;
each (highly) conserved G or C in the stem elements 1 and 2 may be replaced by its complementary nucleotide base C or G, provided that its complementary nucleotide in the corresponding stem is replaced by its complementary nucleotide in parallel; and/or
G, A, T, U, C, R, Y, M, K, S, W, H, B, V, D, and N are nucleotide bases as defined in the following Table:

| abbreviation | Nucleotide bases | remark |
| --- | --- | --- |
| G | G | Guanine |
| A | A | Adenine |
| T | T | Thymine |
| U | U | Uracile |
| C | C | Cytosine |
| R | G or A | Purine |
| Y | T/U or C | Pyrimidine |
| M | A or C | Amino |
| K | G or T/U | Keto |
| S | G or C | Strong (3H bonds) |
| W | A or T/U | Weak (2H bonds) |
| H | A or C or T/U | Not G |
| B | G or T/U or C | Not A |
| V | G or C or A | Not T/U |
| D | G or A or T/U | Not C |
| N | G or C or T/U or A | Any base |
| * | Present or not | Base may be present or not |

In this context, it is particularly preferred that the histone stem-loop sequence according to at least one of the formulae (I) or (Ia) to (Ih) or (II) or (IIa) to (IIh) of the present invention is selected from a naturally occurring histone stem-loop sequence, more particularly preferred from protozoan or metazoan histone stem-loop sequences, and even more particularly preferred from vertebrate and mostly preferred from mammalian histone stem-loop sequences especially from human histone stem-loop sequences.

Further preferably, the histone stem-loop sequence according to at least one of the specific formulae (I) or (Ia) to (Ih) or (II) or (IIa) to (IIh) of the present invention is a histone stem-loop sequence comprising at each nucleotide position the most frequently occurring nucleotide, or either the most frequently or the second-most frequently occurring nucleotide of naturally occurring histone stem-loop sequences in metazoa and protozoa (FIG. 1), protozoa (FIG. 2), metazoa (FIG. 3), vertebrates (FIG. 4) and humans (FIG. 5) as shown in FIGS. 1-5. In this context, it is particularly preferred that at least 80%, preferably at least 85%, or most preferably at least 90% of all nucleotides correspond to the most frequently occurring nucleotide of naturally occurring histone stem-loop sequences.

Further preferably, the histone stem-loop sequence according to at least one of the specific formulae (I) or (Ia) to (Ih) of the present invention may be selected from following histone stem-loop sequences or corresponding RNA sequences (without stem-bordering elements) representing histone stem-loop sequences as generated according to Example 1:

```
    (SEQ ID NO: 1403 according to formula (Ic))
VGYYYYHHTHRVVRCB (SEQ ID NO: 1404 according to formula (Ic))
SGYYYTTYTMARRRCS (SEQ ID NO: 1405 according to formula (Ic))
SGYYCTTTTMAGRRCS (SEQ ID NO: 1406 according to formula (Ie))
DGNNNBNNTHVNNNCH (SEQ ID NO: 1407 according to formula (Ie))
RGNNNYHBTHRDNNCY (SEQ ID NO: 1408 according to formula (Ie))
RGNDBYHYTHRDHNCY (SEQ ID NO: 1409 according to formula (If))
VGYYYTYHTHRVRRCB (SEQ ID NO: 1410 according to formula (If))
SGYYCTTYTMAGRRCS (SEQ ID NO: 1411 according to formula (If))
SGYYCTTTTMAGRRCS (SEQ ID NO: 1412 according to formula (Ig))
GGYYCTTYTHAGRRCC (SEQ ID NO: 1413 according to formula (Ig))
GGCYCTTYTMAGRGCC (SEQ ID NO: 1414 according to formula (Ig))
GGCTCTTTTMAGRGCC (SEQ ID NO: 1415 according to formula (Ih))
DGHYCTDYTHASRRCC (SEQ ID NO: 1416 according to formula (Ih))
GGCYCTTTTHAGRGCC (SEQ ID NO: 1417 according to formula (Ih))
GGCYCTTTTMAGRGCC
```

Furthermore, in this context, following histone stem-loop sequences (with stem bordering elements) as generated according to Example 1 according to one of specific formulae (II) or (IIa) to (IIh) and the corresponding RNA sequences are particularly preferred:

```
    (SEQ ID NO: 1418 according to formula (IIc))
H*H*HHVVGYYYYHHTHRVVRCBVHH*N*N*

(SEQ ID NO: 1419 according to formula (IIc))
M*H*MHMSGYYYTTYTMARRRCSMCH*H*H*

(SEQ ID NO: 1420 according to formula (IIc))
M*M*MMMSGYYCTTTTMAGRRCSACH*M*H*

(SEQ ID NO: 1421 according to formula (IIe))
N*N*NNNDGNNNBNNTHVNNNCHNHN*N*N*

(SEQ ID NO: 1422 according to formula (IIe))
N*N*HHNRGNNNYHBTHRDNNCYDHH*N*N*

(SEQ ID NO: 1423 according to formula (IIe))
N*H*HHVRGNDBYHYTHRDHNCYRHH*H*H*

(SEQ ID NO: 1424 according to formula (IIf))
H*H*MHMVGYYYTYHTHRVRRCBVMH*H*N*

(SEQ ID NO: 1425 according to formula (IIf))
M*M*MMMSGYYCTTYTMAGRRCSMCH*H*H*

(SEQ ID NO: 1426 according to formula (IIf))
M*M*MMMSGYYCTTTTMAGRRCSACH*M*H*

(SEQ ID NO: 1427 according to formula (IIg))
H*H*MAMGGYYCTTYTHAGRRCCVHN*N*M*

(SEQ ID NO: 1428 according to formula (IIg))
H*H*AAMGGCYCTTYTMAGRGCCVCH*H*H*
```

-continued

```
    (SEQ ID NO: 1429 according to formula (IIg))
M*M*AAMGGCTCTTTTMAGRGCCMCY*M*M*

(SEQ ID NO: 1430 according to formula (IIh))
N*H*AAHDGHYCTDYTHASRRCCVHB*N*H*

(SEQ ID NO: 1431 according to formula (IIh))
H*H*AAMGGCYCTTTTHAGRGCCVMY*N*M*

(SEQ ID NO: 1432 according to formula (IIh))
H*M*AAAGGCYCTTTTMAGRGCCRMY*H*M*
```

A particular preferred histone stem-loop sequence is the sequence according to SEQ ID NO: 1433 (CAAAGGCTCTTTTCAGAGCCACCA) or the corresponding RNA sequence.

Thus, in a particularly preferred embodiment, the artificial nucleic acid molecule according to the present invention comprises (a.) at least one 5'UTR element as described above; (b.) at least one open reading frame; and (c.) at least one histone-stem loop which comprises or consists of a sequence having a sequence identity of at least about 75%, preferably of at least about 80%, preferably at least about 85%, more preferably at least about 90%, even more preferably at least about 95% to the sequence according to SEQ ID NO. 1433 or the corresponding RNA sequence, wherein preferably positions 6, 13 and 20 of the sequence having a sequence identity of at least about 75%, preferably of at least about 80%, preferably at least about 85%, more preferably at least about 90%, even more preferably at least about 95% to the sequence according to SEQ ID NO. 1433 or the corresponding RNA sequence are conserved, i.e. are identical to the nucleotides at positions 6, 13 and 20 of SEQ ID NO. 1433.

According to a further preferred embodiment, the inventive artificial nucleic acid molecule comprises or codes for at least one histone stem-loop sequence showing at least about 80%, preferably at least about 85%, more preferably at least about 90%, or even more preferably at least about 95% sequence identity with the not to 100% conserved nucleotides in the histone stem-loop sequences according to at least one of specific formulae (I) or (Ia) to (Ih) or (II) or (IIa) to (IIh) or with a naturally occurring histone stem-loop sequence.

Furthermore, the artificial nucleic acid molecule according to the present invention may comprise more than one histone stem-loop as described herein. For example, the artificial nucleic acid molecule according to the present invention may comprise one, two, three, four or more histone stem-loops, wherein the individual histone stem-loops may be the same or they may be different. For example, the artificial nucleic acid molecule according to the present invention may comprise two histone stem-loops, wherein each histone stem-loop sequence may be selected from the group consisting of SEQ ID NOs. 1391-1433.

In a particularly preferred embodiment, the present invention provides an artificial nucleic acid molecule comprising:
   a. at least one 5'-untranslated region element (5'UTR element) which comprises or consists of a nucleic acid sequence which is derived from the 5'UTR of a TOP gene or which is derived from a variant of the 5'UTR of a TOP gene as described above;
   b. at least one open reading frame (ORF); and
   c. at least one histone stem-loop, wherein preferably the sequence of the histone stem-loop is selected from the group consisting of sequences according to formulae (I) or (Ia) to (Ih) or (II) or (IIa) to (IIh), such as a sequence selected from the group consisting of SEQ ID NOs: 1391-1433, preferably from the group consisting of SEQ ID NOs. 1403-1433.

Thus, for example, the artificial nucleic acid molecule according to the present invention may comprise at least one 5'UTR element which is derived from the 5'UTR of a sequence selected from the group consisting of SEQ ID NOs. 1-1363, SEQ ID NO. 1435, SEQ ID NO. 1461 or SEQ ID NO. 1462, from a homolog thereof, from a variant thereof, or from a corresponding RNA sequence, such as a 5'UTR element which comprises or consists of a nucleic acid sequence which has an identity of at least about 40%, preferably of at least about 50%, preferably of at least about 60%, preferably of at least about 70%, more preferably of at least about 80%, more preferably of at least about 90%, even more preferably of at least about 95%, even more preferably of at least about 99% to a nucleic acid sequence extending from nucleotide position 5 to the nucleotide position immediately 5' to the start codon (located at the 3' end of the sequences), e.g. the nucleotide position immediately 5' to the ATG sequence, of a nucleic acid sequence selected from SEQ ID NOs. 1-1363, SEQ ID NO. 1435, SEQ ID NO. 1461 or SEQ ID NO. 1462, or a corresponding RNA sequence, or at least one 5'UTR element which comprises or consists of a fragment of a nucleic acid sequence which has an identity of at least about 40%, preferably of at least about 50%, preferably of at least about 60%, preferably of at least about 70%, more preferably of at least about 80%, more preferably of at least about 90%, even more preferably of at least about 95%, even more preferably of at least about 99% to a nucleic acid sequence extending from nucleotide position 5 to the nucleotide position immediately 5' to the start codon (located at the 3' end of the sequences), e.g. the nucleotide position immediately 5' to the ATG sequence, of a nucleic acid sequence selected from SEQ ID NOs. 1-1363, SEQ ID NO. 1435, SEQ ID NO. 1461 or SEQ ID NO. 1462, or a corresponding RNA sequence, preferably lacking the 5'TOP motif, wherein, preferably, the fragment is as described above, i.e. being a continuous stretch of nucleotides representing at least 20% etc. of the full-length 5'UTR the fragment is derived from, (b.) at least one open reading frame, and (c.) at least one histone stem-loop sequence selected from the group consisting of SEQ ID NOs: 1391-1433, preferably from the group consisting of SEQ ID NOs: 1403-1433, preferably wherein the at least one histone-stem loop comprises or consists of a sequence having a sequence identity of at least about 75%, preferably of at least about 80%, preferably at least about 85%, more preferably at least about 90%, even more preferably at least about 95% to the sequence according to SEQ ID NO. 1433 or the corresponding RNA sequence, wherein preferably positions 6, 13 and 20 of the sequence having a sequence identity of at least about 75%, preferably of at least about 80%, preferably at least about 85%, more preferably at least about 90%, even more preferably at least about 95% to the sequence according to SEQ ID NO. 1433 or the corresponding RNA sequence are conserved, i.e. are identical to the nucleotides at positions 6, 13 and 20 of SEQ ID NO. 1433.

Furthermore, for example, the artificial nucleic acid molecule according to the present invention may comprise at least one 5'UTR element which comprises or consists of a nucleic acid sequence which is derived from a 5'UTR of a TOP gene encoding a ribosomal protein or from a variant of a 5'UTR of a TOP gene encoding a ribosomal protein, e.g. which comprises or consists of a nucleic acid sequence which is derived from a 5'UTR of a nucleic acid sequence according to any of SEQ ID NOs: 170, 232, 244, 259, 1284, 1285, 1286, 1287, 1288, 1289, 1290, 1291, 1292, 1293, 1294, 1295, 1296, 1297, 1298, 1299, 1300, 1301, 1302, 1303, 1304, 1305, 1306, 1307, 1308, 1309, 1310, 1311, 1312, 1313, 1314, 1315, 1316, 1317, 1318, 1319, 1320, 1321, 1322, 1323, 1324, 1325, 1326, 1327, 1328, 1329, 1330, 1331, 1332, 1333, 1334, 1335, 1336, 1337, 1338, 1339, 1340, 1341, 1342, 1343, 1344, 1346, 1347, 1348, 1349, 1350, 1351, 1352, 1353, 1354, 1355, 1356, 1357, 1358, 1359, or 1360; a corresponding RNA sequence, a homolog thereof, or a variant thereof as described herein, and at least one histone stem-loop sequence selected from the group consisting of SEQ ID NOs: 1391-1433, preferably from the group consisting of SEQ ID NOs: 1403-1433, preferably wherein the at least one histone-stem loop comprises or consists of a sequence having a sequence identity of at least about 75%, preferably of at least about 80%, preferably at least about 85%, more preferably at least about 90%, even more preferably at least about 95% to the sequence according to SEQ ID NO. 1433 or the corresponding RNA sequence, wherein preferably positions 6, 13 and 20 of the sequence having a sequence identity of at least about 75%, preferably of at least about 80%, preferably at least about 85%, more preferably at least about 90%, even more preferably at least about 95% to the sequence according to SEQ ID NO. 1433 or the corresponding RNA sequence are conserved, i.e. are identical to the nucleotides at positions 6, 13 and 20 of SEQ ID NO. 1433.

In a further embodiment, the artificial nucleic acid molecule according to the present invention may comprise at least one 5'UTR element which comprises or consists of a nucleic acid sequence which is derived from a 5'UTR of a TOP gene encoding a ribosomal Large protein or from a variant of a 5'UTR of a TOP gene encoding a ribosomal Large protein, e.g. which comprises or consists of a nucleic acid sequence which is derived from a 5'UTR of a nucleic acid sequence according to any of SEQ ID NOs: 67, 259, 1284-1318, 1344, 1346, 1348-1354, 1357, 1461 and 1462, a corresponding RNA sequence, a homolog thereof, or a variant thereof as described herein, and at least one histone stem-loop sequence selected from the group consisting of SEQ ID NOs: 1391-1433, preferably from the group consisting of SEQ ID NOs: 1403-1433, preferably wherein the at least one histone histone-stem loop comprises or consists of a sequence having a sequence identity of at least about 75%, preferably of at least about 80%, preferably at least about 85%, more preferably at least about 90%, even more preferably at least about 95% to the sequence according to SEQ ID NO. 1433 or the corresponding RNA sequence, wherein preferably positions 6, 13 and 20 of the sequence having a sequence identity of at least about 75%, preferably of at least about 80%, preferably at least about 85%, more preferably at least about 90%, even more preferably at least about 95% to the sequence according to SEQ ID NO. 1433 or the corresponding RNA sequence are conserved, i.e. are identical to the nucleotides at positions 6, 13 and 20 of SEQ ID NO. 1433.

As preferred example, the artificial nucleic acid molecule according to the present invention may comprise a 5'UTR element which comprises or consists of a nucleic acid sequence which has an identity of at least about 90%, preferably of at least about 95%, even more preferably of at least about 99% to the nucleic acid sequence according to SEQ ID NO: 1368 or SEQ ID NOs: 1452-1460 and a histone stem-loop sequence selected from the group consisting of SEQ ID NOs: 1403-1433, e.g. according to SEQ ID NO: 1433, or wherein the histone histone-stem loop comprises or consists of a sequence having a sequence identity of about 90%, even more preferably at least about 95% to the sequence according to SEQ ID NO. 1433 or the corresponding RNA sequence, wherein positions 6, 13 and 20 of the sequence having a sequence identity of at least about 90%, even more preferably at least about 95% to the sequence according to SEQ ID NO. 1433 or the corresponding RNA sequence are conserved, i.e. are identical to the nucleotides at positions 6, 13 and 20 of SEQ ID NO. 1433.

In some embodiments, the histone stem-loop sequence according to component (c.) is not derived from a mouse histone gene, e.g. from mouse histone gene H2A614. In one embodiment, the artificial nucleic acid molecule of the invention neither contains a mouse histone stem-loop sequence nor contains mouse histone gene H2A614. Furthermore, in one embodiment, the inventive artificial nucleic acid molecule does not contain a stem-loop processing signal, more specifically, a mouse histone processing signal and, most specifically, does not contain mouse histone stem-loop processing signal H2kA614. Also, in one embodiment, the inventive nucleic acid molecule may contain at least one mammalian histone gene. However, in one embodiment, the at least one mammalian histone gene is not Seq. ID No. 7 of WO 01/12824.

Preferably, the inventive artificial nucleic acid molecule comprises no histone downstream element (HDE).

The term "histone downstream element (HDE)" refers to a purine-rich polynucleotide stretch of about 15 to 20 nucleotides 3' of naturally occurring stem-loops, which represents the binding site for the U7 snRNA involved in processing of histone pre-mRNA into mature histone mRNA. For example in sea urchins the HDE is CAAGAAAGA (Dominski, Z. and W. F. Marzluff (2007), Gene 396(2): 373-90).

Preferably, the artificial nucleic acid molecule according to the present invention further comprises a poly(A) sequence or a poly(A) signal.

Therefore, it is particularly preferred that the inventive artificial nucleic acid molecule comprises or codes for (a.) at least one 5'UTR element as described above, (b.) at least one open reading frame, preferably encoding a peptide or protein; (c.) at least one histone stem-loop as described herein, and (d.) a poly(A) sequence or a polyadenylation signal.

A polyadenylation signal is defined herein as a signal which conveys polyadenylation to a (transcribed) mRNA by specific protein factors (e.g. cleavage and polyadenylation specificity factor (CPSF), cleavage stimulation factor (CstF), cleavage factors I and II (CF I and CF II), poly(A) polymerase (PAP)).

Preferably, the polyadenylation signal comprises the consensus sequence NN(U/T)ANA, with N=A or U, preferably AA(U/T)AAA or A(U/T)(U/T)AAA. Such consensus sequence may be recognised by most animal and bacterial cell-systems, for example by the polyadenylation-factors, such as cleavage/polyadenylation specificity factor (CPSF) cooperating with CstF, PAP, PAB2, CFI and/or CFII. The polyadenylation signal is preferably located within the artificial nucleic acid molecule such that the above described machinery is able to effect polyadenylation of the artificial nucleic acid molecule. For example, the polyadenylation signal may be located less than about 50 nucleotides, more preferably less than about 30 nucleotides, most preferably less than about 25 nucleotides, for example 21 nucleotides, upstream of the 3'-end of the artificial nucleic acid molecule.

Additionally or alternatively to the polyadenylation signal, in some embodiments, the artificial nucleic acid molecule according to the present invention may further comprise a poly(A) sequence. The length of the poly(A) sequence may vary. For example, the poly(A) sequence may have a length of about 20 adenine nucleotides up to about 400 adenine nucleotides, such as about 20 adenine nucleotides up to about 300 adenine nucleotides, preferably about 40 to about 200 adenine nucleotides, more preferably about 50 to about 100 adenine nucleotides, such as about 60, 70, 80, 90 or 100 adenine nucleotides. The term about refers to a deviation of ±10%.

The poly(A) sequence is preferably located 3' to the ORF. For example, the poly(A) sequence may be connected to the 3'-end of the ORF directly or via a linker, for example via a stretch of nucleotides, such as 2, 4, 6, 8, 10, 20 etc. nucleotides, such as via a linker of 1-50, preferably 1-20 nucleotides, e.g. comprising one or more restriction sites, or the poly(A) sequence may be located within or between or downstream of other structures located 3' to the ORF, such as between a 3'UTR element and a poly(C) sequence, or down-stream of a 3'UTR element and/or a poly(C) sequence, or the poly(A) sequence may be located at the 3'-end of the artificial nucleic acid molecule. The term "located at the 3'-end" also includes embodiments, wherein the poly(A) sequence is followed in 3'-direction by few nucleotides which remain, e.g. after a restriction enzyme cleavage.

It is particularly preferred that the inventive artificial nucleic acid molecule comprises in 5'- to 3'-direction or codes in 5'- to 3'-direction for
(a.) at least one 5'UTR element derived from a TOP gene as described herein;
(b.) at least one open reading frame, preferably encoding a peptide or protein;
(c.) at least one histone stem-loop, optionally without a histone downstream element 3' to the histone stem-loop, as described herein; and
(d.) a poly(A) sequence and/or a polyadenylation signal.

In another particularly preferred embodiment, the inventive nucleic acid molecule according to the present invention comprises in 5'- to 3'-direction or codes in 5'- to 3'-direction for:
(a.) at least one 5'UTR element derived from a TOP gene as described above;
(b.) at least one open reading frame, preferably encoding a peptide or protein;
(d.) a poly(A) sequence; and
(c.) at least one histone stem-loop as described herein.

Thus, the poly(A) sequence and the histone stem-loop of an artificial nucleic acid molecule according to the present invention may be positioned in any desired order from 5' to 3'. Particularly, the poly(A) sequence may be located 5' as well as 3' of the histone stem-loop.

Accordingly, in one embodiment, the artificial nucleic acid molecule according to the present invention comprises
(a.) at least one 5'-untranslated region element (5'UTR element) which comprises or consists of a nucleic acid sequence which is derived from the 5'UTR of a TOP gene or which is derived from a variant of the 5'UTR of a TOP gene;
(b.) at least one open reading frame (ORF);
(c.) a histone stem-loop; and
(d.) a poly(A) sequence and/or a polyadenylation signal, wherein the poly(A) sequence is located 5' or 3' of the histone stem-loop.

In a further preferred embodiment, the artificial nucleic acid molecule according to the present invention further comprises a poly(C) sequence. A poly(C) sequence in the context of the present invention preferably consists of about 10 to about 200 cytidine nucleotides, more preferably of about 10 to about 100 cytidine nucleotides, more preferably of about 10 to about 50 cytidine nucleotides, even more preferably of about 20 to about 40 cytidine nucleotides, such as about 20, about 25, about 30, about 35, about 40, preferably about 30 cytidine nucleotides. The poly(C) sequence is preferably located 3' to the ORF of the artificial nucleic acid molecule. For example, the poly(C) sequence may be connected to the 3'-end of the ORF directly or via a linker of a stretch of nucleotides, such as 2, 4, 6, 8, 10, 20 etc. nucleotides, such as via a linker of 1-50, preferably of 1-20 nucleotides, e.g. comprising one or more restriction sites, or the poly(C) sequence may be located within, between or downstream of any other structures located 3' to the ORF. For example, the poly(C) sequence may be part of a 3'UTR element or may be located between a poly(A) sequence and a histone stem-loop, or the poly(C) sequence may be located at the 3'-end of the artificial nucleic acid molecule. The term "located at the 3'-end" also includes embodiments, wherein the poly(C) sequence is followed in 3'-direction by a few nucleotides which remain, e.g., after a restriction enzyme cleavage. In a particularly preferred embodiment, the poly(C) sequence is located between a poly(A) sequence and a histone stem-loop.

In a particularly preferred embodiment, the poly(C) sequence is located 5' to the histone stem-loop.

Thus, in a particularly preferred embodiment, the artificial nucleic acid molecule according to the present application comprises the structure 5'-[ORF]-[optional linker]-[3'UTR element]-[optional linker]-[poly(A) sequence]-[optional linker]-[poly(C) sequence]-[optional linker]-[histone stem-loop]-3', wherein the optional linkers may be independently of each other present or absent and may be a stretch of 1-50 nucleotides, e.g. comprising one or more restriction sites.

In a further embodiment, the artificial nucleic acid molecule according to the present invention further comprises a 3'UTR element. Thus, in some embodiments, the artificial nucleic acid molecule according to the present invention may comprise at least one 5'UTR element as described above, at least one open reading frame, at least one histone stem-loop as described herein and at least one 3'UTR element as described herein. Furthermore, in some embodiments, the artificial nucleic acid molecule according to the present invention may comprise at least one 5'UTR element as described above, at least one open reading frame, at least one histone stem-loop as described herein, at least one 3'UTR element as described herein, and a poly(A) sequence and/or a polyadenylation signal as described herein. In some embodiments, the histone stem-loop may be part of the 3'UTR element.

The term '3'UTR element' refers to a nucleic acid sequence which comprises or consists of a nucleic acid sequence that is derived from a 3'UTR or from a variant of a 3'UTR. A 3'UTR element in the sense of the present invention may represent the 3'UTR of an mRNA, e.g., in the event that the artificial nucleic acid molecule is an mRNA, or it may represent a sequence in a nucleic acid construct, such as a vector construct, that when transcribed represents the 3'UTR of the transcription product, such as the mRNA. Thus, in the sense of the present invention, preferably, a 3'UTR element may be the 3'UTR of an mRNA, preferably of an artificial mRNA, or it may be the transcription template for a 3'UTR of an mRNA. Thus, a 3'UTR element preferably is a nucleic acid sequence which corresponds to the 3'UTR of an mRNA, preferably to the 3'UTR of an artificial mRNA, such as an mRNA obtained by transcription of a genetically engineered vector construct. Preferably, the 3'UTR element fulfils the function of a 3'UTR or encodes a sequence which fulfils the function of a 3'UTR. The term '3UTR element' furthermore refers to a fragment or part of a 3'UTR of an artificial nucleic acid sequence, such as an artificial mRNA, or which codes for a part or fragment of a 3'UTR of an artificial nucleic acid molecule. This means that the 3'UTR element in the sense of the present invention may be comprised in the 3'UTR of an artificial nucleic acid sequence, such as an artificial mRNA, or which codes for a 3'UTR of an artificial nucleic acid molecule.

In the context of the present invention, the 3'UTR element may be derived from any 3'UTR of a gene or from a variant thereof, such as from a 3'UTR which is naturally associated with the ORF of the artificial nucleic acid molecule according to the present invention or any other 3'UTR of a naturally occurring gene or of a variant thereof.

Preferably, the 3'UTR element is functionally linked to the ORF. This means preferably that the 3'UTR element is associated with the ORF such that it may exert a function, such as a stabilizing function on the expression of the ORF or a stabilizing function on the artificial nucleic acid molecule. Preferably, the ORF and the 3'UTR element are associated in 5'→3' direction. Thus, preferably, the artificial nucleic acid molecule comprises the structure 5'-ORF-(optional)linker-3'UTR element-3', wherein the linker may be present or absent. For example, the linker may be one or more nucleotides, such as a stretch of 1-50 or 1-20 nucleotides, e.g., comprising or consisting of one or more restriction enzyme recognition sites (restriction sites).

Preferably, the at least one 5'UTR element and the at least one 3'UTR element are functionally linked to the ORF. This means preferably that the 5'UTR element and the 3'UTR element are associated with the ORF such that they may exert a function, preferably in an additive, more preferably in a synergistic manner, such as a stabilizing function on the expression of the ORF, a protein production increasing function for the protein encoded by the ORF, or a stabilizing function on the artificial nucleic acid molecule. Preferably, the 5'UTR element, the ORF, and the 3'UTR element are associated in 5'→3' direction. Thus, preferably, the artificial nucleic acid molecule comprises the structure 5'-5'UTR element-(optional)linker-ORF-(optional)linker-3'UTR element-3', wherein the linker may be present or absent. For example, the linker may be one or more nucleotides, such as a stretch of 1-50 or 1-20 nucleotides, e.g., comprising or consisting of one or more restriction enzyme recognition sites (restriction sites).

In a particularly preferred embodiment, the 5'UTR element and the 3'UTR element are heterologous, e.g. preferably the 5'UTR and the 3'UTR are derived from different genes of the same or of different species. Preferably, the 3'UTR is not derived from the TOP gene the 5'UTR is derived from.

In a preferred embodiment, the 3'UTR element is chosen such that it exerts at least an additive, preferably a synergistic function with the 5'UTR element on the protein production from the ORF of the artificial nucleic acid molecule. Preferably, the protein production is increased in at least an additive, preferably a synergistic way by the 3'UTR element and the 5'UTR element. Thus, the protein amount of the protein encoded by the ORF, such as a reporter protein, e.g. luciferase, at a certain time point after initiation of expression of the ORF, e.g. after transfection of a test cell or cell line, is preferably at least the same, preferably higher than what would be expected if the protein production increasing effects of the 3'UTR element and the 5'UTR element were purely additive. The additive, preferably the synergistic effect may, for example, be determined by the following assay. Four artificial nucleic acid molecules, e.g. mRNAs, comprising an ORF encoding, e.g. a reporter protein such as luciferase, are generated, i.e. (i) lacking UTR elements (E0), (ii) containing a 5'UTR element derived from a 5'UTR of a TOP gene or of a variant thereof (E1), (iii) containing a test 3'UTR element (E2), and (iv) containing both the 5'UTR element and the test 3'UTR element (E1E2). Expression of the ORF contained in the artificial nucleic acid molecules is initiated, for example, by transfecting a test cell line, such as a mammalian cell line, e.g. HELA cells, or primary cells, e.g. HDF cells. Samples are taken at specific time points after initiation of expression, for example, after 6 hours, 24 hours, 48 hours, and 72 hours and the amount of protein produced by expression of the ORF contained in the artificial nucleic acid molecules is measured, for example, by an ELISA assay or a luciferase test, depending on the type of protein encoded by the ORF. The predicted amount of protein at a certain time point after initiation of expression obtained by construct E1E2 if the effects of the 3'UTR element and the 5'UTR element were purely additive (PPA) may be calculated as follows:

$$PPA_x = (E1_x - E0_x) + (E2_x - E0_x) + E0_x,$$

E0 is the amount of protein obtained for the construct E0 (lacking UTRs), E1 is the amount of protein obtained for the construct E1, E2 is the protein amount obtained for the construct E2, and x is the time point after initiation of expression. The effect on increasing protein production is additive if $E1E2_x = PPA_x$ and synergistic in the sense of the present invention if $E1E2_x > PPA_x$, wherein $E1E2_x$ is the amount of protein obtained from construct E1E2 at time point x. Preferably, E1E2 is at least 1.0, preferably at least 1.1, more preferably at least 1.3, more preferably at least 1.5, even more preferably at least 1.75 times PPA at a given time point post initiation of expression, such as 24 hours, 48 hours or 72 hours post initiation of expression.

Thus, in a preferred embodiment, the present invention provides an artificial nucleic acid molecule comprising (a.) at least one 5'UTR element which comprises or consists of a nucleic acid sequence which is derived from the 5'UTR of a TOP gene or which is derived from a variant of the 5'UTR of a TOP gene; (b.) at least one open reading frame (ORF); (c.) at least one histone stem-loop, and at least one 3'UTR element, wherein preferably the 3'UTR element and the 5'UTR element act at least additively, preferably synergistically to increase protein production from the ORF, preferably wherein E1E2 PPA, preferably E1E2 is at least 1.0 times PPA, preferably E1E2 is at least 1.1 times PPA, more preferably E1E2 is at least 1.3 times PPA, even more preferably wherein E1E2 is at least 1.5 times PPA at a given time point post initiation of expression of the ORF, for example 24 hours, preferably 48 hours post initiation of expression, wherein E1E2 and PPA are as described above.

Furthermore, it is preferred that the 3'UTR element and the 5'UTR element have at least an additive, preferably a synergistic effect on the total protein production from the artificial nucleic acid molecule in a certain time span, such as within 24 hours, 48 hours, or 72 hours post initiation of expression. The additive or the synergistic effect may be determined as described above, with the difference that the area under the curve (AUC) for the amount of protein over time predicted for E1E2 if the effects were purely additive is compared to the actual AUC measured for E1E2.

In a preferred embodiment, the 3'UTR element comprises or consists of a nucleic acid sequence which is derived from the 3'UTR of a stable mRNA or from a variant of the 3'UTR of a stable mRNA. Thus, in a preferred embodiment, the 3'UTR element comprises or consists of a sequence which is derived from a gene providing a stable mRNA or from a variant of a 3'UTR of a gene providing a stable mRNA. The term "stable mRNA", preferably refers to mRNAs which exhibit a longer half-life in mammalian cells than the average half-life of mRNA molecules in mammalian cells. Preferably, a stable mRNA in the sense of the present application refers to an mRNA which exhibits a half-life of more than 5 hours, preferably more than 8 hours, in a mammalian cell, such as in a mammalian cell line, e.g. in HELA cells, or in primary cells, e.g. in HDF cells, preferably determined by using a transcription inhibitor such as actinomycin D.

For example, the half-life of an mRNA in mammalian cells, such as HELA or HDF cells, may be determined by culturing the cells in presence of a transcription inhibitor, e.g. actinomycin D, 5,6-dichloro-1-β-D-ribofuranosylbenzimidazole (DRB), or α-amanitin, harvesting the cells at different time points after inhibition of transcription, and determining the amount of the mRNA present in the cell samples by methods well known to the person skilled in the art, e.g. by quantitative RT-PCR. The half-life of a particular mRNA may be calculated based on the amounts of the particular mRNA measured at the different time points post inhibition of transcription. Alternatively, pulse-chase methods, e.g. using radioactively labelled nucleotides, or constructs comprising inducible promoters may be used for determining the half-life of an mRNA in mammalian cells.

It is particularly preferred that the enhanced stability of a stable mRNA in the sense of the present invention is affected by its 3'UTR. Thus, preferably, the 3'UTR element comprises or consists of a nucleic acid sequence which is derived from the 3'UTR of a stable mRNA which exhibits a half-life of more than 5 hours, preferably more than 8 hours, in a mammalian cell, such as in a mammalian cell line, e.g. in HELA cells, or in mammalian primary cells, such as HDF cells, preferably determined by using a transcription inhibitor such as actinomycin D, wherein the enhanced stability of said stable mRNA is effected by its 3'UTR. The ability of a 3'UTR for enhancing stability may be tested as described herein, e.g. by using a reporter open reading frame such as a luciferase encoding open reading frame. Alternatively, an artificial construct encoding the test stable mRNA may be generated, wherein the 3'UTR of the stable mRNA is replaced with a reference 3'UTR, such as a 3'UTR of a short lived mRNA, e.g. a Myc 3'UTR. The stability of the wild type stable mRNA and the 3'UTR modified mRNA may be determined as described above. In the event the 3'UTR modified mRNA exhibits a shorter half-life than the wild type stable mRNA, it may be concluded that a stability enhancing effect is exerted by the 3'UTR of the stable mRNA.

In a particularly preferred embodiment, the 3'UTR element comprises or consists of a nucleic acid sequence which is derived from a 3'UTR of a gene selected from the group consisting of an albumin gene, an α-globin gene, a β-globin gene, a tyrosine hydroxylase gene, a lipoxygenase gene, and a collagen alpha gene, such as a collagen alpha 1(I) gene, or from a variant of a 3'UTR of a gene selected from the group consisting of an albumin gene, an α-globin gene, a β-globin gene, a tyrosine hydroxylase gene, a lipoxygenase gene, and a collagen alpha gene, such as a collagen alpha 1(I) gene. In a particularly preferred embodiment, the 3'UTR element comprises or consists of a nucleic acid sequence which is derived from a 3'UTR of an albumin gene, preferably a vertebrate albumin gene, more preferably a mammalian albumin gene, most preferably a human albumin gene. In another particularly preferred embodiment, the 3'UTR element comprises or consists of a nucleic acid sequence which is derived from a 3'UTR of an α-globin gene, preferably a vertebrate α-globin gene, more preferably a mammalian α-globin gene, most preferably a human α-globin gene. For example, the 3'UTR element may comprise or consist of the center, α-complex-binding portion of the 3'UTR of an α-globin gene, such as of a human α-globin gene.

Preferably, the at least one 3'UTR element comprises or consists of a nucleic acid sequence which is derived from the 3'UTR of a vertebrate albumin gene, a vertebrate α-globin gene, a vertebrate β-globin gene, a vertebrate tyrosine hydroxylase gene, a vertebrate lipoxygenase gene, and a vertebrate collagen alpha gene, such as a vertebrate collagen alpha 1(I) gene, or from a variant thereof, preferably from the 3'UTR of a mammalian albumin gene, a mammalian α-globin gene, a mammalian β-globin gene, a mammalian tyrosine hydroxylase gene, a mammalian lipoxygenase gene, and a mammalian collagen alpha gene, such as a mammalian collagen alpha 1(I) gene, or from a variant thereof, more preferably from the 3'UTR of a human albumin gene, a human α-globin gene, a human β-globin gene, a human tyrosine hydroxylase gene, a human lipoxygenase gene, and a human collagen alpha gene, such as a human collagen alpha 1(I) gene, or from a variant thereof, even more preferably from the 3'UTR of the human albumin gene according to GenBank Accession number NM_000477.5 or from a variant thereof. In a preferred embodiment, the 3'UTR element is not derived from the 3'UTR of a *Xenopus* albumin gene. Preferably, the 3'UTR element does not comprise a poly(A) limiting element B (PLEB) of a 3'UTR from a *Xenopus* albumin gene. Preferably, the 3'UTR element does not consist of a PLEB of a 3'UTR from a *Xenopus* albumin gene.

In one embodiment, the 3'UTR element and the at least one open reading frame are heterologous, e.g. preferably the 3'UTR element and the ORF are derived from different genes of the same or of different species. Preferably, the ORF does not encode an α-globin protein if the 3'UTR element is derived from an α-globin gene. Preferably, the ORF does not encode a β-globin protein if the 3'UTR element is derived from a β-globin gene. Preferably, the ORF does not encode an albumin protein if the 3'UTR element is derived from an albumin gene. Preferably, the ORF does not encode a tyrosine hydroxylase protein if the 3'UTR element is derived from a tyrosine hydroxylase gene. Preferably, the ORF does not encode a lipoxygenase protein if the 3'UTR element is derived from a lipoxygenase gene. Preferably, the ORF does not encode a collagen alpha protein if the 3'UTR element is derived from a collagene alpha gene. In one embodiment, the artificial nucleic acid molecule may consist of at least two sequence parts that are derivable from two different genes, the 5'UTR element which is derivable from a TOP gene and the open reading frame and the 3'UTR which may be derivable from the gene encoding the desired protein product. More preferably, the artificial nucleic acid molecule consists of three sequence parts that are derivable from three different genes: the 5'UTR element which is derivable from a TOP gene, the open reading frame which is derivable from the gene encoding the desired gene product and the 3'UTR element which may be derivable from a gene that relates to an mRNA with an enhanced half-life, for example a 3'UTR element as defined and described below.

In some embodiments, the 3'UTR element consists of a histone stem-loop. In some embodiments, the 3'UTR element of the artificial nucleic acid molecule may comprise a histone stem-loop in addition to the nucleic acid sequence derived from the 3'UTR of a gene, such as of a gene providing a stable mRNA, such as of an albumin gene, an α-globin gene, a β-globin gene, a tyrosine hydroxylase gene, a lipoxygenase gene, or a collagen alpha gene, such as a collagen alpha 1(I) gene as described above. Such artificial nucleic acid molecule according to the present invention, for example, may comprise in 5'-to-3'-direction a 5'UTR element, an ORF, a 3'UTR element, preferably comprising a polyadenylation signal, a histone stem-loop and an optional poly(A) sequence. It may also comprise in 5'-to-3'-direction a 5'UTR element as described above, an ORF, a 3'UTR element, e.g. comprising a polyadenylation signal, a poly(A) sequence and a histone stem-loop.

The term 'a nucleic acid sequence which is derived from the 3'UTR of a [ . . . ] gene' preferably refers to a nucleic acid sequence which is based on the 3'UTR sequence of a [ . . . ] gene or on a part thereof, such as on the 3'UTR of an albumin gene, an α-globin gene, a β-globin gene, a tyrosine hydroxylase gene, a lipoxygenase gene, or a collagen alpha gene, such as a collagen alpha 1(I) gene, preferably of an albumin gene or an α-globin gene on a part thereof. This term includes sequences corresponding to the entire 3'UTR sequence, i.e. the full length 3'UTR sequence of a gene, and sequences corresponding to a fragment of the 3'UTR sequence of a gene, such as an albumin gene, α-globin gene, β-globin gene, tyrosine hydroxylase gene, lipoxygenase gene, or collagen alpha gene, such as a collagen alpha 1(I) gene, preferably of an albumin or α-globin gene. A fragment in this context preferably consists of a continuous stretch of nucleotides corresponding to a continuous stretch of nucleotides in the full-length 3'UTR, which represents at least 20%, preferably at least 30%, more preferably at least 40%, more preferably at least 50%, even more preferably at least 60%, even more preferably at least 70%, even more preferably at least 80%, and most preferably at least 90% of the full-length 3'UTR. Such a fragment, in the sense of the present invention, is preferably a functional fragment as described herein. The term '3'UTR of a [ . . . ] gene' preferably refers to the 3'UTR of a naturally occurring gene, such as of a naturally occurring albumin gene, α-globin gene, β-globin gene, tyrosine hydroxylase gene, lipoxygenase gene, or collagen alpha gene, such as a collagen alpha 1(I) gene, preferably of a naturally occurring albumin or α-globin gene.

The terms 'variant of the 3'UTR of a [ . . . ] gene' and 'variant thereof' in the context of a 3'UTR refers to a variant of the 3'UTR of a naturally occurring gene, such as a naturally occurring albumin gene, a naturally occurring α-globin gene, a naturally occurring β-globin gene, a naturally occurring tyrosine hydroxylase gene, a naturally occurring lipoxygenase gene, or a naturally occurring collagen alpha gene, such as a collagen alpha 1(I) gene, preferably to a variant of the 3'UTR of a vertebrate albumin gene, a vertebrate α-globin gene, a vertebrate β-globin gene, a vertebrate tyrosine hydroxylase gene, a vertebrate lipoxygenase gene, and a vertebrate collagen alpha gene, such as a vertebrate collagen alpha 1(I) gene, preferably to a variant of the 3'UTR of a mammalian albumin gene, a mammalian α-globin gene, a mammalian β-globin gene, a mammalian tyrosine hydroxylase gene, a mammalian lipoxygenase gene, and a mammalian collagen alpha gene, such as a mammalian collagen alpha 1(I) gene, or to a variant of the 3'UTR of a human albumin gene, a human α-globin gene, a human β-globin gene, a human tyrosine hydroxylase gene, a human lipoxygenase gene, and a human collagen alpha gene, such as a human collagen alpha 1(I) gene. Such variant may be a modified 3'UTR of a gene. For example, a variant 3'UTR may exhibit one or more nucleotide deletions, insertions, additions and/or substitutions compared to the naturally occurring 3'UTR from which the variant is derived. Preferably, a variant of a 3'UTR is at least 40%, preferably at least 50%, more preferably at least 60%, more preferably at least 70%, even more preferably at least 80%, even more preferably at least 90%, most preferably at least 95% identical to the naturally occurring 3'UTR the variant is derived from. Preferably, the variant is a functional variant as described herein. The term 'a nucleic acid sequence which is derived from a variant of the 3'UTR of a [ . . . ] gene' preferably refers to a nucleic acid sequence which is based on a variant of the 3'UTR sequence of a gene, such as on a variant of the 3'UTR of an albumin gene, an α-globin gene, a β-globin gene, a tyrosine hydroxylase gene, a lipoxygenase gene, or a collagen alpha gene, such as a collagen alpha 1(I) gene, or on a part thereof as described above. This term includes sequences corresponding to the entire sequence of the variant of the 3'UTR of a gene, i.e. the full length variant 3'UTR sequence of a gene, and sequences corresponding to a fragment of the variant 3'UTR sequence of a gene. A fragment in this context preferably consists of a continuous stretch of nucleotides corresponding to a continuous stretch of nucleotides in the full-length variant 3'UTR, which represents at least 20%, preferably at least 30%, more preferably at least 40%, more preferably at least 50%, even more preferably at least 60%, even more preferably at least 70%, even more preferably at least 80%, and most preferably at least 90% of the full-length variant 3'UTR. Such a fragment of a variant, in the sense of the present invention, is preferably a functional fragment of a variant as described herein.

The terms 'functional variant', 'functional fragment', and 'functional fragment of a variant' (also termed 'functional variant fragment') in the context of the present invention, mean that the fragment of the 5'UTR or the 3'UTR, the variant of the 5'UTR or the 3'UTR, or the fragment of a variant of the 5'UTR or the 3'UTR of a gene fulfils at least one, preferably more than one, function of the naturally occurring 5'UTR or 3'UTR of the gene of which the variant, the fragment, or the fragment of a variant is derived. Such function may be, for example, stabilizing mRNA and/or stabilizing and/or prolonging protein production from an mRNA and/or increasing protein production from an mRNA, preferably in a mammalian cell, such as in a human cell. It is particularly preferred that the variant, the fragment, and the variant fragment in the context of the present invention fulfil the function of stabilizing an mRNA, preferably in a mammalian cell, such as a human cell, compared to an mRNA comprising a reference 5'UTR or lacking a 5'UTR and/or a 3'UTR, and/or the function of stabilizing and/or prolonging protein production from an mRNA, preferably in a mammalian cell, such as in a human cell, compared to an mRNA comprising a reference 5'UTR or lacking a 5'UTR and/or a 3'UTR, and/or the function of increasing protein production from an mRNA, preferably in a mammalian cell, such as in a human cell, compared to an mRNA comprising a reference 5'UTR or lacking a 5'UTR and/or a 3'UTR. A reference 5'UTR may be, for example, a 5'UTR naturally occurring in combination with the ORF. Furthermore, a functional variant, a functional fragment, or a functional variant fragment of a 5'UTR or of a 3'UTR of a gene preferably does not have a substantially diminishing effect on the efficiency of translation of the mRNA which comprises such variant of a 5'UTR and/or such variant of a 3'UTR compared to the wild type 5'UTR and/or 3'UTR from which the variant is derived. A particularly preferred function of a "functional fragment", a "functional variant" or a "functional fragment of a variant" of the 3'UTR of a gene, such as an albumin gene, α-globin gene, β-globin gene, tyrosine hydroxylase gene, lipoxygenase gene, or collagen alpha gene, such as a collagen alpha 1(I) gene, in the context of the present invention is the stabilization and/or prolongation of protein production by expression of an mRNA carrying the functional fragment, functional variant or functional fragment of a variant as described above. A particularly preferred function of a "functional fragment", a "functional variant" or a "functional fragment of a variant" of the 5'UTR in the context of the present invention is the protein production increasing function.

Preferably, the efficiency of the one or more functions exerted by the functional variant, the functional fragment, or the functional variant fragment, such as mRNA and/or protein production stabilizing efficiency and/or the protein production increasing efficiency, is at least 40%, more preferably at least 50%, more preferably at least 60%, even more preferably at least 70%, even more preferably at least 80%, most preferably at least 90% of the mRNA and/or protein production stabilizing efficiency and/or the protein production increasing efficiency exhibited by the naturally occurring 5'UTR and/or 3'UTR of which the variant, the fragment or the variant fragment is derived.

In the context of the present invention, a fragment or part of the 3'UTR of a gene, such as an albumin gene, α-globin gene, β-globin gene, tyrosine hydroxylase gene, lipoxygenase gene, or collagen alpha gene, such as a collagen alpha 1(I) gene, or of a variant thereof preferably exhibits a length of at least about 40 nucleotides, preferably of at least about 50 nucleotides, preferably of at least about 75 nucleotides, more preferably of at least about 100 nucleotides, even more preferably of at least about 125 nucleotides, most preferably of at least about 150 nucleotides. Preferably, such fragment of the 3'UTR of a gene or of a variant of the 3'UTR of a gene is a functional fragment as described above.

In the context of the present invention, a fragment or part of the 5'UTR of a TOP gene or of a variant thereof preferably exhibits a length of at least about 20 nucleotides, preferably of at least about 30 nucleotides, more preferably of at least about 50 nucleotides. Preferably, such fragment of the 5'UTR of a TOP gene or of a variant of the 5'UTR of a TOP gene is a functional fragment as described above.

In some embodiments, the 3'UTR element of the artificial nucleic acid molecule according to the present invention comprises or consists of a "functional fragment", a "functional variant" or a "functional fragment of a variant" of the 3'UTR of a gene, such as of an albumin gene, α-globin gene, β-globin gene, tyrosine hydroxylase gene, lipoxygenase gene, or collagen alpha gene, such as a collagen alpha 1(I) gene, or of a variant thereof.

In some embodiments, the at least one 5'UTR element of the artificial nucleic acid molecule according to the present invention comprises or consists of a "functional fragment", a "functional variant" or a "functional fragment of a variant" of the 5'UTR of a TOP gene.

Preferably, the 3'UTR element of the artificial nucleic acid molecule according to the present invention increases the stability of the artificial nucleic acid molecule, e.g. increases the stability of an mRNA according to the present invention, compared to a respective mRNA (reference mRNA) lacking a 3'UTR element. Preferably, the at least one 3'UTR element of the artificial nucleic acid molecule according to the present invention increases the stability of protein production from the artificial nucleic acid molecule according to the present invention, e.g. from an mRNA according to the present invention, compared to a respective mRNA lacking a 3'UTR element. Preferably, the at least one 3'UTR element of the artificial nucleic acid molecule according to the present invention prolongs protein production from the artificial nucleic acid molecule according to the present invention, e.g. from an mRNA according to the present invention, compared to a respective mRNA lacking a 3'UTR element. Preferably, the at least one 3'UTR element of the artificial nucleic acid molecule according to the present invention increases the protein production from the artificial nucleic acid molecule according to the present invention, e.g. from an mRNA according to the present invention, compared to a respective mRNA lacking a 3'UTR element. Preferably, the at least one 3'UTR element of the artificial nucleic acid molecule according to the present invention does not negatively influence translational efficiency of an mRNA compared to the translational efficiency of a respective mRNA lacking a 3'UTR element. The term 'respective mRNA' in this context means that—apart from the different 3'UTR—the reference mRNA is comparable, preferably identical, to the mRNA comprising the 3'UTR element.

Preferably, the at least one 5'UTR element of the artificial nucleic acid molecule according to the present invention increases the stability of the artificial nucleic acid molecule, e.g. increases the stability of an mRNA according to the present invention, compared to a respective mRNA (reference mRNA) lacking a 5'UTR element or comprising a reference 5'UTR element, such as a 5'UTR naturally occurring in combination with the ORF. Preferably, the at least one 5'UTR element of the artificial nucleic acid molecule according to the present invention increases protein production from the artificial nucleic acid molecule according to the present invention, e.g. from an mRNA according to the present invention, compared to a respective mRNA lacking a 5'UTR element or comprising a reference 5'UTR element, such as a 5'UTR naturally occurring in combination with the ORF. The term 'respective mRNA' in this context means that—apart from the different 5'UTR—the reference mRNA is comparable, preferably identical, to the mRNA comprising the inventive 5'UTR element.

Preferably, the histone stem-loop of the artificial nucleic acid molecule according to the present invention increases the stability of the artificial nucleic acid molecule, e.g. increases the stability of an mRNA according to the present invention, compared to a respective mRNA (reference mRNA) lacking a histone stem-loop. Preferably, the histone stem-loop of the artificial nucleic acid molecule according to the present invention increases protein production from the artificial nucleic acid molecule according to the present invention, e.g. from an mRNA according to the present invention, compared to a respective mRNA lacking a histone stem-loop. The term 'respective mRNA' in this context means that—apart from the histone stem loop—the reference mRNA is comparable, preferably identical, to the mRNA comprising the a histone stem-loop.

Preferably, the at least one 5'UTR element and the at least one 3'UTR element act synergistically to increase protein production from the artificial nucleic acid molecule according to the present invention, e.g. from an mRNA according to the present invention, as described above.

Preferably, the at least one 5'UTR element and the histone stem-loop act synergistically to increase protein production from the artificial nucleic acid molecule according to the present invention, e.g. from an mRNA according to the present invention, as described above.

The term 'stabilizing and/or prolonging protein production from an mRNA' preferably means that the protein production from the mRNA is stabilized and/or prolonged compared to the protein production from a reference mRNA, e.g. lacking a 3'UTR element.

'Stabilized protein expression' in this context preferably means that there is more uniform protein production from the artificial nucleic acid molecule according to the present invention over a predetermined period of time, such as over 24 hours, more preferably over 48 hours, even more preferably over 72 hours, when compared to a reference nucleic acid molecule, for example, lacking a 3'UTR element. Thus, the level of protein production, e.g. in a mammalian system, from the artificial nucleic acid molecule comprising a 3'UTR element according to the present invention, e.g. from an mRNA according to the present invention, preferably does not drop to the extent observed for a reference nucleic acid molecule. For example, the amount of a protein (encoded by the ORF) observed 6 hours after initiation of expression, e.g. 6 hours post transfection of the artificial nucleic acid molecule according to the present invention into a cell, such as a mammalian cell, may be comparable to the amount of protein observed 48 hours after initiation of expression, e.g. 48 hours post transfection. Thus, the ratio of the amount of protein encoded by the ORF, such as of a reporter protein, e.g., luciferase, observed at 48 hours post initiation of expression, e.g. 48 hours post transfection, to the amount of protein observed 6 hours after initiation of expression, e.g. 6 hours post transfection, is preferably above 0.4, preferably above 0.5, more preferably above 0.6, even more preferably above 0.7, e.g. between about 0.4 and about 4, preferably between about 0.65 and about 3, more preferably between about 0.7 and 2 for a nucleic acid molecule according to the present invention. Thus, in one embodiment, the present invention provides an artificial nucleic acid molecule as described above, wherein the ratio of the (reporter) protein amount observed 48 hours after initiation of expression to the (reporter) protein amount observed 6 hours after initiation of expression, preferably in a mammalian expression system, such as in mammalian cells, is preferably between about 0.4 and 4, preferably between about 0.65 and about 3, more preferably between about 0.7 and 2.

'Increased protein expression' in the context of the present invention may refer to increased protein expression at one time point after initiation of expression compared to a reference molecule or to an increased total protein production within a certain time period after initiation of expression. Thus, the protein level observed at a certain time point after initiation of expression, e.g. after transfection, of the artificial nucleic acid molecule according to the present invention, e.g. after transfection of an mRNA according to the present invention, for example, 24, 48, or 72 hours post transfection, or the total protein produced in a time span of, e.g. 24, 48 or 72 hours, is preferably higher than the protein level observed at the same time point after initiation of expression, e.g. after transfection, or the total protein produced within the same time span, for a reference nucleic acid molecule, such as a reference mRNA comprising a reference 5'UTR element or lacking a 5'UTR element and/or 3'UTR element and/or a histone stem-loop. As set forth above, it is a particularly preferred function of the 5'UTR element and the histone stem-loop to effect an increase in protein production from the artificial nucleic acid molecule. Preferably, the increase in protein production effected by the 5'UTR element and the histone stem-loop compared to a reference nucleic acid molecule lacking such 5'UTR element and a histone stem-loop at a given time point post initiation of expression is at least 1.5-fold, more preferably at least 2-fold, more preferably at least 3-fold, more preferably at least 4-fold, more preferably at least 5-fold, even more preferably at least 10-fold, even more preferably at least 15-fold of the protein production observed for a reference nucleic acid molecule lacking the 5'UTR element and a histone stem-loop. The same holds preferably for the total protein production in a given time period, for example in a time period of 24, 48 or 72 hours post initiation of expression.

Said increase in stability of the artificial nucleic acid molecule, said increase in stability of protein production, said prolongation of protein production and/or said increase in protein production is preferably determined by comparison with a respective reference nucleic acid molecule lacking a 5'UTR element and/or a 3'UTR element and/or a histone stem-loop, e.g. an mRNA lacking a 5'UTR element and/or a 3'UTR element and/or a histone stem-loop, or a reference nucleic acid molecule comprising a reference 5'UTR element and/or a reference 3'UTR element, such as a 3'UTR and/or a 5'UTR naturally occurring with the ORF or a 5'UTR and/or a 3'UTR of a reference gene.

The mRNA and/or protein production stabilizing effect and efficiency and/or the protein production increasing effect and efficiency of the variants, fragments and/or variant fragments of the 3'UTR of an albumin gene as well as the mRNA and/or protein production stabilizing effect and efficiency and/or the protein production increasing effect and efficiency of the 3'UTR element, the at least one 5'UTR element, or the histone stem-loop of the artificial nucleic acid molecule according to the present invention may be determined by any method suitable for this purpose known to the skilled person. For example, artificial mRNA molecules may be generated comprising a coding sequence for a reporter protein, such as luciferase, and no 3'UTR and/or no 5'UTR and/or no histone stem-loop, a 5'UTR derived from a TOP gene and/or a 3'UTR derived from a gene as described above and/or a histone stem-loop as described above, a 5'UTR derived from a reference gene and/or a 3'UTR derived from a reference gene (i.e., a reference 3'UTR or a reference 5'UTR, such as a 5'UTR or a 3'UTR naturally occurring with the ORF), as 3'UTR a variant of a 3'UTR of a gene as described above, as 3'UTR a fragment of a 3'UTR of a gene as described above, or as 3'UTR a fragment of a variant of a 3'UTR of a gene as described above, as 5'UTR a variant of a 5'UTR of a TOP gene, as 5'UTR a fragment of a 5'UTR of a TOP gene, or as 5'UTR a fragment of a variant of a 5'UTR of a TOP gene. Such mRNAs may be generated, for example, by in vitro transcription of respective vectors such as plasmid vectors, e.g. comprising a T7 promoter and a sequence encoding the respective mRNA sequences. The generated mRNA molecules may be transfected into cells by any transfection method suitable for transfecting mRNA, for example they may be electroporated into mammalian cells, such as HELA or HDF cells, and samples may be analyzed certain time points after transfection, for example, 6 hours, 24 hours, 48 hours, and 72 hours post transfection. Said samples may be analyzed for mRNA quantities and/or protein quantities by methods well known to the skilled person. For example, the quantities of reporter mRNA present in the cells at the sample time points may be determined by quantitative PCR methods. The quantities of reporter protein encoded by the respective mRNAs may be determined, e.g., by ELISA assays or reporter assays such as luciferase assays depending on the reporter protein used. The effect of stabilizing protein expression and/or prolonging protein expression may be, for example, analyzed by determining the ratio of the protein level observed 48 hours post transfection and the protein level observed 6 hours post transfection. The closer said value is to 1, the more stable the protein expression is within this time period. Said value may also be above 1 if the protein level is higher at the later time point. Such measurements may of course also be performed at 72 or more hours and the ratio of the protein level observed 72 hours post transfection and the protein level observed 6 hours post transfection may be determined to determine stability of protein expression.

Preferably, the 3'UTR element of the artificial nucleic acid molecule according to the present invention comprises or consists of a nucleic acid sequence which has an identity of at least about 40%, preferably of at least about 50%, preferably of at least about 60%, preferably of at least about 70%, more preferably of at least about 80%, more preferably of at least about 90%, even more preferably of at least about 95%, even more preferably of at least about 99%, most preferably of 100% to a nucleic acid sequence selected from SEQ ID NOs. 1369-1377 and 1434 and corresponding RNA sequences, wherein the variants of the sequences according to SEQ ID NOs. 1369-1377 and 1434 are preferably functional variants as described above. SEQ ID NOs. 1369, 1371 and 1434, variants thereof, and corresponding RNA sequences are particularly preferred.

The 3'UTR element of the artificial nucleic acid molecule according to the present invention may also comprise or consist of a fragment of a nucleic acid sequence which has an identity of at least about 40%, preferably of at least about 50%, preferably of at least about 60%, preferably of at least about 70%, more preferably of at least about 80%, more preferably of at least about 90%, even more preferably of at least about 95%, even more preferably of at least about 99%, most preferably of 100% to the nucleic acid sequence according to SEQ ID No. 1369-1377 and 1434 and of corresponding RNA sequences, wherein the fragment is preferably a functional fragment or a functional variant fragment as described above. Preferably, the fragment is as described above, i.e. being a continuous stretch of nucleotides representing at least 20% etc. of the full-length 3'UTR the fragment is derived from. Such fragment preferably exhibits a length of at least about 40 nucleotides, preferably of at least about 50 nucleotides, preferably of at least about 75 nucleotides, more preferably of at least about 100 nucleotides, even more preferably of at least about 125 nucleotides, most preferably of at least about 150 nucleotides.

For example, such fragment may exhibit a nucleic acid sequence according to SEQ ID Nos. 1378-1390, such as:

```
                                        (SEQ ID No. 1378)
AAAAGCATCT CAGCCTACCA TGAGAATAAG AGAAAGAAAA

TGAAGATCAA AAGCTTATTC ATCTGTTTTT CTTTTTCGTT

GGTGTAAAGC CAACACCCTG TCTAAAAAAC ATAAATTTCT

TTAATCATTT TGCCTCTTTT CTCTGTGCTT CAATT (SEQ ID No. 1379)
CATCACATTT AAAAGCATCT CAGCCTACCA TGAGAATAAG

AGAAAGAAAA TGAAGATCAA AAGCTTATTC ATCTGTTTTT

CTTTTTCGTT GGTGTAAAGC CAACACCCTG (SEQ ID No. 1380)
AAAAGCATCT CAGCCTACCA TGAGAATAAG AGAAAGAAAA

TGAAGATCAA AAGCTTATTC ATCTGTTTTT CTTTTTCGTT

GGTGTAAAGC CAACACCCTG TCTAAAAAAC (SEQ ID No. 1381)
CAGCCTACCA TGAGAATAAG AGAAAGAAAA TGAAGATCAA

AAGCTTATTC ATCTGTTTTT CTTTTTCGTT GGTGTAAAGC

CAACACCCTG TCTAAAAAAC ATAAATTTCT (SEQ ID No. 1382)
TGAGAATAAG AGAAAGAAAA TGAAGATCAA AAGCTTATTC

ATCTGTTTTT CTTTTTCGTT GGTGTAAAGC CAACACCCTG

TCTAAAAAAC ATAAATTTCT TTAATCATTT (SEQ ID No. 1383)
AGAAAGAAAA TGAAGATCAA AAGCTTATTC ATCTGTTTTT

CTTTTTCGTT GGTGTAAAGC CAACACCCTG TCTAAAAAAC

ATAAATTTCT TTAATCATTT TGCCTCTTTT (SEQ ID No. 1384)
TGAAGATCAA AAGCTTATTC ATCTGTTTTT CTTTTTCGTT

GGTGTAAAGC CAACACCCTG TCTAAAAAAC ATAAATTTCT

TTAATCATTT TGCCTCTTTT CTCTGTGCTT (SEQ ID No. 1385)
AAGCTTATTC ATCTGTTTTT CTTTTTCGTT GGTGTAAAGC

CAACACCCTG TCTAAAAAAC ATAAATTTCT TTAATCATTT

TGCCTCTTTT CTCTGTGCTT CAATTAATAA (SEQ ID No. 1386)
ATCTGTTTTT CTTTTTCGTT GGTGTAAAGC CAACACCCTG

TCTAAAAAAC ATAAATTTCT TTAATCATTT TGCCTCTTTT

CTCTGTGCTT CAATTAATAA AAAATGGAAA (SEQ ID No. 1387)
CAGCCTACCA TGAGAATAAG AGAAAGAAAA TGAAGATCAA

AAGCTTATTC ATCTGTTTTT CTTTTTCGTT GGTGTAAAGC

CAACACCCTG TCTAAAAAAC ATAAATTTCT TTAATCATTT

TGCCTCTTTT CTCTGTGCTT CAATTAATAA A (SEQ ID No. 1388)
TGAAGATCAA AAGCTTATTC ATCTGTTTTT CTTTTTCGTT

GGTGTAAAGC CAACACCCTG TCTAAAAAAC ATAAATTTCT

TTAATCATTT TGCCTCTTTT CTCTGTGCTT CAATTAATAA

A (SEQ ID No. 1389)
CTTTTTCGTT GGTGTAAAGC CAACACCCTG TCTAAAAAAC

ATAAATTTCT TTAATCATTT TGCCTCTTTT CTCTGTGCTT

CAATTAATAA A (SEQ ID No. 1390)
AAGCTTATTC ATCTGTTTTT CTTTTTCGTT GGTGTAAAGC

CAACACCCTG TCTAAAAAAC
``` or the corresponding RNA sequence, or a nucleic acid sequence which is at least 40%, preferably at least about 50%, preferably at least about 60%, preferably at least about 70%, more preferably at least about 80%, more preferably at least about 90%, even more preferably at least about 95%, even more preferably at least about 99% identical to said nucleic acid sequences or the corresponding RNA sequence. Thus, the at least one 3'UTR element of the artificial nucleic acid molecule according to the present invention may comprise or consist of a nucleic acid fragment as described above. Obviously, the thymidine nucleotides comprised in the fragments according to SEQ ID Nos. 1378-1390 may be replaced by uridine nucleotides.

Preferably, said variants, fragments or variant fragments are functional variants, functional fragments, or functional variant fragments as described above, exhibiting at least one function of the nucleic acid sequence according to SEQ ID Nos. 1369-1377 and 1434, such as stabilization of the artificial nucleic acid molecule according to the invention, stabilizing and/or prolonging protein expression from the artificial nucleic acid molecule according to the invention, and/or increasing protein production, preferably with an efficiency of at least 40%, more preferably of at least 50%, more preferably of at least 60%, even more preferably of at least 70%, even more preferably of at least 80%, most preferably of at least 90% of the stabilizing efficiency and/or protein production increasing efficiency exhibited by the nucleic acid sequence according to SEQ ID Nos. 1369-1377 and 1434. Preferably, variants, fragments or variant fragments are functional variants, functional fragments, or functional variant fragments exhibit the function of acting synergistically with the 5'UTR element to increase protein production from the artificial nucleic acid molecule.

Preferably, the 3'UTR element of the artificial nucleic acid molecule according to the present invention exhibits a length of at least about 40 nucleotides, preferably of at least about 50 nucleotides, preferably of at least about 75 nucleotides, more preferably of at least about 100 nucleotides, even more preferably of at least about 125 nucleotides, most preferably of at least about 150 nucleotides. For example, the 3'UTR may exhibit a length of about 50 to about 300 nucleotides, preferably of about 100 to about 250 nucleotides, more preferably of about 150 to about 200 nucleotides.

Furthermore, the artificial nucleic acid molecule according to the present invention may comprise more than one 3'UTR elements as described above. For example, the artificial nucleic acid molecule according to the present invention may comprise one, two, three, four or more 3'UTR elements, wherein the individual 3'UTR elements may be the same or they may be different. For example, the artificial nucleic acid molecule according to the present invention may comprise two essentially identical 3'UTR elements as described above, e.g. two 3'UTR elements comprising or consisting of a nucleic acid sequence which is derived from the 3'UTR of an albumin gene or an α-globin gene or from a variant of the 3'UTR of an albumin gene or of an α-globin gene, such as a nucleic acid sequence according to SEQ ID No. 1369, 1371, 1376, or 1434, functional variants thereof, functional fragments thereof, or functional variant fragments thereof as described above.

In a preferred embodiment, the artificial nucleic acid molecule comprises (a.) at least one 5'UTR element which comprises or consists of a nucleic acid sequence which is derived from the 5'UTR of a TOP gene encoding a ribosomal protein as described above, for example, encoding a ribosomal Large protein, or from a variant thereof, (b.) at least one open reading frame, (c.) at least one histone stem-loop as described herein, such as at least one histone stem-loop according to SEQ ID NOs. 1391-1433, optionally (d.) a poly(A) sequence or a poly(A) signal, optionally (e.) a poly(C) sequence, and optionally (f.) at least one 3'UTR element, preferably derived from a gene providing a stable mRNA, e.g., which comprises or consists of a nucleic acid sequence which is derived from the 3'UTR of an albumin gene or an α-globin gene, such as a sequence selected from the group consisting of SEQ ID NOs: 1369, 1371, and 1434 or a variant thereof as described herein.

Preferably, the sequence of elements of the artificial nucleic acid molecule in 5'-to-3'-direction is 5'-[at least one 5'UTR]-[ORF]-[optional at least one 3'UTR]-[optional poly (A) sequence]-[optional poly(C) sequence]-[at least one histone stem-loop]-3'.

In a particularly preferred embodiment, the artificial nucleic acid molecule comprises (a.) at least one 5'UTR element which comprises or consists of a nucleic acid sequence which is derived from the 5'UTR of a ribosomal protein Large 32 gene (RPL32), a ribosomal protein Large 35 gene (RPL35), a ribosomal protein Large 21 gene (RPL21), an ATP synthase, H+ transporting, mitochondrial F1 complex, alpha subunit 1, cardiac muscle (ATP5A1) gene, an hydroxysteroid (17-beta) dehydrogenase 4 gene (HSD17B4), an androgen-induced 1 gene (AIG1), cytochrome c oxidase subunit VIc gene (COX6C), or a N-acylsphingosine amidohydrolase (acid ceramidase) 1 gene (ASAH1) or from a variant thereof, preferably from a vertebrate ribosomal protein Large 32 gene (RPL32), a vertebrate ribosomal protein Large 35 gene (RPL35), a vertebrate ribosomal protein Large 21 gene (RPL21), a vertebrate ATP synthase, H+ transporting, mitochondrial F1 complex, alpha subunit 1, cardiac muscle (ATP5A1) gene, a vertebrate hydroxysteroid (17-beta) dehydrogenase 4 gene (HSD17B4), a vertebrate androgeninduced 1 gene (AIG1), a vertebrate cytochrome c oxidase subunit VIc gene (COX6C), or a vertebrate N-acylsphingosine amidohydrolase (acid ceramidase) 1 gene (ASAH1) or from a variant thereof, more preferably from a mammalian ribosomal protein Large 32 gene (RPL32), a ribosomal protein Large 35 gene (RPL35), a ribosomal protein Large 21 gene (RPL21), a mammalian ATP synthase, H+ transporting, mitochondrial F1 complex, alpha subunit 1, cardiac muscle (ATP5A1) gene, a mammalian hydroxysteroid (17-beta) dehydrogenase 4 gene (HSD17B4), a mammalian androgen-induced 1 gene (AIG1), a mammalian cytochrome c oxidase subunit VIc gene (COX6C), or a mammalian N-acylsphingosine amidohydrolase (acid ceramidase) 1 gene (ASAH1) or from a variant thereof, most preferably from a human ribosomal protein Large 32 gene (RPL32), a human ribosomal protein Large 35 gene (RPL35), a human ribosomal protein Large 21 gene (RPL21), a human ATP synthase, H+ transporting, mitochondrial F1 complex, alpha subunit 1, cardiac muscle (ATP5A1) gene, a human hydroxysteroid (17-beta) dehydrogenase 4 gene (HSD17B4), a human androgeninduced 1 gene (AIG1), a human cytochrome c oxidase subunit VIc gene (COX6C), or a human N-acylsphingosine amidohydrolase (acid ceramidase) 1 gene (ASAH1) or from a variant thereof, wherein preferably the 5'UTR element does not comprise the 5'TOP of said gene, such as the sequence according to SEQ ID NO: 1368 or SEQ ID NOs 1452-1460 or a variant thereof, (b.) at least one open reading frame, (c.) at least one histone stem-loop, such as at least one histone stem-loop according to SEQ ID NOs. 1391-1433, optionally (d.) a poly(A) sequence and/or a poly(A) signal, optionally (e.) a poly(C) sequence, and optionally (f.) at least one 3'UTR element which comprises or consists of a nucleic acid sequence which is derived from an albumin gene or an α-globin gene, such as a sequence selected from the group consisting of SEQ ID NOs: 1369, 1371, and 1434 or a variant thereof as described herein.

In a particularly preferred embodiment, the artificial nucleic acid molecule according to the present invention comprises:

(a.) at least one 5'UTR element which comprises or consists of a nucleic acid sequence which has an identity of at least about 40%, preferably of at least about 50%, preferably of at least about 60%, preferably of at least about 70%, more preferably of at least about 80%, more preferably of at least about 90%, even more preferably of at least about 95%, even more preferably of at least about 99% to the nucleic acid sequence according to SEQ ID No. 1368 or SEQ ID NOs. 1452-1460, or a corresponding RNA sequence, (b.) at least one open reading frame, (c.) at least one histone stem-loop as described herein, such as a histone stem-loop sequence according to any one of SEQ ID NOs. 1391-1433, preferably a histone stem-loop sequence having a sequence identity of at least about 75%, preferably of at least about 80%, preferably at least about 85%, more preferably at least about 90%, even more preferably at least about 95% to the sequence according to SEQ ID NO. 1433 or a corresponding RNA sequence, wherein preferably positions 6, 13 and 20 of the sequence having a sequence identity of at least about 75%, preferably of at least about 80%, preferably at least about 85%, more preferably at least about 90%, even more preferably at least about 95% to the sequence according to SEQ ID NO. 1433 or the corresponding RNA sequence are conserved, i.e. are identical to the nucleotides at positions 6, 13 and 20 of SEQ ID NO. 1433, (d.) optionally, a poly(A) sequence or a poly(A) signal as described herein, (e.) optionally, a poly(C) sequence, and (f.) optionally, a 3'UTR element, preferably a 3'UTR element which is derived from a gene providing a stable mRNA, such as a 3'UTR element which comprises or consists of a nucleic acid sequence which has an identity of at least about 40%, preferably of at least about 50%, preferably of at least about 60%, preferably of at least about 70%, more preferably of at least about 80%, more preferably of at least about 90%, even more preferably of at least about 95%, even more preferably of at least about 99%, most preferably of 100% to the nucleic acid sequence according to SEQ ID No. 1369, 1371, or 1434 or a corresponding RNA sequence.

Thus, in a particularly preferred embodiment, the present invention provides an artificial nucleic acid molecule comprising a 5'UTR element which comprises or consists of a nucleic acid sequence which has an identity of at least about 90% to the nucleic acid sequence according to SEQ ID No. 1368 or SEQ ID NOs. 1452-1460, or a corresponding RNA sequence, a histone stem-loop comprising a sequence which has an identity of at least about 90% to the sequence according to SEQ ID NO. 1434 or a corresponding RNA sequence, optionally a poly(A) sequence and/or a poly(A) signal as described herein, optionally a poly(C) sequence, and optionally a 3'UTR element which comprises or consists of a nucleic acid sequence which has an identity of at least about 90% to the nucleic acid sequence according to SEQ ID No. 1369, 1371 or 1434.

Preferably, the artificial nucleic acid molecule according to the present invention does not contain one or two or at least one or all but one or all of the components of the group consisting of: a sequence encoding a ribozyme (preferably a self-splicing ribozyme), a viral nucleic acid sequence, a histone stem-loop processing signal, in particular a histone stem-loop processing sequence derived from mouse histon H2A614 gene, a Neo gene, an inactivated promoter sequence and an inactivated enhancer sequence. Even more preferably, the nucleic acid according to the invention does not contain a ribozyme, preferably a self-splicing ribozyme, and one of the group consisting of: a Neo gene, an inactivated promotor sequence, an inactivated enhancer sequence, a histon stem-loop processing signal, in particular a histon-stem loop processing sequence derived from mouse histon H2A614 gene. Accordingly, the nucleic acid may in a preferred mode neither contain a ribozyme, preferably a self-splicing ribozyme, nor a Neo gene or, alternatively, neither a ribozyme, preferably a self-splicing ribozyme, nor any resistance gene (e.g. usually applied for selection). In an other preferred mode, the nucleic acid molecule of the invention may neither contain a ribozyme, preferably a self-splicing ribozyme, nor a histone stem-loop processing signal, in particular a histone stem-loop processing sequence derived from mouse histone H2A614 gene.

Furthermore, it is preferred that the inventive artificial nucleic acid molecule according to the present invention does not comprise an intron.

The artificial nucleic acid molecule according to the present invention may be RNA, such as mRNA, DNA, such as a DNA vector, or may be a modified RNA or DNA molecule. It may be provided as a double-stranded molecule having a sense strand and an anti-sense strand, for example, as a DNA molecule having a sense strand and an anti-sense strand.

The invention also provides an artificial nucleic acid molecule which is an mRNA molecule comprising a, 5'UTR element, an open reading frame, a histone stem-loop as described herein, an optional 3'UTR element as described herein and an optional poly(A) sequence.

The artificial nucleic acid molecule according to the present invention may further comprise a 5'-cap. The optional 5'-cap is preferably attached to the 5'-side of the 5'UTR element.

The invention provides an artificial nucleic acid molecule which may be a template for an RNA molecule, preferably for an mRNA molecule, which is stabilised and optimized with respect to translation efficiency. In other words, the artificial nucleic acid molecule may be a DNA or RNA which may be used for production of an mRNA. The obtainable mRNA, may, in turn, be translated for production of a desired peptide or protein encoded by the open reading frame. If the artificial nucleic acid molecule is a DNA, it may, for example, be used as a double-stranded storage form for continued and repetitive in vitro or in vivo production of mRNA.

Potential transcription systems are in vitro transcription systems or cellular transcription systems etc. Accordingly, transcription of an artificial nucleic acid molecule according to the invention, e.g. transcription of an artificial nucleic acid molecule comprising a 5'UTR element, an open reading frame, a histone stem-loop, a 3'UTR element, and a poly-adenylation-signal, may result in an mRNA molecule comprising a 5'UTR element, an open reading frame, a histone stem-loop, a 3'UTR element and a poly(A) sequence.

For example, the artificial nucleic acid molecule according to the present invention may comprise a nucleic acid sequence corresponding to the DNA sequence (SEQ ID No. 1377)
CATCACATTT AAAAGCATCT CAGCCTACCA TGAGAATAAG

AGAAAGAAAA TGAAGATCAA AAGCTTATTC ATCTGTTTTT

CTTTTTCGTT GGTGTAAAGC CAACACCCTG TCTAAAAAAC

```
ATAAATTTCT TTAATCATTT TGCCTCTTTT CTCTGTGCTT

CAATTAATAA AAAATGGAAA GAATCTAGAT CTAAAAAAAA

AAAAAAAAAA AAAAAAAAAA AAAAAAAAAA AAAAAAAAAA

AAAAAAAAAA AAAAAA.
```

Transcription of such a sequence may result in an artificial nucleic acid molecule comprising a corresponding RNA sequence.

Such artificial RNA molecule may also be obtainable in vitro by common methods of chemical synthesis without being necessarily transcribed from a DNA progenitor.

In a particularly preferred embodiment, the artificial nucleic acid molecule according to the present invention is an RNA molecule, preferably an mRNA molecule comprising in 5'-to-3'-direction a 5'UTR element as described above, an open reading frame, an optional 3'UTR element as described above, an optional poly(A) sequence, an optional poly(C) sequence, and a histone stem-loop as described herein.

In some embodiments, the artificial nucleic acid molecule comprises further elements such as an IRES-motif. An internal ribosome entry side (IRES) sequence or IRES-motif may separate several open reading frames, for example if the artificial nucleic acid molecule encodes for two or more peptides or proteins. An IRES-sequence may be particularly helpful if the mRNA is a bi- or multicistronic RNA.

Furthermore, the artificial nucleic acid molecule may comprise additional 5'-elements such as a promoter or enhancer sequence. The promoter may drive and or regulate transcription of the artificial nucleic acid molecule according to the present invention, for example of an artificial DNA molecule according to the present invention.

In preferred embodiments, the invention provides artificial nucleic acid molecules, preferably mRNA molecules, comprising in 5'-to-3'-direction at least one of the following structures:

5'-cap—5'UTR element—ORF—3'UTR element—histone stem-loop—poly(A) sequence

5'-cap—5'UTR element—ORF—3'UTR element—poly(A) sequence—histone stem-loop

5'-cap—5'UTR element—ORF—IRES—ORF—3'UTR element—histone stem-loop—poly(A) sequence 5'-cap—5'UTR element—ORF—IRES—ORF—3'UTR element—poly(A) sequence—histone stem-loop 5'-cap—5'UTR element—ORF—3'UTR element—poly(A) sequence—poly(C) sequence—histone stem-loop 5'-cap—5'UTR element—ORF—IRES—ORF—3'UTR element—poly(A) sequence—poly(C) sequence—histone stem-loop 5'-cap—5'UTR element—ORF—IRES—ORF—3'UTR element—histone stem-loop—poly(A) sequence—poly(C) sequence More preferably, the inventive artificial nucleic acid molecule comprises or codes for (a.) a 5'UTR-element; (b.) an open reading frame, preferably encoding a peptide or protein; (c.) at least one histone stem-loop, optionally (d.) a poly(A) sequence and/or polyadenylation signal; (e.) optionally a poly(C) sequence; and (f.) optionally a 3'UTR element, preferably for increasing the expression level of an encoded protein, wherein the encoded protein is preferably no histone protein, no reporter protein and/or no marker or selection protein, as defined above. The elements (c.) to (f.) of the inventive artificial nucleic acid molecule may occur in the inventive artificial nucleic acid molecule in any sequence, i.e. the elements (a.), (b.), (c.), (d.), (e.) and (f.) may, for example, occur in the sequence (a.), (b.), (c.), (d.), (e.) and (f.), or (a.), (b.), (d.), (c.), (e.) and (f.), or (a.), (b.), (c.), (d.), (f.) and (e.), or (a.), (b.), (d.), (c.), (f.) and (e.), or (a.), (b.), (e.), (d.), (c.) and (f.), or (a.), (b.), (e.), (d.), (f.) and (c.), or (a.), (b.), (c.), (f.), (e.) and (d.) etc., wherein further elements as described herein, may also be contained, such as a 5'-CAP structure, stabilization sequences, IRES sequences, etc. Each of the elements (a.) to (f.) of the inventive artificial nucleic acid molecule, particularly b), may occur in di- or multicistronic constructs and/or each of the elements (a.), (c.) and (f.) may also be repeated at least once, preferably twice or more in the inventive artificial nucleic acid molecule. As an example, the inventive artificial nucleic acid molecule may comprise its sequence elements (a.), (b.), (c.) and optionally (d.) in e.g. the following order. In all cases the artificial nucleic acid molecule may additionally comprise one or more optional 3'UTR element(s) and/or a poly(C) sequence as defined herein:

5'UTR—ORF—histone stem-loop—3'; or

5'UTR—ORF—ORF—histone stem-loop—3'; or

5' UTR—ORF—IRES—ORF—histone stem-loop—3'; or

5' UTR—ORF—histone stem-loop—poly(A) sequence—3'; or

5' UTR—ORF—histone stem-loop—polyadenylation signal—3'; or

5' UTR—ORF—ORF—histone stem-loop—polyadenylation signal—3'; or

5' UTR—ORF—histone stem-loop—histone stem-loop—3'; or

5' UTR—ORF—histone stem-loop—histone stem-loop—poly(A) sequence—3'; or

5' UTR—ORF—histone stem-loop—histone stem-loop—polyadenylation signal—3'; or

5' UTR—ORF—histone stem-loop—poly(A) sequence—histone stem-loop—3'; or

5' UTR—ORF—poly(A) sequence—histone stem-loop—3'; or

5' UTR—ORF—poly(A) sequence—histone stem-loop—histone stem-loop—3'; etc.

It is preferred that the above sequences comprise a poly(C) sequence. Preferably, this poly(C) sequence is located 5' to the histone stem-loop, preferably between the poly(A) sequence and the histone stem-loop sequence.

In this context, it is particularly preferred that the inventive artificial nucleic acid molecule comprises or codes for a) a 5'UTR element, b) an open reading frame, preferably encoding a peptide or protein; c) at least one histone stem-loop, and d) a poly(A) sequence or polyadenylation sequence; preferably for increasing the expression level of an encoded protein, wherein the encoded protein is preferably no histone protein, no reporter protein (e.g. Luciferase, GFP, EGFP, β-Galactosidase, particularly EGFP) and/or no marker or selection protein (e.g. alpha-Globin, Galactokinase and Xanthine:Guanine phosphoribosyl transferase (GPT)).

The open reading frame of the artificial nucleic acid molecule is not particularly limited. For example, the open reading frame may encode a protein or peptide that may be used for therapy of a disease. The particular choice of the protein or peptide depends on the disease to be treated and is not the subject of the invention. Accordingly, the artificial nucleic acid molecule may be for use in treatment of a disease that is treatable with the protein or peptide that is encoded by the open reading frame. The open reading frame may also encode a protein or peptide that may be used as an antigen for vaccination. Again, the particular choice of the protein or peptide depends on the disease or infection to be prevented. Accordingly, the artificial nucleic acid molecule may be for use in prevention of a disease by inducing a specific immune response.

However, the encoded protein is preferably no histone protein. In the context of the present invention, such a histone protein is typically a strongly alkaline protein found in eukaryotic cell nuclei, which package and order the DNA into structural units called nucleosomes. Histone proteins are the chief protein components of chromatin, act as spools around which DNA winds, and play a role in gene regulation. Without histones, the unwound DNA in chromosomes would be very long (a length to width ratio of more than 10 million to one in human DNA). For example, each human cell has about 1.8 meters of DNA, but wound on the histones it has about 90 millimeters of chromatin, which, when duplicated and condensed during mitosis, result in about 120 micrometers of chromosomes. More preferably, in the context of the present invention, such a histone protein is typically defined as a highly conserved protein selected from one of the following five major classes of histones: H1/H5, H2A, H2B, H3, and H4", preferably selected from mammalian histone, more preferably from human histones or histone proteins. Such histones or histone proteins are typically organised into two super-classes defined as core histones, comprising histones H2A, H2B, H3 and H4, and linker histones, comprising histones H1 and H5.

In this context, linker histones, are preferably excluded from the scope of protection of the pending invention, preferably mammalian linker histones, more preferably human linker histones, are typically selected from H1, including H1F, particularly including H1F0, H1FNT, H1FOO, H1FX, and H1H1, particularly including HIST1H1A, HIST1H1B, HIST1H1C, HIST1H1D, HIST1H1E, HIST1H1T.

Furthermore, in some embodiments, core histones which are preferably excluded from the scope of protection of the pending invention, preferably mammalian core histones, more preferably human core histones, are typically selected from H2A, including H2AF, particularly including H2AFB1, H2AFB2, H2AFB3, H2AFJ, H2AFV, H2AFX, H2AFY, H2AFY2, H2AFZ, and H2A1, particularly including HIST1H2AA, HIST1H2AB, HIST1H2AC, HIST1H2AD, HIST1H2AE, HIST1H2AG, HIST1H2AI, HIST1H2AJ, HIST1H2AK, HIST1H2AL, HIST1H2AM, and H2A2, particularly including HIST2H2AA3, HIST2H2AC; H2B, including H2BF, particularly including H2BFM, H2BFO, H2BFS, H2BFWT H2B1, particularly including HIST1H2BA, HIST1H2BB, HIST1H2BC, HIST1H2BD, HIST1H2BE, HIST1H2BF, HIST1H2BG, HIST1H2BH, HIST1H2BI, HIST1H2BJ, HIST1H2BK, HIST1H2BL, HIST1H2BM, HIST1H2BN, HIST1H2B0, and H2B2, particularly including HIST2H2BE; H3, including H3A1, particularly including HIST1H3A, HIST1H3B, HIST1H3C, HIST1H3D, HIST1H3E, HIST1H3F, HIST1H3G, HIST1H3H, HIST1H3I, HIST1H3J, and H3A2, particularly including HIST2H3C, and H3A3, particularly including HIST3H3; H4, including H41, particularly including HIST1H4A, HIST1H4B, HIST1H4C, HIST1H4D, HIST1H4E, HIST1H4F, HIST1H4G, HIST1H4H, HIST1H4I, HIST1H4J, HIST1H4K, HIST1H4L, and H44, particularly including HIST4H4, and H5.

Preferably, the protein encoded by the open reading frame is no reporter protein (e.g. Luciferase, Green Fluorescent Protein (GFP), Enhanced Green Fluorescent Protein (EGFP), β-Galactosidase) and no marker or selection protein (e.g. alpha-globin, Galactokinase and Xanthine:guanine phosphoribosyl transferase (GPT)). Preferably, the artificial nucleic acid molecule of the invention does not contain a (bacterial) Neo gene sequence (Neomycin resistance gene).

Preferably, the ORF does not code for a protein selected from the group consisting of albumin proteins, α-globin proteins, β-globin proteins, tyrosine hydroxylase proteins, lipoxygenase proteins, and collagen alpha proteins.

In a preferred embodiment, the open reading frame does not code for human albumin, provided that the 3'UTR element is identical to the 3'UTR of human albumin. In some further embodiment, it is preferred that the open reading frame does not code for human albumin according to GenBank Accession number NM_000477.5 provided that the 3'UTR element is identical to the 3'UTR of human albumin. In some further embodiments, it is preferred that the open reading frame does not code for human albumin or variants thereof provided that the 3'UTR element is a sequence which is identical to SEQ ID No. 1369 or to a corresponding RNA sequence.

Furthermore, in some embodiments, it is preferred that the open reading frame does not code for a reporter protein selected from the group consisting of globin proteins, luciferase proteins, GFP proteins or variants thereof, for example, variants exhibiting at least 70% sequence identity to a globin protein, a luciferase protein, or a GFP protein.

Preferably, the artificial nucleic acid molecule, preferably the open reading frame, is at least partially G/C modified. Thus, the inventive artificial nucleic acid molecule may be thermodynamically stabilized by modifying the G (guanosine)/C (cytidine) content of the molecule. The G/C content of the open reading frame of an artificial nucleic acid molecule according to the present invention may be increased compared to the G/C content of the open reading frame of a corresponding wild type sequence, preferably by using the degeneration of the genetic code. Thus, the encoded amino acid sequence of the nucleic acid molecule is preferably not modified by the G/C modification compared to the coded amino acid sequence of the particular wild type sequence. The codons of a coding sequence or a whole nucleic acid molecule, e.g. an mRNA, may therefore be varied compared to the wild type coding sequence, such that they include an increased amount of G/C nucleotides while the translated amino acid sequence is maintained. In respect to the fact that several codons code for one and the same amino acid (so-called degeneration of the genetic code), the most favourable codons for the stability can be determined (so-called alternative codon usage).

Depending on the amino acid to be encoded by the coding region of the inventive nucleic acid molecule as defined herein, there are various possibilities for modification of the nucleic acid sequence, e.g. the open reading frame, compared to its wild type coding region. In the case of amino acids which are encoded by codons which contain exclusively G or C nucleotides, no modification of the codon is necessary. Thus, the codons for Pro (CCC or CCG), Arg (CGC or CGG), Ala (GCC or GCG) and Gly (GGC or GGG) require no modification, since no A or U/T is present.

In contrast, codons which contain A and/or U/T nucleotides may be modified by substitution of other codons which code for the same amino acids but contain no A and/or U/T. For example the codons for Pro can be modified from CC(U/T) or CCA to CCC or CCG;

the codons for Arg can be modified from CG(U/T) or CGA or AGA or AGG to CGC or CGG;

the codons for Ala can be modified from GC(U/T) or GCA to GCC or GCG;

the codons for Gly can be modified from GG(U/T) or GGA to GGC or GGG.

In other cases, although A or (U/T) nucleotides cannot be eliminated from the codons, it is however possible to decrease the A and (U/T) content by using codons which contain a lower content of A and/or (U/T) nucleotides. Examples of these are:

The codons for Phe can be modified from (U/T)(U/T)(U/T) to (U/T) (U/T)C;

the codons for Leu can be modified from (U/T) (U/T)A, (U/T) (U/T)G, C(U/T) (U/T) or C(U/T)A to C(U/T)C or C(U/T)G;

the codons for Ser can be modified from (U/T)C(U/T) or (U/T)CA or AG(U/T) to (U/T)CC, (U/T)CG or AGC;

the codon for Tyr can be modified from (U/T)A(U/T) to (U/T)AC;

the codon for Cys can be modified from (U/T)G(U/T) to (U/T)GC;

the codon for His can be modified from CA(U/T) to CAC;

the codon for Gln can be modified from CAA to CAG;

the codons for Ile can be modified from A(U/T)(U/T) or A(U/T)A to A(U/T)C;

the codons for Thr can be modified from AC(U/T) or ACA to ACC or ACG;

the codon for Asn can be modified from AA(U/T) to AAC;

the codon for Lys can be modified from AAA to AAG;

the codons for Val can be modified from G(U/T)(U/T) or G(U/T)A to G(U/T)C or G(U/T)G;

the codon for Asp can be modified from GA(U/T) to GAC;

the codon for Glu can be modified from GAA to GAG;

the stop codon (U/T)AA can be modified to (U/T)AG or (U/T)GA.

In the case of the codons for Met (A(U/T)G) and Trp ((U/T)GG), on the other hand, there is no possibility of sequence modification without altering the encoded amino acid sequence.

The substitutions listed above can be used either individually or in all possible combinations to increase the G/C content of the open reading frame of the inventive nucleic acid sequence as defined herein, compared to its particular wild type open reading frame (i.e. the original sequence). Thus, for example, all codons for Thr occurring in the wild type sequence can be modified to ACC (or ACG).

Preferably, the G/C content of the open reading frame of the inventive artificial nucleic acid molecule as defined herein is increased by at least 7%, more preferably by at least 15%, particularly preferably by at least 20%, compared to the G/C content of the wild type coding region. According to a specific embodiment at least 5%, 10%, 20%, 30%, 40%, 50%, 60%, more preferably at least 70%, even more preferably at least 80% and most preferably at least 90%, 95% or even 100% of the substitutable codons in the open reading frame of the inventive artificial nucleic acid molecule or a fragment, variant or derivative thereof are substituted, thereby increasing the G/C content of said open reading frame.

In this context, it is particularly preferable to increase the G/C content of the open reading frame of the inventive nucleic acid sequence as defined herein, to the maximum (i.e. 100% of the substitutable codons), compared to the wild type open reading frame.

Furthermore, the open reading frame is preferably at least partially codon-optimized. Codon-optimization is based on the finding that the translation efficiency may be determined by a different frequency in the occurrence of transfer RNAs (tRNAs) in cells. Thus, if so-called "rare codons" are present in the coding region of the inventive artificial nucleic acid molecule as defined herein, to an increased extent, the translation of the corresponding modified nucleic acid sequence is less efficient than in the case where codons coding for relatively "frequent" tRNAs are present.

Thus, the open reading frame of the inventive nucleic acid sequence is preferably modified compared to the corresponding wild type coding region such that at least one codon of the wild type sequence which codes for a tRNA which is relatively rare in the cell is exchanged for a codon which codes for a tRNA which is comparably frequent in the cell and carries the same amino acid as the relatively rare tRNA. By this modification, the open reading frame of the inventive artificial nucleic acid molecule as defined herein, is modified such that codons for which frequently occurring tRNAs are available may replace codons which correspond to rare tRNAs. In other words, according to the invention, by such a modification all codons of the wild type open reading frame which code for a rare tRNA may be exchanged for a codon which codes for a tRNA which is more frequent in the cell and which carries the same amino acid as the rare tRNA. Which tRNAs occur relatively frequently in the cell and which, in contrast, occur relatively rarely is known to a person skilled in the art; cf. e.g. Akashi, Curr. Opin. Genet. Dev. 2001, 11(6): 660-666. Accordingly, preferably, the open reading frame is codon-optimized, preferably with respect to the system in which the nucleic acid molecule according to the present invention is to be expressed, preferably with respect to the system in which the nucleic acid molecule according to the present invention is to be translated. Preferably, the codon usage of the open reading frame is codon-optimized according to mammalian codon usage, more preferably according to human codon usage. Preferably, the open reading frame is codon-optimized and G/C-content modified.

For further improving degradation resistance, e.g. resistance to in vivo degradation by an exo- or endonuclease, and/or for further improving protein production from the artificial nucleic acid molecule according to the present invention, the artificial nucleic acid molecule may further comprise modifications, such as backbone modifications, sugar modifications and/or base modifications, e.g., lipid-modifications or the like. Preferably, the transcription and/or the translation of the artificial nucleic acid molecule according to the present invention is not significantly impaired by said modifications.

Nucleotide analogues/modifications that may be used in the context of the present invention may be selected, for example, from 2-amino-6-chloropurineriboside-5'-triphosphate, 2-aminoadenosine-5'-triphosphate, 2-thiocytidine-5'-triphosphate, 2-thiouridine-5'-triphosphate, 4-thiouridine-5'-triphosphate, 5-aminoallylcytidine-5'-triphosphate, 5-aminoallyluridine-5'-triphosphate, 5-bromocytidine-5'-triphosphate, 5-bromouridine-5'-triphosphate, 5-iodocytidine-5'-triphosphate, 5-iodouridine-5'-triphosphate, 5-methylcytidine-5'-triphosphate, 5-methyluridine-5'-triphosphate, 6-azacytidine-5'-triphosphate, 6-azauridine-5'-triphosphate, 6-chloropurineriboside-5'-triphosphate, 7-deazaadenosine-5'-triphosphate, 7-deazaguanosine-5'-triphosphate, 8-azaadenosine-5'-triphosphate, 8-azidoadenosine-5'-triphosphate, benzimidazole-riboside-5'-triphosphate, N1-methyladenosine-5'-triphosphate, N1-methylguanosine-5'-triphosphate, N6-methyladenosine-5'-triphosphate, O6-methylguanosine-5'-triphosphate, pseudouridine-5'-triphosphate, or puromycin-5'-triphosphate, xanthosine-5'- triphosphate. Particular preference is given to nucleotides for base modifications selected from the group of base-modified nucleotides consisting of 5-methylcytidine-5'-triphosphate, 7-deazaguanosine-5'-triphosphate, 5-bromo-cytidine-5'-triphosphate, and pseudouridine-5'-triphosphate.

Further, lipid-modified artificial nucleic acid molecules may typically comprise at least one linker which is covalently linked with the artificial nucleic acid molecule, and at least one lipid which is covalently linked with this linker. Alternatively, a lipid-modified artificial nucleic acid molecule may comprise at least one artificial nucleic acid molecule as defined herein and at least one, preferably bifunctional lipid which is covalently linked, preferably without a linker, with that artificial nucleic acid molecule. According to a third alternative, a lipid-modified artificial nucleic acid molecule may comprise an artificial nucleic acid molecule as defined herein, at least one linker which is covalently linked with that artificial nucleic acid molecule, at least one lipid which is covalently linked with this linker, and additionally at least one, preferably bifunctional lipid which is covalently linked, preferably without a linker, with the artificial nucleic acid molecule.

In a further aspect, the present invention provides a vector comprising
(a.) at least one 5'-untranslated region element (5'UTR element) which comprises or consists of a nucleic acid sequence which is derived from the 5'UTR of a TOP gene or which is derived from a variant of the 5'UTR of a TOP gene;
(b.) at least one open reading frame and/or at least one cloning site; and
(c.) optionally, at least one histone stem-loop.

The cloning site may be suitable for accepting an open reading frame, i.e. an open reading frame coding for a protein or peptide to be expressed may be cloned into the vector via the cloning site.

The at least one 5'UTR element, the at least one ORF, and the at least one optional histone stem-loop are as described herein for the artificial nucleic acid molecule according to the present invention. The cloning site may be any sequence that is suitable for introducing an open reading frame or a sequence comprising an open reading frame, such as one or more restriction sites.

Thus, the vector comprising a cloning site is preferably suitable for inserting an open reading frame into the vector. Preferably, it may be suitable for inserting an open reading frame between the 5'UTR element and a desired 3' structure such as a histone stem loop, a polyl(A) sequence, a poly-adenylation signal and/or a 3'UTR element, more preferably it is suitable for insertion 5' to the 3' structure and 3' to the 5'UTR element. For example the 3' structure may comprise a histone stem-loop, a poly(A) sequence or a polyadenylation signal and/or a 3'UTR element as described above. Thereby the histone stem loop, the poly(A) sequence and/or the polyadenylation signal and the 3'UTR element may occur in any order that may be desired. Preferably, the cloning site or the ORF is located 5' to the 3'UTR structure, preferably in close proximity to the 5'-end of the histone stem-loop, poly(A) sequence, polyadenylation signal and/or a 3'UTR element as described above. For example, the cloning site or the ORF may be directly connected to the 5'-end of the histone stem-loop, poly(A) sequence, polyadenylation signal and/or a 3'UTR element or they may be connected via a stretch of nucleotides, such as by a stretch of 2, 4, 6, 8, 10, 20 etc. nucleotides as described above for the artificial nucleic acid molecule according to the present invention. Preferably, the cloning site or the ORF is located 3' to the 5'UTR element, preferably in close proximity to the 3'-end of the 5'UTR element. For example, the cloning site or the ORF may be directly connected to the 3'-end of the 5'UTR element or they may be connected via a stretch of nucleotides, such as by a stretch of 2, 4, 6, 8, 10, 20 etc. nucleotides as described above for the artificial nucleic acid molecule according to the present invention.

Preferably, the vector according to the present invention is suitable for producing the artificial nucleic acid molecule according to the present invention, preferably for producing an artificial mRNA according to the present invention, for example, by optionally inserting an open reading frame or a sequence comprising an open reading frame into the vector and transcribing the vector. Thus, preferably, the vector comprises elements needed for transcription, such as a promoter, e.g. an RNA polymerase promoter. Preferably, the vector is suitable for transcription using eukaryotic, prokaryotic, viral or phage transcription systems, such as eukaryotic cells, prokaryotic cells, or eukaryotic, prokaryotic, viral or phage in vitro transcription systems. Thus, for example, the vector may comprise a promoter sequence, which is recognizes by a polymerase, such as by an RNA polymerase, e.g. by a eukaryotic, prokaryotic, viral, or phage RNA polymerase. In a preferred embodiment, the vector comprises a phage RNA polymerase promoter such as an SP6 or T7, preferably a T7 promoter. Preferably, the vector is suitable for in vitro transcription using a phage based in vitro transcription system, such as a T7 RNA polymerase based in vitro transcription system.

The vector may further comprise a poly(A) sequence and/or a polyadenylation signal and/or a poly(C) sequence as described above for the artificial nucleic acid molecule according to the present invention.

The vector may be an RNA vector or a DNA vector. Preferably, the vector is a DNA vector. The vector may be any vector known to the skilled person, such as a viral vector or a plasmid vector. Preferably, the vector is a plasmid vector, preferably a DNA plasmid vector.

In a preferred embodiment, the vector according to the present invention comprises or codes for the artificial nucleic acid molecule according to the present invention.

Preferably, a vector according to the present invention comprises a sequence according to SEQ ID NOs. 1-1363, SEQ ID NO. 1435, SEQ ID NO. 1461, SEQ ID NO. 1462, or a sequence according to SEQ ID NOs. 1368 or 1452-1460, a fragment thereof as described above, or a corresponding RNA sequence, or a sequence having an identity of at least about 40%, preferably of at least about 50%, preferably of at least about 60%, preferably of at least about 70%, more preferably of at least about 80%, more preferably of at least about 90%, even more preferably of at least about 95%; even more preferably of at least about 99% to a sequence according to any one of SEQ ID NOs. 1-1363, SEQ ID NO. 1435, SEQ ID NO. 1461, SEQ ID NO. 1462, or a sequence according to SEQ ID NOs. 1368 or 1452-1460, a fragment thereof as described above, preferably a functional fragment thereof, or a corresponding RNA sequence.

Preferably, a vector according to the present invention comprises a sequence according to any one of SEQ ID Nos. 1369-1390 and 1434, a fragment thereof as described above or a corresponding RNA sequence, or a sequence having an identity of at least about 40%, preferably of at least about 50%, preferably of at least about 60%, preferably of at least about 70%, more preferably of at least about 80%, more preferably of at least about 90%, even more preferably of at least about 95%; even more preferably of at least about 99% to a sequence according to any one of SEQ ID Nos. 1369-1390 and 1434 or a fragment thereof as described above, preferably a functional fragment thereof, or a corresponding RNA sequence.

Preferably, a vector according to the present invention comprises a sequence according to any one of SEQ ID Nos. 1391-1433 or a corresponding RNA sequence, or a sequence having an identity of at least about 75%, preferably of at least about 80%, more preferably of at least about 85%, even more preferably of at least about 90%; even more preferably of at least about 95% to a sequence according to SEQ ID Nos. 1433 as described above or a corresponding RNA sequence.

Preferably, the vector is a circular molecule. Preferably, the vector is a double-stranded molecule, such as a double stranded DNA molecule. Such circular, preferably double stranded DNA molecule may be used conveniently as a storage form for the inventive artificial nucleic acid molecule. Furthermore, it may be used for transfection of cells, for example, cultured cells. Also it may be used for in vitro transcription for obtaining an artificial RNA molecule according to the invention.

Preferably, the vector, preferably the circular vector, is linearizable, for example, by restriction enzyme digestion. In a preferred embodiment, the vector comprises a cleavage site, such as a restriction site, preferably a unique cleavage site, located immediately 3' to the open reading frame or—if present—to the histone stem-loop, or—if present—to the poly(A) sequence or the polyadenylation signal, or—if present—to the 3'UTR element, or—if present—to the poly (C) sequence. Thus, preferably, the product obtained by linearizing the vector terminates at the 3'end with the 3'-end of the open reading frame, or—if present—with the 3'-end of the histone stem loop, or—if present—with the 3'-end of the poly(A) sequence or the 3'-end of the polyadenylation signal, or—if present—with the 3'-end of a 3'UTR element, plus some optional nucleotides, e.g. remaining from the restriction site after cleavage.

In a further aspect, the present invention relates to a cell comprising the artificial nucleic acid molecule according to the present invention or the vector according to the present invention. The cell may be any cell, such as a bacterial cell, insect cell, plant cell, vertebrate cell, e.g. a mammalian cell. Such cell may be, e.g., used for replication of the vector of the present invention, for example, in a bacterial cell. Furthermore, the cell may be used for transcribing the artificial nucleic acid molecule or the vector according to the present invention and/or translating the open reading frame of the artificial nucleic acid molecule or the vector according to the present invention. For example, the cell may be used for recombinant protein production.

The cells according to the present invention are, for example, obtainable by standard nucleic acid transfer methods, such as standard transfection methods. For example, the artificial nucleic acid molecule or the vector according to the present invention may be transferred into the cell by electroporation, lipofection, e.g. based on cationic lipids and/or liposomes, calcium phosphate precipitation, nanoparticle based transfection, virus based transfection, or based on cationic polymers, such as DEAE-dextran or polyethylenimine etc.

Preferably, the cell is a mammalian cell, such as a cell of a human subject, a domestic animal, a laboratory animal, such as a mouse or rat cell. Preferably the cell is a human cell. The cell may be a cell of an established cell line, such as a CHO, BHK, 293T, COS-7, HELA, HEK etc. cell, or the cell may be a primary cell, such as a HDF cell, preferably a cell isolated from an organism. In a preferred embodiment, the cell is an isolated cell of a mammalian subject, preferably of a human subject. For example, the cell may be an immune cell, such as a dendritic cell, a cancer or tumor cell, or any somatic cell etc., preferably of a mammalian subject, preferably of a human subject.

In a further aspect, the present invention provides a pharmaceutical composition comprising the artificial nucleic acid molecule according to the present invention, the vector according the present invention, or the cell according to the present invention. The pharmaceutical composition according to the invention may be used, e.g., as a vaccine, for example, for genetic vaccination. Thus, the ORF may, e.g., encode an antigen to be administered to a patient for vaccination. Thus, in a preferred embodiment, the pharmaceutical composition according to the present invention is a vaccine. Furthermore, the pharmaceutical composition according to the present invention may be used, e.g., for gene therapy.

Preferably, the pharmaceutical composition further comprises one or more pharmaceutically acceptable excipients, vehicles, fillers and/or diluents. In the context of the present invention, a pharmaceutically acceptable vehicle typically includes a liquid or non-liquid basis for the inventive pharmaceutical composition. In one embodiment, the pharmaceutical composition is provided in liquid form. In this context, preferably, the vehicle is based on water, such as pyrogen-free water, isotonic saline or buffered (aqueous) solutions, e.g phosphate, citrate etc. buffered solutions. The buffer may be hypertonic, isotonic or hypotonic with reference to the specific reference medium, i.e. the buffer may have a higher, identical or lower salt content with reference to the specific reference medium, wherein preferably such concentrations of the afore mentioned salts may be used, which do not lead to damage of mammalian cells due to osmosis or other concentration effects. Reference media are e.g. liquids occurring in "in vivo" methods, such as blood, lymph, cytosolic liquids, or other body liquids, or e.g. liquids, which may be used as reference media in "in vitro" methods, such as common buffers or liquids. Such common buffers or liquids are known to a skilled person. Ringer-Lactate solution is particularly preferred as a liquid basis.

One or more compatible solid or liquid fillers or diluents or encapsulating compounds suitable for administration to a patient may be used as well for the inventive pharmaceutical composition. The term "compatible" as used herein preferably means that these components of the inventive pharmaceutical composition are capable of being mixed with the inventive nucleic acid, vector or cells as defined herein in such a manner that no interaction occurs which would substantially reduce the pharmaceutical effectiveness of the inventive pharmaceutical composition under typical use conditions.

The pharmaceutical composition according to the present invention may optionally further comprise one or more additional pharmaceutically active components. A pharmaceutically active component in this context is a compound that exhibits a therapeutic effect to heal, ameliorate or prevent a particular indication or disease. Such compounds include, without implying any limitation, peptides or proteins, nucleic acids, (therapeutically active) low molecular weight organic or inorganic compounds (molecular weight less than 5000, preferably less than 1000), sugars, antigens or antibodies, therapeutic agents already known in the prior art, antigenic cells, antigenic cellular fragments, cellular fractions, cell wall components (e.g. polysaccharides), modified, attenuated or de-activated (e.g. chemically or by irradiation) pathogens (virus, bacteria etc.).

Furthermore, the inventive pharmaceutical composition may comprise a carrier for the artificial nucleic acid molecule or the vector. Such a carrier may be suitable for mediating dissolution in physiological acceptable liquids, transport and cellular uptake of the pharmaceutical active artificial nucleic acid molecule or the vector. Accordingly, such a carrier may be a component which may be suitable for depot and delivery of an artificial nucleic acid molecule or vector according to the invention. Such components may be, for example, cationic or polycationic carriers or compounds which may serve as transfection or complexation agent.

Particularly preferred transfection or complexation agents in this context are cationic or polycationic compounds, including protamine, nucleoline, spermine or spermidine, or other cationic peptides or proteins, such as poly-L-lysine (PLL), poly-arginine, basic polypeptides, cell penetrating peptides (CPPs), including HIV-binding peptides, HIV-1 Tat (HIV), Tat-derived peptides, Penetratin, VP22 derived or analog peptides, HSV VP22 (Herpes simplex), MAP, KALA or protein transduction domains (PTDs), PpT620, prolin-rich peptides, arginine-rich peptides, lysinerich peptides, MPG-peptide(s), Pep-1, L-oligomers, Calcitonin peptide(s), Antennapedia-derived peptides (particularly from *Drosophila antennapedia*), pAntp, pIsl, FGF, Lactoferrin, Transportan, Buforin-2, Bac715-24, SynB, SynB(1), pVEC, hCT-derived peptides, SAP, or histones.

Furthermore, such cationic or polycationic compounds or carriers may be cationic or polycationic peptides or proteins, which preferably comprise or are additionally modified to comprise at least one —SH moiety. Preferably, a cationic or polycationic carrier is selected from cationic peptides having the following sum formula (III):

$$\{(Arg)_l;(Lys)_m;(His)_n;(Orn)_o;(Xaa)_x\}; \quad \text{formula (III)}$$

wherein l+m+n+o+x=3-100, and l, m, n or o independently of each other is any number selected from 0, 1, 2, 3, 4, 5, 6, 7, 8, 9, 10, 11, 12, 13, 14, 15, 16, 17, 18, 19, 20, 21-30, 31-40, 41-50, 51-60, 61-70, 71-80, 81-90 and 91-100 provided that the overall content of Arg (Arginine), Lys (Lysine), His (Histidine) and Orn (Ornithine) represents at least 10% of all amino acids of the oligopeptide; and Xaa is any amino acid selected from native (=naturally occurring) or non-native amino acids except of Arg, Lys, His or Orn; and x is any number selected from 0, 1, 2, 3, 4, 5, 6, 7, 8, 9, 10, 11, 12, 13, 14, 15, 16, 17, 18, 19, 20, 21-30, 31-40, 41-50, 51-60, 61-70, 71-80, 81-90, provided, that the overall content of Xaa does not exceed 90% of all amino acids of the oligopeptide. Any of amino acids Arg, Lys, His, Orn and Xaa may be positioned at any place of the peptide. In this context cationic peptides or proteins in the range of 7-30 amino acids are particular preferred.

Further, the cationic or polycationic peptide or protein, when defined according to formula $\{(Arg)_l;(Lys)_m;(His)_n;(Orn)_o;(Xaa)_x\}$ (formula (III)) as shown above and which comprise or are additionally modified to comprise at least one —SH moiety, may be, without being restricted thereto, selected from subformula (IIIa):

$$\{(Arg)_l;(Lys)_m;(His)_n;(Orn)_o;(Xaa')_x(Cys)_y\} \quad \text{subformula (IIIa)}$$

wherein $(Arg)_l;(Lys)_m;(His)_n;(Orn)_o$; and x are as defined herein, Xaa' is any amino acid selected from native (=naturally occurring) or non-native amino acids except of Arg, Lys, His, Orn or Cys and y is any number selected from 0, 1, 2, 3, 4, 5, 6, 7, 8, 9, 10, 11, 12, 13, 14, 15, 16, 17, 18, 19, 20, 21-30, 31-40, 41-50, 51-60, 61-70, 71-80 and 81-90, provided that the overall content of Arg (Arginine), Lys (Lysine), His (Histidine) and Orn (Ornithine) represents at least 10% of all amino acids of the oligopeptide. Further, the cationic or polycationic peptide may be selected from sub-formula (IIIb):

$$Cys_1\{(Arg)_l;(Lys)_m;(His)_n;(Orn)_o;(Xaa)_x\}Cys_2 \quad \text{subformula (IIIb)}$$

wherein empirical formula $\{(Arg)_l;(Lys)_m;(His)_n;(Orn)_o;(Xaa)_x\}$ (formula (III)) is as defined herein and forms a core of an amino acid sequence according to (semiempirical) formula (III) and wherein $Cys_1$ and $Cys_2$ are Cysteines proximal to, or terminal to $(Arg)_l;(Lys)_m;(His)_n;(Orn)_o;(Xaa)_x$.

Further preferred cationic or polycationic compounds, which can be used as transfection or complexation agent may include cationic polysaccharides, for example chitosan, polybrene, cationic polymers, e.g. polyethyleneimine (PEI), cationic lipids, e.g. DOTMA: [1-(2,3-sioleyloxy)propyl)]-N,N,N-trimethylammonium chloride, DMRIE, di-C14-amidine, DOTIM, SAINT, DC-Chol, BGTC, CTAP, DOPC, DODAP, DOPE: Dioleyl phosphatidylethanol-amine, DOSPA, DODAB, DOIC, DMEPC, DOGS: Dioctadecylamidoglicylspermin, DIMRI: Dimyristo-oxypropyl dimethyl hydroxyethyl ammonium bromide, DOTAP: dioleoyloxy-3-(trimethylammonio)propane, DC-6-14: O,O-ditetradecanoyl-N-(α-trimethylammonioacetyl)diethanolamine chloride, CLIP1: rac-[(2,3-dioctadecyloxypropyl)(2-hydroxyethyl)]-dimethylammonium chloride, CLIP6: rac-[2(2,3-dihexadecyloxypropyl-oxymethyloxy)ethyl]trimethylammonium, CLIPS: rac-[2(2,3-dihexadecyloxypropyl-oxysuccinyloxy)ethyl]-trimethylammonium, oligofectamine, or cationic or polycationic polymers, e.g. modified polyaminoacids, such as β-aminoacid-polymers or reversed polyamides, etc., modified polyethylenes, such as PVP (poly(N-ethyl-4-vinylpyridinium bromide)), etc., modified acrylates, such as pDMAEMA (poly(dimethylaminoethyl methylacrylate)), etc., modified Amidoamines such as pAMAM (poly (amidoamine)), etc., modified polybetaaminoester (PBAE), such as diamine end modified 1,4 butanediol diacrylate-co-5-amino-1-pentanol polymers, etc., dendrimers, such as polypropylamine dendrimers or pAMAM based dendrimers, etc., polyimine(s), such as PEI: poly(ethyleneimine), poly (propyleneimine), etc., polyallylamine, sugar backbone based polymers, such as cyclodextrin based polymers, dextran based polymers, chitosan, etc., silan backbone based polymers, such as PMOXA-PDMS copolymers, etc., block-polymers consisting of a combination of one or more cationic blocks (e.g. selected from a cationic polymer as mentioned above) and of one or more hydrophilic or hydrophobic blocks (e.g polyethyleneglycole); etc.

In this context, it is particularly preferred that the inventive artificial nucleic acid molecule or the inventive vector is complexed at least partially with a cationic or polycationic compound, preferably cationic proteins or peptides. Partially means that only a part of the inventive artificial nucleic acid molecule or the inventive vector is complexed with a cationic or polycationic compound and that the rest of the inventive artificial nucleic acid molecule or the inventive vector is in uncomplexed form ("free"). Preferably the ratio of complexed nucleic acid to: free nucleic acid is selected from a range. of about 5:1 (w/w) to about 1:10 (w/w), more preferably from a range of about 4:1 (w/w) to about 1:8 (w/w), even more preferably from a range of about 3:1 (w/w) to about 1:5 (w/w) or 1:3 (w/w), and most preferably the ratio of complexed nucleic acid to free nucleic acid is selected from a ratio of about 1:1 (w/w).

The pharmaceutical composition according to the present invention may optionally further comprise one or more adjuvants, for example, adjuvants for stimulating the innate immune system or for enhancing cellular uptake of the artificial nucleic acid molecule or vector. In this context, an adjuvant may be understood as any compound, which is suitable to initiate or increase an immune response of the innate immune system, i.e. a non-specific immune response. In other words, when administered, the inventive pharmaceutical composition preferably elicits an innate immune response due to the adjuvant, optionally contained therein. Preferably, such an adjuvant may be an adjuvant supporting the induction of an innate immune response in a mammal. Such an adjuvant may be, for example, an immunostimulatory nucleic acid, i.e. a nucleic acid that may bind to a Toll-like-receptor or the like, preferably an immunostimulatory RNA.

Such adjuvants, preferably such immunostimulatory nucleic acids, may induce an innate, i.e. unspecific, immune response which may support a specific, i.e. adaptive, immune response to the peptide or protein, i.e. the antigen, encoded by the artificial nucleic acid molecule of the pharmaceutical composition, preferably the vaccine.

The inventive pharmaceutical composition may also additionally comprise any further compound, which is known to be immunostimulating due to its binding affinity (as ligands) to human Toll-like receptors TLR1, TLR2, TLR3, TLR4, TLR5, TLR6, TLR7, TLR8, TLR9, TLR10, or due to its binding affinity (as ligands) to murine Toll-like receptors TLR1, TLR2, TLR3, TLR4, TLR5, TLR6, TLR7, TLR8, TLR9, TLR10, TLR11, TLR12 or TLR13.

Further additives which may be included in the inventive pharmaceutical composition are, e.g., emulsifiers, such as, for example, Tween; wetting agents, such as, for example, sodium lauryl sulfate; colouring agents; taste-imparting agents, pharmaceutical carriers; tablet-forming agents; stabilizers; antioxidants; preservatives etc.

The pharmaceutical composition according to the present invention preferably comprises a "safe and effective amount" of the components of the pharmaceutical composition, particularly of the inventive nucleic acid sequence, the vector and/or the cells as defined herein. As used herein, a "safe and effective amount" means an amount sufficient to significantly induce a positive modification of a disease or disorder as defined herein. At the same time, however, a "safe and effective amount" preferably avoids serious side-effects and permits a sensible relationship between advantage and risk. The determination of these limits typically lies within the scope of sensible medical judgment.

In a further aspect, the present invention provides the artificial nucleic acid molecule according to the present invention, the vector according to the present invention, the cell according to the present invention, or the pharmaceutical composition according to the present invention for use as a medicament, for example, as vaccine (in genetic vaccination) or in gene therapy.

The artificial nucleic acid molecule according to the present invention, the vector according to the present invention, the cell according to the present invention, or the pharmaceutical composition according to the present invention are particularly suitable for any medical application which makes use of the therapeutic action or effect of peptides, polypeptides or proteins, or where supplementation of a particular peptide or protein is needed. Thus, the present invention provides the artificial nucleic acid molecule according to the present invention, the vector according to the present invention, the cell according to the present invention, or the pharmaceutical composition according to the present invention for use in the treatment or prevention of diseases or disorders amenable to treatment by the therapeutic action or effect of peptides, polypeptides or proteins or amenable to treatment by supplementation of a particular peptide, polypeptide or protein. For example, the artificial nucleic acid molecule according to the present invention, the vector according to the present invention, the cell according to the present invention, or the pharmaceutical composition according to the present invention may be used for the treatment or prevention of genetic diseases, autoimmune diseases, cancerous or tumour-related diseases, infectious diseases, chronic diseases or the like, e.g., by genetic vaccination or gene therapy.

In particular, such therapeutic treatments which benefit from a stable, prolonged and/or increased presence of therapeutic peptides, polypeptides or proteins in a subject to be treated are especially suitable as medical application in the context of the present invention, since the 5'UTR element in particular in combination with a histone stem-loop provides for increased protein expression from the ORF of the inventive nucleic acid molecule. Thus, a particularly suitable medical application for the artificial nucleic acid molecule according to the present invention, the vector according to the present invention, the cell according to the present invention, or the pharmaceutical composition according to the present invention is vaccination, for example against infections or tumours. Thus, the present invention provides the artificial nucleic acid molecule according to the present invention, the vector according to the present invention, the cell according to the present invention, or the pharmaceutical composition according to the present invention for vaccination of a subject, preferably a mammalian subject, more preferably a human subject. Preferred vaccination treatments are vaccination against infectious diseases, such as bacterial, protozoal or viral infections, and anti-tumour-vaccination. Such vaccination treatments may be prophylactic or therapeutic.

Depending on the disease to be treated or prevented, the ORF may be selected. For example, the open reading frame may code for a protein that has to be supplied to a patient suffering from total lack or at least partial loss of function of a protein, such as a patient suffering from a genetic disease. Additionally, the open reading frame may be chosen from an ORF coding for a peptide or protein which beneficially influences a disease or the condition of a subject. Furthermore, the open reading frame may code for a peptide or protein which effects down-regulation of a pathological overproduction of a natural peptide or protein or elimination of cells expressing pathologically a protein or peptide. Such lack, loss of function or overproduction may, e.g., occur in the context of tumour and neoplasia, autoimmune diseases, allergies, infections, chronic diseases or the like. Furthermore, the open reading frame may code for an antigen or immunogen, e.g. for an epitope of a pathogen or for a tumour antigen. Thus, in preferred embodiments, the artificial nucleic acid molecule or the vector according to the present invention comprises an ORF encoding an amino acid sequence comprising or consisting of an antigen or immunogen, e.g. an epitope of a pathogen or a tumour-associated antigen, a 5'UTR element as described above, preferably a histone stem-loop as described herein, and optional further components, such as a 3'UTR element and/or a poly(A) sequence and/or a poly(C) sequence etc. as described herein.

In the context of medical application, in particular, in the context of vaccination, it is preferred that the artificial nucleic acid molecule according to the present invention is RNA, preferably mRNA, since DNA harbours the risk of eliciting an anti-DNA immune response and tends to insert into genomic DNA. However, in some embodiments, for example, if a viral delivery vehicle, such as an adenoviral delivery vehicle is used for delivery of the artificial nucleic acid molecule or the vector according to the present invention, e.g., in the context of gene therapeutic treatments, it may be desirable that the artificial nucleic acid molecule or the vector is a DNA molecule.

The artificial nucleic acid molecule according to the present invention, the vector according to the present invention, the cell according to the present invention, or the pharmaceutical composition according to the present invention may be administered orally, parenterally, by inhalation spray, topically, rectally, nasally, buccally, vaginally or via an implanted reservoir. The term parenteral as used herein includes subcutaneous, intravenous, intramuscular, intra-articular, intra-synovial, intrasternal, intrathecal, intrahepatic, intralesional, intracranial, transdermal, intradermal, intrapulmonal, intraperitoneal, intracardial, intraarterial, and sublingual injection or infusion techniques.

Preferably, the artificial nucleic acid molecule according to the present invention, the vector according to the present invention, the cell according to the present invention, or the pharmaceutical composition according to the present invention is administered parenterally, e.g. by parenteral injection, more preferably by subcutaneous, intravenous, intramuscular, intra-articular, intra-synovial, intrasternal, intrathecal, intrahepatic, intralesional, intracranial, transdermal, intradermal, intrapulmonal, intraperitoneal, intracardial, intraarterial, sublingual injection or via infusion techniques. Particularly preferred is intradermal and intramuscular injection. Sterile injectable forms of the inventive pharmaceutical composition may be aqueous or oleaginous suspension. These suspensions may be formulated according to techniques known in the art using suitable dispersing or wetting agents and suspending agents.

The artificial nucleic acid molecule according to the present invention, the vector according to the present invention, the cell according to the present invention, or the pharmaceutical composition according to the present invention may also be administered orally in any orally acceptable dosage form including, but not limited to, capsules, tablets, aqueous suspensions or solutions.

The artificial nucleic acid molecule according to the present invention, the vector according to the present invention, the cell according to the present invention, or the pharmaceutical composition according to the present invention may also be administered topically, especially when the target of treatment includes areas or organs readily accessible by topical application, e.g. including diseases of the skin or of any other accessible epithelial tissue. Suitable topical formulations are readily prepared for each of these areas or organs. For topical applications, the artificial nucleic acid molecule according to the present invention, the vector according to the present invention, the cell according to the present invention, or the pharmaceutical composition according to the present invention may be formulated in a suitable ointment suspended or dissolved in one or more carriers.

In one embodiment, the use as a medicament comprises the step of transfection of mammalian cells, preferably in vitro transfection of mammalian cells, more preferably in vitro transfection of isolated cells of a subject to be treated by the medicament. If the use comprises the in vitro transfection of isolated cells, the use as a medicament may further comprise the (re)administration of the transfected cells to the patient. The use of the inventive artificial nucleic acid molecules or the vector as a medicament may further comprise the step of selection of successfully transfected isolated cells. Thus, it may be beneficial if the vector further comprises a selection marker. Also, the use as a medicament may comprise in vitro transfection of isolated cells and purification of an expression-product, i.e. the encoded peptide or protein from these cells. This purified peptide or protein may subsequently be administered to a subject in need thereof.

The present invention also provides a method for treating or preventing a disease or disorder as described above comprising administering the artificial nucleic acid molecule according to the present invention, the vector according to the present invention, the cell according to the present invention, or the pharmaceutical composition according to the present invention to a subject in need thereof.

Furthermore, the present invention provides a method for treating or preventing a disease or disorder comprising transfection of a cell with an artificial nucleic acid molecule according to the present invention or with the vector according to the present invention. Said transfection may be performed in vitro or in vivo. In a preferred embodiment, transfection of a cell is performed in vitro and the transfected cell is administered to a subject in need thereof, preferably to a human patient. Preferably, the cell which is to be transfected in vitro is an isolated cell of the subject, preferably of the human patient. Thus, the present invention provides a method of treatment comprising the steps of isolating a cell from a subject, preferably from a human patient, transfecting the isolated cell with the artificial nucleic acid molecule according to the present invention or the vector according to the present invention, and administering the transfected cell to the subject, preferably the human patient.

The method of treating or preventing a disorder according to the present invention is preferably a vaccination method and/or a gene therapy method as described above.

As described above, the 5'UTR element, preferably, the histone stem-loop, and optionally the poly(A)sequence and/or the 3'UTR element are capable of increasing protein production from an artificial nucleic acid molecule, such as an mRNA or vector, comprising these elements and an ORF, preferably in an at least additive, preferably in a synergistic manner. Thus, in a further aspect, the present invention relates to a method for increasing protein production from an artificial nucleic acid molecule comprising the step of associating the artificial nucleic acid molecule, preferably an ORF contained within the artificial nucleic acid molecule, with (i) at least one 5'-untranslated region element (5'UTR element) which comprises or consists of a nucleic acid sequence which is derived from the 5'UTR of a TOP gene or which is derived from a variant of the 5'UTR of a TOP gene as described above, preferably (ii) at least one histone stem-loop as described herein, and optionally one or more further elements, such as a poly(A)sequence and/or polyadenylation signal, and/or a poly(C) sequence, and/or a 3'UTR element, which comprises or consists of a nucleic acid sequence derived from the 3'UTR of a chordate gene, preferably a vertebrate gene, more preferably a mammalian gene, most preferably a human gene, or from a variant of the 3'UTR of a chordate gene, preferably a vertebrate gene, more preferably a mammalian gene, most preferably a human gene as described above.

Associating the artificial nucleic acid molecule or the vector with a 5'UTR element and preferably a histone stem-loop as well as optional further elements in the context of the present invention preferably means functionally associating or functionally combining an artificial nucleic acid molecule, e.g. comprising an ORF, such as an mRNA or a vector, with the 5'UTR element and optionally the histone stem-loop and/or the poly(A) sequence and/or the 3'UTR element. This means that the artificial nucleic acid molecule, preferably the ORF contained within the artificial nucleic acid molecule, the 5'UTR element and preferably the histone stem-loop and the optional further elements, such as the poly(A)sequence and/or the 3'UTR element as described above, are associated or coupled such that the function of the 5'UTR element and the histone stem-loop and the optional further elements, e.g. protein production increasing function, is exerted. Typically, this means that the 5'UTR element and the histone stem-loop and optionally the poly(A)sequence and/or the 3'UTR element are integrated into the artificial nucleic acid molecule, preferably into the mRNA molecule or the vector, such that the open reading frame is positioned between the 5'UTR element and the optional histone stem-loop and the optional poly(A)sequence and/or the optional 3'UTR element.

The product of said method is preferably the artificial nucleic acid molecule according to the present invention or the vector according to the present invention. Thus, e.g. the nature and sequence of the elements, such as the 5'UTR element, the histone stem-loop, the poly(A) sequence, the polyadenylation signal, the poly(C) sequence, and the 3'UTR element are as described above for the artificial nucleic acid molecule according to the present invention or the vector according to the present invention.

In a further aspect, the present invention provides the use of at least one 5'-untranslated region element (5'UTR element) which comprises or consists of a nucleic acid sequence which is derived from the 5'UTR of a TOP gene or which is derived from a variant of the 5'UTR of a TOP gene as described above, preferably at least one histone stem-loop, and optionally further elements, such as a poly(A) sequence and/or a polyadenylation signal, and/or a poly(C) signal), and/or a 3'UTR element which comprises or consists of a nucleic acid sequence derived from the 3'UTR of a chordate gene, preferably a vertebrate gene, more preferably a mammalian gene, most preferably a human gene, or from a variant of the 3'UTR of a chordate gene, preferably a vertebrate gene, more preferably a mammalian gene, most preferably a human gene as described above for increasing protein production from an artificial nucleic acid molecule, such as an mRNA or a vector.

The use according to the present invention preferably comprises associating the artificial nucleic acid molecule with the 5'UTR element, preferably the histone stem-loop and optional further elements, such as a poly(A)sequence or 3'UTR element etc., as described above.

The compounds and ingredients of the inventive pharmaceutical composition may also be manufactured and traded separately of each other. Thus, the invention relates further to a kit or kit of parts comprising an artificial nucleic acid molecule according to the invention, a vector according to the present invention, a cell according to the invention, and/or a pharmaceutical composition according to the invention. Preferably, such kit or kit of parts may, additionally, comprise instructions for use, cells for transfection, an adjuvant, a means for administration of the pharmaceutical composition, a pharmaceutically acceptable carrier and/or an pharmaceutically acceptable solution for dissolution or dilution of the artificial nucleic acid molecule, the vector, the cells or the pharmaceutical composition.

The following Figures, Sequences and Examples are intended to illustrate the invention further. They are not intended to limit the subject-matter of the invention thereto.

FIG. 1: shows the histone stem-loop consensus sequence generated from metazoan and protozoan stem-loop sequences (as reported by Dávila López, M., & Samuelsson, T. (2008), RNA (New York, N.Y.), 14(1), 1-10. doi:10.1261/rna.782308). 4001 histone stem-loop sequences from metazoa and protozoa were aligned and the quantity of the occurring nucleotides is indicated for every position in the stem-loop sequence. The generated consensus sequence representing all nucleotides present in the sequences analyzed is given using the single-letter nucleotide code. In addition to the consensus sequence, sequences are shown representing at least 99%, 95% and 90% of the nucleotides present in the sequences analyzed.

FIG. 2: shows the histone stem-loop consensus sequence generated from protozoan stem-loop sequences (as reported by Dávila López, M., & Samuelsson, T. (2008), RNA (New York, N.Y.), 14(1), 1-10. doi:10.1261/rna.782308). 131 histone stem-loop sequences from protozoa were aligned and the quantity of the occurring nucleotides is indicated for every position in the stem-loop sequence. The generated consensus sequence representing all nucleotides present in the sequences analyzed is given using the single-letter nucleotide code. In addition to the consensus sequence, sequences are shown representing at least 99%, 95% and 90% of the nucleotides present in the sequences analyzed.

Figure 3:
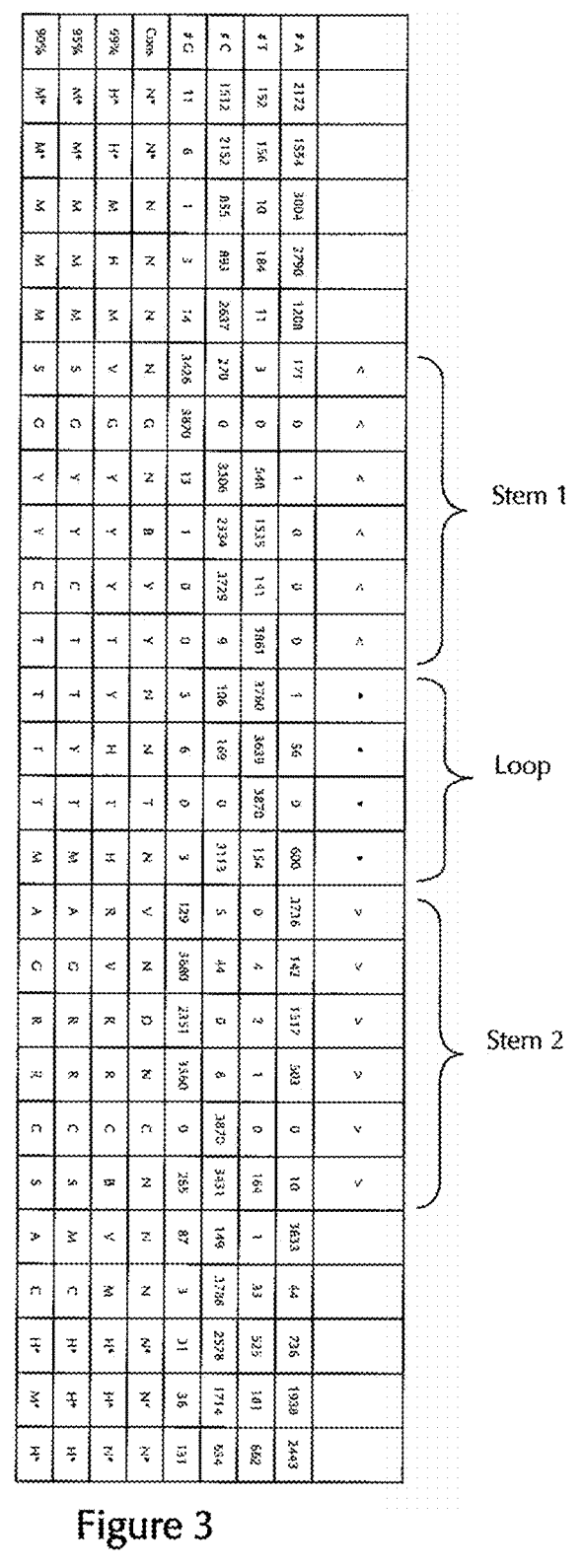

FIG. 3: shows the histone stem-loop consensus sequence generated from metazoan stem-loop sequences (as reported by Dávila López, M., & Samuelsson, T. (2008), RNA (New York, N.Y.), 14(1), 1-10. doi:10.1261/rna.782308). 3870 histone stem-loop sequences from metazoa were aligned and the quantity of the occurring nucleotides is indicated for every position in the stem-loop sequence. The generated consensus sequence representing all nucleotides present in the sequences analyzed is given using the single-letter nucleotide code. In addition to the consensus sequence, sequences are shown representing at least 99%, 95% and 90% of the nucleotides present in the sequences analyzed.

Figure 4:
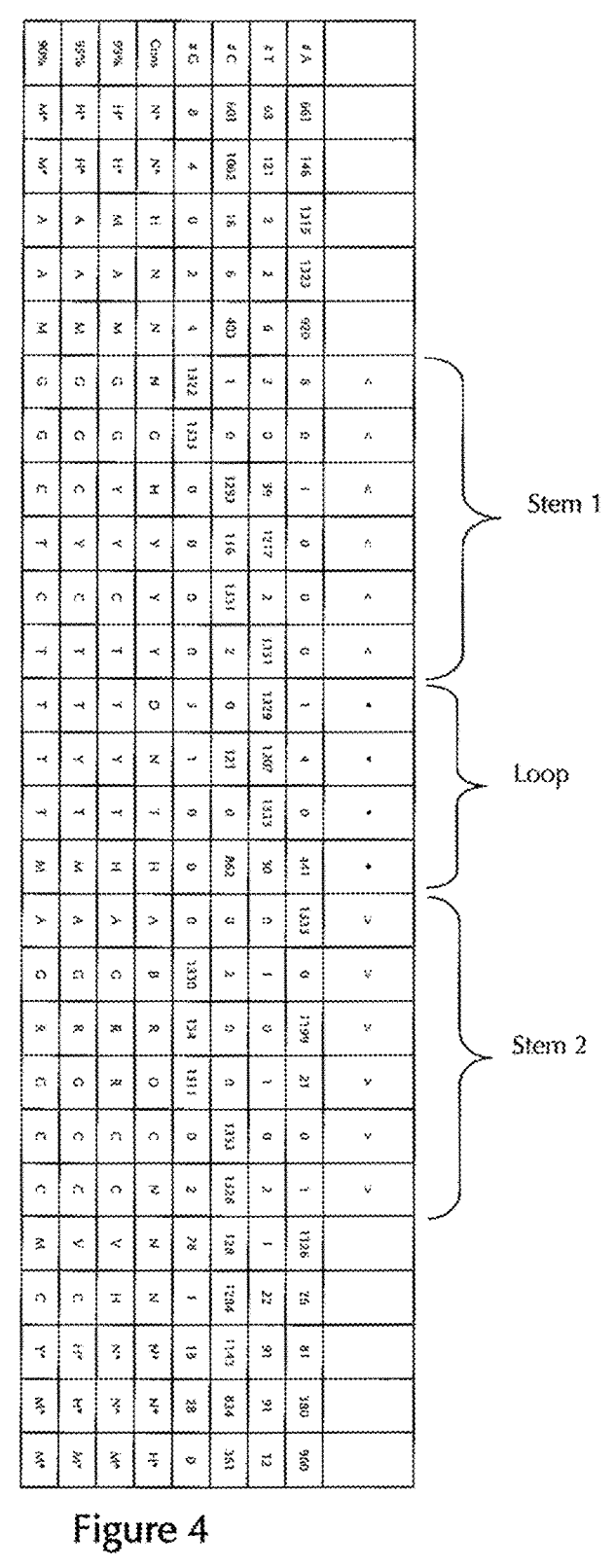

FIG. 4: shows the histone stem-loop consensus sequence generated from vertebrate stem-loop sequences (as reported by Dávila López, M., & Samuelsson, T. (2008), RNA (New York, N.Y.), 14(1), 1-10. doi:10.1261/rna.782308). 1333 histone stem-loop sequences from vertebrates were aligned and the quantity of the occurring nucleotides is indicated for every position in the stem-loop sequence. The generated consensus sequence representing all nucleotides present in the sequences analyzed is given using the single-letter nucleotide code. In addition to the consensus sequence, sequences are shown representing at least 99%, 95% and 90% of the nucleotides present in the sequences analyzed.

FIG. 5: shows the histone stem-loop consensus sequence generated from human (*Homo sapiens*) stem-loop sequences (as reported by Dávila López, M., & Samuelsson, T. (2008), RNA (New York, N.Y.), 14(1), 1-10. doi:10.1261/rna.782308). 84 histone stem-loop sequences from humans were aligned and the quantity of the occurring nucleotides is indicated for every position in the stem-loop sequence. The generated consensus sequence representing all nucleotides present in the sequences analyzed is given using the single-letter nucleotide code. In addition to the consensus sequence, sequences are shown representing at least 99%, 95% and 90% of the nucleotides present in the sequences analyzed.

FIG. 6 shows the nucleotide sequence of a *Photinus pyralis* luciferase encoding nucleic acid molecule PpLuc (GC)—ag—A64. This artificial construct does not comprise a 5'UTR element or a histone stem loop. The coding region for PpLuc(GC) is depicted in italics. The sequence depicted in FIG. 6 corresponds to SEQ ID No. 1364.

FIG. 7 shows the nucleotide sequence of RPL32—PpLuc (GC)—ag—A64—C30—histoneSL. The 5'UTR of human ribosomal protein Large 32 lacking the 5' terminal oligopyrimidine tract was inserted 5' of the ORF. A histoneSL was appended 3' of A64 poly(A). The coding region for PpLuc (GC) is depicted in italics. The 5'UTR element sequence and the histone stem-loop sequence are underlined. The sequence depicted in FIG. 7 corresponds to SEQ ID No. 1365.

Figure 8:
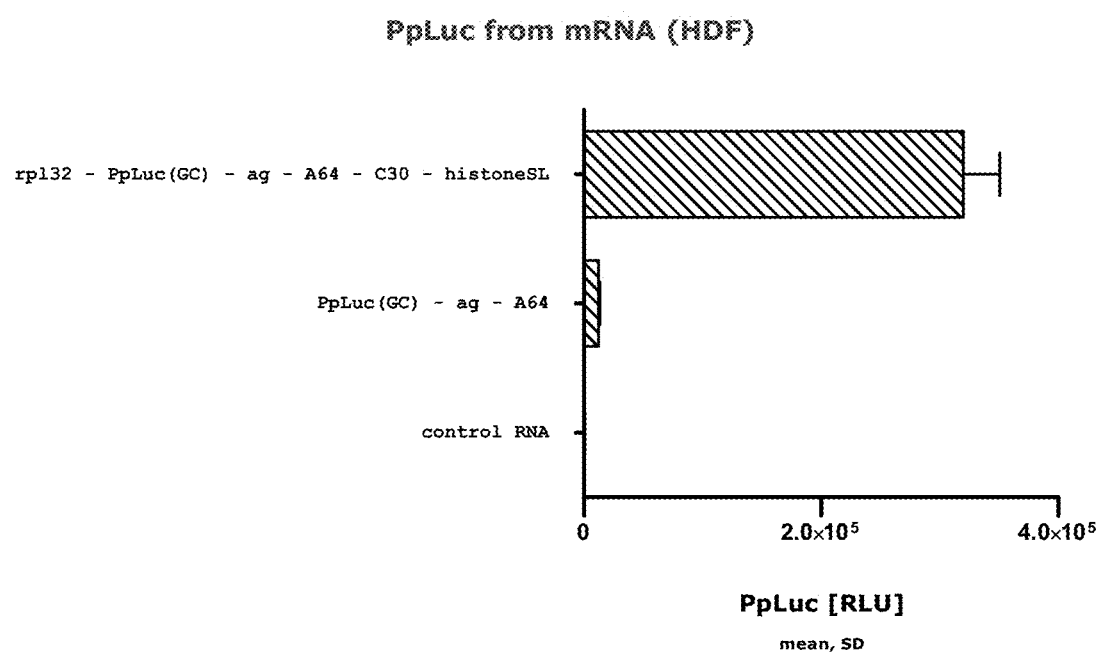

FIG. 8 shows that the combination of the 5'UTR element derived from the 5'UTR of the TOP gene RPL32 and a histone stem-loop increases protein production from mRNA strongly. The effect of the combination of the 5'UTR element and the histone stem-loop on luciferase expression from mRNA was examined. To this end, different mRNAs were transfected into human dermal fibroblasts (HDF) by lipofection. Luciferase levels were measured at 24 hours after transfection. Luciferase was clearly expressed from mRNA having neither 5'UTR element nor histoneSL. Strikingly however, the combination of 5'UTR element and histoneSL strongly increased the luciferase level. The magnitude of the rise in luciferase level due to combining 5'UTR element and histoneSL in the same mRNA indicates that they are acting synergistically. Data are graphed as mean RLU±SD (relative light units±standard deviation) for duplicate transfections. RLU are summarized in Example 5.1.

FIG. 9 shows the nucleotide sequence of PpLuc(GC)—ag—A64—histoneSL. A histoneSL was appended 3' of A64 poly(A). The coding region for PpLuc(GC) is depicted in italics. The histone stem-loop sequence is underlined. The sequence depicted in FIG. 9 corresponds to SEQ ID No. 1464.

FIG. 10 shows the nucleotide sequence of rpl32—PpLuc (GC)—ag—A64. The 5'UTR of human ribosomal protein Large 32 lacking the 5' terminal oligopyrimidine tract was inserted 5' of the ORF. The coding region for PpLuc(GC) is depicted in italics. The 5'UTR element sequence is underlined. The sequence depicted in FIG. 10 corresponds to SEQ ID No. 1463.

FIG. 11 shows the nucleotide sequence of rpl32—PpLuc (GC)—ag—A64—histoneSL. The 5'UTR of human ribosomal protein Large 32 lacking the 5' terminal oligopyrimidine tract was inserted 5' of the ORF. A histoneSL was appended 3' of A64 poly(A). The coding region for PpLuc (GC) is depicted in italics. The 5'UTR element sequence and the histone stem-loop sequence are underlined. The sequence depicted in FIG. 11 corresponds to SEQ ID No. 1480.

Figure 12:
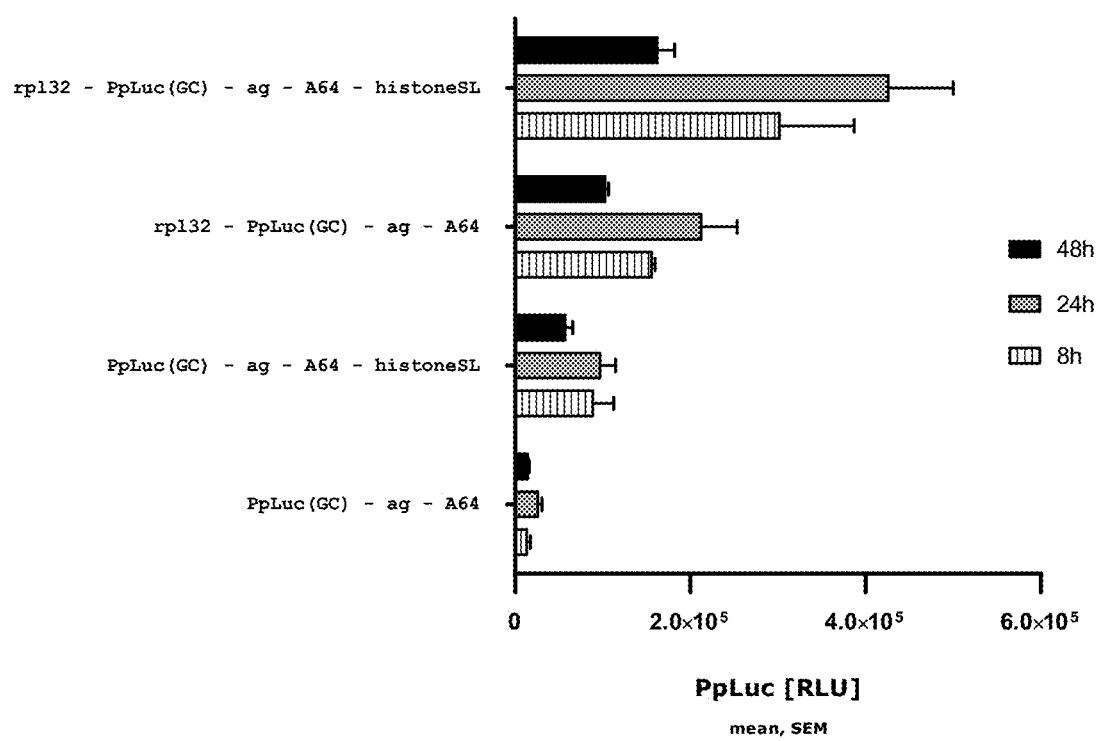

FIG. 12 is a graphical representation of the effect of the 5'UTR element derived from the 5'UTR of the TOP gene RPL32, the histone stem-loop, and the combination of the 5'UTR element and the histone stem-loop on luciferase expression from mRNA. A variety of mRNAs were transfected into human dermal fibroblasts (HDF) by lipofection. Luciferase levels were measured at 8, 24, and 48 hours after transfection. Both, either the histone stem-loop or the 5'UTR element increase luciferase levels compared to mRNA lacking both these elements. Strikingly, the combination of 5'UTR element and histone stem-loop further strongly increases the luciferase level, much above the level observed with either of the individual elements, thus acting synergistically. Data are graphed as mean RLU±SEM (relative light units±standard error) for triplicate transfections. RLU are summarized in Example 5.2.

FIG. 13 shows the nucleotide sequence of rpl32—PpLuc (GC)—albumin7—A64—C30—histoneSL. The albumin7 3'UTR element replaced the alpha-globin 3'UTR element in the construct shown in FIG. 7 (which contains the rpl32 5'UTR element). The 5'UTR element sequence is underlined. The sequence depicted in FIG. 13 corresponds to SEQ ID No. 1481.

FIG. 14 shows the nucleotide sequence of rpl35—PpLuc (GC)—albumin7—A64—C30—histoneSL. The 5'UTR of human ribosomal protein Large 35 lacking the 5' terminal oligopyrimidine tract replaced the rpl32 5'UTR element in the construct shown in FIG. 13. The 5'UTR element sequence is underlined. The sequence depicted in FIG. 14 corresponds to SEQ ID No. 1436.

FIG. 15 shows the nucleotide sequence of rpl21—PpLuc (GC)—albumin7—A64—C30—histoneSL. The 5'UTR of human ribosomal protein Large 21 lacking the 5' terminal oligopyrimidine tract replaced the rpl32 5'UTR element in the construct shown in FIG. 13. The 5'UTR element sequence is underlined. The sequence depicted in FIG. 15 corresponds to SEQ ID No. 1437.

FIG. 16 shows the nucleotide sequence of atp5a1—PpLuc (GC)—albumin7—A64—C30—histoneSL. The 5'UTR of human ATP synthase, H+ transporting, mitochondrial F1 complex, alpha subunit 1 lacking the 5' terminal oligopyrimidine tract replaced the rpl32 5'UTR element in the construct shown in FIG. 13. The 5'UTR element sequence is underlined. The sequence depicted in FIG. 16 corresponds to SEQ ID No. 1438.

FIG. 17 shows the nucleotide sequence of HSD17B4—PpLuc(GC)—albumin7—A64—C30—histoneSL. The 5'UTR of human hydroxysteroid (17-beta) dehydrogenase 4 lacking the 5' terminal oligopyrimidine tract replaced the rpl32 5'UTR element in the construct shown in FIG. 13. The 5'UTR element sequence is underlined. The sequence depicted in FIG. 17 corresponds to SEQ ID No. 1439.

FIG. 18 shows the nucleotide sequence of AIG1—PpLuc (GC)—albumin7—A64—C30—histoneSL. The 5'UTR of human androgen-induced 1 lacking the 5' terminal oligopyrimidine tract replaced the rpl32 5'UTR element in the construct shown in FIG. 13. The 5'UTR element sequence is underlined. The sequence depicted in FIG. 18 corresponds to SEQ ID No. 1440.

FIG. 19 shows the nucleotide sequence of COX6C—PpLuc(GC)—albumin7—A64—C30—histoneSL. The 5'UTR of human cytochrome c oxidase subunit VIc lacking the 5' terminal oligopyrimidine tract replaced the rpl32 5'UTR element in the construct shown in FIG. 13. The 5'UTR element sequence is underlined. The sequence depicted in FIG. 19 corresponds to SEQ ID No. 1441.

FIG. 20 shows the nucleotide sequence of ASAH1—PpLuc(GC)—albumin7—A64—C30—histoneSL. The 5'UTR of human N-acylsphingosine amidohydrolase (acid ceramidase) 1 lacking the 5' terminal oligopyrimidine tract replaced the rpl32 5'UTR element in the construct shown in FIG. 13. The 5'UTR element sequence is underlined. The sequence depicted in FIG. 20 corresponds to SEQ ID No. 1442.

Figure 21:
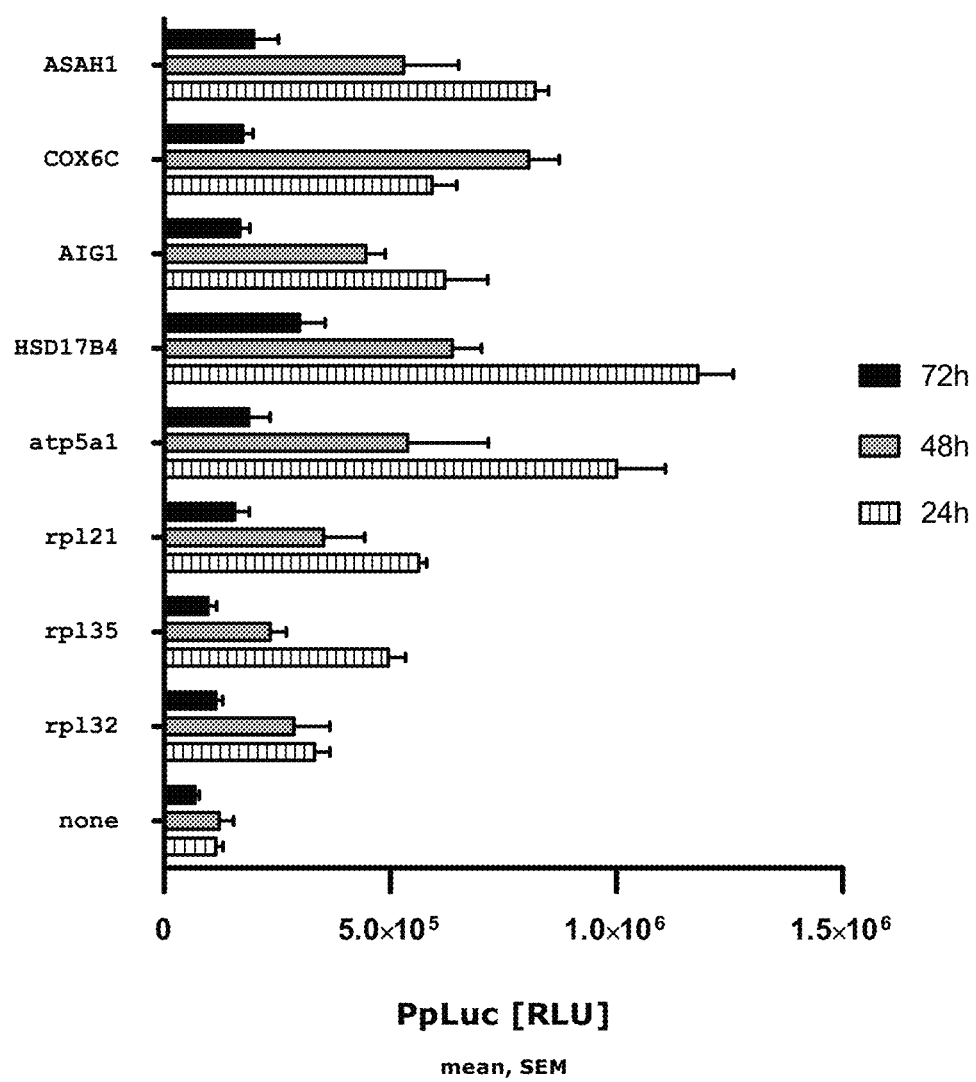

FIG. 21 is a graphical representation of the effect of the 5'UTR element derived from the TOP genes RPL32, RPL35, RPL21, ATP5A1, HSD17B4, AIG1, COX6C and ASAH1 on luciferase expression from mRNA. The mRNAs were transfected into human dermal fibroblasts (HDF) by lipofection. Luciferase levels were measured at 24, 48, and 72 hours after transfection. The 5'UTR elements strongly increase luciferase levels compared to mRNA lacking a 5'UTR element. Data are graphed as mean RLU±SEM (relative light units±standard error) for triplicate transfections. RLU are summarized in Example 5.3.

FIG. 22 shows the nucleotide sequence of rpl35—PpLuc (GC)—ag—A64. The 5'UTR of human ribosomal protein Large 35 lacking the 5' terminal oligopyrimidine tract replaced the rpl32 5'UTR element in the construct shown in FIG. 10. The coding region for PpLuc(GC) is depicted in italics. The 5'UTR element sequence is underlined. The sequence depicted in FIG. 22 corresponds to SEQ ID No. 1466.

FIG. 23 shows the nucleotide sequence of rpl21—PpLuc (GC)—ag—A64. The 5'UTR of human ribosomal protein Large 21 lacking the 5' terminal oligopyrimidine tract replaced the rpl32 5'UTR element in the construct shown in FIG. 10. The coding region for PpLuc(GC) is depicted in italics. The 5'UTR element sequence is underlined. The sequence depicted in FIG. 23 corresponds to SEQ ID No. 1467.

FIG. 24 shows the nucleotide sequence of atp5a1—PpLuc (GC)—ag—A64. The 5'UTR of human ATP synthase, H+ transporting, mitochondrial F1 complex, alpha subunit 1 lacking the 5' terminal oligopyrimidine tract replaced the rpl32 5'UTR element in the construct shown in FIG. 10. The coding region for PpLuc(GC) is depicted in italics. The 5'UTR element sequence is underlined. The sequence depicted in FIG. 24 corresponds to SEQ ID No. 1468.

FIG. 25 shows the nucleotide sequence of HSD17B4—PpLuc(GC)—ag—A64. The 5'UTR of human hydroxysteroid (17-beta) dehydrogenase 4 lacking the 5' terminal oligopyrimidine tract replaced the rpl32 5'UTR element in the construct shown in FIG. 10. The coding region for PpLuc(GC) is depicted in italics. The 5'UTR element sequence is underlined. The sequence depicted in FIG. 25 corresponds to SEQ ID No. 1469.

FIG. 26 shows the nucleotide sequence of AIG1—PpLuc (GC)—ag—A64. The 5'UTR of human androgen-induced 1 lacking the 5' terminal oligopyrimidine tract replaced the rpl32 5'UTR element in the construct shown in FIG. 10. The coding region for PpLuc(GC) is depicted in italics. The 5'UTR element sequence is underlined. The sequence depicted in FIG. 26 corresponds to SEQ ID No. 1470.

FIG. 27 shows the nucleotide sequence of COX6C—PpLuc(GC)—ag—A64. The 5'UTR of human cytochrome c oxidase subunit VIc lacking the 5' terminal oligopyrimidine tract replaced the rpl32 5'UTR element in the construct shown in FIG. 10. The coding region for PpLuc(GC) is depicted in italics. The 5'UTR element sequence is underlined. The sequence depicted in FIG. 27 corresponds to SEQ ID No. 1471.

FIG. 28 shows the nucleotide sequence of ASAH1—PpLuc(GC)—ag—A64. The 5'UTR of human N-acylsphingosine amidohydrolase (acid ceramidase) 1 lacking the 5' terminal oligopyrimidine tract replaced the rpl32 5'UTR element in the construct shown in FIG. 10. The coding region for PpLuc(GC) is depicted in italics. The 5'UTR element sequence is underlined. The sequence depicted in FIG. 28 corresponds to SEQ ID No. 1472.

FIG. 29 shows the nucleotide sequence of rpl35—PpLuc (GC)—ag—A64—histoneSL. The 5'UTR of human ribosomal protein Large 35 lacking the 5' terminal oligopyrimidine tract replaced the rpl32 5'UTR element in the construct shown in FIG. 11. The coding region for PpLuc(GC) is depicted in italics. The 5'UTR element sequence and the histone stem-loop sequence are underlined. The sequence depicted in FIG. 29 corresponds to SEQ ID No. 1473.

FIG. 30 shows the nucleotide sequence of rpl21—PpLuc (GC)—ag—A64—histoneSL. The 5'UTR of human ribosomal protein Large 21 lacking the 5' terminal oligopyrimidine tract replaced the rpl32 5'UTR element in the construct shown in FIG. 11. The coding region for PpLuc(GC) is depicted in italics. The 5'UTR element sequence and the histone stem-loop sequence are underlined. The sequence depicted in FIG. 30 corresponds to SEQ ID No. 1474.

FIG. 31 shows the nucleotide sequence of atp5a1—PpLuc (GC)—ag—A64—histoneSL. The 5'UTR of human ATP synthase, H+ transporting, mitochondrial F1 complex, alpha subunit 1 lacking the 5' terminal oligopyrimidine tract replaced the rpl32 5'UTR element in the construct shown in FIG. 11. The coding region for PpLuc(GC) is depicted in italics. The 5'UTR element sequence and the histone stem-loop sequence are underlined. The sequence depicted in FIG. 31 corresponds to SEQ ID No. 1475.

FIG. 32 shows the nucleotide sequence of HSD17B4—PpLuc(GC)—ag—A64—histoneSL. The 5'UTR of human hydroxysteroid (17-beta) dehydrogenase 4 lacking the 5' terminal oligopyrimidine tract replaced the rpl32 5'UTR element in the construct shown in FIG. 11. The coding region for PpLuc(GC) is depicted in italics. The 5'UTR element sequence and the histone stem-loop sequence are underlined. The sequence depicted in FIG. 32 corresponds to SEQ ID No. 1476.

FIG. 33 shows the nucleotide sequence of AIG1—PpLuc (GC)—ag—A64—histoneSL. The 5'UTR of human androgen-induced 1 lacking the 5' terminal oligopyrimidine tract replaced the rpl32 5'UTR element in the construct shown in FIG. 11. The coding region for PpLuc(GC) is depicted in italics. The 5'UTR element sequence and the histone stem-loop sequence are underlined. The sequence depicted in FIG. 33 corresponds to SEQ ID No. 1477.

FIG. 34 shows the nucleotide sequence of COX6C—PpLuc(GC)—ag—A64—histoneSL. The 5'UTR of human cytochrome c oxidase subunit VIc lacking the 5' terminal oligopyrimidine tract replaced the rpl32 5'UTR element in the construct shown in FIG. 11. The coding region for PpLuc(GC) is depicted in italics. The 5'UTR element sequence and the histone stem-loop sequence are underlined. The sequence depicted in FIG. 34 corresponds to SEQ ID No. 1478.

FIG. 35 shows the nucleotide sequence of ASAH1—PpLuc(GC)—ag—A64—histoneSL. The 5'UTR of human N-acylsphingosine amidohydrolase (acid ceramidase) 1 lacking the 5' terminal oligopyrimidine tract replaced the rpl32 5'UTR element in the construct shown in FIG. 11. The coding region for PpLuc(GC) is depicted in italics. The 5'UTR element sequence and the histone stem-loop sequence are underlined. The sequence depicted in FIG. 35 corresponds to SEQ ID No. 1479.

Figure 36:
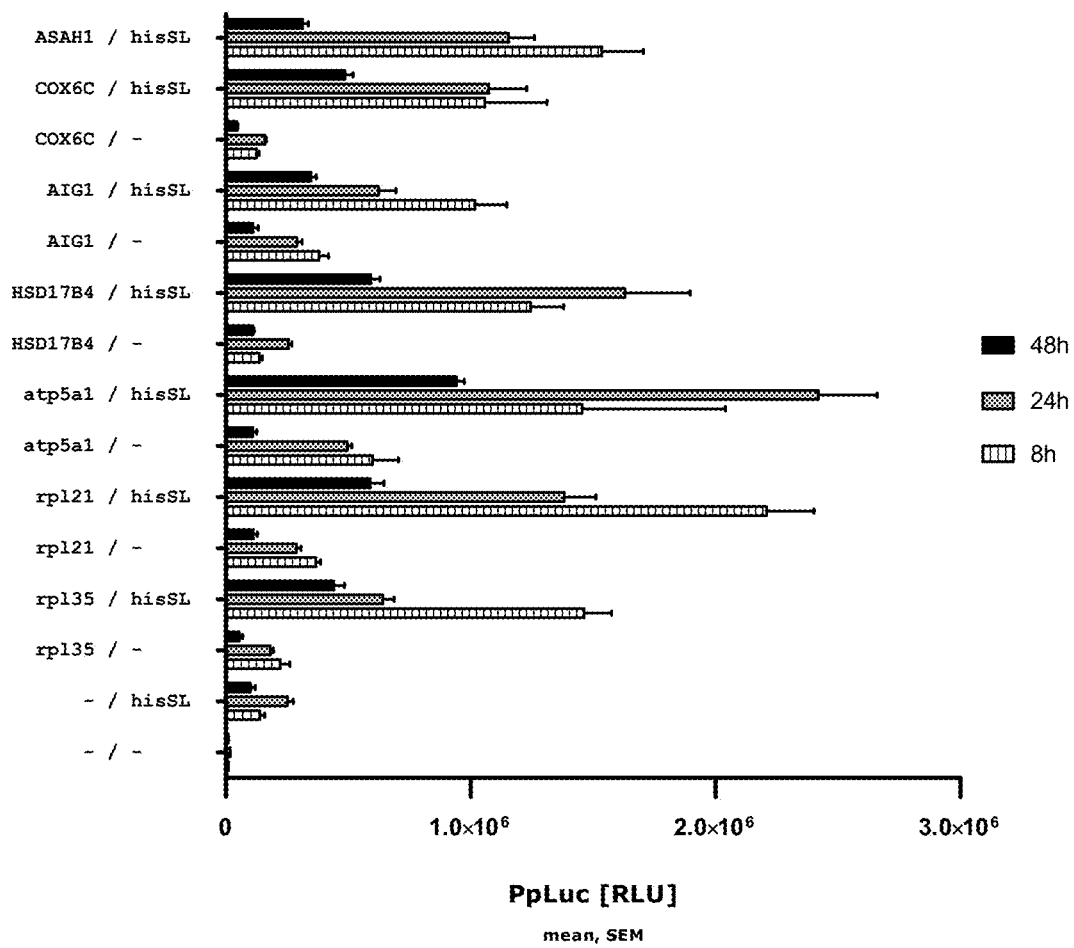

FIG. 36 is a graphical representation of the effect of 5'UTR elements derived from 5'UTRs of the TOP genes RPL35, RPL21, ATP5A1, HSD17B4, AIG1, COX6C and ASAH1, the histone stem-loop, and the combination of 5'UTR elements and histone stem-loop on luciferase expression from mRNA. The different mRNAs were transfected into human dermal fibroblasts (HDF) by lipofection. Luciferase levels were measured at 8, 24, and 48 hours after transfection. Both, either the histone stem-loop or the 5'UTR elements increase luciferase levels compared to mRNA lacking both these elements. Strikingly, the combination of 5'UTR elements and histone stem-loop further strongly increases the luciferase level, much above the level observed with either of the individual elements, thus acting synergistically. Data are graphed as mean RLU±SEM (relative light units±standard error) for triplicate transfections. The synergy between 5'UTR elements and histone stem-loop is summarized in example 5.4.

FIG. 37 shows the nucleotide sequence of mrpl21—PpLuc(GC)—albumin7—A64—C30—histoneSL. The 5'UTR of murine ribosomal protein Large 21 lacking the 5' terminal oligopyrimidine tract replaced the rpl32 5'UTR element in the construct shown in FIG. 13. The 5'UTR element sequence is underlined. The sequence depicted in FIG. 36 corresponds to SEQ ID No. 1443.

FIG. 38 shows the nucleotide sequence of mrpl35A—PpLuc(GC)—albumin7—A64—C30—histoneSL. The 5'UTR of murine ribosomal protein Large 35A lacking the 5' terminal oligopyrimidine tract replaced the rpl32 5'UTR element in the construct shown in FIG. 13. The 5'UTR element sequence is underlined. The sequence depicted in FIG. 37 corresponds to SEQ ID No. 1444.

Figure 39:
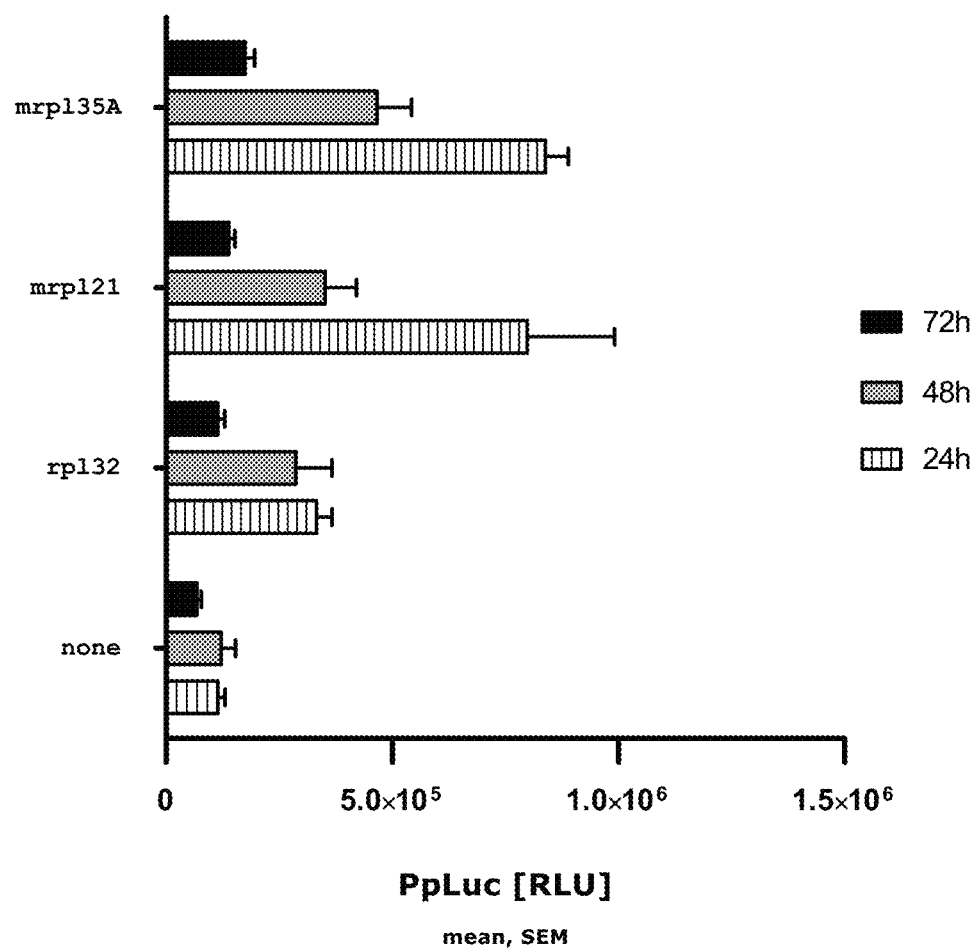

FIG. 39 is a graphical representation of the effect of the 5'UTR elements derived from 5'UTRs of mouse TOP genes on luciferase expression from mRNA. mRNAs containing either a mouse or a human 5'UTR element were transfected into human dermal fibroblasts (HDF) by lipofection. Luciferase levels were measured at 24, 48, and 72 hours after transfection. Mouse 5'UTR elements strongly increase luciferase levels compared to mRNA lacking a 5'UTR element, similarly as the human 5'UTR element. Data are graphed as mean RLU±SEM (relative light units±standard error) for triplicate transfections. RLU are summarized in Example 5.5.

SEQ ID No. 1-1363. 1435, and 1461-1462 sequences comprising 5'UTRs of TOP genes
SEQ ID No. 1364 PpLuc(GC)—ag—A64 (FIG. 6)
SEQ ID No. 1365 RPL32—PpLuc(GC)—ag—A64—C30—histoneSL (FIG. 7)
SEQ ID No. 1366 fragment of the 5'UTR of human ribosomal protein Large 32
SEQ ID No. 1367 fragment of the 5'UTR of human ribosomal protein Large 32
SEQ ID No. 1368 5'UTR of human ribosomal protein Large 32 lacking the 5' terminal oligopyrimidine tract
SEQ ID No. 1369 Human albumin 3'UTR
SEQ ID No. 1370 3'UTR of *Homo sapiens* hemoglobin, alpha 1 (HBA1)
SEQ ID No. 1371 3'UTR of *Homo sapiens* hemoglobin, alpha 2 (HBA2)
SEQ ID No. 1372 3'UTR of *Homo sapiens* hemoglobin, beta (HBB)
SEQ ID No. 1373 3'UTR of *Homo sapiens* tyrosine hydroxylase (TH)
SEQ ID No. 1374 3'UTR of *Homo sapiens* arachidonate 15-lipoxygenase (ALOX15)
SEQ ID No. 1375 3'UTR of *Homo sapiens* collagen, type I, alpha 1 (COL1A1)
SEQ ID No. 1376 albumin? 3'UTR
SEQ ID No. 1377 Human albumin 3'UTR+poly(A) sequence
SEQ ID No. 1378 Human albumin 3'UTR fragment 1
SEQ ID No. 1379 Human albumin 3'UTR fragment 2
SEQ ID No. 1380 Human albumin 3'UTR fragment 3
SEQ ID No. 1381 Human albumin 3'UTR fragment 4
SEQ ID No. 1382 Human albumin 3'UTR fragment 5
SEQ ID No. 1383 Human albumin 3'UTR fragment 6
SEQ ID No. 1384 Human albumin 3'UTR fragment 7
SEQ ID No. 1385 Human albumin 3'UTR fragment 8
SEQ ID No. 1386 Human albumin 3'UTR fragment 9
SEQ ID No. 1387 Human albumin 3'UTR fragment 10
SEQ ID No. 1388 Human albumin 3'UTR fragment 11
SEQ ID No. 1389 Human albumin 3'UTR fragment 12
SEQ ID No. 1390 Human albumin 3'UTR fragment 13
SEQ ID NO. 1391 Sequence according to formula (Ic)
SEQ ID NO. 1392 Sequence according to formula (IIc):
SEQ ID NO. 1393 Sequence according to formula (Id):
SEQ ID NO. 1394 Sequence according to formula (IId)
SEQ ID NO. 1395 Sequence according to formula (Ie)
SEQ ID NO. 1396 Sequence according to formula (IIe)
SEQ ID NO. 1397 Sequence according to formula (If)
SEQ ID NO. 1398 Sequence according to formula (IIf)
SEQ ID NO. 1399 Sequence according to formula (Ig)
SEQ ID NO. 1400 Sequence according to formula (IIg)
SEQ ID NO. 1401 Sequence according to formula (Ih)
SEQ ID NO. 1402 Sequence according to formula (IIh)
SEQ ID NO. 1403 Sequence according to formula (Ic)
SEQ ID NO. 1404 Sequence according to formula (Ic)
SEQ ID NO. 1405 Sequence according to formula (Ic)
SEQ ID NO. 1406 Sequence according to formula (Ie)
SEQ ID NO. 1407 Sequence according to formula (Ie)
SEQ ID NO. 1408 Sequence according to formula (Ie)
SEQ ID NO. 1409 Sequence according to formula (If)
SEQ ID NO. 1410 Sequence according to formula (If)
SEQ ID NO. 1411 Sequence according to formula (If)
SEQ ID NO. 1412 Sequence according to formula (Ig)
SEQ ID NO. 1413 Sequence according to formula (Ig)
SEQ ID NO. 1414 Sequence according to formula (Ig)
SEQ ID NO. 1415 Sequence according to formula (Ih)
SEQ ID NO. 1416 Sequence according to formula (Ih)
SEQ ID NO. 1417 Sequence according to formula (Ih)
SEQ ID NO. 1418 Sequence according to formula (IIc)
SEQ ID NO. 1419 Sequence according to formula (IIc)
SEQ ID NO. 1420 Sequence according to formula (IIc)
SEQ ID NO. 1421 Sequence according to formula (IIe)
SEQ ID NO. 1422 Sequence according to formula (IIe)
SEQ ID NO. 1423 Sequence according to formula (IIe)
SEQ ID NO. 1424 Sequence according to formula (IIf)
SEQ ID NO. 1425 Sequence according to formula (IIf)
SEQ ID NO. 1426 Sequence according to formula (IIf)
SEQ ID NO. 1427 Sequence according to formula (IIg)
SEQ ID NO. 1428 Sequence according to formula (IIg)
SEQ ID NO. 1429 Sequence according to formula (IIg)
SEQ ID NO. 1430 Sequence according to formula (IIh)
SEQ ID NO. 1431 Sequence according to formula (IIh)
SEQ ID NO. 1432 Sequence according to formula (IIh)
SEQ ID NO. 1433 Example histone stem-loop sequence
SEQ ID NO. 1434 Center, α-complex-binding portion of the 3'UTR of an α-globin gene
SEQ ID NO. 1435 ATP synthase lipid-binding protein, mitochondrial (atp5g2)
SEQ ID NO. 1436 RPL35—PpLuc(GC)—albumin7—A64—C30—histoneSL (FIG. 14)
SEQ ID NO. 1437 RPL21—PpLuc(GC)—albumin7—A64—C30—histoneSL (FIG. 15)
SEQ ID NO. 1438 ATP5A1—PpLuc(GC)—albumin7—A64—C30—histoneSL (FIG. 16)
SEQ ID NO. 1439 HSD17B4—PpLuc(GC)—albumin7—A64—C30—histoneSL (FIG. 17)
SEQ ID NO. 1440 AIG1—PpLuc(GC)—albumin7—A64—C30—histoneSL (FIG. 18)
SEQ ID NO. 1441 COX6C—PpLuc(GC)—albumin7—A64—C30—histoneSL (FIG. 19)
SEQ ID NO. 1442 ASAH1—PpLuc(GC)—albumin7—A64—C30—histoneSL (FIG. 20)
SEQ ID NO. 1443 mRPL21—PpLuc(GC)—albumin7—A64—C30—histoneSL (FIG. 37)

SEQ ID NO. 1444 mRPL35A—PpLuc(GC)—albumin7—A64—C30—histoneSL (FIG. 38)
SEQ ID NO. 1445 RPL35—PpLuc(GC)—A64—C30—histoneSL
SEQ ID NO. 1446 RPL21—PpLuc(GC)—A64—C30—histoneSL
SEQ ID NO. 1447 ATP5A1—PpLuc(GC)—A64—C30—histoneSL
SEQ ID NO. 1448 HSD17B4—PpLuc(GC)—A64—C30—histoneSL
SEQ ID NO. 1449 AIG1—PpLuc(GC)—A64—C30—histoneSL
SEQ ID NO. 1450 COX6C—PpLuc(GC)—A64—C30—histoneSL
SEQ ID NO. 1451 ASAH1—PpLuc(GC)—A64—C30—histoneSL
SEQ ID NO. 1452 5'UTR of human ribosomal protein Large 35 (RPL35) lacking the 5' terminal oligopyrimidine tract
SEQ ID NO. 1453 5'UTR of human ribosomal protein Large 21 (RPL21) lacking the 5' terminal oligopyrimidine tract
SEQ ID NO. 1454 5'UTR of human ATP synthase, H+ transporting, mitochondrial F1 complex, alpha subunit 1, cardiac muscle (ATP5A1) lacking the 5' terminal oligopyrimidine tract
SEQ ID NO. 1455 5'UTR of human hydroxysteroid (17-beta) dehydrogenase 4 (HSD17B4) lacking the 5' terminal oligopyrimidine tract
SEQ ID NO. 1456 5'UTR of human androgen-induced 1 (AIG1) lacking the 5' terminal oligopyrimidine tract
SEQ ID NO. 1457 5'UTR of human cytochrome c oxidase subunit VIc (COX6C) lacking the 5' terminal oligopyrimidine tract
SEQ ID NO. 1458 5'UTR of human N-acylsphingosine amidohydrolase (acid ceramidase) 1 (ASAH1) lacking the 5' terminal oligopyrimidine tract
SEQ ID NO. 1459 5'UTR of mouse ribosomal protein Large 21 (mRPL21) lacking the 5' terminal oligopyrimidine tract
SEQ ID NO. 1460 5'UTR of mouse ribosomal protein large 35A (mRPL35A) lacking the 5' terminal oligopyrimidine tract
SEQ ID NO. 1461 Mouse ribosomal protein Large 21 (mRPL21)
SEQ ID NO. 1462 Mouse ribosomal protein large 35A (mRPL35A)
SEQ ID NO. 1463 RPL32—PpLuc(GC)—ag—A64 (FIG. 10)
SEQ ID NO. 1464 PpLuc(GC)—ag—A64—histoneSL (FIG. 9)
SEQ ID NO. 1465 PpLuc(GC)—albumin7—A64—C30—histoneSL
SEQ ID NO. 1466 RPL35—PpLuc(GC)—ag—A64 (FIG. 22)
SEQ ID NO. 1467 RPL21—PpLuc(GC)—ag—A64 (FIG. 23)
SEQ ID NO. 1468 atp5a1—PpLuc(GC)—ag—A64 (FIG. 24)
SEQ ID NO. 1469 HSD17B4—PpLuc(GC)—ag—A64 (FIG. 25)
SEQ ID NO. 1470 AIG1—PpLuc(GC)—ag—A64 (FIG. 26)
SEQ ID NO. 1471 COX6C—PpLuc(GC)—ag—A64 (FIG. 27)
SEQ ID NO. 1472 ASAH1—PpLuc(GC)—ag—A64 (FIG. 28)
SEQ ID NO. 1473 RPL35—PpLuc(GC)—ag—A64—histoneSL (FIG. 29)
SEQ ID NO. 1474 RPL21—PpLuc(GC)—ag—A64—histoneSL (FIG. 30)
SEQ ID NO. 1475 atp5a1—PpLuc(GC)—ag—A64—histoneSL (FIG. 31)
SEQ ID NO. 1476 HSD17B4—PpLuc(GC)—ag—A64—histoneSL (FIG. 32)
SEQ ID NO. 1477 AIG1—PpLuc(GC)—ag—A64—histoneSL (FIG. 33)
SEQ ID NO. 1478 COX6C—PpLuc(GC)—ag—A64—histoneSL (FIG. 34)
SEQ ID NO. 1479 ASAH1—PpLuc(GC)—ag—A64—histoneSL (FIG. 35)
SEQ ID NO. 1480 RPL32—PpLuc(GC)—ag—A64—histoneSL (FIG. 11)
SEQ ID NO. 1481 RPL32—PpLuc(GC)—albumin7—A64—C30—histoneSL (FIG. 13)

EXAMPLES

1. Preparation of DNA-Templates

A vector for in vitro transcription was constructed containing a T7 promoter followed by a GC-enriched sequence coding for Photinus pyralis luciferase (PpLuc(GC)) and an A64 poly(A) sequence. The poly(A) sequence was followed by a restriction site used for linearization of the vector before in vitro transcription. mRNA obtained from this vector accordingly by in vitro transcription is designated as "PpLuc (GC)—A64".

This vector was modified to include untranslated sequences 5' or 3' of the open reading frame. In summary, vectors comprising the following mRNA encoding sequences have been generated:

SEQ ID No. 1364 PpLuc(GC)—ag—A64 (FIG. 6)
SEQ ID No. 1365 RPL32—PpLuc(GC)—ag—A64—C30—histoneSL (FIG. 7):
SEQ ID NO. 1436 RPL35—PpLuc(GC)—albumin7—A64—C30—histoneSL (FIG. 14)
SEQ ID NO. 1437 RPL21—PpLuc(GC)—albumin7—A64—C30—histoneSL (FIG. 15)
SEQ ID NO. 1438 ATP5A1—PpLuc(GC)—albumin7—A64—C30—histoneSL (FIG. 16)
SEQ ID NO. 1439 HSD17B4—PpLuc(GC)—albumin7—A64—C30—histoneSL (FIG. 17)
SEQ ID NO. 1440 AIG1—PpLuc(GC)—albumin7—A64—C30—histoneSL (FIG. 18)
SEQ ID NO. 1441 COX6C—PpLuc(GC)—albumin7—A64—C30—histoneSL (FIG. 19)
SEQ ID NO. 1442 ASAH1—PpLuc(GC)—albumin7—A64—C30—histoneSL (FIG. 20)
SEQ ID NO. 1443 mRPL21—PpLuc(GC)—albumin7—A64—C30—histoneSL (FIG. 37)
SEQ ID NO. 1444 mRPL35A—PpLuc(GC)—albumin7—A64—C30—histoneSL (FIG. 38)
SEQ ID NO. 1445 RPL35—PpLuc(GC)—A64—C30—histoneSL
SEQ ID NO. 1446 RPL21—PpLuc(GC)—A64—C30—histoneSL
SEQ ID NO. 1447 ATP5A1—PpLuc(GC)—A64—C30—histoneSL
SEQ ID NO. 1448 HSD17B4—PpLuc(GC)—A64—C30—histoneSL
SEQ ID NO. 1449 AIG1—PpLuc(GC)—A64—C30—histoneSL
SEQ ID NO. 1450 COX6C—PpLuc(GC)—A64—C30—histoneSL
SEQ ID NO. 1451 ASAH1—PpLuc(GC)—A64—C30—histoneSL SEQ ID NO. 1463 RPL32—PpLuc(GC)—ag—A64 (FIG. 10)

SEQ ID NO. 1464 PpLuc(GC)—ag—A64—histoneSL (FIG. 9)

SEQ ID NO. 1465 PpLuc(GC)—albumin7—A64—C30—histoneSL

SEQ ID NO. 1466 RPL35—PpLuc(GC)—ag—A64 (FIG. 22)

SEQ ID NO. 1467 RPL21—PpLuc(GC)—ag—A64 (FIG. 23)

SEQ ID NO. 1468 atp5a1—PpLuc(GC)—ag—A64 (FIG. 24)

SEQ ID NO. 1469 HSD17B4—PpLuc(GC)—ag—A64 (FIG. 25)

SEQ ID NO. 1470 AIG1—PpLuc(GC)—ag—A64 (FIG. 26)

SEQ ID NO. 1471 COX6C—PpLuc(GC)—ag—A64 (FIG. 27)

SEQ ID NO. 1472 ASAH1—PpLuc(GC)—ag—A64 (FIG. 28)

SEQ ID NO. 1473 RPL35—PpLuc(GC)—ag—A64—histoneSL (FIG. 29)

SEQ ID NO. 1474 RPL21—PpLuc(GC)—ag—A64—histoneSL (FIG. 30)

SEQ ID NO. 1475 atp5a1—PpLuc(GC)—ag—A64—histoneSL (FIG. 31)

SEQ ID NO. 1476 HSD17B4—PpLuc(GC)—ag—A64—histoneSL (FIG. 32)

SEQ ID NO. 1477 AIG1—PpLuc(GC)—ag—A64—histoneSL (FIG. 33)

SEQ ID NO. 1478 COX6C—PpLuc(GC)—ag—A64—histoneSL (FIG. 34)

SEQ ID NO. 1479 ASAH1—PpLuc(GC)—ag—A64—histoneSL (FIG. 35)

SEQ ID NO. 1480 RPL32—PpLuc(GC)—ag—A64—histoneSL (FIG. 11)

SEQ ID NO. 1481 RPL32—PpLuc(GC)—albumin7—A64—C30—histoneSL (FIG. 13)

2. In Vitro Transcription

The DNA-template according to Example 1 was linearized and transcribed in vitro using T7-Polymerase. The DNA-template was then digested by DNase-treatment. mRNA transcripts contained a 5'-CAP structure obtained by adding an excess of N7-Methyl-Guanosine-5'-Triphosphate-5'-Guanosine to the transcription reaction. mRNA thus obtained was purified and resuspended in water.

3. Luciferase Expression by mRNA Lipofection

Human dermal fibroblasts (HDF) were seeded in 24 well plates at a density of $5 \times 10^4$ cells per well. The following day, cells were washed in opti-MEM and then transfected with 50 ng per well of Lipofectamine2000-complexed PpLuc-encoding mRNA in opti-MEM. As a control, mRNA not coding for PpLuc was lipofected separately. mRNA coding for Renilla reniformis luciferase (RrLuc) was transfected together with PpLuc mRNA to control for transfection efficiency (20 ng of RrLuc mRNA per well). 90 minutes after start of transfection, opti-MEM was exchanged for medium. 24, 48, 72 hours after transfection, medium was aspirated and cells were lysed in 200 µl of lysis buffer (25 mM Tris, pH 7.5 (HCl), 2 mM EDTA, 10% glycerol, 1% Triton X-100, 2 mM DTT, 1 mM PMSF). Lysates were stored at $-20°$ C. until luciferase activity was measured.

Alternatively, HDF were seeded in 96 well plates one to three days before transfection at a density of $10^4$ cells per well. Immediately before lipofection, cells were washed in opti-MEM. Cells were lipofected with 25 ng of PpLuc-encoding mRNA per well complexed with Lipofectamine2000. In some experiments, mRNA coding for Renilla reniformis luciferase (RrLuc) was transfected together with PpLuc mRNA to control for transfection efficiency (2.5 ng of RrLuc mRNA per well). 90 minutes after start of transfection, opti-MEM was exchanged for medium. At various time points post transfection, medium was aspirated and cells were lysed in 100 µl of lysis buffer (Passive Lysis Buffer, Promega). Lysates were stored at $-80°$ C. until luciferase activity was measured.

4. Luciferase Measurement

Luciferase activity was measured as relative light units (RLU) in a BioTek SynergyHT plate reader. PpLuc activity was measured at 15 seconds measuring time using 50 µl of lysate and 200 µl of luciferin buffer (75 µM luciferin, 25 mM Glycylglycin, pH 7.8 (NaOH), 15 mM MgSO4, 2 mM ATP). RrLuc activity was measured at 15 seconds measuring time using 50 µl of lysate and 200 µl of coelenterazin buffer (40 µM coelenterazin in phosphate buffered saline adjusted to 500 mM NaCl).

Alternatively, luciferase activity was measured as relative light units (RLU) in a Hidex Chameleon plate reader. PpLuc activity was measured at 2 seconds measuring time using 20 µl of lysate and 50 µl of luciferin buffer (Beetle-Juice, PJK GmbH). RrLuc activity was measured at 2 seconds measuring time using 20 µl of lysate and 50 µl of coelenterazin buffer (Renilla-Juice, PJK GmbH).

Results 5.1 the Combination of 5'UTR Elements Derived from 5'UTRs of TOP Genes and Histone Stem-Loop Increases Protein Expression Strongly.

To investigate the effect of the combination of a 5'UTR element derived from a 5'UTR of a TOP gene and a histone stem-loop (histoneSL) on protein expression from mRNA, mRNAs with different UTRs were synthesized: mRNAs either lacked both 5'UTR element and histoneSL, or contained both 5'UTR element and histoneSL. Luciferase-encoding mRNAs or control mRNA were transfected into human dermal fibroblasts (HDF). Luciferase levels were measured at 24 hours after transfection (see following Table 1 and FIG. 8).

TABLE 1

| mRNA | RLU at 24 hours |
| --- | --- |
| control RNA | 588 |
| PpLuc(GC)-ag-A64 | 12246 |
| RPL32-PpLuc(GC)-ag-A64-C30-histoneSL | 319840 |

Luciferase was clearly expressed from mRNA having neither 5'UTR element nor histoneSL. Strikingly however, the combination of 5'UTR element and histoneSL strongly increased the luciferase level. The magnitude of the rise in luciferase level due to combining 5'UTR element and histoneSL in the same mRNA indicates that they are acting synergistically.

5.2 the Combination of 5'UTR Elements Derived from 5'UTRs of TOP Genes and Histone Stem-Loop Increases Protein Expression from mRNA in a Synergistic Manner To investigate the effect of the combination of a 5'UTR element derived from a 5'UTR of a TOP gene and histone stem-loop on protein expression from mRNA, mRNAs with different UTRs were synthesized: mRNAs either lacked both 5'UTR element and histone stem-loop, or contained either a 5'UTR element or a histone stem-loop, or both 5'UTR element and histone stem-loop. Luciferase-encoding mRNAs were transfected into human dermal fibroblasts (HDF). Luciferase levels were measured at 8, 24, and 48 hours after transfection (see following Table 2 and FIG. 12).

TABLE 2

| mRNA | RLU at 8 hours | RLU at 24 hours | RLU at 48 hours |
|---|---|---|---|
| PpLuc(GC)-ag-A64 | 13110 | 25861 | 14362 |
| PpLuc(GC)-ag-A64-histoneSL | 88640 | 97013 | 57026 |
| rpl32-PpLuc(GC)-ag-A64 | 155654 | 212245 | 102528 |
| rpl32-PpLuc(GC)-ag-A64-histoneSL | 301384 | 425825 | 161974 |

Luciferase was clearly expressed from mRNA having neither 5'UTR element nor histone stem-loop. Both, either the histone stem-loop or the 5'UTR element increased luciferase levels compared to mRNA lacking both these elements. Strikingly however, the combination of 5'UTR element and histone stem-loop further strongly increased the luciferase level, much above the level observed with either of the individual elements. The magnitude of the rise in luciferase level due to combining 5'UTR element and histone stem-loop in the same mRNA demonstrates that they are acting synergistically.

The synergy between 5'UTR element and histone stem-loop was quantified by dividing the signal from mRNA combining both elements by the sum of the signal from mRNA lacking both elements plus the rise in signal effected by the 5'UTR element plus the rise in signal effected by the histone stem-loop. This calculation was performed for the three time points individually and for total protein expressed from 0 to 48 hours calculated from the area under the curve (AUC) (see following Table 3).

TABLE 3

| rpl32 | histoneSL | RLU | Δ RLU | RLU predicted (additive) | synergy |
|---|---|---|---|---|---|
| 8 h | | | | | |
| - | - | 13110 | | | |
| - | + | 88640 | 75530 | | |
| + | - | 155654 | 142544 | | |
| + | + | 301384 | | 231184 | 1.30 |
| 24 h | | | | | |
| - | - | 25861 | | | |
| - | + | 97013 | 71152 | | |
| + | - | 212245 | 186384 | | |
| + | + | 425825 | | 283397 | 1.50 |
| 48 h | | | | | |
| - | - | 14362 | | | |
| - | + | 57026 | 42664 | | |
| + | - | 102528 | 88166 | | |
| + | + | 161974 | | 145192 | 1.12 |
| AUC 0-48 hours | | | | | |
| - | - | 846881 | | | |
| - | + | 3688000 | 2841119 | | |
| + | - | 7343000 | 6496119 | | |
| + | + | 14080000 | | 10184119 | 1.38 |

The synergy thus calculated specifies how much higher the luciferase level from mRNA combining 5'UTR element and histone stem-loop is than would be expected if the effects of 5'UTR element and histone stem-loop were purely additive. This result confirms that the combination of 5'UTR element and histone stem-loop effects a markedly synergistic increase in protein expression.

5.3 5'UTR Elements Derived from 5'UTRs of TOP Genes Increase Protein Expression from mRNA.

To investigate the effect of 5'UTR elements derived from 5'UTRs of TOP genes on protein expression from mRNA, mRNAs with one of different 5'UTR elements were synthesized. In addition, mRNAs contained the albumin? 3'UTR element. Luciferase-encoding mRNAs were transfected into human dermal fibroblasts (HDF). Luciferase levels were measured at 24, 48, and 72 hours after transfection (see following Table 4 and FIG. 21).

TABLE 4

| 5'UTR | RLU at 24 hours | RLU at 48 hours | RLU at 72 hours |
|---|---|---|---|
| none | 114277 | 121852 | 68235 |
| rpl32 | 332236 | 286792 | 114148 |
| rpl35 | 495917 | 234070 | 96993 |
| rpl21 | 563314 | 352241 | 156605 |
| atp5a1 | 1000253 | 538287 | 187159 |
| HSD17B4 | 1179847 | 636877 | 299337 |
| AIG1 | 620315 | 446621 | 167846 |
| COX6C | 592190 | 806065 | 173743 |
| ASAH1 | 820413 | 529901 | 198429 |

Luciferase was clearly expressed from mRNA lacking a 5'UTR element. Strikingly however, all 5'UTR elements strongly increased the luciferase level.

5.4 the Combination of 5'UTR Elements Derived from 5'UTRs of TOP Genes and Histone Stem-Loop Increases Protein Expression from mRNA in a Synergistic Manner.

To investigate the effect of the combination of 5'UTR elements derived from the 5'UTRs of TOP genes and histone stem-loop on protein expression from mRNA, mRNAs with different UTRs were synthesized: mRNAs either lacked both 5'UTR element and histone stem-loop, or contained a histone stem-loop, or contained one of different 5'UTR elements derived from 5'UTRs of TOP genes, or contained both one of different 5'UTR elements and a his tone stem-loop. In addition, mRNAs contained the alpha-globin 3'UTR element. Luciferase-encoding mRNAs were transfected into human dermal fibroblasts (HDF). Luciferase levels were measured at 8, 24, and 48 hours after transfection (see FIG. 36). Luciferase was clearly expressed from mRNA having neither 5'UTR element nor histone stem-loop. The histone stem-loop increased the luciferase level. All 5'UTR elements also increased the luciferase level. Strikingly however, the combinations of 5'UTR element and histone stem-loop further strongly increased the luciferase level, much above the level observed with either of the individual elements. The magnitude of the rise in luciferase level due to combining 5'UTR element and histone stem-loop in the same mRNA demonstrates that they are acting synergistically.

The synergy between 5'UTR element and histone stem-loop was quantified by dividing the signal from mRNA combining both elements by the sum of the signal from mRNA lacking both elements plus the rise in signal effected by the 5'UTR element plus the rise in signal effected by the histone stem-loop. This calculation was performed for total protein expressed from 0 to 48 hours calculated from the area under the curve (AUC) (see following Table 5).

TABLE 5

| TOP 5'UTR | Synergy with histone stem-loop |
|---|---|
| 35L | 2.50 |
| 21L | 3.25 |

TABLE 5-continued

| TOP 5'UTR | Synergy with histone stem-loop |
|---|---|
| atp5a1 | 3.00 |
| HSD17B4 | 3.55 |
| AIG1 | 1.52 |
| COX6C | 3.19 |

The synergy thus calculated specifies how much higher the luciferase level from mRNA combining 5'UTR element and histone stem-loop is than would be expected if the effects of 5'UTR element and histone stem-loop were purely additive. The luciferase level from mRNA combining 5'UTR element and histone stem-loop was up to more than three times higher than if their effects were purely additive. This result confirms that the combination of 5'UTR element and histone stem-loop effects a markedly synergistic increase in protein expression.

5.5 5'UTR Elements Derived from 5'UTRs of Mouse TOP Genes Increase Protein Expression from mRNA.

To investigate the effect of TOP 5'UTR elements derived from 5'UTRs of mouse TOP genes on protein expression from mRNA, mRNAs with two different mouse 5'UTR elements were synthesized. In addition, mRNAs contained the albumin? 3'UTR element. Luciferase-encoding mRNAs were transfected into human dermal fibroblasts (HDF). For comparison, mRNA containing the human rpl32 5'UTR element was transfected. Luciferase levels were measured at 24, 48, and 72 hours after transfection (see following Table 6 and FIG. 39).

TABLE 6

| 5'UTR | RLU at 24 hours | RLU at 48 hours | RLU at 72 hours |
|---|---|---|---|
| none | 114277 | 121852 | 68235 |
| rpl32 | 332236 | 286792 | 114148 |
| mrpl21 | 798233 | 351894 | 139249 |
| mrpl35A | 838609 | 466236 | 174949 |

Luciferase was clearly expressed from mRNA lacking a 5'UTR element. Both mouse 5'UTR elements strongly increased the luciferase level, similarly as the human 5'UTR element.

```
Homo sapiens alpha-2-macroglobulin (A2M):
                                                        (Seq ID No: 1)
gctccttctttctg
caacatg Homo sapiens acyl-CoA dehydrogenase, C-4 to C-12 straight chain
(ACADM):
                                                        (Seq ID No: 2)
ggctctctttccgcgctgcggtcagcctcggcgtcccacagagagggccagaggtggaaa
cgcagaaaaccaaaccaggactatcagagattgcccgagaggggatg Homo sapiens arylsulfatase E (chondrodysplasia punctata 1)
(ARSE):
                                                        (Seq ID No: 3)
cttcctcttcttgatcggggattcaggaaggagcccaggagcagag
gaagtagagagagagacaacatg Homo sapiens Bruton agammaglobulinemia tyrosine kinase
(BTK):
                                                        (Seq ID No: 4)
tgtccttcctctctggactgtaagaatatgtctccagggccag
tgtctgctgcgatcgagtcccaccttccaagtcctggcatctcaatgcatctgggaagc
tacctgcattaagtcaggactgagcacacaggtgaactccagaaagaagaagctatg Homo sapiens complement component 2 (C2):
                                                        (Seq ID No: 5)
tgac
cttttccctcccgcggctctctacctctcgccgccccctagggaggacaccatg Homo sapiens cyclin-dependent kinase 4 (CDK4):
                                                        (Seq ID No: 6)
gggcctctctagcttgcggcctgtgtctatggtcgggccctctgcgtccagctgctccg
gaccgagctcgggtgtatgggccgtaggaaccggctccggggccccgataac
gggccgcccccacagcaccccgggctggcgtgagggtctcccttgatctgagaatg Homo sapiens
cytochrome P450, family 17, subfamily A, polypeptide
1 (CYP17A1):
                                                        (Seq ID No: 7)
agctcttctactccactgctgtctatcttgcctgccggcacc
cagccaccatg Homo sapiens endoglin (ENG):
                                                        (Seq ID No: 8)
cttcctctacccggttgg
caggcggcctggcccagcccttctctaaggaagcg
catttcctgcctccctgggccggccgggctggatg Homo sapiens excision repair cross-complementing rodent repair
``` deficiency, complementation group 3 (ERCC3):

(Seq ID No: 9)

tcttctctctgctgctgtagctgccatg

Homo sapiens excision repair cross-complementing rodent repair deficiency, complementation group 5 (ERCC5):

(Seq ID No: 10)

ctgtctttcttccgggaggcggtgacagctgctgagacgtgttgcagccagag
tctctccgctttaatgcgctcccattagtgccgtcccccactggaaaac
cgtggcttctgtattatttgccatctttgttgtgtaggag
cagggagggcttcctcccggggtcctaggcggcggtgcagtccgtcgtagaagaatt
agagtagaagttgtcggggtccgctcttaggacgcagccgcctcatg Homo sapiens ferritin, light polypeptide (FTL):

(Seq ID No: 11)

cgtcccctcgcagttcggcggtcccgcgggtctgtctcttgcttcaacagtgtttggacg
gaacagatccggggactctcttccagcctccgaccgccctccgatttcctctccgcttgc
aacctccgggaccatcttctcggccatcctgcttctgggacctgccagcaccgttttt
gtggttagctccttcttgccaaccaaccatg Homo sapiens galactosylceramidase (GALC):

(Seq ID No: 12)

ccgcctccctgggcgccggagtcatgtgacccacacaatg

Homo sapiens gap junction protein, alpha 1, 43 kDa (GJA1):

(Seq ID No: 13)

ttttctttcattaggggggaaggcgtgaggaaagtaccaaacagcagcggag
ttttaaactttaaatagacaggtctgagtgcctgaactt
gcctttcatttttacttcatcctccaaggagttcaatcacttggcgtgacttcac
tactttaagcaaaagagtggtgcccaggcaacatg Homo sapiens gap junction protein, beta 1, 32 kDa (GJB1):

(Seq ID No: 14)

cattctctgggaaagggcagcagcagccaggtgtggcag
tgacagggaggtgtgaatgaggcaggatg

Homo sapiens glucose-6-phosphate isomerase (GPI):

(Seq ID No: 15)

cgctccttcctcctcggctcgcgtctcactcagtgtaccttctagtcccgccatg

Homo sapiens hydroxyacyl-CoA dehydrogenase/3-ketoacyl-CoA thiolase/ enoyl-CoA hydratase (trifunctional protein), alpha subunit (HADHA):

(Seq ID No: 16)

ctgtcctcttcagctcaa
gatg

Homo sapiens hydroxyacyl-CoA dehydrogenase/3-ketoacyl-CoA thiolase/enoyl-CoA hydratase (trifunctional protein), beta subunit (HADHB):

(Seq ID No: 17)

gggccctttctgggcag
gacccgcccttggtcccgcagagccttggtacttggacctgaaccttgctccga
gagggagtcctcgcggacgtcagccaagattccagaatg Homo sapiens complement factor H (CFH):

(Seq ID No: 18)

cttccttttgcag
caagttctttcctgcactaatcacaattcttggaagaggagaactggacgtt
gtgaacagagttagctggtaaatgtcctcttaaaagatccaaaaaatg Homo sapiens sarcoglycan, gamma (35 kDa dystrophin-associated glycoprotein) (SGCG):

(Seq ID No: 19)

agcccttctccagggacagttgctgaagcttcatcctttgctctcattctg
taagtcatagaaaagtttgaaacattctgtctgtggtagagctcgggccagctgtag
ttcattcgccagtgtgcttttcttaatatctaagatg Homo sapiens lipase A, lysosomal acid, cholesterol esterase (LIPA):

(Seq ID No: 20)

ggtcccctatccgcaccccggcccctgagagctggcactgcgactcgaga
cagcggcccggcaggacagctccagaatg Homo sapiens lipoprotein lipase (LPL):

(Seq ID No: 21)

cccctcttcctcctcctcaagggaaagctgcccactttctagctgccctgccatcccctt
taaagggcgacttgctcagcgccaaac
cgcggctccagccctctccagcctccggctcagccggctcatcagtcggtccgcgcctt
gcagctcctccagagggacgcgccccgagatg -continued

*Homo sapiens* mutL homolog 1, colon cancer, nonpolyposis type 2 (*E. coli*) (MLH1):

(Seq ID No: 22)

ggctcttctggcgccaaaatg

*Homo sapiens* Niemann-Pick disease, type C1 (NPC1):

(Seq ID No: 23)

cttccttcctgaccggcgcgcg
cagcctgctgccgcggtcagcgcctgctcctgctcctccgctcctcctgcgcggggtgct
gaaacagcccggggaagtagagccgcctccggggagcccaaccagccgaac
gccgccggcgtcagcagccttgcgcggccacagcatg

*Homo sapiens* peroxisomal biogenesis factor 12 (PEX12):

(Seq ID No: 24)

gcgcctctcttccgccaggcatcccagaggtcctggtggtttcatttccgggtgcggctt
ctgtcataaagcggagacctcccttcaaacgtggcgtcgtgggttgttt
gcgcctcgcctggggtcagcgagcaaggacgggcgcgggcggggatactcaaa
gccaacagctggagtcagcccttgtgtcccgggctcacagtggcac
gactgaatcctcagagtcggctggcttttgagctctcacgattggggag
gaggggggcgtttctggttcgcagctccagag
gattgcgttccttcccccatacctgtcccccacagtcacgctctgccctgacgtgcag
catttgacaagttaccccctcgccacatactacttccacccacgtccgagttaacttt
gttcttaaccttcttgagactaccctcggcctccaggtcttttttttcccag
ttcattttttgcccataagattgagtttcgagtttcagatatcatgcagaaagtttac
ctttaagactgagcacccatctgatactcttcctcccgaaaaagttcatgctcacgaga
gagtttgtgggaaaagtgaaagccagtacacgcaggaaactatg

*Homo sapiens* peroxisomal biogenesis factor 6 (PEX6):

(Seq ID No: 25)

cgctccttcaccctcctcgttggtgtcctgtcaccatg

*Homo sapiens* phosphofructokinase, muscle (PFKM):

(Seq ID No: 26)

gagccttctt
gtcagcatctgttagtggaggttgggaagcctctcctccttcccctccctcttt
gcctccac
ctggctcctccccatgttcgtccatcaccctccccccttccccaaggacaatctgcaa
gaaagcagcggcggaggagagctaagactaaaagagtggatcatg

*Homo sapiens* serpin peptidase inhibitor, clade A (alpha-
1 antiproteinase, antitrypsin), member 1 (SERPINA1):

(Seq ID No: 27)

ctgtctcctcagcttcaggcaccaccactgacctgggacagtgaatcgacaatg

*Homo sapiens* phosphatase and tensin homolog (PTEN):

(Seq ID No: 28)

agttctctcctctcggaagctgcagccatgatggaagtttgagagttgagccgctgtgag
gcgaggccgggctcaggcgagggagatgagagacggcggcggccgcggcccggagcccct
ctcagcgcctgtgagcagccgcgggggcagcgccctcggggagccggccggcctgcggcg
gcggcagcggcggcgtttctcgcctcctcttcgtcttttctaaccgtgcagcctcttcct
cggcttctcctgaaagggaaggtggaagccgtgggctcgggcgggagccggctgaggcgc
ggcggcggcggcggcacctcccgctcctggagcgggggggagaagcggcggcggcggcgg
ccgcggcggctgcagctccagggaggggtctgagtcgcctgtcaccatttccaggctg
ggaacgccggagagttggtctctcccccttctactgcctccaaacacggcggcggcggcggc
ggcacatccagggacccgggccggttttaaacctcccgtccgccgccgccgaccccccg
tggcccgggctccggaggccgccggcggaggcagccgttcggaggattattcgtcttctc
cccattccgctgccgccgctgccaggcctctggctgctgaggagaagcaggcccagtcgc
tgcaaccatccagcagccgccgcagcagccattaccggctgcggtccagagccaagcgg
cggcagagcgaggggcatcagctaccgccaagtccagagccatttccatcctgcagaaga
agccccgccaccagcagcttctgccatctctctcctcctttttcttcagccacaggctcc
cagacatg

*Homo sapiens* solute carrier family 3 (cystine,
dibasic and neutral amino acid transporters, activator
of cystine, dibasic and neutral amino acid transport), member
1 (SLC3A1):

(Seq ID No: 29)

cctcccttactgcaggaaggcactccgaagacataagtcggtga
gacatg

*Homo sapiens* aldehyde dehydrogenase 3 family, member A2
(ALDH3A2):

(Seq ID No: 30)

ccgcctcccactccccagcgccccggaccgtgcagttctctgcag
gaccaggccatg

*Homo sapiens* bleomycin hydrolase (BLMH):

(Seq ID No: 31)

gtttctcccagcctcagcctccccgccgccgccgccgccgccgagccggtttcc
ttttttccggcgctccgggtgcgagagacaggtcgggcccctaggcagcgagcc -continued cagcgcaatcccggcgctcgcccaaggaccctggaagctaccgttaccccgccggg
cagcgtgggcgccatg

*Homo sapiens* cathepsin K (CTSK):

(Seq ID No: 32)

cctcctcctcttacccaaattttccagccgatcactggagctgacttccg
caatcccgatggaataaatctagcacccctgatggtgtgcccacacttt
gctgccgaaacgaagccagacaacagatttccatcagcaggatg

*Homo sapiens* GM2 ganglioside activator (GM2A):

(Seq ID No: 33)

gcttctttgcg
taaccaatactggaaggcatttaaaggcacctctgccgccacagaccttgcag
ttaactccgccctgacccaccttcccgatg

*Homo sapiens* hydroxysteroid (17-beta) dehydrogenase 4 (HSD17B4):

(Seq ID No: 34)

ccgcctcctcctgtcccgcagtcggcgtccagcggctctgctt
gttcgtgtgtgtgtcgttgcaggccttattcatg

*Homo sapiens* neutrophil cytosolic factor 2 (NCF2):

(Seq ID No: 35)

ctctctctgcttctttccttttctctctcatggtagggttatgagtcagttgccaaaagg
tggggacatttcctgatgcatttgcaacactgagaagttatcttaagggaggctgggccc
cattctactcatctggcccagaaagtgaacaccttgggggccactaaggcagccctgcta
ggggagacgctccaacctgtcttctctctgtctcctggcagctctcttggcctcctagtt
tctacctaatcatg

*Homo sapiens* 3-oxoacid CoA transferase 1 (OXCT1):

(Seq ID No: 36)

cagcctcctcctgcctcaccgcccgaagatg

*Homo sapiens* sulfite oxidase (SUOX):

(Seq ID No: 37)

ccgccccttctcgagaactcg
cagagctgggctggtaaaattgcagtgctgaagacactggacccg
caaaaggctgtccctcccaaacctgggattctgggctcactgagttcacctgcgag
tcagccctacctgcactgctctggtctagtacaaacaggctgctggcattgagggac
ggagtctccaactcctggcctctagcagtcctcctgtgtaggtctcccaaagtgctag
tgtgtccggaattggtgggttcttggtctcactgacttcaagaatgaagccgcg
gaccctcgcagtctgctacaatg

*Homo sapiens* albumin (ALB):

(Seq ID No: 38)

ttttctcttctgtcaacccca
cacgcctttggcacaatg

*Homo sapiens* arylsulfatase A (ARSA):

(Seq ID No: 39)

ctccctctagcgccttcccccgggccgactccgctggtcagcgccaagtgacttac
gcccccgaccctgagcccggaccgctaggcgaggaggatcagatctccgctcga
gaatctgaaggtgccctggtcctggaggagttccgtcccagoccgcggtctcccgg
tactgtcggccccggccctctggagcttcaggaggcggccgtcagggtcggggag
tatttgggtccggggtctcagggaagggcggcgcctgggtctgcggtatcggaaa
gagcctgctggagccaagtagccctccctctcttgggacagacccctcggtcccatg

*Homo sapiens* elastin (ELN):

(Seq ID No: 40)

ctccctccctctttccctcacagccgac
gaggcaacaattaggctttggggataaaacgaggtgcggagagcgggctgggg
catttctccccgagatg

*Homo sapiens* hemoglobin, alpha 2 (HBA2):

(Seq ID No: 41)

cactcttctggtcccca
cagactcagagagaacccaccatg

*Homo sapiens* hexosaminidase B (beta polypeptide) (HEXB):

(Seq ID No: 42)

cttcctctgatccgggccgggcgggaagtcgggtcccgaggctccggctcggcagac
cgggcggaaagcagccgagcggccatg

*Homo sapiens* mannosidase, alpha, class 2B, member 1 (MAN2B1):

(Seq ID No: 43)

cggccttttccagggccggggaaccccaggaggaagctgctgagccatg

*Homo sapiens* recombination activating gene 2 (RAG2):

-continued

*Homo sapiens* CD53 molecule (CD53):

(Seq ID No: 45)
tctcctttacacaaatagccccg
gatatctgtgttaccagccttgtctcggccacctcaaggataatcac
taaattctgccgaaaggactgaggaacggtgcctggaaaagggcaagaatatcacgg
catg

*Homo sapiens* Fc fragment of IgG, low affinity IIIa, receptor (CD16a) (FCGR3A):

(Seq ID No: 46)
tggtcccttagggctccggatatctttggtgacttgtc
cactccagtgtggcatcatg

*Homo sapiens* interleukin 1, beta (IL1B):

(Seq ID No: 47)
aaac
ctcttcgaggcacaaggcacaacaggctgctctgggattctcttcagccaatcttcatt
gctcaagtgtctgaagcagccatg

*Homo sapiens* CD4 molecule (CD4):

(Seq ID No: 48)
ctgtctctcttcatttaagcac
gactctgcagaaggaacaaagcaccctccccactgggctcctggtt
gcagagctccaagtcctcacacagatacgcctgtttgagaagcagcgggcaagaaagac
gcaa
gcccagaggccctgccatttctgtgggctcaggtccctactggctcaggcccctgcctcc
ctcggcaaggccacaatg

*Homo sapiens* serpin peptidase inhibitor, Glade A (alpha-1 antiproteinase, antitrypsin), member 5 (SERPINA5):

(Seq ID No: 49)
agccctctgccctttctgagcccgagggactgccacctccactgtgtgcacactcagc
tacgggacacatttcaggtatccaaggcagcagaggtgag
tgggtcccccgagctctgtgaccttatgctccacactaactctgg
cagagcctccgtttcctcatagaacaaagaacagccaccatg

*Homo sapiens* vitronectin (VTN):

(Seq ID No: 50)
tgccctcctccctgtctctgcctctccctcccttcctcaggcatcagagcgga
gacttcagggagaccagagcccagcttgccaggcactgagctagaagccctgccatg

*Homo sapiens* aldehyde dehydrogenase 9 family, member A1 (ALDH9A1):

(Seq ID No: 51)
ccgcccctcccgcggccccgcccctcccgcggcccgtcagcctctgccgcg
gagctgcgtccgccactcatg

*Homo sapiens* annexin A1 (ANXA1):

(Seq ID No: 52)
cttcctttaaaatcc
tataaaatcagaagcccaagtctccactgccagtgtgaaatcttcagagaa
gaatttctctttagttctttgcaagaaggtagagataaagacacttttcaaaaatg

*Homo sapiens* ATPase, Na+/K+ transporting, alpha 1 polypeptide (ATP1A1):

(Seq ID No: 53)
ttttctctctgattctccagcgacaggacccggcgccgggcactgag
caccgccaccatg

*Homo sapiens* ATPase, Na+/K+ transporting, alpha 2 polypeptide (ATP1A2):

(Seq ID No: 54)
ctttctctgtctgccagggtctccgactgtcccagac
gggctggtgtgggcttgggatcctcctggtgacctctcccgctaaggtccctcagccac
tctgccccaagatg

*Homo sapiens* calcium channel, voltage-dependent, beta 3 subunit (CACNB3):

(Seq ID No: 55)
ccctccttcgcgctctctcgctccctgccgccgcccgcagggctgcggggctcggtggca
tctcccgggcgcggcccgcagtcctt
gccctgcctccgggccgctcccgcccccggcgccgctcgctcccccgacccg
gactcccccatg -continued

*Homo sapiens* cholinergic receptor, nicotinic, alpha 7 (neuronal) (CHRNA7):

(Seq ID No: 56)

gtgcctctgtggccgcaggcgcaggcccgggcgacagccga
gacgtggagcgcgccggctcgctgcagctccgggactcaacatg

*Homo sapiens* cytochrome P450, family 51, subfamily A, polypeptide 1 (CYP51A1):

(Seq ID No: 57)

gcttctctcgttccgtcgattgggaggagcggtggcgac
ctcggccttcagtgtttccgacggagtgaatg

*Homo sapiens* glutamate decarboxylase 1 (brain, 67 kDa) (GAD1):

(Seq ID No: 58)

atctctctcttctcctggcgctcgcgtgcgagagggaactagcgagaac
gaggaagcagctggaggtgacgccgggcagattacgcctgtcagggccgagccgagcg
gatcgctgggcgctgtgcagaggaaaggcgggagtgcccggctcgctgtcg
cagagccgagcctgtttctgcgccggaccagtcgaggactctggacag
tagaggccccgggacgaccgagctgatg

*Homo sapiens* gamma-glutamyl carboxylase (GGCX):

(Seq ID No: 59)

aattctcctggcggcctccgttcagacgcggcagctgtgacccacctgcctcctccg
cagagcaatg

*Homo sapiens* glutamate receptor, metabotropic 3 (GRM3):

(Seq ID No: 60)

tcccctctttccccaacctcctccctctcttctactccaccctccgttttcccac
tccccactgactcggatgcctggatgttctgccaccgggcagtggtccagcgtg
cagccgggaggggcagggcaggggcactgtgacaggaagctgcgcgcacaagtt
ggccatttcgagggcaaaataagttctcccttggatttggaaaggacaaagccagtaa
gctacctcttttgtgtcggatgaggaggaccaaccatgagccagagcccgggtg
caggctcaccgccgccgctgccaccgcggtcagctccagttcctgccaggagtt
gtcggtgcgaggaattttgtgacaggctctgttagtctgttcctcccttattt
gaaggacaggccaaagatccagtttggaaatgagagaggactagcatgacacatt
ggctccaccattgatatctcccagaggtacagaaacaggattcatgaagatg

*Homo sapiens* guanylate cyclase 1, soluble, alpha 3 (GUCY1A3):

(Seq ID No: 61)

ggttcctttgggggtgatcaaagagggagacacagacacagagagagacaaaggcaaggagga
ctgtctgggagccacgcgggcgatacagtttccgaggcacgccgcgtcccgcctagcctg
ttgaacaggtagacatgagcgacccaagctgcggatttgcgaggcgcgccctggagctgc
tagagatccggaagcacagccccgaggtgtgcgaagccaccaagtcaagttcctaacgag
tcttcagaggaggcagcaggaagctcagagagctgcaaagcaaccgtgcccatctgtcaa
gacattcctgagaagaacatacaagaaagtcttcctcaaagaaaaaccagtcggagccga
gtctatcttcacactttggcagagagtatttgcaaactgattttcccagagtttgaacgg
ctgaatgttgcacttcagagaacattggcaaagcacaaaataaaagaaagcaggaaatct
ttggaaagagaagactttgaaaaaacaattgcagagcaagcagttgcagcaggagttcca
gtggaggttatcaaagaatctcttggtgaagaggttttaaaatatgttacgaggaagat
gaaaacatccttgggggtggttggaggcacccttaaagatttttaaacagcttcagtacc
cttctgaaacagagcagccattgccaagaagcaggaaaaaggggcaggcttgaggacgcc
tccattctatgcctggataaggaggatgattttctacatgtttactacttcttccctaag
agaaccacctccctgattcttcccggcatcataaaggcagctgctcacgtattatatgaa
acggaagtggaagtgtcgttaatg

*Homo sapiens* 3-hydroxy-3-methylglutaryl-CoA reductase (HMGCR):

(Seq ID No: 62)

ggctccttccgctccgcgactgcgttaactg
gagccaggctgagcgtcggcgccggggttcggtggcctctagtgagatctggag
gatccaaggattctgtagctacaatg

*Homo sapiens* IMP (inosine 5'-monophosphate) dehydrogenase 2 (IMPDH2):

(Seq ID No: 63)

aggtctctgcggcgcggtcctcggagacacgcggcggtgtcctgtgtt
ggccatg

*Homo sapiens* leukotriene A4 hydrolase (LTA4H):

(Seq ID No: 64)

acttcctttcccggcgtgcaccgcgaatccctcctcctcttctttac
ctctctccctcctcctcaggttctctatcgacgagtctggtagctgagcgttgggctg
taggtcgctgtgctgtgtgatcccccagagccatg -continued

*Homo sapiens* neuropeptide Y receptor Y1 (NPY1R):

(Seq ID No: 65)
ccttctttaa
taagcaggagcgaaaaagacaaattccaaagaggattgttcagttcagggaatgaa
gaattcagaataattttggtaaatggattccaatatggggaataagaataa
gctgaacagttgacctgctttgaagaaacatactgtccatttgtctaaaa
taatctataacaaccaaaccaatcaaaatg

*Homo sapiens* pyruvate dehydrogenase (lipoamide) beta (PDHB):

(Seq ID No: 66)
cggcccctctgttgtcgtttggcagcggatagaggacacgaccaagatg

*Homo sapiens* ribosomal protein L36a-like (RPL36AL):

(Seq ID No: 67)
cttccctttcctgttaggcgagagctgcgaaaggcga
gagctgcgaagggccaggtgtcgggcgctgtttctcgttttcatcatataga
caaaacagccctgctgcaaagatg

*Homo sapiens* ATPase, Ca++ transporting, type 2C, member 1 (ATP2C1):

(Seq ID No: 68)
gcttcttctcacgccgggagcaggctcccgcctcgcac
cgctgccccgcgag
cagctcctcttctcccgaggcgcgcggggcgcccccgcgagcccgcggctga
gaccccgcagcctggaggagggctgtccggggcttt
ggatgctgctgctaggggtggtgggagcagccgtgggacgcgtggccgg
gagcgggggtgacagcctgggattccgggggcttctcttcctt
gtcctcctcctctcctctctattcccagtgtggccgtggctgacactaaagacttt
gtagccatcaacccgagtgcagtttcgatggaaaatg

*Homo sapiens* UDP-glucose pyrophosphorylase 2 (UGP2):

(Seq ID No: 69)
ccgcctctttcattgaagaaatttaagttcgtgtggttttacctttccgggagtctcca
gctggccctcatttgtgtccggagctcaggagttcccaaaccgactcagtcgcaccaagt
ttccgtcttttggaattgggaaggagtttctttctttctttttcttgagccag
ttttaatcgctttgaataaatactcccttaagtagttaaatataggaggagaaagaatac
atcggttgttaaagcaggagaggaagagagacctgccctgtagcgtgactcctctagaaa
aaaaaaaaaaaagccggagtatttactaagcccctaaaatg

*Homo sapiens* ATPase, Na+/K+ transporting, beta 1 polypeptide (ATP1B1):

(Seq ID No: 70)
cctcctcctgctcctgccttggctcctccgccgcgcgtctcgcac
tccgagagccgcagcggcagcggcgcgtcctgcctgcagagagccaggccggagaa
gccgagcggcgcagaggacgccagggcgcgcgccgcagccacccaccctccggac
cgcggcagctgctgacccgccatcgccatg

*Homo sapiens* glycoprotein M6B (GPM6B):

(Seq ID No: 71)
ctgtctttatggaccag
taggcagagcgaaattgacgctgacaagacttttgcatcttggaagggactg
taatctactgtagtgaagaacagagcctctcaatcagacgggtgtaaataagagac
ggaggggagtccaaaagaaaaggaagaggaggaaaaacaagtgtgtgttgggggg
gaacaggggaaaagcatttttggtggatggtatg

*Homo sapiens* wntless homolog (*Drosophila*) (WLS):

(Seq ID No: 72)
gctcctttaa
gcgtccacaggcggcggagcggccacaatcacagctccgggcattgggg
gaacccgagccggctgcgccgggg
gaatccgtgcgggcgccttccgtcccggtcccatcctcgccgcgctccagcac
ctctgaagtttgcagcgcccagaaaggaggcgaggaaggagggagtgtgtgagag
gagggagcaaaaagctcaccctaaaacatttatttcaaggagaaaa
gaaaaaggggggcgcaaaatg

*Homo sapiens* flavin containing monooxygenase 3 (FMO3):

(Seq ID No: 73)
ttttctctttcaaactgcccagacggttggacaggacgtagacacacagaagaaaa
gaagacaaagaacgggtaggaaaattaaaaaggttaccatg

*Homo sapiens* multiple C2 domains, transmembrane 1 (MCTP1):

(Seq ID No: 74)
cagcctcttttgccggtattcagtgaagaaagcaagtctaaatatgcagttctctcac
tggagtgaaagatgttttgttcatttctaatcaactatg

*Homo sapiens* structural maintenance of chromosomes 4 (SMC4):

(Seq ID No: 75)
ccgcctctcggcgagcccgcctcttctgaagaggcgtttctggaccac
tgagcccgcctcccactgtgagcggaaccctac
cgttttaaaaaaatctttttcaaacttgccaggttgtcttccaaatatttttaa
taatagtgctgctgctgtagaccacagagaaaagaatccctgctcttccttttcac -continued
```
ttagtagaaacttctaccgcgtaggtcccgccaggagttcgcgcatgcgcag
gagcgacaataagatggcggtgataatcgccgcacttttttcaaattagtg
gatcccagaaatcattgcgcgcatttgtaacgaatttccgttcgagttt
gtattttaggcgccattttcgagtgaaggacccggagccgaaacaccggtaggagcggg
gaggtgggtactacacaacgtctccagccttggtctgagtggactgtcctgcagcgac
catg
```

Homo sapiens GLE1 RNA export mediator homolog (yeast) (GLE1):

(Seq ID No: 76)
```
tggccttcccggcggctgattcgagggcttgtttggtcagaaggggggcgtcagagaagc
tgccccttagccaaccatg
```

Homo sapiens tripartite motif containing 6 (TRIM6):

(Seq ID No: 77)
```
gag
tctttcggcctgggtggaggacgcggctgcttcaagtcctt
ggctctgatccaggccacagattccaggattctacaggcaggaaacatctta
gaaatcaggggttgggcaggcaggagccaggagagtagctacaatg
```

Homo sapiens ecotropic viral integration site 2A (EVI2A):

(Seq ID No: 78)
```
tatccttttttactgcagatttacttaaggctcatattctccaagtc
tattctgctttaaaaagaagacaagaaaagaagtggtttatcaaaatcac
gttataatcagattttgaccaagcatttgtaagtatacaaatgtcagccaatgacata
taacaacccatttcttataaaaccttgatgttcaaaagcctgactagcagtggcatccatg
```

Homo sapiens heterogeneous nuclear ribonucleoprotein L (HNRNPL):

(Seq ID No: 79)
```
tgctcttttcgatccgggacggccggtcaggctcgccgccgagctgga
gaactacgatgacccgcacaaaaccctgcctccccagtt
gtccacatcaggggcctgattgacggtgtggtggaagcagaccttgtggaggcctt
gcaggagtttggacccatcagctatgtggtggtaatg
```

Homo sapiens mitochondrial translational initiation factor 2 (MTIF2):

(Seq ID No: 80)
```
cattcttccgggtccagaaggtgatctccgcccgtgctcagaatccaggggcccggggct
gtagattccttgacaaggatatcctagcggcgaaacaacaccgtactgggagtcagaac
gtctgggttctagtcttgactgccattaactagcggtatgacattggagaagctttttt
gaccttctggatttccgttcctttctgtaaaatgaggagcttggaagatccg
gaaaatgaggcccataggaaacaagtgacttgctgagtccagataacac
tgactgtcagagagaaacatg
```

Homo sapiens nuclear factor of kappa light polypeptide gene enhancer in B-cells inhibitor, zeta (NFKBIZ):

(Seq ID No: 81)
```
tggcctcctctt
gccacgaggtcagacggcgagttcttaga
gaaaaaggctgcttagctgctgcttatcatgtaac
ctcaaaaggaaactgatcgtctttctcatgctgtcacgtactt
gggttattatcgctgattacagctggaaacaattgatttgctcttacgtattt
gtgtgacttgactcttcaaacacaaaggttaacaggaa
gatctcgagggccctggctgaacttcaccttttggctttctt
ggcctgatgctgaactctcgaggttgagccccatatg
```

Homo sapiens v-erb-b2 erythroblastic leukemia viral oncogene homolog 3 (avian) (ERBB3):

(Seq ID No: 82)
```
atccctccccg
gactccggctccggctccgattgcaatttgcaacctccgctgccgtcgccgcag
cagccaccaattcgccagcggttcaggtggctctt
gcctcgatgtcctagcctaggggcccccgggccggactt
ggctgggctcccttcaccctctgcggagtcatg
```

Homo sapiens podoplanin (PDPN):

(Seq ID No: 83)
```
ccgcctcctcgggagagataaatg
```

Homo sapiens ribonucleotide reductase M1 (RRM1):

(Seq ID No: 84)
```
gcgccccttt
gtgcgtcacgggtggcgggcgcgggaaggggatttggattgttgcgcctctgctctgaa
gaaagtgctgtctggctccaactccagttctttcccctgagcagcgcctggaac
ctaaccccttcccactctgtcaccttctcgatcccgccggcgctttagagccgcag
tccagtcttggatccttcagagcctcagccactagctgcgatg
```

Homo sapiens solute carrier family 2 (facilitated

-continued glucose transporter), member 4 (SLC2A4):

(Seq ID No: 85)
gcgtctttccccccagcccgctccaccagatccgcgggagccccac
tgctctccgggtccttggcttgtggctgtgggtcccatcgggccgccctcgcac
gtcactccgggaccccgcggcctccgcaggtctgcgctccaggccggagtcaga
gactccaggatcggttctttcatcttcgccgccctgcgcgtccagctcttctaagac
gagatg Homo sapiens steroid-5-alpha-reductase, alpha polypeptide 1
(3-oxo-5 alpha-steroid delta 4-dehydrogenase alpha 1)
(SRD5A1):

(Seq ID No: 86)
aacccctttctgcagagtcccggcagtgcgggactccgg
tagccgcccctccggtagccgcccctcctgccccgcgccgccgccctatatgtt
gcccgccgcggcctctggggcatggagcacgctgcccagccctggcgatg Homo sapiens thromboxane A synthase 1 (platelet) (TBXAS1):

(Seq ID No: 87)
gttcccttttctacctgcagagcacggttcccataagggcggcga
gatcagcctcctgtctcatctggaagaccaccactctggggtctcagaggaatg Homo sapiens transketolase (TKT):

(Seq ID No: 88)
ctatctctgtgtgtccgcgtgtgcgcccggtccccgcctgccgcaccatg

Homo sapiens
tumor necrosis factor receptor superfamily, member
1A (TNFRSF1A):

(Seq ID No: 89)
cctcctcctccagctcttcctgtcccgctgttgcaacac
tgcctcactcttcccctcccac
cttctctccctcctctctgctttaattttctcagaattctctggactgaggctccag
ttctggcctttggggttcaagatcactgggaccaggccgtgatctctatgcccgag
tctcaaccctcaactgtcaccccaaggcacttgggacgtcctggacagaccgag
tcccgggaagcccagcactgccgctgccacactgccctgagcccaaatgggggagtga
gaggccatagctgtctggcatg Homo sapiens tubulin, beta 2A class IIa (TUBB2A):

(Seq ID No: 90)
ag
gtctctgcgcagcccagcccgccggtccacgccgcgcac
cgctccgagggccagcgccacccgctccgcagccggcaccatg Homo sapiens actin, beta (ACTB):

(Seq ID No: 91)
tcgcctttt
gccgatccgccgcccgtccacacccgccgccagctcaccatg

Homo sapiens adenylosuccinate synthase (ADSS):

(Seq ID No: 92)
ggctccttcttcctctgcatgtggctggcggccgcagagcagttcagttcgctcac
tcctcgccggccgcctctccttcgggctctcctcgcgtcactggagccatg Homo sapiens alanyl (membrane) aminopeptidase (ANPEP):

(Seq ID No: 93)
cgttctctgcctggcctgaggctccctgagccgcctccccaccatcaccatg

Homo sapiens beaded filament structural protein 1, filensin
(BFSP1):

(Seq ID No: 94)
gcctcctttctttctcagcccagacctggccctctggagagggtttt
ggagtcctgggtaggcagggtacctcaggcagcaggcagcacacctt
ggatgtgagctgaatggattttcaaatttcacagaaggagcctccatgctgga
gaaagtatgtatg Homo sapiens basic transcription factor 3 (BTF3):

(Seq ID No: 95)
cggcctcccttttagctgccatctt
gcgtccccgcgtgtgtgcgcctaatctcaggtggtccacccgagacccctttgagcac
caaccctagtccccgcgcggcccccttattcgctccgacaagatg Homo sapiens
complement component 1, q subcomponent binding protein
(C1QBP):

(Seq ID No: 96)
ttgtcctttgcatctgcacgtgttcgcagtcgtttccgcgatg

Homo sapiens calsequestrin 1 (fast-twitch, skeletal muscle)
(CASQ1):

(Seq ID No: 97)
tttcctttcttaatatggcgatgagctcttaggccagtgtggggac

-continued cggggctgaggtgccctggacactggaggaggggagggaaggagcccctgg
gagcctggggtagaagtgtaggaggtggggaggattccggcccg
catggagctgtcctggcctcagaaggttatccgtctctcctgccaaccatggaga
catatttagacaggaccaggtggggactgaggggtgccaatttcaggggg
cagctccggttccctccccgcccctgctcctattcctccacctgacccttttcccctt
ggctctgtcggcagtttctccaggacccagcagtgccctctgtccac
tgctctgggccattccccaatcccccctcccacttgagccctaactcagaatctgg
gacccaggggcccctccctaccccagctaacctcttctggaccagga
gagccaacccagatcccactacctccatg

*Homo sapiens* caveolin 3 (CAV3):

(Seq ID No: 98)

gtctctctgcccctctctgccccaagtattttcagcccagccggccacacagctcg
gatctcctcctgtggatcccccagctctgcgatg

*Homo sapiens* serpin peptidase inhibitor, clade H
(heat shock protein 47), member 1, (collagen
binding protein 1) (SERPINH1):

(Seq ID No: 99)

aggtctttggctttttttggcggagctggggcgccctccggaagcgtttccaactttcca
gaagtttctcgggacgggcaggaggggtggggactgccatatatagatcccgggagcag
gggagcgggctaagagtagaatcgtgtcgcggctcgagagcgagtcacgtcccggcgc
tagcccagcccgacccaggccaccgtggtgcacgcaaaccacttcctggccatg

*Homo sapiens* CD68 molecule (CD68):

(Seq ID No: 100)

tttcctccttctccaaga
gagggctgagggagcagggttgagcaactggtgcagacagcctagctggacttt
gggtgaggcggttcagccatg

*Homo sapiens* cell division cycle 20 homolog (*S. cerevisiae*)
(CDC20):

(Seq ID No: 101)

gggtccctttctgtccctgagcac
cgtcgcctcctttcctccagggctccgtaggcaccaactg
caaggacccctcccctgcgggcgctcccatg

*Homo sapiens* cadherin 13, H-cadherin (heart) (CDH13):

(Seq ID No: 102)

gagcctctcctcaaagcctggctcccacgaaaatatgctcagtgcagccgcgtg
catgaatgaaaacgccgccgggcgcttctagtcggacaaaatg

*Homo sapiens* regulator of chromosome condensation
(RCC1) and BTB (POZ) domain containing protein 2 (RCBTB2):

(Seq ID No: 103)

cgctcccttcgtttccgtctcggccgggcacccgagcg
catcccgccgaggcggggccgtttcagggg
gaggcgccaactcatcgcggcgccgggcccctgaccgtgcagtaaccgctacccag
gaggcggagcggacaaggctccggcctgcgaggagtcacattaactttgctctagaaga
caactttacaaggatctaaaaggaacaggattaaagatgactgaa
tactgggttccagaaatttaaaacaatcagcttagcaaatcatatattcttctgtg
gagctgagaattgatgtccgctcttccccgtgatttggaactttccaatcccaga
gaaaagttgacaaagggactgccaggactgagtccatatg

*Homo sapiens* cold inducible RNA binding protein (CIRBP):

(Seq ID No: 104)

ccccccctcactcgcgcgttaggaggctcgggtcgttgtggtgcgctgtcttcccgctt
gcgtcagggacctgcccgactcagtggccgccatg

*Homo sapiens* LIM domain binding 2 (LDB2):

(Seq ID No: 105)

cctcctctcctctccctctcctctcctgctatagagggctccgacagcag
ttcccagccagcgtgttcagcctgcctgcctgcctctgtgtgtgtgagcgtgtg
tgcgtgcgtctactttgtactgggaagaacacagccatgtgctctgcatggac
gttactgatactctgtttagcttgattttcgaaaagcaggcaagatg

*Homo sapiens* chloride channel, nucleotide-sensitive, 1A
(CLNS1A):

(Seq ID No: 106)

ctgcctcttccagggcgggcggtgtggtgcacgcatt
gctgtgctccaactccctcagggcctgtgttgccgcactctgctgctatg

*Homo sapiens* collapsin response mediator protein 1 (CRMP1):

(Seq ID No: 107)

cctcctccttctcccgccctcctcgccgatccgggcggtgctggcagccg
gagcggcggcgggcgggcgagcagccggggcagccgcgcgtgggcatccac
gggcgccgagcctccgtccgtgtctctatccctcccgggccttt
gtcagcgcgcccgctgggagcggggccgagagcgccggttccagtcagacagcccg
caggtcagcggccgggccgagggcgccagaggggggccatg

*Homo sapiens* catenin (cadherin-associated protein), delta 1

-continued (CTNND1):
(Seq ID No: 108)
```
ttgcctttggctgggtgcaacttccatttaggtgttggatctgagggg
gaaaaaaagagagagggagagagagaaagaagagcaggaaagatcccgaaaggag
gaagaggtggcgaaaaatcaactgccctgctggatttgtctttctcagcaccttt
ggcgaagccttgggtttctttcttaaaggactgattttttagaactccacatttt
gaggtgtgtggcttttgaagaaaatgtatgtactgacgggaaaaggaggataa
gcaagtcgaattttttgtcttacgctctctccttcctgcttcctcctt
gctgtggtggctgggatgcttcttccatgattttttgaatcta
gactgggctgttctctgtgttaaaccaatcagttgcgaccttctcttaacag
tgtgaagtgaggggtctctctccctccttctccttcctctgtgattcac
cttccttttaccctgccctgcggcggctccgccccttaccttcatg
```

*Homo sapiens* diacylglycerol kinase, alpha 80 kDa (DGKA):
(Seq ID No: 109)
```
ccgtcccctccagcccagctcgggctccagctccagcgccggcgcttcagctgcgac
cgcgagccctctcaagcaagatataacttccccaagtcacacagtggtatcagagctaa
gaatgggacccagatatgactgatctagttctgttccaaaaccgtgctgtatta
tattaacgcctaccctctgaagaggtccaagcaacggaagtactactacgaa
gctgcctttctggccatccttgagaaaaatagacagatgagttcctgccagtgag
tccctaggcctccatctctctcccttgctgtaccaccttcaccac
catccatgcgaccccaagagccttaatgactctagaagagactccaggcagggaa
gctgaaaggaccttttcactcccttactttttggccagggccttctgtgccacctgccaa
gaccagcaggcctaccctctgaagaggtccaagcaacggaagtactactacgaa
gctgcctttctggccatccttgagaaaaatagacagatg
```

*Homo sapiens* aspartyl-tRNA synthetase (DARS):
(Seq ID No: 110)
```
cgatctttctg
gagccgcacctccacgcggagtccgagcgcgtgtgctgagaccccagggtcgg
gagggcggagactgggaggagggagaagccccttggcctgccttacggaa
gcctgcagggagggtggtgtccactgccagttccgtgtcccgatg
```

*Homo sapiens* dynein, cytoplasmic 1, intermediate chain 2 (DYNC1I2):
(Seq ID No: 111)
```
agttcttctcgatcgtgtcagtttgtaaggcgagggcggaagttggat
tcctggcctgagaatattaggcgtagttttccagttttttggcaaagcggaaa
tacttaaggcccctgggttgactggttctttgttttatctaccggcttctgctttac
gacaggtcacaaacatg
```

*Homo sapiens* dedicator of cytokinesis 1 (DOCK1):
(Seq ID No: 112)
```
tttcctccccatcctgtcgcggctcgaaaggaatggaaaatggcggcctagacgcggag
tttcctgcccgacccgcggcggctccggcggcgccatg
```

*Homo sapiens* dihydropyrimidinase-like 2 (DPYSL2):
(Seq ID No: 113)
```
ctctctcttttttttccgccctagctggggctgtgttggaggagaggaagaaagagaga
cagaggattgcattcatccgttacgttcttgaaatttcctaatagcaagaccagcgaa
gcggttgcacccttttcaatctt
gcaaaggaaaaaaacaaaacaaaacaaaaaaaacccaagtccccttcccggcagttttt
gccttaaagctgccctcttgaaattaatttttcccaggagagagatg
```

*Homo sapiens* developmentally regulated GTP binding protein 2 (DRG2):
(Seq ID No: 114)
```
tgttctctttggcttccgggcgcacgctactctgtcgccgccgtcagaccg
gaattgccggtgccgccgccaccgctgtctgtgcgcccacctctgctgctaccatg
```

*Homo sapiens* eukaryotic translation elongation factor 1 alpha 1 (EEF1A1):
(Seq ID No: 115)
```
cgttctttttcgcaacgggttt
gccgccagaacacaggtgtcgtgaaaactacccctaaaagccaaatg
```

*Homo sapiens* eukaryotic translation elongation factor 1 gamma (EEF1G):
(Seq ID No: 116)
```
tctcctctttccccctcccttctctcccgggcggcttactttgcgg
cagcgccgagaaccccaccccctttctttgcggaatcaccatg
```

*Homo sapiens* eukaryotic translation initiation factor 2, subunit 3 gamma, 52 kDa (EIF2S3):
(Seq ID No: 117)
```
atttccttcctcttttggcaacatggcgggc
```

*Homo sapiens* eukaryotic translation initiation factor 4B

-continued (EIF4B):

(Seq ID No: 118)

gggtcttttgcgttctctttccctctcccaacatg

*Homo sapiens*
eukaryotic translation initiation factor 4 gamma,
2 (EIF4G2):

(Seq ID No: 119)

tattcttttgaagattcttcgttgtcaagccgccaaagtg

*Homo sapiens* epithelial membrane protein 1 (EMP1):

(Seq ID No: 120)

cttcccctcagtgcggtcacatacttccagaagagcggaccagggctgctgccagcac
ctgccactcagagcgcctctgtcgctgggacccttcagaactctctt
gctcacaagttaccaaaaaaaaaagagccaacatg

*Homo sapiens* fibrillarin (FBL):

(Seq ID No: 121)

cgctcttttccacgtgcgaaagccccg
gactcgtggagttgtgaacgccgcggactccggagccgcacaaaccagggctcgccatg

*Homo sapiens* exostoses (multiple)-like 2 (EXTL2):

(Seq ID No: 122)

ctgtcccctt
gctccaggcgctcactttgcgggcggcacttttttccaggttgttaatccagctaatgga
gaaggatagatgcacgctacttggtttagaaaaaaaaacaaaaatgagcaaacgagac
gcccccttccgttttatgataactaagctgcagggaaataaatcggctggccctactg
caatctactgcactcgagaaacatcacagaaaattctttgatttatcttaa
tagtgacaagtgagcctgcttctgtcaattactgaagctataaggagat
ttttttaaaaattaaacttcaacacaatg

*Homo sapiens* solute carrier family 37 (glucose-
6-phosphate transporter), member 4 (SLC37A4):

(Seq ID No: 123)

ccgcctctgttcaggacactgggtcccttggagcctccccaggcttaatgattgtccag
aaggcggctataaagggagcctggaggctgggtggaggagggagcagaaaaaacccaac
tcagcagatctgggaactgtgagagcggcaagcaggaactgtggtcagaggctgtgcgtc
ttggctggtagggcctgctcttttctaccatg

*Homo sapiens* GDP dissociation inhibitor 2 (GDI2):

(Seq ID No: 124)

agccctcccctcctcgctccctcccctcctctccccgcccag
ttcttctcttcccgtctgaggtggcggtcggtctcgcctt
gtcgccagctccattttcctctctctttctcttcccctttccttcgcgcccaa
gagcgcctcccagcctcgtagggtggtcacggagcccctgcgccttttcctt
gctcgggtcctgcgtccgcgcctgccccgccatg

*Homo sapiens*
UDP-Gal:betaGlcNAc beta 1,4-galactosyltransferase,
polypeptide 1 (B4GALT1):

(Seq ID No: 125)

caccccttcttaaagcggcggcgggaagatg

*Homo sapiens* GDP-mannose 4,6-dehydratase (GMDS):

(Seq ID No: 126)

ggccctccctgcac
ggcctcccgtgcgcccctgtcagactgtggcggccggtcgcgcggtgcgctctccctcc
tgcccgcagcctggagaggcgcttcgtgctgcacaccccgcgttcctgccggcac
cgcgcctgccctctgccgcgctccgccctgccgccgaccgcacgcccgccgcgggacatg

*Homo sapiens* histone deacetylase 2 (HDAC2):

(Seq ID No: 127)

ggccccctcctcgcgagttggtgccgctgccacctccgattccgagctttcggcac
ctctgccgggtggtaccgagccttcccggcgcccctcctctcctcccac
cggcctgccctcccccgcgggactatcgcccccac
gtttccctcagccctttctctcccggccgagccgcggcggcagcagcagcagcagcag
cagcaggaggaggagcccggtggcggcggtggccggggagcccatg

*Homo sapiens* protein arginine methyltransferase 2 (PRMT2):

(Seq ID No: 128)

gggccttcccggctgacggcctgcgtgcactgcgcttgcgcgggtt
gagggcggtggctcaggctcctggaaaggaccgtccaccctccgcgctggcggtgtg
gacgcggaactcagcggagaaacgcgattgagagcagtgtgtggattacactatcactg
gaaaaatacgaattgagaagaaggaaaagactggaagatgcagaccttt
ggttcctgttagtggaaacactgtaaggtcccagaaatggaaaagaaaatgaaa
taaatcagcagttatgaggcagagcctaagagaactatg

*Homo sapiens* immunoglobulin (CD79A) binding protein 1
(IGBP1):

(Seq ID No: 129)

gttcctctctccccaagatg

-continued

*Homo sapiens*
eukaryotic translation initiation factor 3, subunit
E (EIF3E):

(Seq ID No: 130)

actcccttttctttggcaagatg

*Homo sapiens* activated leukocyte cell adhesion molecule (AL-
CAM):

(Seq ID No: 131)

gtccctctactcagagcagcccggagaccgctgccgccgctgccgctgctaccaccgctg
ccacctgaggagacccgccgcccccgtcgccgcctcctgcgagtccttcttagcacct
ggcgtttcatgcacattgccactgccattattattatcattccaatacaaggaaaataaa
agaagataccagcgaaaagaaccgcttacacctttccgaattactcaagtgtctcctgga
aacagagggtcgttgtccccggaggagcagccgaagggcccgtgggctggtgttgaccgg
gagggaggaggagtggggggcattgcgtggtggaaagttgcgtgcggcagagaaccgaag
gtgcagcgccacagcccaggggacggtgtgtctgggagaagacgctgcccctgcgtcggg
acccgccagcgcgcgggcaccgcggggccgggacgacgcccctcctgcgggcgtggact
ccgtcagtggcccaccaagaaggaggaggaatatg

*Homo sapiens* acyloxyacyl hydrolase (neutrophil) (AOAH):

(Seq ID No: 132)

tttctttatcctgcagtcttttacctcagcagaaccgcacac
cacagactccctccagctctttgtgtgtggctctctcagggtccaacaagagcaa
gctgtgggtctgtgagtgtttatgtgtgcttttattcacttcacac
ttattgaaaagtgtgtatgtgagagggtggggtgtgtgtcaaagagagtgaggaaga
gaaggagagagagatcaattgattctgcagcctcagctccagcatccctcagttgg
gagcttccaaagccgggtgatcacttggggtgcatagctcggagatg

*Homo sapiens* ADP-ribosylation factor 1 (ARF1):

(Seq ID No: 133)

ccgccccttaccggcgtgccccgcgcccggaggcgctgac
gtggccgccgtcagagccgccatcttgtgggagcaaaaccaacgcctggctcggagcag
cagcctctgaggtgtccctggccagtgtccttccacctgtccacaagcatg

*Homo sapiens* ADP-ribosylation factor 6 (ARF6):

(Seq ID No: 134)

gcgccttttccggcagcggcggcggcagaactgggaggaggagttggaggccg
gagggagcccgcgctcggggcggcggctggaggcagcgcaccgagttcccgcgag
gatccatgacctgacggggccccg
gagccgcgctgcctctcgggtgtcctgggtcggtggggagcccagtgctcg
caggccggcgggcgggccgagggctgcagtctccctcgcggtgagaggaaggcggag
gagcgggaaccgcggcggcgctcgcgcggcgcctgcgggggaagggcag
ttccgggccgggccgcgcctcagcagggcggcggctcccagcgcag
tctcagggcccgggtggcggcggcgactgagaaatcaagtt
gtgcggtcggtgatgcccgagtgagcggggggcctgggcctctgcccttag
gaggcaactcccacgcaggccgcaaaggcgctctcgcggccga
gaggcttcgtttcggtttcgcggcggcggcggcgttgttggctgaggggacccgg
gacacctgaatgccccggccccggctcctccgacgcgatg

*Homo sapiens* ras homolog family member A (RHOA):

(Seq ID No: 135)

cgccctcccgccgcgcccgccctcgctctctcgcgc
taccctcccgccgcccgcggtcctccgtcggttctctcgttagtccac
ggtctggtcttcagctacccgccttcgtctccgagtttgcgactcgcggac
cggcgtcccggcgcgaagaggctggactcggattcgttgcctgagcaatg

*Homo sapiens* ras homolog family member G (RHOG):

(Seq ID No: 136)

cggcctcccgctctcacttccttctcgagcccggagccgctgccgccgcccccagctccc
ccgcctcggggagggcaccaggtcactgcagccagagggtccagaagagagaggaggca
ctgcctccactacagcaactgcacccacgatg

*Homo sapiens*
ATP synthase, H+ transporting, mitochondrial F1 complex,
O subunit (ATP5O):

(Seq ID No: 137)

ctctcttcccactcgggttttgaccta
cagccgcccgggagaagatg

*Homo sapiens* B lymphoid tyrosine kinase (BLK):

(Seq ID No: 138)

ccac
ctctgtctgctgccggcagaaagccacaagccatgaaaactgattgagatgagaa
gaattcatctgggactggcttttgctttaggatggtgttggaagttgctcgtt
gtcgctaggagcctgctccactgtaagggtgtcaggatctgaagagc
tatggtgaaacaccactgaagcattgccaaggatg

*Homo sapiens* B-cell translocation gene 1, anti-proliferative
(BTG1):

(Seq ID No: 139)

-continued
```
gcatctcttcgcctctcggagctggaaatgcagctattga
gatcttcgaatgctgcggagctggaggcggaggcagctgggaggtccgagcgatgtgac
caggccgccatcgctcgtctcttcctctctcctgccgcctcctgtctcgaaaa
taactttttagtctaaagaaagaaagacaaaagtagtcgtccgcccctcac
gccctctcttcctctcagccttccgcccggtgaggaa
gccggggtggctgctccgccgtcggggccgcgccgccgagcccagccgccccgggccg
ccccgcacgccgccccatg
```

*Homo sapiens* calcium modulating ligand (CAMLG):

(Seq ID No: 140)
```
cggcctctag
tcatcgccctcgcagcggcggccaacatcaccgccactgccacccctcccagactgtg
gacgggaggatg
```

*Homo sapiens* calnexin (CANX):

(Seq ID No: 141)
```
aggcctcttggttctgcggcacgtgac
ggtcgggccgcctccgcctctctctttactgcggcgcggggcaaggtgtgcgggcgg
gaaggggcacgggcaccccgcggtccccgggaggctagagatcatg
```

*Homo sapiens* calpain 2, (m/II) large subunit (CAPN2):

(Seq ID No: 142)
```
cgac
ctttctctgcgcagtacggccgccgggaccgcagcatg
```

*Homo sapiens* caveolin 1, caveolae protein, 22 kDa (CAV1):

(Seq ID No: 143)
```
gcgcctttttttccccccatacaatacaagatcttccttcctcagttcccttaaa
gcacagcccagggaaacctcctcacagttttcatccagccacgggccagcatg
```

*Homo sapiens* CD1d molecule (CD1D):

(Seq ID No: 144)
```
cgacctctttgcagctcg
cacagctaagggcgagggcgcccttcggcagaagcagcaaaccgccggcaa
gcccagcgaggagggctgccggggtctgggcttgggaattggctggcacccagcg
gaaagggacgtgagctgagcggcggcggggagaagagtgcgcaggtcagagggcggcgcg
cagcggcgctccgcgaggtccccacgccgggcgatatg
```

*Homo sapiens* CD22 molecule (CD22):

(Seq ID No: 145)
```
tctcctttt
gctctcagatgctgccagggtccctgaagagggaagacacgcggaaacaggctt
gcacccagacacgacaccatg
```

*Homo sapiens* CD37 molecule (CD37):

(Seq ID No: 146)
```
cttcctctttt
ggggttcttcctttctctctcagctctccgtctctcttctctctcagcctctttcttc
tccctgtctcccccactgtcagcacctcttctgtgtggtgagtggaccgcttacccac
taggtgaagatg
```

*Homo sapiens* CD38 molecule (CD38):

(Seq ID No: 147)
```
gcctctctctt
gctgcctagcctcctgccggcctcatcttcgcccagccaaccccgcctggagccctatg
```

*Homo sapiens* CD48 molecule (CD48):

(Seq ID No: 148)
```
cggcctttttctagccaggctctcaactgtctcctgcgttgctgggaagttctg
gaaggaagcatg
```

*Homo sapiens* chromogranin B (secretogranin 1) (CHGB):

(Seq ID No: 149)
```
cttcctttccgcacaggggccgccgagcggggccatg
```

*Homo sapiens* chloride channel, voltage-sensitive 3 (CLCN3):

(Seq ID No: 150)
```
ttcccctttccgtgggtcagggccggtccggtccggaacctgcagccccttttcccag
tgttctagttcgcccgtgacccggaataatgagcaaggagggtgtggtgggttgaaa
gccatcctactttactcccgagttagagcatggattcagttttagtcttaagggg
gaagtgagattggagatttttatttttaattttgggcagaagcaggtt
gactctaggatgctccagagcgagaggatttaacttcatgttgctcccgtgttt
gaaggaggacaataaaagtcccaccgggcaaaattttcgtaacctctgcggtagaaaac
gtcaggtatcttttaaatcgcgatagttttcgctgtgtcaggcttttcttcggtg
gagctccgagggtagctaggttctaggtttgaaacagatgcagaatccaaaggcagcg
caaaaaacagccaccgattttgctatgtctctgagctgcgagataatcagacagc
taaatg
```

*Homo sapiens* colipase, pancreatic (CLPS):

(Seq ID No: 151)
```
ttcccctttccgtgggtcagggccggtccggtccggaacctgcagccccttttcccag
```

```
tgttctagttcgcccgtgacccggaataatgagcaaggagggtgtggtgggttgaaa
gccatcctactttactcccgagttagagcatggattcagtttttagtcttaagggg
gaagtgagattggagattttattttaattttgggcagaagcaggtt
gactctagggatctccagagcgagaggatttaacttcatgttgctcccgtgttt
gaaggaggacaataaaagtcccaccgggcaaaattttcgtaacctctgcggtagaaaac
gtcaggtatcttttaaatcgcgatagttttcgctgtgtcaggcttttcttcggtg
gagctccgagggtagctaggttctaggtttgaaacagatgcagaatccaaaggcagcg
caaaaaacagccaccgattttgctatgtctctgagctgcgagataatcagacagc
taaatg
```

*Homo sapiens* cytochrome c oxidase subunit IV isoform 1 (COX4I1):
(Seq ID No: 152)

```
ctaccctttccgctccacggtgacctccgtgcggccgggtgcgggcg
gagtcttcctcgatcccgtggtgctccgcggcgcgggccttgctctcttccggtcgcgg
gacaccgggtgtagagggcggtcgcggcgggcagtggcggcagaatg
```

*Homo sapiens* cytochrome c oxidase subunit VIIc (COX7C):
(Seq ID No: 153)

```
cttctttcagtccttgcgcaccggggaacaaggtcgtgaaaaaaaaggtcttggtgag
gtgccgccatttcatctgtcctcattctctgcgccttcgcagagcttccagcagcgg
tatg
```

*Homo sapiens* activating transcription factor 2 (ATF2):
(Seq ID No: 154)

```
cagccttttcctccagggggtgctttgtaaacacggctgtgctcagggctcgcgggtgac
cgaaaggatcatgaactagtgacctggaaagggtactagatggaaacttga
gaaaggactgcttattgataacagctaaggtattcctggaagcagagtaaataaa
gctcatggcccaccagctagaaagtattcttgccatgagaaaaagaatgtga
taagttattcaacttatg
```

*Homo sapiens* casein kinase 1, alpha 1 (CSNK1A1):
(Seq ID No: 155)

```
agatccctttcccagagtgctctgcgccgtgaagaagcggctcccggggactggggg
cattttgtgttggctggagctggagtaacaagatggcgtcgtccgcgag
tgacaggggtccctctgggccggagccggcggcagtggtggcagcgg
tatcgccgccctagctcaccgcgcccttttccagcccgcgacgtcgccgcgcaa
gcgaggcagcggcggccgccgagaaacaagtggcccagcctggtaaccgccgagaa
gccccttcacaaactgcggcctggcaaaaagaaac
ctgactgagcggcggtgatcaggttccctctgctgattctgggccccgaacccccgg
taaaggcctccgtgttccgtttcctgccgccctcctccgtagccttgcctagtgtag
gagccccgaggcctccgtcctcttcccagaggtgtcgggcctt
ggccccagcctccatcttcgtctctcaggatg
```

*Homo sapiens* catenin (cadherin-associated protein), beta 1, 88 kDa (CTNNB1):
(Seq ID No: 156)

```
aa
gcctctcggtctgtggcagcagcgttggcccggccccggagcggagagcgaggg
gaggcggagacggaggaaggtctgaggagcagcttcagtccccgccgagccgccaccg
caggtcgaggacggtcggactcccgcggcgggaggagcctgttcccctgagggtattt
gaagtataccatacaactgttttgaaaatccagcgtggacaatg
```

*Homo sapiens* dCMP deaminase (DCTD):
(Seq ID No: 157)

```
ccgcctcctcccccgacttccttccctgagcacggcggcggcggggacgagcac
cggcctgcgcgcggagccggcaccggatgacccaacatg
```

*Homo sapiens* damage-specific DNA binding protein 1, 127 kDa (DDB1):
(Seq ID No: 158)

```
ctgtcttttcgcttgtgtccctctttctagtgtcgcgctcgagtcccgac
gggccgctccaagcctcgacatg
```

*Homo sapiens* desmin (DES):
(Seq ID No: 159)

```
ctgtctcccctcgccgcatccac
tctccggccggccgcctgcccgccgcctcctccgtgcgcccgccagcctcgcccgcgccg
tcaccatg
```

*Homo sapiens* deoxyhypusine synthase (DHPS):
(Seq ID No: 160)

```
cgttccctacttcctgtgctcttgcggagacgcgcgcgtcggggtttaac
gcgtttctgggccgccgtaagcccggcctaggggcagctttgactcgagagccggc
tataggcgcatg
```

*Homo sapiens* dihydrolipoamide S-acetyltransferase (DLAT):
(Seq ID No: 161)

```
cacccttcggatgcctcccctagaaccctaccactttccaccccttccgtctgttatt
tctcccaaacttgcgcccgcacaggcccctctggaacactcctgccccgtagtgcccctc
gtccccgctccgtagagaaagagcgtgcgtgccgcgcattctggcctggggagcgggtg
```

-continued
gagtaaacctgcgggaaccattttacgacaacgtgcggctgtgcggtgtggctgacggca
acgccgctgctcttggagaggtcactccggagacggcgttggttttgggggtgtgggggggt
tggtggcactatg Homo sapiens down-regulator of transcription 1, TBP-binding
(negative cofactor 2) (DR1):

(Seq ID No: 162)

ccttccctggcatctggagggaccaccgtt
gccgcgtcttcggcttccacgatctgcgttcgggctacgcggccacggcggcagccac
tgcgactcccactgtgcctggctctgtccatattag
ttcccaggcggccgtcgccgttccagcagcggcagcggcagcggcagcggcg
gacatgttgtgaggcggcggcgcgggtgtctgaaggatggtttggccgaggcggcgg
caacggctgctggcggcggcggcagcggcagcggggcctcgggctctata
gagccgagcccgctgggtacccgcccggtacccgcggcgaggccagtgcccctggatctt
gcctctgctccgacgccgttggggaccagttaggcgacagcgcccgcccctctgag
gagacacgaaggtggttccccagccgctcaaatttccggaccac
cgcgctttccctcctcagcctgggctgtgctctctctagaatcctcgggccccac
tttcttcccaaactcatcctaaatctctcacacacgcgagtgttcccagccctcaa
gccagctgctcctccgttcattttctgcaccctcttcgcaaagcaccccccgggatcac
tctccgagggcgacttttgagaaatctcggtggagtagtggaccagagctggggag
ttttttaaaagccggggcgcgagaaacaggaaggtactatg Homo sapiens endothelin receptor type A (EDNRA):

(Seq ID No: 163)

ttttcttttcgtgcgagccctcgcgcgcgcgtacagtcatcccgctggtctgac
gattgtggagaggcggtggagaggcttcatccatcccacccggtcgtcgccggg
gattggggtcccagcgagaacctccccgggagaagcagtgcccaggaggttttctgaa
gccggggaagctgtgcagccgaagccgccgccgcgccggagcccgggacac
cggccaccctccgcgccacccaccctcgccggctccggcttcctctggcccaggcgccgc
gcggacccggcagctgtctgcgcacgccgagctccacggtgaaaaaaaagtgaaggtg
taaaagcagcacaagtgcaataagagatatttcctcaaatttgcctcaagatg Homo sapiens
eukaryotic translation elongation factor 1 alpha
2 (EEF1A2):

(Seq ID No: 164)

cagtccctctggctgagacctcggctccggaatcactg
cagccccctcgccctgagccagagcaccccgggtcccgccagcccctcacactcccag
caaaatg Homo sapiens eukaryotic translation elongation factor 2
(EEF2):

(Seq ID No: 165)

cgttctcttccgccgtcgtcgccgccatcctcggcgcgactcgcttctttcggttctac
ctgggagaatccaccgccatccgccaccatg Homo sapiens eukaryotic translation initiation factor 4A2
(EIF4A2):

(Seq ID No: 166)

ctgtcttttcagtcgggcgctgagtggttttttcggatcatg

Homo sapiens egf-like module containing, mucin-like, hormone
receptor-like 1 (EMR1):

(Seq ID No: 167)

gtttcttttctttgaatgacagaactacag
cataatg

Homo sapiens enolase 2 (gamma, neuronal) (ENO2):

(Seq ID No: 168)

gcgcctcctccgcccgccgccgggagccgcagccgccgccgccactgccac
tcccgctctctcagcgccgccgtcgccaccgccaccgccaccgccactaccac
cgtctgagtctgcagtcccgagatcccagccatcatg Homo sapiens esterase D (ESD):

(Seq ID No: 169)

ccgccttttacttcggcccgcttcttctggtcactccgccaccgtagaatcgcctac
catttggtgcaagcaaaaagcaatcagcaattggacaggaaaagaatg Homo sapiens Finkel-Biskis-Reilly murine sarcoma virus
(FBR-MuSV) ubiquitously expressed (FAU):

(Seq ID No: 170)

cttcctctttctcgactccatcttcgcggtagctgggaccgccgttcagtcgccaatatg

Homo sapiens Friend leukemia virus integration 1 (FLI1):

(Seq ID No: 171)

ctgtctcttttcgctccgctacaacaacaaacgtgcacaggggagtgaggg
cagggcgctcgcagggggcac
gcagggagggcccagggcgccaggaggccgcgccgggctaatccgaaggggctgcgagg
tcaggctgtaaccgggtcaatgtgtggaatattgggggggctcggctgcagacttggc
caaatg -continued

*Homo sapiens* fibromodulin (FMOD):

(Seq ID No: 172)
gcccttttcacaatatttgattag
gaatttggggcgggaccctggtctggcacaggcacgcacactctcag
tagactcttcactcctctctctcttcctctctcacac
gttctccaacccaaggaggccagacagagggacgtggtcac
tctctgaaaagttcaacttgagagacaaaatg

*Homo sapiens* ferritin, heavy polypeptide 1 (FTH1):

(Seq ID No: 173)
cgttcttcgccgagagtcgtcggggtttcctgcttcaacagtgcttggac
ggaacccggcgctcgttccccaccccggccggccgcccatagccagccctccgtcac
ctcttcaccgcaccctcggactgccccaaggcccccgccgccgctccagcgccgcg
cagccaccgccgccgccgcctctccttagtcgccgccatg

*Homo sapiens* glyceraldehyde-3-phosphate dehydrogenase (GAPDH):

(Seq ID No: 174)
cgctctctgctcctcctgttcgacagtcagccgcatcttcttt
gcgtcgccagccgagccacatcgctcagacaccatg

*Homo sapiens* glycyl-tRNA synthetase (GARS):

(Seq ID No: 175)
caccctctctg
gacagcccagggccgcaggctcatg

*Homo sapiens* glutamic-oxaloacetic transaminase 2, mitochondrial (aspartate aminotransferase 2) (GOT2):

(Seq ID No: 176)
ctgtccttaccttcagcaggagccggttccctgtgtgtgtgtccgctcgccctctgctcc
gtcctgcggctgcccactgccctcctacggtccaccatg

*Homo sapiens* general transcription factor IIF, polypeptide 1, 74 kDa (GTF2F1):

(Seq ID No: 177)
gcgcctcttccggttac
cttttcccagcgccagaggcgcctagggttggggtcctcgctcaggcacaga
gacccgacaccgagcggcggcttccccgggatcgagggacgcgcacgccagaggagac
gaaaggaacccgggtcggaccagatcggaaccactgaccattgcccatg

*Homo sapiens* glycogen synthase 1 (muscle) (GYS1):

(Seq ID No: 178)
cggcctccttctgcctaggtcccaacgcttcggggcaggggtgcggtcttgcaa
taggaagccgagcgtcttgcaagcttcccgtcgggcaccagctactcggccccg
caccctacctggtgcattcccctagacacctccggggtccctacctggagatccccg
gagccccttcctgcgccagccatg

*Homo sapiens* major histocompatibility complex, class I, C (HLA-C):

(Seq ID No: 179)
cattctccccagaggccgagatg

*Homo sapiens* major histocompatibility complex, class II, DP beta 1 (HLA-DPB1):

(Seq ID No: 180)
gctccctttagcgagtccttctttcctgactg
cagctcttttcattttgccatccttttccagctccatg

*Homo sapiens* 3-hydroxy-3-methylglutaryl-CoA synthase 1 (soluble) (HMGCS1):

(Seq ID No: 181)
ctgtcctttcgtggctcac
tcccttcctctgctgccgctcggtcacgcttgctcttcaccatg

*Homo sapiens* hippocalcin (HPCA):

(Seq ID No: 182)
ccgccttccctgcgcag
tcggtgtctccgcgtcgctgggtgggacttggctcggcggccatg

*Homo sapiens* hydroxysteroid (17-beta) dehydrogenase 2 (HSD17B2):

(Seq ID No: 183)
ctcccttctt
gactctctgttcacagaactcaggctgcctccagccagcctttgccgctagactcac
tggccctgagcacttgaaggtgcagcaagtcactgagaatg

*Homo sapiens* heat shock 60 kDa protein 1 (chaperonin) (HSPD1):

(Seq ID No: 184)

-continued
ctgtccctcactcgccgccgacgacctgtctcgccgagcgcacgcctt
gccgccgccccgcagaaatg

*Homo sapiens* intercellular adhesion molecule 3 (ICAM3):
(Seq ID No: 185)

ccgccttttcccctgcctgcccttcgggcacctcaggaaggcaccttcctctgtca
gaatg

*Homo sapiens* inositol polyphosphate-1-phosphatase (INPP1):
(Seq ID No: 186)

cgtcctctggccgcgcctgcggccgcacgcccagcgcccctcgcctaacctcgcgcccgg
gccgcgcctcctcctcctcctgctccccgccgcttccgtttctcgagggaaaggctgctg
cctcctgctctgtcctcatccccggcttagctgacggcccagagggtgggtgccaattcc
accagcagctgcaactgaaaagcaaggttcagaaatg

*Homo sapiens* interferon regulatory factor 2 (IRF2):
(Seq ID No: 187)

gtttcctctccttgttttgctttcgatctggactgttctcaggcaagccggggag
taacttttagttttgctcctgcgattattcaactgac
gggctttcatttccatttcacatacccctagcaacacttataccttgcggaatt
gtattggtagcgtgaaaaaagcacactgagagggcaccatg

*Homo sapiens* inter-alpha-trypsin inhibitor heavy chain 2
(ITIH2):
(Seq ID No: 188)

ttttcttcttttttcttcttctttctttcttaaagcgaactg
tactcctctgctgttcctttgaacttggttcagtaggaagaagtga
tatcctccccagaccatctgctttggggagcttggcaaaactgtccagcaaaatg

*Homo sapiens* karyopherin (importin) beta 1 (KPNB1):
(Seq ID No: 189)

ccgccttcctccctccctcgctccctccctgcgcgccgcctctcac
tcacagcctcccttcctctttctccctccgcctcccgagcac
cagcgcgctctgagctgcccccagggtccctcccccgccgccagcagcccattt
ggagggaggaagtaagggaagaggagaggaaggggagccggaccgactacccaga
cagagccggtgaatgggttt
gtggtgaccccgcccccacccaccctccctttcccacccgacccccaaccccatccc
cagttcgagccgccgccgaaaggccgggccgtcgtcttaggaggag
tcgccgccgccgccacctccgccatg

*Homo sapiens* karyopherin alpha 3 (importin alpha 4) (KPNA3):
(Seq ID No: 190)

ctctcccccctcctcccccctcccgctccaagattcgccgccgccgccgcagccgcag
gagtagccgccgccggagccgcgcgcagccatg

*Homo sapiens* keratin 19 (KRT19):
(Seq ID No: 191)

gctcctcccgcgaatcg
cagcttctgagaccagggttgctccgtccgtgctccgcctcgccatg

*Homo sapiens* laminin, beta 1 (LAMB1):
(Seq ID No: 192)

attcccttcttt
gggctcgggggctcccggagcagggcgagagctcgcgtcgccggaaaggaagacgggaa
gaaagggcaggcggctcggcgggcgtcttctccactcctctgccgcgtccccgtggctg
cagggagccggcatg

*Homo sapiens* ribosomal protein SA (RPSA):
(Seq ID No: 193)

ctgtcttttccgtgc
tacctgcagaggggtccatacggcgttgttctggattcccgtcg
taacttaaagggaattttcacaatg

*Homo sapiens* lymphocyte cytosolic protein 1 (L-plastin)
(LCP1):
(Seq ID No: 194)

ttttctttcctggctgatgatttgtcattctagtcacttcctgcctt
gtgaccacacacccaggcttgacaaagctgttctgcagatcagaaa
gaagggggttcctggtcatacaccagtactaccaaggacagcttttttcctgcaa
gatctgttacctaaagcaataaaaaatg

*Homo sapiens* lectin, galactoside-binding, soluble, 1
(LGALS1):
(Seq ID No: 195)

ccatctctctcgggtggagtcttctgacagctggtgcgcctgcccgggaacatcctcctg
gactcaatcatg

*Homo sapiens* SH2 domain containing 1A (SH2D1A):
(Seq ID No: 196)

ttctctcttttttgcacatctggctgaactgggagtcaggtggttgactt
gtgcctggctgcagtagcagcggcatctcccttgcacag -continued ttctcctcctcggcctgcccaagagtccaccaggccatg

*Homo sapiens* mannosidase, alpha, class 2A, member 1
(MAN2A1):

(Seq ID No: 197)

tgttcctttcccctccgcttctctgac
ctagctgcgcggccccggcccgggagctgccgaacccgcgcctcccctgggtgaggag
gacacgcctgccctcgtcgagaaaacttttcctgccgactcagttggggcggcggtgg
caggaagtgcgggcagcgacctctcctccgcctgcccgcgcgccctgccg
gaggtcggcgctgagcttgcgatcaagtttgtgggggccccccttcccagtt
gccggcgagtctcgcctcgagaggggcgcccgaccccggggagggcgg
caggccagggcgaaggccaagggcgtgtggtggcgccggagactaggtgcggag
caaggcggggactcgcaccccgcatccgagagcgcggaggtcgcgcagcccggga
gaagggagcctccggcggctgcttcctagagtccacagtgcgctgtctccttt
ggctgaggagagtgtcctggccccgagtctatcgaggaaaatg

*Homo sapiens* myelin basic protein (MBP):

(Seq ID No: 198)

ccgcctcttttcccga
gatgcccgggagggaggacaacaccttcaaagacaggccctctgagtccgac
gagctccagaccatccaagaagacagtgcagccacctccgagagcctggatgtgatg

*Homo sapiens* melanocortin 1 receptor (alpha
melanocyte stimulating hormone receptor) (MC1R):

(Seq ID No: 199)

cattcttcccaggacctcagcgcagccctggcccaggaaggcaggagacagaggccag
gacggtccagaggtgtcgaaatgtcctgggacctgagcagcagccaccagggaa
gaggcagggagggagctgaggaccaggcttggttgtgagaatccctgagcccaggcgg
tagatgccaggaggtgtctggactggctgggccatgcctgggctgac
ctgtccagccagggagagggtgtgaggg
cagatctgggggtgcccagatggaaggaggcaggcatgggg
gacacccaaggcccccctggcagcaccatgaactaagcaggacacctggaggggaa
gaactgtggggacctggaggcctccaacgactccttcctgcttcctggacaggactatg

*Homo sapiens* malic enzyme 1, NADP(+)-dependent, cytosolic
(ME1):

(Seq ID No: 200)

gggcctttcccagtgcggccgccgccgccacagctgcagtcagcac
cgtcaccccagcagcatccgccgcctgcac
cgcgcgtgcgggcccgccccggcctgaccccgccgccgaaccggcgccagccatg

*Homo sapiens* myocyte enhancer factor 2C (MEF2C):

(Seq ID No: 201)

agctctctgctcgctctgctcgcagtcacagacacttgagcacacgcgtacacccagaca
tcttcgggctgctattggattgactttgaaggttctgtgtgggtcgccgtggctgcatgt
ttgaatcaggtggagaagcacttcaacgctggacgaagtaaagattattgttgttatttt
ttttttctctctctctctcttaagaaaggaaaatatcccaaggactaatctgatcggg
tcttccttcatcaggaacgaatgcaggaatttgggaactgagctgtgcaagtgctgaaga
aggagatttgtttggagggaaacaggaaagagaaagaaaaggaaggaaaaaatacataatt
tcagggacgagagagagaagaaaaacggggactatg

*Homo sapiens* mannosyl (alpha-
1,3-)-glycoprotein beta-1,2-N-acetylglucosaminyltransferase
(MGAT1):

(Seq ID No: 202)

agcccttcttggggaagtcagctacccagcagcctgtag
tcctcggctacccacccctcaccgcctggggtcccatggtgagacagctgggtggg
catcaggcttctgcagagggccaggccggagggagctgggcgagggag
tggggctggctcctggcttgcaccggcctcgtggaatccaggcctcagac
ctgatcgctggcgaaactggctctgtgcgctg
gagcccctggtcttctgcgtctgtcctcctcccggccagactttactcctggctcagcga
caggtatttgctatggaagagctgtccctccctccctcggtgggcctggtccac
ctccacctcctcttcaggtccgcaccttcctccccttaaaacaccagccgggcg
cagacccgttctaggcttttccatggtgcttccgccaaagcttgtgaccgag
tccttcccgcctagggctggtgggcctcccctgctgg
taggtctctcttcgctttctttactcagaactgaagctctcattccccacccac
caaggaaaaacaaaagggaagaagccacagctggccccggcttgctttgg
cacaggtgtttcccccccggccccccgtcggg
caccctggttcctgttctgtccctgccccac
gcgaccctgggcctcccacccgggctcctcagcctcccctgggttggggtggggg
gactggctcccagcccttggcctagggtttggtgaacgccttcctg
gactgcgggccacttcaggcgcggctccaggctgggcagctgcgctg
gagggccgaggcaggggtgggtcgggcgtccaccctcaggggttgcgccagggagccg
gaaagccgactcccgaagttgggggtcctgggaaaacttgggtcctgggttgactgagaa
gcggcggggaaaggaggcgggccaggaggagggggcctggcggac
gccggccggggcggggcgcggcggggctgtcggtcacgccccctcag
tccgccccgccccgccctgccggggaagggccacgtt
gcccgcccggccgtccggcccggcgccgcagaaagggctggcgag
tcgaaaggcgaggcggccgcggcagcgcttgggacgcgcctgggcac
cgggctcgctccctgcgccccggagcaggccaagttcggggccaggacgtcgggaggac
ctggtgcatggctgcctcctaatcccatagtccagaggaggcatccctaggactgcggg -continued
caagggagccgggcaagcccagggcagccttgaac
cgtcccctggcctgccctcccggtgggggccaggatg

*Homo sapiens*
mitogen-activated protein kinase kinase kinase 11
(MAP3K11):

(Seq ID No: 203)

ctgcctcccgccccggggccaaagtacaaagggaggaggaa
gaagggagcgggtcggagccgtcggggcaaaggagacggggcaggaacaggcag
tctcggcccaactgcggacgctccctccaccccctgcgcaaaaagaccccaaccggagtt
gaggcgctgcccctgaaggccccaccttacacttggcgggggccg
gagccaggctcccaggactgctccagaaccgagggaagctcgggtccctccaa
gctagccatggtgaggcgcggaggccccggggcccaccccccggcctgaccacac
tgccctgggtgccctcctccagaagcccgagatgcggggggccgggagacaacac
tcctggctcccagagaggcgtgggtctgggctgagggccagggcccg
gatgcccaggttccgggactagggccttggcagccagcggggtggggaccacggg
cacccagagaaggtcctccacacatcccagcgccggctcccggccatg

*Homo sapiens* membrane protein, palmitoylated 1, 55 kDa
(MPP1):

(Seq ID No: 204)

ccgccttctccgcagccccgcaggccccgggccctgtcattcccagcgctgccctgtctt
gcgttccagtgttccagcttctgcgagatg

*Homo sapiens* v-myc myelocytomatosis viral oncogene homolog
(avian) (MYC):

(Seq ID No: 205)

ggccctttataatgcgagggtctggacggctgag
gaccccccgagctgtgctgctcgcggccgccac
cgccgggccccggccgtccctggctcccctcctgcctcgagaaggg
cagggcttctcagaggcttggcgggaaaaagaacggaggggagggatcgcgctgag
tataaaagccggttttcgggctttatctaactcgctgtagtaattccagcga
gaggcagagggagcgagcgggcggccggctagggtggaagagccgggcgag
cagagctgcgctgcgggcgtcctgggaagggagatccggagcgaa
taggggcttcgcctctggcccagcccctcccgctgatcccccagccagcggtccg
caacccttgccgcatccacgaaactttgcccatagcagcgggcgggcactttgcactg
gaacttacaacacccgagcaaggacgcgactctcccgacgcggggaggc
tattctgcccatttggggacacttccccgccgctgccag
gaccgcttctctgaaaggctctccttgcagctgcttagacgctg

*Homo sapiens* nuclear cap binding protein subunit 1, 80 kDa
(NCBP1):

(Seq ID No: 206)

tggcctctcggttccgcggcgcaccggagggcagcatg

*Homo sapiens* necdin homolog (mouse) (NDN):

(Seq ID No: 207)

cttcctctccag
gaatccgcggagggagcgcaggctcgaagagctcctggacgcagaggccctgccctt
gccagacggcgcagacatg

*Homo sapiens* NADH dehydrogenase (ubiqui-
none) 1 beta subcomplex, 5, 16 kDa (NDUFB5):

(Seq ID No: 208)

ccttcttcctcctgcccgtagtagccatg

*Homo sapiens* NADH dehydrogenase (ubiqui-
none) Fe-S protein 4, 18 kDa (NADH-coenzyme Q reductase)
(NDUFS4):

(Seq ID No: 209)

ccgtcctttcatcctggcgtttgcctgcagcaagatg

*Homo sapiens*
nuclear factor of kappa light polypeptide gene enhancer
in B-cells 2 (p49/p100) (NFKB2):

(Seq ID No: 210)

tgcccttccccggccaa
gcccaactccggatctcgctctccaccggatctcacccgccacaccccg
gacaggcggctggaggaggcgggcgtctaaaattctgggaagcagaacctggccg
gagccactagacagagccgggcctagcccagagacatg

*Homo sapiens* non-metastatic cells 2, protein
(NM23B) expressed in (NME2):

(Seq ID No: 211)

gcccctcctccgccgccggctcccgggtgtggtggtcgcac
cagtctctgctctcccagcgcagcgccgccgcccggcccctccagcttcccggaccatg

*Homo sapiens* nucleophosmin (nucleolar
phosphoprotein B23, numatrin) (NPM1):

(Seq ID No: 212)

gcgtcctttccctggtgtgattccgtcctgcgcggttgttctctggagcagcgttcttt

-continued
atctccgtccgccttctctcctacctaagtgcgtgccgccacccgatg

*Homo sapiens* 5'-nucleotidase, ecto (CD73) (NT5E):

(Seq ID No: 213)

cattccttttgtagaaaaacccgtgcctcgaatgaggcgagactcagagag
gacccaggcgcggggcggacccctccaattccttcctcgcgcccccgaaagagcggcg
caccagcagccgaactgccggcgcccaggctccctggtccggccgggatgcggccgg
tacccgctcccgccgggaacaacctctccactcttcctg
cagggagctggtgccagccgacagccgcgccagggccgctccgggtaccagggtcg
gatcgggtgacgtcgcgaacttgcgcctggccgccaagccggcctccaggctgaa
gaaggacccgcccggccttgacccgggccccgcccctccagccggggcac
cgagccccggccctagctgctcgcccctactcgccggcac
tcgcccggctcgcccgctttcgcacccagttcacgcgccacagctatg

*Homo sapiens* phosphatidylethanolamine binding protein 1
(PEBP1):

(Seq ID No: 214)

gcgtcttcccgagccag
tgtgctgagctctccgcgtcgcctctgtcgcccgcgcctggcctaccgcggcac
tcccggctgcacgctctgcttggcctcgccatg

*Homo sapiens* poly(A) binding protein, cytoplasmic 1
(PABPC1):

(Seq ID No: 215)

gcttccccttctccccggcggttagtgctgagagtgcggag
tgtgtgctccgggctcg
gaacacacattttattattaaaaaatccaaaaaaaatctaaaaaaatcttttaaaaaaccc
caaaaaaatttacaaaaaatccgcgtctccccgccgga
gacttttatttttttttcttcctctttttataaaataacccggtgaagcagccgagac
cgacccgcccgcccgcggccccgcagcagctccaagaaggaaccaagagac
cgaggccttcccgctgcccggacccgacaccgccaccctcgctcccgccggcagccgg
cagccagcggcagtggatcgacccccgttctgcggccgttgagtag
ttttcaattccggttgattttttgtccctctgcgctt
gctccccgctcccctcccccggctccggcccccagcccggcac
tcgctctcctcctctcacgaaaggtcgcggcctgtggccctgcgggcagccgtgccga
gatg

*Homo sapiens* proprotein convertase subtilisin/kexin type 2
(PCSK2):

(Seq ID No: 216)

cgctctttctctccggtacacacagctccccacattcg
caccccctgcccgcgcgccgggccgcctgactgcacggcttcccctccagccagatgctg
gagaacacacactgattcgctgctttccaagaccctgttcagtctcttttctctata
caaagatttttttaaaaactatatataagaattctttatttgcaccctccctccgag
tccccctgctccgccagcctgcgcgcctcctagcaccacttttcactcccaaagaaggatg

*Homo sapiens* phosphogluconate dehydrogenase (PGD):

(Seq ID No: 217)

gggtctttccctcactcgtcctccgcgcgtcgccgctcttcggttctgctctgtccgccg
ccatg

*Homo sapiens* phosphoglucomutase 1 (PGM1):

(Seq ID No: 218)

cgctcccctttcccctcccgccggacctgccaggaggtgggctggcgcg
gagggagggccctgtccctgtcccttttaaggaggagggccaaacgccggcctagag
tgcggcgtagccccccaccccgccgtgccctcaccccagagcagctg
cagcctcagccggccgcccctccgccagccaagtccgccgctctgaccccggcag
caagtcgccaccatg

*Homo sapiens* solute carrier family 25 (mitochondrial
carrier; phosphate carrier), member 3 (SLC25A3):

(Seq ID No: 219)

cggcctctgtgagccgcaacctttccaagggagtggtt
gtgtgatcgccatcttagggagtgagtgtggccgggccttctcctgtggcgggtgtggg
gagcggagcccagagctcctgtggggccgctgctttggcggtgggcccagccgggag
cagcctctttcgaaggccgccgtgacctcttcaagggcgtggagacgg
gaaggaaaaggcccggttggggttccagggcgccggtaacgttaaccggcgcctt
gcctgtcctctaaccgtcgctccctcctccctagaaagatg

*Homo sapiens* pim-1 oncogene (PIM1):

(Seq ID No: 220)

cctcccctttactcctggctgcggggcgagccgggcgtctgctg
cagcggccgcgtggctgaggaggcccgagaggagtcggtggcagcggcggcggcgg
gaccggcagcagcagcagcagcagcagcagcaaccac
tagcctcctgccccgcggcgctgccgcacgagccccac
gagccgctcaccccgccgttctcagcgctgcccgaccccgctggcgcgccctccgccgc
cagtcccggcagcgcccctcagttgtcctccgactcgccctcggccttccgcgccagccg
cagccacagccgcaacgccacccg
cagccacagccacagccacagcccaggcatagccttcgg
cacagccccggctccggctcctgcggcagctcctctgggcac
cgtccctgcgccgacatcctggaggttgggatg -continued

*Homo sapiens* pyruvate kinase, muscle (PKM2):

(Seq ID No: 221)

ggatctcttcgtctttgcagcgtagcccgagtcggtcagcgccggaggtgagcggtg
caggaggctacgccatcagtccccaccaagggccagtcgcccggctagtgcg
gaatcccggcgcgccggccggccccgggcacgcaggcagggcggcag
gatccagggcgtctgggatgcagtggagctcagagagaggagaacggctcctcac
gcctggggcctgctcttcagaagtccccagcgccgttccttccagatcaggacctcag
cagccatg

*Homo sapiens* pleiomorphic adenoma gene-like 1 (PLAGL1):

(Seq ID No: 222)

cggcctcctcggcgcagccatcctcttggctgccgcgggcggcaaagcccacggcatctg
ccatttgtcattcagcccgtcggtaccgccccgagccttgatttagacacggctggggcg
tgctctggcctcactctccgggcgggtgctggacggacggacggacggggcagccgtgct
cacagctcagcagcgcggggccttggcgcgcggggcgcttccccgggtcgccgtcatggc
cgcggaggtggcacgcccgagcggcctcgcctgagctccgggggtcgtcgccccgcaggg
attgctgtcacgtctaatgtggctgctgcctcgtgtcacatctgaaactcatctgtacct
cacttagaaagtggttctgattagacaagacttttcgttgcagtcgacagaaacctaatg
ggaccattgaagaattccaaacaggtatttgcataggaatcagaggagttaatcttgtct
cttctcacaggtttgaatcttcagacaaacttctgggaggactcggtccctgcctcgcag
cagatgttccctgtcactcagtaggcatatg

*Homo sapiens* phospholipase D2 (PLD2):

(Seq ID No: 223)

tgctctcttggctccggaaccccgcgggcgctggctccgtctgccagggatg

*Homo sapiens* proteolipid protein 2 (colonic
epithelium-enriched) (PLP2):

(Seq ID No: 224)

cccccttcccggccagacggcggg
caagacagctgggtgtacagcgtcctcgaaaccacgagcaagtgag
cagatcctccgaggcaccagggactccagcccatgccatg

*Homo sapiens* pinin, desmosome associated protein (PNN):

(Seq ID No: 225)

cag
tcctttcgcgcctcggcggcgcggcatagcccggctcggcctgtaaagcagtctcaa
gcctgccgcagggagaagatg

*Homo sapiens* phosphoribosyl pyrophosphate amidotransferase
(PPAT):

(Seq ID No: 226)

ggtccttccacgtgctttcggcggcgacatg

*Homo sapiens*
protein phosphatase 1, catalytic subunit, gamma isozyme
(PPP1CC):

(Seq ID No: 227)

tgttcttctcgtggttccagtggggagagaaggag
gaagtagggagcgggtggcagggggggacccgccggctgctgccaccgccgccac
caccgcctctgctcgtggcgtgggaaaggaggtgtgag
tcccgggcgcgagccggcggcggcgccgctgcgggagggtcggcggtgggaaggcgatg

*Homo sapiens* protein phosphatase 1, regulatory subunit 8
(PPP1R8):

(Seq ID No: 228)

cggtcttccagtttcccggcgtgcttagggcgcgccaaatgggagggg
gagacgcaagatg

*Homo sapiens* protein phosphatase 6, catalytic subunit
(PPP6C):

(Seq ID No: 229)

cggcctccgccgctgccgcgccgctgctacagccgccgccgccgctgtt
gccgcggcttgttattcttaaaatg

*Homo sapiens* protein kinase C substrate 80K-H (PRKCSH):

(Seq ID No: 230)

ctttctttctgcagcaggaaccgcggctgctggacaagagggggtgcggtggatactgac
ctttgctccggcctcgtcgtgaagacacagcgcatctccccgctg
taggcttcctccccacagaacccgtttcgggcctcagagcgtctggtgagatg

*Homo sapiens* mitogen-activated protein kinase 6 (MAPK6):

(Seq ID No: 231)

cgccccctcttcctcgccctctctcgcgggtcggggttacatggcggcgactgcggcaaa
gcgagagcctcggagacgccgctgccgccagcacagccggagacctgagccgacactggg
ggcagtccgcgagccccgcactctctcgatgagtcggagaagtcccgttgtatcagagta
agatggacggtagctttgattgtgattgtggtgagctggagccacctgatcactaacaaa
agacatcttctgttaaccaacagccgccagggcttcctgttgaaataaatatatagcaac
aaaggaaaaaaagaagcaaaacggaaatagtgcttaccagcaccttagaatgatgctgct
caggaccagtccaacactgaatgtatctgcactgtgaggagaatgttcatagaagcctgt

*Homo sapiens* phosphoribosyl pyrophosphate synthetase 2 (PRPS2):

(Seq ID No: 232)

cctcccctteeectacatctagccgccgcgcttteecgctcccgcagcag
cagcctcccgcgtcgctgtcgctgttgcctccgccac
ctcctccgccgccgcgcgccctcggagttccgcgccccaccatg

*Homo sapiens* phosphoribosyl pyrophosphate synthetase-associated protein 1 (PRPSAP1):

(Seq ID No: 233)

ttgcctctggctctgaggcggcggcgccgggcgctgcgaaggctcggccgctgtag
tcagtggtgtggggtgcgcaagggcacggacctcggagctctccccgcttgcgccgag
tttctcagcgccttccccacccaaaccggggtctcgcagtcggaagcactcagagtg
cagccccgcgcggggccggtcgtaaccgcgccgcgggccggacgatg

*Homo sapiens* proteasome (prosome, macropain) subunit, beta type, 5 (PSMB5):

(Seq ID No: 234)

ag
ttctttctgcccacactagacatg

*Homo sapiens* proteasome (prosome, macropain) 26S subunit, non-ATPase, 13 (PSMD13):

(Seq ID No: 235)

tgttcttctgtgccgggggtcttcctgctgtcatg

*Homo sapiens* protein tyrosine phosphatase, receptor type, N (PTPRN):

(Seq ID No: 236)

cagcccctctggcaggctcccgccagcgtcgctgcggctccggcccgg
gagcgagcgcccggagctcggaaagatg

*Homo sapiens* RAB3A, member RAS oncogene family (RAB3A):

(Seq ID No: 237)

ctcccttttgcaggacgtcacggaggactg
caggggcctgagccgctgctgccgccgccgccgcgcagccccacatcaacgcac
cggggtcctgtcaccgccaccgccaaaaaagtcaccgccgctagggtcgccgtt
gcatcggtgcagggcaagatg

*Homo sapiens* RNA binding motif, single stranded interacting protein 2 (RBMS2):

(Seq ID No: 238)

ctctctctctctctctcgctcgttccctaacattaaaga
gaaaatg

*Homo sapiens* reticulocalbin 1, EF-hand calcium binding domain (RCN1):

(Seq ID No: 239)

gcgcccctctgctccggctcggggcgggcactggcggagggactggccag
tcccctcctccgcgccggccccaaccctgtcgctgccgccgcgctccgag
tccccattcccgagctgccgctgtt
gtcgctcgctcagcgtctccctctcggccgccctctcctcgggacgatg

*Homo sapiens* radixin (RDX):

(Seq ID No: 240)

ccgccttttcccgcg
gaggcgccgagcggccatattgcg
gagctgtctgcggtggcggcggcgcctctcgtctcccgcggcccagcgctcgcaccac
cgcttctccctccctgtcgcagccgcgccgccgcgcagcgccccagccacac
gccggcgggcagaagccgcccgctctccggaaagtgataacagaattcattgaagtgga
gaattttttaaagaaggtaacaaaaagagaaagaaaatg

*Homo sapiens* replication factor C (activator 1) 1, 145 kDa (RFC1):

(Seq ID No: 241)

tcgccttcttgcacttcgcgggagaagttgtt
ggcgcgaatggatcctgagcctcgataacagattcctcaac
cggcccaccgccagccagccagcgccttcatcctggggctgccatg

*Homo sapiens* ring finger protein 4 (RNF4):

-continued

```
                                        (Seq ID No: 242)
gcatctttctcgag
gagctctcctgggcggctgaagaaggagcttcttctccggag
tgcgccggcggtggcgcctgcggacctaactagctccaggttaggccgagctttgcgg
gaaagcagcggacttgaaaatactggaaatctgtccggatccaaattattttgcaa
gccagatgagtaaccagagggcatgaaaggttgagaacatttgacttccctgcaaac
cttggtatagatcacttccttttctgtaggaaaggaaaggcaccaaagagcacaatg
```

Homo sapiens ribophorin I (RPN1):

(Seq ID No: 243)

```
tgctcttcccggtcatg
```

Homo sapiens ribosomal protein S27a (RPS27A):

(Seq ID No: 244)

```
cgttcttcctttcgatccgccatctgcggtggagccgccaccaaaatg
```

Homo sapiens secreted and transmembrane 1 (SECTM1):

(Seq ID No: 245)

```
cttcctttagcgtgaaccgcgggtgcggtgcctcccgtgaaaataataaattcac
cgtcacgcttgttgtgaacgcgggtggttcccgaaacttggaggcttccg
taaacccagctccttcctcatctgg
gaggtgggtcccgcgcgggtccgccgcctcctccctggcccctcctctcgtgtctttca
ttttcctggggctccggggcgcggagaagctgcatcccagaggagcgcgtccaggagcg
gacccgggagtgtttcaagagccagtgacaaggaccaggggcccaagtcccaccagc
catg
```

Homo sapiens small glutamine-rich tetratricopeptide repeat
(TPR)-containing, alpha (SGTA):

(Seq ID No: 246)

```
ctttcttttgcg
caggcgtcgcgccctggggccgggccgggcggcaccgcggtgcgcaagcgcaac
cgtcggtgggtcgggatcggtcgcctgagaggtatcacctcttctgggctcaagatg
```

Homo sapiens
SH3 domain binding glutamic acid-rich protein like
(SH3BGRL):

(Seq ID No: 247)

```
agttctccttccaccttcccccacccttctctgccaac
cgctgtttcagccctagctggattccagccattgctg
cagctgctccacagcccttttcaggacccaaacaaccgcagccgctgttcccaggatg
```

Homo sapiens solute carrier family 1 (glutamate/
neutral amino acid transporter), member 4 (SLC1A4):

(Seq ID No: 248)

```
cgccctcctacttccccgtctgcgtccgcgttcgcggctcccgttt
gcatcatccccgtctgcgtccgcgttcgcggctcccgttt
gcatcatctccagccggcggctgctccagggaggctgggcgcgatcctctccgcccgcgg
ctccaacccgcactctgcgcctctcctcgcctttctcgcac
ctgctcctgcgccaggcccggagaccccggggcggcttcccagaacctgcggag
cacaactggccgaccgaccattcattgggaaccccgtcttttgccagagcccac
gtccctgccacctctagctcggagcggcgtgtagcgccatg
```

Homo sapiens
small nuclear RNA activating complex, polypeptide
2, 45 kDa (SNAPC2):

(Seq ID No: 249)

```
ctgcctctttctgagcggcatg
```

Homo sapiens sorting nexin 1 (SNX1):

(Seq ID No: 250)

```
ctatctctcga
taaagttgttgttgcggcttccgccgcgggtggaagaagatg
```

Homo sapiens signal recognition particle 54 kDa (SRP54):

(Seq ID No: 251)

```
ctatctctcatctttccgctcttagctgggagtgctccgcctagtcac
ttttcttaaggtggctcgtcgaggcctgacttcttccccgaaatcacgtccctaga
cagcctcctattttaccactaactttactcctgcagttattcagcggtag
gaaactgaaaccaaaaaccagtgtaagcaagtaaacatctaaactgtttcag
gagccgcgtagaaggaacgcggcggtgtgcccccgaagcggaagtagattctccctata
gaaaggctggactacgcggagtggtgacgtttcctcattgggcggaaggttcgctgg
cactccgttggtcttccagctggtgggagttgacgacgtggtgctgggcgttgg
gaccctactttatctagttcgggaagtttgggttgtgggtcat
acctgtctgtctgctcccagctttcttgggtttcttccgac
ggcgtggggcctcgctaaggaattcccggcccctcagggccac
ggctttagcggtgtcttttgcgagttcttcgtaagtacatcttaaagctgtcaagatg
```

Homo sapiens signal sequence receptor, beta (translocon-
associated protein beta) (SSR2):

(Seq ID No: 252)

```
cggtctttcggatgctgac
```

-continued
gctctcttcctgtctttgtggctccggaaaggcgtttgggatgccaacgatg

*Homo sapiens*
signal transducer and activator of transcription
6, interleukin-4 induced (STAT6):

(Seq ID No: 253)

tttctttttggtggtggtggtg
gaagggggaggtgctagcagggccagccttgaactcgctggacagagctacagac
ctatggggcctggaagtgcccgctgagaaagggagaagacagcagaggggtt
gccgaggcaacctccaagtcccagatcatg

*Homo sapiens* suppressor of Ty 4 homolog 1 (*S. cerevisiae*)
(SUPT4H1):

(Seq ID No: 254)

tgttcttcccatcggcgaagatg

*Homo sapiens* transcription factor 7
(T-cell specific, HMG-box) (TCF7):

(Seq ID No: 255)

ggtccttcccctaaaacttggcactgccgatactcccagcccgttccttcccaagtcagg
aacttgcaggggaccccttggcaattctttttctctcaagagcagacagccttcagtccc
agccgctgccagggctggtgtgtctgaccagctgtggttttccaggcctgaaggcccc
ggagtgcaccagcggcatg

*Homo sapiens* TEA domain family member 4 (TEAD4):

(Seq ID No: 256)

cagtctcctccccgaggtgccggtggccccgccgccac
tccctccggctccctccctcccgccgcggcgcgcatctcattccagccctcattccgcg
cattccagcgtcctcctcgcacactcgaggccaggggcggagggccg
cagctccggcgccgccgcgtcccgccaggtgagaggcgcccgcgcccgccg
caccgccggcgccctcacgggccgcgcgccccacgccgccgcagccgac
cgctcgcgccgcgtgctcggctgctcttttcttccgccgcccgcgttcccgcctt
ggacctctgcgctccgacgcgctccgtcccgac
ctctggcttccctccgcgctccggcgctgctcgctgcccctctcccgcttccctcctgtc
cgccccgcgctcccctcctcgctcccggttgactcactcctccaggaa
tagggatccccgtgttttcccgtcagtcccattctgg
gaaaactcctccctccgcgcgctccgtccgtccgctgggcgcac
cggggccggtcggcgcggggtgggcttggcccgcggccccgccttcac
tgcgccgcccgtcggccccggccggagccggctctgcgcgctgac
gccctgtcgtccccgcagaacgatcgccgcggccggaagagttggcgctcggggcg
gactccttggaactggcttagcgcacccatcccaccttcccgcacctgggaccggtcg
gaacgagctgattgcccgctacatcaagctccggacaggggaagacccgcaccaggaa
gcaggtctccagccacatccaggtgctggctcgtcgcaaagctcgcga
gatccaggccaagctaaaggaccaggcagctaaggacaaggccctgcagagcatg

*Homo sapiens* G protein-coupled receptor 137B (GPR137B):

(Seq ID No: 257)

tttctttcctccagtctcggggctgcaggctgagcgcgatgcgcgga
gaccccgcgggggcggcggcggccgtgagccccgatg

*Homo sapiens* tumor protein, translationally-controlled 1
(TPT1):

(Seq ID No: 258)

cggccttttccgcccgctcccccctcccccgagcgccgctccggctgcac
cgcgctcgctccgagtttcaggctcgtgctaagctagcgccgtcgtcgtctcccttcag
tcgccatcatg

*Homo sapiens* ubiquitin A-52 residue ribosomal protein
fusion product 1 (UBA52):

(Seq ID No: 259)

ctatcttcttttttcttcagcgaggcggccgagctgacg
caaacatg

*Homo sapiens* ubiquinol-cytochrome c reductase core
protein II (UQCRC2):

(Seq ID No: 260)

cggcctccgccaccatcttgctttcctttaatccggcagtgac
cgtgtgtcagaacaatcttgaatcatg

*Homo sapiens* ubiquitin specific peptidase 1 (USP1):

(Seq ID No: 261)

ctgcctttcgtgtctctgcagcgtggagactggaaccggcaatttcaaaggacgccacgt
tcaatcgcagcgctggcgcgggcggaggctaaaacacggggtcctgagactgaggaaaa
cgcgccaagttcccctcggtggcggagtgctaaagaccctagccggttcaggcgttcggcg
agcggggccgctgcttgttgcgctcctggctctccggggcgggcgcagatgggcgccgc
tcccgggatgtagttggtgttggtgcaagacgggagcgagcggcggtcggggttcccgct
cttgggagcggatggtcactcccccgcggggagggcgagccgaccagattttcctgggc
cggggacccggcgggctcggggcagggactcacctgtcgcacccacactcattcgggttg
gacttgccggcgtcaccgccgcggacttcgctttgggccatgaccagatataattggtga
ttacaactttcctctataaattaactcttgacactccttgggatttgaagaaaaaaatg

*Homo sapiens* voltage-dependent anion channel 2 (VDAC2):

(Seq ID No: 262)

gtgtctccttcacttcgccctccagctgctggagctgcagcccgac
cgcgagcgtgccaagcggcttcagcagctagcggagcggtggcggcggccccctcag
gacaccaccagattcccctcttcccgcggcctcgccatg

*Homo sapiens* vimentin (VIM):

(Seq ID No: 263)

gcctcttctccgggagccagtccgcgccac
cgccgccgcccaggccatcgccaccctccgcagccatg

*Homo sapiens* very low density lipoprotein receptor (VLDLR):

(Seq ID No: 264)

ccccctccccgctgctcacccccgctctccggccgccgccggtgcgggtgctccgctac
cggctcctctccgttctgtgctctcttctgctctcggctccccaccccctctcccttccc
tcctctcccttgcctcccctcctctgcagcgcctgcattatttctgcccg
caggctcggcttgcactgctgctgcagcccggggaggtggctgggtgggtggggagga
gactgtgcaagttgtaggg
gagggggtgccctcttcttcccgctcccttcccgccaactccttccctccttctcc
ccctttccctccccgcccccaccttcttcctccttcggaaggactggtaactt
gtcgtgcggagcgaacggcggcggcggcggcggcggcggcaccatccaggcgggcac
catg

*Homo sapiens* wingless-type MMTV integration site
family, member 10B (WNT10B):

(Seq ID No: 265)

agtcctttgctcgccggcttgctagctctctcgatcac
tccctcccttcctcctcccttcctcccggcggccgcggcggcgctggggaa
gcggtgaagaggagtggcccggccctggaagaatgcggctctgacaaggg
gacagaacccagcgcagtctccccacggtttaagcagcactagtgaa
gcccaggcaacccaaccgtgcctgtctcggaccccgcacccaaaccactg
gaggtcctgatcgatctgcccaccggagcctccgggcttcgacatg

*Homo sapiens* CCHC-type zinc finger, nucleic acid
binding protein (CNBP):

(Seq ID No: 266)

cagcctctaccttgcgagccgtcttccccaggcctgcgtccgag
tctccgccgctgcgggcccgctccgacgcggaagatctgactgcagccatg

*Homo sapiens* zinc finger protein 43 (ZNF43):

(Seq ID No: 267)

gggcctttt
gtctctggctgcagttggagctctgcgtctcgtcttcgttcttctgtgtcctctgctgct
agaggtccagcctctgtggctctgtgacctgcgggtattgggggatccacagctaagac
gccaggaccccccggaagcctagaaatg

*Homo sapiens* zinc finger protein 74 (ZNF74):

(Seq ID No: 268)

cagtcctttttgtgggagtccggtctgtccacttgccggtccctcagaccgtcggcggtct
ctgtccgcttcgggacctgtccgctggtcgctccgcgtccgatggctcctggccgcggaa
ccttaggcctggcccctggtctccgagcgcgggttcgccgggaggagcgtggtggcggggt
gtgccggggcgtgagtgcgccgagcatggggctgagcctggtgtggggagtgggtatctg
cggagccggcctgaaccccacctcagccgggcgcggggaggggctccgtgcgtgtgatc
gtgcagctgtgagcgcgtggccgccccgcggggctccgctgcaggcccctcagcccagg
agcagtactcgctcttcagggcctgccctggatcctggaggctacacagctgcccactcc
tcctggggaggctgccgtggaggccatg

*Homo sapiens* zinc finger protein 85 (ZNF85):

(Seq ID No: 269)

gggcctttt
gtctctcgctgcagcctgagctctaggtcttgttttccctgctttt
gtgttttctgctcgtggacgcccagcctctgtggccctgtggcctgcaggtattggga
gatccacagctaagacgccgggaccccctggaagcctagaaatg

*Homo sapiens* zinc finger protein 91 (ZNF91):

(Seq ID No: 270)

gggcctttt
gtctctcgctgccgccggagtttccaggtctcgacttcac
tgctctgtgtcctctgctccaggaggcccagcctgtgtggccctgtgacctg
caggtattggagagccacagctaagatg

*Homo sapiens* zinc finger protein 141 (ZNF141):

(Seq ID No: 271)

gggtctttt
gcgtctggctactaccagaccgcgggttaggggcttcatctctctgcgttctcagtt
gtgggaggccttggtgattcggccacagcctcagcctccgtcgctctgtgacctgcggg
tattggatgattggtagctaagactcccgaatacttcagaagtggggaaatg

*Homo sapiens* zinc finger protein 205 (ZNF205):

(Seq ID No: 272)

tgttctttctagctctgaaatagaaaatg

-continued

*Homo sapiens* transmembrane protein 187 (TMEM187):

(Seq ID No: 273)

ctcccttttcggagatttgaatttcccccagcgaggcgagtgaggcgaaatacccg
tatggtgatagctggccttttcgcgccaatactgaaaaaggcagaac
gttcctccgctggcgccagccaatcagcaggactcctgccttccttcggggcaaggtcg
cagcatctgcctcggaaatcacgaaatcacggggcttctttctgctggctcagccgg
gaggcccagagtgttctgcagaggctgcgtattgaaggctgctctctgaa
gctccctgccccaggtcacgccgccggttccagatg

*Homo sapiens* histone cluster 2, H2be (HIST2H2BE):

(Seq ID No: 274)

acttcttttcttggctaagccgcgtttgtactgtgtcttaccatg

*Homo sapiens* solute carrier family 25 (mitochondrial carrier; oxoglutarate carrier), member 11 (SLC25A11):

(Seq ID No: 275)

ccgcctttgcgctgcgcgcctgcgcccgcgccggcttccagcgggtgtcggacctga
gagctggagggcgtgcgcgcgccctcgctctgttgcgcgcgcggtgtcacctt
gggcgcgagcggggccgcgcgcgcacgggacccggagccgagggccattgagtggcgatg

*Homo sapiens* tyrosylprotein sulfotransferase 2 (TPST2):

(Seq ID No: 276)

cctccccttccccggctgggcggctggagagccgggagtcgctgggtgcgtggggctg
cctcgccgcgtctcgccacgggctctgccagcagacagccttggcacacaggcacaaggg
ctggagcccagagatgagagtgcccaagggagatgtgagcctggcgggctgcccgctaac
ctgtcgctgaagccccagaagcgggcccctcaggccaggcctaccctgcctccggcccag
catg

*Homo sapiens* sorbin and SH3 domain containing 2 (SORBS2):

(Seq ID No: 277)

aagcctcttttatacatctcttcaggaagagagaagcaatgggcatgttagtata
caatgatcacagccacgcaggcctgcaagctgccttttggacaggctgtt
gactgccgttccaattagctgattggagaatgtggaatgcagagtgataatgctgcata
tctgctatcaggcagcagcaaaggttttgtcttgggaaggcaagctttccctgcaa
tattatctcagcagctcccagctgcttaccctgaaaacgagggatccaaac
ggagggtgttgcactctgctaacgctggtcctgtgcgtggctgtggcatatgagcgg
caggtctgaaaaagcaggtgtgtgctgggacgggcactggactggaacgcaggcggac
gctctctgggtttacctgcttcctgttaacagattgtgggctcccagggcatatgtctg
cacgctgaggccgaggcggagaaggggcttcctgagcgtcccagtacactgacagaga
cacttggattggacttaatcttaaacctctggagttcaagac
cttttaaaaaggctaaataaacaatctctacatgtaaaaggccactgactcc
tacttcctctgtatagagcaactgttgaactcagctgcctgtaggaaaactgaa
gactttaataacaaactctccaaggtgaaaatg

*Homo sapiens* G protein-coupled receptor 65 (GPR65):

(Seq ID No: 278)

gtttctcttcttgacttgatgcaggcacagatttatcaagctcctcag
tcaacaaacacatcaccggaagaaatatggaaggaaaggaattttaaaaggaaatac
caatctctgtgcaaacaaagccttgtatattcatgtttgcaccaatctactgtgagat
ttatgaagaaaaacaaattgcggacaactctctatgtacacttacaaatgcctcagtt
gatgcttgtgggctgtttgtcagcgttctgtga
taatgaacacatggacttctgttattaaattcagttgaccccttagccaattgccag
gagcctggattttttacttccaactgctgatatctgtgtaaaaatt
gatctacatccaccctttaaaagcattgatgaattaattagaactttagacaacaaa
gaaaaattgaaaaagaattctcagtaaaagcgaattcgatgttcaaaacaaactacaaa
gagacaagacttctctgtttactttctaagaactaatataattgctac
cttaaaaaggaaaaaatg

*Homo sapiens* nipsnap homolog 1 (*C. elegans*) (NIPSNAP1):

(Seq ID No: 279)

gggccttcctgcaacctttgcggctccaacatg

*Homo sapiens* inhibitor of kappa light polypeptide gene enhancer in B-cells, kinase complex-associated protein (IKBKAP):

(Seq ID No: 280)

gcttctttgcagcgcttcagcgttttcccctggagggcgcctccatcctt
ggaggcctagtgccgtcggagagagagcgggagccgcggacagagacgcgtgcg
caattcggagccgactctgggtgcggactgtgggagctgactctggg
tagccggctgcgcgtggctggggaggcgaggccggacgcacctctgttt
gggggtcctcagagattaatgattcatcaagggatagttgtacttgtctcgtgg
gaatcacttcatcatg

*Homo sapiens* COP9 constitutive photomorphogenic homolog subunit 3 (*Arabidopsis*) (COPS3):

(Seq ID No: 281)

ctgccttcgccgctcgggccgcccggggggaaaacatg

*Homo sapiens* pirin (iron-binding nuclear protein) (PIR):

(Seq ID No: 282)

ccgcctcctctaggccgccggccgcgaagcgctgagtcacggtgaggctactg

```
gacccacactctcttaacctgccctccctgcac
tcgctcccggcggctcttcgcgtcaccccgccgctaaggctccaggtgccgctaccg
cagcgtgagtacctggggctcctgcaggggtccactagccctccatcctc
tacagctcagcatcagaacactctctttttagactccgatatg
```

*Homo sapiens* THO complex 5 (THOC5):

(Seq ID No: 283)
```
ccttccttacttccggttctc
tatggtgcgcgggcaagctttgctccgcctccggcag
tggcttactcccggtgccaggttcttggagctgtgaggaggaacaaccatg
```

*Homo sapiens* RuvB-like 1 (*E. coli*) (RUVBL1):

(Seq ID No: 284)
```
gggcctttt
gcaaaattgccctagtaacggccgcatggtaactcaggcgccgggcgcac
tgtcctagctgctggttttccacgctggttttagctcccggcgtctgcaaaatg
```

*Homo sapiens* Kruppel-like factor 7 (ubiquitous) (KLF7):

(Seq ID No: 285)
```
tttccttttttagttgactgaaacaaaacaaaacaaaagggccactg
gatgtctgccttcttgggggggtgagccaga
cagactgacaaacaaacagccccaactgtgttcggggagggtttcgcctcccgtttt
gcccggcagcagcagcatg
```

*Homo sapiens* USO1 vesicle docking protein homolog (yeast) (USO1):

(Seq ID No: 286)
```
gctccccttttgccttcaaccttcgagccgccacgtaatgccac
gtccccgcgcatgcgcatcttggccgctgctggcggctgtttccgggcttagagggctg
gagtggccgccgagttggaggcggtggtggcagcagtaggagtgtgtagagtgcgg
gattgggggccaggccctgcggagggcggggaagttgtcttcttttttttccg
gaggggccggtaaacctggtggctgaacggcaagatg
```

*Homo sapiens* unc-5 homolog C (*C. elegans*) (UNC5C):

(Seq ID No: 287)
```
cccccttttggcccctgccttttggagaaagtggagtgtggcgcttggtt
gtcgttatttcttcggactgcttcgcggtgcacggattcagcttctgcccag
tggggctttcagctgtttgcgcgtctctctgtcccctccctcccccggcacac
ctctgtctacgatg
```

*Homo sapiens* RNA terminal phosphate cyclase domain 1 (RTCD1):

(Seq ID No: 288)
```
gcttcttccgctttctcgtcaggctcctgcgcccaggcatgaac
caaggtttctgaactactgggcgggagccaacgtctcttctttctcccgctctggcg
gaggctttgtcgctgcgggctgggccccagggtgtccccatg
```

*Homo sapiens* eukaryotic translation initiation factor 3, subunit A (EIF3A):

(Seq ID No: 289)
```
ggctccttccttttccgtctctggccggctgggcgcgggcgactgctggcgaggcgcgtgg
gaccttacgctggttcccttcgtctcctctcccggcccgggccactagagagttcgctg
acgccgggtgagctgagcctgccgccaagatg
```

*Homo sapiens* eukaryotic translation initiation factor 3, subunit D (EIF3D):

(Seq ID No: 290)
```
gtttcctcttttcctggtttctcaagagtgctgctgctaac
gcggtccccggcacgcaccatctgttgccatcccggccggccgaggccattgcagat
tttggaagatg
```

*Homo sapiens* eukaryotic translation initiation factor 3, subunit F (EIF3F):

(Seq ID No: 291)
```
ccgcctccttctttctcgacaagatg
```

*Homo sapiens* eukaryotic translation initiation factor 3, subunit G (EIF3G):

(Seq ID No: 292)
```
cgctctctggccgggcttgggctgcgtggagaatacttttttg
cgatg
```

*Homo sapiens* eukaryotic translation initiation factor 3, subunit H (EIF3H):

(Seq ID No: 293)
```
gtttctctttcttcctgtctgcttggaaagatg
```

*Homo sapiens* eukaryotic translation initiation factor 3, subunit I (EIF3I):

(Seq ID No: 294)
```
aaaccttttccggtcttactcacgttgcggccttcctcgcgtca
```

-continued cagccgggatg

*Homo sapiens* eukaryotic translation initiation factor 3, subunit J (EIF3J):

(Seq ID No: 295)

ctccctctcacacacgctcacacccggctcgagatg

*Homo sapiens* poly(A) binding protein, cytoplasmic 4 (inducible form) (PABPC4):

(Seq ID No: 296)

ccgcctctctccgccccgggtcgctgccgcctccgccgctttcgggcttcgcagcctgag
gaaaaaagagaaaagataaaaaaaatctgaaaacgcttcaaaatcctgaaaaaaaaaa
aggaaaagaaaaaacgaatcctcggagaacccgcggggaagtcactttcgtacgcttccg
gcctgccccgcccgccgccgcagcgcttggcgtccgtcggtctccgtccgtcggtccg
ggggtgagccgcccgcccggcccgccgtgccctcccccgctcgggcccgagcccgcg
ccccgcgcctgccccggcgcaccacgtgtccgtgctgcccttcgccgcccgcccggggct
cgccgagtcggcgcccacaaagatttggtttccctctgccccggcggttgtaatcttaaa
ccgccggagcccgaggcctatatttatagagaaacgcgtgtcccgaggccgccgtgggc
agcgtccggtcgcctcttaaaggattttttaccccttcggaaggggattccccgtttaattt
ttttcctactttgattttttgaaatttggagcttcgcaccaggaccgcggagaagtgcaa
agtcgcggggagggccgtattgtgcggagagccttttgtctgcggtgctgcggccgtggg
agccggccccgcctcccgtttccgtcccgtctccaagccgcgactccagctcgtcct
cgccgcgccggtgccacctgtgagccggcgcgggcccgggctccgaaggcgcccctt
gtcctgcggcgggcccgataagaagtcctcctggcggggctcggggtggtgggggcggg
gagatg

*Homo sapiens* receptor-interacting serine-threonine kinase 2 (RIPK2):

(Seq ID No: 297)

agctcttttcgcggcgctacggcgttggcaccagtctctagaaaa
gaagtcagctctggttcggagaagcagcggctggcgtgggccatccggg
gaatgggcgccctcgtgacctagtgttgcggggcaaaaagggtctt
gccggcctcgctcgtgcaggggcgtatctgggcgcctgagcgcggcgtgggagccttgg
gagccgccgcagcaggggcacacccggaaccggcctgagcgcccgggaccatg

*Homo sapiens* neuropilin 1 (NRP1):

(Seq ID No: 298)

ctttcttttctccaagac
gggctgaggattgtacagctctaggcggagttgggggctcttcggatcgcttagat
tctcctctttgctgcatttccccccacgtcctcgttctcccgcgtctgcctgcg
gacccggagaagggagaatg

*Homo sapiens* guanine monphosphate synthetase (GMPS):

(Seq ID No: 299)

tggtcttctctcccgcggcgctggggcccgcgctccgctgctgtt
gctccattcggcgcttttctggcggctggctcctctccgctgccggctgctcctcgac
caggcctccttctcaacctcagcccgcggcgccgaccccttccgg
caccctcccgccccgtctcgtactgtcgccgtcaccgccgcggctccggccctggccc
cgatg

*Homo sapiens* far upstream element (FUSE) binding protein 1 (FUBP1):

(Seq ID No: 300)

ttttcttctttcttctttcttagctgttagctgagaggaagtctctgaacaggcgg
cagcggctcttatagtgcaaccatg

*Homo sapiens* eukaryotic translation initiation factor 2B, subunit 5 epsilon, 82 kDa (EIF2B5):

(Seq ID No: 301)

gatccttttt
gtccctactgcgtgcggtggcagcttccttgcggaagtggtgaccgtgagagaagaa
gatg

*Homo sapiens* eukaryotic translation initiation factor 2, subunit 2 beta, 38 kDa (EIF2S2):

(Seq ID No: 302)

gtttcctttcgctgatgcaagagcctag
tgcggtggtgggagaggtatcggcagggg
cagcgctgccgccggggcctggggctgacccgtctgacttcccgtccgtgccgagcccac
tcgagccgcagccatg

*Homo sapiens* adaptor-related protein complex 1, sigma 2 subunit (AP1S2):

(Seq ID No: 303)

cctccctctccgcctaa
gcctgccctatgccagccgggtgtcctccccacagcaccacggcttctcttcctcag
cacggcgacaggggcttcccccttcgccgccgccgccgccgccggccaa
gctccgccgcgcccgcggcccgcggccgccatg

*Homo sapiens* suppression of tumorigenicity 13 (colon carcinoma) (Hsp70 interacting protein) (ST13):

-continued (Seq ID No: 304)
cgccccttctgcgcggtcacgccgagccagcgcctgggcctggaaccgggccgtagccc
ccccagtttcgcccaccacctccctaccatg Homo sapiens solute carrier family 7 (cationic
amino acid transporter, y+ system), member 7 (SLC7A7):

(Seq ID No: 305)
ctcccttcttaaatgcttggggtgagagagaagagaggctagggtggggcatggag
gacacagagagagagagtgctgtgtattccttccccgc
tactgtcctgtcctcagctaacttgctctgggacagcttccccagggctacagatactg
cactcagctgactgtcctttcttctgggcccctggtcccagagcagagctgacaaagga
gattcctgagagagcaccttcttatcacagaaagtgctgagccaa
gagctcctagctgccccttttgcagatgtgaagggccagtgaaccttt
ggacccagatggttgcttaatactcctttccccctccctcactccttccttt
gcgggctgcctcacctcctccaccttcttgcttaaatccataggcattt
gtctggccttccctttactgctggctgggaaggaggagcatcagaccacagatcctg
gaaggcacttctctccctgactgctgctcacactgccgtgagaacctgcttatatccag
gaccaaggaggcaatgccaggaagctggtgaagggtttcctctcctccaccatg Homo sapiens paired box 2 (PAX2):

(Seq ID No: 306)
ctcccttttctcctcaagtcctgaagttgagtttgagaggcgacac
ggcggcggcggccgcgctgctcccgctcctctgcctcccccatg Homo sapiens 5-aminoimidazole-4-carboxamide ribonucleotide for
myltransferase/IMP cyclohydrolase (ATIC):

(Seq ID No: 307)
agccctcctacctgcg
cacgtggtgccgccgctgctgcctcccgctcgccctgaacccagtgcctgcagccatg Homo sapiens ATP synthase, H+ transporting, mitochondrial
F1 complex, alpha subunit 1, cardiac muscle (ATP5A1):

(Seq ID No: 308)
ccttcttt
gcggctcggccattttgtcccagtcagtccggaggctgcggctgcagaagtac
cgcctgcggagtaactgcaaagatg Homo sapiens cyclin G1 (CCNG1):

(Seq ID No: 309)
cggccccttcggctccgagctgaccctgatcagggccgagtt
gtctcggcggcgctgccgaggcctccacccaggacag
tcccctccccgggcctctctcctcttgcctacgagtcccctctcctcg
taggcctctcggatctgatatcgtggggtgaggtgagcaggcccggggagggtggttac
cgctgaggagctgcagtctctgtcaagatg Homo sapiens cadherin 16, KSP-cadherin (CDH16):

(Seq ID No: 310)
agctctcttcttgcttggcagctggaccaagggagccagtcttgggcgctg
gagggcctgtcctgaccatg Homo sapiens cyclin-dependent kinase inhibitor 1B
(p27, Kip1) (CDKN1B):

(Seq ID No: 311)
ttttcttcttcgtcagcctcccttccaccgccatattgggccactaaaaaaggggctc
gtcttttcggggtgtttttctcccccctccctgtccccgcttgctcacggctctgcgact
ccgacgccggcaaggtttggagagcggctgggttcgcggaccccgccggcttgcaccgc
ccagactcggacgggctttgccaccctctccgcttgcctggtcccctctcctctccgccc
tcccgctcgccagtccatttgatcagcggagactcggcgccgggccggggcttccccgc
agcccctgcgcgctcctagagctcgggccgtggctcgtcggggtctgtgtcttttggctc
cgagggcagtcgctgggcttccgagaggggttcgggctgcgtaggggcgctttgttttgt
tcggttttgttttttttgagagtgcgagagaggcggtcgtcgtcagacccgggagaaagatg Homo sapiens chimerin (chimaerin) 2 (CHN2):

(Seq ID No: 312)
tctcctcttcttcctttgtgtgtgcgcgagcggagttggggcggagggagaagggg
gaggtcgctctgtctgtccgtctcccgccgcctctgcccggtc
tactcgaagtgcggcggagaggcgggagcccaggagagggtgcgg
gagctggcggggcggctcggagctgccaggacgccctggtcccagccgcgcacaggg
gagcgtggacggcagaggggctcggcgggagccga
gatccgcccgtcccggctgcccctcggcctccctctgctcccac
ctaccccctgacacccatagaaaagcgtgcaaaggcgcgggagcgggacggaaac
cacaaatataatagcggcggcggcagcgcgtcatctggtggagcaggaagtg
caggcagagtccggaggctggtgctttctgcgcgtccccaggactttt
gccatgggctggggccgcggaggctgcgagcggccgggcgaggg
cagcggcggcggcgtccgcaccggggctgagcgagcagcgacgcgaggggcgcgcgga
gatg Homo sapiens citrate synthase (CS):

(Seq ID No: 313)
gggcctccttgag
gaccccgggctgggcgccgccgccggttcgtc

-continued

```
tactctttccttcagccgcctcctttcaacctt
gtcaacccgtcggcgcggcctctggtgcagcggcggcggctcctgttcctgccg
cagctctctcccctttcttacctcccaccagatcccgga
gatcgcccgccatggctttacttactgcggccgcccggctcttgggaac
caaggcacccagtggcaagtactagctgagcatttgggagatgcttgtcttactt
ggctgttgcttctcctgctgctggggaaaaggaatgcatcttgtcttgttctt
gcagcccggcatgccagtgcttcctccacgaatttgaaagacatattggctgacctga
tacctaaggagcaggccagaattaagactttcaggcagcaacatggcaagac
ggtggtgggccaaatcactgtggacatg
```

*Homo sapiens* cathepsin S (CTSS):

(Seq ID No: 314)
```
atttcttttcaagtcaatt
gaactgaaatctccttgttgctttgaaatcttagaagagagcccac
taattcaaggactcttactgtgggagcaactgctggttctatcacaatg
```

*Homo sapiens* deoxynucleotidyltransferase, terminal (DNTT):

(Seq ID No: 315)
```
cagtctccctcccttctggagacaccaccagatgggccagccagaggcagcag
cagcctcttcccatg
```

*Homo sapiens* dual specificity phosphatase 3 (DUSP3):

(Seq ID No: 316)
```
cgctctccgcctcgcttgctcctgccggggcgtgcagggccccgccgccgccatg
```

*Homo sapiens* coagulation factor II (thrombin) receptor-like 2 (F2RL2):

(Seq ID No: 317)
```
catcctttccctgcggaggaccagggcaagtttcctgcctgcacggcacaggagagcaaa
cttctacagacagaccaaggcttccatttgctgctgacacatggaactgaggtgaaattg
tgctccatgattttacagatttcataacgtttaagagacgggactcaggtcatcaaaatg
```

*Homo sapiens* Fc fragment of IgG, receptor, transporter, alpha (FCGRT):

(Seq ID No: 318)
```
cgtcctctcagcatg
```

*Homo sapiens* guanylate binding protein 2, interferon-inducible (GBP2):

(Seq ID No: 319)
```
ttacctcttttcttgtctctcgtcaggtctctgacattgacagagcctg
gacgttggaggaagccccaggacgttggaggggtaaagtaaaagtccacagttac
cgtgagagaaaaagagggagaaagcagtgcagccaaactcggaagaaaagagaggag
gaaaaggactcgactttcacattggaacaaccttctttccag
tgctaaaggatctctgatctggggaacaacaccctggacatg
```

*Homo sapiens* G protein pathway suppressor 1 (GPS1):

(Seq ID No: 320)
```
cgctctttctcccttcagcagccagccagctctgtgtcagggtcgggggtg
cagaaagtcaggacagaatg
```

*Homo sapiens* general transcription factor IIF, polypeptide 2, 30 kDa (GTF2F2):

(Seq ID No: 321)
```
gttcctctttcctcggttcccagtgttctgg
caggtaaggaacgccggctcttcgcctctcagcgcggcttgtcctttgttccggac
gcccgctcctcagccctgcggctcctggggtcgctgctgcatcccgcacgcctccac
cggctgcagacccatg
```

*Homo sapiens* glycogenin 1 (GYG1):

(Seq ID No: 322)
```
cgctccctcccggtgccggcttctctgagtcaccaac
ctgaggctgccccggccgcctgcgcacccggcagcaccatg
```

*Homo sapiens* heat shock 70 kDa protein 9 (mortalin) (HSPA9):

(Seq ID No: 323)
```
agctctttgccgtcggagcgcttgtttgctgcctcgtactcctccatttatccgccatg
```

*Homo sapiens* iron-responsive element binding protein 2 (IREB2):

(Seq ID No: 324)
```
cttccttctttcctcccttgccag
tccgcctgtcttcctcccccgtcttccctgcccggcctccccctccccccgctggccc
cctccccggagggataatatggtctccggcgatg
```

*Homo sapiens* origin recognition complex, subunit 1 (ORC1):

(Seq ID No: 325)
```
ccaccttcttttcatttctagtgagacacacgctttggtcctggctttcggcccgtag
ttgtagaaggagccctgctggtgcaggttagaggtgccgcatcccccg
gagctctcgaagtggaggcggtaggaaacggagggcttgcggctagccggaggaa
gctttggagccggaagccatg
```

-continued

Homo sapiens RAB1A, member RAS oncogene family (RAB1A):

(Seq ID No: 326)

cattcctttctttcgattaccgtggcgcggagagtcagggcggcggctgcggcagcaag
ggcggcggtggcggcggcagctgcagtgacatg Homo sapiens cytohesin 2 (CYTH2):

(Seq ID No: 327)

gagtcttttcagcgctgag
gactggcgctgaggaggcggcggtggctcccggggcgttt
gagcgggctcacccgagcccgcgggccaacgcggatccaggcccgactggcgggac
cgccccggattcccgcgggccttcctagccgccatg Homo sapiens COP9 constitutive photomorphogenic homolog subunit
2 (Arabidopsis) (COPS2):

(Seq ID No: 328)

atttctcctcccctcccggccaagatg

Homo sapiens solute carrier family 9 (sodium/
hydrogen exchanger), member 3 regulator 1 (SLC9A3R1):

(Seq ID No: 329)

ggtcctctctcggctcctcgcggctcgcggcggccgacggttcctgggacacctgctt
gcttggcccgtccggcggctcagggcttctctgctgcgctcccggttcgctggacgg
gaagaagggctgggccgtcccgtcccgtccccatcg
gaaccccaagtcgcgccgctgacccgtcgcagggcgagatg Homo sapiens peptidase (mitochondrial processing) beta
(PMPCB):

(Seq ID No: 330)

ctaccttccttctagcagaaatg

Homo sapiens RAB3D, member RAS oncogene family (RAB3D):

(Seq ID No: 331)

cggcccttcctccgccttctgggcggagcccgcgcgggatccgggtggctg
caggctgctggcttctgcgcgctgcggggtcggggtcgcggccagggccaagccg
cagcgagttcacaggcggaaccccctgcaggcggcgccccctacgcgaggtcacccctgg
gaaggagcgcagcccacccggcccctccgcatccgagcaggac
gcccgtctcctctcccctgaggatttcaggtctccctgtcccaggaggcttgtgccaa
gatg Homo sapiens ATP-binding cassette, sub-family B (MDR/TAP):

(Seq ID No: 332)

tcttctctcggttcctctttcctcgctcaagatg

Homo sapiens N-acylsphingosine amidohydrolase (acid
ceramidase) 1 (ASAH1):

(Seq ID No: 333)

ggctcttctttgcctctgctggagtccggggag
tggcgttggctgctagagcgatg

Homo sapiens cytochrome c oxidase subunit VIc (COX6C):

(Seq ID No: 334)

ttttcctttagtcaggaaggacgttggtgttgaggttagcatacgtatcaaggacag
taactaccatg

Homo sapiens COX15 homolog, cytochrome c oxidase assembly protein
(yeast) (COX15):

(Seq ID No: 335)

gcttctcttttccttggcggaggagggagac
cacagagccctgggttgtggaagaggtggctgttccctgtcatcagtatg Homo sapiens c-src tyrosine kinase (CSK):

(Seq ID No: 336)

cccccttccccgcctttcttccctccgcgaccgggccgtgcgtccgtccccctgcctc
tgcctggcggtccctcctcccctctccttgcacccatacctctttgtaccg
cacccccctggggaccctgcgcccctcccctccccctgaccgcatggaccgtcccg
caggccgctgatgccgcccgcggcgaggtggcccggaccgcagtgccccaaga
gagctctaatggtaccaagtgacaggttggctttactgtgactcggggac
gccagagctcctgagaagatg Homo sapiens versican (VCAN):

(Seq ID No: 337)

gagcctttctggggaa
gaactccaggcgtgcgacgcaacagccgagaacattaggtgttgtggacaggagctgg
gaccaagatcttcggcagcccgcatcctcccgcatcttccagcaccgtcccg
caccctccgcatccttcccggggcaccacgcttcctatgtgaccgcctgggcaac
gccgaacccagtcgcgcgcagcgctgcagtgaattttccccccaaactgcaataa
gccgccttccaaggccaagatg Homo sapiens dystroglycan 1 (dystrophin-
associated glycoprotein 1) (DAG1):

-continued (Seq ID No: 338)
gcgcctcttaggctt
ggcggtggcggcggcggcagcttcgcgccgaatcccggg
gagcggcggtggcggcgtcctggggccaggaggagcgaacac
ctgccgcggtcctcccgccggcgctgggctctgtgtgctccgggatggagcaggtgtg
cagagggtgagaacccagctctgggaccaagtcacttgcttccttacttagcaagac
tatcgacttgagcaaacttggacctgggatg Homo sapiens DEAD (Asp-Glu-Ala-Asp) box helicase 5 (DDX5):

(Seq ID No: 339)
cccctcttttggttacagacgtgagggctctttggagacgtaaacatctccgag
tggcgagggtgggcggggctgggcttgggaaagggcggggtggcttgcttgaggtgtg
gaaagaccagaagaaggtgaggtcaagagagtg
cagaatgaggcattccaatggtgggtgggccctgacctgagagagtggcgcggg
gaggggtgaaagcgcggcgatcctggaacgccagcgggcgttgcggcc
tatgcgcgaggggcggggcgattaggtcatagagcggctcccagcgttccctgcggcg
taggaggcggtccagactataaaagcggctgccggaaagcggccggcac
ctcattcatttctaccggtctctagtagtg
cagcttcggctggtgtcatcggtgtccttcctccgctgccgcccccg
caaggcttcgccgtcatcgaggccatttccagcgacttgtcgcacgcttttctata
tacttcgttccccgccaaccgcaaccattgacgccatg Homo sapiens desmoplakin (DSP):

(Seq ID No: 340)
gctcctctgcgcccttt
gccgccctccgagccacagctttcctcccgctcctgcccccggcccgtcgccgtctccgc
gctcgcagcggcctcgggagggcccaggtagcgagcagcgacctcgcgagccttccg
cactcccgcccggttcccggccgtccgcctatcctt
ggccccctccgctttctccgcgccggcccgcctcgcttatgcctcggcgctgagccgctc
tcccgattgcccgccgacatg Homo sapiens glutamyl-prolyl-tRNA synthetase (EPRS):

(Seq ID No: 341)
cttcctttcgcggggtcctccgtagttctggcacgagccaggcgtactgacaggtggac
cagcggactggtggagatg Homo sapiens acyl-CoA synthetase long-chain family member 4 (ACSL4):

(Seq ID No: 342)
gctcctcctcgtcccagcgctagcgggcacgcggttccttttttgcgagctttccgagtgc
caggcgccggccggctgcgaagacgcggtgggccgcccctccgattgaaatcacagaaga
tattcgtgttcttcttaagagaaaaagaggacattttagctttctcagttgaaggcgtac
tttattgtcggcttccaaagattactaacttttatctgtatcactaagattgaactgcct
tggctgtactgctattcttactgctgcttctattattgccttcttcagcacaataaggct
ttcaaaagccaaagaataacaagaaataagcaccattttagaagcctttccactatg Homo sapiens fibroblast activation protein, alpha (FAP):

(Seq ID No: 343)
tggtccttttcaacggttttcacagatccagtgacccacgctctgaagacagaatt
agctaactttcaaaaacatctggaaaaatg Homo sapiens UDP-N-acetyl-alpha-D-galactosamine:polypeptide N-acetylgalactosaminyltransferase 3 (GalNAc-T3) (GALNT3):

(Seq ID No: 344)
ctgcctctccaggcaacgcgggaggcccagcgggaaggcaggaggcggcggcggaggag
gagctctactgagccgcaactgtggcgacagcaaccggagtcgcagccgccgccacctg
cacctggcgcctagcccac
gtccagcgcctgccggccgccgcttcccgccacccctgccctgcccacccgccaggtact
accattaaagataccttcttctcagcaaatctatgataaaaaatataagtaacagaa
gaagaaataactgttatttgtcaagtgacaagcttttaatgtcagaatg Homo sapiens glypican 3 (GPC3):

(Seq ID No: 345)
acgtctcttgctcctcagggccac
tgccaggcttgccgagtcctgggactgctctcgctccggctgccac
tctcccgcgctctcctagctccctgcgaagcaggatg Homo sapiens interleukin enhancer binding factor 2, 45 kDa (ILF2):

(Seq ID No: 346)
acgcctcttcagttgtctgctactcagaggaaggggcggtt
ggtgcggcctccattgttcgtgttttaaggcgccatg Homo sapiens nucleosome assembly protein 1-like 1 (NAP1L1):

(Seq ID No: 347)
gggtctttttttagcgccatctgctcgcggcgccgcctcctgctcctcccgctgctgctgc
cgctgccgccctgagtcactgcctgcgcagctccggccgcctggctccccatactag
tcgccgatatttggagttcttacaacatg Homo sapiens asparaginyl-tRNA synthetase (NARS):

(Seq ID No: 348)

-continued cgctctctgatgcaacgccggaatcgcggaaaccgccggtgcacgttggagtcataa
gacggcgtcggtgttgcagtctgtgtccttggaggtgaccagggccactgcaggcatg

*Homo sapiens* NADH dehydrogenase (ubiquinone)
1 alpha subcomplex, 10, 42 kDa (NDUFA10):

(Seq ID No: 349)

cgtccccttt
gggtccttgatcctgagctgaccgggtagccatg

*Homo sapiens* NADH dehydrogenase (ubiquinone)
Fe—S protein 2, 49 kDa (NADH-coenzyme Q reductase)
(NDUFS2):

(Seq ID No: 350)

ttctccttcccgcagtctgcagccggagtaagatg

*Homo sapiens* NADH dehydrogenase (ubiquinone)
Fe—S protein 5, 15 kDa (NADH-coenzyme Q reductase)
(NDUFS5):

(Seq ID No: 351)

catcctttacggcaggcgtccgcgtcgctagctagtcgttctgaa
gcggcggccagagaagagtcaagggcacgagcatcgggtagccatg

*Homo sapiens* phosphoenolpyruvate carboxykinase 2 (mitochondrial)
(PCK2):

(Seq ID No: 352)

ccctccttttaa
gcgcctcccgccagcctctgctgtggctcgcttcgccgcgctccctccttcccgccttc
catacctccccggctccgctcggttcctggccaccccgcagcccctgcccaggtgccatg

*Homo sapiens* serpin peptidase inhibitor, clade B (ovalbumin),
member 6 (SERPINB6):

(Seq ID No: 353)

ctcccttcgcgctccggacgggcgacgg
tagctcgagacccgggactccgcccgcctccccgcgagtattt
gaggtccggggcggctccggcgcctctgcccgccgttctgctcgctcgctccccgctctg
gagtctgccatcatg

*Homo sapiens* Rab geranylgeranyltransferase, alpha subunit
(RABGGTA):

(Seq ID No: 354)

ttctctcctcagacttcaagggctaccactggaccettccctgtctt
gaaccctgagccggcaccatg

*Homo sapiens* Rab geranylgeranyltransferase, beta subunit
(RABGGTB):

(Seq ID No: 355)

ctctctcctttccctgttagacatg

*Homo sapiens* small nuclear ribonucleoprotein polypeptide A
(SNRPA):

(Seq ID No: 356)

agttctctccgcacgcgggctggagaagcgggtcctacgcacgctttgtt
gtcgcgctttgcctccgtccttgcccctactcccgccttacctgacttccttttcggag
gaagatccttgagcagccgacgttgggacaaaggatttgga
gaaacccagggctaaagtcacgttttttcctcctttaagacttacctcaacacttcactc
catg

*Homo sapiens* sterol regulatory element binding transcription factor
2 (SREBF2):

(Seq ID No: 357)

cgcccttttctgtgcggcgcccgggcgcaac
gcaaacatggcggcgggtggcacccgtcggtgaggcggtgccgggcgggggtt
gtcgggtgtcatgggcggtggcgacggcaccgcccccgcgtctccctgagcgggacgg
caggggggcttctgcgctgagccgggcgatg

*Homo sapiens* translin (TSN):

(Seq ID No: 358)

ctgccctttggac
gcgcgcctcggttccgaacgcagcggacggcgcctcaggcagcgcgcg
gacagcccgtcctccggcgcgcgccgcgagcctcggaggaccctagcgacggtcgtggcg
taagaccggggggacgcggcggtagcggcggccgttgcgattgattgcgctggtt
gcctgcggcgtccacttccttggccgcccttgctacactggctgattgttgtg
cagccggcgccatg

*Homo sapiens* Fanconi anemia, complementation group G
(FANCG):

(Seq ID No: 359)

ccacccttctcgaggctgtggcctccgcgagagccgagcgggccgcaccgccggccgtg
cgactgcccagtcagacacgaccccggcttctagcccgcctaagcctgtttggggttgc
tgactcgtttcctccccgagtttccgcgggaactaactcttcaagaggaccaaccgcag
cccagagcttcgcagacccggccaaccagaggcgaggttgagagcccggcgggccgcggg -continued gagagagcgtcccatctgtcctggaaagcctgggcgggtggattgggaccccgagagaag
caggggagctcggcggggtgcagaagtgcccaggcccctccccgctggggttgggagctt
gggcaggccagcttcacccttcctaagtccgcttctggtctccgggcccagcctcggcca
ccatg Homo sapiens DEAD (Asp-Glu-Ala-Asp) box polypeptide 39B
(DDX39B):

(Seq ID No: 360)
ttccctccttcgtcgctgtt
gctgccgccatacgcgctctccctgtttagctcttctgttagaaatagtatcttt
gttttcctttgctgttcctcaatcccctactcttcacccttgttttcacctatttt
gcgagaacccatccagatccccttccctttcccctgccggcccagttatg Homo sapiens RAB11A, member RAS oncogene family (RAB11A):

(Seq ID No: 361)
ccgccctttcgctcctcggccgcgcaatg

Homo sapiens SPARC-like 1 (hevin) (SPARCL1):

(Seq ID No: 362)
agctcttcccttttggtttgcaagcactgcctgtaaagccctcgcatga
gaggccagcctgctagggaaatccaggaatctgcaacaaaaacgatgacagtctgaaa
tactctctggtgccaacctccaaattctcgtctgtcacttcagaccccccactagtt
gacagagcagcagaatttcaactccagtagacttgaatatgcctctgggcaaagaa
gcagagctaacgaggaaagggatttaaagagttttcttgggtgttt
gtcaaacttttattccctgtctgtgtgcagaggggattcaacttcaattttctgcag
tggctctgggtccagccccttacttaaagatctggaaagcatg Homo sapiens cyclin B2 (CCNB2):

(Seq ID No: 363)
ctccctttttcag
tccgcgtccctccctgggccgggctggcactcttgccttccccgtccctcatg Homo sapiens cytochrome c oxidase subunit VIIa polypeptide 2 like
(COX7A2L):

(Seq ID No: 364)
ggtccttctctggggcggtcgcgttggcagcggatgcgggaagc
cggactctgggcgtcatg Homo sapiens lysophosphatidic acid receptor 2 (LPAR2):

(Seq ID No: 365)
cgccctctcagcaaccgcacagggcgcacccggacgctctaccgctcccgccgcag
tcgccgggccatgggcctcgagcccgccccgaaccccgcgagcccgcctt
gtctgcggcgtgactggaggcccagatg Homo sapiens adaptor-related protein complex 4, mu 1 subunit
(AP4M1):

(Seq ID No: 366)
cgttcttttgttccggggccgcagggcgggg
caggcccgactttcgccgtcttcttgtctactctccagaacggccatg Homo sapiens budding uninhibited by benzimidazoles 3 homolog
(yeast) (BUB3):

(Seq ID No: 367)
cttcctctccgcctccttcgcctagcctgcgagtgttctgagggaagcaaggaggcggcg
gcggccgcagcgagtggcgagtagtggaaacgttgcttctgaggggagcccaagatg Homo sapiens DEAD (Asp-Glu-Ala-Asp) box helicase 21 (DDX21):

(Seq ID No: 368)
ctacctcttcctctccacgcggttgagaagaccggtcggcctgggcaacctgcgctgaa
gatg Homo sapiens solute carrier family 33 (acetyl-
CoA transporter), member 1 (SLC33A1):

(Seq ID No: 369)
tgctctctgccgcatt
gatagcagcgagagctggaggtgttgggtcgggagaccagccgttcgatcccgccg
caggtaggagctggtttccatcctggcaccacggcacacac
ctccagcctcgagcccggcgctgcccgggggtctccttcaggctctttgac
gccgttccaggggggcacctatccaggcatcctctgggcctctagccagag
gactggctcccggcttcagcactccgggctgcagtaa
gaagtgcccttatcgctctgagccctgccaccatcccgtgaaccac
cgaaaccctggtccagcgcgacagccttggacctgggactggacggatccaaaac
gctcagcctcggccccccacagacggggctctgcatcgtctctgatatg Homo sapiens G protein-coupled receptor 37 like 1 (GPR37L1):

(Seq ID No: 370)
tgctcttcctgggctggctgtctcctgctcatccagccatg

Homo sapiens neuronal regeneration related protein homolog
(rat) (NREP):

(Seq ID No: 371)

-continued ctgtctttctagcatgttgccctttttcaaccacattt
gtgtttcaggtgtagagaggagagagagtgaacagggagcggggcttttgtctgtt
ggtctccctggactgaagagagggagaatagaagcccaagactaagattctcaaaatg Homo sapiens vesicle-associated membrane protein 3 (cellubrevin) (VAMP3):

(Seq ID No: 372)

gcttctctgctgaccctctctcgtcgccgctgccgccgccg
cagctgccaaaatg

Homo sapiens synaptosomal-associated protein, 29 kDa (SNAP29):

(Seq ID No: 373)

cctccttctgtttcccagaccgagagccgcgccggcaccatg

Homo sapiens lon peptidase 1, mitochondrial (LONP1):

(Seq ID No: 374)

cccctcttctccgcgtaggcccagctccctgaagcggctgtttcgagccac
gcgcccatcgggtaccgaggcacgcgccgggcgtcacgtgcgtttcgcggcgagcg
gaaatgacgcgagttgtgtgagccgccagtatggccgggctatg Homo sapiens kinesin family member 3B (KIF3B):

(Seq ID No: 375)

ctgtctctccccatccggggcagcggg
gaatggctgagccaggggttcgccgccccgccgccgccgccgccgccgccgccgcc
gccgcccgcttcggctcgggcctcaggaccgtagcatcctgagacattttgaatt
gacacttctcaagatttgactggatcagagttcatcatg Homo sapiens transmembrane 9 superfamily member 2 (TM9SF2):

(Seq ID No: 376)

cttcctttatctctggcggccttgtagtcgtctccgagactccccacccctccttccctc
ttgacccctaggtttgattgccctttccccgaaacaactatcatg Homo sapiens cytosolic iron-sulfur protein assembly 1 (CIAO1):

(Seq ID No: 377)

gagcctctgtcggccgcggaagcctggagtgggcggtacgcagac
gcgcgcggtgagacccgctgtctgctcagcggactctgcccgcccccac
ctcccctgcgtcgggccgacatg Homo sapiens GRB2-related adaptor protein 2 (GRAP2):

(Seq ID No: 378)

caccctctttcagagtggtacatggaagacagcacaaagtg
gatccatactctgaaatgcagtaactctgatgcttgaatttgtctcccttctt
gccagaaaggattctaataactcggtgtcaaagccaaga
cataaactcaacccccttctcttccaaaagcttcacgttacagcatg Homo sapiens leupaxin (LPXN):

(Seq ID No: 379)

gtaccttctcgggggtgtctgcg
taactgcccagacttgccttggtttggtcagatgacacctcctctgg
gactggctagccagcgttcatg Homo sapiens SH3-domain binding protein 5 (BTK-associated) (SH3BP5):

(Seq ID No: 380)

tttcctctgctccgccgcggccggaggtatccg
catcggcgagctgcgtctcccgggtgtcggccccggcggctccccgac
cgtgcccggctgtggcgaggcggctccagcccagcctgtgg
cagccgcgaccccggggcgctccggagcccactgcgcggcgcgcgtgccggctgcctg
catg Homo sapiens phosphatidylinositol glycan anchor biosynthesis, class B (PIGB):

(Seq ID No: 381)

ctttcttccgccttaggaaggtggcggccagggatg

Homo sapiens lipopolysaccharide-induced TNF factor (LITAF):

(Seq ID No: 382)

cggccctttctcggggcgcccgagaggccagctcagacctcccggctcgacaggcggcg
cgggcggcggtgagtgcggcgcggggacgccggggcgcggggaccagcgggagacagcgg
ggggccggtggcgccagcacctgctgggggccccggcactgagcccttggctgggcct
cctgggatgccaggggggcgcggtcggtcgcgggcatcgaggcgcggcggagggcgtgg
gggcccggccggggcgggtccggcctcccagcgctggtcccggccgcgtctccggttgg
gttcagctcctgcgtcccagagtggcccgatcgcgcgtggcggggtcgtccggcccccac
ccgaacgagcgcccttcgcgggcccgccgcgtcccctccccgagaggacgggccctggg
ctttttagaaaaaggcgcgattctctctagtgactcaggttgagatttcagaaatatcc
cccgggggttcagaaacaaaaccaaaacaaacaaaaaaaaccccaacgaattcccaaatgc
tatttgccaaacatttgacttctaggggcgcgggtacccgcgtttctctccctgcccccg
cgacttcgcgcaagatccgggaaggacacccgaggccctggggagaccctggggaggtga
aaatcagagagcgaagcggggccgtggcccctaggcctgaccccctccccgcggggtaaggc -continued gggcaccccgcgagcgcaggggtcctcttactgctgatggcacccagctctgggcccaga
cgccgctcaccgtccaccgccggtgctgggtaaaatg Homo sapiens etoposide induced 2.4 mRNA (EI24):

(Seq ID No: 383)

ccacccctccggctctgggccccgcctcgtggtgccggctggttcttcgcgctcgcccga
cttcccagcggcccccgtgcggcccgggcatgcccagtgcgggcg
cagcggccccggccctggaagcgcccggcggagctggcctgcggtgggctagggg
cagggccggagccgcggcggcgagctgtggatccttcatgatgagagatttggg
gacacttctctctcctgtgtgtagttgatagtttggtggtgaagagatg Homo sapiens chromosome 14 open reading frame 2 (C14orf2):

(Seq ID No: 384)

tgacctttccgagttggctgcagattt
gtggtgcgttctgagccgtctgtcctgcgccaagatg

Homo sapiens peroxiredoxin 6 (PRDX6):

(Seq ID No: 385)

attcctccgcgcgctgg
gacaggctgcttcttcgccagaaccaaccggttgctt
gctgtcccagcggcgcccctcatcaccgtcgccatg Homo sapiens solute carrier family 29 (nucleoside transporters), member 1 (SLC29A1):

(Seq ID No: 386)

ctctcttccgcccggcggcccacac
cggtcaggcccggcgcgggctgcgctctccagctgtggctatggcccagccccga
gatgaggagggagagaactaggggcccgcaggcctgggaatttccgtcccccac
caagtccggatgctcactccaaagtctcag
cagcccctgagggagggagctgtcagccagggaaaaccgagaacaccatcaccatg Homo sapiens heterogeneous nuclear ribonucleoprotein F (HNRNPF):

(Seq ID No: 387)

cgaccttcctgccgggccggcggtccgaggctgctggagtgccgtgag
caggccgcgggaacgtcgccgtcacctt
gtctcggggcctcggcgctgcttcccgccaaaacacgtttac
cgcgcgcccgggcctcccaccttgcggaagggaccccaccaccacttggatttctgtt
gcaggttgagaacaaaaacatgcacctggagtttccccggagccctctgcgtggtt
gagcttcggtggaatttcggggctcttggctgccagccgcgcttgcctggtag
caacagaaaccagtcctgctcgcctccgtggacatttcattac
catccagaagtgtctcccactgaaggcatccgtggttgtttttaagccacaaaaaa
gccacacccaagatcacctgacacccaccctgacaagtgtccatg Homo sapiens islet cell autoantigen 1, 69 kDa (ICA1):

(Seq ID No: 388)

ccgcccctttccctcgccttcggctgacgctgacgtcggatgagtgatccggagggac
gctccgaccgcggccgggaggctcctgggggccggggctccgaggttataa
tataacttatcctctcatgcttttttcctgcccctttctccccaaatcatcaacaa
tagaagaagaagaaacatg Homo sapiens PWP2 periodic tryptophan protein homolog (yeast) (PWP2):

(Seq ID No: 389)

gtgtctctgtgggcggccgccgggttgagctgcggcacacgtg
cgacggccgtgatg

Homo sapiens glutaminyl-tRNA synthetase (QARS):

(Seq ID No: 390)

gtttctttag
tttccggtgtctctgcaatg

Homo sapiens stearoyl-CoA desaturase (delta-9-desaturase) (SCD):

(Seq ID No: 391)

cggcctctgtctcctcccctcccgcccttacctccacgcgggac
cgcccgcgccagtcaactcctcgcactttgcccctgcttggcagcgga
taaaaggggctgaggaaataccggacacggtcacccgtt
gccagctctagcctttaaattcccggctcggggacctccacgcac
cgcggctagcgccgacaaccagctagcgtgcaaggcgccgcggctcagcgcgtac
cggcgggcttcgaaaccgcagtcctccggcgaccccgaactccgctccg
gagcctcagcccctggaaagtgatcccggcatccgagagccaagatg Homo sapiens fragile X mental retardation, autosomal homolog 1 (FXR1):

(Seq ID No: 392)

cggcctttgcggttccaacatg

Homo sapiens musculin (MSC):

(Seq ID No: 393)

tagccttttcaaaaggcgcagcttac

-continued cgcggtgcgcgcggattctggacttgggcgcaactcgtagtccac
gctccccggggtcagcagaggggcgctcacgctctcgccacccac
ctcgctttctcaccccgcgcttcccggcctgggttttagtcttcctt
ggagcgctctctggcctccgcctccgccagggagcggaaggcggagacagcga
gactggccagggggaggaaagaggacgcgtgtgggcaaggggacaacgggatg

*Homo sapiens* RNA binding motif protein 8A (RBM8A):

(Seq ID No: 394)

cgaccttccccctctgcgacagtttcccgaggtacctagtgtctgagcggca
cagacgagatctcgatcgaaggcgagatg

*Homo sapiens* heparan sulfate (glucosamine)
3-O-sulfotransferase 1 (HS3ST1):

(Seq ID No: 395)

ggtcctctgcgccctgg
cagccaggagtcgccgccacgaccgccgggtctcag
tgggtgcctgcgccttctcccgcccgcctgccccgggccatccagaaacttgctc
tacccgccgcgggtgctcggcagtgctgcccatggcccagcccaggagcc
tatttagggcgccggacgggctggacagaggcgcggctcagtaattgaaggcctgaaac
gcccatgtgccactgactaggaggcttccctgctgcggcac
ttcatgacccagcggcgcgcggcccagtgaagccaccgtggtgtccagcatg

*Homo sapiens* solute carrier family 12 (potassium/
chloride transporters), member 6 (SLC12A6):

(Seq ID No: 396)

ctgtctctt
gtaggcagggatcacagtctgaaacgacagcaaggaa
gaggtaggcagggaaaactaactggaaggaagtttaaatacagaaagag
caaagtattatctaactataacaatg

*Homo sapiens* apelin receptor (APLNR):

(Seq ID No: 397)

cttcctccagggtctgga
gaacccagaggcagctcctcctgagtgctgggaaggactctggg
catcttcagcccttcttactctctgaggctcaagccagaaattcaggctgcttgcagag
tgggtgacagagccacggagctggtgtccctgggaccctctgcccgtcttctctccac
tccccagcatg

*Homo sapiens* calpain 1, (mu/I) large subunit (CAPN1):

(Seq ID No: 398)

cgctcttcctggttgggccctgccctgagctgccaccgggaagccagcctcagggactgc
agcgaccccccaaacacccctcccccaggatg

*Homo sapiens* cyclin C (CCNC):

(Seq ID No: 399)

cttccttcgccgtcgccgccgcggagcg
gagtcgagccgagctgatttgatcgaggagcgcggttaccggacgggctgggtc
tatggtcgctccgcgggccgctccgccggctggtgcttttttatcagggcaa
gctgtgttccatg

*Homo sapiens* glutamate dehydrogenase 1 (GLUD1):

(Seq ID No: 400)

cttcctccctagtcgcggggagtctgagaaagcgcgcctgtttcgcgaccatcacgcac
ctccccctccgcttgtggccatg

*Homo sapiens* guanine nucleotide binding protein-like 1
(GNL1):

(Seq ID No: 401)

cctccttcctcgccgccggggcgccctctcggtgccactggctctcac
gtgccagtagcccaccccgcatcatcctctcgcctcgctcctggagggaagtgacta
tatctcccccgtccgccttccatcgccgcgcggcgg
taattctgtcgggcccgcccgctgacgtcac
ctgctagccccgcctcctcagggtcccgggcccctgcggcggggctgccccgggggg
cagtcagttgaggcggcgggagctcggcggagggcgggccaggtgactggtccgggc
catg

*Homo sapiens* lysophosphatidic acid receptor 4 (LPAR4):

(Seq ID No: 402)

aggccttttgtgtcctgtttgctaaaggcatgcgggctacagcattcaagagagggag
tcgttaacaaagggaaagagataaatgtaaataa
gctcacatttacagaatgagcggtttgcagtaaaaagctgcggcagcccagagtctgc
tactttaggctgggctaacctttccctg
taaaaaaaaaaaaaaaaaaaaaaaaaaaaaatggataaaaatatgcac
ttccaaagggcgagttgcccatttacatgtttattagctaattatctacaggcatcag
cacattctctcatctagcacactctttcttggggaggaaaatatttcctaccggtcca
tagtgtcagagtggtgaaccctgcagccagcaggcctcctgaaaaaaaagtccatg

*Homo sapiens* G protein-coupled receptor kinase 5 (GRK5):

(Seq ID No: 403)

gctcctctttgcagagggggaaactcttgggctgagagcaggaataatgcgg
taggcaaggcgggctgctggctcccccggctccggcagcagcggcggcagcccgag -continued cagcggcagcagcagcggcagcaccccaggcgctgacagcccgccggccggctccgtt
gctgaccgccgactgtcaatg

*Homo sapiens* glutamic-pyruvate transaminase (alanine
aminotransferase) (GPT):

(Seq ID No: 404)

agcccttctgtccctcccag
tgaggccagctgcggtgaagagggtgctctcttgcctggagttccctctgctac
ggctgccccctcccagcccggcccactaagccagacccagctgtcgccattcccac
ttctggtcctgccacctcctgagctgccttcccgcctggtctgggtagagtcatg

*Homo sapiens* hydroxyacyl-CoA dehydrogenase (HADH):

(Seq ID No: 405)

gggtctcctcgctgtcgccgccgctgccacaccatg

*Homo sapiens* high density lipoprotein binding protein
(HDLBP):

(Seq ID No: 406)

tcttctcctttaccaagatggcggcttgtccctgtttcgccacagttcctaccttatgag
ctcggttttcttatgcttataagagtggaacagcaaaagctgg
caggctgacagaggcggcctcaggacggaccttctggctactgaccgtttt
gctgtggttttcccggattgtgtaggtgtgagatcaaccatg

*Homo sapiens* histidine triad nucleotide binding protein 1
(HINT1):

(Seq ID No: 407)

gttcctcccttcttccgagcctctcctctggccgccgcgcgggagagagg
ccgagatg

*Homo sapiens* heat shock 70 kDa protein 1A (HSPA1A):

(Seq ID No: 408)

ctaccttttcgagagtgactcccgttgtcccaaggcttcccagagcgaacctgtg
cggctgcaggcaccggcgcgtcgagtttccggcgtccggaaggaccgagctcttctcgcg
gatccagtgttccgtttccagcccccaatctcagagcggagccgacagagag
cagggaaccggcatg

*Homo sapiens* nucleolin (NCL):

(Seq ID No: 409)

cagtctttcgcctcag
tctcgagctctcgctggccttcgggtgtacgtgctccgggatcttcag
caccccgcggccgccatcgccgtcgcttggcttcttctggactcatctgcgccactt
gtccgcttcacactccgccgccatcatg

*Homo sapiens* nuclear factor, interleukin 3 regulated
(NFIL3):

(Seq ID No: 410)

ccgcccctttctttctcctcgccggcccgagagcaggaacacgataac
gaaggaggcccaacttcattcaataaggagcctgacggatttatcccagacgg
tagaacaaaaggaagaatattgatggattttaaaccagagttttttaaagagcttgagaa
tacgggaaattaatttgttctcctacacacatagatagggtaaggttgtttctgatg

*Homo sapiens* protein phosphatase 1, regulatory subunit 3C
(PPP1R3C):

(Seq ID No: 411)

cagtctctcccagcgaccgccgcgggggcaaggcctg
gagctgtggttcgaatttgtg
caggcagcgggtgctggcttttagggtccgccgcctctctgcctaatg

*Homo sapiens* protein tyrosine phosphatase, non-receptor type
14 (PTPN14):

(Seq ID No: 412)

agttctttccaacttttctcggcggagtgagcgcagcgggcgcagactcggggggcaggt
tgctgtgcttctccgggctcagccgcctgctctcctggctcaggtcctcggggagccta
gacagacatcaagtggccactggcgctccttcccctcccagctgagccatcctccccggc
ctcctcgggcgggacagccccgtgcttaggttttttctccttttctccccggtgcgcctc
tgctcggactctcgcgccgggatcgcggcggaaacctccctcccctttcgcctcctgcgg
ctccttcccttcgccctcctccgccagtcactggaatcaattccgtggggaatcggctc
cgccgccgcgaaggacagcctttccgcgcgggactccggggcgcacggggccatgtaa
gcagctatcttccagagggccacactgggcatggacacccttttccctgcctggaggagc
acaggtgatagtgtaattttccagtcacgaaactgctaaggccatctcagggggcgtgtgc
gccaggataggcgggcggcgtccgaggaccacatagccatg

*Homo sapiens* selenoprotein P, plasma, 1 (SEPP1):

(Seq ID No: 413)

ctttcttttaagttgataacaatcagctcaggggtttgctctgcttgcaaggtcactgca
agaatgaacattgaactttggactatacctgaggggtgaggtaaacaacaggactataaa
tatcagagtgtgctgtgtgcttgtggagctgccagagtaaagcaaaga
gaaaggaagcaggcccgttggaagtggttgtgacaacccagcaatg

*Homo sapiens* serine hydroxymethyltransferase 2 (mitochondrial)
(SHMT2):

-continued

*Homo sapiens* tyrosine kinase with immunoglobulin-like and EGF-like domains 1 (TIE1):

(Seq ID No: 414)
agctcttctcgcgcatgcgttctccgaac
ggtcttcttccgacagcttgctgccctagaccagagttggtggctggac
ctcctgcgacttccgagttgcgatg (Seq ID No: 415)
tttcctcttcctccccagcaccgacccacactgac
caacacaggctgagcagtcaggcccacag
catctgaccccaggcccagctcgtcctggctggcctgggtcggcctctggagtatg

*Homo sapiens* coiled-coil domain containing 6 (CCDC6):

(Seq ID No: 416)
cctcctttccccagcccgccgcggccatg

*Homo sapiens* nuclear receptor coactivator 4 (NCOA4):

(Seq ID No: 417)
ggacctttcgcactcgggtcaggggtaaagcagcctgtcgcttgccgggcagc
tggtgagtcggtgacctggcctgtgaggagcagtgaggagaatg

*Homo sapiens* chromatin assembly factor 1, subunit B (p60) (CHAF1B):

(Seq ID No: 418)
gtgcctctgactgtccgggtccctccagcattt
gcagctttctcctgtcttgaagaagtagaacggtgcccgagaaac
gtttttccccttcgagactcaggaggatgaaagtcatcacttgtgaaatagcctgg
cacaacaaggagcccgtgtacagcctggacttccagcatg

*Homo sapiens* 3'-phosphoadenosine 5'-phosphosulfate synthase 1 (PAPSS1):

(Seq ID No: 419)
agccccgccccgctcgctggcctgccctcctcttgctaccctcccggcg
cagagaaccccggctgctcagcgcgctccgcggtcatg

*Homo sapiens* Fas apoptotic inhibitory molecule 3 (FAIM3):

(Seq ID No: 420)
tgccctcctcttgctaccctcccggcgcaga
gaaccccggctgctcagcgcgctccgcggtcatg

*Homo sapiens* N-acetylated alpha-linked acidic dipeptidase 2 (NAALAD2):

(Seq ID No: 421)
cagcctcctgccagcgcgctctctgtttctctgcagccccgaa
gctcgcgaatgtagcaggcgccccaagctcggtcctcaagaagccatggcg
gaatccaggggccgtctgtacctttggatgtgcttggctgctgcgctgg
catctttcctgatgggatttatggtgggtaagt

*Homo sapiens* abl-interactor 1 (ABI1):

(Seq ID No: 422)
ctgtctctttaacgcgagag
gaagcgatgcagagggggtggaaaatg

*Homo sapiens* potassium voltage-gated channel, Isk-related family, member 3 (KCNE3):

(Seq ID No: 423)
cttccttttctgccttctctcctgctttctagctctgggctttcccagctccgaagtcaa
tactgagatcccagatgtgtccagagacatcctgaagaggctcgggggtggag
gagccttagtgtgtccacaaagggactcctgaaactgactgagagccagt

*Homo sapiens* target of myb1 (chicken)-like 1 (TOM1L1):

(Seq ID No: 424)
ggccctctggcgctaccatg

*Homo sapiens* ubiquitin-like modifier activating enzyme 2 (UBA2):

(Seq ID No: 425)
cgcccttccccacccgcttccggccgcggctcggttctcccgcctccgcctccgccgcg
gctcgtggttgtcccgccatg

*Homo sapiens* scavenger receptor class B, member 2 (SCARB2):

(Seq ID No: 426)
ctccctccttgcagttggatccctggcgggtgcggcccggcccggcccgtgagcggcg
cacagaatg

*Homo sapiens* insulin induced gene 1 (INSIG1):

(Seq ID No: 427)
actcctcctttcccccgccccgcctccgttcgga
gagccggcgggcgggcgcctctcggccaggaagcgcctcttggacgcgtgtgaccgatg

*Homo sapiens* kinesin family member C3 (KIFC3):

-continued

```
aggcctcttctgaggctctaggtgccccagtagcagggccttctgcagcaaggccgg
gaactgctgcaccattggtgtgttttaccttaagggactccaggcagcttccttgctgg
gaagatattcatttgctggggtggggctgggggtgcagaggtaggaagtgctgtggcta
gaaggcggcctggccagcgagtaggtggtggagcgagtgagagcgtgtgcgctg
taaacagtgtgagtgcatg
```
(Seq ID No: 428)

Homo sapiens LIM domain kinase 2 (LIMK2):

(Seq ID No: 429)
```
aggcctcttctgaggctctaggtgccccagtagcagggccttctgcagcaaggccgggaa
ctgctgcaccattggtgtgttttaccttaagggactccaggcagcttccttgctgggaag
atattcatttgctggggtggggctgggggtgcagaggtaggaagtgctgtggctagaagg
cggcctggccagcgagtaggtggtggagcgagtgagagcgtgtgcgctgtaaacagtgtg
agtgcatgtgcgccagcgcgtgcaaggacacggtaagggatgtacatgtattgtctcgtg
agtaagagcttgtgtgtgtgttgggatgggaagacacgtactggtatgagagcccgcgtg
agaagtgtatgtgtgagtactcgcgtggaagttttgcactcgggtttgaggctgtgcaaa
agtacgcatggctcaccaggtgtgggctgtgtgggctgcctcgtgtgtgccagcccgtg
tgcaggcctgttttgtgagagccttcagggaacgcatgagcacgtgtgccagtgcgagtg
cgggacgcggggaggcgggagagaccgagtgggaggccccgcgaaggagtgggagtggga
gtgggagtgccggcgggagacctgcggggcgcgcccggctgacgcgtgcgcgccagtg
cgcgtgagtgcgggcgcgccgccgccccccgccggggtcggagccggttgccatggga
acgcgccgcgggcccgagttaatcatttcctgtggaaagtgttgagtgcaggggccgagcgg
gctggccgaggaggaggcggcggcgtggagctgcctcctgccggcgggccgggccgggcc
gagccccgggcgctgcggcgacgcctggatcctgcctccgccaggccggctgcctggtgc
cccgaggaggctgctgagcccaggccatg
```

Homo sapiens lectin, mannose-binding, 1 (LMAN1):

(Seq ID No: 430)
cctcctccgcgttccagaatccaagatg

Homo sapiens MRE11 meiotic recombination 11 homolog A
(S. cerevisiae) (MRE11A):

(Seq ID No: 431)
```
cgttctctcccgcggaattcaggtttac
ggccctgcgggttctcagaggcaagttcagaccgtgttgttttcttttcac
ggatcctgcccttcttcccgaaaagaagacagcctt
gggtcgcgattgtggggcttcgaagagtccagcagtgggaatttctagaattt
ggaatcgagtgcattttctgacatttgagtacagtacccaggggttcttggagaagaac
ctggtcccagaggagcttgactgaccataaaaatg
```

Homo sapiens nascent polypeptide-associated complex alpha subunit
(NACA):

(Seq ID No: 432)
```
cttccttctgcaacaggcgtgggtcac
gctctcgctcggtctttctgccgccatcttggttccgcgttccctgcacag
taagtactttctgtgccgctactgtctatccgcagccatccgcctttctttcgggctaa
gccgccccggggactgagagttaaggagagttggaggctttactgggccacagggttcc
tactcgcccctgggcctccggacaaaatggggtctgcggttggtgtcctggcaaaa
gcagggtagaagggctgcggggcgggcccagaatccgagcctgcagagatgggagcag
ttgcagtgttgagggcggaagaggagtgcgtcttgttttgggaactgcttcacag
gatccagaaaaggaaatg
```

Homo sapiens claudin 11 (CLDN11):

(Seq ID No: 433)
```
cgcccttcgccgctgagctcg
cagcctccggcgcccacctccacctccag
tgtcccgcctcgggccgtcgccctccagcggctcgcgagcgtgggagacgtacctggg
caggcactgtccagcccaggcccaggcacagccgtgaggggcgaggcacggg
gacatcctggcggccaccatg
```

Homo sapiens retinoblastoma binding protein 4 (RBBP4):

(Seq ID No: 434)
ccgcccctcccgcaacgctcgaccccaggattccccggctcgcctgcccgccatg

Homo sapiens acyl-CoA synthetase medium-chain family member 3
(ACSM3):

(Seq ID No: 435)
```
ccctcttctttagactgccacgaggaaaaagcagatgtga
gaactcaaggttcagggctgctcttctaagaaacaagtctgcca
taatctccatctgtgttggaatctgttaactaatgaactggtctctgtg
caaatcctgagtgctaaagcttccaacaagactgatg
```

Homo sapiens syndecan binding protein (syntenin) (SDCBP):

(Seq ID No: 436)
```
cgctctcttacactcgggcctcagaagtccgtgccagtgaccg
gaggcggcggcggcgagcggttccttgtgggctagaagaatcctgcaaaaatg
```

Homo sapiens serum/glucocorticoid regulated kinase 1 (SGK1):

(Seq ID No: 437)
```
agtccttctcattccttgcccccgcccaaggctctcttcaccttccccgcggggtcctc
tcgttttctgtctcccaaatgctggcttcccgccttttcctccccgcttatttacttaat
```

-continued

```
taaggccctggggctgcaccccaccggcagctccttcggggtgtggccgaagagctccg
agggcggggctgaccgagccatattcgggcgtggccggtggtgattggtgagggcgggc
ctgccgcaggggcggggcctgcaggtttggcccccgcagggagcgcagctggcgccgct
gggagctggtggcggcgcaggtcccggccgagtgtggcgcagcagtggcggcgcttcc
cattcgccatgcgccggggtgggtgcccgaaggttgcatgatggaatttgaacattact
tcaagaggttttgtatttggattagttaattgggtttgtcctctgctgactgtttcttc
ggatgcattttttggtgtgctcttgagggattaaatg
```

*Homo sapiens* Wolf-Hirschhorn syndrome candidate 2 (WHSC2):

(Seq ID No: 438)

```
cgtccttccggctctcggcttttgccacaaaagcttcccgaagacgcggccgctacccgga
gacgcggtcgccacccagaagcgctctcccgggaagcccgctcgtgggaccgcgccac
ctgcgccgcctctgcgcccgcagcccgacgggcgccgccatgtt
ggggtcctagcgagggacgcgtaggtgtcttcataagatg
```

*Homo sapiens* nuclear receptor subfamily 1, group H, member 3 (NR1H3):

(Seq ID No: 439)

```
cagtcctttgcaagagctgctaagagcgctgggtaaggagaggaaggg
gagagacatggaacttggctggtctgcagggaaatgccactgttttggccgggag
tagggggcgggagtggcgggagaggggtggccggctggggaggagccagcctggtgga
gaagctgccctgtgggcggggtgaggaggggagggctgtggtcaccaggcag
gaaggaggggtggcctgacccctcggcagtcccctccctcagcctttccccaaattgc
tacttctctgggctccaggtcctgcttgtgctcagctcagctcactggctggccac
cgagacttctggacaggaaactgcaccatcctcttctcccagcaaggggctccaga
gactgcccacccaggaagtctggtggcctggggatttggtgggtctgctccttag
```

*Homo sapiens* glypican 6 (GPC6):

(Seq ID No: 440)

```
cctcctttctccttccctctt
gcctccagtgactgtctccaggatttctctcttcctatttcaggag
gactctcacaggctcccacagcctgtgttaagctgaggtttcccctagatctcg
tatatccccaacacatacctccacgcacacacatccccaagaacctcgagctcacac
caacagacacacgcgcgcatacacactcgctctcgcttgtccatctccctcccggg
gagccggcgcgcgctcccaccttgccgcacactccggcgagccgagcccg
cagcgctccaggattctgcggctcggaactcg
gattgcagctctgaaccccatggtggttttttaaacac
ttcttttccttctcttcctcgttttgattgcaccgtttccatctgggggctagaggag
caaggcagcagcctcccagccagccctgttggctt
gccatcgtccatctggcttataaaagtttgctgagcgcag
tccagagggctgcgctgctcgtcccctcggctggcagaagggggtgacgctggg
cagcggcgaggagcgcgccgctgcctctggcgggctttcggcttgaggggcaaggtgaa
gagcgcaccggccgtgggggtttaccgagctggatttgtatgttgcaccatg
```

*Homo sapiens* peptidylprolyl isomerase F (PPIF):

(Seq ID No: 441)

```
cggccttctgggcgcgcgcgacgtcagtttgag
ttctgtgttctccccgcccgtgtcccgcccgacccgcgcccgcgatg
```

*Homo sapiens* ARP1 actin-related protein 1 homolog A, centractin alpha (yeast) (ACTR1A):

(Seq ID No: 442)

```
agttccttccccagaaggaga
gattcctctgccatg
```

*Homo sapiens* tripartite motif containing 28 (TRIM28):

(Seq ID No: 443)

```
ggctctttctgcgagcgggcgcgcgggcgagcggttgtgcttgtgctt
gtggcgcgtggtgcgggtttcggcggcggctgaggaagaagcgcgggcggcgccttcgg
gaggcgagcaggcagcagttggccgtgccgtagcagcgtcccgcgcgcggggg
cagcggcccaggaggcgcgtggcggcgctcggcctcgcggcggcggcggcgg
cagcggcccagcagtt
ggcggcgagcgcgtctgcgcctgcgcggcgggccccgcgcccctcctcccccctgggcg
ccccggcggcgtgtgaatg
```

*Homo sapiens* aminoadipate-semialdehyde synthase (AASS):

(Seq ID No: 444)

```
cggccttccatcccagtttcttctaggaattcggagcctcccctgcagcgactcggaa
gattcgaggcggcggggggacaagtcggcgcccccagagcggacgagtcaccaggtgtcaa
gatg
```

*Homo sapiens* cornichon homolog (*Drosophila*) (CNIH):

(Seq ID No: 445)

```
ccgcctttctccgctggcaacggcgccgctccccgctcctcctcccccagccatg
```

*Homo sapiens* M-phase phosphoprotein 10
(U3 small nucleolar ribonucleoprotein) (MPHOSPH10):

(Seq ID No: 446)

```
ctcccttcccttgcatgctgcattgtgtcggagttgctgacagccatg
```

*Homo sapiens* ubiquitin specific peptidase like 1 (USPL1):

-continued

```
                                               (Seq ID No: 447)
ccgccttcctagtggagacgcgagtgggggaggagcagtccgaggggaacgtgggtt
gaacgttgcaactagggtggagatcaagctggaacaggagttccgatcgacccggtac
caagaaggggagtgcccgcggcagggttcattgaaaaaatccttagtga
tattgacatgtctcaagtgacataaattagccaatgactcggaatg
```

*Homo sapiens* solute carrier family 23 (nucleobase transporters), member 1 (SLC23A1):

```
                                               (Seq ID No: 448)
tggcctttt
gtcaagtcatccctcttctcctcaggaactgctcaaacctgtgccccaaagatg
```

*Homo sapiens* splicing factor 3b, subunit 4, 49 kDa (SF3B4):

```
                                               (Seq ID No: 449)
ggatctctttcgccatg
```

*Homo sapiens* DnaJ (Hsp40) homolog, subfamily A, member 2 (DNAJA2):

```
                                               (Seq ID No: 450)
ctgtctccctcggcctgtgccgccgccgacgccgctt
gtgggcccgactccgctctgtctgcttcgccaccttctccccgagcac
tgcccggccggccgccatg
```

*Homo sapiens* calicin (CCIN):

```
                                               (Seq ID No: 451)
catcctctcttccaccctctcttctccctggtcaaccgctctgcaaacaac
catcaatctgatcccacaggcctgagaaagtctgctctccagtac
ctgctgctgatctgtttcagccgacaagaggcaccatg
```

*Homo sapiens* mannosidase, beta A, lysosomal (MANBA):

```
                                               (Seq ID No: 452)
ctgcctttcgatctctccacatctcggtggcgcgggatctcaagatg
```

*Homo sapiens* microtubule-associated protein 1B (MAP1B):

```
                                               (Seq ID No: 453)
aatcctttctcctgccgcagtggagaggagcggccggagcgagacac
ttcgccgaggcacagcagccggcaggatg
```

*Homo sapiens* malate dehydrogenase 1, NAD (soluble) (MDH1):

```
                                               (Seq ID No: 454)
gagccttttctcgctaacaccgctcgccctctccgagtcagttccgcggtagaggtgac
ctgactctctgaggctcattttgcagttgttgaaattgtccccgcagttttcaatcatg
```

*Homo sapiens* microfibrillar-associated protein 1 (MFAP1):

```
                                               (Seq ID No: 455)
gtttctctatcagtcgcgcagctgtgttcgcggactcaggtg
gaaggaatttcttctcttcgttgacgttgctggtgttcactgtttggaattag
tcaagtttcgggaatcaccgtcgctgccatcaacatg
```

*Homo sapiens* chaperonin containing TCP1, subunit 3 (gamma) (CCT3):

```
                                               (Seq ID No: 456)
ggttctctctctccagaaggttctgccggttcccccagctctggg
tacccggctctgcatcgcgtcgccatg
```

*Homo sapiens* tubulin, alpha 1a (TUBA1A):

```
                                               (Seq ID No: 457)
caacctctcctcttcgtctccgccatcagctcggcagtcgcgaagcagc
aaccatg
```

*Homo sapiens* CD164 molecule, sialomucin (CD164):

```
                                               (Seq ID No: 458)
ctttctcccgaacgccagcgctgaggacacgatg
```

*Homo sapiens* cysteine-rich secretory protein 3 (CRISP3):

```
                                               (Seq ID No: 459)
ctctctctgcaccttccttctgtcaatagatg
```

*Homo sapiens* SMYD family member 5 (SMYD5):

```
                                               (Seq ID No: 460)
cggcctccatgtgcgac
gtgttctccttctgcgtgggcgtggcgggccgcgcgcgggtctccgtg
gaagtccgtttcgtgagcagcgccaaggtgaggtcggggcgggtcctgccgg
gagcctctccccagtccggccatg
```

*Homo sapiens* kelch repeat and BTB (POZ) domain containing 10 (KBTBD10):

```
                                               (Seq ID No: 461)
ctgccttttacagctagacctgtgtgctg
caaggagctaaggccttcagtgtccccttccttacccaggttttctcacagaatg
```

*Homo sapiens* aldo-keto reductase family 1, member A1 (aldehyde reductase) (AKR1A1):

(Seq ID No: 462)

ccgccccttgcaccgcccacgtggccagcgccacctgcctcattgtgcccaggagttctc
caaaccccgcgctgcggagtgagtgaccaagttccggccagttcgacctcgaggatccaga
ggtggagacggtactacctcccagctctgttttcatcccccttcaggtccttcctcggga
ggcggcgaaggcggtccaccctgcgcgtgatcctttatgcccggcccctgccctccctc
cgggtggaacttccccctcaccgccagacttaagctgaggatcgttggatctctggcggg
gtgcagaactgagcccaggccacagtaccctattcacgctctgtgcttgtgccaaggttt
caagtgatcctcccgcctcagcctgcccaggtgctgagattacatgtatgagccactgca
cctggaaaggagccagaaatgtgaagtgctagctgaaggatgagcagcagctagccaggc
aaaggggggcaatg

*Homo sapiens* TRK-fused gene (TFG):

(Seq ID No: 463)

tgttcttcccccacctgccac
gtacagagcccaagttctcgctaggcttgtt
gggtcagcgcgattggccggggcccgcgcagcctgcgagcgaggtgcggcggtcgcgaa
gggcaaccgaggggggccgtgaccaccgcctcccccgcgacgcccccagtccag
tggcctcgcgtccgccattcagcggagacctgcggagaggcggcggccgcggcctccg
caagccgtctttctctagagttgtatatatagaacatcctggagtccaccatg

*Homo sapiens* 3'(2'), 5'-bisphosphate nucleotidase 1 (BPNT1):

(Seq ID No: 464)

catccttctcaaaagacttattgacagtgccaaagctcggtactggacacaac
gagggacctgggtctacgataacgcgcttttgctcctcctgaagtgtctttggtccaac
gttgttccagagtgtaccatg

*Homo sapiens* guanine nucleotide binding protein (G protein):

(Seq ID No: 465)

tttttctctctctctttcactgcaaggcggcggcaggagaggttgtggtgctag
ttctctaagccatccagtgccatcctcgtcgctgcagcgacacac
gctctcgccgccgccatg

*Homo sapiens* major histocompatibility complex, class II, DM alpha (HLA-DMA):

(Seq ID No: 466)

caccctctcggggagggagttggggaagctgggttggctgggtt
ggtagctcctacctactgtgtggcaagaaggtatg

*Homo sapiens* transmembrane protein 50B (TMEM50B):

(Seq ID No: 467)

tctccttcctgcgcgcgcgcctgaagtcggcgtgggcgtttgaggaagctgggatacag
catttaatgaaaaatttatgcttaagaagtaaaaatg

*Homo sapiens* lactoperoxidase (LPO):

(Seq ID No: 468)

cagtctttcctgctaa
gcctcagcgtctcctccaa
gccacatcaaaatctttccttctgggccttctcccagaagtgaattcttgctg
gaaggtataaaagaccagctcctccaagcagagcaactccctggctgccgtgaaaaga
caaggcactgggcagtgatg

*Homo sapiens* NEL-like 2 (chicken) (NELL2):

(Seq ID No: 469)

ctgcctttacaaca
gagggagacgatggactgagctgatccgcaccatg

*Homo sapiens* nucleobindin 1 (NUCB1):

(Seq ID No: 470)

cgccctctgcggtgaaggaga
gaccacactgccatg

*Homo sapiens* paired box 9 (PAX9):

(Seq ID No: 471)

aagcctctttcatcggggcacagacttccttttacttcttccttttgccctctcgcctcc
tcctcctgggaagaagcggaggcgccggcggtcggccgggatagcaacaggccgggccac
tgaggcggtgcggaaagtttctgtctgggagtgcggaactgggggccgggttggtgtactg
ctcggagcaatg

*Homo sapiens* cyclin-dependent kinase 16 (CDK16):

(Seq ID No: 472)

cgcccttttattcttgctcggcctcgccacagagag
caaatcagattggctgggcgacaacctcaaagggcggggctgcacacgttcactacgg
gaatgaggtagcggtggaggggcagttgggcgggataggccgtcctagctaaggtgg
taaaggccaataactcttcaggctgcctctcctcgaaaagtcatcttctcgcgaac
ctttaaaatgccttcctccccaagcacctcaaggggactagaactgagtgctcattt
gtcttttttcctccttgcaaaagtcccgtttgccaccatggggatgtaccaagtgagac
cgagtagggggaacgagtggtgattgacgcgccaggttactggccactgctcac
ctaggcgctagcaaaacttctgccaagatcggaactgagtactaaacagcctccacag
ttctccctggtgccgtctccggcttggcgccg -continued
```
catcctcctctgggctcgcgatggccgcgtcccctcccgctgcggacgggtcctttgg
tacatg
```

*Homo sapiens* serpin peptidase inhibitor, clade E (nexin, plasminogen activator inhibitor type 1), member 2 (SERPINE2):

(Seq ID No: 473)
```
ctgcctctttccggctgtgaccctcctcgccgccgccgctt
ggctgcgtcctccgactccccgccgccgagaccaggctcccgctccggttgcggccg
caccgccctccgcggccgcccctggggatccagcgagcgcggtcgtccttggtg
gaaggaaccatg
```

*Homo sapiens* pancreatic lipase-related protein 1 (PNLIPRP1):

(Seq ID No: 474)
```
aactcctttcccctgctgtgacgtacaggtgaggtaaacag
tactgaagtccagggcgtcggtgctcactgctctggcaatgcccggtga
gactgaattatgtttaaatttattgtagatg
```

*Homo sapiens* peripherin (PRPH):

(Seq ID No: 475)
```
ggctccttcccagccccggcctagctctgcgaacggtgactgcccatccttggccg
caatg
```

*Homo sapiens* RAD21 homolog (*S. pombe*) (RAD21):

(Seq ID No: 476)
```
gaccctttcccctcccgggccaccagcccgcccaactcccagcggagag
caaggttttcttctgttttcatagccagcagaacaatg
```

*Homo sapiens* signal sequence receptor, delta (SSR4):

(Seq ID No: 477)
```
ttttcttttcctctaggcagagaagaggcgatg
```

*Homo sapiens* tissue factor pathway inhibitor (lipoprotein-associated coagulation inhibitor) (TFPI):

(Seq ID No: 478)
```
ctccctctttt
gctctaacagacagcagcgactttaggctggataatagtcaaattcttac
ctcgctctttcactgctagtaagatcagattgcgtttctttcag
ttactcttcaatcgccagtttcttgatctgcttctaaaagaagaagtagagaaga
taaatcctgtcttcaatacctggaaggaaaaacaaaataacctcaactccgtttt
gaaaaaaacattccaagaactttcatcagagattttacttagatg
```

*Homo sapiens* ubiquinol-cytochrome c reductase binding protein (UQCRB):

(Seq ID No: 479)
```
gcttctctttctggtcaaaatg
```

*Homo sapiens* mitogen-activated protein kinase kinase kinase 12 (MAP3K12):

(Seq ID No: 480)
```
ccgccttttgtgctgcggccgcggagcccccgagggcccagtgttcac
catcataccaggggccagaggcgatg
```

*Homo sapiens* sushi-repeat containing protein, X-linked (SRPX):

(Seq ID No: 481)
```
tggtctcttcggtctcctgccgccccccgggaa
gcgcgctgcgctgccgaggcgagctaagcgcccgctcgccatg
```

*Homo sapiens* aminopeptidase puromycin sensitive (NPEPPS):

(Seq ID No: 482)
```
cccctctccctccctcctt
gcgggccctcctcccctccctccctccgccccccttccccg
taggcagcccgcccgccagtccgcccgcac
cgcctccttcccagcccctagcgctccggctgggtctctccccgcccccaggctcccc
cggtcgctctcctccggcggtcgcccgcgctcggtggatg
```

*Homo sapiens* fibulin 5 (FBLN5):

(Seq ID No: 483)
```
tcgccttctgcccgggcgctcg
cagccgagcgcggccggggaagggctctcctcccagcgccgagcactgggccctgg
cagacgcccaagattgttgtgaggagtctagccagttggtgagcgctgtaatctgaac
cagctgtgtccagactgaggcccatttgcattgtttaacatactta
gaaaatgaagtgttcattttaacattcctcctccaatt
ggtttaatgctgaattactgaagagggctaagcaaaaccaggtgctt
gcgctgagggctctgcagtggctggaggaccccggcgctctccccgtgtcctctccac
gactcgctcggccctctggaataaaacacccgcgagcccgagggcccagag
gaggccgacgtgcccgagctcctccgggggtcccgcccgcgagctttcttctcgccttcg
catctcctcgcgcgtcttggacatg
```

*Homo sapiens* lysophospholipase I (LYPLA1):

(Seq ID No: 484)

-continued
cgctcttccttccgcttgcgctgtgagctgaggcggtgtatg

*Homo sapiens* high mobility group nucleosomal binding domain 4
(HMGN4):

(Seq ID No: 485)

tcgtcttctctgtcttagggctggtgctggccctgcccac
gcctagggctccggcgcgtcacgggcctcagctgggattccgcgcccctcggac
ggccacgagactcggacatctttccaggaacagcgtgaggaggacagaa
gcacccaacaggactgctcaagccacctgcgaacactgctgctaccatg

*Homo sapiens* eukaryotic translation initiation factor 3, subunit
M (EIF3M):

(Seq ID No: 486)

agttccctttccggtcggcgtggtcttgcgagtggag
tgtccgctgtgcccgggcctgcaccatg

*Homo sapiens* Sec23 homolog A (*S. cerevisiae*) (SEC23A):

(Seq ID No: 487)

cctcctcttgacgtggcagaggcggcgccagccatg

*Homo sapiens* cartilage associated protein (CRTAP):

(Seq ID No: 488)

cgtcctctttccttccttctccctcccctttccccttccttcgtcccttccttccttcc
tttcgccgggcgcgatg

*Homo sapiens* vesicle amine transport protein 1 homolog
(*T. californica*) (VAT1):

(Seq ID No: 489)

ccgcccctcccgctggatcccg
cagccgcggctcttcccgacgcgttccgccttccccagctgtgcac
tctccatccagctgtgcgctctcgtcgggagtcccagccatg

*Homo sapiens* importin 7 (IPO7):

(Seq ID No: 490)

gcttctctttcctttcgcgccggtt
gccgctgcggagcgcggcgggtccatgtgcgcagtgagtggcgctattcctggcccag
tagcacccgagcccgggtttgaccgagtccgcgctgcgatg

*Homo sapiens* ATG7 autophagy related 7 homolog
(*S. cerevisiae*) (ATG7):

(Seq ID No: 491)

gctcctttgcgcacgcgcgccgcttcccagtgg
caagcgcgggcaggaccgcgttgcgtcatcggggcgcgcgcctcagaga
gagctgtggttgccggaagttgagcggcggtaagtgagccgcggcgggcgagggtgtag
tggggtcttgctgggccggttttggaggcctggag
tcaagggggcgagctcgccagggagggcgagggtcacagcaagtctcag
gatcctcctctgccagtttctgggtggtcttcctcctccagggactcactgat
tccggctggcgcccttcgtctgtagccgcgtcccctcagactggttcag
tccggggtcttctgacttggaagctcgtgctgat
ttcctaagtcagcccctcctgtcctcttggtaggcagtgctcagaatcttcagtgtt
ggaacacgggagatgggacatttggattcccagcctggctgtgtctggattt
gctgtctctggcacgttccttcccccatctaagctgcttttccatctgcaaaatgg
gaatgataatccgccatttgtttaagtgaggaggttaaataagtttactttctgagaaa
gaagattctcgattccttggttacagggttagaaactaatg

*Homo sapiens* dynactin 2 (p50) (DCTN2):

(Seq ID No: 492)

cgctcccttt
gccgccgccttagcccgggacccgaacccagcctctcccctacccgaacac
cggccccggctccaccgaggcccgggtcccccagcccgtctcgccgccgccatg

*Homo sapiens* acidic (leucine-
rich) nuclear phosphoprotein 32 family, member B
(ANP32B):

(Seq ID No: 493)

agccccttttcccctccatggtttctctccgctcccgtgagtaactt
ggctccgggggctccgctcgcctgcccgcacgccgcccgccacccaggac
cgcgccgccggcctccgccgctagcaaaccctccgacggccctcgctgcgcaagccgg
gacgcctctccccccctccgcccccgccgcggaaagttaagtttgaagaggggggaa
gaggggaacatg

*Homo sapiens* protein C receptor, endothelial (PROCR):

(Seq ID No: 494)

acttctcttttccctagactgcagccagcggagcccgcagccggcccgagccag
gaacccaggtccggagcctcaacttcaggatg

*Homo sapiens* actin related protein 2/3 complex, subunit 1A,
41 kDa (ARPC1A):

(Seq ID No: 495)

cgctccctctgggcttccgtcctccgcccgcgcccgacggagcctgttcgcgtcgactgc
ccagagtccgcgaatcctccgctccgagcccgtccggactcccccgatcccagctttctc -continued tcctttgaaaacactaagaataatg

*Homo sapiens* chaperonin containing TCP1, subunit 4 (delta) (CCT4):

(Seq ID No: 496)

aggccccttctccgcctccgcctcctcccgacgccggcgccgctttctg
gaaggttcgtgaaggcagtgagggcttaccgttattacac
tgcggccggccagaatccgggtccatccgtccttcccgagccaacccagacacagcg
gagtttgccatg

*Homo sapiens* Niemann-Pick disease, type C2 (NPC2):

(Seq ID No: 497)

gcttctttcccgagcttggaacttcgttatccgcgatg

*Homo sapiens* phosphoribosylaminoimidazole carboxylase, phosphoribosylaminoimidazole
succinocarboxamide synthetase (PAICS):

(Seq ID No: 498)

accccctcttttctagagttctgcctcgcttcccggcgcggtcgcagccctcagcccac
ttaggataatg

*Homo sapiens* ST6 (alpha-
N-acetyl-neuraminyl-2,3-beta-galactosyl-1,3)-N-acetylgalactosaminide
alpha-2,6-sialyltransferase 2 (ST6GALNAC2):

(Seq ID No: 499)

ctcccttctgcctgggacgtcagcggacggggcgctcgcgggccggggctgtatg

*Homo sapiens* polymerase (RNA) III
(DNA directed) polypeptide C (62 kD) (POLR3C):

(Seq ID No: 500)

aagccctttccgaggatggcaaaggatctgggaatgcttctccaaagatatgtggatgga
cgaaataggtctctggtgatactgaggcgggtggggacggggaggcaaagacttggctt
cttaggaattggaagaaataagtaaacaatgtttggtagcaatttgtaataaggaagtaa
tcataaaattaactacgtccgtttctgattgtgtcaactttgtcaaggagtagaagttta
agaattgaatactgtcctgcaaacaacgtaacctcatctcctgtttgacacaccctgttg
agaagcagtcctttacctcctaaatttcttttcgaaattatcatttcctttatggactg
agaataacactgcctgttcactcccaccgagctgtgaacagtgaccttaattcttccaag
cagggaagtgtagaaactaaggtctgtgacagaccgcaaaatcatctcccaatctttaag
gaaaatcagaatcacgcataatcccatagagataaatttgatgcatagtctttttcctatg
catacatttttcctttttttttacaataattgaatttttatattttttcagcttgcttct
gtcacttaatatattatgagtaattttttttggttttttttgttttggagacagaatctc
gcactgtcgcccgggttggagtgcagtggcgcgatctcggctcactgcaacctctgcctc
ccggcttcaagcgattctcctgtctcagcctcccctagtagctgggattacaggcacccgc
caccacgcccagctaatttttttgtgtgttttagtagagaaggggtttcactatattgg
ccaggctggtctcaaactcctgacctcatgatacgcccacctcggtctcccaaagtgcta
ggattacaggcctgagccaccgcgccagcctattatgaataattttctacatgaatacgc
atcgtactaaataaactttaaatgttggtgtagtatgccattgtatgggtatggcatcatt
tattgttagacgttagattgtttccactaagtcggtattataaagagaactaatgacttc
attattattagcttttctttctttggacacaatatccaaaaagaaattgttgtttcaaa
gatatgcaagattttttaaggcttttttgatatgtattgtcaaattgccctccagaaagaat
acatgaatttacactcagcagctctgcttccagcgtgaaagactttctattgtaccattt
tggtgtttttcccctagctctcagactccccagtacaatg

*Homo sapiens* influenza virus NS1A binding protein (IVNS1ABP):

(Seq ID No: 501)

gtgtctcccggtcgcgcgtg
gaggtcggtcgctcagagctgctgggcgcag
tttctccgcctgctgcttcggcgcggctgtatcggcgagcgagcgagttcccgcgag
ttctcggtggcgctccccccttcctttcagtctccacggactggcccctcgtccttc
tacttgaccgctcccgtcttccgccgccttctggcgctttccgttgggccgat
tcccgcccgcttcctcctgcttcccatcgaagctcta
gaaatgaatgtttccatctcttcagagatgaaccagat
tatgatgcatcattatcacagaagaaattcgtgtctatagcttttaaggacttgat
tacatcattttcaagcctgatagttttggaatcaccattagagcttaagacacac
ctgccttcatttcaaccacctgtcttcataccctgacgaagtgcaccttttaacac
tcctttgtccttggattacttaagagttcccagaaatacatttgccaccaacagag
tagccaaatttataaggaaaaatg

*Homo sapiens* thioredoxin interacting protein (TXNIP):

(Seq ID No: 502)

accccctcttttttctccaaaggagtgcttgtggagatcggatctttttctccagcaatt
gggggaaagaaggcttttctctgaattcgcttagtgtaaccagcggcg
tatattttttaggcgcccttttcgaaaacctagtagttaatattcattt
gtttaaatcttatttttattttaagctcaaactgcttaagaatac
cttaattcctaaagtgaaataattttttgcaaaggggtttcctcgattt
ggagcttttttttttcttccaccgtcatttctaactcttaaaaccaactcagttccat
catg

*Homo sapiens* ecotropic viral integration site 2B (EVI2B):

(Seq ID No: 503)

-continued ttttcctttcttagccaaatcaccaaaatgtccagttagaacaagaatttagcattctg
caaaagaagttaacagctgagataacgaggaaatattctgaaatg

*Homo sapiens* guanine nucleotide binding protein
(G protein), alpha inhibiting activity polypeptide 3
(GNAI3):

(Seq ID No: 504)

ggttcttctgggcgctaagggagctgacggagagggccaccgcccagcaa
tagacggtgcctcagcctgccgagccgcagtttccgtggtgtgagtgag
tccgggcccgtgtccctctcccgccgccgccatg

*Homo sapiens* polymerase (DNA directed), eta (POLH):

(Seq ID No: 505)

cggcccttcgcagcgggcgcgctgtcagacctcagtctggcggctgcatt
gctgggcgcgccgctctcgtctgatccctgctggggacggttgcccgggcag
gatcctttacgatcccttctcggtttctccgtcgtcacagggaa
taaatctcgctcgaaactcactggaccgctcctagaaaggcgaaaagatattcag
gagcccttccatttttccttccagtaggcaccgaacccagcatttttcggcaac
cgctgctggcagttttgccaggtgtttgttaccttgaaaaatg

*Homo sapiens* solute carrier family 2 (facilitated
glucose transporter), member 1 (SLC2A1):

(Seq ID No: 506)

cgctctctggcaagaggcaagaggtagcaacagcgagcgtgccggtcgctagtcgcgggt
ccccgagtgagcacgccagggagcaggagaccaaacgacgggggtcggagtcagagtcgc
agtgggagtccccgaccggagcacgagcctgagcgggagagcgccgctcgcacgcccgt
cgccaccccgcgtacccggcgcagccagagccaccagcgcagcgctgccatg

*Homo sapiens* zinc finger protein 138 (ZNF138):

(Seq ID No: 507)

gggtctttt
gtctcgctgcagcgggtgctgcaggtctggccttcacttttctgcgtcctcttactccta
gaggcccagcctctgtggcgctgtgatctggttattgggagattcacagctaagac
gccaggatccccggaagcctagaaatg

*Homo sapiens* ubiquitin specific peptidase 3 (USPS):

(Seq ID No: 508)

cttttctttgacgcaagggctcgagacgcagccgccgtcggccgagcgcccggctagaa
gcgacaccagacggagcctccggagttcctccgcccccacctcgccgggtcctg
gagccgcagtcctcccagctgccctcctcgtggccatg

*Homo sapiens* influenza virus NS1A binding protein
(IVNS1ABP):

(Seq ID No: 509)

ctgtctttttctccagtttgagcggggggtgtcgggagcaggcgga
gagctttcctgcgaggctgtggaagcagtgaacactcttctcagcggctcgcctcccag
cagtgctattttttgccatccgccctcaccccccagcacacgcgctcgcacacacac
gcacgcacgcacacacacacacacactcacacagagacctctctgggtttctttt
gccttgagtctcccggggctgtgagaagcaggcgcatctcaaaccgagctgg
cagctccaggctccggagccatgccctgcacggaccctcgtctttaccacgctcctgag
gaatgaaaggaaaccagggaccctcagaaggcagcagtgatgcggaccaaccccccg
gagcctgcaccctccgagggccataggcgacccagggaactggaga
gagctccagaaaggaaatcccagcttttcccaaagtccctgtggatgctgacaaaagga
gacctgaatttttggaagagcctgtactaggttaccggctgcagagtgat
tttcccctccggcactgactctcccctccaaccccagccgtccagagtaccatgaa
gaattatg

*Homo sapiens* guanine nucleotide binding protein
(G protein), beta 5 (GNB5):

(Seq ID No: 510)

ttccctctccgctgcgtccccgcgcgaagatg

*Homo sapiens* chaperonin containing TCP1, subunit 8 (theta)
(CCT8):

(Seq ID No: 511)

cttcctccgcggtcttccgagcggtcgcgtgaactgcttcctgcaggctgg
ccatg

*Homo sapiens* prostaglandin E synthase 3 (cytosolic)
(PTGES3):

(Seq ID No: 512)

cgctcttttccgcgcggtg
cattctggggcccgaggtcgagcccgccgctgccgccgtcgcctgagggaagcgagaa
gaggccgcgaccggagagaaaaagcggagtcgccaccggagagaagtcgactccctag
cagcagccgccgccagagaggcccgcccaccagttcgcccgtcccctgccccgttca
caatg

*Homo sapiens* zinc finger protein 266 (ZNF266):

(Seq ID No: 513)

ttttcttcctggtggcgtttgggcttaatacagctttggcgaggtcggatgacgggtggg
agccagcggtggaagggtggcgaaagtaccggtttgccccaggccgccgaggggcctcc -continued

```
ttagagagaccttgcctgctccgctcgcgtccgccggggccgcgcgggtcctcctggcgc
cgccaggttcaaaaagccactcgagttgtcactgcgacggccctgggccaggagccgttt
cgggatctgtcaaacaacgagttttcgtcgttcgaatcaggttgactggtccttcatccc
cccaatctcccgtacctggcgagtccagctcgtcgcggcaatgctaagaaaagagtgata
tgcaagctgagaccaaaaatatggtatgatttagccatactgaaggggaaggaaataaga
gctgggcaaagcattctgtgaattggctgactccacttctatggtgagagaggaggagtgc
atcaaagattactcccagtagagatggtttcagcatgttggccagtctggtctcagactc
ctgacctcaagtgatccacccacctcggcctcccaaaatgctgggattacaggtataagc
cactgtgcctggccaaagataccgttaaccctggataaagagaatggaggttacctctgt
ccgtgtagattcctaagctgtcctggagtgatccttggagtaaaggaaaggtgctttgaa
gcacattcagccatcagccctgtgggatggcagccactgatttgtcctatggtctttaca
gggacccagtctgccttcaagaaaagacagaagtagaaagggtggtggctgactgttctga
caaattgttatcaggtatgcaggaagtatatccttctccaaaatatcatacttgcatcac
caggtagacacatttccttctacacagaattatcttcagagcttcttaaagcaaataaag
cctgcttcaaggactgagtccctagtcgaattcccggaaggagtggagcctgtcatattg
tgtttatctagcatctgctcaagagtgtgctgcagtggagggaaatcagatgacctccca
gtctggttgtgttacatacaatcatgtgtaagaagtgccattcaagccgtgtcactggag
gggactgacagtgagattcagtgacttttgatgatctggctgtggacttcacccccagaag
aatggacttactgaccccaactcagagaaacctctacagagatgtgatg
```

*Homo sapiens* methylenetetrahydrofolate dehydrogenase
(NADP+ dependent) 2, methenyltetrahydrofolate cyclohydrolase
(MTHFD2):

(Seq ID No: 514)
```
gcttccctcccggcgcagtcaccggcgcggtctatg
```

*Homo sapiens* chemokine (C-C motif) receptor 9 (CCR9):

(Seq ID No: 515)
```
cttcctttctcgtgttgttatcgggtagctgcctgctcagaacccacaaa
gcctgcccctcatcccaggcagagagcaacccagctctttccccagacactga
gagctggtggtgcctgctgtcccagggagagttgcatcgccctccacagagcaggctt
gcatctgactgacccaccatg
```

*Homo sapiens* heat shock 105 kDa/110 kDa protein 1 (HSPH1):

(Seq ID No: 516)
```
cctcccctttgggtcggtagttcagcgccggcgccggtgtgcgagccgcggcagag
tgaggcaggcaacccgaggtgcggagcgacctgcg
gaggctgagccccgctttctcccaggggtttcttatcagccagccgccgctgtccccggggg
gagtaggaggctcctgacaggccgcggctgtctgtgtgtccttctgagtgtcagag
gaacggccagacccgcggggcggagcagaacgcggccagggcagaaagcggcggcag
gagaagcaggcaggggccggaggacgcagaccgagacccgaggcggaggcggac
cgcgagccggccatg
```

*Homo sapiens* StAR-related lipid transfer
(START) domain containing 10 (STARD10):

(Seq ID No: 517)
```
tggtcctttcttttatgattcacaaggaatgaccctcttcatcgcctctcctaattcagt
cctcacaacagtccttttacaaatgggacaacaggttagaggaagtcaggcagatttcca
gcatcatagagagtaaaggaccagggaaggatcaggattcaaggactgcacccaggctct
gcttccagcttgctgtgtgactttgggtaattttgttcccttagggaactgagctttctc
atttgtaaatgcaaacaggctgttgggaggatcaaatgagatccaggggtgaaaacagct
tagtttacttttcaggaatttacccacgcggtatataaaggcaaaatattattatagtcag
gtgattgtagattgaggaacccatttcctcattctgcaaattgcaaacctgagggcccaa
agagggacaggggcttgccccaggtctcagcaggctgtgagcaagagctaaagcctaatc
ctcctgcctttgggcctggagcccttccttgtacccccagggggtcagtgtctttgttggat
acaggcttagattgactgactgtaccctgagaacctagggggagtccctgttcccaattct
tctcctaccccaccttggcctgatgaggaagacccctgctgtgttgagatgagcaccag
agccaagaagctgaggaggatctggagaattctggaggaagaggagagtgttgctggagc
tgtacagaccctgcttctcaggtcccaggaaggtggcgtcagcatctgcagccgcgtcga
cgttgtcggagcctccgcggaggacccaggagagccggactaggaccagggcccctgggcc
tccccacactccccatg
```

*Homo sapiens* UTP14, U3 small nucleolar ribonucleoprotein, homolog
A (yeast) (UTP14A):

(Seq ID No: 518)
```
ctttccttcggcttccgttcttggtccatgtgaga
gaagctggctgctgaaatg
```

*Homo sapiens* SUB1 homolog (*S. cerevisiae*) (SUB1):

(Seq ID No: 519)
```
ggttctctgtcagtcgcgagcgaacgaccaagagggtgttcgactgcta
gagccgagcgaagcgatg
```

*Homo sapiens* minichromosome maintenance complex component 5
(MCM5):

(Seq ID No: 520)
```
ccgcctcttgttttcccgcgaaactcggcggctgagcgtggaggttctt
gtctcccctggtttgtgaagtgcggaaaaccagaggcgcagtcatg
```

*Homo sapiens* RNA binding motif (RNP1, RRM) protein 3 (RBM3):

(Seq ID No: 521)

-continued tactctttatcaatcgtcttccggcgcagccccgtccctgtttttt
gtgctcctccgagctcgctgttcgtccgggttttttacgttttaatttccaggactt
gaactgccatg

*Homo sapiens* KDEL
(Lys-Asp-Glu-Leu) endoplasmic reticulum protein retention receptor
1 (KDELR1):

(Seq ID No: 522)

ctcccctctcgctctcctccctcttcccggctccagctccgccgccagctccagcctt
gctccccctcccaaagtccctcccggagcggagcgcac
ctagggtccctcttccgtcccccagcccagctaccgttcagaccagcagcctcggggg
gcaccccccgccagcctgcctccctcccgctcagccctgccagggttccccagccatg

*Homo sapiens* StAR-related lipid transfer
(START) domain containing 3 (STARD3):

(Seq ID No: 523)

agatcttcttccgctctgaggcgctactgaggccgcggagccggactgcggtt
ggggcgggaagagccggggccgtggctgacatggag
cagccctgctgctgaggccgcgccctcccgccctgaggtgggggcccaccaggatg

*Homo sapiens* heterogeneous nuclear ribonucleoprotein A0
(HNRNPA0):

(Seq ID No: 524)

cggcctctttgtgtggtgcccagatagggagcggaggtggcggcggcggcggtagcggt
ggccttggttgtcttccagtctcctcggctcgcccttttagccggcaccgctcccttcc
tccccctcctctcttccttcctccctcccttcctttttcccgtcggtgag
cggcgggggtggctccagcaacggctgggcccaagctgtgtagaggccttaaccaacgat
aacggggcgacggcgaaacctcggagctcgcagggcgggggcaaggcccgggccttgga
gatg

*Homo sapiens* chromobox homolog 1 (CBX1):

(Seq ID No: 525)

ggctctttt
gttcggctgaggggagggccgttggccggggcctgcggtacgccgcttcagtgagggac
gccactgcggccaccggcttgctgcctcctgggcgccactccccccaggcgacccgac
gcgacgcgccagcagcgcagcaccgattcctctcgggctctt
gggcgctgctctgaggtgaggagcccgctggaggcgggagagctgggg
gaggggcgcggcggcggcggcggcgggagccctgcgtgagggaac
gcgctttcgaggcggaggttaggagcggg
gagcgcgcccgggtccagcgtcctgcttctccgcttcccgcgctgagctcttcgcctgtc
gctgaggcgtcggtgccagctgcgtgaaggatgga
gagggcggggcgcgaatcctgagccagagactgagtgcttgggggtgggccgagcactt
ggggcgctcttcggggcccgggtggtctggaacaatgttgctt
ggctgggcggctgcgggataggggcggaaggggacaggcttgaggcttgga
taggcgtgaggaggcgcatacgaccgcacaacccgaggtttgtaactgtattcggaa
gacgccgggtccggctgggactgccagaggaacctggctttgcaggactacggaggag
taacgtcgagtgaattggaagagggcccagggccgcacaagcagcgtcacccttacac
cagaaagctggcgggcactatg

*Homo sapiens* myeloid/lymphoid or mixed-lineage leukemia
(trithorax homolog, Drosophila); translocated to, 11
(MLLT11):

(Seq ID No: 526)

cgcccttcttaggaggggctgcattgcaggggagag
tgaactgacagactcagtcactgaagagggaaaaggagtgagaagacaaagccgtcaaa
gccccaacagctttgtatttctccagcccggcgcagaccccggagctcccgaggcac
tccctccatctttggaacacgccagtaattgattgataacaggaagctatg

*Homo sapiens* interferon-induced protein 44-like (IFI44L):

(Seq ID No: 527)

ttttctttctttcctagagtctctgaagccacagatctcttaa
gaactttctgtctccaaaccgtggctgctcgataaatcagacagaacag
ttaatcctcaatttaagcctgatctaaccctagaaacagatatagaacaatg

*Homo sapiens* cyclin I (CCNI):

(Seq ID No: 528)

acttcttcctcccttccctctcttcccctccctccccagccttccccgcgagcggacgc
ggcagcgcctctgtctcgcttttttcttatttttccccctttccctttcttttttttt
tttcttttcttttctccctccccccctttcaccatttccctcggaggcgctttccccg
ggcaggggcagagccggtctcaccccccgcctctccccgccccccgccgccctatggcga
gagggagccccctcccaacccgggctcgagcggcggcggcctcaggccggggtcatcat
ggaactaattcgctgaccgacccagcggccgcagccgtgcgtcccgctcgagcgccagcg
cccgcgcccgcgccccgatccgcttccccttctccctcctcagttggccgagtcgtc
ccgcgcgcaccgcctccgcgcgcctatgagaatgaggtggtaacgggccccggatgacc
ccgcgtcaccactgtgaggcctacagctctgccggggaggaggaggaggaggaagaggag
gagaaggtagctacagcaagctgggtagcaggcagatccaaaggatatcatg

*Homo sapiens* methionyl aminopeptidase 2 (METAP2):

(Seq ID No: 529)

cattccctcgcgctctctcgggcaacatg

-continued

*Homo sapiens* leukocyte immunoglobulin-like receptor, subfamily B (with TM and ITIM domains), member 4 (LILRB4):

(Seq ID No: 530)
gtctcttt
gtcctgccggcactgaggactcatccatctgcacagctggggcccctgggaggagacgc
catg

*Homo sapiens* destrin (actin depolymerizing factor) (DSTN):

(Seq ID No: 531)
gggtctctcggtcccgcagccgtgaggaggacggtctgcat
actcgctgcccgccggctcctccccgcgtccctgcgaccgccgcggcgaagatg

*Homo sapiens* eukaryotic translation initiation factor 2D (EIF2D):

(Seq ID No: 532)
gggccttttcgcggccgggcccagcatggctgccccac
ggctgagggcctggcagctgctgcgccctcgctttctt
gacattccctggcttctgtgctctcttccccaggccaccccagcagacatg

*Homo sapiens* histamine N-methyltransferase (HNMT):

(Seq ID No: 533)
ctgtctttctcagaaaaccaaatatg

*Homo sapiens* ras-related C3 botulinum toxin substrate 1 (rho family, small GTP binding protein Rac1) (RAC1):

(Seq ID No: 534)
gtttctctgcagttttcctcagctttgggtggtggccgctgccgggcatcggcttccag
tccgcggagggcgaggcggcgtggacagcggccccggcacccagcgccccgccgcccg
caagccgcgcgcccgtccgccgcgccccgagcccgccgcttcc
tatctcagcgccctgccgccgccgccgcgccccagcgagcggccctgatgcaggccatca
agtgtgtggtgggagacggaaacaagaatctcagtgtaaccgag
caaaatcgcgcgtctcagcgttgcttgtatagagctgtaggtaaaacttgcc
tactgatcagttacacaaccaatgcatttcctggagaatatatccctactgtctttt
gacaattattctgccaatgttatg

*Homo sapiens* signal recognition particle 72 kDa (SRP72):

(Seq ID No: 535)
tcgtctcctccaagatg

*Homo sapiens* zinc finger protein 33B (ZNF33B):

(Seq ID No: 536)
ccgcctttccttttgtttgtctcacgttttgcgtgggaggcggtcccgggat
ttcaggggtctaccggctctcttatggcgaatgcaacccgaagagagtgagctg
tatcttcagagttgtctccgtctttccaagaacagaacaaaatg

*Homo sapiens* zinc finger protein 16 (ZNF16):

(Seq ID No: 537)
gcctcctttccaa
gcgcgacccgttgaggtccttgtcatg

*Homo sapiens* zinc finger protein 33A (ZNF33A):

(Seq ID No: 538)
ccgcctttccttttgttttctcaggttttgcgtgggaggcggtcccgggatttcaaggg
tctacgcgcttttctatggcgaatgcaacccgacgagggagtgggctgtatcttcagagt
tgtctccgtctttccaagaacagaacaaaatg

*Homo sapiens* butyrophilin, subfamily 3, member A3 (BTN3A3):

(Seq ID No: 539)
ctttcttttcctttcttcggaatgagagactcaaccataatagaaagaatggagaac
tattaaccaccattcttcagtgggctgtgattttcagaggggaatactaa
gaaatggttttccatactggaacccaaaggtaaagacactcaaggacagacatttttgg
cagagctgctcactccttgctcagctcagttttctgtgctt
ggaccctctgggcccatcctggccatg

*Homo sapiens* butyrophilin, subfamily 2, member A2 (BTN2A2):

(Seq ID No: 540)
ctctttgggatgctttgttgtctggtggtgactgtgcccatgggtgagttgtatcg
gaaaatcgtcatgtgaggatcagaggggaaaa
gaaaacagaggcctctggtctctgcctgccctgggtgctcatg

*Homo sapiens* nudix (nucleoside diphosphate linked moiety X)-type motif 21 (NUDT21):

(Seq ID No: 541)
acgcctcctcttgcgctgtcctgttaatggcgggcagtagccgctgaggggattgcaga
taaccgcttcccgcacggggaaagtctaccctgcctgccac
tttctgctcgccgtcagcgccggagctcgccagcatg

*Homo sapiens* stathmin-like 2 (STMN2):

(Seq ID No: 542)
tgctcttctctagcac
ggtcccactctgcagactcagtgccttattcag

-continued tcttctctctcgctctctccgctgctgtagccggacccttttgccttcgccac
tgctcagcgtctgcacatccctacaatg

*Homo sapiens* katanin p60 (ATPase containing) subunit A 1
(KATNA1):

(Seq ID No: 543)

cacccctcttccgccgctcccgcccagcgacctcgctcccggggcgac
gccccgcgtgcgccagagtcgccgaggtcgtccccggcaccg
gaagtgaccctggcggggtttgtcttcaaattctcggcgagcaggagccgcgccgg
caggtggtgttgacgattgaactgggcagtactggggccgtgagcggagag
caaagtgggctggactgggtcaggccctccttcctcgctgccgggatctccac
tccgccaatcccctgtgcctggcgttgggcggtttcccgaggagcttgggccgccg
cagcttacagttgaacatg

*Homo sapiens* butyrophilin, subfamily 3, member A2 (BTN3A2):

(Seq ID No: 544)

cttcttctttttcctttcttccggatgagaggctaagccataatagaaagaatgga
gaattattgattgaccgtctttattctgtgggctctgattctccaatgggaatac
caagggatggttttccatactggaacccaaaggtaaagacactcaaggacaga
catttttggcagagcatagatg

*Homo sapiens* CLK4-associating serine/arginine rich protein
(CLASRP):

(Seq ID No: 545)

cggcctttcatttccgcttccggtgcgggccgcgcgcgagcg
cagcggtggaggcggcgaccagccggttgaggcccaggcttggcctcaccacaatg

*Homo sapiens* clathrin, light chain A (CLTA):

(Seq ID No: 546)

ctccctcctggcgcttgtcctcctctcccagtcggcaccacagcggtggctgccgggcgt
ggtgtcggtgggtcggttggttttttgtctcaccgttggtgtccgtgccgttcagttgccc
gccatg

*Homo sapiens* NADH dehydrogenase (ubiquinone)
flavoprotein 1, 51 kDa (NDUFV1):

(Seq ID No: 547)

gcgtctctatcgcgccag
ttcctcagcctcagtgctatgaaggtgacagcgtgaggtgacccatctggcccgccg
cgatg

*Homo sapiens* signal sequence receptor, gamma (translocon-
associated protein gamma) (SSR3):

(Seq ID No: 548)

gggcctttgcccgcctt
ggcggccggctctacgttccctgttctcgcctgcagctccgccatg

*Homo sapiens* valosin containing protein (VCP):

(Seq ID No: 549)

gcttcccttccgatgattcggctcttctcggctcagtctcagcgaagcgtctgcgac
cgtcgtttgagtcgtcgctgccgctgccgctgccactgccactgccacctcgcg
gatcaggagccagcgttgttcgcccgacgcctcgctgccggtgggaggaagcga
gagggaagccgcttgcgggtttgtcgccgctgctcgcccaccgcctggaa
gagccgagccccggcccagtcggtcgcttgccaccgctcg
tagccgttaccgcggggccgccacagccgccggccgggagaggcgcgcgccatg

*Homo sapiens* zinc finger protein 195 (ZNF195):

(Seq ID No: 550)

gggccttt
gtcccgacagagctccacttcctgtccccgcggctctgtgtcccctgctagccg
taggtcgtgtgacccgcaggcaccgggagatccagaagtgaaacgccaggctctctg
gaggccaggagatg

*Homo sapiens* testis-specific kinase 2 (TESK2):

(Seq ID No: 551)

cag
tctttcgcggcccgggagctcagcagagctaccagctgccctgttggcttcgctggtcg
gatcgtcctcctggccccgccaaacaggcgggg
gagcggccccgactgtggggccatggcagtag
tctcctcgttcgccgccgccgctagcctagctgag
tcgccggcttctgcgctagggcctccccaccgcctccgcaggctaaggagccgctgccac
caacgagctgtgagggttactatgctccctctttgccgccgtctcctcctctt
gcccgcgcaggcaccccctctggctgctcctcagtcctgcctcagtgtcaaaccagaaga
gaagtaaaattcaacaaaaatttatgtgtggagttccttcttaaaagaa
gaaaaaagtgattatttagactatg

*Homo sapiens* family with sequence similarity 107, member A
(FAM107A):

(Seq ID No: 552)

agccctccttgctagtctgggacttccggtggagtgaggaacccag
caacacgctcctgacttcccttcccaaggactcgacctgagaaggacacagcag
tctctgaatttcatgctctcctctttgatgtgaagaaaatgaaaagctgaacagttgtg -continued gaactgtggatagagttagacaataaggccgccatg Homo sapiens serine/threonine kinase receptor associated protein (STRAP):

(Seq ID No: 553)

ccctccctccctttccctccctcgtcgactgttgcttgctggtcgcagactccctgaccc
ctccctcacccctccctaacctcggtgccaccggattgcccttcttttcctgttgcccag
cccagccctagtgtcagggcgggggcctggagcagcccgaggcactgcagcagaagagag
aaaagacaacgacgaccctcagctcgccagtccggtcgctggcttcgccgccgccatg Homo sapiens mitochondrial ribosomal protein L3 (MRPL3):

(Seq ID No: 554)

cttctttccgtcgcagagagcatcggccggcgaccgttccggcggccatt
gcgaaaacttccccacggctactgcgtccacgtggcggtggcgtggggactccctgaaa
gcagagcggcagggcgcccggaagtcgtgagtcgagtcttcccgggctaatccatg Homo sapiens zinc fingers and homeoboxes 1 (ZHX1):

(Seq ID No: 555)

ctcccttcccctccgcccccggacggccgctggggcgcgcgcctctcctcg
caccccaccctgagtccccacactccgcggggccaccgagctgctgaggcccctttt
gcgggcccgccgagcggttccgggtttagggttcacaggtcagagtt
gactccctgaaaagtgcagccggtttgaaatgcaagatggcggcggcgtggcgctga
gaggcgcggcggcccctgcaggagaagacagactgctgctttggacctgttgg
taatgatggcctgagctaaacatctaactagaagggatacccttccatttcaaa
gaacagaatgctaaggaagctgtggcaagtgattggagtt
gtgcttcaaaaatttcagaaattcagcagtattttatctgccaacaataa
gctctttacttgattgcaccatgagaaagctgctaatgagacttgttgag
cacaaaaatggacttgaagaaccaaaagccattgttttcaaatgaagaacactgaacag
ttttaagcctcgatgcttttaatcaccactgagcttttcctcataacatcagaatg Homo sapiens calcium binding protein P22 (CHP):

(Seq ID No: 556)

ccttccttccctccttccctcctgtcgccgtctcttctggcgccgctgctcccg
gaggagctcccggcacggcgatg

Homo sapiens ecdysoneless homolog (Drosophila) (ECD):

(Seq ID No: 557)

cttctctcaggatttccgctggcttcaggttccggtcaggcgtcgg
gacagagcctgatccaggcttcggcggccggtggcagctctcgatcagctctcgcag
tcggagaggcggctaaggaaaggtgccacagcagagacgcgaaggagaggccctagaac
cttttcaaagaagaatg Homo sapiens V-set and immunoglobulin domain containing 4 (VSIG4):

(Seq ID No: 558)

gagcctctttggtagcaggaggctggaagaaaggacagaagtagctctgg
ctgtgatg

Homo sapiens prohibitin 2 (PHB2):

(Seq ID No: 559)

tgcccttcttcgccagccttac
gggcccgaaccctcgtgtgaagggtgcagtacctaagccggagcgggg
tagaggcgggccggcacccccttctgacctccagtgccgccggcctcaagatcagacatg Homo sapiens signal transducer and activator of transcription 1, 91 kDa (STAT1):

(Seq ID No: 560)

ctgccttttctcctgccgggtagtttcgctttcctgcgcagagtctgcggaggggctcgg
ctgcaccggggggatcgcgcctggcagaccccagaccgagcagaggcgaccagcgcgct
cgggagaggctgcaccgccgcgccccccgcctagccctccggatcctgcgcgcagaaaag
tttcatttgctgtatgccatcctcgagagctgtctaggttaacgttcgcactctgtgtat
ataacctcgacagtcttggcacctaacgtgctgtgcgtagctgctccttgttgaatcc
ccaggcccttgttggggcacaaggtggcaggatg Homo sapiens heat shock protein 90 kDa alpha (cytosolic), class B member 1 (HSP90AB1):

(Seq ID No: 561)

agctctctcgagtcac
tccggcgcagtgttgggactgtctgggtatcggaaagcaagcctacgttgctcac
tattacgtataatccttttcttttcaagatg Homo sapiens cancer susceptibility candidate 3 (CASC3):

(Seq ID No: 562)

cgttctccgtaagatg

Homo sapiens nuclear cap binding protein subunit 2, 20 kDa (NCBP2):

(Seq ID No: 563)

gcttctctgcactatg

Homo sapiens non-POU domain containing, octamer-binding (NO-

-continued

NO):

(Seq ID No: 564)
cgctcttttctcgggacgggagaggccgtgtagcgtcgccgttactccgagga
gataccagtcggtagaggagaagtcgaggttagagggaactgggaggcacttt
gctgtctgcaatcgaagttgagggtgcaaaaatg

*Homo sapiens* lectin, galactoside-binding, soluble, 9
(LGALS9):

(Seq ID No: 565)
atttctttgttaagtcgttccctctacaaaggacttcctag
tgggtgtgaaaggcagcggtggccacagaggcggcggagagatg

*Homo sapiens* chaperonin containing TCP1, subunit 5 (epsilon)
(CCT5):

(Seq ID No: 566)
cggtctccgccggttgggggaagtaattccggttgttgcaccatg

*Homo sapiens* haloacid dehalogenase-like hydrolase domain containing
1 (HDHD1):

(Seq ID No: 567)
cttcctcctcgcccccacccagacccagaaggcgccaccatg

*Homo sapiens* glutamate dehydrogenase 2 (GLUD2):

(Seq ID No: 568)
cttccttcctagtcgcggggagtctgagaaagcgcacctgttccgcgaccgtcac
gcacccctcctccgcctgccgcgatg

*Homo sapiens* general transcription factor IIIC, polypeptide 3,
102 kDa (GTF3C3):

(Seq ID No: 569)
ggttctctgtcccggttcctgggggttgcacagacagaccct
gtaaacatg

*Homo sapiens* general transcription factor IIIC, polypeptide
5, 63 kDa (GTF3C5):

(Seq ID No: 570)
gggtccctcgctggctagtaggagagactggtgcttgccccgcccggtggactaactcgc
ttaattttaaataaaaagtcgaggacacggcggtcgttttcccgaagacatgggccctcc
catgggccatttgctccctggaggccctcgcgtcttgctgagcccgggagttaggatga
cgcgagcggtgagggagcccggaacgattccttcgcggaacaattgaggcgaggcctttg
ggagtactttgtgggacggaccctggcgggccctgccagacgcacagggatg

*Homo sapiens* ancient ubiquitous protein 1 (AUP1):

(Seq ID No: 571)
ccgccttcccaagagccctgcggccgggcgcgaaaatggcggcggcggcgac
ggccgggcgctcctgaagcagcagttatg

*Homo sapiens* coatomer protein complex, subunit gamma 2
(COPG2):

(Seq ID No: 572)
cggccttcctgcagcctcttccgctcgccggctgcggcgcctgggac
ggttgcggtgggtctgggcgctgggaagtcgtccaagatg

*Homo sapiens* apoptosis antagonizing transcription factor
(AATF):

(Seq ID No: 573)
cggtctctggcggagtcggggaatcggatcaaggcgagaggatccgg
cagggaaggagcttcggggccgggggttgggccgcacatttacgtgcgcgaagcggag
tggaccgggagctggtgacgatg

*Homo sapiens* integrator complex subunit 6 (INTS6):

(Seq ID No: 574)
tctcctctttctccaccacctcgggccccggtgtccccggccagcactatg

*Homo sapiens* F-box and leucine-rich repeat protein 4
(FBXL4):

(Seq ID No: 575)
tcttccttccgggtcgcgctaggccgggcttgcggcggttgtgccg
catctagagagtcggggagccgcccccg
cacccaggccttctcgcgctgcctggtcgctggtgaa
gcccgcggcgcgcgcctctcccggaccctgcagggtaaaagaatgtcacatgtcag
catttgtacctgaagtcagcatgcaaagttcagggtacctggatgaatgccaactttt
gcatttcccatgtgtatcctgtgaccattctatctgggaacatccttcaaagag
ttcatgcatcttactgaggacacctgacctttttgaagcttcataattcacatctagatg

*Homo sapiens* guanine nucleotide binding protein
(G protein), gamma 3 (GNG3):

(Seq ID No: 576)
gctccttctag
catccttcatccttcaggtaccagccatccagacagtgcttgagctgcagaaactga
gaccagacctctggcctggccctccccaggggcctcctttcgtatagtcactgcttctg -continued catcagatactttcagctgcaactccctactgggtgggg
cacccatttcaggcagaaggttttggtaccctccactgacccacacccagggctgc
tactgccgcttgtggcttcaggatg

*Homo sapiens* histidyl-tRNA synthetase 2, mitochondrial (putative)
(HARS2):

(Seq ID No: 577)

aggccttttgttcctgtcccggaaagccggcgtcctgccgcg
cgatg

*Homo sapiens* interleukin enhancer binding factor 3, 90 kDa
(ILF3):

(Seq ID No: 578)

cctcctcctcctcttctcgccattgcagttggacccagcagcccggcgcg
caccgcgtggcttttgggggcagaccccggcgggctgtggcag
gagggcggcggcggcggctgcggtcgaagaaggggacgccgacaagagtt
gaagtattgataacaccaaggaactctatcacaatttgaaaagataagcaaaagttt
gatttccagacactacagaagaagtaaaaatg

*Homo sapiens* polymerase I and transcript release factor
(PTRF):

(Seq ID No: 579)

gtttcctctgctctccgctctcgcccgctagctctcctcccttccgctcctgcttctctc
cgggtctcccgctccagctccagccccaccggccggtcccgcacggctccgggtagc
catg

*Homo sapiens* 5'-3' exoribonuclease 2 (XRN2):

(Seq ID No: 580)

tgccctctgccgctgctcccgtctctttggttac
gctcgtcagccggtcggccgccgcctccagccgtgtgccgctatg

*Homo sapiens* 2-hydroxyacyl-CoA lyase 1 (HACL1):

(Seq ID No: 581)

ccgcctcttccttcccgttgtttaaggcagttggttgccctcctgtccgtcagaggtg
cagtaccagaggtggcgtgctgccgatttcgcgtttgccttgctggatgattccgctt
gtttgccggctgcgtgagtgcttagagcttttcggtggaagatg

*Homo sapiens* zinc finger protein 346 (ZNF346):

(Seq ID No: 582)

ggctctctac
cggtgagggtttgcggggaagatg

*Homo sapiens* microtubule-associated protein, RP/EB family, member
3 (MAPRE3):

(Seq ID No: 583)

cagtctctgtgcgttgaagccggagac
cgcggcggcctcagcgaggaccctccgccccggagccgccggccggagccg
cagcctctgccgcagcgccccgccacctgtcccctcccctccgcctccgccg
gagccgcctcgtgcactctggggtatg

*Homo sapiens* splicing factor 3b, subunit 3, 130 kDa (SF3B3):

(Seq ID No: 584)

gtgccttttccgccgcgcgccaccagaatgtccctgtcttgaggtctaatggcggac
gccagtatgttggagttggtggtggcttaagttttgaagggaggtagcatccgttgga
tatccacaccatccttctcgctgcaggcttttcttggactccgtactgttggtgtaac
caaggcctggaggtctgggtggctcaggtttcctgcagccatg

*Homo sapiens* spondin 2, extracellular matrix protein
(SPON2):

(Seq ID No: 585)

ctgcctctcgctggaggccaggccgtgcagcatcgaagacaggag
gaactggagcctcattggccggcccggggcgccggcctcgggcttaaa
taggagctccgggctctggctgggacccgac
cgctgccggccgcgctcccgctgctcctgccgggtgatg

*Homo sapiens* solute carrier family 13 (sodium/
sulfate symporters), member 4 (SLC13A4):

(Seq ID No: 586)

ttttcttttctgctttgcaggcccaggctcaaggcaaattataagtagggaaccaatttg
agggaaagacatgtgaacagagttaaggtaccacgtcctgggagcgaccagcagccccac
ctgaagtccgcatgcaactctgacaagctcaggtgcttgttttaaggaaaggggctacta
gagtcttaccaacagcgagcccaggtgggagatgaaacaggtactccccaaaataggtca
tccgagggaggaaaactgatggagagcacaatgtgctctgagcgttttaatgtttttaa
gcttttaaatgatttcttcaaggccgagcagcagcagcaaaggtgtggcttaaaggatta
aggggggtttctgctgacacctagaatgaagttactctattactaatcaagccgagaggag
gcccactatgccccgtttatcatcctttcccagttccttttttgctggtcacaaaacgat
gctcatcaatcccacctaaagcaggaggccaggagcccagcctcttgtagaaacagcgag
ggtataactgccctcccgttctgccccaagacgaaggaggactctcggaagccaagaaa
ggtttaagaagtctttctggatagagagcagtgcccaggcaggaagcctttcgccggcag
agcggggtccaaggacgagctggagaggacagaggcgcgatg

*Homo sapiens* PRP6 pre-mRNA processing factor 6 homolog
(*S. cerevisiae*) (PRPF6):

(Seq ID No: 587)

attcctttccttcctagccttggtcgtcgccgc
caccatg

*Homo sapiens* eukaryotic translation initiation factor 3, subunit
K (EIF3K):

(Seq ID No: 588)

ccacctcttcctgttcccgtccttgaggacgccgtgccgggtcag
tgttagcctccagccctggttgtggaaggcgacagaagtcatg

*Homo sapiens* ataxin 10 (ATXN10):

(Seq ID No: 589)

cccccctcccccgcggcgccgtctcctcctcccgcctgaggcgagtctgggctcagccta
gagctctccggcggcggcgcagcttcagggcagcgcgggctg
cagcggcggcggcggttagggctgtgtagggcgaggcctccccctcctcctcgccatcc
tactcctccctcctcgtcatcctccccttcgtcctcctcgccttcctcctcctcgtcag
gctcgacccagctgtgagcggcaagatg

*Homo sapiens* secretogranin III (SCG3):

(Seq ID No: 590)

cttccttcctcac
ttcctctgcaggagggagcgagagtaaagctacgccctggcgcgcag
tctccgcgtcacaggaacttcagcacccacagggcggacagcgctcccctctacctgga
gacttgactcccgcgcgccccaaccctgcttatcccttgaccgtcgagtgtcaga
gatcctgcagccgcccag
tcccggcccctctcccgccccacacccaccctcctggctcttcctgttttactcctcct
tttcattcataacaaaagctacagctccaggagcccagcgccgggctgtgacccaa
gccgagcgtggaagaatg

*Homo sapiens* polymerase (DNA directed), mu (POLM):

(Seq ID No: 591)

cttccttccgtctcgctcggagtttccctctgcgttcgctccgcgctgctg
gaggctgtcgtcccaatg

*Homo sapiens* epsin 1 (EPN1):

(Seq ID No: 592)

cctccttctgtt
gcttcccgtctcctcggcggctcccctcccccgcccggctctccgcgcccccttctgggcg
gcggggcggcggagccgtcggcgtgcggccctcctt
gcgttcgtgcgtgcgcccgtggcccggcgcacgtcccgcgacaccgaggccgagcgggg
caggggggctgaccgccatgaccccccagagcccggcgtgagggggccga
gatgcggtgacctgccagcacctgccgcagccttcgtccgggag
tcgcccccatctctccacgcatcggggccctgtgccccttgctgctgcagccgggcac
catg

*Homo sapiens* Sec61 alpha 1 subunit (*S. cerevisiae*)
(SEC61A1):

(Seq ID No: 593)

gtgtctctcggcggagctgctgtgcagtggaacgcgctgggccgcggg
cagcgtcgcctcacgcggagcagagctgagctgaagcgggacccggagcccgag
cagccgccgccatg

*Homo sapiens* Obg-like ATPase 1 (OLA1):

(Seq ID No: 594)

cgttctctcctccttcctccccgcctccagctgccggcaggacctttctctcgctgccgc
tgggaccccgtgtcatcgcccaggccgagcacgatg

*Homo sapiens* sorting nexin 12 (SNX12):

(Seq ID No: 595)

ag
gcctctgtcccccaccccctttccccggtcccaggctctccttcggaaagatg

*Homo sapiens* LAG1 longevity assurance homolog 2
(*S. cerevisiae*) (LASS2):

(Seq ID No: 596)

cggcctttttttcccggctgggctcgggctcagctcgactgggctcggcgggcggcggcg
gcggcgccggcggctggcggag
gagggagggcgagggcgggcgcgggccggcgggcgggcggaagagggagga
gaggcgcggggagccaggcctcggggcctcggagcaaccacccgagcagacggag
tacacggagcagcggccccggccccgccaacgctgccgccggctactccctctt
gatgccctcccctttgcccctcactcaggatg

*Homo sapiens* cytohesin 4 (CYTH4):

(Seq ID No: 597)

tcatcttttcccca
gaggcgtcggaatg

*Homo sapiens* transportin 2 (TNPO2):

(Seq ID No: 598)

-continued aattctctctctttt
ggctccctccttccgcgcgagtctctggagaagccgcagcgcgagtt
gccgccgctgctgcccggggcgggtaagtgggcctcactcagagcccgaccctctt
ggccccggcttgcgtcgaccccgccgggcac
cgagcctgcgccgcgcgcggcccgggcgtcggggccgcgcccgaccgggaaaggccgg
gaagccggttgggcccgatcctcctggcagctagaacgggccgggcgggggaggggg
gaaccgagcagagcttagggggtggggcctcggagccaggccatgtcggggctcctcaa
gaagagggccagtgggactgctgggtcgggctggagggatctgattgggggaa
gcgtctggggactgcttggggcctgattgggggacgtcgcgaggatcggcttgccttgcgccatg

*Homo sapiens* makorin ring finger protein 1 (MKRN1):

(Seq ID No: 599)

gggcctttgctgtgtgggataaacagtaatg

*Homo sapiens* vinculin (VCL):

(Seq ID No: 600)

ctgtctcttcgccggttcccggccccgtg
gatcctacttctctgtcgcccgcggttcgccgccccgctcgccgccgcgatg

*Homo sapiens* DEAH (Asp-Glu-Ala-His) box polypeptide 38 (DHX38):

(Seq ID No: 601)

cctccttttcctgcccccagactagaggcgggatgtag
tctcttaggctaagagtgattggtcacaaggagactcg
gaagtgtctgatcagagccccagaggaggcctttgagagcctgttggcgtac
cgttccacacttggatccaggaatcgggcgtgttccaggctgctctctatggtagcttt
gggcggatagaggggggcgcgcaaagtattaagggacaa
taatggccgctttcaaggtgtggattttggctccttgagcctgtctgagcgaggggtgg
cagcgccggcgcccagaatccgggacagaagggtcccaagagtcgcgcttggtgaga
gaaatcccagatcctgtgatg

*Homo sapiens* osteoglycin (OGN):

(Seq ID No: 602)

catcctctaagcttttaaatattgcttcgatggtctgaattttatttccagggaaaaag
agagttttgtcccacagtcagcaggccactagtttattaacttccagtcaccttgatttt
tgctaaaatg

*Homo sapiens* NIN1/RPN12 binding protein 1 homolog
(*S. cerevisiae*) (NOB1):

(Seq ID No: 603)

gctcccctctcacgcagccaacatg

*Homo sapiens* nudix (nucleoside
diphosphate linked moiety X)-type motif 5 (NUDT5):

(Seq ID No: 604)

catccttttagcaccgcgagaggcgccggtgtttcgagccgtggcaccgg
catcggctgacactgctgcctccagctag
ttatttcgtcctcttccgttcttcaccctacaccttggaggtgaacttctcac
ctgagggctgtaaagactcgtttgaaaatg

*Homo sapiens* WD repeat domain 91 (WDR91):

(Seq ID No: 605)

cgtccctcaccgcac
caccctaaagacgctagcgctgcgatg

*Homo sapiens* nuclear transcription factor Y, gamma (NFYC):

(Seq ID No: 606)

gggcctctgcattgcccgactccgtaggagcgcggggcggctcctgctcttcctg
gactcctgagcagagttgtcgagatg

*Homo sapiens* protein phosphatase 2, regulatory subunit A, alpha (PPP2R1A):

(Seq ID No: 607)

ccgcccttccttcttctcccagcattgccccccccacgtttcag
cacagcgctggccgcagtctgacaggaaagggacggagccaagatg

*Homo sapiens* vesicle-associated membrane protein 2 (synaptobrevin 2) (VAMP2):

(Seq ID No: 608)

ccatctttccgtcccgggcagccagcgccagtcg
gagccagcgcgagccgccgccgccatcac
tgccgctgccaagtcctccacccgctgcccccgccatg

*Homo sapiens* transmembrane protein 5 (TMEM5):

(Seq ID No: 609)

gat
tctctttccgcccgctccatggcggtggatgcctgactggaagcccgagtgggatg

*Homo sapiens* UDP-GlcNAc:betaGal beta-1,3-N-acetylglucosaminyltransferase
3 (B3GNT3):

-continued

```
                                             (Seq ID No: 610)
aactctttcttcggctcgcgagctgagaggag
caggtagaggggcagaggcgggactgtcgtctggggagccgcccag
gaggctcctcaggccgaccccagaccctggctggccaggatg
```

*Homo sapiens* SEC11 homolog A (*S. cerevisiae*) (SEC11A):
```
                                             (Seq ID No: 611)
gcgccctttcccctgccggtgtcctgctcgccgtccccgccatg
```

*Homo sapiens* RUN and SH3 domain containing 1 (RUSC1):
```
                                             (Seq ID No: 612)
ctccctccccgcgcccgtcctctcccgccctacaggccctagcagggcaggcgggaggt
gagcgcggccatcccgctcccggagttccgggatcctggagtccgtagttcgtggtcctt
cgccggtgtccccggagcccagcggctgtggatg
```

*Homo sapiens* aryl hydrocarbon receptor interacting protein-like 1 (AIPL1):
```
                                             (Seq ID No: 613)
cctccctttctcctgcagccatg
```

*Homo sapiens* tumor necrosis factor, alpha-induced protein 8 (TNFAIP8):
```
                                             (Seq ID No: 614)
cctccttttctcccgccggctctaacccgcgctt
ggctaaggtccgcgggaacccgtgagccaccgagagagcaga
gaactcggcgccgccaaacagcccagctcgcgcttcagcgtcccggcgccgtcgcgccac
tcctccgatg
```

*Homo sapiens* staphylococcal nuclease and tudor domain containing 1 (SND1):
```
                                             (Seq ID No: 615)
gcgtctctttcgctccgtgtcccgctgctgctcctgtgagcgcccggcgag
tccgtcccgtccaccgtccgcagctgg
tagccagcctgcccctcgcctcgactccctttcaccaacaccgacacccacattgacac
ctccagtccggccagccgctccactcgttgcctttgcatctccacacatg
```

*Homo sapiens* DNA segment on chromosome 4 (unique) 234 expressed sequence (D4S234E):
```
                                             (Seq ID No: 616)
cgccctctttt
ggtcgcccctcccaacccagcactaaggagcaccctgctctggtctccgccac
cacccagcgcctcctggacccatcccccaaaccttgaacgtcctcag
gaccccaggtgagcgcggcgcgctgcgggcgggacctctctgcacctccccg
caccctgggggtcgctctgtccctacggtcccgcctcccctttctcctttctaa
gcgcctcgcgcccaggcgccgcccgggtggcgcagcccg
cagccctcccgctccgggcgccctccgccgctccga
gaccccctggggcgcgtcctctcccgctcccctgttccctcccccggctcagggcgggc
gcgtggtcccaggggaggctcccgcccagccccgcactcctttt
gtgcggccgggcgggcgctgcgtcaaggtggaggcgcggccacacgcgcg
cacccacccgcgcgcacccagccccccgggagaggcaggaagggaggcggcggcgcgag
gaggagggagcggccgtg
gagcccaatcgttcgctccccttcccgggtccgcgcgcggcgccgcctccgccatt
gctgcgagcaggagcaggagacgcggagctcggagcgctcagctgacctgccg
gagccgggcgtgggctgcagcctcggagctcccggaacgatg
```

*Homo sapiens* growth hormone inducible transmembrane protein (GHITM):
```
                                             (Seq ID No: 617)
acgtcctttcgatgttgcgtcatgcagtgcgccggag
gaactgtgctctttgaggccgacgctaggggcccg
gaagggaaactgcgaggcgaaggtgaccggggaccgagcatttcagatctgctcgg
tagacctggtgcaccaccaccatg
```

*Homo sapiens* stress-associated endoplasmic reticulum protein 1 (SERP1):
```
                                             (Seq ID No: 618)
tttccttcctctttcactccgcgctcacggcggcggccaaagcggcggcgacggcggcgc
gagaacgacccggcggcagttctcttcctcctgcgcacctgccccgctcggtcagtcag
tcggcggccggcgcccggcttgtgctcagacctcgcgcttgcggcgcccaggcccagcgg
ccgtagctagcgtctggcctgagaacctcggcgctccggcggcgcgggcaccacgagccg
agcctcgcagcggctccagaggaggcaggcgagtgagcgagtccgaggggtggccggggc
aggtggtggcgccgcgaagatg
```

*Homo sapiens* ADP-ribosylation factor interacting protein 1 (ARFIP1):
```
                                             (Seq ID No: 619)
cggtctcctcacttccggcttcgctgctcttggttctggttctg
gaggctgggttgagaggtcgccggtccgactgtcctcggcggttggtcagtgtgaattt
gtgacagctgcagttgctccccgcccccgagcagccgaggagtctaccatg
```

*Homo sapiens* tumor necrosis factor receptor superfamily, member 21 (TNFRSF21):

(Seq ID No: 620)

ccgcccttcggcgccaccac
gtgtgtccctgcgcccggtggccaccgactcagtccctcgccgaccagtctgggcagcg
gaggagggtggttggcagtggctggaagcttcgctatgggaagttgttcctttt
gctctctcgcgcccagtcctcctccctggttctcctcagccgctgtcggaggagag
cacccggagacgcgggctgcag
tcgcggcggcttctccccgcctgggcggccgcgccgctggg
caggtgctgagcgccctagagcctcccttgccgcctccctcctctgcccggccgcag
cagtgcacatgggtgttggaggtagatgggctcccggcccgggaggcggcggtg
gatgcggcgctgggcagaagcagccgccgat
tccagctgccccgcgcccccgggcgcccctgcgagtccccggttcagccatg

*Homo sapiens* sushi-repeat containing protein, X-linked 2 (SRPX2):

(Seq ID No: 621)

cccctcttctgcagcagacggactgag
ttcctctaatccctgtgttccttctccccatctttctaaaacccttctctgagagag
gaataactatagcttcagggataatatagctttaaggaaacttttggcagatgtggac
gtcgtaacatctgggcagtgttaacagaatcccggaggccgggacagaccaggagccac
tcgttctaggaatgttaaagtagaaggttttttccaattgatgagaggagcagagag
gaaggagaaagaggaggagagagaaaaagggcacaaaatacca
taaaacagatcccatatttctgcttcccctcacttttagaagttaatt
gatggctgacttctgaaagtcactttcctttgccctgg
tacttcaggccatatacatcttttcttgtctccataatcctcccctttcaaggatg

*Homo sapiens* HIV-1 Tat specific factor 1 (HTATSF1):

(Seq ID No: 622)

ac
ctcccttttctctgctcagctccagcgtcatttcggcctcttag
ttcttctgaaccctgctcctgagctaggtaggaaacatg

*Homo sapiens* trafficking protein particle complex 2 (TRAPPC2):

(Seq ID No: 623)

gggtctcttccgcggaaactgacattgcgtttccgttgtcggcctcccactgcaggagcc
atatattgaagaccatg

*Homo sapiens* UDP-N-acetyl-alpha-D-galactosamine:polypeptide N-acetylgalactosaminyltransferase 5 (GalNAc-T5) (GALNT5):

(Seq ID No: 624)

ccaccttttcttgggcttgtaggaaggtggacatgggctcccggagacaagacaagtga
tatgttgaactgttcggtggctggaatcaactgctcctggagtgacctaaggccag
tgtttatcagaacttagccagggccagccaagcaggcacagatgctctgc
tatgaaatgccacgcaggcagagactgacaagcggtaggaactgagctttcccctt
ggactgctgcttcctgctgtgttcaggggagggggtcactttctgg
caactctgctgctgctgctgctgctgctacttcagcttcctctccactcaaggtaa
gcaggctaagggagggcaggctgctagggaaagctttgtaccatg

*Homo sapiens* transmembrane protein 97 (TMEM97):

(Seq ID No: 625)

tggcccctcttctcacatcagcgggtccaggcccaaccgacagactatg

*Homo sapiens* EH-domain containing 2 (EHD2):

(Seq ID No: 626)

cgtcctccccgctccgggcccacccggctcagacggctccggacgggaccgcgag
cacaggccgctccgcgggcgcttcggatcctcgcgg
gaccccaccctctcccagcctgcccagcccgctgcagccgccagcgcgcccgtcgg
cagctctccatctgcacgtctctccgtgaaccccgtgagcggtgtgcagccaccatg

*Homo sapiens* tubulin tyrosine ligase-like family, member 4 (TTLL4):

(Seq ID No: 627)

cgccctcttcttccagactctcggtctgtccgctgggggcgcgcgcggtgtgtgg
caggcggcagcggcgctggcggccgagtgcgcttgtcacgcgtggcggtgcgtggtt
gctagggcgcctgaggctgccgggtagcccagcaggccgagggaggaagtagcgtg
gagccggtgccgagccggggcgaagctggatcccctagatagactgtcttcaagctcac
tgatattttcctctgcttgatccattgtgctgttgagagcctctag
taaatttttcagactgacagacttcaaggatgcagctgctactaccggaggtgtgtgg
caccttacctcagcaaggccatgagaccgtgtggccatgatgtgggcccctcatg

*Homo sapiens* basic leucine zipper and W2 domains 1 (BZW1):

(Seq ID No: 628)

acctctccctcctcctggcgttagttccggtcgcagaggagacaccgccgcagtt
gccggtacatcggggatttctggctctttcctcttcgccttaaattcgggtgtcttt
tatg

*Homo sapiens* centrosomal protein 57 kDa (CEP57):

(Seq ID No: 629)

ttgccctttctgtgtaagctgtgagcgtaggcggccctgagggggtgtgtt
gcaggggtttccaagcccagcaccagcacccctt -continued gcccttttccatcaggggttcagcctagggtccccgctggtgggcggctcccgagtctt
ggagaagagcacgagaacctagaccgcccccgaagtgcggagaccccctggg
caggctgaaagatg

*Homo sapiens* family with sequence similarity 115, member A
(FAM115A):

(Seq ID No: 630)

ctgcccctttgcctcctgggcggagaagctgcttcctcctgggaacaaccgcctcccgctc
ctagcaggttgctactgccccgaacccgcgctgcagggaacagcggggcaaacagtgagt
gggggttcagcgtagactctggaccaggagaggcccgcggtgaccgaggcctgggccccgg
aaaccaatagagccatg

*Homo sapiens* ATG13 autophagy related 13 homolog
(*S. cerevisiae*) (ATG13):

(Seq ID No: 631)

agccctctttcaccccccccccccggccattac
cgaagcggatgaaaacaaacactaacgatggcggcgccgggaagcgac
cggctgctgggcttaaggcgggagtgaccgcttaaccagtgagggaagcactgaa
gagcgccagtcgacgtgggtgcgacaactcgcggagtcttaggagcaaaac
gtctggggcctgcgagccaggaccttctgaagccttaggtgtctatcggcgacgtg
tacggtcactgcagctccggagcgcggaaccctcagccag
gaggcgcggctggtcggtcccaggtcccggcctccgtaatgagagcccggaaccac
tctttgtgccgcagcttcgcagcatcttggactcaagtgat
tctcctgcctcagcctcctgagtagctgggactacagattcctataggcaatg

*Homo sapiens* sorting nexin 17 (SNX17):

(Seq ID No: 632)

ccgccttcccacatcg
gatcgcagggctcccaaaatggcgagtgaggctgcggggactcgctgagcagcg
gaggggagcgtgcagagccgctgcggccctcacagtccg
gagcccggccgtgccgtgccgtagggaacatg

*Homo sapiens* phytanoyl-CoA 2-hydroxylase interacting protein
(PHYHIP):

(Seq ID No: 633)

cgttctttctcccttctctgcctctctcctccacgctgctttgat
ttcgctcttgcctctcttcttgcgctgctcagctgggaacatcgtctcaccaggggcag
cagcgacgcgctgcacagccagacaggagctggctgcggggcatggaagcagcctcctt
ggcagccgggagaggagcaagcgcacgccac
tgcccgtgacccaggcgtccggctgctgtccctgccggggagctcatccac
gcagaggtctctccctgtcctccctgcgagcttttcctctgcagagcccagtg
gagccagtccccacaggagacaaccctgacgggagcatg

*Homo sapiens* translocase of outer mitochondrial membrane 20 homolog
(yeast) (TOMM20):

(Seq ID No: 634)

cggcctttctgtgttcctggcccgcggccgtcgggtgtgagctgcgccgac
cgctctgagggttcgtggcccaccgctccttcgcggtccctgccgccaccgtccac
gctcagcgttgtagagaagatg

*Homo sapiens* KIAA0141 (KIAA0141):

(Seq ID No: 635)

cggcctttctagccgctgtcccaagggtt
ggtctcgcgcttttcggctgcgagctctctgtggtgctggcagcgacatg

*Homo sapiens* janus kinase and microtubule interacting protein
2 (JAKMIP2):

(Seq ID No: 636)

ctccctcctttaaacagcttctccgggtctcagcatgggcttccagggcagcgattgagg
agaccttaccaaggagcaccacacagtagatgctgagacatcgtactccaggataagaaa
cagtaacatggcagcacctgcttgaaagaaattaaaaaccaacagactccatttagaaag
gaacaatg

*Homo sapiens* EPM2A (laforin) interacting protein 1
(EPM2AIP1):

(Seq ID No: 637)

cctcctctcccttgcggccttttctaacgttggccctgctcttgtgg
cctcccgcagaatg

*Homo sapiens* centrosomal protein 170 kDa (CEP170):

(Seq ID No: 638)

cggtctttt
gccgttaccgctatgtgtgggcgtgtgtggaataacgttattgcccagcg
gagctgagggccccggagctcgaccgcagcggcagcgacgacaacagcggcgacgac
gacgacgacgaggtggggggaggacggcgtgcgagagactcacgggacgcgac
gcgccccgcctcccccgtccggtccctctctccacggtaaggggatgacgtagctttt
gccaaagacttagaagctaagcagaaaatg

*Homo sapiens* suppressor of Ty 7 (*S. cerevisiae*)-like
(SUPT7L):

(Seq ID No: 639)

-continued aggcctctcgaggtccagacagcgcccagcccgctctgcgacgcag
cagtgaatagtgtggtacctccttgtctcggttcaggtccagac
ctccccgtcttccggctgccctgaacgtcaggcgacctcag
gaccctgtgattggcgcctgcgccggcggaccgtgaccgaggaaaccctg
gagggacttgggcattccttgggctccgtgcctgttcttcgtgctcctttcggg
caaggatctcacattatcagtctttgaccgacacagaatgcctggcatttga
taaatgtttgttgaacttgaagagacatatggacaatg Homo sapiens non-SMC condensin I complex, subunit D2
(NCAPD2):

(Seq ID No: 640)

tttcctttcatttcagcctgactgccggaatcagagccgcgggtga
gatccccagccctgtgagcctgtaggagtagaatg Homo sapiens ring finger protein 10 (RNF10):

(Seq ID No: 641)

ggttctttga
gatgctgtttggcgactcgtcgccattcccggag
caggtcggcctcggcccaggggcgagtatccgttgctgtgtcggagacactag
tccccgacaccgagacagccagccctctccctgcctcgcggcggga
gagcgtgtccgccggccggccggcggggctcgcgcaac
ctccctcgcctccccttccccgcagcctccgccccgccaggcccggcccg
gactcccgagcccggcctcctcgtcctcggtcgccgctgccgccgggcttaacagcccc
gtccgccgcttctcttcctagtttgagaa
gccaaggaaggaaacagggaaaaatgtcgccatgaaggccgagaac
cgctgccgccgaccccgccggccctgaac
gccatgagcctgggtccccgccgcgcccgctccgctccgactgccgtcgccgccgaggcc
cccgttgatg Homo sapiens PAN2 poly(A) specific ribonuclease subunit homolog
(S. cerevisiae) (PAN2):

(Seq ID No: 642)

agcccttcttgattggaagaagcgcctcg
gaccccggtccttggcgccgtagtggttaggttgagccctaggcgtggggga
gaactggggaaactggaatttcccgcggagctgacagcgctt
gcgctcccctactcgttctaattccacgcgctccaaaatatccgccatgga
gaaatcttggcaggatgtccattctaggcccatcggtgctgtcttgctgaaggtt
gggtcaggcatctaaagggactgtggtaagggagggtgtgacacaggtgtaa
gctgccatcgtcatcatg Homo sapiens CD302 molecule (CD302):

(Seq ID No: 643)

gctcctctccggccgcg
cagccgctgccgcccacccgcacccgccgtcatg

Homo sapiens NSA2 ribosome biogenesis homolog
(S. cerevisiae) (NSA2):

(Seq ID No: 644)

gactctttcctgtcccggcctgcgtggtgtgggcttgtgggtctttga
gacccgaaaattgagagcgttttcgcac
tccagcggctgctcctggcggtctgcggccgtcaccatg Homo sapiens DIS3 mitotic control homolog (S. cerevisiae)
(DIS3):

(Seq ID No: 645)

acgccttttgctggaagagcgctgctgggggttaggattctgcgcggcgagg
caagatg

Homo sapiens caspase recruitment domain family, member 8
(CARD8):

(Seq ID No: 646)

cctcctctgcgagcgttatttcaaaagaagttgagaaccagagaaac
cgacctaaggggattctcccatttggcccgtcctaccctaaagtcaccac
ctgctgcttttctggagcgcttaccagtgaccaagaggaacagaacacagag
cagcctggcagtgtccaagcaacaagcctccgctcctccttcctg
caccctggggctcctgaaactcacatgggtaaaaaagatacagtaaagacataaatac
cacatttgacaaatg Homo sapiens epsin 2 (EPN2):

(Seq ID No: 647)

ccgcctctcgagcgctgccggtggccg
cagcggcgcacccacgccggcccggaggagcagagtgttcatttctgtgtcgggcacag
tgctaagtgctgggtgctcactggtgatgaggcagatgaaggttaccaaacttgtg
gacaggagcctcatatcagagacgtggacctcactg
tagcctggtcatggcttccagcttttcgaatctgaggctccaaaggaggaaatgac
cattcagggatcttactccagcttgattacggagactgaaccttcataggggtgcgcac
ttaccaaggacaggaaggtttctctgtttgaagggctttaaacttataacaaagaaaa
taaaaatg Homo sapiens pyridoxal-dependent decarboxylase domain containing
1 (PDXDC1):

-continued (Seq ID No: 648)
ccgcctctcaaccatcaggttcggcagccgcgggcgccgcctgg
cagctcctcctcttctccgccccgccggccgcgggcgcggggac
gtcagcgctgccagcgtggaaggagctgcggggcgcgggaggaggaagtagagcccgg
gaccgccaggccaccaccggccgcctcagccatg

*Homo sapiens* nicotinamide nucleotide adenylyltransferase 2 (NMNAT2):

(Seq ID No: 649)
ccttcctttctccctctgcagacacaacgagacacaaaaaga
gaggcaaccccctagaccaccgcgaaggacccatctgcaccatg

*Homo sapiens* mitochondrial ribosomal protein S27 (MRPS27):

(Seq ID No: 650)
tgttccttttggtacgctccaagatg

*Homo sapiens* leucine-rich repeats and calponin homology (CH) domain containing 1 (LRCH1):

(Seq ID No: 651)
tcccctccttccagcgcctttcggtggagcactgcggcac
tcagcccgagctgccgtttcccctcgcggggaacgctgtgaccccccgcag
gagcggcgggcggggtgggggggcccgggagaagatg

*Homo sapiens* PAS domain containing serine/threonine kinase (PASK):

(Seq ID No: 652)
gctcctttccgtggtgtgtagccggcttggcgtgaccctcgcctgatccagttgttagag
ttggaagcttggcagttggcctcccttcttcccatg

*Homo sapiens* megalencephalic leukoencephalopathy with subcortical cysts 1 (MLC1):

(Seq ID No: 653)
cttcctttcctagttgggttctgacagctccgaggcag
tggtttacacaaccaacacgaaacatttctacgatccacccgattcctcccctcattga
tattcaggaagcagctctccttcccctgccttcagctcaagtttgctgagcttttt
gtttcatttgtgaatacttcttgctggaagtccctcacccagagaccagtgctcccaac
ggcagagcagcggggagataaagaactggtgacacgtggctgtacattcag
cacagctgtggtgtccccaagtgccatg

*Homo sapiens* RRS1 ribosome biogenesis regulator homolog (*S. cerevisiae*) (RRS1):

(Seq ID No: 654)
cttttcttttccggattgggcatcccggcatctg
cacgtggttatgctgccggagtttgggccgccactgtaggaaaagtaacttcagctg
cagccccaaagcgagtgagccgagccggagccatg

*Homo sapiens* formin binding protein 4 (FNBP4):

(Seq ID No: 655)
cgctctctgctcgcgcttgggctcgcgatg

*Homo sapiens* peptidylprolyl isomerase domain and WD repeat containing 1 (PPWD1):

(Seq ID No: 656)
gcgccttttctgacgatgcgaacaacatg

*Homo sapiens* sorting and assembly machinery component 50 homolog (*S. cerevisiae*) (SAMM50):

(Seq ID No: 657)
ccgccttctgccctcagcagcagac
gctctgtcccgcccgggcagctctgcgaggcagcggctggagagggaaccatg

*Homo sapiens* Yip1 domain family, member 3 (YIPF3):

(Seq ID No: 658)
gcttctccttttgtgttccggccgatcccacctctcctcgaccctggacgtctac
cttccggaggcccacatcttgcccactccgcgcgcggggctagcgcgggtttcagcgac
gggagccctcaagggacatg

*Homo sapiens* tectonin beta-propeller repeat containing 1 (TECPR1):

(Seq ID No: 659)
caccctcttgcccggtcccgggagggccggtccgctcctcccggac
gccgaggacctaccaccgcgacttcgccccgcccggcgcgggcccag
gaccctgatgtcgcttttgaacagcccctgcacctggcagcagcgagctactgtag
taggcattgccgactgtttgcataccggatgggagtgacagtgtaatagaaaaacaa
gcaagaaaccttttaggtaggactcctaaggctcagaggaagttacctccagccgctgc
catg

*Homo sapiens* DDB1 and CUL4 associated factor 12 (DCAF12):

(Seq ID No: 660)
ccttcccctttccggctcaagtccttcctcctctctcttcctttctttccgcctatcttttt
tctgctgccgctccgggtccgggccattttccgggccgggcgcactaaggtgcgcggccc -continued cggggcccagtatatgacccgccgtcctgctatccttcgcttccccgcccatgtggct
gcggggccgcggcggcgctgcccactatg

*Homo sapiens* chromosome 3 open reading frame 17 (C3orf17):

(Seq ID No: 661)

ccgcctttcgtaagtcccccgcctcgcatg

*Homo sapiens* LETM1 domain containing 1 (LETMD1):

(Seq ID No: 662)

caac
ctcttctctcccgcttctctcgctgtgaagatg

*Homo sapiens* chordin-like 2 (CHRDL2):

(Seq ID No: 663)

ctcccttctgctggac
cttccttcgtctctccatctctccctcctttccccgcgttctctttccac
cttttctcttcttcccaccttagacctcccttcctgccctcctttcctgcccac
cgctgcttcctggcccttctccgaccccgctctagcagcagac
ctcctggggtctgtgggtt
gatctgtggccctgtgcctccgtgtccttttcgtctcccttcctcccgactccgctccc
ggaccagcggcctgaccctggggaaaggatg

*Homo sapiens* CCR4-NOT transcription complex, subunit 10 (CNOT10):

(Seq ID No: 664)

actcctctagccggaacctgggggcccggagccggggtaggcacagag
ttgtcctcggaggtccaggacagcggccagcccggcggcgggagtcagggccacgccac
ctgcagggaagaacccgagtcgaagcgggaagatg

*Homo sapiens* THUMP domain containing 3 (THUMPD3):

(Seq ID No: 665)

cttcctctt
gcagttgaggccggcgccgagccggacttcaggcggatctcgtggcggagcccatctt
gctccctctcccaggcctttacccgctccctaggattcccgggccctgtaggtgggag
ttgggagacgacagtactgcttttaaagagacagtgttagggatcttggaa
gcacagccaacatg

*Homo sapiens* nipsnap homolog 3A (*C. elegans*) (NIPSNAP3A):

(Seq ID No: 666)

gctcctttccactcgggaaaccttcagaggagtctcagaaaggacac
ggctggctgcttttctcagcgccgaagccgcgccatg

*Homo sapiens* CAP-GLY domain containing linker protein 3 (CLIP3):

(Seq ID No: 667)

gcccctccctctccgcccccacccctgtcggcgtctgggcctcgtccccttctctctgt
ctcccttgcctcccccatcacgtccctgacaccgacacccccattgctcccacag
tctccccagtctccactttggtccccagcgctgtctgcccgaggattt
gcctgaaggctgcccccaactctgcaccgcccccccgagggccaccgaggaccatg

*Homo sapiens* ring finger protein 167 (RNF167):

(Seq ID No: 668)

caccccttcccgaagttttctgtcac
ctgtgttaggctccgtcccctttccgcgttttatccccgtaccagaaaaggata
catttagtgcctcccacccagctccactaaacgggttggatatctcattctttgagtt
ggtgttccttcccccggcgccccatgtagctgggaagtgggacctgggggtggtt
ggaccctgggatcctaaaggaggggcagggagggcgcagaactccgcttctgctcctt
gctaccaggacgcgcggcctcctcagcctcttcctcccgctgccatg

*Homo sapiens* polymerase (RNA) II (DNA directed) polypeptide M (POLR2M):

(Seq ID No: 669)

cgttcttccgggaaaatggcgactcccgctcgtgccccggagtcaccgccgtccgcggat
ccggcgctag
tagcggggcctgccgaggaagccgagtgcccgccgccgcgccagcctcagcccgcgca
gaatg

*Homo sapiens* dihydroxyacetone kinase 2 homolog (*S. cerevisiae*) (DAK):

(Seq ID No: 670)

tcgcctctttccgccagcgcccgcaggacccg
gatgagagcgcacgcttcggggtctccgggaagtcgcggcgccttcggatgtggcg
gatgcggccgtgagccggcggggaggtgctgctgctgcctccactg
tactcagacccaggtagcacaggattgtccatcctccagcagctcagtgcaac
ggtgtgaactcagcctgtttcagagcctccacaccatg

*Homo sapiens* RNA polymerase II associated protein 1 (RPAP1):

(Seq ID No: 671)

cgatctctgcggggcaagatggcggcgcccagacaggcctggagcacggatgaataa
gagggaaccccccacacggagacactgctggagagagtcgtactggggaggcagctggag
cagcaagatg Homo sapiens torsin A interacting protein 1 (TOR1AIP1):

(Seq ID No: 672)

cctcctctttggtgcctccagccaggaggcgggagcgatccacag
cagctgacccagctcaggcactgcctctctcacagccctcaagacacac
catgggcccagaggcaggtttgctacacagcagcgacgac
gcaggcggcggccccagcgactcgcaactgcctccctgaccacagcggccac
cgcccaacaccccgagaagccatcgccaccaccggcaggagaacctagggtccataaa
gccatcttcgcgatcgactaaagctacgtcaacaactatg Homo sapiens SERPINE1 mRNA binding protein 1 (SERBP1):

(Seq ID No: 673)

cccccctctctcggcccggccatcttgtgggaagagctgaagcaggcgctctt
ggctcggcgcggcccgctgcaatccgtggaggaacgcgccgccgagccaccatcatg Homo sapiens N-acetyltransferase 9 (GCN5-related, putative) (NAT9):

(Seq ID No: 674)

caccctttctgcggggacgatttcgtcggtggtaggctgctaccatg

Homo sapiens ribosomal L1 domain containing 1 (RSL1D1):

(Seq ID No: 675)

gcgcctcttcacgaggtggaaacaagatg

Homo sapiens SH3 domain containing, Ysc84-like 1
(S. cerevisiae) (SH3YL1):

(Seq ID No: 676)

cttcctcttcctgggcagcctcgggacggggcg
ccgcggccgggcgggcagcatg

Homo sapiens methylmalonic aciduria (cobalamin deficiency) cblD type, with homocystinuria (MMADHC):

(Seq ID No: 677)

acttcctttgcctgctcaccgccagcgtaggtgctaccac
cgctgccgtcgccgccgccattttgatgcaggaagagtccggttctgggacagctg
gagacagtggtggtgactgaaataactttaccaaaggaaagctattttgcgaac
tatcttctccagcggagatg Homo sapiens glioma tumor suppressor candidate region gene 2 (GLTSCR2):

(Seq ID No: 678)

agttcttcctttgacaagatg

Homo sapiens DDB1 and CUL4 associated factor 8 (DCAF8):

(Seq ID No: 679)

cagtcttctcgagcacatcgtcgcaaacggggccggaaagcgtggcag
cgcaggcgcaagcgcagagagcggaggcggtggtggtggcggccgctggccagttcctt
cagtgaatctacagacctattttctcaggagctcagcctggccttacttcagtga
taaaaggaggaaaggctggctacagcaaacatcattcaagatg Homo sapiens UBX domain protein 1 (UBXN1):

(Seq ID No: 680)

cttcttctcgtcggtgttcccggctgctatagagccgggtgagagagcgag
cgcccgtcggcgggtgtcgagggcgggttgcctcgcgct
gacccttcccgccctccttctcgtcacacaccaggtccccgcggaag
ccgcggtgtcggcgccatg Homo sapiens antizyme inhibitor 1 (AZIN1):

(Seq ID No: 681)

ccgccttctcacac
tttcaggctct
gatcgcggccgcagttttcctttttctctctgccgtcgccttctctgcctcttct
catcctttctcgctctgctgctctgcagtgtgacgagtccgaatcctcttcccacccag
cccgcgcctttcttcttttgcctgcgctgttctatttctccttcggccgccgccgcac
tgctgcacacagctggtgtcggtgccgcgcttttaccccaagtcgttcccgcagcc
tatgcccaggccgccttgggtattctgctcaaggtaaccacatccctctt
taaaaattccgccgaaaagagaagacgctttacccgactctttgggccgttatct
cacggcgaactttctgaccaagtatacaactacccagagggcctaggagaagtgctgta
tagagagcagttcgacttcaacgctgagccaccctgggaacctagctgatgatag
gggggttccatctcccaacttgtccatggaggtcttcacttcagaaatccaagactca
tattcatccagcttggtgtcaagtgggctgttgctgccagaattatcttgtgattattt
gagagatgtatcagtttcttctgaagtacaatcaactgtagaagcctttgtag
cagtttgttgcatattctaaggacccagacatag
gcttggtggccgtctcttgtcttttcctggtttatgactttcggctttgtg
gaatacggctgagatg Homo sapiens cell division cycle 40 homolog (S. cerevisiae) (CDC40):

(Seq ID No: 682)

gcctcttcttcttccgccctggcagggtctccgca
gaagatttgttgccgtcatg

-continued

*Homo sapiens* stathmin-like 3 (STMN3):

(Seq ID No: 683)

gcgcctctccag
cctccgcaggcccaaccgccgccagcaccatg

*Homo sapiens* nudix (nucleoside
diphosphate linked moiety X)-type motif 13 (NUDT13):

(Seq ID No: 684)

tttcctcttttgtgctgattcctgaggactaggaaggtgccccgaaaagaattcagaga
cctgacaatg

*Homo sapiens* calcium homeostasis modulator 2 (CALHM2):

(Seq ID No: 685)

ctctcttttctggagttagattagtctgaagccgccaccagccccaggccccgtgcaga
agaaaagcgggagggaacggcggaggccgccgctgccctgcaccgccctcctggaggcca
cttggagagtccggccccgaggaggccatggccacaagtgcccacagctggccccaggtt
gccagcgtcgctacagcccagaccaaggcagaataatctccggatgagctggtggcaccg
ctgagcctttggtctcaccagggcttcctgttgctggcaggcggggtggagcggagctgc
tgggaggctgctggataggagagggtcacggctgcggaagaggaggttcttcgggacac
ccgtggatggacacggcaaggaaacaccaggccaaccacagctgggataaaatagcaca
accacacctgccgtccagcgcctcccagcctgtgcccttcctagtaccaccagcaacc
atcaatcccgtctcctcctgcctcctcctgcaatccacccgccacgactatcgccat
g

*Homo sapiens* NMD3 homolog (*S. cerevisiae*) (NMD3):

(Seq ID No: 686)

tcttctctgtggcggagacagccaggttggcagctgacgggacagccggggtc
tatttgttgcgggttttcagcaaatccagggctggtctggaggcgcgaaaact
taaggcatacagaacgatg

*Homo sapiens* ATPase, H+ transporting, lysosomal 50/57 kDa, V1 subunit
H (ATP6V1H):

(Seq ID No: 687)

gcgcctctgtcattc
tactgcggccgccctggcttccttctacctgtgcggccctcaacgtctccttggtgcgg
gacccgcttcactttcggctcccggagtctccctccactgctcagacctctggacct
gacaggagacgcctacttggctctgacgcggcgcccag
cccggctgtgtccccggcgccccggaccac
cctccctgccggctttgggtgcgttgtggggtcccgaggattcgcgagatttgtt
gaaagacattcaagattacgaagtttagatg

*Homo sapiens* DPH5 homolog (*S. cerevisiae*) (DPH5):

(Seq ID No: 688)

gggccttttctctgcacggagccggcgcttttgcagttgcttctgcg
gaaaggtggtagttaagaatttgtaaaggccagagaactacctacgattctctcag
cggtctctcttctcctcaagtttgaaatg

*Homo sapiens* polymerase (RNA) I polypeptide D, 16 kDa
(POLR1D):

(Seq ID No: 689)

cctcctccctccttccgtcctccgcgccttccgtcggtcggtccttgcttcctgcttcgc
ctccgcgcctcgcgctatgggacagagcccccgatccgccagcaccacctgaggatcca
gaaaccgccccagcgatg

*Homo sapiens* HMP19 protein (HMP19):

(Seq ID No: 690)

ctgtcctttcagcaccacaag
ctcgggctgaggagggaggactcctggccgtcctcctcctcttcaaattggctt
gaatcttctctgaccccccacgagtgcagcacagtctgggaagaaaggcgtaaggatg

*Homo sapiens* adiponectin receptor 1 (ADIPOR1):

(Seq ID No: 691)

gcgccccttccggcgcggggagggcgct
gaagatcggggccgctcggccgcaggccgcctccagcgccgcgggatgtagcgcgggg
gaccgcggccccagcagagcccgcctgcccggcttgtctaccatcagagggaga
tctctgcccctggggctgagagaccccaaccttccccaagctgaag
ctgcagggtattgaggtaccagccagatg

*Homo sapiens* SH3-domain GRB2-like endophilin B1 (SH3GLB1):

(Seq ID No: 692)

ttttcccttgggacccgggtccacacggcggggtcgcccgtccatctccggctcgcccgc
ggggcccatcgtcgacgttagcggccgttctccgagccgactgacccatccttggcgctg
ccgccgcgcgcttgttctcctccctcgccccgcctttcatcctccccgttcacggaaacga
cagctgcggctgcggggctggcgccgcctccctccacctaccacgtctgccctcgccgct
ctagcctgcgcccagcccggccgggcacctccgcctcgccgccgctaggtcggccgg
ctccgcccgctgccgcctaggatg

*Homo sapiens* anterior pharynx defective 1 homolog A
(*C. elegans*) (APH1A):

(Seq ID No: 693)

-continued

```
gtccctcttcggcttccgtagaggaagtggcgcg
gaccttcatttggggtttcggttcccccccttcccttcccggggtctgggggt
gacattgcaccgcgccctcgtggggtcgcgttgccaccccacgcggactcccag
ctggcgcgccctcccatttgcctgtcctggtcaggccccaccccccttcccacct
gaccagccatg
```

*Homo sapiens* RNA binding motif protein, X-linked 2 (RBMX2):

(Seq ID No: 694)

```
ctgcctttcccgggcgctgattcctgagtgctgagcgcgaacccgaggagatg
```

*Homo sapiens* family with sequence similarity 82, member B (FAM82B):

(Seq ID No: 695)

```
atctcctttagccccgcccgcctccgtagctgcct
gaagtagtgcagggtcagcccgcaagttgcaggtcatg
```

*Homo sapiens* UTP11-like, U3 small nucleolar ribonucleoprotein, (yeast) (UTP11L):

(Seq ID No: 696)

```
tgatcttttccaaggctgtacagacatg
```

*Homo sapiens* chromosome 14 open reading frame 166 (C14orf166):

(Seq ID No: 697)

```
cgccctctcgccgcgtcgccggtgcctgcgcctcccgctccac
ctcgcttcttctctcccggccgaggcccggggaccagagcgagaagcggggaccatg
```

*Homo sapiens* transmembrane emp24 protein transport domain containing 5 (TMED5):

(Seq ID No: 698)

```
gcttctctttcggagggagtgttcgccgccgccgcggccgc
cacctggagtttcttcagactccagatttccctgtcaaccacgaggagtccagagag
gaaacgcggagcggagacaacagtacctgacgcctctttcagcccgggatcgccccag
cagggatg
```

*Homo sapiens* coatomer protein complex, subunit zeta 1 (COPZ1):

(Seq ID No: 699)

```
gtttcttttgcggctccacgtcggcaccagctgcggggcaagat
```

*Homo sapiens* mitochondrial ribosomal protein S16 (MRPS16):

(Seq ID No: 700)

```
ggttctttctgtgtttgttctctgccctgccaaggccgtagag
ctggtgcgtgcgggtagcggggctctccgaggagccgcacgccggcggcaccatg
```

*Homo sapiens* charged multivesicular body protein 3 (CHMP3):

(Seq ID No: 701)

```
ctacctccttttccgcgggccccgcccaggcggctgcccgtgacctgcctgggcgcgggg
aactgaaagccggaaggggcaagacgggttcagttcgtcatggggctgtttggaaagacc
caggagaagccgcccaaagaactgatatccaaagagaagaagaaaaagtgaaacgatctg
tgaaagatgctgccaagaagggccagaaggatgtctgcatagttctggccaaggagatg
```

*Homo sapiens* RNA binding motif protein 7 (RBM7):

(Seq ID No: 702)

```
cgaccttttggccaggttagggaggggggcgacgctgagatg
```

*Homo sapiens* eukaryotic translation initiation factor 3, subunit L (EIF3L):

(Seq ID No: 703)

```
cgctcttttccggcggtgctcgcaagcgaggcagccatg
```

*Homo sapiens* zinc finger protein 706 (ZNF706):

(Seq ID No: 704)

```
ccttcctttccctccggcgtcctctcccggccctctcgcgctgcac
tgtctctccgacgcaagactgtcccggcccggatatg
```

*Homo sapiens* androgen-induced 1 (AIG1):

(Seq ID No: 705)

```
cgccctccttgccgcccag
ccggtccaggcctctggcgaacatg
```

*Homo sapiens* interleukin-1 receptor-associated kinase 4 (IRAK4):

(Seq ID No: 706)

```
cgcccctcgcggcgcttcctagttcggctggttcttctgtcgccggctt
cagcagcccgcgcccgggcaggaatagaagatg
```

*Homo sapiens* transmembrane protein 66 (TMEM66):

(Seq ID No: 707)

```
cgttccttcgccgccgccaggggtagcggtgtagctgcgcagcgtcgcgcgcgctac
cgcacccaggttcggcccgtaggcgtctggcagcccggcgccatcttcatcgagcgc
```

-continued catg

*Homo sapiens* carboxypeptidase Q (CPQ):

(Seq ID No: 708)

ccgcctctcggccccgcggcctggccggcaagcagggctgcagtcacggggcggcgcg
gagggccccagcccagtcaggggtgtggccgccgccaccgtaaggctaggccgcgagct
tagtcctgggagccgcctccgtcgccgccgtcagagccgccctatcagattatct
taacaagaaaaccaactggaaaaaaaaatg

*Homo sapiens* hydroxysteroid (17-beta) dehydrogenase 12 (HSD17B12):

(Seq ID No: 709)

cgctcttttcattcacgaaggtagtgaggcctagtggaaagccatg

*Homo sapiens* protein phosphatase methylesterase 1 (PPME1):

(Seq ID No: 710)

cctcccctcgatg

*Homo sapiens* HemK methyltransferase family member 1 (HEMK1):

(Seq ID No: 711)

cccccttccggcaggctactgggctccgcccacacacctcccggcctggttcctaaacg
ccagctcggagcaatcccttgggctggagccaaatccctgctgtgattttaaggaagac
cggcaggtccgggcccccaagggtcaaccccacacacatccccgcacttcctgtatgca
ggcctgcgagcgtagagggagtggaattcacagcctcccacccatccgcagggtctcc
tgggaggaacccaccagcgataggaacactgaagctgggctacggcgtccgcccgagcct
ttcttaaaggcgccgaccccggaagcggggcgtccgagggagcgcgcgacgggccacgc
acgtccgggcgtccagttcggggcagcttctccggctggtgggtgggtggggcagccttt
caggcagggtggcaaccaactatatctgaggaccagagccattttggggcaccagagctt
gtgacctctccatctccacccagctgggtccaggggccactctcagcactcacctcagca
gctgacatcataaagcagacttgggaacctggaagcactctggagaaccttccctgaga
catg

*Homo sapiens* N(alpha)-acetyltransferase 38, NatC auxiliary subunit (NAA38):

(Seq ID No: 712)

cgcccttcagttctgcttgctgtcggcaccgctgcgttacccg
gaaccgccgggccgaacagcatg

*Homo sapiens* cleavage and polyadenylation specific factor 3, 73 kDa (CPSF3):

(Seq ID No: 713)

ggttcttcctttttatttaccggtggctgtgcttccaatttag
gaagaccccggcgacctgttcctcaccccgcttcgccctcacactttcgggatg

*Homo sapiens* dynactin 4 (p62) (DCTN4):

(Seq ID No: 714)

tcgcctcctccctccccaa
gatg

*Homo sapiens* hydroxysteroid (17-beta) dehydrogenase 11 (HSD17B11):

(Seq ID No: 715)

gttcctccttgctctcgcccctactctttctggtgttagatcgagc
taccctctaaaagcagtttagagtggtaaaaaaaaaaaaaaacacaccaaacgctcg
cagccacaaagggatg

*Homo sapiens* YTH domain family, member 2 (YTHDF2):

(Seq ID No: 716)

tag
tctttccaggtgttagtcgaaac
ctcgtggtgcgaccctggtcgtcccaaaccccctaggccttaatcctggggcggtggggg
cggggaggccgtgagcacggcttccgctcctccaatccgccagagggcg
cagcggccggcctctcccttcccggggttcttcgcgccgggcccttccgcgtgggtgag
tgaatgtgagag
tcagcgctcgccgcgcgcgccgcccgcctccgctgttcggcgctctgctttaggcggt
gggggcgggcgcgcgcgtaaaagcatagagacgggcattgagctcttgggcta
gagcgtcgccgagtcggagccg
gagcctgagccgcgcgcgtgtctccgctgcgtccgccgaggccccgag
tgtcagggacaaaagcctccgcctgctcccg
cagccggggctcatctgccgccgccgccgcgctgaggagag
ttcgccgccgtcgccgcccgtgaggatctgagagccatg

*Homo sapiens* tubulin, epsilon 1 (TUBE1):

(Seq ID No: 717)

agctctctag
cagagcgccgttgctgggggaatgcagaagcggccgcgggctagcaagctcccg
gagcggcggcgcaccaccatg

*Homo sapiens* ubiquitin interaction motif containing 1 (UIMC1):

(Seq ID No: 718)

-continued cctcctttcttcctcagcgggtccgcggcccgctactctccgggaggggcgcttcccga
cgccaaggtaggcctctcccgacgccggggcggcccttcctgatgccggggtgtgtctct
cgcgacgcggggtgggctccggacgccggggctggccttgccgaagtcggggtgggtc
cctccggacgccgaagtgggctcgggatgcggggctggaccctcccgattccggggcgg
attccggacgccgggaccggccattactggtgccgggtttgggcttctccagatgccgggg
ctgggtccttcccaaggttgagacaaaaggatg

*Homo sapiens* TNF receptor-associated protein 1 (TRAP1):

(Seq ID No: 719)

ccgccccttcccatcgtgtacggtcccgcgtggctgcgcgcggcgctctgggag
tacgacatg

*Homo sapiens* cereblon (CRBN):

(Seq ID No: 720)

cagcctcctttgcgggtaaacagacatg

*Homo sapiens* ribosomal L24 domain containing 1 (RSL24D1):

(Seq ID No: 721)

cttcctctcaagcttggcgtttgtttggtggggttacacgcgggttcaacatg

*Homo sapiens* leucine carboxyl methyltransferase 1 (LCMT1):

(Seq ID No: 722)

taccctcttctgtt
gctttctccctgtggctcgcgccgtccccgccgcccgtcgaccccgcttccatgtccct
ggcggacacagctcccaggaacctccacgccatggccactaggcagagggaatcctc
tatcacctcctgctgttccacctcgagctgcgacgcagacgacgagggcgtgcgcgg
cacctgcgaagatg

*Homo sapiens* RAB14, member RAS oncogene family (RAB14):

(Seq ID No: 723)

cccccttctttgtggtccggcccattgcgagggtgacaggaaaccctgtg
cagggagcgccgccatcttggaccagcccgaggaagatactgagggagcacaggagcag
tcaccgctgccactgctactgccgctactgctgccggcgcgtctgcac
ctctcggcctgccagtgtacctgccggcgcctcggtcgac
cgccccgcccctctcccgctgcgtccgcactcctgttcctggtcctgac
gccccctcccgcccggaaagctgcccagccagcaaccccccagtgccaccatg

*Homo sapiens* Enah/Vasp-like (EVL):

(Seq ID No: 724)

cttccttttcctgttt
ggttttaagtaggctataaaaatcaagtt
gctgtcttcagagggtctgtggtcctctgatcaacataggctggtgggagtacag
gactcgcctcctcagggttcctgtgctgccacttttcagccatg

*Homo sapiens* LIM domain and actin binding 1 (LIMA1):

(Seq ID No: 725)

ctctcttcccctctccctctccctctgccgggtggatgctttctccatgtgg
caaggctgtaactgttcacagctgtctgaaacagcagtggaccaggagcagcttggag
ttttaactttcattttacaaagaacaacatgtttgaatgtttcag
caggcaagttataactggcatctacttcttgttcttctagaacac
cgaaaatctctcccagcactttagaaaggggaccctgactgtgttaaagaagaagtgg
gagaacccagggctgggagcagagtctcacacagactctctacggaacagcagcactga
gattaggcacagagcagaccatcctcctgctgaagtgacaagccacgctgcttctg
gagccaaagctgaccaagaagaacaaatccaccccagatctagactcaggtcac
ctcctgaagccctcgttcagggtcgatatccccacatcaaggacggtgaggatcttaaa
gaccactcaacagaaagtaaaaaaatg

*Homo sapiens* ubiquitin-fold modifier conjugating enzyme 1 (UFC1):

(Seq ID No: 726)

gtttctcttgcgccctggtccaagatg

*Homo sapiens* coatomer protein complex, subunit beta 1 (COPB1):

(Seq ID No: 727)

cacccccttccacgtcagccaaggactctggagccgccgccgccgctgctgcggttcata
gccggagtagacggagccgcagtagacggatccgcggctgcaccaaaccactgcccctcg
gagcctggtagtgggccacaa
gcccccagtcccagaggcgtggtgggtcgggcagagtcggaagaactggctttctagctg
gaagatgcggaaggggagcgactaggccgcttgcgtctgggcctgcagaagggaccgga
ttttctggcatccttaaatcttgtgtcaaggattggttataatataaccagaaaccatg

*Homo sapiens* transmembrane protein 9 (TMEM9):

(Seq ID No: 728)

gggtcttt
gcggctgcagcgggcttgtaggtgtccggctttgctggcccagcaagcctgataagcatg

*Homo sapiens* shisa homolog 5 (*Xenopus laevis*) (SHISA5):

(Seq ID No: 729)

cttctttttctccaaaagggggaggaaattgaaactgagtggcccacgatgggaa
gaggggaagcccaggggtacaggaggcctctgggtgaaggcagaggctaacatg

*Homo sapiens* transmembrane protein 69 (TMEM69):

(Seq ID No: 730)

gtgcctttccagtggacctgggctgttgttgcggttgttttccttctctccgtgcaac
gctggcaagtctcaaagtcgccacagaaacatgcccctgattcag
tgcctctgcttagctgtaacatgttaatcagaactacctggcatcttcctgaacaa
gactttcaataggggccagtatg

*Homo sapiens* kelch repeat and BTB (POZ) domain containing 4 (KBTBD4):

(Seq ID No: 731)

agatcttcttccgggcggacgtggagccggaagcggaggttccgggctc
cgggatg

*Homo sapiens* pipecolic acid oxidase (PIPOX):

(Seq ID No: 732)

cgtcctttagccgg
gagcctgtctttgcttgcctttgcctttgaggctctgtggctgtggggctgagtggcat
catg

*Homo sapiens* blocked early in transport 1 homolog (*S. cerevisiae*)-like (BET1L):

(Seq ID No: 733)

agctctttccccgcgactgcgccac
gtctgaggcggctgtggccgcgtcggtgtccgcgtcgaggagccggggcagggcacgatg

*Homo sapiens* zinc finger protein 581 (ZNF581):

(Seq ID No: 734)

ttctctctcttcggccggcgccgccagttcctgggg
cacacccagaggtccccttctcgccgccgcctgcaactgcgaggg
tagcccggggccgcttggagtcgcccggacctgagaggctgctgcac
tgggcctcagccagccctccggatg

*Homo sapiens* armadillo repeat containing, X-linked 1 (ARMCX1):

(Seq ID No: 735)

cgtccttctaatcctagtcttcgtttggtccggttgcactcttcctatagcccagagggc
gagagggcctgtggcctgggggaaggaggacgaggttctgcctggatcccagcagtagga
cgctgtgccatttgggaacaaaggaatagtctgcctggaatccctgcagatcttgggcc
ggaggccagtccaaccccttggagcaggaagaaacgcaaagttgtcaagaaccaagtcgag
ctgcctcagagccggcccgcagtagctgcagactccgcccgcgacgtgtgcgcgcttctc
tgggccagagcgagcctgttttgtgctcgggttaagagatttgtcccagctataccatg

*Homo sapiens* spastic paraplegia 21 (autosomal recessive, Mast syndrome) (SPG21):

(Seq ID No: 736)

cggcctcccgcacgcaccgcgcagcctgctgtgcccgtgggtcccgag
tgctccgccgcccgccccgacccgggcccagccgcctccacggcccgcgctcgtactg
gagcgaagagcggcctcctgaaggaggggaagggacgtggggcggccacggcaggat
taacctccatttcagctaatcatg

*Homo sapiens* staufen, RNA binding protein, homolog 1 (*Drosophila*) (STAU1):

(Seq ID No: 737)

tctcccttttttccttcttccttcccctcctcgccgccac
cgcccaggaccgccggccggggacgagctcggagcagcagccagagtttattaaccac
ttaacctctcagaactgaacaaagacaacattgttcctggaac
gccctcttttaaaaaagaaagcataaccccctactgtagaactaaatgcactgtgcatg

*Homo sapiens* adducin 2 (beta) (ADD2):

(Seq ID No: 738)

cggccttttgtcagcgcg
cagggccaggagagctctcatttcctcccagcctcgtgcgg
gaaatggctttaattctgacggcagggctgtgagggactagcgggaacccgagccttt
gtcaaggaactgcggcgtcggtggccagtcatccccgccgccgcggagccgctgcac
tgctgggggatctcccagcagctctgacgagcgcgggctgcagcatgggcagaaaac
gctgccctgcagattagctgggtggatttttaagcgcaccccaccccccaaaccca
taaaataacaaaaccaacccgcagtggccgaccggagataagctaagatgccgcgcag
gagtttccacctggatgtttgaggttgtgtagatgtggccggccaccccttgagagtg
gagctaggggggtgcagactgagcagtgaacagaaggagcctt
ggacagggctgggccagcctcccgagttccaggagcgaattgcaaacccaccgg
gaaaatg

*Homo sapiens* WD repeat domain 1 (WDR1):

(Seq ID No: 739)

ccgccttccggctccag
tccccgggctcggcctcggcgaggtgtaattcgcagcgcgggccggccccg
gaggctctcggcgagcgcggcgcggtaacaagtgggcgaggatg

*Homo sapiens* family with sequence similarity 20, member A (FAM20A):

-continued

```
cgacctctacttccac
ctctggccccaagtacagcgccagctgcggcctcgggagcgcccgcggggtgcccgtg
caccggccgcgcctcctccctggcgcgggactcggccgcagctgcctcggaccccgg
cacgatcgtgcacaactttccgaaccgagccccggactgaaccggctggcgg
cagccacagcgggtcgagctccaagttgcaggccctcttcgccaccccgctgtacaac
gtcccggaggagccgcctctcctgggagccgaggactcgctcctggccagccag
gaggcgctgcggtattaccggaggaaggtggcccgctggaacaggcctcag
ttcctgcttttgaaaggaagagggggagtctgtgaccctgaggcctcctt
gcaactctgttttccaagcttttgcacatcttccgaattcttcttcaaagtc
taccctaatgaaatatcagacaattttccaagtgtgcttcatgaacttctgg
gaggtgcttcacagtttctgcaaatgattgaattttcactttgaaaaaa
tatactttaaggcgacacaagatg
```

(Seq ID No: 740)

*Homo sapiens* kelch domain containing 4 (KLHDC4):

(Seq ID No: 741)

```
ttttctttcctggtgtcccgtcgcggcttgggacccggcaagatg
```

*Homo sapiens* calcium channel flower domain containing 1 (CACFD1):

(Seq ID No: 742)

```
tgctccctctcccacaaggcagcgcgccggctcggacgcggccggctac
cgagccctttgtgagggctgtgagctgcgcctgacggtggcaccatg
```

*Homo sapiens* zinc finger, CCHC domain containing 8 (ZCCHC8):

(Seq ID No: 743)

```
gaatcttttccacagcccaaaatg
```

*Homo sapiens* kelch-like 24 (*Drosophila*) (KLHL24):

(Seq ID No: 744)

```
gtttcctttt
gttgtgagctgcgcagagactggtggctggaggagacgccggcgctggagag
tgcgctgcgccgcccgcgctgagggaccgcggggttagccactgctggctgcttccag
tgttcgccgagaggtaccgggggtgacagctccgggaccggccgaaaggcgaggaac
cggtgtggaaattaaaagaacacacatattttgactggggctttgatcaac
caaatgctaaaaagccacataaagaagatccctaatagtcatttctcaacaattata
tagtcaactgatgtaacaatg
```

*Homo sapiens* FtsJ homolog 3 (*E. coli*) (FTSJ3):

(Seq ID No: 745)

```
ctccccctttccaccatg
```

*Homo sapiens* dymeclin (DYM):

(Seq ID No: 746)

```
gcttccctcttctctcgccgcctcctggcctccgcaccgacgcggcccgggctg
gagccgagccggggccgagctgcaggccggaccggagccggatctgtacccgctgagac
gtggaaacatggaggcctgagccggtgtgcgccac
ctgggctgcggcggcgacagcgacttctcctgacccctctgccaccctcccatccgtccg
cgggtccgtggagctggagcagatcccccagccggctgagacaggttgtcttt
ggaaatgcaggtttaaggacaaattatctgcttaagctagaagatg
```

*Homo sapiens* zinc finger protein 280D (ZNF280D):

(Seq ID No: 747)

```
cctcctctttctcctcctcctcagggctccagtcaggccgatccgctccgctcac
ggaaggaaaacagaaataacttgctggcttgtctggag
tcacatgtacttaggtgacaatttacagaaagtcatctctgcagcttgatg
```

*Homo sapiens* ankyrin repeat domain 10 (ANKRD10):

(Seq ID No: 748)

```
cgttccttt
gtgctgcggcggcggcttctcgagtcctccccgac
gcgtcctctaggccagcgagccccgcgctctccggtgacggaccatg
```

*Homo sapiens* SWT1 RNA endoribonuclease homolog (*S. cerevisiae*) (SWT1):

(Seq ID No: 749)

```
ctctcctttggcttggggctccggagttgccac
tgccgccggcgctggtaagcttttcaggatg
```

*Homo sapiens* leucine rich repeat containing 49 (LRRC49):

(Seq ID No: 750)

```
tgacctctttcgggtctcttttgaatctccgctgtagcgtcacctggaaggcagatctaac
agagaacctggactgtctcctatcatg
```

*Homo sapiens* F-box and leucine-rich repeat protein 12 (FBXL12):

(Seq ID No: 751)

```
ccgccttctggacttggtcttagttcccagtcgcggccaaatcac
gcctcagccacctcccgcaagcctctcactgcctcagccacgcttttccaggctggtttct
ggtccccatccgcgcggctggtccggccctgggaccgaatcacttcccagcgagaggaaggt
caaatttctcgaccggctacgggaaggtcgcggccgccgcccgtgtcagccgcctcggcgc
```

-continued
ccccaggaccccucgggtctctttaaccggaagcggaagtgcgtgtcggcgggatcatg

*Homo sapiens* WD repeat domain 55 (WDR55):

(Seq ID No: 752)
cagtccttctcagcatg

*Homo sapiens* zinc finger protein 3 (ZNF3):

(Seq ID No: 753)
cgttcttt
gttctgtccccggtgtgtgggtctgtgacagggtccaacagggcctggtccgtgtccggt
cccccaaatctgtcgtccctgcccccaggcattgg
catcaacaaaagtcagaattcccgggaacttgaacagaggctgctaaattcccag
taattgctccttggccttctagggactgacttcaaagaaggaaggaaa
gaatcaggcagtgcttcctcattctcttttaaaacccgcttcccgctgagtctg
cacccaggagaccagagagcaccttgcccttccatg

*Homo sapiens* tetratricopeptide repeat domain 27 (TTC27):

(Seq ID No: 754)
ggttcttctcctaggcggaagccagaccaga
gagcgtgcgtgttttcccagggtgccccgcgctgctgttatggccgcctcctt
gaggtagtatccgcacatggaattctagggccgcaggtgtatttacgg
taactgtcgccactagatttcagcgcctttggactctcctgttttcactttcttttgtt
gactcccgtgtggccctcgtgggagcctgttttggctgcagcggtgtctgggtgatg

*Homo sapiens* THUMP domain containing 1 (THUMPD1):

(Seq ID No: 755)
gtttctctttcctctcagtttgcgcacaccatg

*Homo sapiens* ankyrin repeat and KH domain containing 1
(ANKHD1):

(Seq ID No: 756)
tgctcttctctcgttcccgagatcagcggcggcggtgaccgcgag
tgggtcggcaccgtctccggctccgggtgcgaacaatg

*Homo sapiens* syntabulin (syntaxin-interacting) (SYBU):

(Seq ID No: 757)
cctcctcctggacggcggcagcggcggcgcgaggagccggcgggcagcggcgcgatg

*Homo
sapiens* coiled-coil-helix-coiled-coil-helix domain containing
3 (CHCHD3):

(Seq ID No: 758)
gcgccttctccttgcttctgggggtcgtggcctt
gctcccgctgtgcgggaaaagaatccaggcccttccac
gcgcgtgtgggtgcgggggccccgaagtgctcgtggttccccgctaggtctccgctgggg
caggaaccggaatcatg

*Homo sapiens* HAUS augmin-like complex, subunit 4 (HAUS4):

(Seq ID No: 759)
cctccttcgtcgcggcctctagtgcactttcggctccttcccctcccgggccttcagc
ttggtctttccgggcctcgcttccccagcccctgcgcccggcccgaacgagaggttccg
gagccccggcgcgggcgggttctggggtgtagacgctgctggccagcccgcccccagccga
ggttctcggcaccgccttgagagcttcagctgccccaggattagaatcccaagaaaatca
aatg

*Homo sapiens* solute carrier family 41, member 3 (SLC41A3):

(Seq ID No: 760)
ccgcctcttcccgccgccgcctgggaggg
gacccgggctgccaggcgcccagctgtgcccagatg

*Homo
sapiens* phosphatidylinositol glycan anchor biosynthesis,
class V (PIGV):

(Seq ID No: 761)
cttccttccagcctcccgccctcgtctgcttccggccctgtggcctggtggggctctg
caggctccctcgggagtggtccttgggccgtggcccctctgg
gaggcctgagggagctcaatcctggtagcaacacccctgaattcctggtggtgaaag
gatg

*Homo sapiens* poly (ADP-ribose) polymerase family, member 16
(PARP16):

(Seq ID No: 762)
agttcctttatccctgggcccaac
ctccccgccgacccgcggtccaggcctcggtctctctcttcggcggcagccgcggccca
gaccccggcagaggacacttgtcggcac
gttctcaccccctgtcatctcagccccctgcctagctccaccccaggcttgg
gaacccggccctgacggccattgtccgcgggcccagccccgcgctgaacgcac
gctcgcccttgcccctaaccagcgcgtctaccccggcaacgcgcagtgacctgggatg

*Homo sapiens* thioredoxin-like 4B (TXNL4B):

(Seq ID No: 763)

-continued
```
gtttctttctgcgcttgtgcgttttctgttcggtttccttcccgctagcggggccac
gagggttgctaggcaacagccctgggtgacttggtcttagggtcctgtccggctt
ggggctgatgaaaggagctgtccgcgcccgggctcttccgagaagtggtt
gctgacagccacaaagtgaaagggagtgaggcggcgtggacgagtaaggagtgacag
tgaggattcacatttgggttatttcaagatg
```

Homo sapiens slingshot homolog 3 (*Drosophila*) (SSH3):

(Seq ID No: 764)

```
cgtccttcctggtcctgcgggtccaggactgtccgcggggtt
gagggaaggggccgtgcccggtgccagcccaggtgctcgcggcctggctccatg
```

Homo sapiens zinc finger protein 692 (ZNF692):

(Seq ID No: 765)

```
ctccctctggggcgcgggcctcagttccgggctacagcagccgacgccgagaggcac
cgtttcttcttaaaagagaaacgctgcgcgcgcgaggtgggcccctgtcttccag
cagctccgggcctgctcgctaggcccggggaggcgcaggcgcaggcgcag
tgggggtgagggcgcgtgggggcgcacagcctctggtgcacatg
```

Homo sapiens tRNA-histidine guanylyltransferase 1-like
(*S. cerevisiae*) (THG1L):

(Seq ID No: 766)

```
tggccctttcctttccgcgtgtagaatg
```

Homo sapiens solute carrier family 25, member 38 (SLC25A38):

(Seq ID No: 767)

```
tctcccttctacagagttcctccggcgcttcctccaccccgggatacacagaacctcat
ctcctacggtgctgaagcctgcagcagggcaggatgggcaggagagcagagccgcggagt
ctgcggcgcgggtgaagagcggcgcgtaattcccgcagcaagattgttccgcgcccgcag
cccctggactagcaggatccgaaccccggcggctgcgtgcttataggcgcagacgtcaga
gagcccgcggcttaaagcgcgtcgcctggctagcgccacccctagccttcttcaaggcc
tccagggctgggcccaagcgcccgtcgacggcaccctgggcccagaggactcgcgggcct
catctccaatg
```

Homo sapiens WD repeat domain 13 (WDR13):

(Seq ID No: 768)

```
agttctttctga
tagcaggcagccatcttgcctggagcctgagaaagggaggagagacagaaggaac
cggcgacagtggtctcagggccgctccggggggcctcaagaaccggaggcagccccg
gaggtggtccccgatcccgggctatgctcttggatctgagaaggggaaggcg
gagggcggcggggacaagatgggtggagaatgtcaagcaaggaatgctaggcgggg
gaggggcgttgctatggcgactggg
gaggggcggtgtctgttctgaatcgctgtgtgtcacccgggcgctgcccaggaaggg
cagggctgggtgatgaccatggtaacacccggggggag
ttcgtgacatctccggcgcggagggactcgatgtctatggcaatggtcgcctggtg
gaagggacggaactagatcccttcgctcgggacgctcacattccaggcccttgtcctg
caggctgccgcgggcggacacgccagaggaggaggccggggaatg
```

Homo sapiens chromosome 1 open reading frame 123 (C1orf123):

(Seq ID No: 769)

```
ccgccttttacgacgcgccggaaagcaacggcaagggcggcagccagcaccgggcgga
gagggctaccatg
```

Homo sapiens chromosome 20 open reading frame 11 (C20orf11):

(Seq ID No: 770)

```
ctgcctccttctactcgggcgccccggcggccgccacctctccccagcccagga
gaggctgcggagccgcagccgcccagaccgcgcagcgcgggaggcaggttccgcac
gaaataaatcagaatg
```

Homo sapiens zinc finger protein 446 (ZNF446):

(Seq ID No: 771)

```
ttccccttt
ggggacagatcccgaagttcgagcatccctcgga
taggccgggtgtcaggcctggtctctcaggcccgtccaggcccatcttgacgattccaa
gaccacccccttgagcaagaatg
```

Homo sapiens mitofusin 1 (MFN1):

(Seq ID No: 772)

```
ccgcccttgccac
tccccctgcctcctctccgcctttaacttctcgggaagatgaggcagtttgg
catctgtggccgagttgctgttgccgggtgatagttggagcggagacttagcataatg
```

Homo sapiens phosphotyrosine interaction domain containing 1
(PID1):

(Seq ID No: 773)

```
agtcctctcgcagctgcgccaggacagccggcgcgcggccgtgcccacaagttgccggca
gctgagcgccgcgcctcctcctgctcgcagcccctacgcccaccccggcggcggtggcca
gcgccaggacgcacatcccgcggacaccgaccccagatgtaaagcgggacccccagccct
cgcccccggcgcgatcgacagtctcgccagcgtctcctctgccaaaacccaggctgga
agatgtggcagccggccacggagcgcctgcaggagagatttgcagacacagaagcggcac
agagaaggccattgtgaagatcaaggcagaaaccggagttatggcatcataagccaag
gaatg
```

*Homo sapiens* pleckstrin homology domain interacting protein (PHIP):

(Seq ID No: 774)

tttcctcctcctcctcctccgcctccgccgcgttgcttgaatggtggagccgaagctcg
gctcgtgaacacacactgacagctataggggcaggcggcggcaccgtccccgcttcccctc
ggcggcggggtgtcccgtcggcggccctgaagtgacccataaacatg

*Homo sapiens* LIM and senescent cell antigen-like domains 2 (LIMS2):

(Seq ID No: 775)

tggcctttttt
gggcgtctccctgctccgcggcccgggctggcgggcgggcgctcggctggcggctgcag
cagcagagggagacccgcggcaaccccggcaacccagggctcggcgtcgctgccaccatg

*Homo sapiens* SCY1-like 2 (*S. cerevisiae*) (SCYL2):

(Seq ID No: 776)

aggtcttttag
tcttttccccctcccttactcttcgtccccggtccctccctcccacccctttccttc
tagctccgacgtttgcggccgcgggggcggcggaggatatggagtaaagccagagtcag
tggccaggcacgaaggcagagcaggaacagccaggaggcgtttattagggggcgggggg
gaaagagccccagcaccgccctcctggaagaaggaagaggtaagtgaccggccgccgg
caccgaccgacctccctcaccggcggctctctcgcctgggctcccggagccggcgag
gagggaatggag
gactcgcgcccgggttaggcctcccagggccgctcaggctggtgggtgtt
gcctggtgacgggcctgccggcggccggccgggcgatcggcggtcggcgcccgcgcaaa
gcggggctggacgagcagcgagctccgggagaccggatccgagagggcgag
tcctcgaaagaggccttgaggcgacgggagacccgggatcgaagtcagctgccg
gagggagagccccccatgccggctcgagagctcgggtttcggtggtggagaacgtag
tacctttcggggacattggacactactctaggaccgggtaactataactacccaa
tattgcagccatg

*Homo sapiens* ring finger protein 31 (RNF31):

(Seq ID No: 777)

caccctctctcctagtacttcctgttctcggctaaccctggcgctgggccggggctg
gagagtgaccgtggtctgagtgacctggggcggctgcgtgggccggggtgggcctcaaa
gccgggcaccagacgg
gaggggcggcgctcgggccgcgcgctgcccgcgccgggtcctggcgggcggcgaggctgg
ggctgactcctgcctcaggatg

*Homo sapiens* mediator complex subunit 9 (MED9):

(Seq ID No: 778)

cgac
ctctggctaacctaccccggagccatg

*Homo sapiens* ATP5S-like (ATP5SL):

(Seq ID No: 779)

cggccccttccggttacgaaac
cttagcaagatg

*Homo sapiens* GPN-loop GTPase 2 (GPN2):

(Seq ID No: 780)

tctccttttgcgcgacacggtctcagctgttccgcctgaggcgagtgacgctggccgcca
acgaggtatacgtactgggaccctcgccctcagtctcgtctccggcgcggctacctgccc
cgttttccctgtgagttgacctgctccggggccgcgggccgccaatg

*Homo sapiens* transmembrane protein 48 (TMEM48):

(Seq ID No: 781)

cggtctcctg
tacgccctagactaggggccgccatctccatg

*Homo sapiens* ankyrin repeat and zinc finger domain containing 1 (ANKZF1):

(Seq ID No: 782)

ttgtcctcttcgctgctccgtagtgacggggattgttgtgtt
gcagaaatccggcaatcgacctgaggacttgcgagccgctcagctcccgggacgttt
ggagctgctgctaaataatttctgctcagccatg

*Homo sapiens* notchless homolog 1 (*Drosophila*) (NLE1):

(Seq ID No: 783)

ggctcttttctcctccacgtggggacgcaggatg

*Homo sapiens* cell division cycle associated 8 (CDCA8):

(Seq ID No: 784)

cgctctctctcactggcacagcgaggttttgctcagcccttgtctcgggaccg
cagcctccgccgagcgccatg

*Homo sapiens* polymerase (RNA) III (DNA directed) polypeptide E (80 kD) (POLR3E):

(Seq ID No: 785)

```
cgctcccccccac
gtgtccgccggagtttctccaccagcaacatggccgccgctgagagga
gagccgggccgccgccgtctctgcagcccgcgggtaactgggccgtt
gccgccgtccgcgctcggccccgcggaga
gatcgagctgaaggactgcgcggctggctctcctctagtatg
```

*Homo sapiens* armadillo repeat containing 1 (ARMC1):

(Seq ID No: 786)
```
gagcctttgcccgccagcgccttcgctctttggctccctgagttagtccggttgctt
gcgatcgccgcggccggggctgcgaaccgaagggctcgctccgcgccgcctgggtctc
tacctcatccgtaggtgtggccctgatggtgtggcaggctctggactcctaaagctctg
gagcgaatttaagatttttattcatgtgcatggcatagaagatg
```

*Homo sapiens* transmembrane protein 33 (TMEM33):

(Seq ID No: 787)
```
ccgtctttctg
gaaacaccgctttgatctcggcggtgcgggacaggtac
ctcccggctgctgcgggtgccctggatccagtcggctgcaccaggcgagcga
gacccttccctggtggaggctcagagttccggcaggtg
catccggcctgtgtgtggcgcgaggcagggaagccgg
taccgggtcctggccccagcgctgac
gttttctctccccttttcttctctcttcgcggttgcggcgtcgcagacgctag
tgtgagcccccatg
```

*Homo sapiens* pyridoxamine 5'-phosphate oxidase (PNPO):

(Seq ID No: 788)
```
ccttccttccccggggtagaagtccagggtgagaaatt
ggttccgaactcaaaggaaccagtgccgggccacagccgggtcac
gtggccggcggccccccatg
```

*Homo sapiens* golgi phosphoprotein 3-like (GOLPH3L):

(Seq ID No: 789)
```
attccttctctgcatcgaaggatcaggaagtttgtgctctctgcgtggctaagttttca
cctactaggacgggggtggggtggggagaacaggtgtccttctaaaatacagcacaagct
acagcctgcgtccagccataacccaggagtaacatcagaaacaggtgagaatg
```

*Homo sapiens* regulator of chromosome condensation
(RCC1) and BTB (POZ) domain containing protein 1 (RCBTB1):

(Seq ID No: 790)
```
cgctcctcctcttcgctgccggtgggcaccgccgctcgctcgcacttctgcgcccatt
ggagcttcggagatccctgcggtcccgcgggacggcgcggcagcagctgacctcgcaga
caggatcttgctctcttgcccagactggaatacagtggtgtgaacacggctcactg
cagcctcaacctcctggactcagagatgtcggcttatttataggaattgcttgaa
gccagagtcatg
```

*Homo sapiens* leprecan-like 1 (LEPREL1):

(Seq ID No: 791)
```
cgtcccttaa
gagcggctggccaggcacggcctccgcctctcagtacgcggagcgccggcggtcac
ctggggctcgcggagcggccagatcgcggcggag
tcggcgcgcttcccgagggaaggtgggagaggggacccggacgcgaggtgccccgaa
gccctctcgagcgtaaccgtcccgcgcctctctgaggcggaggatg
```

*Homo sapiens* hedgehog acyltransferase (HHAT):

(Seq ID No: 792)
```
ctgtctctt
ggctcaggcttggaggcctccgagcagcaacatcgtcccaattatacccgttggag
catcttcagatcttccactcttttcacaacgcaatcaaaatcttcgtacccatttt
gcagtagtgatctctgtaagttgctttacaattcataaagtttattctattt
gatcttcactctaatttacaaagaaaagcagggaagtctatttctgttttacagaggtg
tacagggaggctcacagggggtaagttcacacagtaagccctcgaagctgccagggctg
caaagcccaccctcttccaccgcaccgaactacctccttttcgcctacaaaac
gtaggtggggaccactggtgttggaatgacggcccacctcgag
tttcaggtgacttccactctgcaattaacttgcaggcagcccccagacctg
caatgaacacacgggtgggggagagatatgcacgccaggtcagtgggaac
caacagccgaggggtgagcggggctaggggcccgggccgccggcggggcaaac
gcggttcagaaacgcaggccgcgctctggcccgcccctgcagcagcac
ggcctgctcgccatcgcccggagagcgccgcgggttcccgagtccgggcgcg
gagggcgcgcgggcacggcggcaggggcgtgctcggaggac
gcgcgctgcgctgctcctccaaagggcagctccggggaaagagggtggcgtcccggg
gaagcccgcagccgccgccgatgtcgctgggactcggaagtgccgaaagagggtgtt
gggaactcgcggcgcgcgtgaacgttgccgtcgccgccgcccgggacagcccgga
gaaactctcagcgtaggcatcgggaaccttcgtgccaaggagccatg
```

*Homo sapiens* chromosome 11 open reading frame 57 (C11orf57):

(Seq ID No: 793)
```
cctccttttctctcccaaaccacttcttcccccctaccccccgccacgcgaggctgcggcg
cacggtatgggtgtgtttgtgtgtatttgtgtgggagggcgtttggagggaaggttacc
gggagctccgaggccgctgggaacagggatcccggtgacaaagatggggatatttcctc
tgtcttccacttggaaacctcaaccccgcttcaggctccctagatactttctggggccc
aaccgaaggccgtagccatccaaagcgttcccagccttttctggggagtgaaacttacccc
```

-continued cggggttcgtcctagaggagcgtgagcggggaatgcccaggtcaaccgggctgtccgaat
tccgccccggctcagcctccggcctcagtccgggagagagatctgcctgtcggtctgggc
tgggggaaacgcggcagtggcctgggccacaggtgagggcagagtaaccagtgggaaggc
tgcgttttcacgaaggactcgggtgaagctgcagagctgcctttgagccctgactccttg
gcttcctgggtcggaggagatcttgtaatggagtggttcttcgtctcactagcaagatgc
ctgatttcctcaggatcaagggattgaagaatg

*Homo sapiens* high mobility group 20A (HMG20A):

(Seq ID No: 794)

agtccttcgccg
cattggggcaaaataatcccttcattttgtgaaggtaccgtggaaaa
tatttcattttcttctcaccggagcaattgtaaatgctatgcggtaagaggagttac
ctgtggaaaggtggttaagagattaggtaaagaaaaggaaaggacaccaaaa
taaagtgctgcggaagaattttgtccagctgtgagacgacgag
tgcgtgaagtgaaggcgattgagaggggctgagggaattgtcctctgtg
gaagggactttctttggccctaggcccttcctgcccctgtcgtcagcagagtctc
tacaaggaagataacgactgtaaaattctataaagcaaagctacacatcacttgacac
catacaccatcttggttacataatgaagagagatg

*Homo sapiens* checkpoint with forkhead and ring finger domains,
E3 ubiquitin protein ligase (CHFR):

(Seq ID No: 795)

atgtctctt
gacagcggcggcggcgcagccggttccgggttcggcgcggggcggggatgtgaatcc
cgatg

*Homo sapiens* nucleoporin 133 kDa (NUP133):

(Seq ID No: 796)

ccatctcttcccttaggtgtttaagttccgcgcgcaggccaggctgcaacctgac
ggccagatccctcgctgtcctagtcgtgctccttggagtcatg

*Homo sapiens* CNDP dipeptidase 2 (metallopeptidase
M20 family) (CNDP2):

(Seq ID No: 797)

cttccttccaagaaccttcgagatctgcggtct
ggggtctggttgaaagatg

*Homo sapiens* oxoglutarate dehydrogenase-like (OGDHL):

(Seq ID No: 798)

gcaccccttccgcgcagcccctgacctgcagcctccggacctcgctgcagcgcg
gacccggcccgcccgcccgaatg

*Homo sapiens* transmembrane protein 30A (TMEM30A):

(Seq ID No: 799)

ccgcctcttccgctctacagcg
gaggtggctgtggcggtggcgctggtggctgcggcggcggcggcgg
cagcggcgctcgagcggttcctgtcagggtcagccggcgggcccctgggtggtccac
ctgcaaatcgcggagcggcgcccagggatcgatg

*Homo sapiens* elongation protein 2 homolog (*S. cerevisiae*)
(ELP2):

(Seq ID No: 800)

gcgtctcttgtttgtgcggctgaccagttggcgacatg

*Homo sapiens* WD repeat domain 12 (WDR12):

(Seq ID No: 801)

cgttcttttctttgtatttccgcctctcgcctctctctaaaagccgcagttagaggcgag
atttaggaaaaacctctgccgagtgagcctctggttgggaatatgtatgagaaaaaaaa
ctggcaaggcgttagtcaagcaaagctgaaggcagaggaaatttgatatctggctggagt
ctagaggatttaatgcaaataagatactctgagggcagcgtggcaaaaaaagactacaat
tcccggtggtcacagcgtttgagaagcgatgctttctgagacttgtagtaactaggagct
gtgtttgaactatccaggctcaggacagcctcttgaaaaaaaattttttattaataaagc
ggatttgagtggatcttttcctaatcgattacgggcccacacgtatgggaagaattct
aacaatgattaaagggacatgctacctttacgactatcctttctaatcgatgactccta
aatctaggagtaggtagtcgatgtttgtggtctgggcgtctgtagaagggcaaccctgtg
ctttctgcagaggagaccggagggcagaaggcagagtccaggcttagactgcagttcctc
gcttacctgtgcagtctaattttgagctgcctctttgtagtcttaaaaggcaggagcttc
gtgttgtgggtctgctaacccgtacgtttccgtgggcaagtcgtgtgtactcctcgc
catg

*Homo sapiens* tetratricopeptide repeat domain 17 (TTC17):

(Seq ID No: 802)

cgacctcttcaagatggcgggcgccgga
gactagcttccgcttccggtgtgagcggcccggccgggggggcaagatg

*Homo sapiens* proline rich 11 (PRR11):

(Seq ID No: 803)

ttttctttatggcgtggga
gaggccacagcccggactccatcgactcccccggctcttagactaaaatcatg

-continued

*Homo sapiens* TBC1 domain family, member 23 (TBC1D23):

(Seq ID No: 804)

ctccctctttcttccctctggggaagctcagtgctggacttccgaagacctttac
gacattgagtctcggagttggtctcagcgccggatccacttttcggcaaagtgacgtg
gacgtcaacagcaatg

*Homo sapiens* leucine rich repeat neuronal 3 (LRRN3):

(Seq ID No: 805)

gctcctctctggggagtggagggtgttcagttattaatgaccgctgagcaggcagcac
catgtcagtgtgacaactgatcgggtgaacgatgcaccactaaccac
catggaaacaaggaaaaataaagccagctcacaggatctctcttcactggattga
gagcctcagcctgccgactgagaaaaagagttccaggaaaaagaaggaatcccggctg
cagcctcctgccttcctttatattttaaaatagagagataagattgcgtgcatgtgtg
catatctatagtatatattttgtacactttgttacacagacacacaaatgcac
ctatttataccgggcaagaacacaaccatgtgattatctcaaccaaggaactgag
gaatccagcacgcaaggacatcggaggtgggctagcactgaaactgcttttcaa
gcatcatgctgctattcctgcaaatactgaagaagcatgggatttaaa
tattttacttctaaataaatgaattactcaatctcctatgaccatctatacat
actccaccttcaaaaagtacatcaatattatatcattaaggaaatagtaac
cttctcttctccaatatgcatgacattttttggacaatgcaattgtggcactggcac
ttatttcagtgaagaaaaactttgtggttctatggcattcatcatttgacaaatgcaa
gcatcttccttatcaatcagctcctattgaacttactagcactgactgtg
gaatccttaagggcccattacatttctgaagaagaaagctaagatg

*Homo sapiens* MIS18 binding protein 1 (MIS18BP1):

(Seq ID No: 806)

ggccctctctccgcgcggagccgagccggaactgcggcag
tctctccctgccaggctcttcatccaaggtttctgtggatcccttctgaagttc
tatctgaaaattgcgcttaagtgaattttctgttagaagaacttggttgctactttctt
gtcaagatg

*Homo sapiens* LMBR1 domain containing 1 (LMBRD1):

(Seq ID No: 807)

ccgccccttttaacctttagggtgcgcgggtgcagtatatctcgcgctctctcccctttcc
ccctccccttccccaccccgggcgctcaggttggtctggaccggaagcgaagatg

*Homo sapiens* ST6 (alpha-
N-acetyl-neuraminyl-2,3-beta-galactosyl-1,3)-N-acetylgalactosaminide
alpha-2,6-sialyltransferase 1 (ST6GALNAC1):

(Seq ID No: 808)

cttcctctagaacccgacccaccaccatg

*Homo sapiens* spermatogenesis associated 7 (SPATA7):

(Seq ID No: 809)

gctcctcttttccagtcctccactgccggggctgggcccggccgcgggaaggac
cgaaggggatacagcgtgtccctgcggcggctgcaagaggactaagcatg

*Homo sapiens* docking protein 5 (DOK5):

(Seq ID No: 810)

cctcctccttcctcctcctcctcctccttcttctcctccttctcggccgggag
gaggcagggctggatccctcagccgccgccgctcctcctcctggcaggccggccgcg
gagtcagctgac
gccggcgctccagcctcgcctccccgcgccgcgctctgcgctccccgaaagtggctg
caagccggccgcccactgtcagggttgggggggacaga
gaaagtgatgtgcgccttctaaagcctcgcccagcgccgccgaagcagcttcac
ctctccaactttctcccaccgactgcttgtctt
gaccctgccctccaccctccccagagccacttcgggtgcgcgctcttggg
taaagggggggtcaccggctgtctgggatg

*Homo sapiens* glycosyltransferase 8 domain containing 1 (GLT8D1):

(Seq ID No: 811)

tctcctccatcgcctgcagtaagggcggccgcggcgagcctttgaggg
gaacgacttgtcggagccctaaccaggggtatctctgagcctggtgggatcccg
gagcgtcacatcactttccgatcacttcaaagtggttaaaaactaatattta
tatgacagaagaaaaagatg

*Homo sapiens* cullin-associated and neddylation-dissociated 1 (CAND1):

(Seq ID No: 812)

tggccttttgccctagggagcgagtgcggagcgagtgggagcgagac
ggccctgagtggaagtgtctggctcccgtagaggccctctgtac
gccccgccgcccatgagctcgttctcacgcgaacagcgccgtcgttaggctggctctg
tagcctcggcttaccccgggacaggcccacgcctcgccagggaggggg
cagcccgtcgaggcgcctcctagtcagcgtcggcgtcgcgctgcgaccctggaagcgg
gagccgccgcgagcgagaggaggagctccagtggcggcggcggcggcggcagcgg
cagcgggcagcagctccagcagcgccagcaggcgggatcgaggccgtcaacatg

*Homo
sapiens* BRICK1, SCAR/WAVE actin-nucleating complex subunit (BRK1):

-continued cgctcttcctcaggcggcggccatg (Seq ID No: 813)

Homo sapiens zinc finger CCCH-type containing 15 (ZC3H15):
(Seq ID No: 814)
cggtcttcctcctcgtcctgccgcagggccagaacccctgacggtattcagctgcgcg
taagtctggccggtgccatctgtctccgcaatg Homo sapiens polo-like kinase 1 substrate 1 (PLK1S1):
(Seq ID No: 815)
cggtctccttcggcaaccccggccgaacggccacccagaggctgtgctgagctggcgcag
cggcagcagcatg Homo sapiens dysbindin (dystro-
brevin binding protein 1) domain containing 2 (DBNDD2):
(Seq ID No: 816)
gtttctttcctacgcagccgctcctgccgccgtggtcgctggagctttt
gcctctctaggccggcagcgcctctcctccatggtcctgtctgtcagcgctgttttgg
gagcccgccggtgaggccgggccacgctcagacacttcgatcgtcgagtctgtcac
tgggcatg Homo sapiens KIAA1704 (KIAA1704):
(Seq ID No: 817)
gattcttttggatagggttgac
gttcgtggatagactcatatctgtgaccagtgtccgccaccgcggatg Homo sapiens solute carrier family 25, member 37 (SLC25A37):
(Seq ID No: 818)
cccctccctgcccacctcctgcagcctcctgcgccccgccgagctggcggatg Homo sapiens myoneurin (MYNN):
(Seq ID No: 819)
cgtcctcccaagatggcggagacagag
tgaagaaactgtgttcccccccttgggttgctatcgatcaagggtaaaattccattctga
tatcaaaatg Homo sapiens vacuolar protein sorting 33 homolog B (yeast)
(VPS33B):
(Seq ID No: 820)
gcttctttttctggtagaaggcggggttctcctcgtacgctgcggag
tctctgcggggtgtagaccggaatcctgctgacgggcagagtg
gatcaggagggagggtcgagacacggtggctgcaggtctgaga
caaggctgctccgaggtagtagctctcttgcctggaggtggccattcattcctggag
tgctgctgaggagcgagggcccatctggggtctctg
gaagtcggtgcccaggcctgaaggatagccccccctt
gcgcttccctgggctgcggccggccttctcagaac
gaagggcgtcctccaccccgcgggcgcaggtgaccgctgccatg Homo sapiens zinc finger, C4H2 domain containing (ZC4H2):
(Seq ID No: 821)
aggcctctccaagcccctaccgcacaggctcatagccccaagcccggaggaggtggc
tacattgtgtctattgtatcccttggctggtgtatttgtacatctctcgggac
gtgaaattgacagtgaaaagtatg Homo sapiens BAI1-associated protein 2-like 1 (BAIAP2L1):
(Seq ID No: 822)
cttcctctggcggcgtccggccgcttctcctctgctcctcgaa
gaaggccagggcggcgctgccgcaagttttgacattttcgcagcggagacgcgcgcggg
cactctcgggccgacggctgcggcggcggccgaccctccagagccccttag
tcgcgccccggccctcccgctgcccggagtccggcggcac
gaggcccagccgcgtcctcccgcgcttgctcgccggcggccgcagccatg Homo sapiens solute carrier family 25, member 40 (SLC25A40):
(Seq ID No: 823)
cgtcctctcgcgcctcgctctggccctgcaggttgtgtttccgcctctaccccgcctcc
attccgttgctctctcagtctcagacccgggctctcggtccgccgcttcaggtcttggcg
cagcctcagagagttggcgcggctctgtgttgaccaaacctagtggatgcagttagcgcc
ggagcccggcccgccgtcaccagggttattcccgccttctaggtttgccaggactgcc
ggccctgcagctgccttctgccccaggttttttggctactgatgttacaaacaataaaata
ttggagcatagagttgaagaacagactcaaaccaggttttttatttaattagt
taaaaatatg Homo sapiens protocadherin alpha subfamily C, 2 (PCDHAC2):
(Seq ID No: 824)
tttcctttcctccccctggagctgtagcggcagcagcagcaggaa
gccgagccgggttgagcgactcggaggcgagcgaggagctggaatatgggag
tcagcgaggacggtggggccaggagcccttgggagggcctac
ggagggagcggcccaggcgctttctagagcgtgagcggtggggagcaggcg
cagggtggcacgagcggaggcggggcccgggcgtggggcacggctggggaa
gctgccgcctccggccctgccggctgcctccgccgcggccagtggctatg -continued

*Homo sapiens* chondroitin polymerizing factor 2 (CHPF2):

(Seq ID No: 825)

gttccttttgggttagctttggcagtattgagttttacttcctcctcttttagtg
gaagacagaccataatcccagtgtgagtgaaattgattgtttcatttattaccgtttt
ggctgggggttagttccgacaccttcacagttgaagagcaggcagaaggagtt
gtgaagacaggacaatcttcttggggatgctggtcctggaa
gccagcgggcctcgctctgtctttggcctcatt
gaccccaggttctctggttaaaactgaaagcc
tactactggcctggtgcccatcaatccattgatccttgaggctgtgcccctgggg
cacccacctggcagggcctaccaccatg

*Homo sapiens* thioredoxin-related transmembrane protein 3 (TMX3):

(Seq ID No: 826)

gcttctcttccgctccgggtcggctccgtttcccttttccgggcggg
caggcggcggacccagtgtctttatccctcttttgcacagtcagcttctg
cagctctcccgggctagcatg

*Homo sapiens* ras homolog family member F (in filopodia) (RHOF):

(Seq ID No: 827)

cgacctcttggctccgctagtgcccggcgcgccgccgccagtgctgcgggc
tccgggcaatg

*Homo sapiens* amyloid beta
(A4) precursor protein-binding, family B, member 1 interacting protein (APBB1IP):

(Seq ID No: 828)

ctttctctcaggaaactccactcccaactgacaggtgctatttccagccagtcctatgct
gttgcaaatagtgagtccatgaatgccctctgccgtgtgcattacttattttcatcagca
gatcttcgtaacacactcctggaagtgggatgacgggtcaaaaggcgaatccatacata
agttaaatagatattgctcaattctcttccacggggttcagaccattttggatttctacg
agcaatgaagacagtgctattcctctacaccctggccggccaactgagcgtggttaaacg
tggggaggaggagggtgaggttaccaacctgatggttgagaaagggcctccgcccagcg
cgcccttcctccaccccacccgagagacagctgaactccggccgggacgcgcgtgttgc
cagtccagccctgcaccgcgtcccctgagggcgggctgcaggcggcgcgggaagcttgca
caaccggcccaaagaggaagcccagaaagtgctgaagtaaacactttgggagaccgttg
caacataaagcggcctctcagtctttggtggaaccatcactaggccccaatcccttagtc
cctcttgcgtcgaggctgcaaaatggttccattcgccaggagacgctcctgagagaaggg
cgcgcgcggcacaggggccttccttgcacctcggagcaaagcagctcggatagcgccaca
cgtctgcgcgctgcgtgggaagggcagggctgacagcacttcctccccggggcagcgacc
tggagcccgggtgcggcagtctgcaccgcgcgtcgctttccggccggagtctcgccgcc
ttcccgcgccccgcagcgccccgcagagcagtcgagatg

*Homo sapiens* roundabout, axon guidance receptor, homolog 4 (*Drosophila*) (ROBO4):

(Seq ID No: 829)

ccttccctcttcactgtgagctcagagcagcag
gacaaagtgctcgggacaaggacatagggctgagagtagccatg

*Homo
sapiens* translocase of outer mitochondrial membrane 7 homolog (yeast) (TOMM7):

(Seq ID No: 830)

acctcctttcccttcggattcccgacgctgtggtt
gctgtaaggggtcctccctgcgccacacggccgtcgccatg

*Homo
sapiens* major histocompatibility complex, class II, DR alpha (HLA-DRA):

(Seq ID No: 831)

ttttcttttattcttgtctgttctgcctcactcccgagctc
tactgactcccaacagagcgcccaagaagaaaatg

*Homo sapiens* protein arginine methyltransferase 8 (PRMT8):

(Seq ID No: 832)

cctcctctactatctcggtatcaccaaaccccttgccggctcttatg

*Homo sapiens* adducin 3 (gamma) (ADD3):

(Seq ID No: 833)

ctgcctcttatgaagcaa
tactagagaggaaaaacaaaacccattcctttaagaaagattccgcctcctctcataa
gcaagcgcctaatggtaattgtagagtttactaagtcaaacacttactactcagcatt
gagagaa
gctgctgctgctaatgctgctgctgctgctgccgccgccgccgctgctgctgctgtt
ggtctgaggctgcagtaggtttctgtgcagcattgcagaatccacacctaga
gaacagaagacagacacgtacgtctactacccttgttagaaggaagcttt
ggatcttcggtggataacaagagtaatccacagacttaaaacatg

*Homo sapiens* BarH-like homeobox 1 (BARHL1):

(Seq ID No: 834)

```
agccctttt
ggatctaatgcgcagaggaggtt
ggcccagagctcccgggctcccccaaggctgaactccgtccaaggtgcccg
caggctccctgcccgccttcccatgccagcccgcagctaggggcagggg
cagcggcggctggggttgggggtgggtggggagcttttggggaggacaggtcgcagctt
ggctatg
```

*Homo sapiens* intraflagellar transport 46 homolog (*Chlamydomonas*) (IFT46):

(Seq ID No: 835)
```
ttatcttttgcctagcgactgacaacaggctggttgctt
ggcgtggaatcctaaagtggcctggctttgagactggagtga
gaccccagccctaggctggggttcttccattatagaggagacggattcagaagggc
tacagaccaaggttgttgaaaaccagacatatgatgagcgtctagagattaac
gactccgaagaggttgcaagtatttatactccaaccccaagacac
caaggacttcctcgttctgcccatcttcctaacaaggctatg
```

*Homo sapiens* carbonic anhydrase X (CA10):

(Seq ID No: 836)
```
cccccttttcgggag
gagggaggcagggacttgcaggcaagagttgcacctggtctaggaacctgcagagaaaa
gaactctggggtaagtagtgttctggcactggcacggaaaggggtaaagggtggggg
catgagagggacgaaatggagagggcagggaatgaattatgcaaaaaaatctccaa
tatttcgcagcggagggagagcacagcacagcactcccaggatgag
tcctgcctgggtctcccgcgccgaacccgcagcacgaagttcttttttaagaaga
gaaactcgaaaatcctggagggtaacagaggcagccagggcggggcggagtgcg
gaggcggctgccagggactggggccgaggcggccggccaaggtggcctgaa
gctgtgacacccagcctcctcctcctcctcctcatgccgcgctcagcctcac
ctccccgcccgggcctcctgcctccgccccgggtgccgggctgcggagctgacgctgg
gacgcccggcggcggcgaggacgctcacctggccaa
gcctcctctcctcctcccctcccgccccacctgtcctcctcctctctgagttgg
gaagcgtagggatccgtaggcgaggaaataacgacccctgcagttgtattgcg
gaaaatctgacagcggcgctagttgcgggcgatggaa
gccaggcaactgggggttctggggagttcaggaaaatagcagaggagcag
gaagggcgcgcgacctggagatctgtgtgcccccaccgcgcccag
tccccggggcccagcccttccctcggcgccctggacgcactgccggaacccggctga
gaggctgcaggctgcgcgcggacctggggagcagggagggtcggcg
gaggctgccggcggctggcggtttcgggcaa
taatccctgcctctctttctctgtgtgtctgctgtgtctgctccttccccgccccccg
gaagcaggagaagaactgccccggagcgcagcagccaccctccgac
catgccccggtgagggggcggacttcgagggcaacttgccgcg
gactgcctgggcttagccagcgagctacgcgctcccgggagcccggaattgcacggcg
cagcccggcgggggctatcgtctatgtcttcttggggcgccagac
gaatcggggtctcgttttttgctggaagagcccagtgtt
ggtggcttcaggtggctgctgccgccgccgccgccgccgccgctgctag
tgcggtttccgccgctggtgcgaagagaagagacacgcgagcggggagac
ctccaaggcagcgaggcatcggacatgtgtcagcacatctggggcg
cacatccgtcgagcccgagggagatttgccggaacaattcaaactgcga
tattgatcttgggggtgactgtccctggccggctgtcgggtgggagtgcgagtgtgcac
tcgctcggaagtgtgtgcgagtgtg
tatgtgtgtgtgccgtcgggctcccccttccccccgttttccgtcgag
tgatgcacttggaatgagaatcagaggatg
```

*Homo sapiens* dual specificity phosphatase 22 (DUSP22):

(Seq ID No: 837)
```
cctcctccctgtaacatgccatagtgcgcctgcgaccacac
ggccggggcgctagcgttcgccttcagccaccatg
```

*Homo sapiens* olfactomedin-like 3 (OLFML3):

(Seq ID No: 838)
```
gttccttctactctgg
caccactctccaggctgccatg
```

*Homo sapiens* phosphoribosyl transferase domain containing 1 (PRTFDC1):

(Seq ID No: 839)
```
ccgtcttcccttcccgcgttccccgggagaaacatg
```

*Homo sapiens* translocase of outer mitochondrial membrane 22 homolog (yeast) (TOMM22):

(Seq ID No: 840)
```
cctcctttccgcttccggtgtcccta
cagtcatg
```

*Homo sapiens* arrestin, beta 1 (ARRB1):

(Seq ID No: 841)
```
gctcctcctgctggctggg
gattttccagcctgggcgctgacgccgcggacctccctgcgaccgtcgcggaccatg
```

*Homo sapiens* cytokine induced apoptosis inhibitor 1 (CIAPIN1):

-continued

Homo sapiens leucine zipper transcription factor-like 1 (LZTFL1):

(Seq ID No: 843)
taccctccttccccattttctgtggtccaac
taccctcggcgatcccaggcttggcggggcac
cgcctggcctctcccgttcctttaggctgccgccgctgcctgccgccatg Homo sapiens phospholipid scramblase 4 (PLSCR4):

(Seq ID No: 844)
agccctcccttccgcgcgcttactttgtttataacttr
gaaaaatcctctccgtctcccttccctgcctcctttcctttcctttcctctgccag
tacaactagacccggcgtctggcgtccccggtgcccagcattctgcggggcaggcggat
taattggaattcttcaaaatg Homo sapiens ectonucleoside triphosphate diphosphohydrolase 7 (ENTPD7):

(Seq ID No: 845)
cctccttccggctgggcaaggggccgcggggagcagctcgggactgaac
cgagaggtgccgaaggaaccggcgggccgcttgatcccgctgcagacgtagga
gatgcctgggacaaggaggccaccttctcagggcaaaagaaaaa
gaaggtgacaggcgttgagaccaccgaagggaacccatg Homo sapiens fascin homolog 3, actin-bundling protein, testicular (Strongylocentrotus purpuratus) (FSCN3):

(Seq ID No: 846)
agttctctctgg
gaacatctggtgggtactacaggccctattccaggccctatggcctgtggaacctcac
cacgggggggagggctgggccagacggagacatcacctgtggtgtcagccccatg Homo sapiens X-prolyl aminopeptidase (aminopeptidase P) 1, soluble (XPNPEP1):

(Seq ID No: 847)
cctccttcgcgccggcccttccgcgggtgatcagctggtctgcgctcccctgac
gtgggctggggcacgtcaccgccgaatg Homo sapiens REX4, RNA exonuclease 4 homolog (S. cerevisiae) (REXO4):

(Seq ID No: 848)
gggtctcttccggagtcttttcctggac
ggggtccctgcggtgggtgtgtttcggcctggcctgggcaggcgctt
gtgctgccaggcggcgccgggcccggg
gaggccggggtctcgggtggccgccggcccaggcgctggacggcagcaggatg Homo sapiens LYR motif containing 4 (LYRM4):

(Seq ID No: 849)
ttttctttccaaaatg

Homo sapiens DEAD (Asp-Glu-Ala-Asp) box polypeptide 24 (DDX24):

(Seq ID No: 850)
ggttcttcactcgcgactgacggagctgcggtggcgtctccacacgcaac
catg

Homo sapiens transmembrane protein 159 (TMEM159):

(Seq ID No: 851)
ccttcttcctcttgttcctcctcctgcctctcttcgcttcgcctgcaaac
gcggtggggctgctcggcggtcaggagcaggttaccctccgtctgcatgcccac
catcaaggtatgaggatggtagaagctctcgtcgaaccagatggatgaagaccactaac
ggcttttgtttcctctggtaacagcaagagacagagcgacatgagagattggac
cgcgggctgcactgagaatttactggtaggataattcatccctaaaga
gattgaagtgagcttcagaatg Homo sapiens NDRG family member 4 (NDRG4):

(Seq ID No: 852)
cggcctccgcccctg
cagccgcgggcacgcggagggggctcctggctgcccgcacctg
caccccgcgcgtcggcggcgccgaagcccgctccccgcctgcgcgtctgtctcgtccg
catctccgcggcctcctgctccacgacgtgaccatg Homo sapiens pre-B-cell leukemia homeobox interacting protein 1 (PBXIP1):

(Seq ID No: 853)
ttttcttctcgggctgcaaacaaagggaagcctgcaacaagttaa

-continued
gctgaagaccgaagcaagagctggttcaggtggcagccacagcagcctcagggac
ctcagcaactatg

*Homo sapiens* twisted gastrulation homolog 1 (*Drosophila*)
(TWSG1):

(Seq ID No: 854)

ctgtctctttaaggtgcccgaggctcgcgggcgctgcgctgaggggac
ggcgggaggcgcggcctggcctcgcactcaaagccgccg
cagcgcgccccgggctcggccgacccggcggggatctaggggtgggcgacttcgcgg
gaccgtggcgcatgtttcctgggagttactgatcatcttctttgaagaaacatg

*Homo sapiens* zinc finger protein 286A (ZNF286A):

(Seq ID No: 855)

gtccccttt
gtgaggcccggatgggaggtgcccggttcccccagggacagcttcaagcgg
tagggacagacatctgag
gacccagcctcaggatgctgtccccgggcttccaggctccagcgccgtag
gactgaggcagactccacggtgagaaaga
gacccgatctaacccaggcctttcatcagagcccaggagggaaggcaggaagtgggac
cacgaggcccgggggcttctaactcgtctggcagggagatctgaattggggtgaa
gagcagaatctccagaacaaggaggaggtggtgatcatg

*Homo sapiens* S100 calcium binding protein A14 (S100A14):

(Seq ID No: 856)

gctcctcctgtctt
gtctcagcggctgccaacagatcatgagccatcagctcctctggggccagc
tataggacaacagaactctccaccaaaggaccagacacagtgggcaccatg

*Homo sapiens* ANKHD1-EIF4EBP3 readthrough (ANKHD1-EIF4EBP3):

(Seq ID No: 857)

tgctcttctcgttcccgagatcagcggcggcggtgaccgcgagtgggtcggcac
cgtctccggctccgggtgcgaacaatg

*Homo sapiens* KIAA1143 (KIAA1143):

(Seq ID No: 858)

ctgtctttacccagagctaccatg

*Homo sapiens* neuroligin 4, X-linked (NLGN4X):

(Seq ID No: 859)

ctctctttttctt
gcagaaccgtctctctcccttctctgtctcttagcacagagctcttattcagccac
tagcttggcccttcctgcttcaattgtaatgcttgttctgcccgtccacagac
tattggcggcagaaacaacgaatttcctccaaactaggcgtgttggtggctctt
gcattcctctggatgaggaaatctagttggggggttccagaaggg
gaaggctcctgggctttcaatacatcctcctgaatcatacctcgtttcgggttcccta
gaaaaatctggacgtgtaaaaagaactcttaacggccgatgcagctcttccaaa
gctaaggctgccttggagttttcataagaaattgtccctggaggtgtt
ggatgatcacagcttccttggagcattgcagttgctggaatccagtttcaggat
taagggagggctgcctccttgcaatgggctgccaagaaaacggctgtgctt
gttcttaacctcaggctctgtctgtgatcagtctgagagtctctcccaggtc
tactgctccctggaaagccctatctctctgcaggctcgcctctgggctttgtctcctt
ggagccacatcactgggacagctgtggatgtggatgcagatttgaaccatg

*Homo sapiens* mitochondrial antiviral signaling protein
(MAVS):

(Seq ID No: 860)

ccgcctcctcgctgcgg
gaagggtcctgggccccgggcggcggtcgccaggtctcagggccgggggtacccgag
tctcgtttcctctcag
tccatccacccttcatgggccagagccctctctccagaatctgagcagcaatg

*Homo sapiens* serine incorporator 1 (SERINC1):

(Seq ID No: 861)

ctgtctccatctt
gtctgtatccgctgctcttgtgacgttgtggagatg

*Homo sapiens* KIAA1324 (KIAA1324):

(Seq ID No: 862)

cctccccttttttttccgccttctgccagcagaagcagcagccgcagcacctgagccgc
tactgccgctcactcaggacaacgctatg

*Homo sapiens* synaptotagmin IV (SYT4):

(Seq ID No: 863)

ggacctccctcttt
gcctcctccctgttccaggagctggtgccctgggctctgcgctgtt
gttttcagcgctccgaaagccggcgcttgagatccaggcaagtgaatccagccaggcag
ttttcccttcagcacctcggacagaacacgcagtaaaaaatg

*Homo
sapiens* pyruvate dehydrogenase phosphatase catalytic subunit
2 (PDP2):

-continued

Homo sapiens gephyrin (GPHN):

(Seq ID No: 864)
cttccttctggagctgggtcctgactagggac
cgcctgggtgaggtgaggacctggtggccgcagttgtggcactgtgcg
caggcgctgaactgaccggacggagcgggcggctgtggcctcgccagctggtttaaaaa
tatcctttttgctgaaggaacacatttgctggtatagtttcagaatg Homo sapiens gephyrin (GPHN):

(Seq ID No: 865)
ctatcctttcctctcagtcctgccatctagctgccttgggtctcgcgctccgcagagcgt
tccgacactctccggcctcgttctgccgcctccgcgcgctctcccgtgccggccaccgcg
ccccccaagcttgcctccttcttgccggacttggggccgcgcgccctgactccttccct
cccgcggacccgcgcactcccggcgcggcctctccccacgcaggccaccgtgcactctg
tggcctcccctccttcccgctctcctcgcgcttctctggctcctagctgtcgcgctc
tcctcggcgagcgcgctcccggcccgcgcgctccgggctccggtttctcccggctcctgt
cagtgcggtgactgcgctgggaaacatg Homo sapiens deltex homolog 2 (Drosophila) (DTX2):

(Seq ID No: 866)
ccttctcctgagagtcggagccacagccagagccctgcccaggccgagccggagctg
cagcccgagcgcggtggtgccctcagcccgtcctctt
gtcctcctcagcctcggtgccttggaatttgtgtcgctgagtcagcaagcctttcagat
ttgcccggttttgttgtttgtggtttgtatcaagatgg
gaactcaaacaagtcattcctcctaaggagctggtgtcttcatccagaagggacagttt
gtgccagctctccagagagaaaaggatctggtactgttctggagtggcctgtagcaga
cactgaaccaccagccagctgcatttgttgtcctggaagtcattgccaactctgccag
tcacactggggtccccagagaagtcaagatctgccggaggcgctgggcaatgaccccgg
gactccaggccagaggggtctgaagctgtttgggaaagcagcgggactccttgggaa
gatg Homo sapiens melanoma antigen family E, 1 (MAGEE1):

(Seq ID No: 867)
ctgccttttcaccacctctaatttcagcttcagcagttgcttggaactttggttctgg
cagcagcagcaacatcattaccgctagcggcagttttgtgccgaggcacctacacac
ctcccgtcctctctgccagatcgcggggcctgtcggtgtctgctcctacacgccaac
gccggtgggcaggaccatg Homo sapiens G protein-coupled receptor 107 (GPR107):

(Seq ID No: 868)
cgcccttttcaccccggacgtgggcgggagaggaagcggctggtgatgctg
gaacaaacatg Homo sapiens PDZ and LIM domain 1 (PDLIM1):

(Seq ID No: 869)
cgctctttctccgacagctgccgggggtgccctgcaa
gctgttccgcgcgtcctgcccgtctgtccccgcgggtcgtcgcccgccacagccgcgc
catg Homo sapiens thymosin beta 10 (TMSB10):

(Seq ID No: 870)
cgctcttttgtttctt
gctgcagcaacgcgagtgggagcaccaggatctcgggctcggaacgagactgcac
ggattgttttaagaaaatg Homo sapiens phospholipid scramblase 1 (PLSCR1):

(Seq ID No: 871)
agaccctttcagacccttttccggctgacttctgagaaggttgcgcag
cagctgtgcccggcagtctagaggcgcagaagaggaa
gccatcgcctggccccggctctctggaccttgtctcgctcgggagcggaaacagcgg
cagccagagaactgttttaatcatg Homo sapiens eukaryotic translation elongation factor 1 beta 2 (EEF1B2):

(Seq ID No: 872)
gggtccttttcctctcttcagcgtggggcgcccacaattt
gcgcgctctctttctgctgctcccagctctcggatacagccgacaccatg Homo sapiens pyrophosphatase (inorganic) 1 (PPA1):

(Seq ID No: 873)
ggctctctccttgtcagtcggcgccgcgtgcgggctggtggctctgtggcagcggcggcg
gcaggactccggcactatg Homo sapiens X-ray repair complementing defective repair in Chinese hamster cells 5 (double-strand-break rejoining) (XRCC5):

(Seq ID No: 874)
ggctctttccgctatctgccgcttgtccaccggaagcgagttgcgacac
ggcaggttcccgcccggaagaagcgaccaaagcgcctgaggaccggcaacatg Homo sapiens GATA zinc finger domain containing 1 (GATAD1):

*Homo sapiens* enolase-phosphatase 1 (ENOPH1):

(Seq ID No: 876)

ccgccttttccag
ttccaggtgtgcagaagtgtcctctcccacgcgcggcgggctgcactt
ggtcgctggctccgagatcgcgcggggccgccggaagcccaagacggtaccgggggccg
cagccgcagccggcgccgccctccgccctccccaacagcaggccgagtcccgtag
catccggtagggaaatg

*Homo sapiens* regulation of nuclear pre-mRNA domain containing 1B (RPRD1B):

(Seq ID No: 877)

agctctttccggggggcccggggaactactctcctt
gcctcgctctgtctccttcgaaagtgctctgcgcgaggttcagagcggccgccgcctccaa
agggacggttttctagagctccgacgcctctcggtgccctctgctccggccctt
gccctttgacctcgctctcgcggcagggtgagaggtcgggtggccatctt
gtggcggcggcgcggcggctgttactgcggagacccatcccctccccttctcg
caccccctggcagtctgtcagtcggtaaaaagtcccg
cagcctgtcaggtgaggcccggcctcgtgccgtcgctcttcccgccgcac
tgggcggcccaggccgctccctgccggggcctcactgccgccaccatg

*Homo sapiens* family with sequence similarity 60, member A (FAM60A):

(Seq ID No: 878)

ctatctttctagacaaggcagttgaggaggagggagcgcttgagggg
gactggcctggcgtgcactccgcacctcggggacattattgcgcgtggaac
ggctgcttttggaaggcacaacttcctgaatggaccatgactcccaccaaa
gatccctgtctctgattcaccaaacagcttcaaccctgaaaccaggacgagaagtt
gacaacatctgagtggacagctaattgacctaagacttcagaccagac
tattgcccagaagaaaagatg

*Homo sapiens* MID1 interacting protein 1 (MID1IP1):

(Seq ID No: 879)

gggccttttatctcggtgctgccggggggaggcgggaggaggagacaccaggggtggccct
gagcgccggcgacacctttcctggactataaattgagcacctgggatgggtaggggggcca
acgcagtcaccgccgtccgcagtcacagtccagccactgaccgcagcagcgcccttgcgt
agcagccgcttgcagcgagaacactgaattgccaacgagcaggagagtctcaaggcgcaa
gaggaggccagggctcgacccacagagcaccctcagccatcgcgagtttccgggcgccaa
agccaggagaagccgcccatcccgcagggccggtctgccagcgagacgagagttggcgag
ggcggaggagtgccgggaatcccgccacaccggctatagccaggcccccagcgcgggcct
tggagagcgcgtgaaggcgggcatccccttgaccggccgaccatccccgtgcccctgcg
tccctgcgctccaacgtccgcgcggccaccatg

*Homo sapiens* transmembrane protein 35 (TMEM35):

(Seq ID No: 880)

ctctcccttt
gtcattctagctgcctgctgcctccg
cagcgtccccccagctctccctgtgctaactgcctgcaccttggacagagcgggtgcg
caaatcagaaggattagttgggacctgccttggcgaccccatg

*Homo sapiens* Fc fragment of IgG, low affinity IIa, receptor (CD32) (FCGR2A):

(Seq ID No: 881)

cttcctcttttctaagcttgtctcttaaaacccactggacg
ttggcacagtgctgggatg

*Homo sapiens* tribbles homolog 2 (*Drosophila*) (TRIB2):

(Seq ID No: 882)

cttttctcttttttgtttggcttctaacgcgttgggactgag
tcgccgccgtgagctccccgaagactgcacaaactac
cgcgggctcctccgccccgtctgcgattcggaagccggcctgggggtcgcgtcgg
gagccctggcgctgcagctccgcacccttagcagcccgggtactcatccagatccac
gccggggacacacacagagtaactaaaagtgcggcgattctg
cacatcgccgactgctttgggtaacaaaaagacccgagttgcctgccgaccgag
gaccccggggagccgggctcggagcagacgaggtatccggcggcgcccattt
gggggcttctaactcttttctccac
gcagcccctcttctgtccctcccctctcgctcccttttaaaatcagtggcac
cgaggcgcctcagccgcactcgccagcgactcatctctccagcgggttttttttt
gtttgtcgtgtgcgatcctcacactcatg

*Homo sapiens* family with sequence similarity 3, member A (FAM3A):

(Seq ID No: 883)

-continued
cgtcctctccgggggcggagcgggtcggcgggcctgacagggaac
ctccctgaccgagcccacgtctccccacggccagagaaatctccggcccggcccg
catcgccagccccaggcccggaggaacggcccgagcccaggagaac
cacatcttcgtcccagcccggaggctcctgtgggcaagatcgtgagccaac
gggttcctgaggcccctcctggccaggcagggtttccccgcgcgtttccgag
gagccctgcctggccgggcggctggacaaacaggtcgtagcac
cgatcgcgcccgcccccagcagggtcccgcacaggctt
gcccctgaccccacccaaacctgtccttccgctttgccccaaacagtgcactt
gccggcggtcccaacccagcaggagaagtggacatg Homo sapiens exocyst complex component 4 (EXOC4):

(Seq ID No: 884)
ggctctccccgcgtccaagatg

Homo sapiens ELOVL fatty acid elongase 5 (ELOVL5):

(Seq ID No: 885)
gcgccttcctcttcccatcgcgcgggtcctagccaccggtgtctccttctacatccgcct
ctgcgccggctgccacccgcgctccctccgccgccgccgccttgctgctgctcaaagctg
ctgccgccccttgggctaaaaggttttcaaatg Homo sapiens apolipoprotein B mRNA editing enzyme, catalytic polypeptide-like 3G (APOBEC3G):

(Seq ID No: 886)
ctttctctttcccctttgcaattgcctt
gggtcctgccgcacagagcggcctgtctttatcagaggtccctctgccagggg
gagggccccagagaaaaccagaagagggtgagagactgaggaagataaa
gcgtcccagggcctcctacaccagcgcctgagcaggaagcgggaggggccatgactac
gaggccctggggaggtcacttaggagggctgtcctaaaaccagaagcttggag
cagaaagtgaaaccctggtgctccagacaaagatcttagtcgggactagccggccaag
gatg Homo sapiens gamma-aminobutyric acid (GABA) B receptor, 1 (GABBR1):

(Seq ID No: 887)
gctcctcctcctccctccgtcggtcagtcagtccgcgaggagag
tccgcggtggcggcgacggtggcgagagccgcggggggccgtaggaagccaac
cttccctgcttctccggggccctcgcccctcctccccacaaaatcaggatggaggcgc
ctccccggcacccctcttagcagccctccccaggaaaagtgtccccctgagctcctaac
gctccccaacagctaccctgccccccacgccatg Homo sapiens cofilin 2 (muscle) (CFL2):

(Seq ID No: 888)
cctccttctcctcccag
tgccacagagccgaagcccgagctgccgccgcagccacagccgagggcactatg Homo sapiens DEAH (Asp-Glu-Ala-His) box polypeptide 35 (DHX35):

(Seq ID No: 889)
tgaccttttaccccaacatg

Homo sapiens resistance to inhibitors of cholinesterase 8 homolog A (C. elegans) (RIC8A):

(Seq ID No: 890)
ccgccttccccggcgcgccatg

Homo sapiens FK506 binding protein 10, 65 kDa (FKBP10):

(Seq ID No: 891)
ag
ttctttgtagtgcctccctcagactctaacacactcagcctggcccctcctcc
tattgcaaccccctcccccgctcctcccggccaggccagctcag
tcttcccagcccccattccacgtggaccagccagggcgggggtagggaaagaggacag
gaagaggggggagccagttctgggaggcggggggaaggaggtt
ggtggcgactccctcgctcgccctcactgccggcggtcccaactccaggcaccatg Homo sapiens small ArfGAP 1 (SMAP1):

(Seq ID No: 892)
cctcctcccgttccagctgccgctgccgcttcctgggctgag
tccgcccgcggtcccggcggcgccaggtgcgttcac
tctgccggctccagccagcgtccgccgccgccg
tagctgcccaggctccccgccccgctgccgagatg Homo sapiens chromosome 14 open reading frame 93 (C14orf93):

(Seq ID No: 893)
cctccttttgcacacacacgaatacaaagagccatacgaccttcggatgccggaaggtc
cttctgaatcccttccctgttccttaggttgcactagtcgggggttccatgctgggggc
agaaggaatgctctctaccgtctgaaaccgttcatcaggaggccttgatttgtgatgtg
ctaggagagcacaggatctgcaaatagaaggcacctgtctcccttctgcaggccgaggag
aggccgccatgactgtgtgcttcttcatggcttgtttactcttcttcacagaccctac
agcttggggcctgggctcctctgaccatcctcattgagaaaggaaagtgagtccagaa
gttgatgcttcctacctgttggagcggcccagcagtgtaagcgtggttgttactgccca -continued tccgccatg

*Homo sapiens* brevican (BCAN):

(Seq ID No: 894)

cgccctcttccgaatgtcctgcggccccagcctctcctcacgctcgcgcag
tctccgccgcagtctcagctgcagctgcaggactgagccgtgcaccggagga
gaccccggaggaggcgacaaacttcgcagtgccgcgacccaaccccagccctggg
tagcctgcagcatg

*Homo sapiens* H2.0-like homeobox (HLX):

(Seq ID No: 895)

cggcctctcttcctcag
tgcgggcggagaagcgaaagcggatcgtcctcggctgccgccgccttctccgg
gactcgcgcgcccctccccgcgcgcccacccaccccagtccggctggactgcgg
cagccgcgcggctcaccccggcaggatg

*Homo sapiens* v-rel reticuloendotheliosis viral oncogene homolog A (avian) (RELA):

(Seq ID No: 896)

ccgcctctggcgaatggctcgtctgtagtgcac
gccgcgggcccagctgcgaccccggccccgcccccgggaccccggccatg

*Homo sapiens* zinc finger protein 277 (ZNF277):

(Seq ID No: 897)

cctccttttctttttctgccgggtaatg

*Homo sapiens* globoside alpha-1,3-N-acetylgalactosaminyltransferase 1 (GBGT1):

(Seq ID No: 898)

cttcctcttttctgtctggcccgcggccccgctgcctgccctgctccaggctccac
ctgcgccgccgatcgcccgggtatcgcggggcccaggccagctgag
tccgttttccgcgccggggtggcgcccctccaacgtcctaacgccgggccggcag
caaggagtgttcctgggacctcagagaccaggctcagagcctgacatccctgcgaggg
gacagcctcatccgcccaggccagtgggggtctctacaagtgcccaggctcaggtg
cagcccccagcaatg

*Homo sapiens* FXYD domain containing ion transport regulator 6 (FXYD6):

(Seq ID No: 899)

ggtcctcctgggagtctcggaggggaccggctgtgcagacgccatg

*Homo sapiens* nuclear RNA export factor 3 (NXF3):

(Seq ID No: 900)

tcctctc
tatgcttggggaaggaacttcctgtaagcaaggcttgaggcttgctctcgccttcgtcag
cagccctcctcaatcttctccaaactcccgtcccaggccacacagattctcctcaaga
gagccctataaggacattggtaaaatg

*Homo sapiens* chromosome 14 open reading frame 133 (C14orf133):

(Seq ID No: 901)

attcccttccgccccttctctaagctgcacagcctgaatagaagggctggtccagcggc
ggcggaggctggcgctgtcctgagagggagggctctgtgcggaagagtcagggcgaccct
tgggcgctggagtacgcttgggactggggctgcgagtgagcaccagcgattggttcggaa
gcggacatttggttcagaacgagcatttaactctgccagggatccgctgggctctgacga
ctgcggtagatccatggcttcctggacgttcacccgtagagtcatcctagcttaactctt
gttccctggtctcagttcacaagcctcacctgtatcttcctggctcggaagataattgaa
accaagtctgacttctcaatg

*Homo sapiens* X-prolyl aminopeptidase (aminopeptidase P) 3, putative (XPNPEP3):

(Seq ID No: 902)

ctttctcttcccgacgcgtgag
ttaggccgtaatg

*Homo sapiens* death inducer-obliterator 1 (DIDO1):

(Seq ID No: 903)

ggccctctggcaagatggctgctgcggaggcgttggagcgcggaaatctggaaccgg
gatggcgacgtctacactgagtcggaggcgaaggagcttactccacgg
gaacagcctctagataatctgagttgttgaaaatacgaagcctgttactcgtgaacag
tggctgacaacagtgttgttgtgagcctggctgtctgctt
ggacccagagggtttcgtctgccaggttttttggttgtatttaggat
ttcagggaaaagtgtccaagctttcagtgttggagcaggtatg

*Homo sapiens* PERP, TP53 apoptosis effector (PERP):

(Seq ID No: 904)

cggcctcttcgcttttgtggcggcgcccgcgctcgcaggccac
tctctgctgtcgcccgtcccgcgcgctcctccgaccgctccgctccgctccgctcggcc -continued ccgcgccgcccgtcaacatg Homo sapiens tubulointerstitial nephritis antigen-like 1
(TINAGL1):

(Seq ID No: 905)

tcctctcttgactttgagcgtccggcggtcgcagagccaggaggcg
gaggcgcgcgggccagcctgggccccagcccacaccttcaccagggcccaggagccac
catg Homo sapiens eukaryotic translation initiation factor 4H
(EIF4H):

(Seq ID No: 906)

ggttcctctcggagcggagacggcaaatg

Homo sapiens non-SMC condensin I complex, subunit G (NCAPG):

(Seq ID No: 907)

cccctctcgcgggaattatttgaacgttcgagcggtaaa
tactccctggggctgtcatagaagactactcggagagcgctgcctctgggtt
ggcgggctggcaggctgtagccgagcgcgggcaggactcgtcccgg
cagggttccagagccatg Homo sapiens MMS19 nucleotide excision repair homolog
(S. cerevisiae) (MMS19):

(Seq ID No: 908)

tatcccctcccacggtctctagttcgcgttatg

Homo sapiens DnaJ (Hsp40) homolog, subfamily C, member 1
(DNAJC1):

(Seq ID No: 909)

ctgcctctacagctgtgtgtaggcctgggggcgagggtcttcggaac
gtagcgctggctgcggccccgcccgcctacccacccgcccgtccgg
cagccggctcccgccgcctccgcgctctgtctggggccagccac
ctggcgggccgctccggtgcgcctgcccgcgcttttcac
tgacaggcgctgttccccacagccagcgccgcccgccacgtcccagctctcggccaac
ggagctgcgcggcgggtgacctttccgagcccagcgcgatg Homo sapiens stimulated by retinoic acid gene 6 homolog
(mouse) (STRA6):

(Seq ID No: 910)

ctacccttcatctctgcaactccttcctccctgggcctcccttctggtgtgtctgtggg
tctgtctaggtgggcttgggaaaggggaaggaaggggcgtctctttaggcagctcagact
ggacaagccttcttt
gaaaatggtcctttgaacacacgcctgctggtggttggtcagacagatgcgccagcgg
gagccccggggccccaaggggacagctatctctgcaggaccagtgcgatg Homo sapiens 5-azacytidine induced 2 (AZI2):

(Seq ID No: 911)

cagcccctttccggctgagagctcatccacacttccaatcactttccggag
tgcttcccctccctccggcccgtgctggtcccgacggcgggcctgggtctcgcgcgcg
tattgctgggtaac
gggccttctctcgcgtcggcccggcccctcctgcctcggctcgtccctccttccagaac
gtcccgggctcctgccgagtcagaagaaatgggactccctccgcgacgtgcccgag
cagctcccttcgctgtggaagcggcggtgtcttcgaagaaaccggaa
gcccgtggtgaccctggcgacccggtttgttttcggtccgtttccaaacac
taaggaatcgaaactcggcggccttggggcggcccctacgtagcctggcttctggttgt
catg Homo sapiens polymerase (RNA) I polypeptide E, 53 kDa
(POLR1E):

(Seq ID No: 912)

acgccttttccggcccg
cagcgcggcctgggctcccgcgtgtttaaaagtgcgctt
gtggctgctgctgtcttaactcctgtgcttggcggacagacaggcgagatg Homo sapiens mitochondrial ribosomal protein S25 (MRPS25):

(Seq ID No: 913)

agtcctttctcgtcgctgctcggctcgcggcccgtggggtcggccccgccaccgtt
gccgccatg

Homo sapiens TRM2 tRNA methyltransferase 2 homolog A
(S. cerevisiae) (TRMT2A):

(Seq ID No: 914)

cggcctccgccgcacgcgctggcggactaagag
tggctggcgaagcgagcggccggcgcgggcccctggcgggcgggcggtacagccccaa
gcctgagacccggacctgagcatcgcaggttcgagtcccgccccgcctggggcgaa
gccggggtggcggcgacctcgcggcgttgcaccggctctgtgagcac
ctcccctctgagcacttcccttgtgacaggccacttcccttgtgacaggccaggac
gaggtggccaggcggcccccatggcgtccctggtctaggcggagaaccgcctgggcgatg Homo sapiens lipid phosphate phosphatase-related protein type
2 (LPPR2):

```
                                                            (Seq ID No: 915)
ccctccctccacctcggagtctgcgcggcgcggccaggcccggccgaccgcgtctcggtc
ttcgcgtctgccagcctggctggcagtccgtctgtccatcccgccgcgccggggcagtct
aggcggagcgggggctcaggcggcggcggcctcgacgcgagtgagtgtcgtggttggggt
gctggacccagagtgcctaccctcgcctgcctgggcctcagtttccacatctgcacaatg
ggggtgaccatccctgccctgctggctgccaggagcggctgtgagtcttcaggcgtggat
gcagcctgggggaagccatagggcgctttcacaggcctggccttcaccatg
```

Homo sapiens chromosome 11 open reading frame 1 (C11orf1):

```
                                                            (Seq ID No: 916)
gaacctttttcacctcgtctgaaatg
```

Homo sapiens microtubule associated monoxygenase, calponin and LIM domain containing 1 (MICAL1):

```
                                                            (Seq ID No: 917)
cgccctcccacccgctcagac
ctggttgccagcccaacaggaagcggcccctcccggcttcggagccgccgccac
tcatctctgcccagctgctgccctccccaggaggcctccatg
```

Homo sapiens kinesin light chain 2 (KLC2):

```
                                                            (Seq ID No: 918)
gctcctttaaggcagcgaacgggccaagagaagcgtgtttcgcccctccgacgccac
cgaggtagcggcttcacctttaaggcggcgcgggggctgctgggaaggccggcgg
gatggaggcggcgggaccggctcgcgggtgcgggtccgggtgaagcgg
gaggcagccagagtcggagccgggcccgagcaccaggcg
caggcccggcgcccgcctgcccgcaccctcgtcctcacagacgccacagccatg
```

Homo sapiens DNA cross-link repair 1B (DCLRE1B):

```
                                                            (Seq ID No: 919)
acttcctttttctgcccactctgg
taacttattgctctgctgggctctttcccttagggtctctggccctgttcttgccccag
catgacttttatcgggacgccgttgtggaagcctcacgcaggagccctgccccgtgga
gaagatcccactggtgactccaaccctaccaccatg
```

Homo sapiens armadillo repeat containing, X-linked 5 (ARMCX5):

```
                                                            (Seq ID No: 920)
gctcctcccactgccgttgtgggtaacgcggacgtggaagaac
ctcgtctgcggaggaaaaggtagatgttaaatggtaactacgcgcgaggttctgag
gagccctgggaacaggaaggagaaaagaataccaaaagtgacaacagtttgccaatcg
cagtctttaatctgataaagcggttatctcgtcttgagtcccaggtgccgag
tcaatcccatacacagccgccgccattgcctcgagtcctt
gtgtctgactgtctgttcctgctgctgtatgacacagcacctcgaggcaaggaaataa
gaaaactgcctctgatccaagcagagaaggtctgcctgtagatctgctgtagggctt
gtcaccattggaagcaaggtcctacttcagtggcagatctggtggccttggag
tggctgaagaccaccaccctccacagggctgggcccatgcacagccatccttccctac
cttgagtgagcttcctctgcatgttttctatatcactggcagagcctgtagtt
ggaaaggggacagagtgactactggactttgtgtgaaaacaccaaccgg
gacaaaacttcagtcaaggctgagacgggtgggggtatataacttgtccttac
gttaaacttggaacatg
```

Homo sapiens chromosome 12 open reading frame 43 (C12orf43):

```
                                                            (Seq ID No: 921)
aatcctttgcggtggttcaagatg
```

Homo sapiens vacuolar protein sorting 33 homolog A (S. cerevisiae) (VPS33A):

```
                                                            (Seq ID No: 922)
ggtcctcccgtaggaaccggcggactcggtt
ggcgttgtgggcagggggtggtggagcaagatg
```

Homo sapiens arginine/serine-rich coiled-coil 2 (RSRC2):

```
                                                            (Seq ID No: 923)
gggcctcctcgcctttgtgccatccgggtctctcgcgcgagcgatttagtctgaggcgaa
gcttcggagcggccggtactgttgaaagcgacaagtggaggcgccgctctagcggcggg
actctgaactatggcggctagtgatacagagcgagatggactagcccagaaaagacatc
accagatagagataagaaaaaagagcagtcagaagtatctgtttctcctagagcttcaa
acatcattattcaagatcacgatcaaggtcaagagaaagaaaacgaaagtcagataatga
aggaagaaaacacaggagccggagcagaagcaaagagcgtgcttatgcgcgaagagactg
aactgaagacgctgcagactcagatagcaaaataataagcctacttcatgataagggaag
aagacatgaatccaaagatcaaatcctctaagaaacataagtctgaggaacataatgacaa
agaacattcttctgataaaggaagagagcgactaaattcatctgaaaatggtgaggacag
gcacaaacgcaaagaaagaaagtcatcaagaggcagaagtcactcaagatctaggtctcg
tgaaagacgccatcgtagtagaagcagggagcggaagaagtctcgatccaggagtaggga
gcggaagaaatcgagatccagaagcagagagaggaagaaatcgagatccagaagcaggga
aagaaaacggcggatcaggtctcgttcccgctcaagatcaagacacaggcataggactag
aagcaggagtaggacaaggagtaggagtcgagatagaaagaagagaattgaaaagccgag
aagatttagcagaagttttaagccggactccaagtccacctcccttcagaggcagaaacac
agcaatg
```

*Homo sapiens* integrator complex subunit 3 (INTS3):

(Seq ID No: 924)

ccgccttcccaccccccgcccttccactatggccgcttctgtgtggtgtggggagac
gctggtcctcccgtcctcccatagcgcttattgcctcaccctcaccccctaggggccg
gatccaaaggcgctgcactccccaagccttggggcatcagccaggaaggtttcctac
ctcctaattcaggggcaggactcctcttttccccccacgggggaaaa
gaggcagaaacttagggggtttccctcctttcttagggtcagacgctcttagggtccac
ttcttcaggggcggaagcctctcctacccttcccataggggcacaggcctttacccac
tgtacttcggagccaacgcctttccctcagcactgccaccccagagtcaggacccagag
gactgtgccttcgcccccaacgcaggcgcggcctttttggagaggagggaggagtgga
gaggacaggggcccttgctctcccctcccaacttgttcctcttgccccccag
tccctggcaatccagagatcccgatatctaggactgtccatccatccactccctgac
cttttcccggctcctggctgcagccatg

*Homo sapiens* spermatogenesis associated, serine-rich 2 (SPATS2):

(Seq ID No: 925)

tctcctttcctcttctcagacccgggagcgtccgggacgcggagccg
gagctggggcgacgaggcgattgcgggggcctggctagctgctggctaccaatattc
tactttctgtctctatgaatgtgactaccctggttacctcatataatctccctg
gaaaaggagacatgaatgtctgcaatgatacttcctgacaagaagttgatacaa
gaaaaggaaaggagattaacagctagtgagcagaatttcgaaacagcaggatttcg
tattttttgcttccaactgcacacttccgttgcccacttttaaatcagagatac
ctacactcaaaacccagacaaggcaaaaggatacttttcttgtatattttttga
gatcgaagaaacgacaatg

*Homo sapiens* fibroblast growth factor receptor 1 (FGFR1):

(Seq ID No: 926)

ccgccccttcacctcctggctccctcccgggcgatccgcgcccctt
gggtctcccctcccttccctccgtccgcgtctcctgcgcccctccctgcgctcgtcccg
ccgctcttcccgccgcccaacttttcctccaactcgcgctcgg
gagctggcgaggcggcggcggctcctcaggtcagtttgaaaaggaggatcgagctcac
tgtggagtatccatggagatgtggagccttgtcaccaacctctaactgcagaactgg
gatg

*Homo sapiens* FUN14 domain containing 2 (FUNDC2):

(Seq ID No: 927)

ctccctcttccgctgccgccgtgggaatg

*Homo sapiens* ganglioside induced differentiation associated protein 1-like 1 (GDAP1L1):

(Seq ID No: 928)

cctccttctttcctgcctctgattccgggctgtcatg

*Homo sapiens* chromosome 19 open reading frame 43 (C19orf43):

(Seq ID No: 929)

agtcctttgcgcggcacctggcgacaaaatg

*Homo sapiens* MIS12, MIND kinetochore complex component, homolog (*S. pombe*) (MIS12):

(Seq ID No: 930)

ccctctcttctccaccagccaacgtccgggaaaaacgag
taagtacaggttccttctgccaatccccgccggccacagctaactttcccgcccggcccc
tttctgtcataattgaggtgtccacaaccagccaatcaggaacgcgagag
tatcccgcgtttgctttcgctcgccgaggcgcgtatcagtcggaattttggg
gagccaaccgcgccgtctgtccctggcaagccagcggcggtttaaaggagggtggcgg
gaagcctgtgtgtgcttcaaatcgtcaccctcatggtcgctccggtaagtgctgcgggg
cagcattttctctgaggaggagcggggacgggcgagactggcataa
gcgtcttcgcgagggagcaaggcggcctgtgggtcggcctcacccccggcctccgac
ctgaagatcccagcatgcagcgcgggcgcggggcccgacggaagcgggagccggccg
gaagcagttcctgcgctctggcttctgggtcctgtcctgcgcgatcgcggggtcttaga
cagctcaactcgccgagatgacctgggcacctctgcgttgaatcggcaaa
tactgatcaagccgcatttattctgctctcaggaactctaagtctagcagagaa
gatgaggcggtagaagttcatcaatggcttggctggaggacaagcaaattggagacatt
ggcaacggagtgatcaaaatgatagatcatgaggcctaaaatgaataaggaaagaaga
gaagtggcagaggctgagaacagaaagagagggtggagggctgtaaatcttgaa
gattagggtataatatgagtatatgggtaagaattggaagaattgtgtaggaggcag
tagtcaaaaagtagaagcagtttgaagagtagttacaaatatcaa
gagccaggtggctaaaggtggagctataggtcattgaagctcaagaaactgag
tctctagggcattggttaagtcatctgtctagacttcaaagttgtctaggatga
taattcagaagactgatctgtgccaaagtcacaggttttcac
gactgaaaacaacatagcaaaataagccaagatg

*Homo sapiens* DEAD (Asp-Glu-Ala-Asp) box polypeptide 50 (DDX50):

(Seq ID No: 931)

cttcctttcacgctgtcgctgcccgtaggtggttgtggccactgtgcccg
gagggaggcggcggtggccagtaatg

*Homo sapiens* chromosome 7 open reading frame 25 (C7orf25):

(Seq ID No: 932)

```
cggcctctgcgtgcacgcgcctgcgtgctcgcgctcgcggttctggcgctgccggaa
taatgctgacagcatg
```

*Homo sapiens* KxDL motif containing 1 (KXD1):

(Seq ID No: 933)
```
ccgccctttcctgtcgtgacttaacgcacgcaagcggctccagggtacgtccccgccac
gcgcgctcgcaggatcggtgcgtggtgacgtttcgccggcgcgggcgccatcccggaa
gcgcgagcaaggccgccagatgtgcaggcagcggaggaggagaaagagatg
```

*Homo sapiens* defective in sister chromatid cohesion 1 homolog (*S. cerevisiae*) (DSCC1):

(Seq ID No: 934)
```
acttctttcttgcccgccaagcccgcagccacccgggcgcggcgggactcctagacccgg
cgctgcgatg
```

*Homo sapiens* zinc finger protein 426 (ZNF426):

(Seq ID No: 935)
```
cgttcctttgtgacgccggctgtgagcgcctgagagtcttttgcctttcagagttaag
gcctcactggcctgggaaaataattgctgccttttgcatccgcgttggctccgtccccag
gatcttcccggttcagggacctggcgatttctgagtgttccggaatcccaataaccctgt
ttaaagaggaatggagattgccactgtccatttagattaatgaggtgtcctgaagtgatg
gtgacatcaatgaaaggagggttctgacacgttctcacctcgcgggatg
```

*Homo sapiens* TATA box binding protein (TBP)-associated factor, RNA polymerase I, D, 41 kDa (TAF1D):

(Seq ID No: 936)
```
caaccctttttcttccgcacggttggaggaggtcggctggttatcgggagtt
ggagggctgaggtcgggaggtggtgtgtacagagctctaggacaccaggccag
tcgcgggttttgggccgaggcctgggttacaagcagcaagtgcgcggttggggccac
tgcgaggccgttttagaaaactgtttaaaacaaagagcaattgatg
```

*Homo sapiens* PHD finger protein 1 (PHF1):

(Seq ID No: 937)
```
ccgcctcctcctcctgccgctgccgctgctttggctgctgcgtcat
acgccccagagccgccgggacggagggctgggcctgggaccccccggcctccgcctg
cacgccccccacgcccggacgtgccctctccgcgcggggggactcgcctaggtctcc
tacgtctgcccctgcccggctcccggcggcccccagctgtcaccggcccccccaggatg
caatg
```

*Homo sapiens* family with sequence similarity 134, member A (FAM134A):

(Seq ID No: 938)
```
ccccccttccgcctgacgcgcccccggcggcggccgcg
cagccctggctcctcgcgggctcgggcggcggctgcggcggggctatg
```

*Homo sapiens* membrane bound O-acyltransferase domain containing 7 (MBOAT7):

(Seq ID No: 939)
```
ccgcctcctttccggagcccgtctgttccccttcgggtccaaa
gcttttggctcctccttgttccgagcccgaaggcccgcccttcacgtactcg
gagctcggatcccagtgtggacctggactcgaatcccgtt
gccgactcgcgctctcggcttctgctccggggcttcttccctgcccgccggggccctga
ccgtggcttcttccccggcctgatctgcgcagcccggcgggcgcccagaaggag
caggcggcgcggggcgcgctgggcggggaggcgtggccggagctgcggcggcaa
gcgggctgggactgctcggccgcctcctgcccggcgagcagctcagaccatg
```

*Homo sapiens* major facilitator superfamily domain containing 11 (MFSD11):

(Seq ID No: 940)
```
acgccccttttttgctcagccgtcagccccgtctccgtctgaagagtgcttctgccctca
tttgcctctccctgtgaccccggcccctcagactccgctgcgtcgtctctcggccccgt
ccagccgttcctgactgctcttcgccggagtccgcttcccaaccccctttcgccagagcc
cgagagctccgtccggctctgcgtcctggcggattgtcagtggcttcgccccgaggagagc
tgactgccctgggctgctgcctccggcagagctgagccaaaatg
```

*Homo sapiens* thiamine triphosphatase (THTPA):

(Seq ID No: 941)
```
ctcccttccccctctgtgggtcccgcgaggagactctcgggctttgaggtgagacctgaa
gttccgctggccggtagtgtagcaggaaagggcaggtcctcccgggtcgtgagccagtag
cctcctggggtggcaaggtgtagagaggggggcgttgaaaggacaccgctaccggcct
gctttctagggggtctcttttggattgaggacatcagcagcagtggaaggggattttactgga
gacctgtcactgtcagagccttaaaatatcaccgacggggccttaatgtcaccgaggtag
agagaaaagggcagtagcccctagagactattgcgacacag
tgtgcccctcataagttttttccagggagggggttctgtactgagttgacgccccag
gagctgagcaccaggctttgcatccttgggaactcagcaaacgttttgttcagccaatt
gcaggtagcatg
```

*Homo sapiens* acyl-CoA synthetase short-chain family member 3 (ACSS3):

(Seq ID No: 942)

-continued
tactcccttccctcaggccccaggaagttgcaagagtaccatttgtcg
cacactcggggaccgcgggtggccggaggagatg

*Homo sapiens* chromosome 6 open reading frame 211 (C6orf211):

(Seq ID No: 943)

gctcctccttcgcggcggtaccgcctctgtttctgcggcgattgaacagccgagctttt
gcggccgggatcgcggaaagtgatg

*Homo sapiens* transmembrane protein 204 (TMEM204):

(Seq ID No: 944)

atttcctctctgctgagagccagggaaggcgagctctgcgcacacgggcgtccctgcag
cagccactctgctttccaggaccggccaactgccctg
gaggcatccacacaggggcccaggcagcacagaggagctgtgaacccgctccacac
cggccaccctgcccggagcctggcactcacagcaggccggtgctaaggag
tgtggcgcgggctcgactcccactgctgccggcctcccgagtgactctgttttccac
tgctgcaggcgagaagaggcacgcgcggacaggccggcctccgcttccgggaagac
ggcgcactcctggccctgggttcttgctgctgcccaccctctgctccctgg
gatgggccccgaggcgagcagcttcagcacaggcctggccctgctccaggtgcag
gaaggaggataaggccgggccgagaggcggcacacctggac
catcccatgggcctccgcccgcgccgccccgaggatgag
tggtgatgtcctctagccacccctagcagcgtcggctctccctggacgtgcggccgcg
gactgggacttggctttctccggataagcggcggcaccggcgtcagcgatg

*Homo sapiens* DEAR (Asp-Glu-Ala-His) box polypeptide 40 (DHX40):

(Seq ID No: 945)

tcgtctttcccctcccatctcctcagatcggtggacgtgctcgcctccac
tcggggccaggtctatg

*Homo sapiens* importin 4 (IPO4):

(Seq ID No: 946)

cctccccttttcggcccag
tagcggcggctcagttgctgccatg

*Homo sapiens* N-acetyltransferase 10 (GCN5-related) (NAT10):

(Seq ID No: 947)

ccttctctttcggagttgttccgtgctcccacgtgcttcccttctccactggctgg
gatccccgggctcggggcgcagtaataattttcaccatg

*Homo sapiens* lin-28 homolog A (*C. elegans*) (LIN28A):

(Seq ID No: 948)

aaccctttgccttcggacttctccggggccagcagccgcccgaccaggggcccggggcca
cgggctcagccgacgaccatg

*Homo sapiens* CAP-GLY domain containing linker protein family, member 4 (CLIP4):

(Seq ID No: 949)

cggcctttcctccgcgcccccgcgtccccagccggccgctccgagaggacccggag
gaggcaggtggctttctagaagatg

*Homo sapiens* zinc finger, AN1-type domain 1 (ZFAND1):

(Seq ID No: 950)

ccgccccttacggcgccggagagatg

*Homo sapiens* GTPase, IMAP family member 6 (GIMAP6):

(Seq ID No: 951)

cctcccttttctacttccgaggctgcaaagtgcaacagcagactcttctgactcag
gaaggccggtgctcctacccacttcctgttcctccatctccagcggacac
tgctcttttcaagggcaggtctccagcccagctctctgaaaacattttgctgaaaa
tataagcaaacatcggccttgtcctccttgtgttcatacactgtggaa
gcttttctctgcctcctccgtgagagtgcgtggccgggagaccagaaac
gtggtcctttctcttgcctgtgagctggtgcagagatg

*Homo sapiens* thioredoxin domain containing 15 (TXNDC15):

(Seq ID No: 952)

cttcctccggctggcagcacgactcgcgtagccgtgcgccgattgcctctcggcctggg
caatg

*Homo sapiens* asparagine-linked glycosylation 9, alpha-1,2-mannosyltransferase homolog (*S. cerevisiae*) (ALG9):

(Seq ID No: 953)

aattctttttcccccaggcttgccatg

*Homo sapiens* glutathione S-transferase, C-terminal domain containing (GSTCD):

(Seq ID No: 954)

acttcccttttccggtccgccggattatgaatgac
ggccggcgcgagtattttccacataaggtggctgtcgttttctcctggcgtctgtg
gaggcgagtggtctgcgggcagcagctcccagaggcagccttggaattccagctcg
gactgggcgggaaggcgcaggcggcccaggtcgccgacacgctcac -continued
gcaccctccctgcctggccgcgcctctgcgaccaggtgacccaatgaaagaagaaaatg

*Homo sapiens* CXADR-like membrane protein (CLMP):

(Seq ID No: 955)

actccttttctttccaaacagggaaaagtgttccacgaagcgg
tagcgcctttccgcctcgcgttttcctccctgacccctggtcccggctcccgtccgggcgc
cagctggtggggcgagcgccgggagcccatctgcccccaggggcac
ggggcgcggggccggctcccgcccggcacatggctgcagccacctcgcgcg
caccccgaggcgccgcgcccagctcgcccgaggtccgtcggaggcgcccggccgcccg
gagccaagcagcagctgagcggggaagcgcccgcgtccggggatcgggatg

*Homo sapiens* nonhomologous end-joining factor 1 (NHEJ1):

(Seq ID No: 956)

cctcctcttgcggtgggggaaagcggcctcttactctaggcctttcggtttgcgcgagc
gggcaggaaagcgtgcgtgcggctaagagagtgggcgctctcgcggccgctgacgatg

*Homo sapiens* gametogenetin binding protein 2 (GGNBP2):

(Seq ID No: 957)

cctccttcttccactccccgcggcgcgagcggctgactgcccgtagaggaaac
gacattcggagctgcgctcccgcccaggccggccctgacgcgggcctcgtcagccag
taacaggagcagaggtgggagttagcgaggcgaccacgaaaacggtgaaggtcggaac
cgacagcctcctccgagaagggcaggagctgggaggaggcggcagcggcggcgg
cagaaacagcagcggcggcggcggcagctgggaggaggtggtgacggtggcaacgg
cagcgtcgggacgatg

*Homo sapiens* zinc finger protein 672 (ZNF672):

(Seq ID No: 958)

ctttctcttttagccccgcctgcttcccggctccagctggggccggagaggctgag
tggttggtacgctgctcgctggcctcccagtcttcccagcaaccggtgacac
tgcccgcgccagactgaccactagccgacgcgggcgagagggacaggagcgtgac
ctcccccatcccgaggggccggacgctcgggcgcctcccccgcccccactcg
gaggccgcgcgcgcgttagccccttcctcgctccccgccccagtcccgcagtccgg
gaggcggggtcggcagccggctgagtgggaaccgcgcggtgtctgaggaggcag
tcggcgaccggtttccacttcaagcgtgacccttttgcctgtgggatgagctccag
catgggtgaggtacagaagagagacttgaagagcgtgccttgggactcaa
gcgccaaacctgtaccctagcgagtgtcctactccgcatccg
taatggaaggaaatgcacatcttactccagaggcacaagaggaggacatcccatgcggc
tactcctgcccagcgtggtggggcagcagaagctccagagcccagacttgcaggctcac
ggtgcagggtgaacctggccacagctcaccctggaacagccacaatgtctgcccctta
gagaagaaccctgaaatcagaccagttttttgcggcctccccctttcctctctgttacag
tgccctttccaggccttaagagaagtaaaacttagctgcagcgccaggaggtg
gaccccagagtgtgagtggcacgcttccctgtgaacccgtcctcaccatg

*Homo sapiens* N(alpha)-acetyltransferase 60, NatF catalytic subunit (NAA60):

(Seq ID No: 959)

ccgcctccgtcccggctgcggcccctgccggttacataactcgtt
gcgggctccgcgcggtcccacttcccggctcccttcgcctccag
gatgcgctgagcccatacaacaccccagcggccgccggctccccacgaggtgtgaatg

*Homo sapiens* transcription elongation factor A (SII)-like 4 (TCEAL4):

(Seq ID No: 960)

tgccctctgtccccgcggctgggtctcgtctgctccggttcctgggctcctaattctt
ggtccagcttcttccaggtcagtgtgcgggccttccacgctgccagcggaacactg
gaatggcggaagggggaacgggtctgcgcgtctgttgttcccagcgctctgcgaa
gcctgaaaaggaggagcaacctgtccagaatccccgcaggacaggaaaaggaggg
gaaatctcgacatg

*Homo sapiens* progestin and adipoQ receptor family member VI (PAQR6):

(Seq ID No: 961)

tcccctttgtctccccactccccgcccaggcctggcccgcctgcctggccactcttcctc
catcagcctggctggcagcagccttggactccgcccgtggagccctgggcctgttgaccc
accagcttaggagcacccaccaagctctgggtaaggaagctcaccttctggggctcttct
gggaaaatagaaggtcaacgtggaggtaccaggccaccatgctcagtctcaagctgcccca
acttcttcaagtccaccaggtccccgggtgttctgggaagatggcatcatgtctggcta
ccgccgccccaccagctcggctttggactgtgtcctcagctccttccagatgaccaacga
gacggtcaacatctggactcacttcctgcccacctggtgaggggaggctctgccccaggc
cgcggccttgagctcagaggggtaccaggcgggcagggaccgtccaggcccacgggct
gcagcggcagtcgcgggggtccgcggcggcctgagcacgcgcccgccgcaggtacttcct
gtggcggctcctggcgctggcgggcggccccggcttccgtgcgggagccgtaccactggcc
gctgctggtcttcctgctgcccgcctgcctctaccccttcgcgtcgtgctgcgcgcacac
cttcagctccatg

*Homo sapiens* DENN/MADD domain containing 2D (DENND2D):

(Seq ID No: 962)

catccttcttgctcaaccactgggtgcacaggatggaaacttctattccctctctg
gaagacagcgcgtggcttggcttcacagagttgtggctggagaccgaa
gcagccctttctcaggcttactgtcaccagtctgtctgtgttaggggagaggggag
tccgctctgtcctgaaggcccagagatg

*Homo sapiens* family with sequence similarity 188, member A (FAM188A):

(Seq ID No: 963)

ccttcttctttcctgcctcaccttccaattcgttt
gccgccgccgtcccgcagctgctgtttccggagttgcccttccccatgttccgggg
caggagtccgcaaagcgaagatccgcccgccggttcctcatcatg

*Homo sapiens* neurensin 2 (NRSN2):

(Seq ID No: 964)

ccgcctttgctcggcggagacag
caggcagagagatgaggaaactgagacccagaaaggtggaagcacttgtctaaggtcac
gcctccaggaagcagtgtgtccacgactccag
tccaagtggtcaggctccagagcccacagtcccagggtccatg

*Homo sapiens* tripartite motif containing 46 (TRIM46):

(Seq ID No: 965)

agccctcctcacaccccactgggctcctgcattaagcccggggttcgcagccg
cagccgggatcgggcacccaggggcgggcgggcacggtagggccatg

*Homo sapiens* target of EGR1, member 1 (nuclear) (TOE1):

(Seq ID No: 966)

catcctctctgggaatttaccgatgcccagaacgcccttcttcccccacac
gaccctctcctagtctaactcctgggcgtgctttaagctcagctcaggcagcgtcac
cttctctggaaagcccaaacccagccaccccactacccgctacccgcggcccac
gctgatgaagacagcagaacacggaggccccgcgttcccgccgcgagagcaggaga
gaaagattacctcccgcgagctctagcgcgcccggcttccggcgcac
tccaggggcgtggctcgggtccacccgggctgcgagccggcagcacaggccaa
taggcaattagcgcgcgccaggctgccttccccgcgccggacccgggacgtctgaac
ggaagttcgacccatcggcgacccgacggcga
gaccccgcccatccccgactgcctgaaccgcgccaggagacggaccgcaagtccagcg
tacccacagactgactcaggcgggagacgagcggtgtcatg

*Homo sapiens* DBF4 homolog B (*S. cerevisiae*) (DBF4B):

(Seq ID No: 967)

cgttcttttaggggtggagccggcaggaaatttaaactgaagccgcggccgaaaacgcca
agagattgatgctgtagctgccctgagataaccaggactgtggaatcgggaa
gagctcatggagctcgcgaatgtaatacggaggcctctgaggaaggagtac
ggaggccgagaaggagccggcatttgatg

*Homo sapiens* myc target 1 (MYCT1):

(Seq ID No: 968)

atttccttttatg

*Homo sapiens* myosin XIX (MYO19):

(Seq ID No: 969)

ggttcctttcctcactgcacgctctt
gcccctcctcttttctctcctgcccgtgttcttcccgccgcctgac
ctggcccgcccgcctttccagtctggccgggcggggcctgaagcacggcggctcgggcc
gtgggaccgtgttcacacccttttccagaaattcttggctggtaaccgcgaaaccgactgg
agcaggagctgggagaactggagaaaaactgctctaatctcacttgactccagctaggagc
tgatgctgcatcgtaataacatttgcagagcgctttcacaggcgctggagtgacttgtct
gagattcctccagaactgagccctttgttggaaccataccccagcccatggtcccatgac
taggtggatagtactccttgtacctcctgcaacccagaaccctggctgaccactttgaag
gaggatg

*Homo sapiens* KIAA0226-like (KIAA0226L):

(Seq ID No: 970)

cctcccctttctgctgttaccgggagcgcggtggccacggaacgctgcccg
gagccgcgcgagggaggacccgacgcggcgtttacccagcgcagcgttccac
cgctcggggtttggctggataaaataaaaaatggggatattgacctcctgtcactactg
catggactttgatggtttccaatcattactttctcctctgtgtcaatctgcctcttcga
gaaattcatactcctgaatagctctccagaccccagctggccatgtggtgag
ttcagggcccaaatcaagtagtaccagcaatcagggaactcctatctgtttt
gaatggattcacaccagccacaagcctggaaagatg

*Homo sapiens* MUS81 endonuclease homolog (*S. cerevisiae*) (MUS81):

(Seq ID No: 971)

ctccctcttcccccgccccgccctgggccaggtgttcgaatcccgactccagaactggcg
gcgtcccagtcccgcgggcgtggagcgccggaggacccgccctcgggctcatg

*Homo sapiens* zinc finger protein 430 (ZNF430):

(Seq ID No: 972)

gggcctttt
gtccctcgctgtggcctgagctccaggtctcgtcttcagcgctctgtgtcctctgctcct
agaggtccaggctctgtggccctgtgaccccgcaggtattgggagatctacagctaagac
gccaggaaccctggaagcctagaaatg

*Homo sapiens* mutS homolog 5 (*E. coli*) (MSH5):

(Seq ID No: 973)

gctcctttt
gcaggctcgtggcggtcggtcagcggggcgttctcccacctg
tagcgactcaggttactgaaaaggcgggaaaacgctgcgatggcggcagctgggggag
gaggaagataagcgcgtgaggctgggtcctggcgcgtggttggcagaggcagaga
cataagacgtgcac
gactcgcccacagggccctcagaccccttccttccaaaggagcctccaagctcatg

*Homo sapiens* proline rich 3 (PRR3):

(Seq ID No: 974)

gccccttcctcac
taccctccaaatcccgctgcagccattgccgcagacacgatg

*Homo sapiens* sirtuin 2 (SIRT2):

(Seq ID No: 975)

cgcccttaccaacatggctgctgac
gccacgccttctgggactcgtagtccggtcctcgcgcgctttcttac
ctaactggggcgctctgggtgttgtacgaaagcgcgtctgcggccgcaatgtctgctga
gagttgtagttctgtgccctatcacggccactccatttctggtgccgtcacgg
gacagagcagtcggtgacaggacagagcagtcggtgacgggacacagtggttggtgac
gggacagagcggtcggtgacagcctcaagggcttcagcaccgcgcccatgg
cagagccagaccgactcagattcagactctgagggaggagccgctggtggagaagca
gacatg

*Homo sapiens* KIAA1715 (KIAA1715):

(Seq ID No: 976)

ttgtctctctgtcagtggcggctgctgcctgctctggaggcaggctgggcggtggcggcc
gagactggcggggtggacgcccgggccgggctgcgcccgcttctt
gcagctgtgaattcctttggacaattgatgatatttatcattgtgcccagtttc
tacaaataaaagatg

*Homo sapiens* proline-rich transmembrane protein 1 (PRRT1):

(Seq ID No: 977)

ctgccttcatctctccatctctgcgctgctgccggctgcgccatccag
cacccagactccagcaccggccgaggaccccactccggctg
cagggaccctgtcccagcgagaccgcaggcatg

*Homo sapiens* t-complex 1 (TCP1):

(Seq ID No: 978)

ccgccccttccccggagcctcac
ttccgtcacagtcctgtttctctccctgtt
gtccctgcctcttttccttcccgccgtgccccgcggccgggccggggcagccgggaa
gcgggtggggtggtgtgttacccagtagctcctgggacatcgctcgggtacgctccac
gccgtcgcagccactgctgtggtcgccggtcggccgaggggccgcgatactggtt
gcccgcggtgtaagcagaattcgacgtgtatcgctgccgtcaagatg

*Homo sapiens* Yip1 domain family, member 5 (YIPF5):

(Seq ID No: 979)

cgttctttt
ggccctgtgacacgtagcaacggggctggttcagggtctgaaacagagtttgggggtt
gtttgggattagtgaagctactgccttttgccgccagcgcagcctcagagtttgat
tatttgcaatg

*Homo sapiens* glucose-fructose oxidoreductase domain containing 2 (GFOD2):

(Seq ID No: 980)

cctcccttccagagccccagttccttagaaac
caggcggcgcgttcccggtggcggcgccctggactcccgggcccgcg
catcccgccagccttccttaaggcggatgggtggccccgagacccgtcg
gacccatggtttccagtgcagcgcggagtgggcgatgccagcgtgccag
gagccatgtctgaccaggacgtttggaagatcatatccatgccagaggctcttgtgag
gagatgagttggtaaagagagaggctgggatg

*Homo sapiens* apolipoprotein L, 2 (APOL2):

(Seq ID No: 981)

ttcccttttcgaattccagggtatatctgggaggccggaggacgtgtctggttattacaca
gatgcacagctggacgtgggatccacacagctcagaacagttggatcttgctcagtctct
gtcagaggaagatcccttggacaagaggaccctgccttggtgtgagagtgagggaagagg
aagctggaacgagggttaaggaaaaccttccagtctggacagtgactggagagctccaag
gaaagcccctcggtaacccagccgctggcaccatg

*Homo sapiens* microtubule-associated protein 4 (MAP4):

(Seq ID No: 982)

ccgcctcctgcgcccgcccctccggctagctcgctggctcccggctcctcccgac
gtctcctacctcctcac
ggctcttcccggcgctctcctggctcccttctgccccagctccgtctcggcggcggcggg
cagttgcagtggtgcagaatg

*Homo sapiens* exonuclease NEF-sp (LOC81691):

(Seq ID No: 983)

cttccttctttt
gccaggcagacgcccgttgtagccgttggggaaccgttgagaatccgccatg

-continued

*Homo sapiens* ST6 (alpha-
N-acetyl-neuraminyl-2,3-beta-galactosyl-1,3)-N-acetylgalactosaminide
alpha-2,6-sialyltransferase 5 (ST6GALNAC5):

(Seq ID No: 984)

ctgtctctaatctctg
caacagccgcgcttcccgggtcccgcggctcccgcgcgcgatctgccgcggccggctgct
gggcaaaaatcagagccgcctccgccccattaccatcatggaaaccctccag
gaaaaagtggccccggacgcgcgagcctgaggattctgcacaaaagaggtgcccaaaatg

*Homo sapiens* heterogeneous nuclear ribonucleoprotein A1
(HNRNPA1):

(Seq ID No: 985)

tgctcctttctgcccgtggacgccgccgaagaa
gcatcgttaaagtctctcttcaccctgccgtcatg

*Homo sapiens* zinc finger protein 93 (ZNF93):

(Seq ID No: 986)

gggtcctttt
gtctctcggtgcagccggagctccaggtctcctcttcactactctgtgtcctgtgctcc
tacaggcccagcctctgtggccctgtgacctgcaggtattgggagatccacagctaaga
caccaggacccctggaagcctagaaatg

*Homo sapiens* N-terminal EF-hand calcium binding protein 3
(NECAB3):

(Seq ID No: 987)

cggcctctagccacaccgagtccgccgcggcgtccagggtcggcag
caaccgcagccgagcccgagcgggtggcggcgccatg

*Homo sapiens* splicing factor 3b, subunit 5, 10 kDa (SF3B5):

(Seq ID No: 988)

cattcttctgcgacggcgcggacctggagcttccgcgcggtggcttcactctcctg
taaaacgctagagcggcgagttgttacctgcgtcctctgacctgagagcgaaggggaaa
gcggcgagatg

*Homo sapiens* INO80 complex subunit B (INO80B):

(Seq ID No: 989)

gtcccctttcctcgcaggacctcatg

*Homo sapiens* polyamine modulated factor 1 binding protein 1
(PMFBP1):

(Seq ID No: 990)

ctttcttcctcttggcttatattagggatagggatgtggttt
gttacaaaggatgagtattttgatagcttctcattccttgaactattctg
caggtttataacaaagctcagaaaatactaaaggttaaaggagaattga
gagctgccaaggaaatg

*Homo sapiens* pseudouridylate synthase 3 (PUS3):

(Seq ID No: 991)

cttcctttctcggaaacgcggcgcggccggctgccggaaaacagggcagacctgtatggt
tcgtttattcctggggttgtcatatcatg

*Homo sapiens* heterogeneous nuclear ribonucleoprotein D
(AU-rich element RNA binding protein 1, 37 kDa) (HNRNPD):

(Seq ID No: 992)

tattctttttagtgcagcgggagagagcgggagtgtgcgccgcgcgagagtgg
gaggcgaagggggcaggccagggagaggcgcaggagcctttgcagccac
gcgcgcgccttccctgtcttgtgtgcttcgcgaggtagagcgggcgcgcgg
cagcggcggggattactttgctgctagtttcggttcgcggcagcggcgggtgtag
tctcggcggcagcggcggagacactagcactatg

*Homo sapiens* GABA(A) receptor-associated protein like 1
(GABARAPL1):

(Seq ID No: 993)

atttctccatctggctctcctctacctccaggcaggctcacccga
gatccccgccccgaaccccccctgcacactcggcccagcgctgttgcccccggagcg
gacgtttctgcagctattctgagcacaccttgacgtcggctgagggagcgg
gacagggtcagcggcgaaggaggcaggccccgcgcggggatctcggaagccctgcggtg
catcatg

*Homo sapiens* chromosome 22 open reading frame 13 (C22orf13):

(Seq ID No: 994)

ccttcctttccccagtgttgagcgcggtctcgcctccgcttcctcctcac
tccgcctgccggctgggaaactagggcaccagtacgatagttccggcaccggaaaa
gagggctgatgactgggcccggggggccgccgcaacgacccttggggccggcaaa
gagccagagagggtgctcacacttccaagcaccccacaccaaggcacaggctggacgg
caaggcggagacgcggggcttgggccctcagaccggggacagcaggaggtt
gggcaagggccaggacttcccgtcacaatttcatttgttgatcccggcac
cgccaggtaaggggggccctgagtgaggctaggtatctggtacgga
taaagtaggtatagagtagagcggctgcccgctcagggttatccctaaagacagtt
ggaggagagttgcttggggcctcggggatgcactgggcgggatcagggcttacacctag -continued
```
gactggcaaaagagcgggacccggcagaggcggggcttgccgaagggacgagcctc
tattcaggaaatgcacgagctttggggcggggctcaaa
gaaaggggcggggcttccgggcccgcgtcctggtgagctgcgcgtctgcgcgag
gattgggcgagagggtggggccactcaacgctgaggcggcgaatggccggag
cagacttaaatcaagaggctggggacctctaagatcaaagttt
ggggcggggcctaaggaggggcggggcctccagattcgagacctg
gaagggctggggcggcgcttggggcggccctgccgccgcctcccgttctcccctccg
cagcggcggcggtggcggagaaggaactcgacacgcaccgac
cgccctcccgcccagccgaagcggaagctg
tagcccgctctgggccggggccatgggcgcccgcgccgcccgggtcatg
```

*Homo sapiens* lon peptidase 2, peroxisomal (LONP2):

(Seq ID No: 995)
```
ggctcttttgacagcccccagtgcgaaaggctgccagcatg
```

*Homo sapiens* RNA binding motif protein 4B (RBM4B):

(Seq ID No: 996)
```
ggttctctctgacgtgggagccgccgtcgctgccgccacccggaggctcttgtcaggatg
```

*Homo sapiens* protocadherin alpha 3 (PCDHA3):

(Seq ID No: 997)
```
aggtctttctccacaaaagaaataacagcgtgcattacgtattcagatactgctttgctt
catcctctctaaaatttaacaccgaggagtttaagaaatgaaga
taaggaactcgaattattttttaaactttggatcaatgtaaaggcaatctaatatttt
ggaaaatacttgcaatg
```

*Homo sapiens* RAB34, member RAS oncogene family (RAB34):

(Seq ID No: 998)
```
gcctctccttgggcccttctctccccctttcccctccctgctggttcctgg
catcgccagatgctgcgcagcagtctccgattccccatcac
caattcggctggcgtctccgagaccgcggactcccgtagggtccccgtggccccgagtt
gtagtcgggacaccccggccgcgggtgatcgtcgggtctccac
gcgcccgggtcgctgacgcggatccggcctcggcgccttctcagggcgcctg
caaggccgcaggcaggatg
```

*Homo sapiens* cell division cycle associated 7 (CDCA7):

(Seq ID No: 999)
```
gctcctcctgctgtgggaccgctgaccgcgcggctgctccgctctccccgctccaa
gcgccgatctgggcacccgccaccagcatg
```

*Homo sapiens* ArfGAP with GTPase domain, ankyrin repeat and PH domain 3 (AGAP3):

(Seq ID No: 1000)
```
gggtcttttaggagagcactgctgcagccggcagtgga
gagcctgggcagggagacagggagaaaactccggcagcagggtggtctctagggctgac
ctcggagcctggggacaggggagcctatgccgcactgaaggcgggacgctgtaagcgag
gagcagctgggcctgggcggactcctcggccaatcagcctcggtcagcag
caccctcaggcgcagggcactgtttgggcattgcctaga
gatccgacaccccgcccagatcagcgcagggaggcgaaagcgacagccgggcgcgggag
gagaccaggg
cagctgtcccctccgcgagggtggccctcgaggcaatgcgggtggggctggtgag
gaggcggaagggccgaggctgagtgggaggggccggggcgccagggctg
gagcgcgcggctcggggggtggaggctg
cagagccagcgagcgagcgaggggcggggcgcccgggccggcgcgcag
gaggggcgggggcggcggggagggggggctcgggctgcgtgtgccg
gagccggcggggcggcggtgcgtgcgcatgacgcgggggg
gagggcctgggccgcgcgctcccggtcccgttgttgttgccgctg
gaggctgctccgaggcagcgggatcacggcgctgggaagcgctcgg
cagcggcggccacagcgtgcgcggcggcgcctcctggcctcggcctccgccccggccc
ccggctccatgcgctagccccgcgccgccagccagtag
tcccggccccgccagcccgcgctcccgctcgcgcgctgccgccgccgccgccgccgc
ctccgccgccgcccccgggcccgcctcgggcccacggctccgaagccatg
```

*Homo sapiens* potassium channel tetramerisation domain containing 10 (KCTD10):

(Seq ID No: 1001)
```
ctgcctctctcagtccgggtttggagactcctgcgtcctc
cgacttttcatg
```

*Homo sapiens* cyclin B1 (CCNB1):

(Seq ID No: 1002)
```
cattctctgcgaccggcagccgccaatgggaagggagtgagtgccacgaacaggccaata
aggagggagcagtgcggggtttaaatctgaggctaggctggctcttctcggcgtgctgcg
gcggaacggctgttggtttctgctgggtgtaggtccttggctggtcgggcctccggtgtt
ctgcttctccccgctgagctgctgcctggtgaagaggaagccatg
```

*Homo sapiens* eukaryotic translation initiation factor 2A, 65 kDa (EIF2A):

(Seq ID No: 1003)
```
gtttctctttccgggacaacatg
```

*Homo sapiens* protocadherin gamma subfamily B, 7 (PCDHGB7):

(Seq ID No: 1004)

cagcctctagcctgggattccctgcgcagccaacaacagaaaagaaaac
cagctcccacacagaggctcccggctgcgcagaccttgcccagcacac
cagattgccagctccgagacccgg
gactcctcctgtcctgggccgaatgctcttttagcgcggtagagtgcac
tttctccaactggaaaagcggggacccagcgagaacccgagcgaacgatg

*Homo sapiens* acyl-CoA dehydrogenase family, member 11 (ACAD11):

(Seq ID No: 1005)

ggctctttcggcttccttcctcgctgggccggctaaacccggccgcag
cagcaccggggtgataagtgtccagggcaggaggccagcgatgttgccttgctaac
cgggtatctaagagaaacagggtcttttattcttaggctcgacagtctgac
ggccttttctgaacgggaccctgcaggtcttccgcctgctgttgcattaaattt
gggggtggaagaggcttctgcgttgttccttacccgcaacgatgaccatggcttt
gccttctttaaaattgaggcctccaactctgacgctgactggagaatt
gaaacccgaacacacattgggctcttttggcacttgactagagctaaaacctcgggat
tcagcgggcaagcgttgctcagcaacggcgcgtaggctgtgtgcggttggctg
gagccagacccaccccggcctcggcccatgctctagaggggacgtt
gccccaatcctgaaggacttcggcactcgagacctgtggatgccgcgtt
gctgtggcctgcgggggtgatcatg

*Homo sapiens* zinc finger, CCHC domain containing 7 (ZCCHC7):

(Seq ID No: 1006)

ccgtccctctacgcgttttggttcccggttggtgcttcctgttcgcagctgcggcac
ttcaaggttactgactttttatg

*Homo sapiens* zinc finger, MYND-type containing 12 (ZMYND12):

(Seq ID No: 1007)

gggcctttctggacttggactccttgggagtcgtttctcggccatttgacccgtgg
gacttgtgggtttttgtgctgcttttctttctttcttcccttttccaacttcag
caatacacccagatgttagtcgagtcacgtcccgccgccctctgcccttgaaatgctgg
caagtacgcagcccgcgatcgtcacgtgacgccggggttcagcgtatccttgctggg
caaccgtcttagagaccagcactgctggctgcaccatg

*Homo sapiens* forty-two-three domain containing 1 (FYTTD1):

(Seq ID No: 1008)

cgctccctcggtgcggcgggctgcgtgcgcgagtgggaggtgg
caggcctgcgactccgccttgtccgcgcccgctctcggcgcgacgtctccagccatg

*Homo sapiens* SH3-domain GRB2-like (endo-
philin) interacting protein 1 (SGIP1):

(Seq ID No: 1009)

ctcccttttctctcagcatcttcttggtagcctgcctgtaggtgaagaagcaccagcagca
tccatggcctgtctttggcttaacacttatctcctttggctttgacagcggacggaata
gacctcagcagcggcgtggtgaggacttagctgggacctggaatcgtatcctcctgtgtt
ttttcagactccttggaaattaaggaatgcaattctgccaccatg

*Homo sapiens* GTPase activating Rap/RanGAP domain-like 3 (GARNL3):

(Seq ID No: 1010)

cagccctttttgcaaatg

*Homo sapiens* DCN1, defective in cullin neddylation 1, domain containing 5 (*S. cerevisiae*) (DCUN1D5):

(Seq ID No: 1011)

gagcctcttgctt
gctgtgactggtggagctgccgcgctgtccgcgttatctcctcccggtgagaacgaac
cgcagtgtccaccggcgaggagccagccctgtcccggtcagagaaagacgacgagga
tacctgg
gagcgggcggcggccgggctgggccgcgccggtgcgggctggcgactctgctcctccgct
tgctgctgtctctgggaactgggtgccagcgctgagggcttccagcg
gacagggaccccttccccggctccctgccaccctgccggggagggcggaagatg

*Homo sapiens* alkB, alkylation repair homolog 7 (*E. coli*) (ALKBH7):

(Seq ID No: 1012)

tgccctctctcatgacccgctccgggattatg

*Homo sapiens* nitric oxide associated 1 (NOA1):

(Seq ID No: 1013)

ccgccccttt
ggagctacttcctcatg

*Homo sapiens* BTB (POZ) domain containing 10 (BTBD10):

(Seq ID No: 1014)

tcgcctcttcgcattgtgagctctcgcggtaagaggctgaggagccggcctgcaac
ctgccggggcggctccgctacgcgcagccgcctcagtggcttcctccacagccac
ctccggagggatctggctgaggaggaagtggaggtgtcactggccccggccttt
gccccaatcttgtgtgggcactgaaggggactacaggttcgagagttatgggtgc tacatgtgtgctttcagagcagtagtgtgaggaagcttggagtgggatg

*Homo sapiens* zinc finger protein 397 (ZNF397):

(Seq ID No: 1015)

cggtctttt
gtggcttgcagctcggggtgggtggctcatttcctggccgctcctgggcttcgcggaaa
gaagagattactcacactccttcgcaagcacagaaccagttgtactgagcttttt
gctaagctgtttcagccaagaatg

*Homo sapiens* mitochondrial ribosomal protein L45 (MRPL45):

(Seq ID No: 1016)

gctcccttcccggcggcctttgcgggaacaagatg

*Homo sapiens* AKT1 substrate 1 (proline-rich) (AKT1S1):

(Seq ID No: 1017)

cttccttctccatattgtatactggaattgaagccaaggaggtaccattttgctcgaggg
catggcctaagccggtcagctaaggccatgttaatacggggctgtcccatctctctgcgg
ggcgcgacagctggaagagccgaacggataagagaagaggaggtgagaggagctgtacac
cacaagaggcactgagggactcaggataacgggatgaagccgtcagtgccccagaaacg
aagcggccccggacgaatttctgagtcaccgtcgcgagaaagcgggctgagccgccattt
tgaagcctggcaaaccgaagcaagaaatgctgccgtgttggatctttgccagccttcgtg
ccgaatgggagcaggttggagggagggagagccaatatacactatgggctgattaagccc
ggttggctgccatgttgttaacgagcaccgatttcctctactttttgtcgaagaagtttat
tgtgggtcagggacgtcaggtcgcttgccttcgtttactgtggtcatgattgagcatatg
aggacggccattattgttgggggcaaatggaaatgctctaggcggggccatttttcttag
gggcaagctgtcgtcacccttgtcaactggttcggatgaagccctgtggccgccatctt
gatctcgggcggccccgataagggaggcggagtgtgcggagaggaggcgggcaactgcg
cggacgtgacgcaaggcgccgccatgtcttttgagggcggtgacggcgccgggccggcca
tgctggctacgggcacggcgcggatg

*Homo sapiens* transmembrane protein 101 (TMEM101):

(Seq ID No: 1018)

ctgcccttcccaagatg

*Homo sapiens* eukaryotic translation elongation factor 1 delta
(guanine nucleotide exchange protein) (EEF1D):

(Seq ID No: 1019)

ggccctcccttcatcagtcttcccgcgtccgccgattcctcctcctt
ggtcgccgcgtccttggctggcgttagagacagggtttcaacgtgttagccag
gatggtctcagtctccagaccctgtgatccgcccgcctcggcctcccaaagtgttgg
gattacaggtgtgagccaccgtgcctggccgaggctccttcttttatg

*Homo sapiens* ADP-ribosylation factor GTPase activating protein
2 (ARFGAP2):

(Seq ID No: 1020)

cgccctccccgccgtggattggcccgcggcgg
gacccgtcagccgcggttgtgtctgggaaggagagaaaatg

*Homo sapiens* junctophilin 4 (JPH4):

(Seq ID No: 1021)

atttctctcctccctgggggtctcagtg
catctccttctcctctctgcctgcctcctccctcaccgaagggttagcg
gacacccatccttttctgcttggggaccccaccaccaccccgcaacac
tgccgctgtctcttcttcaccgtatccttctc
tacccaccctcttctctcttctcttctccctgccccttttaaatctgcctggcccagcctc
ccccgtgatgctgggatggagcaaacattgatttgtgctgggatggaatcggaatttt
gatttatttttcctctcccaaccataagaagaaaaaataataaaaacacccctctt
gagagcccctcccccttt
gcatccagctcccagctcttcttccctatctccatccaaggcagat
ttttcccctacactattctcatcttcccccaccccttgccactac
ctcgcccccaccccagcctgctcctccagctggggagagaggggactctccg
gactcccccaccctttcctctctgggttggagcagtctctccggaaggggaggggctt
ggcttgtccgggcgaggtgggagtggaggtatcctgccatggatgctgtgccggg
gaggcagcctgagccccagcccacatgagacgccgaagaaccgggg
cagaggggtcctgacagcagccagggaaacgggtgccctacgat
tctgcccagccccctctcaggacccccaaactgccatccacactcgacac
ttcggggttctagccactcag
gatgagggtccggccctgcctgccctcgctggggccccccgcccggccccggtctaact
gcccccgccccgaggcctcgcccggctccaaggcccccagcaggctctccagtcccag
gatgcgctgagccgccggggggctgaggccgcgccaactacatgcatg

*Homo sapiens* embryonal Fyn-associated substrate (EFS):

(Seq ID No: 1022)

ttttctttctcctcctccaaccttggcggaggccac
gactcaggcgccacagctgggggctagaggccgcggaccatggtgcggggcagccac
cgctgaagtcagcaaaaccgagcctggcctgaggcaggctgcgcgggaggccaaagc
catg

*Homo sapiens* GH3 domain containing (GHDC):

(Seq ID No: 1023)

cgctccttctttctggccggatgtgtgctgagacccagag

-continued tcacccaggggtctccgtcacgtgccaggagtaggcagaagtgggctgtgacagatcag
gaaacagagctcagtgcagcccactaaattgctcagggccctacagctaacaagcgg
cagaggcaggatctgcactcaggagctgcttggagatg Homo sapiens acrosin binding protein (ACRBP):

(Seq ID No: 1024)

ggctctctctgcggcttggcccgttagaggcggcttgtgtccacgggacgcgggcg
gatcttctccggccatg

Homo sapiens jagunal homolog 1 (Drosophila) (JAGN1):

(Seq ID No: 1025)

ag
ttctcttcacggagccgcgcggctgcgggggcgcaaatagggtcagtgggccgctt
ggcggtgtcgttgcggtaccaggtccgcgtgaggggttcgggggttctgggcaggca
caatg Homo sapiens ligand of numb-protein X 1, E3 ubiquitin protein
ligase (LNX1):

(Seq ID No: 1026)

gttcctttcctgggcatcagcttgcctgctctcagcctaa
gctctctcgccaaccgtggtggctccttgcgttcctacatcctctcatctga
gaatcagagagcataatcttcttacgggcccgtgatttattaac
gtggcttaatctgaaggttctcagtcaaattctttgtgatctactgattgtggggg
catggcaaggtttgcttaaaggagcttggctggtttgggccctt
gtagctgacagaaggtggccagggagaaggcagcacactgctcggagaatg Homo sapiens cyclin-dependent kinase 2 interacting protein
(CINP):

(Seq ID No: 1027)

tctccttctacggatatctgtggaccttatg

Homo sapiens splA/ryanodine receptor domain and SOCS box containing
2 (SPSB2):

(Seq ID No: 1028)

gcttctttccgcccggctcctcagaggcccggcgac
ctccagggctgggaagtcaaccgagctcccttccaggtcaatccaaactg
gagctcaactttcagaagagaaagacgccccagcaagcctctttcggggag
tcctctagctcctcacctccatg Homo sapiens Berardinelli-Seip congenital lipodystrophy 2
(seipin) (BSCL2):

(Seq ID No: 1029)

cctcctcctttcctccctctactctgacacagcacttag
cacctgaatcttcgtttctctcccagggaccctccattttccatatccag
gaaaatgtgatgcgccacaggtatcagcgtctggatcgccacttcac
gttttagccacaagtgactcagtggaagatccagagtcaacagaggctcgtcaggaa
gatg Homo sapiens tubulin, alpha 1c (TUBA1C):

(Seq ID No: 1030)

caccctttcactacttctcccccggactccttggtagtctgttagtgggagatccttgtt
gccgtcccttcgcctccttcaccgccgcagacccccttcaagttctagtcatg Homo sapiens 1-acylglycerol-3-phosphate O-acyltransferase 9
(AGPAT9):

(Seq ID No: 1031)

tttccttcctctcttcccttcgcagaggtgag
tgccgggctcggcgctctgctcctggagctcccgcgggactgcctggg
gacagggactgctgtggcgctcggccctccactgcggacctctcctgag
tgggtgcgccgagtcatg Homo sapiens 1-acylglycerol-3-phosphate O-acyltransferase 1
(lysophosphatidic acid acyltransferase, alpha) (AGPAT1):

(Seq ID No: 1032)

gccccttctttccttcgcttcctcttttagagaatgtccggattgctattggactttt
ggagcgtatggctccaaatcaactcattggctaaaacttgac
ggaaaatggtggttaggtggccagaatg Homo sapiens abhydrolase domain containing 14B (ABHD14B):

(Seq ID No: 1033)

cggcctcttcccagcgttcctcctccggccccaggtcaccgccagcac
gcgcctgcttcccgtctgcgcgagtccacgcagctcccccagatcaagaa
gctgaggccccaggttacacactaaagtaaatggcagaggcagaaataacac
ctatgtcctcctgaccccaaggcatgttcttaaagttctggaaacctcctg
gaggcttccttgctgctcctctgggactgccaccctggg
cagggtgttctgtggccctcatcatcgtggttttgaaccacaggcccttccaccag
cacagcagcagcaggcatg Homo sapiens protein tyrosine phosphatase, non-receptor type 5
(striatum-enriched) (PTPN5):

(Seq ID No: 1034)

-continued catcctcccgccagcctgcccgcctgctcgccggcgcccggagcccgctctggccgctt
gcttttgctgagaaagcttcctgccctggaagatggcacccttccccatccagacac
cttgggaatg

*Homo sapiens* carbonyl reductase 4 (CBR4):

(Seq ID No: 1035)

cttcctccttttcac
ggcgtcttgcattactattgtgcggctgcaggaggtgtcgagcggcgttatttttttt
gcggtttgccttttttttctttttttttttttggaaccgcggttgtttaaaa
gcctgagggaacctggagaggggctcccactccctaccctctttcctccgagttt
gtgactccgagatg

*Homo sapiens* zinc finger CCCH-type containing 10 (ZC3H10):

(Seq ID No: 1036)

ggctctttgtcgaagctagaggaccggcaggcggcagcagcaactacggcggcggcgg
cagaacccagcagcgatgtggaggtggagacccacaggagccccggacttcacctgagc
tacctcagtggtcaccaagagtggcaagataaagaaaaccctgagttgggcgggaccag
gatg

*Homo sapiens* poly (ADP-ribose) polymerase family, member 10 (PARP10):

(Seq ID No: 1037)

ccgtctttcagtttcacttttgttttcctgctcccagcagggttaggcttgctgaggggc
aggcacaggagtcctggctgagctcatggcctgaggctgcctagcggccacggggaatg

*Homo sapiens* RNA pseudouridylate synthase domain containing 4 (RPUSD4):

(Seq ID No: 1038)

ccgcccttccttgtaagatg

*Homo sapiens* family with sequence similarity 73, member B (FAM73B):

(Seq ID No: 1039)

ctgcccttccgcagcgatggcatcccgggtgag
tatcggccccggccgagcccccaaggcgggcgggcagcgcggcagggccgggactt
gagcggaggaccgagtaggcgcaggtgtccgggcccaacaggaccag
gaaggtgtcggggttggaatgagtgggtacccgggccggggacggtgcga
gagggtgccttgcttgggagcggaacgagaaggtactt
gggtcagggaggtgatgcccgggcctggaacgtggcggggattggagcaggcgcg
caggtacccgatccgaggcggggagagcacccgggatggaaggag
caggcgtgcgggccgtgagcggcgccagagggtacctggctctgtg
gaggggccctctggtatgtgtgtccctgtccttctggggcgtggatggtgcctgg
gacccagctggcaaccagttgaagacgttctccttggaagctcttggccctgag
gactttgcctggggcattggccctgccatg

*Homo sapiens* protein phosphatase 1, regulatory subunit 15B (PPP1R15B):

(Seq ID No: 1040)

gcgtctcttccggcgtctagggggtgtcctgccggcgcgcgggccctgcggccattt
gggcttcgcttccaccgcaccagccggcctacccagtccttccggtatcgcgtt
gctcagggcttttcaaccctctgtcagtcggaaaaccatcgccgaggccgtgggggg
gactcctatccatggtgttgaagcgtcgagccgactagggaacctccttccccgccag
gatggaagtcgcatcagtcgccgcc
tattgcgcgggctgttcttccctgtgttctgccgcccgctgccg
cattcgctgccctctgtggcttttctgctggctcgaagatcggcctggagcagcgac
gccaccgctgggcaaggccgagactctgtaggcttcctccgaatcccgtcgac
ctccagccgctgagcgccgcggccctacctgagagactgtcaagaaaaggagatg

*Homo sapiens* family with sequence similarity 104, member A (FAM104A):

(Seq ID No: 1041)

ccctctcttcgcggagcggcgccgcgtagcttccatccgccagctgc
catg

*Homo sapiens* PRP38 pre-mRNA processing factor 38 (yeast) domain containing A (PRPF38A):

(Seq ID No: 1042)

agcccctttacactac
ggtgtttccggcttcaagatggtcgcctaagctgtttagtgaaacttcttccac
cttttctccattcctctaggtgcttttctgaacctg
gatgtgaggcattaaaggatccgacggaaatagaattgaaggcattctaaaatg

*Homo sapiens* synaptotagmin-like 1 (SYTL1):

(Seq ID No: 1043)

cctcctccgtgtgggg
cagctgctggctgggctgcctgttgagtcagccttcttccctcac
ggctcttctcccggtccctgaaactcggctgccaggggagctggagccac
ctgcgaaggtgtcctcccatactggaccctacaggaagctccgtgtgcccagctgggg
cacagccccagctgatg

*Homo sapiens* ubiquitin associated and SH3 domain containing B (UBASH3B):

(Seq ID No: 1044)

gctccttttcctttttgatccattcaaaaattactcatt
gcaaattcccggactgctaggcgaggagagggaaggggcggaggagacagggctactg
caggcgcagagctgggggcagccgggggcccgagtggctgaggctggtcccg
cagcggccgcttgccggcgttctggctcctgtggcctcaccaggaagcgtcagag
tcccgacactggggaagctcg
gagcgccgcctccgctgccgccgcctcctgcctggctctgggtcccgagcccctcccc
tggcccagcccgactccctcctccttcccgaac
catccggctcgggtccttccctggcgatggctggccgctgagccatg

*Homo sapiens* transmembrane protein 241 (TMEM241):

(Seq ID No: 1045)

ccgtctctgggcggctgctgccgctgccgctgctgctgctgcggggtcgggcggcggcc
aggggatttgggcaggcaccgtggatccccgagaaggggacgagttgacagatg

*Homo sapiens* ataxia, cerebellar, Cayman type (ATCAY):

(Seq ID No: 1046)

gagcctctgccagccctgagctgggaagaagcagctacctcggaggcagggcgcg
caggcgggcggcgatgagaggggcgcagccgcagccccgcgctggggagcccac
cgctaaccctgcaccccaccccctgcacaaaagagctggcgggcgctggccac
gtcgccctgggtgaccttcctcggatgcagaatccgcccctgcgag
catcctcttcctcctaggctctgaaggccggggagcgtgagcgatgcccagctg
cacccgggcagggctcgccttttgttgccagtaaggaggagaggctgtctcagctg
cagaggggtcatccctgcttcaagccagtgcctcttcccagctcccatg

*Homo sapiens* ELL associated factor 1 (EAF1):

(Seq ID No: 1047)

attcctctctcaccccacgcagaggagagaacttgcttctg
gacccgggtgggtgccggctcggctctccttgtcttccagagcggtggcccggaa
gcacagtcctcccagacgccagcgccagaagctcggatcgcggctgcaccggga
gagcgccgatctgggtgcgaggcaggtgcggggccatg

*Homo sapiens* tripartite motif containing 5 (TRIM5):

(Seq ID No: 1048)

gttcctctaggaaaattcctttgtgcagatcaggcccgtggattggtgag
tgaatcctaaccacgtcttccctggcctgtcttcactcttctccccagaatcaccac
ttctgcactggtgtctgaaggtgtattgagtgattttgtggagggcagaagtag
gaagtctttgggacaaaactgtatttaccttgggatctgtgaacaagaggaacctcag
cagccaggacaggcaggagcagtggaatagctactatg

*Homo sapiens* wingless-type MMTV integration site family, member 3A (WNT3A):

(Seq ID No: 1049)

cgccctctcgcgcggcgatg

*Homo sapiens* chromosome 16 open reading frame 45 (C16orf45):

(Seq ID No: 1050)

ctccctccctgcagcccgcaacgggaatggagtaaagggagacccgtcgacctggccac
ggggatcagcgatg

*Homo sapiens* zinc finger protein 502 (ZNF502):

(Seq ID No: 1051)

cattcttccggtttcagaagttaaggctggtgtcctggccccagtccacctctgggagcg
cctgcgccgctccgcggagagtccgtggatctcacagtgaaaaatgtttgctgacccttg
acattgacaaactgctgacagctcagatgatccatgattggaaggatgtggtcatccaca
agatgtctttctttctccggttcccagttttccagacctgaagtgttttccaatcaaa
gcgaagagacgatctgtggatg

*Homo sapiens* armadillo repeat containing 6 (ARMC6):

(Seq ID No: 1052)

ggctctcttgcgcaagcgcgctgtccgcttcttctgggcggacgctctg
gaggcaaaacatttccctgctgggggcggcgaccaccgtgagcgtcccggaaggggcgg
caaagacgcctccgtcgcgcacgaggtggcctcgttggctttacctt
ggttcgcggtcgtccttggttatcgtgagcgtccgcgagtctctgggaggccaa
gcctaggggcgccacagccgctgcgcgcgtacggcggccggaaggggcta
gaggcggctccctgggtgacaaccgcgcgccccaccttttccccacgtggccgcgaagacc
ggctcaggagcatctatcggctgcacgccaacatcaacacaggcgaagatg

*Homo sapiens* post-GPI attachment to proteins 3 (PGAP3):

(Seq ID No: 1053)

gctcctcccccggcggcgagccagggagaaaggatg

*Homo sapiens* histone cluster 3, H2a (HIST3H2A):

(Seq ID No: 1054)

tgccctctt
gttttagtctcgcttttcggttgccgttgtcttttttccttgactcggaaatg

*Homo sapiens* ethanolaminephosphotransferase 1 (CDP-ethanolamine-specific) (EPT1):

(Seq ID No: 1055)

```
ggctctcctaccttctcggg
cagcccagtctttgccatccttgcccagccggtgtggtgcttgtgtgtcacagcctt
gtagccgggagtcgctgccgagtgggcgctcagttttcgggtcgtcatg
```

Homo sapiens F-box and leucine-rich repeat protein 5
(FBXL5):

(Seq ID No: 1056)
```
ccgcctctgccccgcggcgagggtgtctatgga
gaggcggcggccgcggctgctgaggcggaggctgaggcag
tggcgatggcgcccttcctgaagaagtggacgtcttcaccgccccacactggcg
gatgaagcagctggtggggctctactgcgacaagcttttctaaaac
caattttttccaacaacaacgatttccgtgctcttctgcagtctttgtatgc
tactttcaaggagttcaaaatgcatgagcagattgaaaatgaatacattattggttt
gcttcaacaacgcagccagaccatttataatgtacattctgacaataaactctccga
gatgcttagcctctttgaaaagggactgaagaatgttaagcctactactgttgactg
gaagccttaccaataacataaaacaatcgaataacaattatttcatgtatta
tatgtaaaatatatatactggattcttacagtaagaatgaatatgaacag
ttaaattatgcaaaacaactgaaagagagattggaggcttttacaagagat
tttcttcctcacatg
```

Homo sapiens major histocompatibility complex, class II, DP
alpha 1 (HLA-DPA1):

(Seq ID No: 1057)
```
ctgcctccactcggcctcagttcctcatcactgttcctgtgctcacagtcatcaattata
gaccccacaacatg
```

Homo sapiens secretory carrier membrane protein 1 (SCAMP1):

(Seq ID No: 1058)
```
tcgtctctctctctgcgcctgggtcggtgggtgacgccgagagccagagagatg
```

Homo sapiens chromosome 15 open reading frame 57 (C15orf57):

(Seq ID No: 1059)
```
ccgcccctcccgatttcctccgggctacaggcgacagagctgagccaa
gcgtttactgggcagctgttacggtaagtgaggaggggctggggtgcccagcgtttt
ggatctcccactctggcccggccccggaataccacatagaggccttgggacctgat
tcatcccgtccagacagccctagagacctgagcgactgaggcctgggatctggacgccg
gaatttcctgcgtggttctggacgccctgccctgggctcagattccaaatg
```

Homo sapiens WD repeat and FYVE domain containing 2 (WDFY2):

(Seq ID No: 1060)
```
cctcctcttgtagtggcgccggcttgcatcccaggtcgtggcggttttggtgcctgaagc
agggagcgcggagtcgttcccgagagaggcggccaggctatgctcgccggtttccggcgt
tccgctccggccagccagagtctctgtctcaac
ctgtgtccgtgctccagcagtctcctcagcccggccccgcggcgcggtt
ggcggcggcgccccaggcgcgccccctcctccgatg
```

Homo sapiens topoisomerase (DNA) I, mitochondrial (TOP1MT):

(Seq ID No: 1061)
```
cgctcttttcccggaggctggcagatg
```

Homo sapiens intraflagellar transport 122 homolog (Chlamydomonas)
(IFT122):

(Seq ID No: 1062)
```
cttccctttcggacatgcgcgctcggagcaaggcgccctcg
cactcagcttaccgcgcatgtacgttgccaggggtaacgcaggtagccaaagtggctt
gtggagtggcgaccgttagtgaggcggttgctgagacagacgctgaggcgggtaggag
gagcccgagccgtaagggaagccgtgatg
```

Homo sapiens mitochondrial ribosomal protein L53 (MRPL53):

(Seq ID No: 1063)
```
agttcttccggggcggaggtcaccatg
```

Homo sapiens T-cell activation RhoGTPase activating protein
(TAGAP):

(Seq ID No: 1064)
```
ccgccccttcgcttataatgcagagcatgtgaagggagac
cggctcggtctctctctctcccagtggactagaaggagcagagag
ttatgctgtttctcccattctttacagctcaccggatgtaaaagaactctggctaga
gaccctccaaggacagaggcacagccacacgggagtgaaatccaccctggacag
tcagccgcaatactgatgaagctgagaagcagccacaatgcttcaaaaacactaaac
gccaataatatggagacactaatcgaatgtcaatcagagggtga
tatcaaggaacatcccctgttggcatcatgtgagagtgaagacagtattt
gccagctcattggacattctcactattctatgcctttaaaggcccttcaacggaaggga
tattcaggagagcagccaacgagaaagcccgtaaggagctgaaggag
gagctcaactctggggatgcggtggatctggagaggctccccgtgcac
ctcctcgctgtggtctttaaggacttcctcagaagtatcccccggaagctactttcaa
gcgacctctttgaggagtggatg
```

Homo sapiens phosphoserine aminotransferase 1 (PSAT1):

(Seq ID No: 1065)
```
ggtcctccttggctgactcaccgccctggccgccgcaccatg
```

*Homo sapiens* CD97 molecule (CD97):

(Seq ID No: 1066)

ccccctccttcataaagtcctggcctcgggacagcctgcacagctgcctagcctgtggag
acgggacagccctgtcccactcactctttcccctgccgctcctgccggcagctccaac
catg

*Homo sapiens* protein tyrosine phosphatase, non-receptor type 2
(PTPN2):

(Seq ID No: 1067)

cgctctccccggatcgtgcggggcctgagcctctccgccggcg
caggctctgctcgcgccagctcgctcccgcagccatg

*Homo sapiens* chromosome 20 open reading frame 112
(C20orf112):

(Seq ID No: 1068)

gcccctctcccgggcagccgcggcggcagcagcagcagcagctggagctgtgggc
tgtcaccgccgccgccccgctcactcgcggatcccgaccgccatctccgcctcgcttc
cagcccaggatgagacttctgtgagcagcgaggattttgatatg

*Homo sapiens* APEX nuclease (multifunctional
DNA repair enzyme) 1 (APEX1):

(Seq ID No: 1069)

cacccttctttgtgctcgggttag
gaggagctaggctgccatcgggccggtgcagatacggggttgctcttttgctcataa
gagggggcttcgctggcagtctgaacggcaagcttgagtcaggacccttaattaa
gatcctcaattggctggagggcagatctcgcgagtagggcaacgcggtaaaaa
tattgcttcggtgggtgacgcggtacagctgcccaagggcgttcgtaacgggaatg

*Homo sapiens* intermediate filament family orphan 1 (IFFO1):

(Seq ID No: 1070)

tttcctcttgagccatcatgcacatctgactgcagccccagcgagcccttccttcctt
gtctgactgctcttcttctcgatttcttcttgttctgccttctcggttt
gcagccctgaccccgctgtgtgtctggcccctt
ggtgactgtccgtgtttctgttcctgtcatt
gtaactgtgactttctctctgtctgcccccccttcc
tactggttcatgcttctcccccattcccaccctctctgcccggcctcccgctcccgccct
ttctcctcatgcacccggcctcgtctctgtagtctctgcactt
gtctcccattaaggtcccatccatg

*Homo sapiens* neuralized homolog 2 (*Drosophila*) (NEURL2):

(Seq ID No: 1071)

cagtcttcctcccgccccttcttggtccctacggac
ctggggggcggtggcggtcaatgccgggtcaaggtccgcgggcctcgcagatcg
tagcccgggcgcacgcgatcagatgatcctgttgtggacggctaagttgtaggcgg
gatggctgagaaagcggcgctaggaccccgggcagaggctcggggaagggag
tcagggggaaatgccttacaaggtcgccttgcggtcaccatcatt
gcccgccgcccaaaatagccccggcgccagctggcctgccctatggccgagagatg

*Homo sapiens* drebrin 1 (DBN1):

(Seq ID No: 1072)

ctccctctttccctccctcctcctccgtccgcccgtccgtccgcgcgtctgtccgttcgg
cccggtccggcccgaagcatg

*Homo sapiens* WW domain containing adaptor with coiled-coil
(WAC):

(Seq ID No: 1073)

cagcctcccttatttagtccgcgatggcttccctcgcgccccaccgtcctcttccggaag
gcggctccctccctgcgcagcccggagcccctgagatcagcctcgagcaggcgcccgagc
gagactatccctaaacgggaacggcggttggccgactcgcagtgaggaaaagaaggaaag
ggcagactggtcgcgaagagaagatccaggcctcagaggaggagaaaggccggagccagc
cgaggtttgccgagggcggtgttccggacccgcgcggtgcggggaggaaggccgagggtg
ggagaggaggggcccggcggaaactgccgaggtttcccgaaggcggcagcgtccgagttg
cccggatgtagttggtggagcggcagcggcggcaccagcggcggcgggcaagggaaaag
aggaggaggagaagaaggaccaggcggcggcagcagcggcggcggcgggggagagggg
aggagcggcggagcaggaggaggagaaggcggaggaggcagtcgctctccgcggggctg
agccggacgcgtcgtcttgccccctcccccggttcgcggtgccgccgtgtagttggcg
ccgctgccccggctgagagtgagcgtggtgtcgacggagggagatgccccgggacgccg
gcgccagtaactgggagctgatgagagtcgccgagggcgcgccgggcccaggtgccgggg
ctgcccgccgccgccgccgccgcctgcgcgcccgcccgcctttcgcggccgctctc
ccccctccccgacacacactcacaggccgggcattgatg

*Homo sapiens* kelch-like 6 (*Drosophila*) (KLHL6):

(Seq ID No: 1074)

cgctccttcag
tctcgatg

*Homo sapiens* GTPase, IMAP family member 1 (GIMAP1):

(Seq ID No: 1075)

cagccttctgcactcacagccgaagggaaagcagcaggttggggcttctt
gtggccaacttcagagcctgtcaccaggaaaggtaagcatg -continued

*Homo sapiens* RAB24, member RAS oncogene family (RAB24):

(Seq ID No: 1076)

cgccctctagccccctcccgcgggagtcgcggcgctgcgggtaggagccgggttgcgg
gagaccccaggttcggttgggattcccagccagaacggagcttaagccggg
caggcgagcgaatgacggagtagcgagctgcacggcggcgtgctgcgctgttgaggac
gctgtcccgcgcgctcccaggccgccccgaggcttgggtcttcgaagga
taatcggcgcccggggccgaacagcgggggcacacggggcgctgccgaagtg
caaggccacggccagagctcgagcccgacgcgctgtctggagtcgtaggaccctgac
gtggctgaagcggccccgggagcatg

*Homo sapiens* adaptor-related protein complex 2, alpha 1 subunit (AP2A1):

(Seq ID No: 1077)

agccctccccgcggccggctcggctcctt
ggcgctgcctggggtcctttccgcccggtccccgctt
gccagccccgctgctctgtgccctgtccggccaggcctggagccgacaccaccgccat
catg

*Homo sapiens* copine IV (CPNE4):

(Seq ID No: 1078)

ctccctcttttctcag
taccctcctctttactctccgagttaactgagagccgac
ctgacatctccaacatttcaccctcttccccaccccatcaccgagaatggag
tcagggtttccggagagaccgaactctgctctcagcacctttcccagccgctgtt
gctaaactgacctcggaggacgagaggggaaggaggtgcgacgcccttacatcag
tacataactaccacaccaaccacctccacttcaaagccgatttt
gcatcctgggggcgggacagaccctcgtcccgggctgaattctctctccactcttcga
gattggcacacccagaatg

*Homo sapiens* synaptosomal-associated protein, 25 kDa (SNAP25):

(Seq ID No: 1079)

ctgtctttccttccctccctgctcggcggctccaccacagttgcaacctgcagaggcccg
gagaacacaaccctcccgagaagcccaggtccagagccaaacccgtcactgaccccccag
cccaggcgcccagccactccccaccgctaccatg

*Homo sapiens* cAMP responsive element binding protein 3-like 4 (CREB3L4):

(Seq ID No: 1080)

aggtctcttgactctttccgccttt
gtttacaaccctgccatgatctccctcttgcaaaagcgagggc
tacagaacaggcattcaggagtcctgtgctccag
tcacagccttttctgttcttcagctaggagacaccaaacctcaggaagatttacta
tagctaagagaaaactgcagcagaaagggcgcggctacctacttcttaaattccgttt
gtggaccctcagactcttagtcccctactcccagatacagcggccctac
cgtggctcctggcaaggtggcatccacttttgtagtaagcatg

*Homo sapiens* leucine-rich pentatricopeptide repeat containing (LRPPRC):

(Seq ID No: 1081)

ctgtccttctggcggagcgtgcttcccgctgcggggacgttcgagcaatg

*Homo sapiens* zinc finger protein 418 (ZNF418):

(Seq ID No: 1082)

cgttctctgg
tagcgaccattttggttaatgttgggtgtgtttctgcggtttgtgaggtga
gaggcgctggagctatgggtccgaaccgcggtgtctgaacccagaaggtgaagag
tccttcttgctgcacagaggcagatcttaggcccgtaacggcgcccgccgctcccgg
cagtgctttccccgcgtactcgg
gatggcggcggccgcgctgaggctcccggctcaggcatcatctggctgcaaagaaga
gaacacactgtgtttgagggaggaggaaggaggatcagagtttaaactcctgccataatg

*Homo sapiens* tetratricopeptide repeat domain 14 (TTC14):

(Seq ID No: 1083)

gtttcttccgcttcctgtaccacccggctcaagtagcggacacggaacagggaac
tatcagcccgtcggcctccgggccctgcattctctagccatg

*Homo sapiens* BMP binding endothelial regulator (BMPER):

(Seq ID No: 1084)

agccctttcgactgtgagctgcggcagctgagcagaggcggcggcgcgggacctgcag
tcgccagggattccctccaggtgacgatg

*Homo sapiens* zinc finger protein 384 (ZNF384):

(Seq ID No: 1085)

cccccttttcgtttccggcgctcccgccttctctccgcagagctcttctctgagcctgtt
gggggaggggaggggggcgtggaggaactgggggttcgcgggagcacgagctgcagcacca
cttccgggtgagtgcaaggggaggggcagcaaggaggggggccaccccactacctcgcgcc
cccgccctgcgggtgtctcgcgcgcgttccgtgcgtgtgagtgtgtgggtctgtctcgct
ccagaagtgcgtgcccgcgcgctgcgccttgcgctttttcccctccctcgccccttcctg
gtcctcccaccctcctcggctccctcctttcccagcaaacgccgcccctcccgcgccctg -continued
```
gctcaggctctggcgccgccgcagccgtcgccgcccgaaagttcaggagccctggaaagg
agaaggaataagacggcaggaggaagagagagagagggtagaatg
```

Homo sapiens RAD51-like 3 (S. cerevisiae) (RAD51L3): (Seq ID No: 1086)

```
ctctcctttctcctccggcagccagcgcgcctgtgtcctctctaggaaggggtaggggag
gggcgtctggagaggacccccgcgaatgcccacgtgacgtgcag
tcccccctggggctgttccggcctgcggggaacatg
```

Homo sapiens CD99 molecule-like 2 (CD99L2): (Seq ID No: 1087)

```
gctcctcctcccgctcctcctcggcctccccttcgggcgctctcgcgctaactgtgctcc
tccggggcccctccgcctgctcccagccatg
```

Homo sapiens glucosamine-6-phosphate deaminase 2 (GNPDA2): (Seq ID No: 1088)

```
gcgcctttatctgcatccgggtccgtgggattcgcgctccac
tggtcagctggggtcgctctcgggtggttgggtgttgctt
gttcccgctgttccagcgtcgaagaaccattgggtctgccggtttgaacttgttctg
gaagctgtgcgtcaccgtaatg
```

Homo sapiens methionyl-tRNA synthetase 2, mitochondrial
(MARS2): (Seq ID No: 1089)

```
ccgcctcctccgcttgcggccggtctgcaccatg
```

Homo sapiens chromosome 12 open reading frame 57 (C12orf57): (Seq ID No: 1090)

```
tttccttccgctcccaggggcgttgggaacggttgtaggac
gtggctctttattcgtgagttttccatttacctccgctgaacctagagcttcagac
gccctatg
```

Homo sapiens tRNA-yW synthesizing protein 3 homolog
(S. cerevisiae) (TYW3): (Seq ID No: 1091)

```
ggacctttcggccaccgctcgcttcaa
tatggctgccccagggagagacgaggctaccatgaaggagccgagcgcagaccctgag
tccgtcacccatg
```

Homo sapiens Sp1 transcription factor (SP1): (Seq ID No: 1092)

```
ctccctcctccttaccccccctccctgtccggtccgggttcgctt
gcctcgtcagcgtccgcgttttcccggcccccccaaccccccccggacag
gaccccttgagcttgtccctcagctgccaccatg
```

Homo sapiens histidine triad nucleotide binding protein 3
(HINT3): (Seq ID No: 1093)

```
cgccctctagtggcagccggttttgaggccggcctccggcttt
gaagttcctcaccgcgtctccttccctctcccaaagcctggatcac
cgcccagcgtcaggcgaggggcgacgtctcgaggtaaaacggaggaggtgcgggacgcg
gagactgcgcgggcccggtagccctgga
gaggccgaggctctaggccgcgaggggcgggtgcaatg
```

Homo sapiens M-phase specific PLK1 interacting protein
(MPLKIP): (Seq ID No: 1094)

```
agttctctgcggagggccggttgatacagttccggtgggagaac
gcggctgcgaggttttcggctttggctcctgatatg
```

Homo sapiens palmitoyl-protein thioesterase 2 (PPT2): (Seq ID No: 1095)

```
cacccttcccccgccaccgtgggttccagacttgggataagtaaacagcgggtggagcg
aggcctacggacccaggccaggtgggagtctgcactcttcaaggggcctgggctgctgct
cacgggtattaaagaactccgcgttgttcatggctgaggcgatgcattaggaagatcctg
gacctagagaacaagtcccccgaacgctgagttggaggcgggacttcgggtgcgcgttgg
cgggagcatg
```

Homo sapiens BCL2-like 14 (apoptosis facilitator) (BCL2L14): (Seq ID No: 1096)

```
aagcctcttttcaggctgagtcctaaacctgaagaaagttta
gagcctggggctctaaactacctgagtcttttccaaacgacaagccaagaagacctgtt
gaaagtttcctcttaagtttcgtggagagagactcaggtatagaaa
tatccttactgccacctgacctgaagcagaagaaatcacagacagcttccagac
caggcccaacatg
```

Homo sapiens galactose mutarotase (aldose 1-epimerase)
(GALM): (Seq ID No: 1097)

```
acgccccttctcctgtaaacttgggtcgcctctagcttagcgagcgctg
gagtttgaagagcgggcagtggctgcacacgccaaactttccctatg
```

*Homo sapiens* carboxymethylenebutenolidase homolog (*Pseudomonas*) (CMBL):

(Seq ID No: 1098)

cttccttcccttccccgactttgcagat
ttctcttccccaggcctccctcctccacctctccgccccctccgggctt
ggctctcccaggaggctacgactggagccactggtcccgcag
gatcccgcgtcctcggtcgcgcgtccacgtccctctcgcgtcccgcccggcgccac
gccgcctcctctgggttcggcctccgcgcggtgcagcgcagtctcaggccgcgggacaa
gcccgacttaaatctctgcaatg

*Homo sapiens* chromosome 7 open reading frame 31 (C7orf31):

(Seq ID No: 1099)

cgtccttctcccgcccccgccctgcctgccagctccaccgggccgtaggtgcggac
gacctcaaaattcctcggcccgcgaaggccgccagctgcggggaggggaggg
gaggcgcggtcccg
cagcgcccccaggctcatgtcccaggtatgtccagaccccgaggcaccgcttgcaggg
cagtgacagcccgtgaggctcggcctcgaccctggcacccttggtcccagctac
gccggctcctggccttcccccaagtccgagagagaggtgggattctccccgacgcagtt
ggaaaccgggaatcccctttagggtcccgttcgtgctgcactactgactccaccatctg
caaagggattcttgtccagaatccccgaaggctttaggacagcgcttatttgtt
gaatgaagagtctctaattttcggaaagaccacaggctaaaagtcaagtt
gtgccttttagccaagaagcatg

*Homo sapiens* secretory carrier membrane protein 5 (SCAMP5):

(Seq ID No: 1100)

cggcctttcggcagccgaacggccgcggcagttcaggacaaagaggtgtggg
caggccactgggccagctggtaacatcatg

*Homo sapiens* mitogen-activated protein kinase 10 (MAPK10):

(Seq ID No: 1101)

tgctcctttcggttgccatagcaaccccattccccaagccctctgtccgtctcctctggt
aggttccacaatggtacaggcagcatcacgctgcacaatggtttccaggcagtgaaagag
ggtgattcagcaagccactcttcttctatttctttaacctcccccttcacttttatttt
tatggggtgggtggtgcttgctatatgcttaccttttctttttcttttttcattttac
aaatttcctttttgtcctcacccctcaattcctaggggcttgagtgagtttaagattgg
gttttcttggaaatcacctgtccatcgttaattttaaacaatctccatatctccaaagaa
tctcttccatgttagtctggaatgtggttaatgaaaaacaagtagggaggatttctgggg
caaacactgccggatcaggatcgtagttctcaggcacggaaggctagtgtgagaaacac
caacagcaggcccatctcagatcttcactatggcaacttatgcaagaaactgttgaatta
gacccgtttcctatagatgagaaaccatacaagctgtggtatttatgagcctccatttct
tatactactgcagtgaaccaacattggatgtgaaaattgcctttgtcaggtgtgtgttc
cttacaggtaaaacaagggattcgataaacaagtggatgtgtcatatattgccaaacatt
acaacatg

*Homo sapiens* beta-site APP-cleaving enzyme 2 (BACE2):

(Seq ID No: 1102)

cgtcctccccgccgccgccggtccggtgcgcgcccatccctgcccg
cagccccgcgcgccggccgagtcgctgagccgcggctgccggacgggacgggac
cggctaggctgggcgcgccccccgggccccgccgtgggcatg

*Homo sapiens* SWI/SNF related, matrix associated, actin dependent regulator of chromatin, subfamily d, member 1 (SMARCD1):

(Seq ID No: 1103)

acgccttttccgctagtcgccccgctctatccca
tagtctcgctgccctgagcctcccgtgccggccggccggccgggg
gaacaggcgggcgctcgggggggcgctcgggggggcgggggag
ttccggttccggttctttgtgcggctgcatcggcggctccgggaagatg

*Homo sapiens* family with sequence similarity 175, member A (FAM175A):

(Seq ID No: 1104)

cgtcctcttgtgtagcctgaggcggcggtagcatg

*Homo sapiens* adenosine deaminase domain containing 1 (testis-specific) (ADAD1):

(Seq ID No: 1105)

aggcctcttttgaaa
gatgcggccctgaccctgtgaacctcgcgcagagcggcctgaagcgagaggtt
gaggctggggaggtgagaaaatg

*Homo sapiens* acyl-CoA synthetase short-chain family member 2 (ACSS2):

(Seq ID No: 1106)

gcccctctacggaggccccgcctctagttcggcctgttttctcag
tcccggcacccgccgcgaccgcaaaggcggccgcggttctaggaacttgacgtgatg

*Homo sapiens* multiple coagulation factor deficiency 2 (MCFD2):

(Seq ID No: 1107)

cttcccttactcaccggtgtccggaaaggtgaac

-continued gctgcgctcgggctgcctcgcctgttacctccgccgccgggcatg

*Homo sapiens* SPOC domain containing 1 (SPOCD1):
(Seq ID No: 1108)

gctcctttcagctagtgggtggaacccaggagggaaaactcagggaa
gcccagggcccgtgttgtgcttttggcccaggtaggtggacagacatg

*Homo sapiens* LY6/PLAUR domain containing 1 (LYPD1):
(Seq ID No: 1109)

agttccttcagtctcagccgccaactccggaggcgcggtgctcggcccgggagcgcgagc
ggggaggagcagagacccgcagccgggagcccgagcgcgggcgatgcaggctccgcgagcg
gcacctgcggctcctctaagctacgaccgtcgtctccgcgggcagcagcgcgggcccagc
agcctcggcagccacagccgctgcagccggggcagcctccgctgctgtcgcctcctctga
tgcgcttgccctctccggccccgggactccgggagaatg

*Homo sapiens* cytochrome b5 domain containing 1 (CYB5D1):
(Seq ID No: 1110)

cattctttcatactgcctcctcccttgttttctgtctcagagaga
tagtctgtcctaaatatcccatgtagcccaggccactgaattaaaacggagcg
tattcgttctctgccccacccgcaactcctgaaagcggcgcaactcaattactt
gatcctatatgccccacgcgggactcatactacgtttcccgtgaacacgtgcag
tccaaacccgcccctgatatttatctcagtggacggtggccg
gaaaaggacaatggtttccatgtcagcggataaacgctctccctcggctcccggac
gcgacggaggtcgtagtagtagtgagtacgtgctgaggagcaaaggagtaaccaaga
gatccagtgaccgacagagcaagagccatg

*Homo sapiens* synaptoporin (SYNPR):
(Seq ID No: 1111)

tctcctcctttgcttcataaaaa
gagggacaagtggctggtgctgtggacagagaagctttattttttagtatgagacaac
ctctattttcttcaggagagggaagttggattatcaattcttttgtaaatg

*Homo sapiens* heterogeneous nuclear ribonucleoprotein U-like 1 (HNRPUL1):
(Seq ID No: 1112)

ccccccctttccccccttcgcctcctgacaggaaaggtttaagggg
gacagagccctgggaggccgggccgggctcggggggccaccccgggggcccgggccatg

*Homo sapiens* schlafen family member 5 (SLFN5):
(Seq ID No: 1113)

ggttctctgctctggacttgggaggctccgttgcctgctcccggagggagac
gcgctgccgaggagaacccagcgggagaacatttcaggataggaa
taggccaagtgctgagaagatg

*Homo sapiens* MAS-related GPR, member F (MRGPRF):
(Seq ID No: 1114)

ccatctcttccagcaggagagggctctactctgagctcc
tatttttccaaggctccgggccgcgctcggcgctggcctgctgccccggcgggtccgccgg
ccggaggcgggagtcacaggaagagccctccacaaaaggaggcctcggcggatcag
gacagctgcaggtgggtgtgcagactggtgagctgccagcaggggcccagac
gcgcaggcctggagatg

*Homo sapiens* ubiquitin-like domain containing CTD phosphatase 1 (UBLCP1):
(Seq ID No: 1115)

cggtctctcagcggccggtttctgcgtccgctgccgcaggttccac
cgcgctccaggtattttttttttctgaaggaaagctgcttcctcatatgtttcaagaatg

*Homo sapiens* Rab interacting lysosomal protein-like 2 (RILPL2):
(Seq ID No: 1116)

cctccttttccgttgtcccttcgcgccccaaaccacatcctggagcg
cactctccagcgtggctggcagcggggacggtgcgccggggcgcaggcccaagag
tcgcgtgcgcggccccttgcaccatcccccgggcccaccccgggccgcgctgattggg
caggtagggactctgcccagcggaaagttttgggtgccgggaggaagtctaaccttttgg
gagactccaagacagcagctccgaggtcggcgggggtctgggtggccatg

*Homo sapiens* zinc finger with UFM1-specific peptidase domain (ZUFSP):
(Seq ID No: 1117)

acttctttttccgtggggagtaaggaagtgcttttgaatgaggtactgagggccaaggtgtt
ggaagttcctaattcttttcctcggttaactgtgaaactctgcgtattgggaaggcctggc
ctcagtcatcaggccaggagaggtactggacgccgcgcacgcactcgtctgccagcgagg
cccaaaggggaagcctagcggagctcagtgtggcagctgctggcctctgggccgctactt
gtcaataccatg

*Homo sapiens* mitogen-activated protein kinase kinase 5 (MAP2K5):
(Seq ID No: 1118)

ccgccttcctcctcctcctctcgccgctaccgccgtcgccgccgccg
cagccgccgccggtccgcgcggccctcgggtggccg -continued gagctcagcctgcgcgcgccgcgccctgtgtctccgggtggggcagaa
gactcgcccttgaacctcccgcggggactctccgtggtgtggcggccctgggctcttt
cttaatagccccggactgagtcccctccagtcgaggaccctctcctagtccactgacgag
cggtggacacctgccgctgtatctcccccaaaccgagtccttgccctgctgcctcctcat
acccacacggcggcagagaccttcaccatagcgttcgctcaactccagaaccttccgacc
tccgctagttcctgcgggcctttgcccgcttcccggtgcacccteecegggagacacctc
agaccccgacagcctgggcaggctcggtgcctgcgggtgcgttcctgatcacccctccc
ctcttccctcccccctcatcctccattcccttgttttcaccctctgtcctctgcccgtcac
tccccttgtcacctcttggagcccectcctaaccagcggccagtgggtttcccataccec
aggatgtgagcctctttaacctgtaatg

*Homo sapiens* solute carrier family 2 (facilitated
glucose transporter), member 12 (SLC2A12):

(Seq ID No: 1119)

cactcttctttag
catgctattatgggaaagtgaccactcctgggagcgggggtggtcggggcggttt
ggtggcggggaagcggctgtaacttctacgtgaccatg

*Homo sapiens* mitochondrial ribosomal protein L30 (MRPL30):

(Seq ID No: 1120)

cttcctctgctctgcttcccttcggag
gaaaatttcaggctgaaggtttagcgggtgccgcctctaaagagagcaatcactacact
tatg

*Homo sapiens* tripartite motif containing 11 (TRIM11):

(Seq ID No: 1121)

gctcctcttcctgccggcatccgggatccctacgtcccgcgtcccccgagcgctcg
gagcctacgcgcccagcgctaccgaaacccagagtcctgcgccctggag
tccccgcgcccccggagcccgagcacccgggagtcccgagcctcgcgcccccggag
tgcccgagcctgcgccgccgcacccgga
taccccgcgtccccgcgagctgccgaggccgcccgccgccgccccgcggacagtac
cgccttcctcccctctgtccgcgccatg

*Homo sapiens* proline-rich transmembrane protein 2 (PRRT2):

(Seq ID No: 1122)

ctccctccctagctgacttgctccctcccgggctgcggctgctgcaaaagccagcagcgg
cagcgggagctgtccggaggccggcgtcgagggtttgccgctgtctctgctattccatcc
tccccatagggctctctcccctctcccatctcaagatg

*Homo sapiens* zinc finger protein 626 (ZNF626):

(Seq ID No: 1123)

cggcctttgtctctcgctgcagtcagagctccaggtctggttcttctcctaaaggcccag
gctgtgtggccccgtgtcctgcaggtattgggagatccacagctaagacaccgggacctc
ctggaagccaaaaatg

*Homo sapiens* solute carrier family 25, member 43 (SLC25A43):

(Seq ID No: 1124)

cggtcttccgggcccgggtcggggctcgatg

*Homo sapiens* crystallin, zeta (quinone reductase)-like 1
(CRYZL1):

(Seq ID No: 1125)

ggctctctgacgaaggactggaaggtggcggtggtgaaggtg
caggccgttggggcggctcagaggcaggtgactatg

*Homo sapiens* mitogen-activated protein kinase kinase kinase
7 (MAP3K7):

(Seq ID No: 1126)

ctgcctctaccccgccacggatcgccgggtagtaggactgcgcggctccaggctgaggg
tcggtccggaggcgggtgggcgcgggtctcacccggattgtccgggtggcaccgttcccg
gccccaccgggcgccgcgagggatcatg

*Homo sapiens* septin 6 (SEPT6):

(Seq ID No: 1127)

cttttctctttgtcggag
gagctcctctgtttcctgtgcagtagctcccgttgcggcggcacccgtgg
cagccctggcggacgcaggagcgatg

*Homo sapiens* myotrophin (MTPN):

(Seq ID No: 1128)

ctgcctctcctcggccaggcggaac
ctctctgctgggcccggtggccgcaaaagaactttctttctcccgcccgaac
ggtcgccgcggccaactgcctcgcccgcctgg
cagcctaaccctccttctcttcttctcctctccggcttcgcgcggccctgcctccctctc
gcccggcggcatccgcttgctgctgccaccgcctcctcatcttctgcccggccaac
cggcctgccccgctgcagtgatg

*Homo sapiens* annexin A11 (ANXA11):

(Seq ID No: 1129)

ccctcccttgcactgcctctgg
cacctggggcagccgcgcccgcggagttttccgcccggcgctgac

-continued

```
ggctgctgcgcccgcggctccccagtgccccgagtgcccgcgggcccgcgagcgg
gagtgggacccagccctaggcagaacccaggcgccgcgcccgggacgccgcggaga
gagccactcccgccacgtccatttcgccctcgcgtccggag
tccccgtggccagggattattggacctgcctggtttaaactattgtcttagttaatttt
gtgctgctctaacaaaatatcacagactgagtaatttataagcaatagtacttattt
ggctcacagttctggaggctgagaagatcgtgaggctgcatctggcaagggccttctt
gctgcttcataacatggcagaagacatcatgcgggtgtgtgtctggggaaga
gacttacagaagtggagttgctgagtcaaagatctaaccatg
```

*Homo sapiens* RNA binding protein, fox-1 homolog
(*C. elegans*) 1 (RBFOX1):

(Seq ID No: 1130)
```
ttttctttctttcctctcccggcgttgatgag
tgcttggctcctgacagaagggatttggctcccagctttgtagttcggaagaagtt
gggtctatagatttcccctaactctccattgatgtgttgagcttcagagggaataa
taactctacgtaaagcatg
```

*Homo sapiens* prefoldin subunit 5 (PFDN5):

(Seq ID No: 1131)
```
cttcctcttcgttaagtcggccttcccaacatg
```

*Homo sapiens* high mobility group AT-hook 1 (HMGA1):

(Seq ID No: 1132)
```
cgctcttttaagctcccctgagccggtgctgcgctcctctaattgggactccgagccgg
ggctatttctggcgctggcgcggctccaagaaggcatccgcatttgctaccagcggcggc
cgcggcggagccaggccggtcctcagcgcccagcac
cgccgctcccggcaacccggagcgcgcaccgcaggccggcggccgagctcgcg
catcccagccatcactcttccacctgctccttagagaagggaagatg
```

*Homo sapiens* zinc finger protein 323 (ZNF323):

(Seq ID No: 1133)
```
cggcctt
gcggttgatcggtcattggggtgctgcagccccgccacctgttccgtagctt
gccggtgccccgaaggtgtcttctcctaaggaagat
taaatcagaaaatttaaatcacagttatccctttacttaaagccagagtaa
gccttccaaattaaccccaggaatg
```

*Homo sapiens* tumor protein p53 inducible protein 3 (TP53I3):

(Seq ID No: 1134)
```
ctttctcttctcttagcagcacccagcttgcccacccatgctcaagatgggcgggatgcc
agcctgttacataaatgtgccaaaagcctggccatgcctggaaaatggaccaatccgccc
gccaagaggttgggtctcgttccctagaga
gaaggaagtttcctctccttgaagtgagagctagaatcgcactttctgtcaagctgaga
gaaagactcttttccagaggctaaaaggacaagaaaatctgatttgctt
gcttctaactttgcgttttaaaggggggaaggaggaaaggaaagagggg
gagggtggttctgcttagccccaccctccggc
taccccaggtccagccgtccattccggtggaggcagaggcag
tcctggggctctggggctcggctttgtcaccgggaccgcaggagccagaaccac
tcggcgccgcctggtgcatgggaggggagccgggccaggaacaatatg
```

*Homo sapiens* ceramide synthase 5 (CERS5):

(Seq ID No: 1135)
```
ccgcctccccgcgggttccgttggctgtggcggcagctgacgctt
gtggcggcggtggcttcggggtgggcgtaagatg
```

*Homo sapiens* TRAF3 interacting protein 2 (TRAF3IP2):

(Seq ID No: 1136)
```
tgttcttctacttacctgggccggagaaggtggagggagacgagaagccgccga
gagccgactaccctccgggcccagtctgtctgtccgtggtggatctaagaaactagaatg
```

*Homo sapiens* Smith-Magenis syndrome chromosome region, candidate 7
(SMCR7):

(Seq ID No: 1137)
```
ggtccttcac
gttccattcccaggctggtctgagctccggggccgtggtcccgctgcctcctccggtcgt
cgtgcggaagctgcgacgcaggcagaccatg
```

*Homo sapiens* mitochondrial ribosomal protein L10 (MRPL10):

(Seq ID No: 1138)
```
cattcttccggtggagatggctgcggccgtggcggg
gatgctgcgaggggtctcctgccccaggcgggctagagtgcagtggcatg
```

*Homo sapiens* proteasome (prosome,
macropain) subunit, alpha type, 1 (PSMA1):

(Seq ID No: 1139)
```
acttctctgtagatcgctgagcgatactttcggcagcacctccttgattctcagttttgc
tggaggccgcaaccaggcccgcgccgccaccatg
```

*Homo sapiens* sorting nexin 5 (SNX5):

(Seq ID No: 1140)
```
cggtcttttctctagac
```

-continued

```
gcgtcttgctgggagagtgtccgttgcttcccgtccgtgtcgcggccctgcggtt
ggcggcctcctcgtggagcggagcaaggccaggcggcccctgctcgagtcccgcgtcgc
catg
```

*Homo sapiens* zinc finger protein 276 (ZNF276):

(Seq ID No: 1141)

```
gggcccctccgcgcgtactgcgggcccacgggtgttagtggcggggcggcagagtcc
gggtgggttgtcgcgacggagccgggcctcttcgccgtcttgagacggggctggcgagaa
gggcccctcacggagttgccatgggcgtctaaccgcggcagccaggcccctctctacgtg
agacccggccccctcccctttctgcagcccgcccgccacctgcgcggccgcgtggcctc
cgccggcgcctgcccgccccgcgcctccgtctcccacggagcaggccgggctctcgc
catg
```

*Homo sapiens* zinc finger protein 561 (ZNF561):

(Seq ID No: 1142)

```
ccatcttttccggcgctggctcctctccgtcagtgcggtttcgccttatggtggtg
gagtctgcccaggctgtggaccgcaaataaccctgtacaaagaggaatgga
gattgcctctatccacctagattcataagctggcctgaggtgatcttgg
catcaaggaagggatgcacatcatcacaccatcagcttcagagaatg
```

*Homo sapiens* mucin 7, secreted (MUC7):

(Seq ID No: 1143)

```
ctttctcttctttt
gcttctagttaccatcctcaaaggattggctaaaagcaagcaactg
gattgaacaccctaagaagaaagattcacactgcaccaggagacatcagaaagaatg
```

*Homo sapiens* threonyl-tRNA synthetase (TARS):

(Seq ID No: 1144)

```
gcgcctttcgattgcatcagctggtccagccgaggccaagtcccgggcgctagcccac
ctcccacccgcctctt
ggctcctctcctctaggccgtcgctttcgggttctctcatcgcttcgtcgttcgccaatg
```

*Homo sapiens* ATPase, Na+/K+ transporting, alpha 3 polypeptide (ATP1A3):

(Seq ID No: 1145)

```
cagcctctgtgcggtgggaccaacggacggacggacggacgcgcgcac
ctaccgaggcgcgggcgctgcagaggctcccagcccaa
gcctgagcctgagcccgccccgaggtccccgccccgcccgcctggctctctcgccgcg
gagccgccaagatg
```

*Homo sapiens* chromosome 11 open reading frame 46 (C11orf46):

(Seq ID No: 1146)

```
cgtcctctcagtggtagcgcggggactggctgggaagcggtcggtcgag
tgtggcctgtgtggactcgcatcttgcccgaagccgggcggaggagagctcaa
gctaagggtgatcagcccatgacctaaacctccagacaaaataaaacggaaaattt
gctagaatcaagaatg
```

*Homo sapiens* chromosome 17 open reading frame 45 (C17orf45):

(Seq ID No: 1147)

```
tgaccttttcattcccgttgttatggaggtaggctctctaggaatctgggagtagtagct
gggggggcaagagcaaataaagagctcgagcttctgtggtctctggggagatg
```

*Homo sapiens* AHA1, activator of heat shock 90 kDa protein ATPase homolog 2 (yeast) (AHSA2):

(Seq ID No: 1148)

```
gggccttctggcagtttctgg
gagctgcgaacgcgccgccccggggctcggcggccggaaacgctggcttcg
gagccttaggcgccgcggcctttccttgttttccgcccagtccac
gccgccatggccaagtggggccaggggaaccccccactggatcgtggaggagcgggag
gacgggaccaacgtgaacaactggcgctggcgcggctggcggcggcctccttccgg
gatctggggagggccgggccgcgg
gagccggggctgccctgggtctgtgcggggccgcggggccagggggtcaggggccgcc
cccccctcagctgctggacgcagggctcggccttcgcctctcggctcgggagagtcctt
gagtacggagaccggctaggagggttgcagctgcctcttttttgaaagttgggtt
gggcccaagagtgacttccgacagacctttccactcccac
cgtctgtggcctgagggccttcccttctcctcccgcccaccccctctggatgtttcggg
gagttagaagggagctggattgagagactgtgttaggggcggggtatggaacgtagtg
gaaagggcagaaatttggatctcagttcgcgcccaccccg
caggcgcctcccgcgagccgggccctctgtgagtgagacaagctccccttccttac
gcgcctcacctggcgcgtggggagaggtcggcagcccctccgccgcagaacctccg
gaagggatgtcctctgccctgcgcctctggccggggctgtggtccctccaggccgtcgag
gggatgctgaggccggtccccagaggagcatgacttggctggtccggag
gagctctgagggcatgggcaatcttggctcgctgcaacctcagcttccagagttcaa
gcgagtctcctgcttcagcctcatgagtagctgggactacagatgcgtgccactac
gtccgtctgatgtttgtatttttagtagagacagggtttcaccatgtt
ggtcaggctgctctcgaactccagatctcgtgatccgcccgcctgggcctacta
aagtgctgggattacaggcgtgagctagatctgacttttctagtgtcctagcctt
ggcccgatggacatgtcatttctctcagctcgtttctgtcccctaaagtgagaa
tattgcctgggaagattacattagacgatgtatatgcgaagacacttgatagctgg
tatttgtcatgattctgattagttcactactgctactttccctgtggcctaggctttgcc
tatttccagtgggcgagctagctagatcctcctcccttaaataagccag
```

```
tgtttttaagacagaatactacttgcatagtggacaataatatcttaaagaactgag
caggatgaaaagaatttgatagaaagcaggtttgaggagcacattggaggttgg
caggtttcgaggctgcttgagaggacttgggccgatctgggctgggcttggac
gtgaccctggcacccaggcaggtggatcccagctggggcttccattcac
gactttctggtccctggcaggacagagcgggatgccaccagctt
gtccaaaggggaagttccaggagctcctggtgggcatcgttgtggagaatgac
gctggccgcggcgagatcaacgagttgaagcaggtggaaggggaggcttcgtgcag
cagccgcaaaggaaagctgattttcttctatgagtggaacatcaaactgggctg
gaaaggcatcgttaaagaatctggagtgaagcacaagggattgattgaaa
tacccaatcttctgaggaaaatgaagtagatgacactgagaatttacaacgggaatg
```

*Homo sapiens* GrpE-like 2, mitochondrial (*E. coli*) (GRPEL2):

(Seq ID No: 1149)
```
ctgcctctcagcccaaattggaaacatg
```

*Homo sapiens* xyloside xylosyltransferase 1 (XXYLT1):

(Seq ID No: 1150)
```
ccgccccttcatggccgccgcctggcgccggggctaagtggccgccggcgtccgggtac
ccgagggctctcccgcgttgctggcaccgctggcgccgcggtctcgtagcgcatg
```

*Homo sapiens* chromosome 7 open reading frame 60 (C7orf60):

(Seq ID No: 1151)
```
cctcctctggctgctgcctccgcagctccctcctcctacccacctcctccatctggg
gagcgtctgcggggggcctgaggggcggcggcggcggcggctgcgatatg
```

*Homo sapiens* tetratricopeptide repeat domain 39B (TTC39B):

(Seq ID No: 1152)
```
ccctcctttgcgctgggctgagcccagagccgagagcaggggtcggctctgag
ttccctgcttggtttttgggtggcagcagccagaggaggaatatg
```

*Homo sapiens* motile sperm domain containing 2 (MOSPD2):

(Seq ID No: 1153)
```
cacccttctctgtctacctctgggcgggactgccgggtgatgaga
tactcggtcggcgacggtagaacgggcgacggcgacaaccgcaatcacatccacgac
ggtgatcatg
```

*Homo sapiens* major facilitator superfamily domain containing 6-like (MFSD6L):

(Seq ID No: 1154)
```
ggccccttcggtccaacggcaggac
ctgggggctgtggccgggggcggccgttgacctggtgaccgcggcgccgccccagac
cggggggcgcagtcccactcgctccgagccccggtcccccaagcctccctcccgggtac
ctgggccgcgcccgccctgcgcccagctccgccctccgtcggcccaggcctgacagagc
ccggcagccatg
```

*Homo sapiens* consortin, connexin sorting protein (CNST):

(Seq ID No: 1155)
```
cttcctctctagccgccagtgctc
tatgctccgcggtcgcgggccgccagcctccagccggccagccgcgaggggtgcg
cagagggaggcggggcggaaaggcgagaggtgtctcctccaccggagccaggga
gacccgagcaagctccgtgacagcacgtcggccgccatgtcgccgagtggggctg
gaaacagaccggcgcccagcggtagccctccttgcgcctccgattcccaga
catggaaggtctttaatgtaactttaaatggttcaccaaaggatgctctaatg
```

*Homo sapiens* zinc finger protein 92 (ZNF92):

(Seq ID No: 1156)
```
gggccttt
gtctctcgctgcagccggcgctccacgtctagtcttcactgctctgcgtcctgtgctga
taaaggctcgccgctgtgaccctgttacctgcaagaacttggaggttcacagctaagac
gccaggaccccctggaagcctagaaatg
```

*Homo sapiens* DnaJ (Hsp40) homolog, subfamily C, member 18 (DNAJC18):

(Seq ID No: 1157)
```
ccccccttctctttcagcctcgggcacggggggaggctcggcggac
ctgctgattgggaaccgatatg
```

*Homo sapiens* polymerase (RNA) I polypeptide D, 16 kDa (POLR1D):

(Seq ID No: 1158)
```
cctcctccctccttccgtcctccgcgccttccgtcggtcggtccttgcttcctgcttcgc
ctccgcgcctcgcgctatgggacagagcccccgatccgccagcaccacctgaggatccag
aaaccgccccagcgatg
```

*Homo sapiens* ring finger protein 182 (RNF182):

(Seq ID No: 1159)
```
ac
ctccctcccctcccaggcgccgccgcagccg
gagcggctcccgggccctgggccgccgccggccaggaagaaatacttgtgttggctg
catttccagggatgctaccagagctcaaggctgtcacctggtcttgcccagaa
gagccgttcttagaggcaggacttgatgaaggctttcctgctgatggaataggttt
```

-continued

```
gctagagctggccttggaattagaaccctccatgtggcctttataaatatgcgttt
gagacagagttatatgcagaagttgaaaatgcctggaagatttctggtttctttcac
tacttatcctgccttttgcatcgctgccagatttggatgatatgatattcagagggg
caccttaatcaaagccattcttcaacaagacccacctggcataa
gattgcacacataattcaagatg
```

Homo sapiens transmembrane protein 18 (TMEM18):

(Seq ID No: 1160)
```
cctcctctgtg
gattctggccaggccgggttcggcggttgctgtgagagcgggcttcccaacaccatg
```

Homo sapiens Hermansky-Pudlak syndrome 4 (HPS4):

(Seq ID No: 1161)
```
ag
gcctctctgccgcgcgcgcaggtacggggcagaagtcg
caggtacccagctgctgcccacatttctggtccagagtcccgaaccccgagcactgg
gatgcctggctactccgagccaaggcactgatgtttgaactggaaacttcaaaac
gtttaataagagtcttcaggatgggtttgaactagacaagctagaaatttcttta
gaacaccagctctagcatgcatctcccacttttggctttcctggagaggagcttgaa
gaggtggttctgcagacagccacagtgatacttaggaaaccagaggaatggattt
gacttttctgctaggattctctgttatagtttctccctgagttgtaagaggcatggaaa
tatacatgaaactgaagaacctgcaaggaagggaagtggaactttccatgctgag
tgaaaactaaccaagtggcagttgtgactgaaaacactgaaacctaccacgtccagat
tcactggattggggatagaggaacggtcacagctagggagaaagaagtgataccg
gaaaagaaaacctaaatgaagagaatgaggatgactgcacagtagatg
```

Homo sapiens PTK7 protein tyrosine kinase 7 (PTK7):

(Seq ID No: 1162)
```
agctccttttcctgagcccgccgcgatg
```

Homo sapiens kelch repeat and BTB (POZ) domain containing 6 (KBTBD6):

(Seq ID No: 1163)
```
agttctcctgggcgcctagcattgtcgcccacgctgcag
tagcggcttctgcggctccaagccagcgggtcctgtgaaggcgagcagacgcgga
gaaaggacgcgggagtgagagagggtgagtcagccactgtctaaacgataacgg
gaggcggctctgcggggtagggttgaattcag
taaatgggctcgtgctgctgtctcttcggagacgctgc
tatcttagcgtcagcgagggaaggttgaggaggagcagagccgggtcctg
cagcgtttctcgccatcagcgcccgtcgccatctccaccatg
```

Homo sapiens sperm antigen with calponin homology and coiled-coil domains 1 (SPECC1):

(Seq ID No: 1164)
```
ctttctttgactggagcggacccgccggacgcaac
cgcctcgccagccggagccagcgcgagctcggcacggtggacacccggtccgaggccgg
caagccggctggtgcccgagtcggccaagcatg
```

Homo sapiens ST6 (alpha-N-acetyl-neuraminyl-2,3-beta-galactosyl-1,3)-N-acetylgalactosaminide alpha-2,6-sialyltransferase 3 (ST6GALNAC3):

(Seq ID No: 1165)
```
ggtcccttatttggatctgcgggaatgtgggctggagaggtcctgccgtggtac
cagcctccagcctgccccaggactgcccctgacccaggcgcgcccgctgctcggtgg
caggagggccggcggagcgccatg
```

Homo sapiens transportin 1 (TNPO1):

(Seq ID No: 1166)
```
gattctctttgttccg
cagccatttcaggccccggacaggaggcag
tgccgcttcggccgaaggcccgagcgcccgaggcgtctgggatg
```

Homo sapiens heat shock 70 kDa protein 8 (HSPA8):

(Seq ID No: 1167)
```
cttccttcgttattggagccaggcctacaccccagcaaccatg
```

Homo sapiens hyaluronoglucosaminidase 1 (HYAL1):

(Seq ID No: 1168)
```
ggctccttcctccaggagtctctggtgcagctggggtg
gaatctggccaggccctgcttaggcccccatcctggggtcaggaaatttggagga
taaggcccttcagccccaaggacatcctggctgccatacctgctcctgacttctcagggc
tggcagtcatcgactgggaggcatggcgcccacgctgggccttcaactgggacac
caaggacatttaccggcagcgctcacgggcactggtacaggcacag
caccctgattggccagctcctcaggtggaggcagtagcccaggaccag
ttccagggagctgcacgggcctggatg
```

Homo sapiens STE20-related kinase adaptor alpha (STRADA):

(Seq ID No: 1169)
```
agtcctcccggtcgccccactgcgcatggcacgttgcgtactcccctcccagcaac
cggtctggcggcggcgcggcagtaaaactgaggaggcggagccaagac
ggtcggggctgcttgctaactccaggaacaggtttaagttttttgaaactgaagtaggcc
```

-continued tacacagtaggaactcatg

Homo sapiens transmembrane protein 161B (TMEM161B):

(Seq ID No: 1170)

ccctctctttcgctgtttgagagtctctcggctcaaggaccgggaggtaagaggtttgg
gactgccccggcaactccagggtgtctggtccacgacctatcctaggcgccatg Homo sapiens Usher syndrome 1C (autosomal recessive, severe)
(USH1C):

(Seq ID No: 1171)

ggctctttccagctcctggcagccgggcacccgaaggaacgggtcgtg
caacgacgcagctggacctggcccagccatg Homo sapiens interleukin 12 receptor, beta 1 (IL12RB1):

(Seq ID No: 1172)

cag
tcttttctccttgctcagcttcaatgtgttccggagtggggacggggtggctgaac
ctcgcaggtggcagagaggctccctggggctgtggggctctacgtggatccgatg Homo sapiens Meis homeobox 2 (MEIS2):

(Seq ID No: 1173)

atcccttcctctctttttctgttcgccctcttctccctgctcttttttccctttccacccc
ctcctctgttctccctcacctcctgcgccccctccccttcccggggttctgacagtac
gatgagctgccccattacggcgggatg Homo sapiens G elongation factor, mitochondrial 2 (GFM2):

(Seq ID No: 1174)

ttttcttttcgtttagatacattgccttttgcctaggctggcgtcgagactt
gaggccgttgcagactttggcgcggctcgcgcctcctgcttcaagagcccagcggtga
gagctggcctgcggcacgcggcctaatgccagacagtaacagtttggaggatcaagatg Homo sapiens lamin A/C (LMNA):

(Seq ID No: 1175)

gagcctttt
gccccggccgtcggtgactcagtgttcgcgggagcgccgcacctacac
cagccaacccagatcccgaggtccgacagcgcccggcccagatccccacgcctgccag
gagcaagccgagagccagccggccggcgcactccgactccgagcag
tctctgtccttcgacccgagccccgcgcccttccgggacccctgccccgcggg
cagcgctgccaacctgccggccatg Homo sapiens calcium/calmodulin-dependent protein kinase II delta
(CAMK2D):

(Seq ID No: 1176)

cgctctttctctcgccgcgccgtcttgaa
gccgcgcgggctcgtgagcagcgcgaggccgccaaggtgcctcgcttcgccg
gagccgctgccgcccgccggagggaagccggcctcgggcgcgcacgctcgtcg
gagccccggcgcgccccgcgcctgagcctgctgacagccggcgctgggctcaggctgtcc
gctctgggctccgcggcctcggccccgctgcactccacctccgccccctcg
gactccctcccctctgcttctactcctcctgctccagtgcggatcgtttcg
caactgcttgccac
tcgtcccgtgcctggctgttttccatttcccggccccctcttcttgag
tactttaccccctgcatttggggacagggactggaaaaggggcgggtggagcgtccag
tggagaagaaggaagcgaggcccgcaggaggaggaggatcggcgactgtggggagga
gaccccacgccaccttctggtcatctccctccgccccgcccctgcgcacac
tccctcgcgggcgagctactttcggaccaggaaagtaa
gagcggccctgggtgacagcgccgcggggccag
tcccggggttagccgcgcgtctgctcgcttctggtccgtcgcgctcccagccaggg
cacagcccggaccgaggatg Homo sapiens calcium/calmodulin-dependent protein kinase II gamma
(CAMK2G):

(Seq ID No: 1177)

ccgtctcctcctcttgctccctcggccgggcggcggtgactgtg
caccgacgtcggcgcgggctgcaccgccgcgcgtccgcccgcccgccagcatg Homo sapiens interleukin 15 (IL15):

(Seq ID No: 1178)

ttttcttttcgccaggggttgggactccgggtggcaggcgcccggggaatcccagctga
ctcgctcactgccttcgaagtccggcgcccccgggagggaactgggtggccgcaccctc
ccggctgcggtggctgtcgcccccaccctgcagccaggactcgatggagaatccattcc
aatatatggccatgtggctcttttggagcaatgttccatcatgttccatgctgctgacgtc
acatggagcacagaaatcaatgttagcagatagccagcccatacaagatcgttttcaact
agtggcccactgtgtccggaattgatggttcttggtctcactgacttcaagaatgaag
ccgcggaccctcgcggtgagtgttacagctcttaaggtggcgcatctggagtttgttcct
tctgatgttcggatgtgttcggagtttcttccttctggtgggttcgtggtctcgctggct
caggagtgaagctacagaccttcgcggaggcattgtggatggatggctgctggaaacccc
ttgccatagccagctcttcttcaatacttaaggatttaccgtggctttgagtaatgagaa
tttcgaaaccacatttgagaagtatttccatccagtgctacttgtgtttacttctaaaca
gtcattttctaactgaagctggcattcatgtcttcatttgggatgcagctaatataccc
agttggcccaaagcacctaacctatagttatataatctgactctcagttcagttttactc
tactaatgccttcatg -continued Homo sapiens protein O-fucosyltransferase 1 (POFUT1):

(Seq ID No: 1179)

gtccctccttccctccccgactgtgcgccgcggctggctcggggttcccgggccgacatg

Homo sapiens calpain 3, (p94) (CAPN3):

(Seq ID No: 1180)

cac
tctctttctctctccctctggcatgcatgctgctggtaggagaccccccaagtcaacatt
gcttcagaaatcctttagcactcatttctcagga
gaacttatggcttcagaatcacagctcggttttttaagatggacataacctgtacgac
cttctgatgggctttcaactttgaactggatgtggacac
ttttctctcagatgacagaattactccaacttccccctttgcagttgcttcctttcctt
gaaggtagctgtatcttatttttcttaaaaagcttttttcttccaaagccacttgccatg Homo sapiens PTK2B protein tyrosine kinase 2 beta (PTK2B):

(Seq ID No: 1181)

agcccttttactcagccacagcctccggagccgttgcacacctac
ctgcccggccgacttacctgtacttgcgccgtcccggctcacctggcggtgcccgag
gagtagtcgctggagtccgcgcctccctgggactg
caatgtgccgatcttagctgctgcctgagaggatg Homo sapiens ST6 beta-galactosamide alpha-2,6-sialyltranferase 1 (ST6GAL1):

(Seq ID No: 1182)

cttccttccttctccagtcccttccac
tgtgcgtcttctgtccccgttcttccccagcggaccctctttcgagactccctag
tggggtccccagctcccgggcgatcctgcccttgccgagcgcgttttctggagtcac
ctgggggagggagtcctgggcagggccgggctggggaagacgcctggggcac
tgccggcgttaacaaaggagccgataccgaccggcgtgggcgcg
gagcgggcggccgccaccgagcgtgctgagcaaccgcagcctccgcggccgagagtg
cagcgagcaaggggagagccagttgcgcagagccctgcaaccagcagtccaggga
gaagtggtgaatgtcatggagcccagctgaaatggactggcccccctt
gagcctgtcccaagccctggtgccaggtgtccatccccgtgctgagatgagtttt
gatcatcctgagaaaaatgggccttggcctgcagacccaataaac
cttccctcccatggataatagtgctaattcctgaggac
ctgaagggcctgccgcccctgggggattagccagaagcagatgatcatgacgcag
tcctgaggtttaatggggcacccacagccaacttccaacaagatgtgggcacaaaaac
taccattcgcctgatg Homo sapiens ubiquitin-conjugating enzyme E2Q family member 2 (UBE2Q2):

(Seq ID No: 1183)

ctccccttccgcgcccggctcccccttccgcgccccctcccgccggagat
gaggggaagatg

Homo sapiens membrane magnesium transporter 1 (MMGT1):

(Seq ID No: 1184)

gcttcttttgctgggctgctgctccttcggcatcatg

Homo sapiens PAP associated domain containing 4 (PAPD4):

(Seq ID No: 1185)

cggtcttccgggtgtctttgacagggttttctacgccgcttttttcggcgacttttttgctc
ttccgcttttttgccaccgcccccaaccttctatatccttgcagccctac
cttttcttgtgttgctcctcccctggcagccgtgaggggggttagatctcagccg
gagcggagctgggcctagctgtcccacgggccaccactacctcctttggttcggga
gaaagctacgaccaagtacgcccagctcgggcctttagaacttctgaacgggcag
tgcgggtaggccctgcttagcccttcccggaggacacctgaccaaaagaggaaga
tagtcttgggacccttgcatggtgttttcaaagggtggtgaagaactaaggtagaa
gaatacatgttcacttccagtgaacaagagcatg Homo sapiens chromosome 3 open reading frame 23 (C3orf23):

(Seq ID No: 1186)

ctcccttctggtgtactgggtgggaggtggaactagtcggacaaagccctcgcgtcg
gacccttgccagaactcaattaatggatgcctcgaagttgacgtacatatatattca
gaaatg Homo sapiens mucosa associated lymphoid tissue lymphoma translocation gene 1 (MALT1):

(Seq ID No: 1187)

cgcccctttt
gcgcggctggcgcggccagccggccaggctcccctcggcaaacctgtctaatt
ggggcggggagcggagcttcctcctctgaggggccgtgccgcgctgccagattt
gttcttccgccctgcctccgcgggctcggaggcgagcg
gaaggtgccccggggccgaggcccgtgacggggcgggcgggagccccggcag
tccggggtcgccggcgagggccatg Homo

*sapiens* UDP glycosyltransferase 3 family, polypeptide A2 (UGT3A2):

(Seq ID No: 1188)

ctacctctacccacagccagtgcctttggcgcactgaggtg
cacagggtcccttagccgggcgcagggcgcgcagcccaggctgagatccgcggcttccg
tagaagtgagcatg

*Homo sapiens* sodium channel, voltage-gated, type IV, beta subunit (SCN4B):

(Seq ID No: 1189)

cctcctctcgctctctgcccgctaactttcccgagccccgac
cggcggcgcagagctccggggtagctttgtggccgaacgccgacctcgggcgga
gagcgcggctgtgcccagtatcccatcccgcgaccccgcgcgctccggagagaacag
gactatg

*Homo sapiens* JAZF zinc finger 1 (JAZF1):

(Seq ID No: 1190)

tcccctctgcctcccggtggctcctcgctctccttccatctctctcgcccctctccctc
cgtcccgtcctcgccgctcccctcaccccgcctctctcccctcccccagccctcctct
cctcaccccacccggcctccctccctcccctcgcccgcccggcgctcgcagagccgacac
caggggggctctcgatgtagcaccatg

*Homo sapiens* chromosome 15 open reading frame 55 (C15orf55):

(Seq ID No: 1191)

ttcccttccttggatccctgtgcacctactggagccaggttactctgggtcctggac
ctgactgcctcattctggaggcttccagacagccacagttagtgcccaaacctgagag
gatg

*Homo sapiens* ras homolog family member C (RHOC):

(Seq ID No: 1192)

cgccctctcttcctgcagcctgggaacttcagccggctggagcccaccatg

*Homo sapiens* CTP synthase II (CTPS2):

(Seq ID No: 1193)

cattctctttccttttccttctctcctgagcgctcctgcagttcctggggcgtag
tagggatccacaagcgtttgtgaccagtgaagttctttacaagggtgagatctgcac
gggaggacccgagcgagggtctcggcttgccaggaagccggggttcccccgggaagcgtg
gagttcaccccgcgcactcgaagtgcctttgcaaaattatatctgggtgttgg
cacccagccactattctgccaatg

*Homo sapiens* PRP4 pre-mRNA processing factor 4 homolog B (yeast) (PRPF4B):

(Seq ID No: 1194)

agctcttttccttcttcctccacttcccctaccctccac
cgtccgggagccgccgccaccgccgccgaggagtcaggaagttcaagatg

*Homo sapiens* molybdenum cofactor synthesis 2 (MOCS2):

(Seq ID No: 1195)

gcgcctttgcggccgtgattcggtcccgctgtcctaggcgg
gatggtgccgctgtgccaggtaagggtggcgggtgtgcgtgccgggcctgggtgcg
gagccctcctcgacgtgtctctcccgccctttccctccacataccagccttggtcag
tcggacctcccccactagccccccaacctggccggcgtctt
gggttcgggggcgcccccgcccccgcccccgggcccttcctgtctccgggctttactgcg
actgccccagcagaagtcgggtcctctccgagaacctcttgtcagctcacggcag
caaggacggactcgttctgaaggcgcctccaccttttatgaccacctctttcccagat
tattcgttttgatgaagctaaaatttaatctaaaaagaaatgcacctcatgga
gaattcttgtgaagaactgtgcttcatctgtggatttctacacccttgatcattt
gcaaacctgtaattatttcgtaaagagttgtttgcacggagtgacaggtt
gaagtattgtattttgcaaaaagtgctgaaataacaggagttcgttcagagac
catttctgtgcctcaagaaataaaagcgttgcagctgtggaaggagata
gaaactcgacatcctggattggctgatgttagaaatcagataatattt
gctgttcgtcaagaatatg

*Homo sapiens* cat eye syndrome chromosome region, candidate 1 (CECR1):

(Seq ID No: 1196)

tttccttttccggagggagatg

*Homo sapiens* solute carrier family 13 (sodium-dependent citrate transporter), member 5 (SLC13A5):

(Seq ID No: 1197)

ctgcccctcactcgtctcgcccgccagtctccctcccgcgcgatg

*Homo sapiens* armadillo repeat containing, X-linked 3 (ARMCX3):

(Seq ID No: 1198)

agtcctcttgtcctggtcgttgttcccgtctgagtaccagctcccactgccctgaggg
cgggccggcctgcggcggagggaaaaaggaagaggagaaggaaattgtcccgaatccctg
cagtgggtccaagcctctcccggggtggccagtctttctgtaggttgcggcacaacgccag
gcaaaagaagaggaaggaatttaatcctaatcggtggaggtcgatttgagggtctgctgt -continued agcaggtggctccgcttgaagcgagggaggaagtttcctccgatcagtagagattggaaa
gattgttgggagtggcacaccactagggaaaagaagaaggggcgaactgcttgtcttgag
gaggtcaaccccagaatcagctcttgtggccttgaagtggctgaagacgatcaccctcc
acaggcttgagcccagtcccacagccttcctcccccagcctgagtgactactctattcct
tggtccctgctattgtcggggacgattgcatg Homo sapiens armadillo repeat containing, X-linked 2
(ARMCX2):

(Seq ID No: 1199)

cgtcctcctctgggtaccaactctattgcg
cagctcgctgccgtgcgtttaacccaggcgaggaggaggaggagaaaattcccccagat
tcgggcaggcccgcaccccacattccgtcctgttttgagaggaggagggaagagaaa
taaacgtggcagcgcatagaaggccagcagggagactgctttccagacac
ctccggcccacacagccgttcaccccccgtcttttcagtcctg
gaaaaggaattcggtctgtccttaggatgaagctctaactgaactgaagtaagga
gaaacagccttgaatctttggagggtctgtcttccttttgggctctgtgcaactgcagc
tacagtggaaaaaagcaaactgctcttgatcccaggccctgcctaagcctcag
cagaacttgtaagcctaaactgaagagcctcaccggacgagcaggcatcccttaac
cttaagcaatccagttccacgccctggatcagtgaataaccccagctgcaccatg Homo sapiens UBA domain containing 2 (UBAC2):

(Seq ID No: 1200)

cgccctctggggctccgagcccggcgggaccatgttcaccagcaccggctccag
tgggctctgtgagtaccggcctccgccatcctggctgcccctacac
gccaccctaggcacctctttgaggaggctggggcagcggggaccctcgggtttgccg
gaggtggtggggccgaccctccagacccgcgtccgaaccctgctagttcccggtctt
gggggtcagcggaaaccgcccccatttcggcctgaggggcgaatggggacaaa
gccccgccgccccgaccccaccctggtatccccaggtgctctgcccaggag
tctcttggggccgctgcaagtggg
caggtgccctggtgttctcgtgggccggcccaggcccttgcg
gagcgtgccgcgctgaaggaaggggccgtcccccttac
catgccccattcttttaggcttggggggaccgaactaactcccccgcccccactt
gcaaagttcagcctccgctttagaagctgacctctcagtttcacttggatg Homo sapiens cancer susceptibility candidate 4 (CASC4):

(Seq ID No: 1201)

cctcctccctcggccggccctggggccgtgtccgccggg
caactccagccgaggcctgggcttctgcctgcaggtgtctgcggcgaggcccctaggg
tacagcccgatttggccccatg Homo sapiens protein phosphatase, Mg2+/Mn2+ dependent, 1G
(PPM1G):

(Seq ID No: 1202)

cgctccctcacagctcccgtcccgttac
cgcctcctggccggcctcgcgcctttcaccggcacctt
gcgtcggtcgcgccgcggggcctgctcctgccgcgcg
caccccggggcttcggctccggcacgggtcgcgcccagcttttcctgcac
ctgaggccgccggccagccgccgccatg Homo sapiens StAR-related lipid transfer
(START) domain containing 13 (STARD13):

(Seq ID No: 1203)

cttctttttaaaaatcgctgggtctgttgagctgtcctgggctgggtgcctt
gctctttgactgagactggagacagacggcaacagccacaggcagactgaggtggcaa
taggaaatctgccgagatg Homo sapiens tubulin, beta class I (TUBB):

(Seq ID No: 1204)

gattctcccgcctcccagcccggcgcacgcgcgccccgcccagcctgctttccctccgc
gccctcccctctcctttctccctctcagaaccttcctgccgtcgcgtttgcacctcgctg
ctccagcctctggggcgcattccaac
cttccagcctgcgacctgcggagaaaaaaattacttattttcttgccccatacat
accttgaggcgagcaaaaaaattaaattttaaccatg Homo
sapiens cytochrome P450, family 4, subfamily X, polypeptide
1 (CYP4X1):

(Seq ID No: 1205)

tttccttcttcccgcgagtcagaagcttcgcgagggcccaga
gaggcggtggggtgggcgaccctacgccagctccgggcgggagaaa
gcccaccctctcccgcgccccaggaaaccgccggcgttcggcgctgcgcagagccatg Homo sapiens doublecortin (DCX):

(Seq ID No: 1206)

ttttctttctctctcag
catctccacccaaccagcagaaaaccggtgagtgggcttttaagtgattttcaagaa
gaatgtaacagatgtcaaacgggaaaagcacaaggcaaa
gcctgctctctctgtctctctgtctcctcttctccttttttgccttattctatccgat
ttttccctaagcttctacctgggattttcctttggaaaagtctctgaggttccac
caaaatatg

*Homo sapiens* protein phosphatase 2, regulatory subunit B', gamma (PPP2R5C):

(Seq ID No: 1207)

ttgtctttttttttttaaactaaaatggaggctggtttctt
gccttaaggagcccattgcctttcccgctgaagtctagatg

*Homo sapiens* solute carrier family 9, subfamily B (cation proton antiporter 2), member 2 (SLC9B2):

(Seq ID No: 1208)

ccacctttccgggg
gaagccacgcgcaccaggcatcgcacgcggctctgcacccgcgccgcggac
ctgaaacccggcggagggcacacggggctgccgctgcgggccccggac
caacccatgcttactccggagcctgtaccggcgccgacgggtcggac
ctccctgcgcggtgtcgcccagcgggttcgtgcgaaaggcggggccgactacac
gcggtgccgcgccctgagaccgtttatctgcagtcaac
gcagcctccggctcagcctgggaagatgcgcgaatcgg
gaacccagagcgcggtggctagac
cgggctccgccgcctcccccacagccccttcctaatcgttcagac
ggagcctggtcgacttcgccgga
gactgccagatctcgttcctcttcctgtgtcatcttcttaattataaataatg

*Homo sapiens* hypoxia inducible factor 1, alpha subunit (basic helix-loop-helix transcription factor) (HIF1A):

(Seq ID No: 1209)

caccctcttcgtcgcttcggccagtgtgtcgggctgggccctgacaagccacctgagga
gaggctcggagccgggcccggaccccggcgattgccgcccgcttctctctagtctcac
gaggggtttcccgcctcgcacccccacctctggactt
gcctttccttctcttctccgcgtgtggagggagccagcgcttaggccg
gagcgagcctggggccgcccgccgtgaagacatcgcggggaccgattcaccatg

*Homo sapiens* interleukin 21 receptor (IL21R):

(Seq ID No: 1210)

cctcctcttcctccccactctgcacatgcggctgggtggcagccagcggcctcaga
cagacccactggcgtctctctgctgagtgaccgtaa
gctcggcgtctggccctctgcctgcctctccctgagtgtggctgacagccac
gcagctgtgtctgtctgtctgcggcccgtgcatccctgctgcggccgcctggtac
cttccttgccgtctcttcctctgtctgctgctctgtgggacacctgcctg
gaggcccagctgcccgtcatcagag
tgacaggtcttatgacagcctgattggtgactcgggctgggtgtggat
tctcaccccaggcctctgcctgctttctcagaccctcatctgtcaccccac
gctgaacccagctgccaccccagaagcccatcagactgccccagcacac
ggaatggatttctgagaaagaagccgaaacagaagatgaggcaatgaggctgcga
gaggtagagtgattttccctcggtgactcaactgggacgtagcaggtcgggcagtcaa
gccaggtgaccccatg

*Homo sapiens* DDB1 and CUL4 associated factor 4 (DCAF4):

(Seq ID No: 1211)

tggtcttttccgggtccttgcacgcttcgctccaactcctgcagagctgagccggaggg
gaatccggaagggacacgctgaacaggtctgactcccgggcagcacagcccgctcac
gattccggccacggtgatgacgagtctccgtcaacctcgtctggcacagctgggac
ctcctctgtgccagagctacctgggttttactttgaccctgaaaagaaacgc
tacttccgcttgctccctggacataacaactgcaaccccctgacgaaagagag
catccggcagaaggagatg

*Homo sapiens* oxidation resistance 1 (OXR1):

(Seq ID No: 1212)

ccgcctctt
gtgaggcgcgcggagccgcctcccctgggtcaggtctgatgggccggtgggcgcgctag
tggtggccgccaccgccgaaaccgtcgacctcctgggcccccag
ttccgcgtccagccccgcggcagcatg

*Homo sapiens* cut-like homeobox 1 (CUX1):

(Seq ID No: 1213)

cccccctctctat
cagccgctcactccgtctcaatatgtctcaagatg

*Homo sapiens* atlastin GTPase 1 (ATL1):

(Seq ID No: 1214)

ctccctttcctccccac
tccttcccaccagcgccacagcaacatcctcagag
tctgagcgaactgcgcccagcgcgggcacggagcctcccaccgccagcaac
ctgcggccccggagaaggcagcgagcgcagtgacagcgcctcaccgccaccagctcctg
gaccaccatg

*Homo sapiens* chemokine-like factor superfamily 5 (CKLFSF5):

(Seq ID No: 1215)

ctgccttctctcccggggcccgtgggcaagcctcctgcttcac
tttcaggtttctcgaagtgccttcttgctcctgtctgtttccccatcctgccagat
ttctgtttctcttgctgggcttttggcagtagggggctgtgttggtgggccctacgaa
gatg -continued

*Homo sapiens* transmembrane emp24 protein transport domain containing 7 (TMED7):

(Seq ID No: 1216)

```
aggccttttccgcttctcttttacctccccaggtccgcccgtctgcgcccctcacaggaa
gccggagggtcgctctgatcccgaatctcccacaggcgtgaacctgctctgctgtgtatc
tttgcgggtggcctgcgctgaggcctgccgcgcgcggtgagtccgcgcagacctgaccc
tgcgtctcgcagctcggttgaggccgccgccgccttctcgggatg
```

*Homo sapiens* ubiquitin-conjugating enzyme E2D 3 (UBE2D3):

(Seq ID No: 1217)

```
cttcctttac
cttcctcccatggtctccttccggttctcgatgcttctctgagcctaagggtttccgcca
ctcgttcaccctcccccagctcatgatcctcctcccccccgccctcctggtccaatc
tccgatctgtttagtaagaaggtgctgttccgagaagaaggaaagggcttgacac
gtattcactcggccccggacgtgggaagcaa
gccgtctggcttcggcctcacatcggtcttgtgctcgggacggcggcgttggcg
gactgatccgcggcggtgaagagaggccgggaagttaaacttgtagccaccac
ctccgctcttcccgtcaccctcgcccccacttcgggccgaaagcacgg
tacagaggctgttggtggcttttgccacgccacccaccccaccccg
gatcgcggctgtcttaagggacctggattcatcagggctcttcggggcctgtgcgag
tgctgatctgctccgttttttgcaaaaggcgctgtgtctggcagagctggtgtgagac
gagacaatcctgccccgccgccgggataatcaagagttttggccggaccttgagcata
caccgagagagtgaggagccagacgacaagcacacactatg
```

*Homo sapiens* zinc finger protein 595 (ZNF595):

(Seq ID No: 1218)

```
tttcctctggctcctgcgagggctt
ggtttagggcttcagctctctgcgttctcggctccgggaggcctcggtgat
tcagccacagcctctgcctcccgttgctctgtgacctgagggtattggacaattt
gtagctaagactcccggataccctgaagtcgggaaatg
```

*Homo sapiens* acyl-CoA synthetase medium-chain family member 2B (ACSM2B):

(Seq ID No: 1219)

```
tgctctcttccaaggctgtaggagttctggagctgctggctggagag
gagggtggacgaagctctctccagaaagacatcctgagaggacttggcagcctg
cagatggcctattgtgggaccttgtgatcatgcctgaacatg
```

*Homo sapiens* SRSF protein kinase 2 (SRPK2):

(Seq ID No: 1220)

```
tttccctttatagcaccattgaatcccagtcctaacagaagtactgcgaatctt
gtggcctcattctgaacaaaagggattagagaagaaaaatctcttgatataaggctt
gaaagcaagggcaggcaatcttggttgtgaatattttctgattttttccagaaatcaa
gcagaagattgagctgctgatg
```

*Homo sapiens* synaptophysin-like 1 (SYPL1):

(Seq ID No: 1221)

```
tgcccttcctcgccac
cgggctgctctggtctcgtcggtcccctcctccgccccgtcgtcctgactctctctccct
cctttcctcagaggatg
```

*Homo sapiens* thioredoxin reductase 1 (TXNRD1):

(Seq ID No: 1222)

```
aacccttcac
ctcagttttcttcactccggcatttgcagcagagcgaaaggtggtcgag
tcctgaaggagggcctgatgtcttcatcattctcaaattcttgtaa
gctctgcgtcgggtgaaaccagacaaagccgcgagcccagggatgggagcacgcgggg
gacggcctgccggcggggacgacagcattgcgcctgggtgcagcagtgtgcgtctcggg
gaagggaagatattttaaggcgtgtctgagcagacggg
gaggcttttccaaacccaggcagcttcgtggcgtgtgcggtttcgacccggtcacacaaa
gcttcagcatgtcatgtggcttatcaggagggcagacttcaaaagctactaaaaatg
```

*Homo sapiens* minichromosome maintenance complex component 7 (MCM7):

(Seq ID No: 1223)

```
tgtccttccgcgcggcggccgcgggagagagctgcggcccggggggcgtgcctgggatcc
ggagcttcgctcgggcccgggaaaggcggcagtgggctgggatcgcggtgtctctgggtg
tgatggccaatggctggactggctcccgccctgggcggaggaatcccgagctgtgaagcg
gctggaatccgggcccatgtgcttctttgtttactaagagcggaagcgatggcgggagcg
ggggtggggtgcggtggcggggtgcggtggcggaggtcccggtgaaatcaggggctaagg
ggacccaaagaaggcggggggatcatagggtggaaagaaaagctgagaaccttgagaccgg
agtgtgaggggccaacggggaagggcgctagaatttaaactaaagtagggaccggaatt
cccctggggagatgttggatgccctgtgcactgccacgggctctttattcttcgctggt
tagaaacagacttgtgaaaaagagttatgcccactttgggagacttcgaaaaggttaag
aagttcttacaagagttctaccaggatgatgaactcgggaagaagcagttcaagtatggg
aaccagttggttcggctggctcatcgggaacaggtggctctgtatgtggacctggacgac
gtagccgaggatgaccccgagttggtggactcaatttgtgagaatgccaggcgctacgcg
aagctctttgctgatgccgtacaagagctgctgcctcagtacaaggagagggaagtggta
aataaagatgtcctggacgtttacattgagcatcggctaatgatggagcagcggagtcgg
```

-continued
```
gaccctgggatggtccgaagcccccagaaccagtaccctgctgaactcatgcgcagattg
tgagtggtctctgtcgggaaagatgtagggattggttctccaggatcttgtttgtgactg
ttttctccccttagtgagctgtattttcaaggccctagcagcaacaagcctcgtgtgatc
cgggaagtgcgggctgactctgtggggaagttggtaactgtgcgtggaatcgtcactcgt
gtctctgaagtcaaacccaagatg
```

*Homo sapiens* pre-B-cell colony enhancing factor 1 (PBEF1):

(Seq ID No: 1224)

```
tttccccctctcccctcctccgccgaccgagcagtgacttaagcaac
ggagcgcggtgaagctcattttttctccttcctcg
cagccgcgccagggagctcgcggcgcgcggcccctgtcctccggcccgagatg
```

*Homo sapiens* cyclin B1 interacting protein 1, E3 ubiquitin protein ligase (CCNB1IP1):

(Seq ID No: 1225)

```
ctttctttccctctccgttttggtgggctggtt
gaagatgaaatccactgaggagggaagtccagcaccctgtgtgccag
tccagaactggcccatctgtagaccccctgaaaatcatatgggcttggatttgga
tattctcaacagaaagggttaaaggctgatggtacctaaagcctggtacttgaatttt
gatcaagataagctgccttaagttctcttcattacacaaatgatcctagataattgata
gatcctgtggttcaactggatttctagatagaagctggattcatgtgatgccagaggag
taaaatttcaagagactgaaaccagatctgagtttcgctgttccagtctggacctcttt
ggtgctgtaaatcctggatatactgtagatgag
tactgcgttttctttatggcctctcttcagcttctggagacctcactatcctattatg
```

*Homo sapiens* STEAP family member 3, metalloreductase (STEAP3):

(Seq ID No: 1226)

```
ccgccttcgccgcggaccttcagctgccgcggtcgctccgagcggcgggccgcagagatg
acatttattcatttatgcatcctgggttctactggtcgtcccacctcagttcctgtagc
aaagagacttgagtctgagccactaattatcacccgtgaggtttcctccccgagcaggaa
gcagcaggccagagctgcgctctctcagtgcactctccaaccaagcatcagtcaccactc
ccggtccagcccctgtggcaagagctggcgtgcaggctgcggaggcagctggctgtgc
aagaccctggcagggcctcgcctcctgagaaaccgagagtcagaaccaaagccaggctg
tcctggttggagactgagccagaaagggtggctcacctcacggtgaggctgtcgagtgac
ctgagagcctcagaccctcacgtcagccggatg
```

*Homo sapiens* nicotinamide nucleotide transhydrogenase (NNT):

(Seq ID No: 1227)

```
tgttcttccggttggaggcgcagcgccgcggggcccaa
gcccgggtctgccagcgcgacgtcctctcgcggccctcaggg
cacagcccaaggctgtcagcctcccggcccagtgatttgccttcaaggaaactggggag
tcagaaaattgggaactcatatcaacatg
```

*Homo sapiens* SHC (Src homology 2 domain containing) transforming protein 1 (SHC1):

(Seq ID No: 1228)

```
gtccctctccctccccag
gacttctgtgactcctgggccacagaggtccaaccaggctaagggcctgggga
taccccctgcctggcccccttgcccaaactggcagggggccaggctgggcag
cagcccctcttcacctcaactatg
```

*Homo sapiens* bromodomain containing 8 (BRD8):

(Seq ID No: 1229)

```
cggcccttcca
gaccgtctctcctcagggttggagacttcggggccaagatg
```

*Homo sapiens* ring finger protein 13 (RNF13):

(Seq ID No: 1230)

```
tcgcctctttag
taggtcgggtgagtgtagtgtgcagggaagagac
gcgtcagcgccagggccaggcccgcccggggcagcccggcagccgaatcttgggc
tactctgtcccaacagccggagcagatcagaccgac
cggccctgcccgctcggtcccgcgcccctccagacccctacggtctccgtttctagggg
cacatggttagcggcaggcgcccacagccaatccactt
gccagcctgccccttcctctgccaagagcagcttcttcagccgcgctccagttccg
cagacgcctgccccaccctgctcttccctttccagggaagacggatcacgcggccaa
gaacgagactcgcaaactgggcatttctccgagccgggctagagcaagtagcga
gactccgcgtgagagtgggaaagagccttaacaggcaaccatgttgcccag
tgggttttctgtgcctttgggtgcggaccaatgaggcgcgtggggcgg
gacttccgcttcgcctaggtgttgtcgtccctgctag
tactccgggctgtgggggtcggtgcggatattcagtcatgaaatcaggg
tagggacttctcccgcagcgacgcggctggcaagactgtttgtgttgcggggccg
gacttcaagagagaaagagagagtgggcagacatcgaagccaaacagcagtatcccg
gaagcactcatgcaactttggtggcggccactcagttttctctgccagtgtctggtgat
tttacaacgagatg
```

*Homo sapiens* aldolase A, fructose-bisphosphate (ALDOA):

(Seq ID No: 1231)

-continued
```
ccgcctcctgcgccgcccttccgaggctaaatcggctgcgttcctctcggaac
gcgccgcagaaggggtcctggtgacgagtcccgcgttctctccttgaatccac
tcgccagccgccgccctctgccgccgcaccctgcacaccgcccctctcctgtgccag
gaacttgctactaccagcaccatg
```

Homo sapiens LY6/PLAUR domain containing 6 (LYPD6):

(Seq ID No: 1232)

```
cgctccttccctgagctcccgggctccggcagcgcgctggcggggcgccgcatt
gcacactctgggggcgccgcagtgttcgtgggatggggcagcgggctg
cagctggcggccggaatccgcgcgcagcccgggtgcaagttctctcctgttgccctgag
tgcccactcccaggccctctgtatgagtgacacttcagtctgccatg
```

Homo sapiens butyrophilin, subfamily 3, member A1 (BTN3A1):

(Seq ID No: 1233)

```
cagtctctgctttcttttttcctttcttccagaaggagatttaaccatagtagaaa
gaatggagaactattaactgcctttcttctgtgggctgtgattttcagaggg
gaatgctaagaggtgattttcaatgttgggactcaaaggtgaagacac
tgaaggacagaattttttggcagaggaaagatcttcttcggtcaccatacttgag
ttagctctagggaagtggaggtttccatttggaattc
tatagcttcttccaggtcatagtgtctgcccccaccttccagtatctcctga
tatgcagcatgaatg
```

Homo sapiens lipoic acid synthetase (LIAS):

(Seq ID No: 1234)

```
ctgtcctttcccgg
gagttagcgatccctcaacccctgcactgcgctagtcctaaagaggaaatg
```

Homo sapiens C-type lectin domain family 7, member A (CLEC7A):

(Seq ID No: 1235)

```
gattctcttttgtccacagacagtcatctcaggagcagaaagaaaa
gagctcccaaatgctatatctattcaggggctctcaagaacaatg
```

Homo sapiens CD247 molecule (CD247):

(Seq ID No: 1236)

```
actccttttctcctaac
cgtcccggccac
cgctgcctcagcctctgcctcccagcctctttctgagggaaaggacaagatg
```

Homo sapiens myeloid zinc finger 1 (MZF1):

(Seq ID No: 1237)

```
aa
gcctttctccattttgcggtctaggaagtagcagaggcccccttcctgtaggagtt
gccatggagacgcggtggggcaccgacggagttctaatgacggccgtgattggtgcag
gatcctgctaatctcaggaaggcccgtagagaagtgaggaaaacgtggtgggggg
catgcgcgatctggtaggcggtgctgccgtctgttgtacctgagaggcttgcg
catgccgacgcacggattcgaggcgggagcatgggaagaagcggccaggagtatgac
ctgatcattgcgaccaccgctaggggaagggaggagagggtgtagaaacggggac
gagggtgggggaagggcaaggaggcgctcgagctggtgcgcggagcatcctgggagac
gtagtccagcgggaggggggaagtcgaagactgcgcgtgctcaggagcgcg
gagcggcccgctgagcgcagaggggcagacactggcctcagatacctgacctgg
taccctctatg
```

Homo sapiens E2F transcription factor 6 (E2F6):

(Seq ID No: 1238)

```
cctcctcttttccgtctgcgtcgggagctcccgggcac
gtgaggccgtgccgcgtttactggcggggcgggacggcctagccgggcggcgcctcggag
gaagccgcggacccttaggtgctgggccctt
ggaaatcggcgcgtggggggcggtgctcgagctgagcgcgagagggcggga
gagctcgtgggtgcgaggggagcaggacgcccggccgggcagcatg
```

Homo sapiens purinergic receptor P2Y, G-protein coupled, 10 (P2RY10):

(Seq ID No: 1239)

```
cttcctctttcaacaacaaatgtgtcagttatcagcaggatccatgccgccagagtaaag
ctttctaccctttactccctgcaaagaaacaagagtgcttatcccagctaagctccaggg
taatgttatcatgacagcttcaacttttagaccacaggcaaatgctttgttaaaactcta
tgctggtcattcccttcaggatttggcactcaccaacataccttctttcaagtgaaaag
gcatctcttttaatggtcctgaccttggaataggaagcatgtaccctggacagagcact
tcaaactagaggaaccataaatccatg
```

Homo sapiens chromosome 9 open reading frame 85 (C9orf85):

(Seq ID No: 1240)

```
catccttttgcctgctcccggcgaggggtggctttgatttcggcgatg
```

Homo sapiens ERGIC and golgi 3 (ERGIC3):

(Seq ID No: 1241)

```
cgtcccttccggccggtccccatg
```

Homo sapiens ankyrin repeat domain 46 (ANKRD46):

(Seq ID No: 1242)

-continued
```
ccctcccctccgcccgtcaccgcctccttgaa
gctgccgctgtcgctgctgctcgttcgagtcgcagatccttgccagcacattacagaa
tattttttgttgaaccttcttgagaattcagagaaactgctgagtgaccactgaac
gaaaagatctaatcttaaggcttacgcctcactttgatgcccaggctggag
tgctgtggctcaatcacagctcatcgcaacctcgac
ctcccgggctcaagtgatcctctcacctcagcgtcccgaacaggcgtgttccatccac
cacatcagaacaatg
```

Homo sapiens Ras and Rab interactor-like (RINL):

(Seq ID No: 1243)
```
tcctctctccacttcctgctactgcaggcctctcctccga
gaacagaggccaggtcatgactcactggcttcctgcaacctgac
gatggcccagccagaagacaaggcac
ctgaagtccccacagagggggtgaggtgaacaaagcagacag
gaccectctaggggtcctcagcacectagagccacttactcgcctgcagag
gacatgggggggtgtggcatgtgccagagctggatacccaggatgcggaggccctt
gtggggctgtggccactagggagtttcttggtcacaggac
gtgaccccagccaggccctggtgttgaggtcaggacctttaccaggagaagtcaatac
ctaccagatccagaagattcccagaggtgtgtccctggaatcctccaacctctgcatg
```

Homo sapiens embigin (EMB):

(Seq ID No: 1244)
```
ccgccttttcttcagcgtcctacccgcgg
cactggctgcgagcgccgggccacctgcgagtgtgcgcagggactctg
gacacccgcggcggcgagctgagggagcagtctccacgaggacccaggcg
gaccctctggcgccatg
```

Homo sapiens MMS22-like, DNA repair protein (MMS22L):

(Seq ID No: 1245)
```
ccgccttttccggagcgcgggcgcgcggtggcgggaatttcgcctgtttgcggttta
gaccccaaagattcctgttggtggtctgggtcacaggaggcaggtttcgggagctg
gaaatgtgagcgggtacgacaggcaccgcgggtaaccgacgccccgggtccttgctg
cagccgggtacgcgggataccggcaccccgccttctccgcccgag
tgctgccaggcgtgggcctggaatctcttcacaccttctctttggagcccttaatga
tacgacgaaccccaagtgtttcagaacatgaagtaaacaatg
```

Homo sapiens chromosome 19 open reading frame 54 (C19orf54):

(Seq ID No: 1246)
```
actcctttccttttttccagtggttatcgcggcgccaccggcctctgatctctgagtctt
ctccaacccacagacgttttttgttgctctggttccaggaccttctccacaactaggcca
ttttccctgccaggtgtcctttttgacctcttgacctctgactcaaagggcctgctcccc
ctcatgtcttcggcctggagaagagccagctcctgaaggaggcctttgataaggccggcc
cggtccccaagggcagagaagatgtgaagaggcttctgaaactacacaaggaccggttcc
gaggtgacctgcggtggatcctcttctgtgcagacctgccgtccctcatccaagaaggcc
ctcaatg
```

Homo sapiens zinc finger protein 621 (ZNF621):

(Seq ID No: 1247)
```
cgccctccggctcggcctttagttagtgaccagctcctcggcgttctg
cagagcgtgggtttcagcgagttctac
gtgccaggtccgcccggtgccggcttcctcgctgcccctggcggctcgtcagccccac
taccccctgaacttggtcccaatggcggccgccccctcttcaccggaccgtggg
catctgggcctcgccgaagccgtcaaggtggctgctcgggcttcta
gagcccgtgtccagccctttgccaccgaggcctgatcctcttttctgccctaaa
gaacttgccctgacagcctctggctcccgctcttgaggatcttgctt
gtccaaacccagaagacagtgcatgaagccaggggacatccgccatg
```

Homo sapiens family with sequence similarity 73, member A (FAM73A):

(Seq ID No: 1248)
```
ccgccttctccatg
```

Homo sapiens RNA binding motif protein 43 (RBM43):

(Seq ID No: 1249)
```
ccgccctttcttcgtagcctccaagggagctggaacaaaaaacgaaaccaaaac
ctgcctgctcgctcctctcccatcgcctgcgttccgctggtt
gtgggctttctgcgccgctgagggcgcgtctcccctccgccatg
```

Homo sapiens spermatogenesis and centriole associated 1 (SPATC1):

(Seq ID No: 1250)
```
caccctccttcagcccaggcaaggcctggggccctggg
cagcctccaggtgcagtgccctcccgtgggccgcacccttgccactgccccagggcatg
```

Homo sapiens carbonic anhydrase XIII (CA13):

(Seq ID No: 1251)
```
ctttctcttccttccaccccgagggaccatg
```

Homo sapiens transglutaminase 2
(C polypeptide, protein-glutamine-gamma-glutamyltransferase)
(TGM2):

-continued

```
cgctctccgcctcggcagtgccagccgccagtggtcgcactt
ggagggtctcgccgccagtggaaggagccaccgccccgcccgaccatg
```
(Seq ID No: 1252)

Homo sapiens NOP2/Sun domain family, member 4 (NSUN4):

(Seq ID No: 1253)
```
atttcctttcccttttttcgctcgtgtcccgccgggtggcgctcaccacctccccg
gaacacgcgagtctcctgtcgcggttccggtcggaattaccccgtggagcacgccga
tatg
```

Homo sapiens mitochondrial ribosome recycling factor (MRRF):

(Seq ID No: 1254)
```
gagtctttccttagtaacctgggcgatagctgtggatgtttccaaggattgtcttcagt
catg
```

Homo sapiens PHD finger protein 17 (PHF17):

(Seq ID No: 1255)
```
cttcctccataacaagccaaacgccagaccgagagtgcctccgtgcgcgagtgcccggtg
tgtgcgcgccggcgagagcaggggcccgcccggctccccgcccgccgcggcccgaactca
tgcagctccgagcgagcgagcggcgcccagcccagcgcctcggccgaaccccctccgcagc
aggctgcctgctgtttccggggagatcatg
```

Homo sapiens prolylcarboxypeptidase (angiotensinase C) (PRCP):

(Seq ID No: 1256)
```
cctccttttcgccctcccacccgcactgcagtctccagcctgagccatg
```

Homo sapiens proteolipid protein 1 (PLP1):

(Seq ID No: 1257)
```
aagcccttttcatt
gcaggagaagaggacaaagatactcagagagaaaaagtaaaagaccgaa
gaaggaggctggagagaccaggatccttccagctgaacaaagtcagccacaaa
gcagactagccagccggctacaattggagtcagagtcccaaagacatg
```

Homo sapiens coiled-coil domain containing 80 (CCDC80):

(Seq ID No: 1258)
```
cagccttctcactcctcactgagtccactctgaacgtgctaaaatgg
gaaggaggcggtgttttgctgatctgttaaattcttagtgaagtttccttgatttccag
tggctgctgttgtttgagtttggtttggagcaaaactgaggtagtcctaacatttctgg
gactgaatccaggcaagagaaagaagaaaaagaagaagaaaaagaggag
gaaaaaggtagggagaaataaagggaggagagaagcacagtgaaa
gaaaaaaaagtccttttcgacatcacattcctgtgttttccctcagcctg
gaaaacatattaatcccagtgcttttacgcccggaaacaaagagactaagccagac
tatggggaaagggagataagaaggatcctggaactttaaagagggaaagagtgagat
tcagaaatcgccaggactggactttaagggacgtcctgtgtcagcacaagggactgg
cacacacagacacgagaccgaggagaaactgcagacaaatggagatacaaagactta
gaaggacagctcctttcacctcatcctacttgtccagaaggtaaaaaga
cacagccagaaagaaaaggcatcggctcagctctcagatcaggacaggctgtg
gatctgtggcggtactctgaaagctggagctgcagcacaccccttt
gtattgctcaccctcggtaaagagagagagggctgggaggaaaagtagttcatctag
gaaactgtcctgggaaccaaacttctgatttcttttgcaaccctctgcattccatctc
tatgagccaccattggattacacaatg
```

Homo sapiens chromosome 20 open reading frame 44 (C20orf44):

(Seq ID No: 1259)
```
cgacctctttgcgcctgcgcccccccttgccagtcttttcgccggcaaaaggaggac
gtagaaaaggggacaccggaaaactcactcttcacccggaaatggttattgaggaacatg
```

Homo sapiens tryptophanyl tRNA synthetase 2, mitochondrial (WARS2):

(Seq ID No: 1260)
```
cgcccttctcaagatg
```

Homo sapiens myotubularin related protein 2 (MTMR2):

(Seq ID No: 1261)
```
cttcccctgtgctgccctgccgcgcgatggagaagagctcgagctgcgagagtcttggc
tcccagccggcggcggctcggccgcccagcgtggactccttgtccagttaatgtgttaag
agccattgacatttgaagatcatcagaagtgaagataaaacatctcaaaaattataattg
cctccacttctcattcagagaattcagtgcatacaaaatcagcttctgttgtatcatcag
attccatttcaacttctgccgacaacttttctcctgatttgaggagggagtctcgctcta
tcccctaggctggagtgcattggcgccatctcggctcatttgcaacctctgtctcccggg
ttcaagcgattctccctgcctcagcttcccgaggagctgggattacaggtcctgagggagt
ctaacaagttagcagaaatg
```

Homo sapiens reticulon 3 (RTN3):

(Seq ID No: 1262)
```
cgccctctagctgcgctcggctgag
tcagtcagtctgtcggagtctgtcctcggagcaggcggagtaaagggactt
gagcgagccagttgccggattattctatttcccctccctctctcccgccccg
tatctcttttcaccttctcccaccctcgctcgcgtagccatg
```

*Homo sapiens* G protein-coupled receptor 56 (GPR56):

(Seq ID No: 1263)

gtccctccctctccgcactagctgtctgccctgccctgccgtaggagatgggctgg
gagcctcccacgctctccagctcactcggcaggcagcggggaccagggctgg
caggttaagcctctgggggtggatcctgaaaggtggtccagccgcctggccctgcgtgg
gaccctccacctggcagcagacagggtctcgctctgtcacacaggctggagtgcag
tggtgtgatcttggctcatcgtaacctccacctcccgggttcaagtgat
tctcatgcctcagcctcccgagtagctgggattacaggtggtgacttccaagag
tgactccgtcggaggaaaatg

*Homo sapiens* immunoglobulin superfamily containing leucine-rich repeat (ISLR):

(Seq ID No: 1264)

gctcctccctgccgcctcctctcagtg
gatggttccaggcaccctgtctggggcagggagggcacaggcctg
cacatcgaaggtggggtgggaccaggctgcccctcgcccagcatccaagtcctccctt
gggcgcccgtggccctgcagactctcagggctaaggtcctctgttgcttttt
ggttccaccttagaagaggctccgcttgactaagagtagcttgaaggaggcaccatg

*Homo sapiens* glycoprotein M6A (GPM6A):

(Seq ID No: 1265)

atttcttttccccattttaaatgcaaagcaagactt
gtgaatcatagtgtctctgctcctgggattcagac
caaatttccccccaaaattctcaggctatttgtttgaatacctgcttacagtgg
tacacaatgggcagctttgagaagaaaaattgataatcttcacggaagagtaattt
gaatgaaattacacttgacagcctgtctccaagcaaacaagaggaac
gagggagcctgagctaagctctgaggacttgcccaagccactgctgtt
ggagcttcccaggaaaaaaaaaaaaaaaaaaaaaaaaaaaaaaaaaaaaaaacaccag
tttttccaacatctaattgagcttttgattaattccgtgtaccagattctactgaa
gaaaggtagccatg

*Homo sapiens* splicing factor 1 (SF1):

(Seq ID No: 1266)

ctccctctttt
gtgcgtctcgcgccgccgccgcccgcgcgtgagaggacgggctccgcgcgctccgg
cagcgcattcgggtcccctccccccgggaggcttgcgaaggagaagccgccgcagag
gaaaagcaggtgccggtgcctgtcccggggggcgccatg

*Homo sapiens* cell cycle associated protein 1 (CAPRIN1):

(Seq ID No: 1267)

ccgcccctcgcgacccagagggctgctggctggctaagtccctcccgctcccggctctcg
cctcactaggagcggctctcggtgcagcgggacagggcgaagcggcctgcgcccac
ggagcgcgcgacactgcccggaagggaccgccacccttgcccctcagctgcccac
tcgtgatttccagcggcctccgcgcgcgcacgatg

*Homo sapiens* hypothetical protein FLJ90297 (LOC388152):

(Seq ID No: 1268)

ctgccctcttgcgtgccccggccaccccgggcggcttgtagccggtgcgcggggtggct
ggggctacgtgcagagctgtcgcggagccggaacagcagcggtgaagcccctcggctcgg
ccgagaccgccgtgcccattgctcgcctcggttgccgccgctttagccgcagccgctgct
gccgccgccgggggagaggcagcctattgtctttctccgcggcgaaggtgaggagctgtc
tcggctcggcccgcggggagcccgggagccgcacggagatggaggaggacatctggac
agtgagcaggaggcgcctcggcccatg

*Homo sapiens* kelch-like ECH-associated protein 1 (KEAP1):

(Seq ID No: 1269)

cgccctctcccgcctccttttcgggcgtcccgaggccgctccccaaccgacaaccaa
gaccccgcaggccacgcagccctggagccgaggccccccgacggcg
gaggcgcccgcgggtcccctacagccaaggtccctgagtgccagaggtggtggtgtt
gcttatcttctggaaccccatg

*Homo sapiens* F-box protein 38 (FBXO38):

(Seq ID No: 1270)

ctccctctcaaccacaa
taacaggcggagggtcggcgtaggtactttgaactcaagtaaacaaaagggaagat
tttctcgttgatactggagactgcacaacaatg

*Homo sapiens* musculoskeletal, embryonic nuclear protein 1 (MUSTN1):

(Seq ID No: 1271)

agatcttttccagcagctgctgcctgccagagaggcgccttcaga
gacccagcgcttacacaatacccaccatg

*Homo sapiens* QKI, KH domain containing, RNA binding (QKI):

(Seq ID No: 1272)

cctcctctccggcggcggcggcggcggcgggcggagtgagctgcggagcctg
gaatatg

*Homo sapiens* protein phosphatase 1, catalytic subunit, beta isoform

-continued (PPP1CB):

(Seq ID No: 1273)

gggcctctctt
gtttatttatttattttccgtgggtgcctccgagtgtgcgcgcgctctcgc
tacccggcggggaggggtgggggagggcccgggaaaaggggagtt
ggagccgggtcgaaacgccgcgtgacttgtaggtgagagaaccgcgagccgtcgccg
cagcctccgccgccgagaagcccttgttcccgctgctgggaaggagag
tctgtgccgacaagatg

*Homo sapiens* methyltransferase like 21B (METTL21B):

(Seq ID No: 1274)

cagcctc
tacccgctccggatccggatctgagcgccggccgcggtgcccaggcactcccctt
ggcgggccggatg

*Homo sapiens* adaptor-related protein complex 3, mu 1 subunit
(AP3M1):

(Seq ID No: 1275)

cggccttctcggcttctccagcttcggtaggagag
gatccggcgccgaatcactgactggcacaggtgttgggatagtgtctcactt
ggtcacccaggctggagtgcagtggcgcaatcttagctctc
tacagcgtcgatcttcctcctgggctcaagcaattctcctgcttcatcctcctgagtac
ctaggactacagaaaatg

*Homo sapiens* muscleblind-like splicing regulator 1 (MBNL1):

(Seq ID No: 1276)

cagtcttttcactgcagctgaatgagttgtggcgcccacaatgctcccatgacaaggagc
tgacaagttccattttccgtcgcgggcatcttggaatcatgactcccacaatgccttggg
cacttggtcgacagtggggccgcctctgaaaaaaaatgtgagaggttggtactaagaag
tgcctttcctgacgtctctgctgcttggaaccgcttctagagcagtctctgcttttgcct
tgcttgccagctagactgtgacgacagcacatccaccctccacctctagcccagaca
ccccatttctacttataatcaagagaaaagctcaagtatctggcattgccctaggctg
ctttagtgttaaaagaaaagtttgctgaaaaagtaagatatcttctgccaggaaatcaag
gaggaaaaaaaaatcattttctcgattttgctctaaactgctgcatctgtctatgccaa
actaatcaataccgattgcaccaccaaactccattgcaaattcagctgtgaggagattcc
ctttcagacaactttgctgaaagcagcttggaaattcggtgtcgaagggtctgccacgtt
ttcatgcttgcattttgggctccaaattggcactgggaaggggttactgagagcacaagg
ctgataccaggccctactttttaaacgttcatctacttacaatcctagtatttctctaaaa
accaaaacctctttgaattaacagtttcatgctgtgaatttctagtggggatcttttcc
ttgatattgacgacacaattttccatgtacttttaaagcagggagtggggaaaagtattt
tgaggggacattttcatcatcagttcagcttttttttttttggttgttgctctttttggg
ggggttgggtttgttggtttcactgaaacatttaactacctgtaaaatctaaacatg

*Homo
sapiens* lipid phosphate phosphatase-related protein type
1 (LPPR1):

(Seq ID No: 1277)

cagccttttgctctttcctttcattaaacaaacaggagatcctgaaac
ctggaccctgtgcaagctgcagcgccaggaggaggcagcggaggaagcagagcgcgg
gatgggcgcccagcggcatctgtgatcccgcgcacctccgccccacgggcgcgcg
cacaaacacggacacacacatacacacactcgcgcacacactcgcacaaacacacac
tcgtacacgcccgcgccgctcgctcgccggcttgctctcccacgcaagcggaatgcag
cagcgcctggagagcgtgtctcggaccgccgcctgaatgtacctcgctcccgggagccg
gacggcccagtagggcgcactggaggacgctccgctgcgggagcctggacagttttt
gacggtgcagtcttgctatatggtgtgagaaatg

*Homo sapiens* muscleblind-like splicing regulator 2 (MBNL2):

(Seq ID No: 1278)

ctgtctttgcttcatcatctgaaggtaaaattttccagatacggcagac
ggctttcagagtacaataaacagggaatgagaac
tatttacatggaagtttctttctcatgatgcggtggagaagcctcggccactt
ggttctgccagatgttcctggggttactgtaaatgg
gaaggacaggcagagctaaacaaggtttatcatttaaaagtgcctgtgtgaagtcac
ttttgctggaaaactgcagcttgggagcttttctttgtattcacatcccac
tcttctgtcaagtacacttacccctgaccttatgagtggatgaagataccctcagtt
gtctgactttgccaattgcttaatttcagaatttaaaaaggggaaa
gaaaaacatcctgctaaaatatgaacatctgagtgtcttattttccaacatcgtcaa
tagctgtgagcgtcagcattaaatattctcccaaggagtgccatgatattgaagtcac
tttattaataacagctgtatctgcaaaacagtcaagagactcggacgttgaaagccaga
gatgacactgagcatgcttttattgcggcctaccatctttaagtgg
gacatattgattgatgagtgattgcctgtccatacactctctcatcatcctgttcctt
ggattggacttcactaagcaatttatcactcacctttcagacttacatgtgggag
ttttcacaacagtagttttggaatcattagaacttggattgat
ttcatcatttaacagaaacaaacagcccaaattactttatcaccatg

*Homo sapiens* chromosome 3 open reading frame 25 (C3orf25):

(Seq ID No: 1279)

gcgcctttcgcacgacttggagttacggtttatctgataccgcggtaccccctacgcaa
gcaagcccacatcgacacacattcacacacgcccttcagcacccccctcccagcaccac
gaccatg -continued Homo sapiens testis expressed 19 (TEX19):
(Seq ID No: 1280)
cctcctcctttccctgggtgcccacatgaacagagacaccaggatgctctcctgagacca
cagcaactgcagaagctgaagacatttccagaagttcaagcttccaccctctg
caggtccccactgagctgggacccaggtcatccaccccaccccaaatccctgga
taggaaaccccttctcctcctgctccttgtcccttcatccctgccgcccagcatcc
tactggcctcagcacctgtggccagaccgtccaagatctctgaaggcccagctcttgct
gtccaccccggcagtaggcaggcagcctggccatg Homo sapiens protein kinase C, beta (PRKCB):
(Seq ID No: 1281)
gcctccctccccg
cagctggggccagcggtgccaagcgcagctggacgagcggcagcagctgggcgag
tgacagccccggctccgcgcgccgcggccgccagagccggcgcaggggaa
gcgcccgcggccccgggtgcagcagcggccgccgcctcccgcgcctcccggcccg
cagcccgcggtcccgcggcccggggccggcacctctcgggctccggctccccgcgcg
caagatg Homo sapiens protein kinase N1 (PKN1):
(Seq ID No: 1282)
ccctccctccgcgcggg
gaccctggcgggcggcaggaggacatg Homo sapiens hemochromatosis type 2 (juvenile) (HFE2):
(Seq ID No: 1283)
ccttctctggttccctgacctcagtgagacagcagccggcctggggacctggggaga
cacggaggaccccctggctggagctgacccacagagtagggaatcatggctggagaatt
ggatagcagagtaatgtttgacctctggaaacatcac
ttacagggcttccggtcaaaattcactaggtaggagggtcatcagctgggaagaac
cggcgcctgggaaacctggctggataggtatg Homo sapiens ribosomal protein L9 (RPL9):
(Seq ID No: 1284)
cgttctttctttt
gctgcgtctactgcgagaatg Homo sapiens ribosomal protein L3 (RPL3):
(Seq ID No: 1285)
cggcctcttcggcgg
gatttgatggcgtgatg Homo sapiens ribosomal protein L4 (RPL4):
(Seq ID No: 1286)
acttcctttcctgtgg
cagcagccgggctgagaggagcgtggctgtcctctctccgccatg Homo sapiens ribosomal protein L5 (RPL5):
(Seq ID No: 1287)
tggccctttcccaccccctagcgccgctgggcctgcaggtctctgtcgagcagcggac
gccggtctctgttccgcaggatg Homo sapiens ribosomal protein L6 (RPL6):
(Seq ID No: 1288)
aattctctttcccatcttgcaagatg Homo sapiens ribosomal protein L7 (RPL7):
(Seq ID No: 1289)
cttcctcttttttccggctggaaccatg Homo sapiens ribosomal protein L7a (RPL7A):
(Seq ID No: 1290)
ctttcctttctctctcctcccgccgcccaagatg Homo sapiens ribosomal protein L11 (RPL11):
(Seq ID No: 1291)
ctttctcttcctgctctccatcatg Homo sapiens ribosomal protein L12 (RPL12):
(Seq ID No: 1292)
cggcctctcggctttcggctcggaggaggccaaggtgcaacttccttcggtcgtcccgaa
tccgggttcatccgacaccagccgcctccaccatg Homo sapiens ribosomal protein L13 (RPL13):
(Seq ID No: 1293)
gcttcctttccgctcggctgttttcctgcgcaggagccgcagggccgtaggcagccatg Homo sapiens ribosomal protein L23 (RPL23):
(Seq ID No: 1294)
acttcctttttctttttccggcgttcaagatg Homo sapiens ribosomal protein L18 (RPL18):

*Homo sapiens* ribosomal protein L18a (RPL18A):

(Seq ID No: 1296)
acttcctttt
gcgggtggcggcgaacgcggagagcacgccatg

*Homo sapiens* ribosomal protein L19 (RPL19):

(Seq ID No: 1297)
agctctttcctttcgctgctgcggccgcagccatg

*Homo sapiens* ribosomal protein L21 (RPL21):

(Seq ID No: 1298)
gcctctttcctttcggccggaaccgccatcttccagtaattcgccaaaatg

*Homo sapiens* ribosomal protein L22 (RPL22):

(Seq ID No: 1299)
ac
ctcccttctaactccgctgccgccatg

*Homo sapiens* ribosomal protein L23a (RPL23A):

(Seq ID No: 1300)
agaccctttttca
caagatg

*Homo sapiens* ribosomal protein L17 (RPL17):

(Seq ID No: 1301)
cgctcttcctctctttccctaagcagcctgagggttgactg
gattggtgaggcccgtgtggctacttctgtggaagcagtgctgtagttactggaaga
taaaagggaaagcaagcccttggtgggggaaagtatggctgcgatgatgg
catttcttaggacacctttggattaataatgaaaacaactactctctgag
cagctgttcgaatcatctgatatttatactgaatgagttactgtaagtac
gtattgacagaattacactgtactttcctctaggtgatctgtgaaaatg

*Homo sapiens* ribosomal protein L24 (RPL24):

(Seq ID No: 1302)
ttctctctttcttttcgccatctttttgtctttccgtggagctgtcgccatg

*Homo sapiens* ribosomal protein L26 (RPL26):

(Seq ID No: 1303)
agttctcttcccttttgcggccatcaccgaagcgggagcggccaaaatg

*Homo sapiens* ribosomal protein L27 (RPL27):

(Seq ID No: 1304)
ctttccttttt
gctggtagggccgggtggttgctgccgaaatg

*Homo sapiens* ribosomal protein L30 (RPL30):

(Seq ID No: 1305)
aagtctttcctttctcgttccccggccatcttagcggctgctgttggtt
gggggccgtcccgctcctaaggcaggaagatg

*Homo sapiens* ribosomal protein L27a (RPL27A):

(Seq ID No: 1306)
ccttccttttcgtctgggctgccaacatg

*Homo sapiens* ribosomal protein L28 (RPL28):

(Seq ID No: 1307)
cttcctctttccgtctcaggtcgccgctgcgaagggagccgccgccatg

*Homo sapiens* ribosomal protein L29 (RPL29):

(Seq ID No: 1308)
cagccctttctcttccggttctaggcgcttcgggagccgcggcttatggtgcagacatg

*Homo sapiens* ribosomal protein L31 (RPL31):

(Seq ID No: 1309)
cgctcttcctttccaacttggacgctgcagaatg

*Homo sapiens* ribosomal protein L32 (RPL32):

(Seq ID No: 1310)
ccgtcccttctctcttcctcggcgctgcctacggaggtggcagccatctccttctcgg
catcatg

*Homo sapiens* ribosomal protein L35a (RPL35A):

(Seq ID No: 1311)
cgtccttctcttaccgccatcttggctcctgtggaggcctgctgggaacgg
gacttctaaaaggaactatg

*Homo sapiens* ribosomal protein L37 (RPL37):

-continued

```
                                                 (Seq ID No: 1312)
ccttctcttccggtctttctggtctcggccgcagaagcgagatg
```

Homo sapiens ribosomal protein L37a (RPL37A):
```
                                                 (Seq ID No: 1313)
gcgtctcttcctttctgggctcggacctaggtcgcggcgacatg
```

Homo sapiens ribosomal protein L38 (RPL38):
```
                                                 (Seq ID No: 1314)
cgttcttttcgtcctttccccggttgctgcttgctgtgagtgtctctagggtgatac
gtgggtgagaaaggtcctggtccgcgccagagcccagcgcgcctcgtcgccatg
```

Homo sapiens ribosomal protein L39 (RPL39):
```
                                                 (Seq ID No: 1315)
ccctcctcttcctttctccgccatcgtggtgtgttcttgactccgctgctcgccatg
```

Homo sapiens ribosomal protein, large, P0 (RPLP0):
```
                                                 (Seq ID No: 1316)
ag
gcccttctctcgccaggcgtcctcgtggaagtgacatcgtctttaaaccctgcgtgg
caatccctgacgcaccgccgtgatg
```

Homo sapiens ribosomal protein, large, P1 (RPLP1):
```
                                                 (Seq ID No: 1317)
cggtccttccgaggaagctaaggctgcgttggggtgaggccctcac
ttcatccggcgactagcaccgcgtccggcagcgccagccctacactcgcccgcgccatg
```

Homo sapiens ribosomal protein, large, P2 (RPLP2):
```
                                                 (Seq ID No: 1318)
ccttcctttcctccctgtcgccaccgaggtcgcacgcgtgagacttctccgccgcctcc
gccgcagacgccgccgcgatg
```

Homo sapiens ribosomal protein S3 (RPS3):
```
                                                 (Seq ID No: 1319)
acttcctttcctttcagcggagcgcggcggcaagatg
```

Homo sapiens ribosomal protein S3A (RPS3A):
```
                                                 (Seq ID No: 1320)
ccgccctttt
ggctctctgaccagcaccatg
```

Homo sapiens ribosomal protein S4, X-linked (RPS4X):
```
                                                 (Seq ID No: 1321)
ggtcctctttccttgcctaacgcagccatg
```

Homo sapiens ribosomal protein S4, Y-linked 1 (RPS4Y1):
```
                                                 (Seq ID No: 1322)
gat
tctcttccgtcgcagagtttcgccatg
```

Homo sapiens ribosomal protein S5 (RPS5):
```
                                                 (Seq ID No: 1323)
ttttcttcccag
ttaaaagtgttggcccgcggcgcgcggcctcttcctgtctgtac
cagggcggcgcgtggtctacgccgagtgacagagacgctcaggctgtgttctcaggatg
```

Homo sapiens ribosomal protein S6 (RPS6):
```
                                                 (Seq ID No: 1324)
ggccctcttttccgtggcgcctcggaggcgttcagctgcttcaagatg
```

Homo sapiens ribosomal protein S7 (RPS7):
```
                                                 (Seq ID No: 1325)
gggtctcttcctaa
gccggcgctcggcaagttctcccaggagaaagccatg
```

Homo sapiens ribosomal protein S8 (RPS8):
```
                                                 (Seq ID No: 1326)
gtttctctttccagccagcgccgagcgatg
```

Homo sapiens ribosomal protein S9 (RPS9):
```
                                                 (Seq ID No: 1327)
gcgcctctttctcag
tgaccgggtggtttgcttaggcgcagacggggaagcggagccaacatg
```

Homo sapiens ribosomal protein S10 (RPS10):
```
                                                 (Seq ID No: 1328)
gctccttcctttccagccccggtaccggaccctgcagccgcagagatg
```

Homo sapiens ribosomal protein S11 (RPS11):
```
                                                 (Seq ID No: 1329)
ctgcccctttctttttttcaggcggccgggaagatg
```

*Homo sapiens* ribosomal protein S12 (RPS12):

(Seq ID No: 1330)

ag
gcctctttccctgccgccgccgagtcgcgcggaggcggaggcttgggtgcgttcaagat
tcaacttcacccgtaacccaccgccatg

*Homo sapiens* ribosomal protein S13 (RPS13):

(Seq ID No: 1331)

cgctctcctttcgtt
gcctgatcgccgccatcatg

*Homo sapiens* ribosomal protein S15 (RPS15):

(Seq ID No: 1332)

cgatctcttctgag
gatccggcaagatg

*Homo sapiens* ribosomal protein S15a (RPS15A):

(Seq ID No: 1333)

cgtcctcttcccgccatctttccgcgccggtgagtagcactctctga
gagctccaatttcatccgtctgccatcggcgccatcctgcaatctaagccacaatg

*Homo sapiens* ribosomal protein S16 (RPS16):

(Seq ID No: 1334)

cttcctttcggttgcggcgccgcgcggtgaggttgtctagtccacgctcggagc
catg

*Homo sapiens* ribosomal protein S19 (RPS19):

(Seq ID No: 1335)

cgttcccttcccctggctggcagcgcggaggccgcacgatg

*Homo sapiens* ribosomal protein S20 (RPS20):

(Seq ID No: 1336)

ccaccccttcttttgaggaagacgcggtcgtaagggctgaggattttggtccgcac
gctcctgctcctgactcaccgctgttcgctctcgccgaggaacaagtcggtcaggaa
gcccgcgcgcaacagccatg

*Homo sapiens* ribosomal protein S21 (RPS21):

(Seq ID No: 1337)

gcttcctttctctctcgcgcgcggtgtggtggcagcaggcgcagcccagcctcgaaatg

*Homo sapiens* ribosomal protein S23 (RPS23):

(Seq ID No: 1338)

gcttctctcttccgctcaggcccgtggcgccgacaggatg

*Homo sapiens* ribosomal protein S25 (RPS25):

(Seq ID No: 1339)

gcttcctttttt
gtccgacatcttgacgaggctgcggtgtctgctgctattctccgagcttcgcaatg

*Homo sapiens* ribosomal protein S26 (RPS26):

(Seq ID No: 1340)

ccgtctcctctctccggtccgtgcctccaagatg

*Homo sapiens* ribosomal protein S27 (RPS27):

(Seq ID No: 1341)

cgctcctttccggcggtgacgacctacgcacacgagaacatg

*Homo sapiens* ribosomal protein S28 (RPS28):

(Seq ID No: 1342)

actcctctccgcca
gaccgccgccgcgccgccatcatg

*Homo sapiens* ribosomal protein S29 (RPS29):

(Seq ID No: 1343)

gcttcttcctttac
ctcgttgcactgctgagagcaagatg

*Homo sapiens* ribosomal protein L15 (RPL15):

(Seq ID No: 1344)

agctctttccttccgtctggcggcagccatcaggtaagccaagatg

*Homo sapiens* ribosomal protein S2 (RPS2):

(Seq ID No: 1345)

cgttcttcttttccgacaaaacaccaaatg

*Homo sapiens* ribosomal protein L14 (RPL14):

(Seq ID No: 1346)

gggtcttcttccttctcgcctaacgccgccaacatg

*Homo sapiens* ribosomal protein S14 (RPS14):

-continued (Seq ID No: 1347)
ctctctttccggtgtggagtctggagacgacgtgcagaaatg

Homo sapiens ribosomal protein L10 (RPL10):
(Seq ID No: 1348)
gcgcctcttccccttcggtgtgccactgaagatcctggtgtcgccatg Homo sapiens ribosomal protein L10a (RPL10A):
(Seq ID No: 1349)
tag
tctcttttccggttagcgcggcgtgagaagccatg Homo sapiens ribosomal protein L35 (RPL35):
(Seq ID No: 1350)
tcctctttccctcg
gagcgggcggcggcgttggcggcttgtgcagcaatg Homo sapiens ribosomal protein L13a (RPL13A):
(Seq ID No: 1351)
cctcctcctttccaagcggctgccgaagatg Homo sapiens ribosomal protein L36 (RPL36):
(Seq ID No: 1352)
cagcccttccgccac
ggccgtctctggagagcagcagccatg Homo sapiens ribosomal protein L36a (RPL36A):
(Seq ID No: 1353)
gtttctttctttccgcgccgatagcgctcacgcaagcatg Homo sapiens ribosomal protein L41 (RPL41):
(Seq ID No: 1354)
tcgcc tttctctcggccttagcgccatttttttggaaacctctgcgccatg Homo sapiens ribosomal protein S18 (RPS18):
(Seq ID No: 1355)
cgctctctcttcca
caggaggcctacacgccgccgcttgtgctgcagccatg Homo sapiens ribosomal protein S24 (RPS24):
(Seq ID No: 1356)
ggttctcttttcctccttggctgtctgaagatagatcgccatcatg Homo sapiens ribosomal protein L8 (RPL8):
(Seq ID No: 1357)
tttcctctttcggccgcgctggtgaacaggtaggtcatccttgcggccttgcggcatg Homo sapiens ribosomal protein L34 (RPL34):
(Seq ID No: 1358)
cttcctcttccggg
gacgttgtctgcaggtatg Homo sapiens ribosomal protein S17 (RPS17):
(Seq ID No: 1359)
gtttcctcttttac
caaggacccgccaacatg Homo sapiens ribosomal protein SA (RPSA):
(Seq ID No: 1360)
ctgtcttttccgtgc
tacctgcagaggggtccatacggcgttgttctggattcccgtcg
taacttaaagggaaattttcacaatg Homo sapiens eukaryotic translation initiation factor 3, subunit C (EIF3C):
(Seq ID No: 1361)
cttctctctcggcgtttccgctgtcagggccctgcggtgtgactcgcgggctcagctggt
ccggccgtagcacctccgcgccgtcgccatg Homo sapiens poly(A) binding protein, cytoplasmic 1 (PABPC1):
(Seq ID No: 1362)
cgctctcctcctctcacggaaaggtcgcggcctgtggccctgcgggcag
ccgtgccgagatg Homo sapiens tubulin, beta 1 class VI (TUBB1):
(Seq ID No: 1363)
cac
tcccttccaaaagcatgacaggcagaaagcagagaagggccag
gactggctgagggcggggagctgggcctctggggtggacacacccttggtcacatt -continued

```
gtgagggtagcttggttggccagtcccaccactgcagtgaccacagttgtgtt
gggctcacaccagtgaaccgaagctctggattctgagagtctgaggattccgtgaa
gatctcagacttgggctcagagcaaggatg
```

PpLuc(GC)-ag-A64

(SEQ ID No: 1364)

```
GGGAGAAAGCTTGAGGATGGAGGACGCCAAGAACATCAAGAAGGGCCCGGCGCCCTTCTA
CCCGCTGGAGGACGGGACCGCCGGCGAGCAGCTCCACAAGGCCATGAAGCGGTACGCCCT
GGTGCCGGGCACGATCGCCTTCACCGACGCCCACATCGAGGTCGACATCACCTACGCGGA
GTACTTCGAGATGAGCGTGCGCCTGGCCGAGGCCATGAAGCGGTACGGCCTGAACACCAA
CCACCGGATCGTGGTGTGCTCGGAGAACAGCCTGCAGTTCTTCATGCCGGTGCTGGGCGC
CCTCTTCATCGGCGTGGCCGTCGCCCCGGCGAACGACATCTACAACGAGCGGGAGCTGCT
GAACAGCATGGGGATCAGCCAGCCGACCGTGGTGTTCGTGAGCAAGAAGGGCCTGCAGAA
GATCCTGAACGTGCAGAAGAAGCTGCCCATCATCCAGAAGATCATCATCATGGACAGCAA
GACCGACTACCAGGGCTTCCAGTCGATGTACACGTTCGTGACCAGCCACCTCCCGCCGGG
CTTCAACGAGTACGACTTCGTCCCGGAGAGCTTCGACCGGGACAAGACCATCGCCCTGAT
CATGAACAGCAGCGGCAGCACCGGCCTGCCGAAGGGGGTGGCCCTGCCGCACCGGACCGC
CTGCGTGCGCTTCTCGCACGCCCGGGACCCCATCTTCGGCAACCAGATCATCCCGGACAC
CGCCATCCTGAGCGTGGTGCCGTTCCACCACGGCTTCGGCATGTTCACGACCCTGGGCTA
CCTCATCTGCGGCTTCCGGGTGGTCCTGATGTACCGGTTCGAGGAGGAGCTGTTCCTGCG
GAGCCTGCAGGACTACAAGATCCAGAGCGCGCTGCTCGTGCCGACCCTGTTCAGCTTCTT
CGCCAAGAGCACCCTGATCGACAAGTACGACCTGTCGAACCTGCACGAGATCGCCAGCGG
GGGCGCCCCGCTGAGCAAGGAGGTGGGCGAGGCCGTGGCCAAGCGGTTCCACCTCCCGGG
CATCCGCCAGGGCTACGGCCTGACCGAGACCACGAGCGCGATCCTGATCACCCCCGAGGG
GGACGACAAGCCGGGCGCCGTGGGCAAGGTGGTCCCGTTCTTCGAGGCCAAGGTGGTGGA
CCTGGACACCGGCAAGACCCTGGGCGTGAACCAGCGGGGCGAGCTGTGCGTGCGGGGGCC
GATGATCATGAGCGGCTACGTGAACAACCCGGAGGCCACCAACGCCCTCATCGACAAGGA
CGGCTGGCTGCACAGCGGCGACATCGCCTACTGGGACGAGGACGAGCACTTCTTCATCGT
CGACCGGCTGAAGTCGCTGATCAAGTACAAGGGCTACCAGGTGGCGCCGGCCGAGCTGGA
GAGCATCCTGCTCCAGCACCCCAACATCTTCGACGCCGGCGTGGCCGGGCTGCCGGACGA
CGACGCCGGCGAGCTGCCGGCCGCGGTGGTGGTGCTGGAGCACGGCAAGACCATGACGGA
GAAGGAGATCGTCGACTACGTGGCCAGCCAGGTGACCACCGCCAAGAAGCTGCGGGGCGG
CGTGGTGTTCGTGGACGAGGTCCCGAAGGGCCTGACCGGGAAGCTCGACGCCCGGAAGAT
CCGCGAGATCCTGATCAAGGCCAAGAAGGGCGGCAAGATCGCCGTGTAAGACTAGTTATA
AGACTGACTAGCCCGATGGGCCTCCCAACGGGCCCTCCTCCCCTCCTTGCACCGAGATTA
ATAGATCTAAAAAAAAAAAAAAAAAAAAAAAAAAAAAAAAAAAAAAAAAAAAAAAAAAAA
AAAAAAAAAAAA
```

RPL32-PpLuc(GC)-ag-A64-C30-histoneSL (SEQ ID No: 1365)

```
GGGGCGCTGCCTACGGAGGTGGCAGCCATCTCCTTCTCGGCATCAAGCTTGAGGATGGAG
GACGCCAAGAACATCAAGAAGGGCCCGGCGCCCTTCTACCCGCTGGAGGACGGGACCGCC
GGCGAGCAGCTCCACAAGGCCATGAAGCGGTACGCCCTGGTGCCGGGCACGATCGCCTTC
ACCGACGCCCACATCGAGGTCGACATCACCTACGCGGAGTACTTCGAGATGAGCGTGCGC
CTGGCCGAGGCCATGAAGCGGTACGGCCTGAACACCAACCACCGGATCGTGGTGTGCTCG
GAGAACAGCCTGCAGTTCTTCATGCCGGTGCTGGGCGCCCTCTTCATCGGCGTGGCCGTC
GCCCCGGCGAACGACATCTACAACGAGCGGGAGCTGCTGAACAGCATGGGGATCAGCCAG
CCGACCGTGGTGTTCGTGAGCAAGAAGGGCCTGCAGAAGATCCTGAACGTGCAGAAGAAG
CTGCCCATCATCCAGAAGATCATCATCATGGACAGCAAGACCGACTACCAGGGCTTCCAG
TCGATGTACACGTTCGTGACCAGCCACCTCCCGCCGGGCTTCAACGAGTACGACTTCGTC
CCGGAGAGCTTCGACCGGGACAAGACCATCGCCCTGATCATGAACAGCAGCGGCAGCACC
GGCCTGCCGAAGGGGGTGGCCCTGCCGCACCGGACCGCCTGCGTGCGCTTCTCGCACGCC
CGGGACCCCATCTTCGGCAACCAGATCATCCCGGACACCGCCATCCTGAGCGTGGTGCCG
TTCCACCACGGCTTCGGCATGTTCACGACCCTGGGCTACCTCATCTGCGGCTTCCGGGTG
GTCCTGATGTACCGGTTCGAGGAGGAGCTGTTCCTGCGGAGCCTGCAGGACTACAAGATC
CAGAGCGCGCTGCTCGTGCCGACCCTGTTCAGCTTCTTCGCCAAGAGCACCCTGATCGAC
AAGTACGACCTGTCGAACCTGCACGAGATCGCCAGCGGGGGCGCCCCGCTGAGCAAGGAG
GTGGGCGAGGCCGTGGCCAAGCGGTTCCACCTCCCGGGCATCCGCCAGGGCTACGGCCTG
ACCGAGACCACGAGCGCGATCCTGATCACCCCCGAGGGGGACGACAAGCCGGGCGCCGTG
GGCAAGGTGGTCCCGTTCTTCGAGGCCAAGGTGGTGGACCTGGACACCGGCAAGACCCTG
GGCGTGAACCAGCGGGGCGAGCTGTGCGTGCGGGGGCCGATGATCATGAGCGGCTACGTG
AACAACCCGGAGGCCACCAACGCCCTCATCGACAAGGACGGCTGGCTGCACAGCGGCGAC
ATCGCCTACTGGGACGAGGACGAGCACTTCTTCATCGTCGACCGGCTGAAGTCGCTGATC
AAGTACAAGGGCTACCAGGTGGCGCCGGCCGAGCTGGAGAGCATCCTGCTCCAGCACCCC
AACATCTTCGACGCCGGCGTGGCCGGGCTGCCGGACGACGACGCCGGCGAGCTGCCGGCC
GCGGTGGTGGTGCTGGAGCACGGCAAGACCATGACGGAGAAGGAGATCGTCGACTACGTG
GCCAGCCAGGTGACCACCGCCAAGAAGCTGCGGGGCGGCGTGGTGTTCGTGGACGAGGTC
CCGAAGGGCCTGACCGGGAAGCTCGACGCCCGGAAGATCCGCGAGATCCTGATCAAGGCC
AAGAAGGGCGGCAAGATCGCCGTGTAAGACTAGTTATAAGACTGACTAGCCCGATGGGCC
TCCCAACGGGCCCTCCTCCCCTCCTTGCACCGAGATTAATAGATCTAAAAAAAAAAAAAA
AAAAAAAAAAAAAAAAAAAAAAAAAAAAAAAAAAAAAAAAAAAAATGCATCCCCC
CCCCCCCCCCCCCCCCCCCCCCCAAAGGCTCTTTTCAGAGCCACCAGAATT
``` fragment of the 5'UTR of human ribosomal protein Large 32

(SEQ ID No: 1366)

ACGGAGGTGGCAGCCATCTCCTTCTCGGCATC fragment of the 5'UTR of human ribosomal protein Large 32

(SEQ ID No: 1367)

GGCGCTGCCTACGGAGGTGGCAGCCATCTCCT

-continued

5'UTR of human ribosomal protein Large 32 lacking the 5' terminal oligopyrimidine tract (SEQ ID No. 1368)

GGCGCTGCCTACGGAGGTGGCAGCCATCTCCTTCTCGGCATC

Human albumin 3'UTR (SEQ ID No: 1369)

CATCACATTT AAAAGCATCT CAGCCTACCA TGAGAATAAG AGAAAGAAAA
TGAAGATCAA AAGCTTATTC ATCTGTTTTT CTTTTTCGTT GGTGTAAAGC
CAACACCCTG TCTAAAAAAC ATAAATTTCT TTAATCATTT TGCCTCTTTT
CTCTGTGCTT CAATTAATAA AAAATGGAAA GAATCT

3'UTR of Homo sapiens hemoglobin, alpha 1 (HBA1)

(SEQ ID No: 1370)

gctggagcctcggtggccatgcttcttgcccctt
gggcctcccccagcccctcctcccctttcctgcacccgtaccccgtggtctttgaa
taaagtctgagtgggcggc 3'UTR of Homo sapiens hemoglobin, alpha 2 (HBA2)

(SEQ ID No: 1371)

gctggagcctcggtagccgttcctcctgcccgctgggcctcccaac
gggcctcctcccctccttgcaccggcccttcctggtctttgaataaagtctgagtgggcag 3'UTR of Homo sapiens hemoglobin, beta (HBB)

(SEQ ID No: 1372)

Gctcgctttcttgctgtccaatttctattaaaggttcctttgttccctaagtccaactacta
aactgggggatattatgaagggccttgagcatctggattctgcctaa
taaaaaacatttattttcattgc 3'UTR of Homo sapiens tyrosine hydroxylase (TH)

(SEQ ID No: 1373)

gtgcacggcgtccctgagggcccttcccaacctcccctggtcctgcactgtcccg
gagctcaggccctggtgaggggctgggtcccgggtgccccccatgccctccctgctgcca
ggctcccactgcccctgcacctgcttctcagcg
caacagctgtgtgtgcccgtggtgaggtt
gtgctgcctgtggtgaggtcctgtcctggctcccagggtcctgggggctgctgcac
tgccctccgcccttccctgacactgtctgctgccccaatcaccgtcacaataaaa
gaaactgtggtctcta 3'UTR of Homo sapiens arachidonate 15-lipoxygenase (ALOX15)

(SEQ ID No: 1374)

gcgtcgccaccctttggttatttcagcccccatcacccaagccacaagctgacccttcg
tggttatagccctgccctcccaagtcccaccctcttcccatgtcccaccctccctagagg
ggcaccttttcatggtctctgcacccagtgaacacattttactctagaggcatcacctgg
gaccttactcctctttccttcctcctcctttcctatcttccttcctctctctcttcctc
tttcttcattcagatctatatggcaaatagccacaattatataaatcatttcaagactag
aataggggatataatacatattactccacaccttttatgaatcaaatatgatttttttg
ttgttgttaagacagagtctcactttgacacccaggctggagtgcagtggtgccatcacc
acggctcactgcagcctcagcgtcctgggctcaaatgatcctcccacctcagcctcctga
gtagctgggactacaggctcatgccatcatgcccagctaatattttttattttcgtgga
gacggggcctcactatgttgcctaggctggaaataggattttgaacccaaattgagttta
acaataataaaaagttgttttacgctaaagatggaaaagaactaggactgaactatttta
aataaaatattggc 3'UTR of Homo sapiens collagen, type I, alpha 1 (COL1A1)

(SEQ ID No: 1375)

actccctccatcccaacctggctccctcccacccaaccaactttccccccaacccg
gaaacagacaagcaacccaaactgaacccccctcaaaagccaaaaaatgggaga
caatttcacatggactttggaaaatatttttttcctttgcattcatctctcaaacttag
ttttatctttgaccaaccgaacatgaccaaaaaccaaaagtgcattcaaccttac
caaaaaaaaaaaaaaaaaaagaataaataaataacttttttaaaaaaggaagctt
ggtccacttgcttgaagacccatgcggggtaagtcccttttctgcccgtt
gggcttatgaaaccccaatgctgcccttctgctcctttctccacaccccccctt
ggggcctcccctccactccttcccaaatctgtctccccagaagacacag
gaaacaatgtattgtctgcccag
caatcaaaggcaatgctcaaacacccaagtggcccccaccctcagcccgctcctgccgc
ccagcacccccaggccctgggggacctgggttctcagactgccaaagaagcctt
gccatctggcgctcccatggctcttgcaacatctccccttcgttttt
gaggggtcatgccggggagccaccagcccctcactgggttcggaggagagtcag
gaagggccacgacaaagcagaaacatcggatttggggaacgcgtgtcaatccctt
gtgccgcagggctggcgggagagactgttctgttccttgtgtaactgtgttgctgaaa
gactacctcgttcttgtcttgatgtgtcaccggggcaactgcctgggggcggg
gatggggcagggtggaagcggctccccattttataccaaaggtgc
tacatctatgtgatgggtgggtggggagggaatcactggtgctatagaaattga
gatgccccccaggccagcaaatgttcctttttgttcaaagtctatttttattccttga
tatttttctttttttttttttttttttgtggatgggactt
gtgaattttctaaaggtgctatttaacatgggagga
gagcgtgtgcggctccagcccagcccgctgctcacttttcacccctctctccac
ctgcctctggcttctcaggcctctgctctccgac
ctctctcctctgaaaccctcctccacagctgcagcccatcctcccggctccctcctag
tctgtcctgcgtcctctgtccccgggtttcagagacaacttcccaaagcacaaagcag -continued

```
tttttcccctaggggtgggaggaagcaaaagactctgtacctattttgtatgtg
tataataatttgagatgtttttaattattttgattgctggaataaagcatgtg
gaaatgacccaaacataa
``` albumin7 3'UTR (SEQ ID No: 1376)

```
CATCACATTTAAAAGCATCTCAGCCTACCATGAGAATAAGAGAAAGAAAATGAA
GATCAATAGCTTATTCATCTCTTTTTCTTTTTCGTTGGTGTAAA
GCCAACACCCTGTCTAAAAAACATAAATTTCTTTAATCATTTT
GCCTCTTTTCTCTGTGCTTCAATTAATAAAAAATGGAAAGAACCT
```

Human albumin 3'UTR + poly(A) sequence (SEQ ID No: 1377)

```
CATCACATTT AAAAGCATCT CAGCCTACCA TGAGAATAAG AGAAAGAAAA TGAA
GATCAA AAGCTTATTC ATCTGTTTTT CTTTTTCGTT GGTGTAAAGC
CAACACCCTG TCTAAAAAAC ATAAATTTCT TTAATCATTT TGCCTCTTTT
CTCTGTGCTT CAATTAATAA AAATGGAAA GAATCTAGAT CTAAAAAAAA
AAAAAAAAAA AAAAAAAAA AAAAAAAAA AAAAAAAAA AAAAAAAAA
AAAAAA
```

Human albumin 3'UTR fragment 1

(SEQ ID No: 1378)

```
AAAAGCATCT CAGCCTACCA TGAGAATAAG AGAAAGAAAA TGAAGATCAA AA
GCTTATTC ATCTGTTTTT CTTTTTCGTT GGTGTAAAGC CAACACCCTG
TCTAAAAAAC ATAAATTTCT TTAATCATTT TGCCTCTTTT CTCTGTGCTT CAATT
```

Human albumin 3'UTR fragment 2

(SEQ ID No: 1379)

```
CATCACATTT AAAAGCATCT CAGCCTACCA TGAGAATAAG AGAAAGAAAA
TGAAGATCAA AAGCTTATTC ATCTGTTTTT CTTTTTCGTT GGTGTAAAGC
CAACACCCTG
```

Human albumin 3'UTR fragment 3

(SEQ ID No: 1380)

```
AAAAGCATCT CAGCCTACCA TGAGAATAAG AGAAAGAAAA TGAAGATCAA
AAGCTTATTC ATCTGTTTTT CTTTTTCGTT GGTGTAAAGC CAACACCCTG
TCTAAAAAAC
```

Human albumin 3'UTR fragment 4

(SEQ ID No: 1381)

```
CAGCCTACCA TGAGAATAAG AGAAAGAAAA TGAAGATCAA AAGCTTATTC
ATCTGTTTTT CTTTTTCGTT GGTGTAAAGC CAACACCCTG TCTAAAAAAC
ATAAATTTCT
```

Human albumin 3'UTR fragment 5

(SEQ ID No: 1382)

```
TGAGAATAAG AGAAAGAAAA TGAAGATCAA AAGCTTATTC ATCTGTTTTT
CTTTTTCGTT GGTGTAAAGC CAACACCCTG TCTAAAAAAC ATAAATTTCT
TTAATCATTT
```

Human albumin 3'UTR fragment 6

(SEQ ID No: 1383)

```
AGAAAGAAAA TGAAGATCAA AAGCTTATTC ATCTGTTTTT CTTTTTCGTT
GGTGTAAAGC CAACACCCTG TCTAAAAAAC ATAAATTTCT TTAATCATTT
TGCCTCTTTT
```

Human albumin 3'UTR fragment 7

(SEQ ID No: 1384)

```
TGAAGATCAA AAGCTTATTC ATCTGTTTTT CTTTTTCGTT GGTGTAAAGC
CAACACCCTG TCTAAAAAAC ATAAATTTCT TTAATCATTT TGCCTCTTTT
CTCTGTGCTT
```

Human albumin 3'UTR fragment 8

(SEQ ID No: 1385)

```
AAGCTTATTC ATCTGTTTTT CTTTTTCGTT GGTGTAAAGC CAACACCCTG
TCTAAAAAAC ATAAATTTCT TTAATCATTT TGCCTCTTTT CTCTGTGCTT
CAATTAATAA
```

Human albumin 3'UTR fragment 9

(SEQ ID No: 1386)

```
ATCTGTTTTT CTTTTTCGTT GGTGTAAAGC CAACACCCTG TCTAAAAAAC
ATAAATTTCT TTAATCATTT TGCCTCTTTT CTCTGTGCTT CAATTAATAA
AAAATGGAAA
```

Human albumin 3'UTR fragment 10

(SEQ ID No: 1387)

```
CAGCCTACCA TGAGAATAAG AGAAAGAAAA TGAAGATCAA AAGCTTATTC
ATCTGTTTTT CTTTTTCGTT GGTGTAAAGC CAACACCCTG TCTAAAAAAC
ATAAATTTCT TTAATCATTT TGCCTCTTTT CTCTGTGCTT CAATTAATAA A
```

Human albumin 3'UTR fragment 11

-continued

```
TGAAGATCAA AAGCTTATTC ATCTGTTTTT CTTTTTCGTT GGTGTAAAGC    (SEQ ID No: 1388)
CAACACCCTG TCTAAAAAAC ATAAATTTCT TTAATCATTT TGCCTCTTTT
CTCTGTGCTT CAATTAATAA A
```

Human albumin 3'UTR fragment 12

(SEQ ID No: 1389)
```
CTTTTTCGTT GGTGTAAAGC CAACACCCTG TCTAAAAAAC ATAAATTTCT
TTAATCATTT TGCCTCTTTT CTCTGTGCTT CAATTAATAA A
```

Human albumin 3'UTR fragment 13

(SEQ ID No: 1390)
```
AAGCTTATTC ATCTGTTTTT CTTTTTCGTT GGTGTAAAGC CAACACCCTG
TCTAAAAAAC
```

Sequence according to formula (Ic)

(SEQ ID NO: 1391)
NGNNNNNNUNNNNNCN

Sequence according to formula (IIc):

(SEQ ID NO: 1392)
N*N*NNNNGNNNNNNUNNNNNCNNNN*N*N*

Sequence according to formula (Id):

(SEQ ID NO: 1393)
NCNNNNNNUNNNNNGN

Sequence according to formula (IId)

(SEQ ID NO: 1394)
N*N*NNNNCNNNNNNUNNNNNGNNNN*N*N*

Sequence according to formula (Ie)

(SEQ ID NO: 1395)
DGNNNNNNUNNNNNCH

Sequence according to formula (IIe)

(SEQ ID NO: 1396)
N*N*NNNDGNNNNNNUNNNNNCHNNN*N*N*

Sequence according to formula (If)

(SEQ ID NO: 1397)
NGNBYYNNUNVNDNCN

Sequence according to formula (IIf)

(SEQ ID NO: 1398)
N*N*NNNNGNBYYNNUNVNDNCNNNN*N*N*

Sequence according to formula (Ig)

(SEQ ID NO: 1399)
NGHYYYDNUHABRDCN

Sequence according to formula (IIg)

(SEQ ID NO: 1400)
N*N*HNNNGHYYYDNUHABRDCNNNN*N*H*

Sequence according to formula (Ih)

(SEQ ID NO: 1401)
DGHYCUDYUHASRRCC

Sequence according to formula (IIh)

(SEQ ID NO: 1402)
N*H*AAHDGHYCUDYUHASRRCCVHB*N*H*

Sequence according to formula (Ic)

(SEQ ID NO: 1403)
VGYYYYHHTHRVVRCB

Sequence according to formula (Ic)

(SEQ ID NO: 1404)
SGYYYTTYTMARRRCS

Sequence according to formula (Ic)

(SEQ ID NO: 1405)
SGYYCTTTTMAGRRCS

Sequence according to formula (Ie)

(SEQ ID NO: 1406)
DGNNNBNNTHVNNNCH

Sequence according to formula (Ie)

(SEQ ID NO: 1407)

-continued

RGNNNYHBTHRDNNCY

Sequence according to formula (Ie)  (SEQ ID NO: 1408)
RGNDBYHYTHRDHNCY

Sequence according to formula (If)  (SEQ ID NO: 1409)
VGYYYTYHTHRVRRCB

Sequence according to formula (If)  (SEQ ID NO: 1410)
SGYYCTTYTMAGRRCS

Sequence according to formula (If)  (SEQ ID NO: 1411)
SGYYCTTTTMAGRRCS

Sequence according to formula (Ig)  (SEQ ID NO: 1412)
GGYYCTTYTHAGRRCC

Sequence according to formula (Ig)  (SEQ ID NO: 1413)
GGCYCTTYTMAGRGCC

Sequence according to formula (Ig)  (SEQ ID NO: 1414)
GGCTCTTTTMAGRGCC

Sequence according to formula (Ih)  (SEQ ID NO: 1415)
DGHYCTDYTHASRRCC

Sequence according to formula (Ih)  (SEQ ID NO: 1416)
GGCYCTTTTHAGRGCC

Sequence according to formula (Ih)  (SEQ ID NO: 1417)
GGCYCTTTTMAGRGCC

Sequence according to formula (IIc)  (SEQ ID NO: 1418)
H*H*HHVVGYYYYHHTHRVVRCBVHH*N*N*

Sequence according to formula (IIc)  (SEQ ID NO: 1419)
M*H*MHMSGYYYTTYTMARRRCSMCH*H*H*

Sequence according to formula (IIc)  (SEQ ID NO: 1420)
M*M*MMMSGYYCTTTTMAGRRCSACH*M*H*

Sequence according to formula (IIe)  (SEQ ID NO: 1421)
N*N*NNNDGNNNBNNTHVNNNCHNHN*N*N*

Sequence according to formula (IIe)  (SEQ ID NO: 1422)
N*N*HHNRGNNNYHBTHRDNNCYDHH*N*N*

Sequence according to formula (IIe)  (SEQ ID NO: 1423)
N*H*HHVRGNDBYHYTHRDHNCYRHH*H*H*

Sequence according to formula (IIf)  (SEQ ID NO: 1424)
H*H*MHMVGYYYTYHTHRVRRCBVMH*H*N*

Sequence according to formula (IIf)  (SEQ ID NO: 1425)
M*M*MMMSGYYCTTYTMAGRRCSMCH*H*H*

Sequence according to formula (IIf)  (SEQ ID NO: 1426)
M*M*MMMSGYYCTTTTMAGRRCSACH*M*H*

Sequence according to formula (IIg)  (SEQ ID NO: 1427)
H*H*MAMGGYYCTTYTHAGRRCCVHN*N*M*

-continued

Sequence according to formula (IIg)

(SEQ ID NO: 1428)

H*H*AAMGGCYCTTYTMAGRGCCVCH*H*M*

Sequence according to formula (IIg)

(SEQ ID NO: 1429)

M*M*AAMGGCTCTTTTMAGRGCCMCY*M*M*

Sequence according to formula (IIh)

(SEQ ID NO: 1430)

N*H*AAHDGHYCTDYTHASRRCCVHB*N*H*

Sequence according to formula (IIh)

(SEQ ID NO: 1431)

H*H*AAMGGCYCTTTTHAGRGCCVMY*N*M*

Sequence according to formula (IIh)

(SEQ ID NO: 1432)

H*M*AAAGGCYCTTTTMAGRGCCRMY*H*M*

Specific histone stem-loop sequence (SEQ ID NO: 1433)

CAAAGGCTCTTTTCAGAGCCACCA

Center, α-complex-binding portion of the 3'UTR of an α-globin gene (SEQ ID NO: 1434)

GCCCGATGGGCCTCCCAACGGGCCCTCCTCCCCTCCTTGCACCG

ATP synthase lipid-binding protein, mitochondrial (atp5g2)

(SEQ ID NO: 1435)

tagttt ctcctctcga acgccaggtg gagcaaccgg ccggataccg ccacagccct ggcaggcggc gctgtgatg RPL35-PpLuc(GC)-albumin7-A64-C30-histoneSL (SEQ ID NO: 1436)

GGGGAGCGGGCGGCGGCGTTGGCGGCTTGTGCAGCAAAGCTTGAGGATGGAGGACGCCAA
GAACATCAAGAAGGGCCCGGCGCCCTTCTACCCGCTGGAGGACGGGACCGCCGGCGAGCA
GCTCCACAAGGCCATGAAGCGGTACGCCCTGGTGCCGGGCACGATCGCCTTCACCGACGC
CCACATCGAGGTCGACATCACCTACGCGGAGTACTTCGAGATGAGCGTGCGCCTGGCCGA
GGCCATGAAGCGGTACGGCCTGAACACCAACCACCGGATCGTGGTGTGCTCGGAGAACAG
CCTGCAGTTCTTCATGCCGGTGCTGGGCGCCCTCTTCATCGGCGTGGCCGTCGCCCCGGC
GAACGACATCTACAACGAGCGGGAGCTGCTGAACAGCATGGGGATCAGCCAGCCGACCGT
GGTGTTCGTGAGCAAGAAGGGCCTGCAGAAGATCCTGAACGTGCAGAAGAAGCTGCCCAT
CATCCAGAAGATCATCATCATGGACAGCAAGACCGACTACCAGGGCTTCCAGTCGATGTA
CACGTTCGTGACCAGCCACCTCCCGCCGGGCTTCAACGAGTACGACTTCGTCCCGGAGAG
CTTCGACCGGGACAAGACCATCGCCCTGATCATGAACAGCAGCGGCAGCACCGGCCTGCC
GAAGGGGGTGGCCCTGCCGCACCGGACCGCCTGCGTGCGCTTCTCGCACGCCCGGGACCC
CATCTTCGGCAACCAGATCATCCCGGACACCGCCATCCTGAGCGTGGTGCCGTTCCACCA
CGGCTTCGGCATGTTCACGACCCTGGGCTACCTCATCTGCGGCTTCCGGGTGGTCCTGAT
GTACCGGTTCGAGGAGGAGCTGTTCCTGCGGAGCCTGCAGGACTACAAGATCCAGAGCGC
GCTGCTCGTGCCGACCCTGTTCAGCTTCTTCGCCAAGAGCACCCTGATCGACAAGTACGA
CCTGTCGAACCTGCACGAGATCGCCAGCGGGGGCGCCCCGCTGAGCAAGGAGGTGGGCGA
GGCCGTGGCCAAGCGGTTCCACCTCCCGGGCATCCGCCAGGGCTACGGCCTGACCGAGAC
CACGAGCGCGATCCTGATCACCCCCGAGGGGGACGACAAGCCGGGCGCCGTGGGCAAGGT
GGTCCCGTTCTTCGAGGCCAAGGTGGTGGACCTGGACACCGGCAAGACCCTGGGCGTGAA
CCAGCGGGGCGAGCTGTGCGTGCGGGGGCCGATGATCATGAGCGGCTACGTGAACAACCC
GGAGGCCACCAACGCCCTCATCGACAAGGACGGCTGGCTGCACAGCGGCGACATCGCCTA
CTGGGACGAGGACGAGCACTTCTTCATCGTCGACCGGCTGAAGTCGCTGATCAAGTACAA
GGGCTACCAGGTGGCGCCGGCCGAGCTGGAGAGCATCCTGCTCCAGCACCCCAACATCTT
CGACGCCGGCGTGGCCGGGCTGCCGGACGACGACGCCGGCGAGCTGCCGGCCGCGGTGGT
GGTGCTGGAGCACGGCAAGACCATGACGGAGAAGGAGATCGTCGACTACGTGGCCAGCCA
GGTGACCACCGCCAAGAAGCTGCGGGGCGGCGTGGTGTTCGTGGACGAGGTCCCGAAGGG
CCTGACCGGGAAGCTCGACGCCCGGAAGATCCGCGAGATCCTGATCAAGGCCAAGAAGGG
CGGCAAGATCGCCGTGTAAGACTAGTGCATCACATTTAAAAGCATCTCAGCCTACCATGA
GAATAAGAGAAAGAAAATGAAGATCAATAGCTTATTCATCTCTTTTTCTTTTCGTTGGT
GTAAAGCCAACACCCTGTCTAAAAAACATAAATTTCTTTAATCATTTTGCCTCTTTTCTC
TGTGCTTCAATTAATAAAAAATGGAAAGAACCTAGATCTAAAAAAAAAAAAAAAAAAAAA
AAAAAAAAAAAAAAAAAAAAAAAAAAAAAAAAAAAATGCATCCCCCCCCCCCC
CCCCCCCCCCCCCCCCCAAAGGCTCTTTTCAGAGCCACCAGAATT

RPL21-PpLuc(GC)-albumin7-A64-C30-histoneSL (SEQ ID NO: 1437)

GGGGCCGGAACCGCCATCTTCCAGTAATTCGCCAAAAAGCTTGAGGATGGAGGACGCCAA
GAACATCAAGAAGGGCCCGGCGCCCTTCTACCCGCTGGAGGACGGGACCGCCGGCGAGCA
GCTCCACAAGGCCATGAAGCGGTACGCCCTGGTGCCGGGCACGATCGCCTTCACCGACGC
CCACATCGAGGTCGACATCACCTACGCGGAGTACTTCGAGATGAGCGTGCGCCTGGCCGA
GGCCATGAAGCGGTACGGCCTGAACACCAACCACCGGATCGTGGTGTGCTCGGAGAACAG
CCTGCAGTTCTTCATGCCGGTGCTGGGCGCCCTCTTCATCGGCGTGGCCGTCGCCCCGGC
GAACGACATCTACAACGAGCGGGAGCTGCTGAACAGCATGGGGATCAGCCAGCCGACCGT

-continued

```
GGTGTTCGTGAGCAAGAAGGGCCTGCAGAAGATCCTGAACGTGCAGAAGAAGCTGCCCAT
CATCCAGAAGATCATCATCATGGACAGCAAGACCGACTACCAGGGCTTCCAGTCGATGTA
CACGTTCGTGACCAGCCACCTCCCGCCGGGCTTCAACGAGTACGACTTCGTCCCGGAGAG
CTTCGACCGGGACAAGACCATCGCCCTGATCATGAACAGCAGCGGCAGCACCGGCCTGCC
GAAGGGGGTGGCCCTGCCGCACCGGACCGCCTGCGTGCGCTTCTCGCACGCCCGGGACCC
CATCTTCGGCAACCAGATCATCCCGGACACCGCCATCCTGAGCGTGGTGCCGTTCCACCA
CGGCTTCGGCATGTTCACGACCCTGGGCTACCTCATCTGCGGCTTCCGGGTGGTCCTGAT
GTACCGGTTCGAGGAGGAGCTGTTCCTGCGGAGCCTGCAGGACTACAAGATCCAGAGCGC
GCTGCTCGTGCCGACCCTGTTCAGCTTCTTCGCCAAGAGCACCCTGATCGACAAGTACGA
CCTGTCGAACCTGCACGAGATCGCCAGCGGGGCGCCCCGCTGAGCAAGGAGGTGGGCGA
GGCCGTGGCCAAGCGGTTCCACCTCCCGGGCATCCGCCAGGGCTACGGCCTGACCGAGAC
CACGAGCGCGATCCTGATCACCCCCGAGGGGGACGACAAGCCGGGCGCCGTGGGCAAGGT
GGTCCCGTTCTTCGAGGCCAAGGTGGTGGACCTGGACACCGGCAAGACCCTGGGCGTGAA
CCAGCGGGGCGAGCTGTGCGTGCGGGGGCCGATGATCATGAGCGGCTACGTGAACAACCC
GGAGGCCACCAACGCCCTCATCGACAAGGACGGCTGGCTGCACAGCGGCGACATCGCCTA
CTGGGACGAGGACGAGCACTTCTTCATCGTCGACCGGCTGAAGTCGCTGATCAAGTACAA
GGGCTACCAGGTGGCGCCGGCCGAGCTGGAGAGCATCCTGCTCCAGCACCCCAACATCTT
CGACGCCGGCGTGGCCGGGCTGCCGGACGACGACGCCGGCGAGCTGCCGGCCGCGGTGGT
GGTGCTGGAGCACGGCAAGACCATGACGGAGAAGGAGATCGTCGACTACGTGGCCAGCCA
GGTGACCACCGCCAAGAAGCTGCGGGGCGGCGTGGTGTTCGTGGACGAGGTCCCGAAGGG
CCTGACCGGGAAGCTCGACGCCCGGAAGATCCGCGAGATCCTGATCAAGGCCAAGAAGGG
CGGCAAGATCGCCGTGTAAGACTAGTGCATCACATTTAAAAGCATCTCAGCCTACCATGA
GAATAAGAGAAAGAAAATGAAGATCAATAGCTTATTCATCTCTTTTTCTTTTTCGTTGGT
GTAAAGCCAACACCCTGTCTAAAAAACATAAATTTCTTTAATCATTTTGCCTCTTTTCTC
TGTGCTTCAATTAATAAAAAATGGAAAGAACCTAGATCTAAAAAAAAAAAAAAAAAAAA
AAAAAAAAAAAAAAAAAAAAAAAAAAAAAAAAAATGCATCCCCCCCCCCCCCC
CCCCCCCCCCCCCCCCCCCAAAGGCTCTTTTCAGAGCCACCAGAATT
```

ATP5A1-PpLuc(GC)-albumin7-A64-C30-histoneSL (SEQ ID NO: 1438)

```
GGGCGGCTCGGCCATTTTGTCCCAGTCAGTCCGGAGGCTGCGGCTGCAGAAGTACCGCCT
GCGGAGTAACTGCAAAGAAGCTTGAGGATGGAGGACGCCAAGAACATCAAGAAGGGCCCG
GCGCCCTTCTACCCGCTGGAGGACGGGACCGCCGGCGAGCAGCTCCACAAGGCCATGAAG
CGGTACGCCCTGGTGCCGGGCACGATCGCCTTCACCGACGCCCACATCGAGGTCGACATC
ACCTACGCGGAGTACTTCGAGATGAGCGTGCGCCTGGCCGAGGCCATGAAGCGGTACGGC
CTGAACACCAACCACCGGATCGTGGTGTGCTCGGAGAACAGCCTGCAGTTCTTCATGCCG
GTGCTGGGCGCCCTCTTCATCGGCGTGGCCGTCGCCCCGGCGAACGACATCTACAACGAG
CGGGAGCTGCTGAACAGCATGGGGATCAGCCAGCCGACCGTGGTGTTCGTGAGCAAGAAG
GGCCTGCAGAAGATCCTGAACGTGCAGAAGAAGCTGCCCATCATCCAGAAGATCATCATC
ATGGACAGCAAGACCGACTACCAGGGCTTCCAGTCGATGTACACGTTCGTGACCAGCCAC
CTCCCGCCGGGCTTCAACGAGTACGACTTCGTCCCGGAGAGCTTCGACCGGGACAAGACC
ATCGCCCTGATCATGAACAGCAGCGGCAGCACCGGCCTGCCGAAGGGGGTGGCCCTGCCG
CACCGGACCGCCTGCGTGCGCTTCTCGCACGCCCGGGACCCCATCTTCGGCAACCAGATC
ATCCCGGACACCGCCATCCTGAGCGTGGTGCCGTTCCACCACGGCTTCGGCATGTTCACG
ACCCTGGGCTACCTCATCTGCGGCTTCCGGGTGGTCCTGATGTACCGGTTCGAGGAGGAG
CTGTTCCTGCGGAGCCTGCAGGACTACAAGATCCAGAGCGCGCTGCTCGTGCCGACCCTG
TTCAGCTTCTTCGCCAAGAGCACCCTGATCGACAAGTACGACCTGTCGAACCTGCACGAG
ATCGCCAGCGGGGCGCCCCGCTGAGCAAGGAGGTGGGCGAGGCCGTGGCCAAGCGGTTC
CACCTCCCGGGCATCCGCCAGGGCTACGGCCTGACCGAGACCACGAGCGCGATCCTGATC
ACCCCCGAGGGGGACGACAAGCCGGGCGCCGTGGGCAAGGTGGTCCCGTTCTTCGAGGCC
AAGGTGGTGGACCTGGACACCGGCAAGACCCTGGGCGTGAACCAGCGGGGCGAGCTGTGC
GTGCGGGGGCCGATGATCATGAGCGGCTACGTGAACAACCCGGAGGCCACCAACGCCCTC
ATCGACAAGGACGGCTGGCTGCACAGCGGCGACATCGCCTACTGGGACGAGGACGAGCAC
TTCTTCATCGTCGACCGGCTGAAGTCGCTGATCAAGTACAAGGGCTACCAGGTGGCGCCG
GCCGAGCTGGAGAGCATCCTGCTCCAGCACCCCAACATCTTCGACGCCGGCGTGGCCGGG
CTGCCGGACGACGACGCCGGCGAGCTGCCGGCCGCGGTGGTGGTGCTGGAGCACGGCAAG
ACCATGACGGAGAAGGAGATCGTCGACTACGTGGCCAGCCAGGTGACCACCGCCAAGAAG
CTGCGGGGCGGCGTGGTGTTCGTGGACGAGGTCCCGAAGGGCCTGACCGGGAAGCTCGAC
GCCCGGAAGATCCGCGAGATCCTGATCAAGGCCAAGAAGGGCGGCAAGATCGCCGTGTAA
GACTAGTGCATCACATTTAAAAGCATCTCAGCCTACCATGAGAATAAGAGAAAGAAAATG
AAGATCAATAGCTTATTCATCTCTTTTTCTTTTTCGTTGGTGTAAAGCCAACACCCTGTC
TAAAAAACATAAATTTCTTTAATCATTTTGCCTCTTTTCTCTGTGCTTCAATTAATAAAA
AATGGAAAGAACCTAGATCTAAAAAAAAAAAAAAAAAAAAAAAAAAAAAAAAAAAAAA
AAAAAAAAAAAAAAAAAAAAATGCATCCCCCCCCCCCCCCCCCCCCCCCCCCCCC
AAAGGCTCTTTTCAGAGCCACCAGAATT
```

HSD17B4-PpLuc(GC)-albumin7-A64-C30-histoneSL (SEQ ID NO: 1439)

```
GGGTCCCGCAGTCGGCGTCCAGCGGCTCTGCTTGTTCGTGTGTGTGTCGTTGCAGGCCTT
ATTCAAGCTTGAGGATGGAGGACGCCAAGAACATCAAGAAGGGCCCGGCGCCCTTCTACC
CGCTGGAGGACGGGACCGCCGGCGAGCAGCTCCACAAGGCCATGAAGCGGTACGCCCTGG
TGCCGGGCACGATCGCCTTCACCGACGCCCACATCGAGGTCGACATCACCTACGCGGAGT
ACTTCGAGATGAGCGTGCGCCTGGCCGAGGCCATGAAGCGGTACGGCCTGAACACCAACC
ACCGGATCGTGGTGTGCTCGGAGAACAGCCTGCAGTTCTTCATGCCGGTGCTGGGCGCCC
TCTTCATCGGCGTGGCCGTCGCCCCGGCGAACGACATCTACAACGAGCGGGAGCTGCTGA
ACAGCATGGGGATCAGCCAGCCGACCGTGGTGTTCGTGAGCAAGAAGGGCCTGCAGAAGA
TCCTGAACGTGCAGAAGAAGCTGCCCATCATCCAGAAGATCATCATCATGGACAGCAAGA
CCGACTACCAGGGCTTCCAGTCGATGTACACGTTCGTGACCAGCCACCTCCCGCCGGGCT
TCAACGAGTACGACTTCGTCCCGGAGAGCTTCGACCGGGACAAGACCATCGCCCTGATCA
TGAACAGCAGCGGCAGCACCGGCCTGCCGAAGGGGGTGGCCCTGCCGCACCGGACCGCCT
GCGTGCGCTTCTCGCACGCCCGGGACCCCATCTTCGGCAACCAGATCATCCCGGACACCG
```

-continued

```
CCATCCTGAGCGTGGTGCCGTTCCACCACGGCTTCGGCATGTTCACGACCCTGGGCTACC
TCATCTGCGGCTTCCGGGTGGTCCTGATGTACCGGTTCGAGGAGGAGCTGTTCCTGCGGA
GCCTGCAGGACTACAAGATCCAGAGCGCGCTGCTCGTGCCGACCCTGTTCAGCTTCTTCG
CCAAGAGCACCCTGATCGACAAGTACGACCTGTCGAACCTGCACGAGATCGCCAGCGGGG
GCGCCCCGCTGAGCAAGGAGGTGGGCGAGGCCGTGGCCAAGCGGTTCCACCTCCCGGGCA
TCCGCCAGGGCTACGGCCTGACCGAGACCACGAGCGCGATCCTGATCACCCCCGAGGGGG
ACGACAAGCCGGGCGCCGTGGGCAAGGTGGTCCCGTTCTTCGAGGCCAAGGTGGTGGACC
TGGACACCGGCAAGACCCTGGGCGTGAACCAGCGGGGCGAGCTGTGCGTGCGGGGGCCGA
TGATCATGAGCGGCTACGTGAACAACCCGGAGGCCACCAACGCCCTCATCGACAAGGACG
GCTGGCTGCACAGCGGCGACATCGCCTACTGGGACGAGGACGAGCACTTCTTCATCGTCG
ACCGGCTGAAGTCGCTGATCAAGTACAAGGGCTACCAGGTGGCGCCCGGCCGAGCTGGAGA
GCATCCTGCTCCAGCACCCCAACATCTTCGACGCCGGCGTGGCCGGGCTGCCGGACGACG
ACGCCGGCGAGCTGCCGGCCGCGGTGGTGGTGCTGGAGCACGGCAAGACCATGACGGAGA
AGGAGATCGTCGACTACGTGGCCAGCCAGGTGACCACCGCCAAGAAGCTGCGGGGCGGCG
TGGTGTTCGTGGACGAGGTCCCGAAGGGCCTGACCGGGAAGCTCGACGCCCGGAAGATCC
GCGAGATCCTGATCAAGGCCAAGAAGGGCGGCAAGATCGCCGTGTAAGACTAGTGCATCA
CATTTAAAAGCATCTCAGCCTACCATGAGAATAAGAGAAAGAAAATGAAGATCAATAGCT
TATTCATCTCTTTTTCTTTTTCGTTGGTGTAAAGCCAACACCCTGTCTAAAAAACATAAA
TTTCTTTAATCATTTTGCCTCTTTTCTCTGTGCTTCAATTAATAAAAAATGGAAAGAACC
TAGATCTAAAAAAAAAAAAAAAAAAAAAAAAAAAAAAAAAAAAAAAAAAAAAAAAAAAAA
AAAAAAAAAATGCATCCCCCCCCCCCCCCCCCCCCCCCCCCCCCCAAAGGCTCTTTTC
AGAGCCACCAGAATT
```

AIG1-PpLuc(GC)-albumin7-A64-C30-histoneSL (SEQ ID NO: 1440)

```
GGGCCGCCCAGCCGGTCCAGGCCTCTGGCGAACAAGCTTGAGGATGGAGGACGCCAAGAA
CATCAAGAAGGGCCCGGCGCCCTTCTACCCGCTGGAGGACGGGACCGCCGGCGAGCAGCT
CCACAAGGCCATGAAGCGGTACGCCCTGGTGCCGGGCACGATCGCCTTCACCGACGCCCA
CATCGAGGTCGACATCACCTACGCGGAGTACTTCGAGATGAGCGTGCGCCTGGCCGAGGC
CATGAAGCGGTACGGCCTGAACACCAACCACCGGATCGTGGTGTGCTCGGAGAACAGCCT
GCAGTTCTTCATGCCGGTGCTGGGCGCCCTCTTCATCGGCGTGGCCGTCGCCCCGGCGAA
CGACATCTACAACGAGCGGGAGCTGCTGAACAGCATGGGGATCAGCCAGCCGACCGTGGT
GTTCGTGAGCAAGAAGGGCCTGCAGAAGATCCTGAACGTGCAGAAGAAGCTGCCCATCAT
CCAGAAGATCATCATCATGGACAGCAAGACCGACTACCAGGGCTTCCAGTCGATGTACAC
GTTCGTGACCAGCCACCTCCCGCCGGGCTTCAACGAGTACGACTTCGTCCCGGAGAGCTT
CGACCGGGACAAGACCATCGCCCTGATCATGAACAGCAGCGGCAGCACCGGCCTGCCGAA
GGGGGTGGCCCTGCCGCACCGGACCGCCTGCGTGCGCTTCTCGCACGCCCGGGACCCCAT
CTTCGGCAACCAGATCATCCCGGACACCGCCATCCTGAGCGTGGTGCCGTTCCACCACGG
CTTCGGCATGTTCACGACCCTGGGCTACCTCATCTGCGGCTTCCGGGTGGTCCTGATGTA
CCGGTTCGAGGAGGAGCTGTTCCTGCGGAGCCTGCAGGACTACAAGATCCAGAGCGCGCT
GCTCGTGCCGACCCTGTTCAGCTTCTTCGCCAAGAGCACCCTGATCGACAAGTACGACCT
GTCGAACCTGCACGAGATCGCCAGCGGGGGCGCCCCGCTGAGCAAGGAGGTGGGCGAGGC
CGTGGCCAAGCGGTTCCACCTCCCGGGCATCCGCCAGGGCTACGGCCTGACCGAGACCAC
GAGCGCGATCCTGATCACCCCCGAGGGGGACGACAAGCCGGGCGCCGTGGGCAAGGTGGT
CCCGTTCTTCGAGGCCAAGGTGGTGGACCTGGACACCGGCAAGACCCTGGGCGTGAACCA
GCGGGGCGAGCTGTGCGTGCGGGGGCCGATGATCATGAGCGGCTACGTGAACAACCCGGA
GGCCACCAACGCCCTCATCGACAAGGACGGCTGGCTGCACAGCGGCGACATCGCCTACTG
GGACGAGGACGAGCACTTCTTCATCGTCGACCGGCTGAAGTCGCTGATCAAGTACAAGGG
CTACCAGGTGGCGCCGGCCGAGCTGGAGAGCATCCTGCTCCAGCACCCCAACATCTTCGA
CGCCGGCGTGGCCGGGCTGCCGGACGACGACGCCGGCGAGCTGCCGGCCGCGGTGGTGGT
GCTGGAGCACGGCAAGACCATGACGGAGAAGGAGATCGTCGACTACGTGGCCAGCCAGGT
GACCACCGCCAAGAAGCTGCGGGGCGGCGTGGTGTTCGTGGACGAGGTCCCGAAGGGCCT
GACCGGGAAGCTCGACGCCCGGAAGATCCGCGAGATCCTGATCAAGGCCAAGAAGGGCGG
CAAGATCGCCGTGTAAGACTAGTGCATCACATTTAAAAGCATCTCAGCCTACCATGAGAA
TAAGAGAAAGAAAATGAAGATCAATAGCTTATTCATCTCTTTTTCTTTTTCGTTGGTGTA
AAGCCAACACCCTGTCTAAAAAACATAAATTTCTTTAATCATTTTGCCTCTTTTCTCTGT
GCTTCAATTAATAAAAAATGGAAAGAACCTAGATCTAAAAAAAAAAAAAAAAAAAAAAAA
AAAAAAAAAAAAAAAAAAAAAAAAAAAAAAAAAAATGCATCCCCCCCCCCCCCCC
CCCCCCCCCCCCCCCAAAGGCTCTTTTCAGAGCCACCAGAATT
```

COX6C-PpLuc(GC)-albumin7-A64-C30-histoneSL (SEQ ID NO: 1441)

```
GGAGTCAGGAAGGACGTTGGTGTTGAGGTTAGCATACGTATCAAGGACAGTAACTACCAA
GCTTGAGGATGGAGGACGCCAAGAACATCAAGAAGGGCCCGGCGCCCTTCTACCCGCTGG
AGGACGGGACCGCCGGCGAGCAGCTCCACAAGGCCATGAAGCGGTACGCCCTGGTGCCGG
GCACGATCGCCTTCACCGACGCCCACATCGAGGTCGACATCACCTACGCGGAGTACTTCG
AGATGAGCGTGCGCCTGGCCGAGGCCATGAAGCGGTACGGCCTGAACACCAACCACCGGA
TCGTGGTGTGCTCGGAGAACAGCCTGCAGTTCTTCATGCCGGTGCTGGGCGCCCTCTTCA
TCGGCGTGGCCGTCGCCCCGGCGAACGACATCTACAACGAGCGGGAGCTGCTGAACAGCA
TGGGGATCAGCCAGCCGACCGTGGTGTTCGTGAGCAAGAAGGGCCTGCAGAAGATCCTGA
ACGTGCAGAAGAAGCTGCCCATCATCCAGAAGATCATCATCATGGACAGCAAGACCGACT
ACCAGGGCTTCCAGTCGATGTACACGTTCGTGACCAGCCACCTCCCGCCGGGCTTCAACG
AGTACGACTTCGTCCCGGAGAGCTTCGACCGGGACAAGACCATCGCCCTGATCATGAACA
GCAGCGGCAGCACCGGCCTGCCGAAGGGGGTGGCCCTGCCGCACCGGACCGCCTGCGTGC
GCTTCTCGCACGCCCGGGACCCCATCTTCGGCAACCAGATCATCCCGGACACCGCCATCC
TGAGCGTGGTGCCGTTCCACCACGGCTTCGGCATGTTCACGACCCTGGGCTACCTCATCT
GCGGCTTCCGGGTGGTCCTGATGTACCGGTTCGAGGAGGAGCTGTTCCTGCGGAGCCTGC
AGGACTACAAGATCCAGAGCGCGCTGCTCGTGCCGACCCTGTTCAGCTTCTTCGCCAAGA
GCACCCTGATCGACAAGTACGACCTGTCGAACCTGCACGAGATCGCCAGCGGGGGCGCCC
CGCTGAGCAAGGAGGTGGGCGAGGCCGTGGCCAAGCGGTTCCACCTCCCGGGCATCCGCC
AGGGCTACGGCCTGACCGAGACCACGAGCGCGATCCTGATCACCCCCGAGGGGGACGACA
```

-continued

```
AGCCGGGCGCCGTGGGCAAGGTGGTCCCGTTCTTCGAGGCCAAGGTGGTGGACCTGGACA
CCGGCAAGACCCTGGGCGTGAACCAGCGGGGCGAGCTGTGCGTGCGGGGGCCGATGATCA
TGAGCGGCTACGTGAACAACCCGGAGGCCACCAACGCCCTCATCGACAAGGACGGCTGGC
TGCACAGCGGCGACATCGCCTACTGGGACGAGGACGAGCACTTCTTCATCGTCGACCGGC
TGAAGTCGCTGATCAAGTACAAGGGCTACCAGGTGGCGCCGGCCGAGCTGGAGAGCATCC
TGCTCCAGCACCCCAACATCTTCGACGCCGGCGTGGCCGGGCTGCCGGACGACGACGCCG
GCGAGCTGCCGGCCGCGGTGGTGGTGCTGGAGCACGGCAAGACCATGACGGAGAAGGAGA
TCGTCGACTACGTGGCCAGCCAGGTGACCACCGCCAAGAAGCTGCGGGGCGGCGTGGTGT
TCGTGGACGAGGTCCCGAAGGGCCTGACCGGGAAGCTCGACGCCCGGAAGATCCGCGAGA
TCCTGATCAAGGCCAAGAAGGGCGGCAAGATCGCCGTGTAAGACTAGTGCATCACATTTA
AAAGCATCTCAGCCTACCATGAGAATAAGAGAAAGAAAATGAAGATCAATAGCTTATTCA
TCTCTTTTTCTTTTCGTTGGTGTAAAGCCAACACCCTGTCTAAAAAACATAAATTTCTT
TAATCATTTTGCCTCTTTTCTCTGTGCTTCAATTAATAAAAAATGGAAAGAACCTAGATC
TAAAAAAAAAAAAAAAAAAAAAAAAAAAAAAAAAAAAAAAAAAAAAAAAAAAAAAAAAA
AAAAATGCATCCCCCCCCCCCCCCCCCCCCCCCCCCCCCCCAAAGGCTCTTTTCAGAGCC
ACCAGAATT
```

ASAH1-PpLuc(GC)-albumin7-A64-C30-histoneSL (SEQ ID NO: 1442)

```
GGGCCTCTGCTGGAGTCCGGGGAGTGGCGTTGGCTGCTAGAGCGAAGCTTGAGGATGGAG
GACGCCAAGAACATCAAGAAGGGCCCGGCGCCCTTCTACCCGCTGGAGGACGGGACCGCC
GGCGAGCAGCTCCACAAGGCCATGAAGCGGTACGCCCTGGTGCCGGGCACGATCGCCTTC
ACCGACGCCCACATCGAGGTCGACATCACCTACGCGGAGTACTTCGAGATGAGCGTGCGC
CTGGCCGAGGCCATGAAGCGGTACGGCCTGAACACCAACCACCGGATCGTGGTGTGCTCG
GAGAACAGCCTGCAGTTCTTCATGCCGGTGCTGGGCGCCCTCTTCATCGGCGTGGCCGTC
GCCCCGGCGAACGACATCTACAACGAGCGGGAGCTGCTGAACAGCATGGGGATCAGCCAG
CCGACCGTGGTGTTCGTGAGCAAGAAGGGCCTGCAGAAGATCCTGAACGTGCAGAAGAAG
CTGCCCATCATCCAGAAGATCATCATCATGGACAGCAAGACCGACTACCAGGGCTTCCAG
TCGATGTACACGTTCGTGACCAGCCACCTCCCGCCGGGCTTCAACGAGTACGACTTCGTC
CCGGAGAGCTTCGACCGGGACAAGACCATCGCCCTGATCATGAACAGCAGCGGCAGCACC
GGCCTGCCGAAGGGGGTGGCCCTGCCGCACCGGACCGCCTGCGTGCGCTTCTCGCACGCC
CGGGACCCCATCTTCGGCAACCAGATCATCCCGGACACCGCCATCCTGAGCGTGGTGCCG
TTCCACCACGGCTTCGGCATGTTCACGACCCTGGGCTACCTCATCTGCGGCTTCCGGGTG
GTCCTGATGTACCGGTTCGAGGAGGAGCTGTTCCTGCGGAGCCTGCAGGACTACAAGATC
CAGAGCGCGCTGCTCGTGCCGACCCTGTTCAGCTTCTTCGCCAAGAGCACCCTGATCGAC
AAGTACGACCTGTCGAACCTGCACGAGATCGCCAGCGGGGCGCCCCGCTGAGCAAGGAG
GTGGGCGAGGCCGTGGCCAAGCGGTTCCACCTCCCGGGCATCCGCCAGGGCTACGGCCTG
ACCGAGACCACGAGCGCGATCCTGATCACCCCCGAGGGGGACGACAAGCCGGGCGCCGTG
GGCAAGGTGGTCCCGTTCTTCGAGGCCAAGGTGGTGGACCTGGACACCGGCAAGACCCTG
GGCGTGAACCAGCGGGGCGAGCTGTGCGTGCGGGGGCCGATGATCATGAGCGGCTACGTG
AACAACCCGGAGGCCACCAACGCCCTCATCGACAAGGACGGCTGGCTGCACAGCGGCGAC
ATCGCCTACTGGGACGAGGACGAGCACTTCTTCATCGTCGACCGGCTGAAGTCGCTGATC
AAGTACAAGGGCTACCAGGTGGCGCCGGCCGAGCTGGAGAGCATCCTGCTCCAGCACCCC
AACATCTTCGACGCCGGCGTGGCCGGGCTGCCGGACGACGACGCCGGCGAGCTGCCGGCC
GCGGTGGTGGTGCTGGAGCACGGCAAGACCATGACGGAGAAGGAGATCGTCGACTACGTG
GCCAGCCAGGTGACCACCGCCAAGAAGCTGCGGGGCGGCGTGGTGTTCGTGGACGAGGTC
CCGAAGGGCCTGACCGGGAAGCTCGACGCCCGGAAGATCCGCGAGATCCTGATCAAGGCC
AAGAAGGGCGGCAAGATCGCCGTGTAAGACTAGTGCATCACATTTAAAAGCATCTCAGCC
TACCATGAGAATAAGAGAAAGAAAATGAAGATCAATAGCTTATTCATCTCTTTTTCTTTT
TCGTTGGTGTAAAGCCAACACCCTGTCTAAAAAACATAAATTTCTTTAATCATTTTGCCT
CTTTTCTCTGTGCTTCAATTAATAAAAAATGGAAAGAACCTAGATCTAAAAAAAAAAAAA
AAAAAAAAAAAAAAAAAAAAAAAAAAAAAAAAAAAAAAAAAAAAAAAAATGCATCCCC
CCCCCCCCCCCCCCCCCCCCCCCCCAAAGGCTCTTTTCAGAGCCACCAGAATT
``` mRPL21-PpLuc(GC)-albumin7-A64-C30-histoneSL (SEQ ID NO: 1443)

```
GGGGCCGCCGCAGCCATCTTCCAGTAACTCGCCAAAAAGCTTGAGGATGGAGGACGCCAA
GAACATCAAGAAGGGCCCGGCGCCCTTCTACCCGCTGGAGGACGGGACCGCCGGCGAGCA
GCTCCACAAGGCCATGAAGCGGTACGCCCTGGTGCCGGGCACGATCGCCTTCACCGACGC
CCACATCGAGGTCGACATCACCTACGCGGAGTACTTCGAGATGAGCGTGCGCCTGGCCGA
GGCCATGAAGCGGTACGGCCTGAACACCAACCACCGGATCGTGGTGTGCTCGGAGAACAG
CCTGCAGTTCTTCATGCCGGTGCTGGGCGCCCTCTTCATCGGCGTGGCCGTCGCCCCGGC
GAACGACATCTACAACGAGCGGGAGCTGCTGAACAGCATGGGGATCAGCCAGCCGACCGT
GGTGTTCGTGAGCAAGAAGGGCCTGCAGAAGATCCTGAACGTGCAGAAGAAGCTGCCCAT
CATCCAGAAGATCATCATCATGGACAGCAAGACCGACTACCAGGGCTTCCAGTCGATGTA
CACGTTCGTGACCAGCCACCTCCCGCCGGGCTTCAACGAGTACGACTTCGTCCCGGAGAG
CTTCGACCGGGACAAGACCATCGCCCTGATCATGAACAGCAGCGGCAGCACCGGCCTGCC
GAAGGGGGTGGCCCTGCCGCACCGGACCGCCTGCGTGCGCTTCTCGCACGCCCGGGACCC
CATCTTCGGCAACCAGATCATCCCGGACACCGCCATCCTGAGCGTGGTGCCGTTCCACCA
CGGCTTCGGCATGTTCACGACCCTGGGCTACCTCATCTGCGGCTTCCGGGTGGTCCTGAT
GTACCGGTTCGAGGAGGAGCTGTTCCTGCGGAGCCTGCAGGACTACAAGATCCAGAGCGC
GCTGCTCGTGCCGACCCTGTTCAGCTTCTTCGCCAAGAGCACCCTGATCGACAAGTACGA
CCTGTCGAACCTGCACGAGATCGCCAGCGGGGCGCCCCGCTGAGCAAGGAGGTGGGCGA
GGCCGTGGCCAAGCGGTTCCACCTCCCGGGCATCCGCCAGGGCTACGGCCTGACCGAGAC
CACGAGCGCGATCCTGATCACCCCCGAGGGGGACGACAAGCCGGGCGCCGTGGGCAAGGT
GGTCCCGTTCTTCGAGGCCAAGGTGGTGGACCTGGACACCGGCAAGACCCTGGGCGTGAA
CCAGCGGGGCGAGCTGTGCGTGCGGGGGCCGATGATCATGAGCGGCTACGTGAACAACCC
GGAGGCCACCAACGCCCTCATCGACAAGGACGGCTGGCTGCACAGCGGCGACATCGCCTA
CTGGGACGAGGACGAGCACTTCTTCATCGTCGACCGGCTGAAGTCGCTGATCAAGTACAA
GGGCTACCAGGTGGCGCCGGCCGAGCTGGAGAGCATCCTGCTCCAGCACCCCAACATCTT
CGACGCCGGCGTGGCCGGGCTGCCGGACGACGACGCCGGCGAGCTGCCGGCCGCGGTGGT
```

-continued
```
GGTGCTGGAGCACGGCAAGACCATGACGGAGAAGGAGATCGTCGACTACGTGGCCAGCCA
GGTGACCACCGCCAAGAAGCTGCGGGGCGGCGTGGTGTTCGTGGACGAGGTCCCGAAGGG
CCTGACCGGGAAGCTCGACGCCCGGAAGATCCGCGAGATCCTGATCAAGGCCAAGAAGGG
CGGCAAGATCGCCGTGTAAGACTAGTGCATCACATTTAAAAGCATCTCAGCCTACCATGA
GAATAAGAGAAAGAAAATGAAGATCAATAGCTTATTCATCTCTTTTTCTTTTTCGTTGGT
GTAAAGCCAACACCCTGTCTAAAAAACATAAATTTCTTTAATCATTTTGCCTCTTTTCTC
TGTGCTTCAATTAATAAAAAATGGAAAGAACCTAGATCTAAAAAAAAAAAAAAAAAAAAA
AAAAAAAAAAAAAAAAAAAAAAAAAAAAAAAAAAAAAAAAAAAATGCATCCCCCCCCCCC
CCCCCCCCCCCCCCCCCCAAAGGCTCTTTTCAGAGCCACCAGAATT
``` mRPL35A-PpLuc(GC)-albumin7-A64-C30-histoneSL (SEQ ID NO: 1444)
```
GGGCCATCTTGGCGCCTGTGGAGGCCTGCTGGGAACAGGACTTCTAACAGCAAGTAAGCT
TGAGGATGGAGGACGCCAAGAACATCAAGAAGGGCCCGGCGCCCTTCTACCCGCTGGAGG
ACGGGACCGCCGGCGAGCAGCTCCACAAGGCCATGAAGCGGTACGCCCTGGTGCCGGGCA
CGATCGCCTTCACCGACGCCCACATCGAGGTCGACATCACCTACGCGGAGTACTTCGAGA
TGAGCGTGCGCCTGGCCGAGGCCATGAAGCGGTACGGCCTGAACACCAACCACCGGATCG
TGGTGTGCTCGGAGAACAGCCTGCAGTTCTTCATGCCGGTGCTGGGCGCCCTCTTCATCG
GCGTGGCCGTCGCCCCGGCGAACGACATCTACAACGAGCGGGAGCTGCTGAACAGCATGG
GGATCAGCCAGCCGACCGTGGTGTTCGTGAGCAAGAAGGGCCTGCAGAAGATCCTGAACG
TGCAGAAGAAGCTGCCCATCATCCAGAAGATCATCATCATGGACAGCAAGACCGACTACC
AGGGCTTCCAGTCGATGTACACGTTCGTGACCAGCCACCTCCCGCCGGGCTTCAACGAGT
ACGACTTCGTCCCGGAGAGCTTCGACCGGGACAAGACCATCGCCCTGATCATGAACAGCA
GCGGCAGCACCGGCCTGCCGAAGGGGGTGGCCCTGCCGCACCGGACCGCCTGCGTGCGCT
TCTCGCACGCCCGGGACCCCATCTTCGGCAACCAGATCATCCCGGACACCGCCATCCTGA
GCGTGGTGCCGTTCCACCACGGCTTCGGCATGTTCACGACCCTGGGCTACCTCATCTGCG
GCTTCCGGGTGGTCCTGATGTACCGGTTCGAGGAGGAGCTGTTCCTGCGGAGCCTGCAGG
ACTACAAGATCCAGAGCGCGCTGCTCGTGCCGACCCTGTTCAGCTTCTTCGCCAAGAGCA
CCCTGATCGACAAGTACGACCTGTCGAACCTGCACGAGATCGCCAGCGGGGCGCCCCGC
TGAGCAAGGAGGTGGGCGAGGCCGTGGCCAAGCGGTTCCACCTCCCGGGCATCCGCCAGG
GCTACGGCCTGACCGAGACCACGAGCGCGATCCTGATCACCCCCGAGGGGGACGACAAGC
CGGGCGCCGTGGGCAAGGTGGTCCCGTTCTTCGAGGCCAAGGTGGTGGACCTGGACACCG
GCAAGACCCTGGGCGTGAACCAGCGGGGCGAGCTGTGCGTGCGGGGCCGATGATCATGA
GCGGCTACGTGAACAACCCGGAGGCCACCAACGCCCTCATCGACAAGGACGGCTGGCTGC
ACAGCGGCGACATCGCCTACTGGGACGAGGACGAGCACTTCTTCATCGTCGACCGGCTGA
AGTCGCTGATCAAGTACAAGGGCTACCAGGTGGCGCCGGCCGAGCTGGAGAGCATCCTGC
TCCAGCACCCCAACATCTTCGACGCCGGCGTGGCCGGGCTGCCGGACGACGACGCCGGCG
AGCTGCCGGCCGCGGTGGTGGTGCTGGAGCACGGCAAGACCATGACGGAGAAGGAGATCG
TCGACTACGTGGCCAGCCAGGTGACCACCGCCAAGAAGCTGCGGGGCGGCGTGGTGTTCG
TGGACGAGGTCCCGAAGGGCCTGACCGGGAAGCTCGACGCCCGGAAGATCCGCGAGATCC
TGATCAAGGCCAAGAAGGGCGGCAAGATCGCCGTGTAAGACTAGTGCATCACATTTAAAA
GCATCTCAGCCTACCATGAGAATAAGAGAAAGAAAATGAAGATCAATAGCTTATTCATCT
CTTTTTCTTTTTCGTTGGTGTAAAGCCAACACCCTGTCTAAAAAACATAAATTTCTTTAA
TCATTTTGCCTCTTTTCTCTGTGCTTCAATTAATAAAAAATGGAAAGAACCTAGATCTAA
AAAAAAAAAAAAAAAAAAAAAAAAAAAAAAAAAAAAAAAAAAAAAAAAAAAAAAAAAAAA
AATGCATCCCCCCCCCCCCCCCCCCCCCCCCCCCAAAGGCTCTTTTCAGAGCCACC
AGAATT
```

RPL35-PpLuc(GC)-A64-C30-histoneSL (SEQ ID NO: 1445)
```
GGGGAGCGGGCGGCGGCGTTGGCGGCTTGTGCAGCAAAGCTTGAGGATGGAGGACGCCAA
GAACATCAAGAAGGGCCCGGCGCCCTTCTACCCGCTGGAGGACGGGACCGCCGGCGAGCA
GCTCCACAAGGCCATGAAGCGGTACGCCCTGGTGCCGGGCACGATCGCCTTCACCGACGC
CCACATCGAGGTCGACATCACCTACGCGGAGTACTTCGAGATGAGCGTGCGCCTGGCCGA
GGCCATGAAGCGGTACGGCCTGAACACCAACCACCGGATCGTGGTGTGCTCGGAGAACAG
CCTGCAGTTCTTCATGCCGGTGCTGGGCGCCCTCTTCATCGGCGTGGCCGTCGCCCCGGC
GAACGACATCTACAACGAGCGGGAGCTGCTGAACAGCATGGGGATCAGCCAGCCGACCGT
GGTGTTCGTGAGCAAGAAGGGCCTGCAGAAGATCCTGAACGTGCAGAAGAAGCTGCCCAT
CATCCAGAAGATCATCATCATGGACAGCAAGACCGACTACCAGGGCTTCCAGTCGATGTA
CACGTTCGTGACCAGCCACCTCCCGCCGGGCTTCAACGAGTACGACTTCGTCCCGGAGAG
CTTCGACCGGGACAAGACCATCGCCCTGATCATGAACAGCAGCGGCAGCACCGGCCTGCC
GAAGGGGGTGGCCCTGCCGCACCGGACCGCCTGCGTGCGCTTCTCGCACGCCCGGGACCC
CATCTTCGGCAACCAGATCATCCCGGACACCGCCATCCTGAGCGTGGTGCCGTTCCACCA
CGGCTTCGGCATGTTCACGACCCTGGGCTACCTCATCTGCGGCTTCCGGGTGGTCCTGAT
GTACCGGTTCGAGGAGGAGCTGTTCCTGCGGAGCCTGCAGGACTACAAGATCCAGAGCGC
GCTGCTCGTGCCGACCCTGTTCAGCTTCTTCGCCAAGAGCACCCTGATCGACAAGTACGA
CCTGTCGAACCTGCACGAGATCGCCAGCGGGGCGCCCCGCTGAGCAAGGAGGTGGGCGA
GGCCGTGGCCAAGCGGTTCCACCTCCCGGGCATCCGCCAGGGCTACGGCCTGACCGAGAC
CACGAGCGCGATCCTGATCACCCCCGAGGGGGACGACAAGCCGGGCGCCGTGGGCAAGGT
GGTCCCGTTCTTCGAGGCCAAGGTGGTGGACCTGGACACCGGCAAGACCCTGGGCGTGAA
CCAGCGGGGCGAGCTGTGCGTGCGGGGCCGATGATCATGAGCGGCTACGTGAACAACCC
GGAGGCCACCAACGCCCTCATCGACAAGGACGGCTGGCTGCACAGCGGCGACATCGCCTA
CTGGGACGAGGACGAGCACTTCTTCATCGTCGACCGGCTGAAGTCGCTGATCAAGTACAA
GGGCTACCAGGTGGCGCCGGCCGAGCTGGAGAGCATCCTGCTCCAGCACCCCAACATCTT
CGACGCCGGCGTGGCCGGGCTGCCGGACGACGACGCCGGCGAGCTGCCGGCCGCGGTGGT
GGTGCTGGAGCACGGCAAGACCATGACGGAGAAGGAGATCGTCGACTACGTGGCCAGCCA
GGTGACCACCGCCAAGAAGCTGCGGGGCGGCGTGGTGTTCGTGGACGAGGTCCCGAAGGG
CCTGACCGGGAAGCTCGACGCCCGGAAGATCCGCGAGATCCTGATCAAGGCCAAGAAGGG
CGGCAAGATCGCCGTGTAAGACTAGTAGATCTAAAAAAAAAAAAAAAAAAAAAAAAAAAA
AAAAAAAAAAAAAAAAAAAAAAAAAAAAAAAATGCATCCCCCCCCCCCCCCCCCCCC
CCCCCCCCCCCCAAAGGCTCTTTTCAGAGCCACCAGAATT
```

RPL21-PpLuc(GC)-A64-C30-histoneSL
(SEQ ID NO: 1446)

GGGGCCGGAACCGCCATCTTCCAGTAATTCGCCAAAAAGCTTGAGGATGGAGGACGCCAA
GAACATCAAGAAGGGCCCGGCGCCCTTCTACCCGCTGGAGGACGGGACCGCCGGCGAGCA
GCTCCACAAGGCCATGAAGCGGTACGCCCTGGTGCCGGGCACGATCGCCTTCACCGACGC
CCACATCGAGGTCGACATCACCTACGCGGAGTACTTCGAGATGAGCGTGCGCCTGGCCGA
GGCCATGAAGCGGTACGGCCTGAACACCAACCACCGGATCGTGGTGTGCTCGGAGAACAG
CCTGCAGTTCTTCATGCCGGTGCTGGGCGCCCTCTTCATCGGCGTGGCCGTCGCCCCGGC
GAACGACATCTACAACGAGCGGGAGCTGCTGAACAGCATGGGGATCAGCCAGCCGACCGT
GGTGTTCGTGAGCAAGAAGGGCCTGCAGAAGATCCTGAACGTGCAGAAGAAGCTGCCCAT
CATCCAGAAGATCATCATCATGGACAGCAAGACCGACTACCAGGGCTTCCAGTCGATGTA
CACGTTCGTGACCAGCCACCTCCCGCCCGGGCTTCAACGAGTACGACTTCGTCCCGGAGAG
CTTCGACCGGGACAAGACCATCGCCCTGATCATGAACAGCAGCGGCAGCACCGGCCTGCC
GAAGGGGGTGGCCCTGCCGCACCGGACCGCCTGCGTGCGCTTCTCGCACGCCCGGGACCC
CATCTTCGGCAACCAGATCATCCCGGACACCGCCATCCTGAGCGTGGTGCCGTTCCACCA
CGGCTTCGGCATGTTCACGACCCTGGGCTACCTCATCTGCGGCTTCCGGGTGGTCCTGAT
GTACCGGTTCGAGGAGGAGCTGTTCCTGCGGAGCCTGCAGGACTACAAGATCCAGAGCGC
GCTGCTCGTGCCGACCCTGTTCAGCTTCTTCGCCAAGAGCACCCTGATCGACAAGTACGA
CCTGTCGAACCTGCACGAGATCGCCAGCGGGGCGCCCCGCTGAGCAAGGAGGTGGGCGA
GGCCGTGGCCAAGCGGTTCCACCTCCCGGGCATCCGCCAGGGCTACGGCCTGACCGAGAC
CACGAGCGCGATCCTGATCACCCCCGAGGGGACGACAAGCCGGGCGCCGTGGGCAAGGT
GGTCCCGTTCTTCGAGGCCAAGGTGGTGGACCTGGACACCGGCAAGACCCTGGGCGTGAA
CCAGCGGGGCGAGCTGTGCGTGCGGGGGCCGATGATCATGAGCGGCTACGTGAACAACCC
GGAGGCCACCAACGCCCTCATCGACAAGGACGGCTGGCTGCACAGCGGCGACATCGCCTA
CTGGGACGAGGACGAGCACTTCTTCATCGTCGACCGGCTGAAGTCGCTGATCAAGTACAA
GGGCTACCAGGTGGCGCCCGGCCGAGCTGGAGAGCATCCTGCTCCAGCACCCCAACATCTT
CGACGCCGGCGTGGCCGGGCTGCCGGACGACGACGCCGGCGAGCTGCCGGCCGCGGTGGT
GGTGCTGGAGCACGGCAAGACCATGACGGAGAAGGAGATCGTCGACTACGTGGCCAGCCA
GGTGACCACCGCCAAGAAGCTGCGGGGCGGCGTGGTGTTCGTGGACGAGGTCCCGAAGGG
CCTGACCGGGAAGCTCGACGCCCGGAAGATCCGCGAGATCCTGATCAAGGCCAAGAAGGG
CGGCAAGATCGCCGTGTAAGACTAGTAGATCTAAAAAAAAAAAAAAAAAAAAAAAAAAAA
AAAAAAAAAAAAAAAAAAAAAAAAAAAAAAAAAATGCATCCCCCCCCCCCCCCCCCC
CCCCCCCCCCCCAAAGGCTCTTTTCAGAGCCACCAGAATT

ATP5A1-PpLuc(GC)-A64-C30-histoneSL
(SEQ ID NO: 1447)

GGGCGGCTCGGCCATTTTGTCCCAGTCAGTCCGGAGGCTGCGGCTGCAGAAGTACCGCCT
GCGGAGTAACTGCAAAGAAGCTTGAGGATGGAGGACGCCAAGAACATCAAGAAGGGCCCG
GCGCCCTTCTACCCGCTGGAGGACGGGACCGCCGGCGAGCAGCTCCACAAGGCCATGAAG
CGGTACGCCCTGGTGCCGGGCACGATCGCCTTCACCGACGCCCACATCGAGGTCGACATC
ACCTACGCGGAGTACTTCGAGATGAGCGTGCGCCTGGCCGAGGCCATGAAGCGGTACGGC
CTGAACACCAACCACCGGATCGTGGTGTGCTCGGAGAACAGCCTGCAGTTCTTCATGCCG
GTGCTGGGCGCCCTCTTCATCGGCGTGGCCGTCGCCCCGGCGAACGACATCTACAACGAG
CGGGAGCTGCTGAACAGCATGGGGATCAGCCAGCCGACCGTGGTGTTCGTGAGCAAGAAG
GGCCTGCAGAAGATCCTGAACGTGCAGAAGAAGCTGCCCATCATCCAGAAGATCATCATC
ATGGACAGCAAGACCGACTACCAGGGCTTCCAGTCGATGTACACGTTCGTGACCAGCCAC
CTCCCGCCCGGGCTTCAACGAGTACGACTTCGTCCCGGAGAGCTTCGACCGGGACAAGACC
ATCGCCCTGATCATGAACAGCAGCGGCAGCACCGGCCTGCCGAAGGGGGTGGCCCTGCCG
CACCGGACCGCCTGCGTGCGCTTCTCGCACGCCCGGGACCCCATCTTCGGCAACCAGATC
ATCCCGGACACCGCCATCCTGAGCGTGGTGCCGTTCCACCACGGCTTCGGCATGTTCACG
ACCCTGGGCTACCTCATCTGCGGCTTCCGGGTGGTCCTGATGTACCGGTTCGAGGAGGAG
CTGTTCCTGCGGAGCCTGCAGGACTACAAGATCCAGAGCGCGCTGCTCGTGCCGACCCTG
TTCAGCTTCTTCGCCAAGAGCACCCTGATCGACAAGTACGACCTGTCGAACCTGCACGAG
ATCGCCAGCGGGGCGCCCCGCTGAGCAAGGAGGTGGGCGAGGCCGTGGCCAAGCGGTTC
CACCTCCCGGGCATCCGCCAGGGCTACGGCCTGACCGAGACCACGAGCGCGATCCTGATC
ACCCCCGAGGGGACGACAAGCCGGGCGCCGTGGGCAAGGTGGTCCCGTTCTTCGAGGCC
AAGGTGGTGGACCTGGACACCGGCAAGACCCTGGGCGTGAACCAGCGGGGCGAGCTGTGC
GTGCGGGGGCCGATGATCATGAGCGGCTACGTGAACAACCCGGAGGCCACCAACGCCCTC
ATCGACAAGGACGGCTGGCTGCACAGCGGCGACATCGCCTACTGGGACGAGGACGAGCAC
TTCTTCATCGTCGACCGGCTGAAGTCGCTGATCAAGTACAAGGGCTACCAGGTGGCGCCG
GCCGAGCTGGAGAGCATCCTGCTCCAGCACCCCAACATCTTCGACGCCGGCGTGGCCGGG
CTGCCGGACGACGACGCCGGCGAGCTGCCGGCCGCGGTGGTGGTGCTGGAGCACGGCAAG
ACCATGACGGAGAAGGAGATCGTCGACTACGTGGCCAGCCAGGTGACCACCGCCAAGAAG
CTGCGGGGCGGCGTGGTGTTCGTGGACGAGGTCCCGAAGGGCCTGACCGGGAAGCTCGAC
GCCCGGAAGATCCGCGAGATCCTGATCAAGGCCAAGAAGGGCGGCAAGATCGCCGTGTAA
GACTAGTAGATCTAAAAAAAAAAAAAAAAAAAAAAAAAAAAAAAAAAAAAAAAAAAAAA
AAAAAAAAAAAAAAAAATGCATCCCCCCCCCCCCCCCCCCCCCCCCCCCCCCCAAAGGCT
CTTTTCAGAGCCACCAGAATT

HSD17B4-PpLuc(GC)-A64-C30-histoneSL
(SEQ ID NO: 1448)

GGGTCCCGCAGTCGGCGTCCAGCGGCTCTGCTTGTTCGTGTGTGTGTCGTTGCAGGCCTT
ATTCAAGCTTGAGGATGGAGGACGCCAAGAACATCAAGAAGGGCCCGGCGCCCTTCTACC
CGCTGGAGGACGGGACCGCCGGCGAGCAGCTCCACAAGGCCATGAAGCGGTACGCCCTGG
TGCCGGGCACGATCGCCTTCACCGACGCCCACATCGAGGTCGACATCACCTACGCGGAGT
ACTTCGAGATGAGCGTGCGCCTGGCCGAGGCCATGAAGCGGTACGGCCTGAACACCAACC
ACCGGATCGTGGTGTGCTCGGAGAACAGCCTGCAGTTCTTCATGCCGGTGCTGGGCGCCC
TCTTCATCGGCGTGGCCGTCGCCCCGGCGAACGACATCTACAACGAGCGGGAGCTGCTGA
ACAGCATGGGGATCAGCCAGCCGACCGTGGTGTTCGTGAGCAAGAAGGGCCTGCAGAAGA
TCCTGAACGTGCAGAAGAAGCTGCCCATCATCCAGAAGATCATCATCATGGACAGCAAGA

-continued

```
CCGACTACCAGGGCTTCCAGTCGATGTACACGTTCGTGACCAGCCACCTCCCGCCGGGCT
TCAACGAGTACGACTTCGTCCCGGAGAGCTTCGACCGGGACAAGACCATCGCCCTGATCA
TGAACAGCAGCGGCAGCACCGGCCTGCCGAAGGGGGTGGCCCTGCCGCACCGGACCGCCT
GCGTGCGCTTCTCGCACGCCCGGGACCCCATCTTCGGCAACCAGATCATCCCGGACACCG
CCATCCTGAGCGTGGTGCCGTTCCACCACGGCTTCGGCATGTTCACGACCCTGGGCTACC
TCATCTGCGGCTTCCGGGTGGTCCTGATGTACCGGTTCGAGGAGGAGCTGTTCCTGCGGA
GCCTGCAGGACTACAAGATCCAGAGCGCGCTGCTCGTGCCGACCCTGTTCAGCTTCTTCG
CCAAGAGCACCCTGATCGACAAGTACGACCTGTCGAACCTGCACGAGATCGCCAGCGGGG
GCGCCCCGCTGAGCAAGGAGGTGGGCGAGGCCGTGGCCAAGCGGTTCCACCTCCCGGGCA
TCCGCCAGGGCTACGGCCTGACCGAGACCACGAGCGCGATCCTGATCACCCCCGAGGGGG
ACGACAAGCCGGGCGCCGTGGGCAAGGTGGTCCCGTTCTTCGAGGCCAAGGTGGTGGACC
TGGACACCGGCAAGACCCTGGGCGTGAACCAGCGGGGCGAGCTGTGCGTGCGGGGGCCGA
TGATCATGAGCGGCTACGTGAACAACCCGGAGGCCACCAACGCCCTCATCGACAAGGACG
GCTGGCTGCACAGCGGCGACATCGCCTACTGGGACGAGGACGAGCACTTCTTCATCGTCG
ACCGGCTGAAGTCGCTGATCAAGTACAAGGGCTACCAGGTGGCGCCCGGCCGAGCTGGAGA
GCATCCTGCTCCAGCACCCCAACATCTTCGACGCCGGCGTGGCCGGGCTGCCGGACGACG
ACGCCGGCGAGCTGCCGGCCGCGGTGGTGGTGCTGGAGCACGGCAAGACCATGACGGAGA
AGGAGATCGTCGACTACGTGGCCAGCCAGGTGACCACCGCCAAGAAGCTGCGGGGCGGCG
TGGTGTTCGTGGACGAGGTCCCGAAGGGCCTGACCGGGAAGCTCGACGCCCGGAAGATCC
GCGAGATCCTGATCAAGGCCAAGAAGGGCGGCAAGATCGCCGTGTAAGACTAGTAGATCT
AAAAAAAAAAAAAAAAAAAAAAAAAAAAAAAAAAAAAAAAAAAAAAAAAAAAAAAAAAAA
AAAATGCATCCCCCCCCCCCCCCCCCCCCCCCCCCCCCCCAAAGGCTCTTTTCAGAGCCA
CCAGAATT
```

AIG1-PpLuc(GC)-A64-C30-histoneSL (SEQ ID NO: 1449)

```
GGGCCGCCCAGCCGGTCCAGGCCTCTGGCGAACAAGCTTGAGGATGGAGGACGCCAAGAA
CATCAAGAAGGGCCCGGCGCCCTTCTACCCGCTGGAGGACGGGACCGCCGGCGAGCAGCT
CCACAAGGCCATGAAGCGGTACGCCCTGGTGCCGGGCACGATCGCCTTCACCGACGCCCA
CATCGAGGTCGACATCACCTACGCGGAGTACTTCGAGATGAGCGTGCGCCTGGCCGAGGC
CATGAAGCGGTACGGCCTGAACACCAACCACCGGATCGTGGTGTGCTCGGAGAACAGCCT
GCAGTTCTTCATGCCGGTGCTGGGCGCCCTCTTCATCGGCGTGGCCGTCGCCCCGGCGAA
CGACATCTACAACGAGCGGGAGCTGCTGAACAGCATGGGGATCAGCCAGCCGACCGTGGT
GTTCGTGAGCAAGAAGGGCCTGCAGAAGATCCTGAACGTGCAGAAGAAGCTGCCCATCAT
CCAGAAGATCATCATCATGGACAGCAAGACCGACTACCAGGGCTTCCAGTCGATGTACAC
GTTCGTGACCAGCCACCTCCCGCCGGGCTTCAACGAGTACGACTTCGTCCCGGAGAGCTT
CGACCGGGACAAGACCATCGCCCTGATCATGAACAGCAGCGGCAGCACCGGCCTGCCGAA
GGGGGTGGCCCTGCCGCACCGGACCGCCTGCGTGCGCTTCTCGCACGCCCGGGACCCCAT
CTTCGGCAACCAGATCATCCCGGACACCGCCATCCTGAGCGTGGTGCCGTTCCACCACGG
CTTCGGCATGTTCACGACCCTGGGCTACCTCATCTGCGGCTTCCGGGTGGTCCTGATGTA
CCGGTTCGAGGAGGAGCTGTTCCTGCGGAGCCTGCAGGACTACAAGATCCAGAGCGCGCT
GCTCGTGCCGACCCTGTTCAGCTTCTTCGCCAAGAGCACCCTGATCGACAAGTACGACCT
GTCGAACCTGCACGAGATCGCCAGCGGGGGCGCCCCGCTGAGCAAGGAGGTGGGCGAGGC
CGTGGCCAAGCGGTTCCACCTCCCGGGCATCCGCCAGGGCTACGGCCTGACCGAGACCAC
GAGCGCGATCCTGATCACCCCCGAGGGGGACGACAAGCCGGGCGCCGTGGGCAAGGTGGT
CCCGTTCTTCGAGGCCAAGGTGGTGGACCTGGACACCGGCAAGACCCTGGGCGTGAACCA
GCGGGGCGAGCTGTGCGTGCGGGGGCCGATGATCATGAGCGGCTACGTGAACAACCCGGA
GGCCACCAACGCCCTCATCGACAAGGACGGCTGGCTGCACAGCGGCGACATCGCCTACTG
GGACGAGGACGAGCACTTCTTCATCGTCGACCGGCTGAAGTCGCTGATCAAGTACAAGGG
CTACCAGGTGGCGCCGGCCGAGCTGGAGAGCATCCTGCTCCAGCACCCCAACATCTTCGA
CGCCGGCGTGGCCGGGCTGCCGGACGACGACGCCGGCGAGCTGCCGGCCGCGGTGGTGGT
GCTGGAGCACGGCAAGACCATGACGGAGAAGGAGATCGTCGACTACGTGGCCAGCCAGGT
GACCACCGCCAAGAAGCTGCGGGGCGGCGTGGTGTTCGTGGACGAGGTCCCGAAGGGCCT
GACCGGGAAGCTCGACGCCCGGAAGATCCGCGAGATCCTGATCAAGGCCAAGAAGGGCGG
CAAGATCGCCGTGTAAGACTAGTAGATCTAAAAAAAAAAAAAAAAAAAAAAAAAAAAAAA
AAAAAAAAAAAAAAAAAAAAAAAAAAAAATGCATCCCCCCCCCCCCCCCCCCCCCCCCCC
CCCCCCCCCAAAGGCTCTTTTCAGAGCCACCAGAATT
```

COX6C-PpLuc(GC)-A64-C30-histoneSL (SEQ ID NO: 1450)

```
GGAGTCAGGAAGGACGTTGGTGTTGAGGTTAGCATACGTATCAAGGACAGTAACTACCAA
GCTTGAGGATGGAGGACGCCAAGAACATCAAGAAGGGCCCGGCGCCCTTCTACCCGCTGG
AGGACGGGACCGCCGGCGAGCAGCTCCACAAGGCCATGAAGCGGTACGCCCTGGTGCCGG
GCACGATCGCCTTCACCGACGCCCACATCGAGGTCGACATCACCTACGCGGAGTACTTCG
AGATGAGCGTGCGCCTGGCCGAGGCCATGAAGCGGTACGGCCTGAACACCAACCACCGGA
TCGTGGTGTGCTCGGAGAACAGCCTGCAGTTCTTCATGCCGGTGCTGGGCGCCCTCTTCA
TCGGCGTGGCCGTCGCCCCGGCGAACGACATCTACAACGAGCGGGAGCTGCTGAACAGCA
TGGGGATCAGCCAGCCGACCGTGGTGTTCGTGAGCAAGAAGGGCCTGCAGAAGATCCTGA
ACGTGCAGAAGAAGCTGCCCATCATCCAGAAGATCATCATCATGGACAGCAAGACCGACT
ACCAGGGCTTCCAGTCGATGTACACGTTCGTGACCAGCCACCTCCCGCCGGGCTTCAACG
AGTACGACTTCGTCCCGGAGAGCTTCGACCGGGACAAGACCATCGCCCTGATCATGAACA
GCAGCGGCAGCACCGGCCTGCCGAAGGGGGTGGCCCTGCCGCACCGGACCGCCTGCGTGC
GCTTCTCGCACGCCCGGGACCCCATCTTCGGCAACCAGATCATCCCGGACACCGCCATCC
TGAGCGTGGTGCCGTTCCACCACGGCTTCGGCATGTTCACGACCCTGGGCTACCTCATCT
GCGGCTTCCGGGTGGTCCTGATGTACCGGTTCGAGGAGGAGCTGTTCCTGCGGAGCCTGC
AGGACTACAAGATCCAGAGCGCGCTGCTCGTGCCGACCCTGTTCAGCTTCTTCGCCAAGA
GCACCCTGATCGACAAGTACGACCTGTCGAACCTGCACGAGATCGCCAGCGGGGGCGCCC
CGCTGAGCAAGGAGGTGGGCGAGGCCGTGGCCAAGCGGTTCCACCTCCCGGGCATCCGCC
AGGGCTACGGCCTGACCGAGACCACGAGCGCGATCCTGATCACCCCCGAGGGGGACGACA
AGCCGGGCGCCGTGGGCAAGGTGGTCCCGTTCTTCGAGGCCAAGGTGGTGGACCTGGACA
CCGGCAAGACCCTGGGCGTGAACCAGCGGGGCGAGCTGTGCGTGCGGGGGCCGATGATCA
```

-continued

```
TGAGCGGCTACGTGAACAACCCGGAGGCCACCAACGCCCTCATCGACAAGGACGGCTGGC
TGCACAGCGGCGACATCGCCTACTGGGACGAGGACGAGCACTTCTTCATCGTCGACCGGC
TGAAGTCGCTGATCAAGTACAAGGGCTACCAGGTGGCGCCGGCCGAGCTGGAGAGCATCC
TGCTCCAGCACCCCAACATCTTCGACGCCGGCGTGGCCGGGCTGCCGGACGACGACGCCG
GCGAGCTGCCGGCCGCGGTGGTGGTGCTGGAGCACGGCAAGACCATGACGGAGAAGGAGA
TCGTCGACTACGTGGCCAGCCAGGTGACCACCGCCAAGAAGCTGCGGGGCGGCGTGGTGT
TCGTGGACGAGGTCCCGAAGGGCCTGACCGGGAAGCTCGACGCCCGGAAGATCCGCGAGA
TCCTGATCAAGGCCAAGAAGGGCGGCAAGATCGCCGTGTAAGACTAGTAGATCTAAAAAA
AAAAAAAAAAAAAAAAAAAAAAAAAAAAAAAAAAAAAAAAAAAAAAAAAAAAAAAAAATG
CATCCCCCCCCCCCCCCCCCCCCCCCCCCCCCCCAAAGGCTCTTTTCAGAGCCACCAGAA
TT
```

ASAH1-PpLuc(GC)-A64-C30-histoneSL (SEQ ID NO: 1451)

```
GGGCCTCTGCTGGAGTCCGGGGAGTGGCGTTGGCTGCTAGAGCGAAGCTTGAGGATGGAG
GACGCCAAGAACATCAAGAAGGGCCCGGCGCCCTTCTACCCGCTGGAGGACGGGACCGCC
GGCGAGCAGCTCCACAAGGCCATGAAGCGGTACGCCCTGGTGCCGGGCACGATCGCCTTC
ACCGACGCCCACATCGAGGTCGACATCACCTACGCGGAGTACTTCGAGATGAGCGTGCGC
CTGGCCGAGGCCATGAAGCGGTACGGCCTGAACACCAACCACCGGATCGTGGTGTGCTCG
GAGAACAGCCTGCAGTTCTTCATGCCGGTGCTGGGCGCCCTCTTCATCGGCGTGGCCGTC
GCCCCGGCGAACGACATCTACAACGAGCGGGAGCTGCTGAACAGCATGGGGATCAGCCAG
CCGACCGTGGTGTTCGTGAGCAAGAAGGGCCTGCAGAAGATCCTGAACGTGCAGAAGAAG
CTGCCCATCATCCAGAAGATCATCATCATGGACAGCAAGACCGACTACCAGGGCTTCCAG
TCGATGTACACGTTCGTGACCAGCCACCTCCCGCCGGGCTTCAACGAGTACGACTTCGTC
CCGGAGAGCTTCGACCGGGACAAGACCATCGCCCTGATCATGAACAGCAGCGGCAGCACC
GGCCTGCCGAAGGGGGTGGCCCTGCCGCACCGGACCGCCTGCGTGCGCTTCTCGCACGCC
CGGGACCCCATCTTCGGCAACCAGATCATCCCGGACACCGCCATCCTGAGCGTGGTGCCG
TTCCACCACGGCTTCGGCATGTTCACGACCCTGGGCTACCTCATCTGCGGCTTCCGGGTG
GTCCTGATGTACCGGTTCGAGGAGGAGCTGTTCCTGCGGAGCCTGCAGGACTACAAGATC
CAGAGCGCGCTGCTCGTGCCGACCCTGTTCAGCTTCTTCGCCAAGAGCACCCTGATCGAC
AAGTACGACCTGTCGAACCTGCACGAGATCGCCAGCGGGGGCGCCCCGCTGAGCAAGGAG
GTGGGCGAGGCCGTGGCCAAGCGGTTCCACCTCCCGGGCATCCGCCAGGGCTACGGCCTG
ACCGAGACCACGAGCGCGATCCTGATCACCCCCGAGGGGGACGACAAGCCGGGCGCCGTG
GGCAAGGTGGTCCCGTTCTTCGAGGCCAAGGTGGTGGACCTGGACACCGGCAAGACCCTG
GGCGTGAACCAGCGGGGCGAGCTGTGCGTGCGGGGGCCGATGATCATGAGCGGCTACGTG
AACAACCCGGAGGCCACCAACGCCCTCATCGACAAGGACGGCTGGCTGCACAGCGGCGAC
ATCGCCTACTGGGACGAGGACGAGCACTTCTTCATCGTCGACCGGCTGAAGTCGCTGATC
AAGTACAAGGGCTACCAGGTGGCGCCGGCCGAGCTGGAGAGCATCCTGCTCCAGCACCCC
AACATCTTCGACGCCGGCGTGGCCGGGCTGCCGGACGACGACGCCGGCGAGCTGCCGGCC
GCGGTGGTGGTGCTGGAGCACGGCAAGACCATGACGGAGAAGGAGATCGTCGACTACGTG
GCCAGCCAGGTGACCACCGCCAAGAAGCTGCGGGGCGGCGTGGTGTTCGTGGACGAGGTC
CCGAAGGGCCTGACCGGGAAGCTCGACGCCCGGAAGATCCGCGAGATCCTGATCAAGGCC
AAGAAGGGCGGCAAGATCGCCGTGTAAGACTAGTAGATCTAAAAAAAAAAAAAAAAAAAA
AAAAAAAAAAAAAAAAAAAAAAAAAAAAAAAAAAAAAAAAAAAATGCATCCCCCCCCCCC
CCCCCCCCCCCCCCCCCCCAAAGGCTCTTTTCAGAGCCACCAGAATT
```

5'UTR of human ribosomal protein Large 35 (RPL35) lacking the 5'
terminal oligopyrimidine tract (SEQ ID NO: 1452)

GGAGCGGGCGGCGGCGTTGGCGGCTTGTGCAGCA

5'UTR of human ribosomal protein Large 21 (RPL21) lacking the 5'
terminal oligopyrimidine tract (SEQ ID NO: 1453)

GGCCGGAACCGCCATCTTCCAGTAATTCGCCAAA

5'UTR of human ATP synthase, H+ transporting, mitochondrial F1
complex, alpha subunit 1, cardiac muscle (ATP5A1) lacking the 5'
terminal oligopyrimidine tract (SEQ ID NO: 1454)

GCGGCTCGGCCATTTTGTCCCAGTCAGTCCGGAGGCTGCGGCTGCAGAAGTACCGCCTGCG
GAGTAACTGCAAAG

5'UTR of human hydroxysteroid (17-beta) dehydrogenase 4 (HSD17B4)
lacking the 5' terminal oligopyrimidine tract (SEQ ID NO: 1455)

GTCCCGCAGTCGGCGTCCAGCGGCTCTGCTTGTTCGTGTGTGTGTCGTTGCAGGCCTTATTC

5'UTR of human androgen-induced 1 (AIG1) lacking the 5' terminal
oligopyrimidine tract (SEQ ID NO: 1456)

GCCGCCCAGCCGGTCCAGGCCTCTGGCGAAC

5'UTR of human cytochrome c oxidase subunit VIc (COX6C) lacking
the 5' terminal oligopyrimidine tract (SEQ ID NO: 1457)

AGTCAGGAAGGACGTTGGTGTTGAGGTTAGCATACGTATCAAGGACAGTAACTACC

5'UTR of human N-acylsphingosine amidohydrolase (acid ceramidase)
(ASAH1) lacking the 5' terminal oligopyrimidine tract (SEQ ID NO: 1458)

-continued

<u>GCCTCTGCTGGAGTCCGGGGAGTGGCGTTGGCTGCTAGAGCG</u>

5'UTR of mouse ribosomal protein Large 21 (mRPL21) lacking the 5'
terminal oligopyrimidine tract (SEQ ID NO: 1459)

GGCCGCCGCAGCCATCTTCCAGTAACTCGCCAAA

5'UTR of mouse ribosomal protein large 35A (mRPL35A) lacking the
5' terminal oligopyrimidine tract (SEQ ID NO: 1460)

GCCATCTTGGCGCCTGTGGAGGCCTGCTGGGAACAGGACTTCTAACAGCAAGT

Mouse ribosomal protein Large 21 (mRPL21)

(SEQ ID NO: 1461)

TCCTCCTTTCGGCCGCCGCAGCCATCTTCCAGTAACTCGCCAAAATGCCATCTTCCAG
TAACTCGCCAAAATG mouse ribosomal protein large 35A (mRPL35A)

(SEQ ID NO: 1462)

CTTCCTCTTTCCGCCATCTTGGCGCCTGTGGAGGCCTGCTGGGAACAGGACTTCTAACAG
CAAGTATG

RPL32-PpLuc(GC)-ag-A64

(SEQ ID NO: 1463)

GGGGCGCTGCCTACGGAGGTGGCAGCCATCTCCTTCTCGGCATCAAGCTTGAGGATGGAG
GACGCCAAGAACATCAAGAAGGGCCCGGCGCCCTTCTACCCGCTGGAGGACGGGACCGCC
GGCGAGCAGCTCCACAAGGCCATGAAGCGGTACGCCCTGGTGCCGGGCACGATCGCCTTC
ACCGACGCCCACATCGAGGTCGACATCACCTACGCGGAGTACTTCGAGATGAGCGTGCGC
CTGGCCGAGGCCATGAAGCGGTACGGCCTGAACACCAACCACCGGATCGTGGTGTGCTCG
GAGAACAGCCTGCAGTTCTTCATGCCGGTGCTGGGCGCCCTCTTCATCGGCGTGGCCGTC
GCCCCGGCGAACGACATCTACAACGAGCGGGAGCTGCTGAACAGCATGGGGATCAGCCAG
CCCGACCGTGGTGTTCGTGAGCAAGAAGGGCCTGCAGAAGATCCTGAACGTGCAGAAGAAG
CTGCCCATCATCCAGAAGATCATCATCATGGACAGCAAGACCGACTACCAGGGCTTCCAG
TCGATGTACACGTTCGTGACCAGCCACCTCCCGCCGGGCTTCAACGAGTACGACTTCGTC
CCGGAGAGCTTCGACCGGGACAAGACCATCGCCCTGATCATGAACAGCAGCGGCAGCACC
GGCCTGCCGAAGGGGGTGGCCCTGCCGCACCGGACCGCCTGCGTGCGCTTCTCGCACGCC
CGGGACCCCATCTTCGGCAACCAGATCATCCCGGACACCGCCATCCTGAGCGTGGTGCCG
TTCCACCACGGCTTCGGCATGTTCACGACCCTGGGCTACCTCATCTGCGGCTTCCGGGTG
GTCCTGATGTACCGGTTCGAGGAGGAGCTGTTCCTGCGGAGCCTGCAGGACTACAAGATC
CAGAGCGCGCTGCTCGTGCCGACCCTGTTCAGCTTCTTCGCCAAGAGCACCCTGATCGAC
AAGTACGACCTGTCGAACCTGCACGAGATCGCCAGCGGGGGCGCCCCGCTGAGCAAGGAG
GTGGGCGAGGCCGTGGCCAAGCGGTTCCACCTCCCGGGCATCCGCCAGGGCTACGGCCTG
ACCGAGACCACGAGCGCGATCCTGATCACCCCCGAGGGGGACGACAAGCCGGGCGCCGTG
GGCAAGGTGGTCCCGTTCTTCGAGGCCAAGGTGGTGGACCTGGACACCGGCAAGACCCTG
GGCGTGAACCAGCGGGGCGAGCTGTGCGTGCGGGGGCCGATGATCATGAGCGGCTACGTG
AACAACCCGGAGGCCACCAACGCCCTCATCGACAAGGACGGCTGGCTGCACAGCGGCGAC
ATCGCCTACTGGGACGAGGACGAGCACTTCTTCATCGTCGACCGGCTGAAGTCGCTGATC
AAGTACAAGGGCTACCAGGTGGCGCCGGCCGAGCTGGAGAGCATCCTGCTCCAGCACCCC
AACATCTTCGACGCCGGCGTGGCCGGGCTGCCGGACGACGACGCCGGCGAGCTGCCGGCC
GCGGTGGTGGTGCTGGAGCACGGCAAGACCATGACGGAGAAGGAGATCGTCGACTACGTG
GCCAGCCAGGTGACCACCGCCAAGAAGCTGCGGGGCGGCGTGGTGTTCGTGGACGAGGTC
CCGAAGGGCCTGACCGGGAAGCTCGACGCCCGGAAGATCCGCGAGATCCTGATCAAGGCC
AAGAAGGGCGGCAAGATCGCCGTGTAAGACTAGTTATAAGACTGACTAGCCCGATGGGCC
TCCCAACGGGCCCTCCTCCCCTCCTTGCACCGAGATTAATAGATCTAAAAAAAAAAAAAA
AAAAAAAAAAAAAAAAAAAAAAAAAAAAAAAAAAAAAAAAAAAAA

PpLuc(GC)-ag-A64-histoneSL (SEQ ID NO: 1464)

GGGGCGCTGCCTACGGAGGTGGCAGCCATCTCCTTCTCGGCATCAAGCTTGAGGATGGAG
GACGCCAAGAACATCAAGAAGGGCCCGGCGCCCTTCTACCCGCTGGAGGACGGGACCGCC
GGCGAGCAGCTCCACAAGGCCATGAAGCGGTACGCCCTGGTGCCGGGCACGATCGCCTTC
ACCGACGCCCACATCGAGGTCGACATCACCTACGCGGAGTACTTCGAGATGAGCGTGCGC
CTGGCCGAGGCCATGAAGCGGTACGGCCTGAACACCAACCACCGGATCGTGGTGTGCTCG
GAGAACAGCCTGCAGTTCTTCATGCCGGTGCTGGGCGCCCTCTTCATCGGCGTGGCCGTC
GCCCCGGCGAACGACATCTACAACGAGCGGGAGCTGCTGAACAGCATGGGGATCAGCCAG
CCCGACCGTGGTGTTCGTGAGCAAGAAGGGCCTGCAGAAGATCCTGAACGTGCAGAAGAAG
CTGCCCATCATCCAGAAGATCATCATCATGGACAGCAAGACCGACTACCAGGGCTTCCAG
TCGATGTACACGTTCGTGACCAGCCACCTCCCGCCGGGCTTCAACGAGTACGACTTCGTC
CCGGAGAGCTTCGACCGGGACAAGACCATCGCCCTGATCATGAACAGCAGCGGCAGCACC
GGCCTGCCGAAGGGGGTGGCCCTGCCGCACCGGACCGCCTGCGTGCGCTTCTCGCACGCC
CGGGACCCCATCTTCGGCAACCAGATCATCCCGGACACCGCCATCCTGAGCGTGGTGCCG
TTCCACCACGGCTTCGGCATGTTCACGACCCTGGGCTACCTCATCTGCGGCTTCCGGGTG
GTCCTGATGTACCGGTTCGAGGAGGAGCTGTTCCTGCGGAGCCTGCAGGACTACAAGATC
CAGAGCGCGCTGCTCGTGCCGACCCTGTTCAGCTTCTTCGCCAAGAGCACCCTGATCGAC
AAGTACGACCTGTCGAACCTGCACGAGATCGCCAGCGGGGGCGCCCCGCTGAGCAAGGAG
GTGGGCGAGGCCGTGGCCAAGCGGTTCCACCTCCCGGGCATCCGCCAGGGCTACGGCCTG
ACCGAGACCACGAGCGCGATCCTGATCACCCCCGAGGGGGACGACAAGCCGGGCGCCGTG
GGCAAGGTGGTCCCGTTCTTCGAGGCCAAGGTGGTGGACCTGGACACCGGCAAGACCCTG
GGCGTGAACCAGCGGGGCGAGCTGTGCGTGCGGGGGCCGATGATCATGAGCGGCTACGTG
AACAACCCGGAGGCCACCAACGCCCTCATCGACAAGGACGGCTGGCTGCACAGCGGCGAC
ATCGCCTACTGGGACGAGGACGAGCACTTCTTCATCGTCGACCGGCTGAAGTCGCTGATC

AAGTACAAGGGCTACCAGGTGGCGCCGGCCGAGCTGGAGAGCATCCTGCTCCAGCACCCC
AACATCTTCGACGCCGGCGTGGCCGGGCTGCCGGACGACGACGCCGGCGAGCTGCCGGCC
GCGGTGGTGGTGCTGGAGCACGGCAAGACCATGACGGAGAAGGAGATCGTCGACTACGTG
GCCAGCCAGGTGACCACCGCCAAGAAGCTGCGGGGCGGCGTGGTGTTCGTGGACGAGGTC
CCGAAGGGCCTGACCGGGAAGCTCGACGCCCGGAAGATCCGCGAGATCCTGATCAAGGCC
AAGAAGGGCGGCAAGATCGCCGTGTAAGACTAGTTATAAGACTGACTAGCCCGATGGGCC
TCCCAACGGGCCCTCCTCCCCTCCTTGCACCGAGATTAATAAAAAAAAAAAAAAAAAAAA
AAAAAAAAAAAAAAAAAAAAAAAAAAAAAAAAAAAAAAAAAAAAATGCATCAAAGGCTCTT
TTCAGAGCCACCA

PpLuc(GC)-albumin7-A64-C30-histoneSL                             (SEQ ID NO: 1465)

GGGGCGCTGCCTACGGAGGTGGCAGCCATCTCCTTCTCGGCATCAAGCTTGAGGATGGAG
GACGCCAAGAACATCAAGAAGGGCCCGGCGCCCTTCTACCCGCTGGAGGACGGGACCGCC
GGCGAGCAGCTCCACAAGGCCATGAAGCGGTACGCCCTGGTGCCGGGCACGATCGCCTTC
ACCGACGCCCACATCGAGGTCGACATCACCTACGCGGAGTACTTCGAGATGAGCGTGCGC
CTGGCCGAGGCCATGAAGCGGTACGGCCTGAACACCAACCACCGGATCGTGGTGTGCTCG
GAGAACAGCCTGCAGTTCTTCATGCCGGTGCTGGGCGCCCTCTTCATCGGCGTGGCCGTC
GCCCCGGCGAACGACATCTACAACGAGCGGGAGCTGCTGAACAGCATGGGGATCAGCCAG
CCGACCGTGGTGTTCGTGAGCAAGAAGGGCCTGCAGAAGATCCTGAACGTGCAGAAGAAG
CTGCCCATCATCCAGAAGATCATCATCATGGACAGCAAGACCGACTACCAGGGCTTCCAG
TCGATGTACACGTTCGTGACCAGCCACCTCCCGCCGGGCTTCAACGAGTACGACTTCGTC
CCGGAGAGCTTCGACCGGGACAAGACCATCGCCCTGATCATGAACAGCAGCGGCAGCACC
GGCCTGCCGAAGGGGGTGGCCCTGCCGCACCGGACCGCCTGCGTGCGCTTCTCGCACGCC
CGGGACCCCATCTTCGGCAACCAGATCATCCCGGACACCGCCATCCTGAGCGTGGTGCCG
TTCCACCACGGCTTCGGCATGTTCACGACCCTGGGCTACCTCATCTGCGGCTTCCGGGTG
GTCCTGATGTACCGGTTCGAGGAGGAGCTGTTCCTGCGGAGCCTGCAGGACTACAAGATC
CAGAGCGCGCTGCTCGTGCCGACCCTGTTCAGCTTCTTCGCCAAGAGCACCCTGATCGAC
AAGTACGACCTGTCGAACCTGCACGAGATCGCCAGCGGGGCGCCCCGCTGAGCAAGGAG
GTGGGCGAGGCCGTGGCCAAGCGGTTCCACCTCCCGGGCATCCGCCAGGGCTACGGCCTG
ACCGAGACCACGAGCGCGATCCTGATCACCCCCGAGGGGGACGACAAGCCGGGCGCCGTG
GGCAAGGTGGTCCCGTTCTTCGAGGCCAAGGTGGTGGACCTGGACACCGGCAAGACCCTG
GGCGTGAACCAGCGGGGCGAGCTGTGCGTGCGGGGGCCGATGATCATGAGCGGCTACGTG
AACAACCCGGAGGCCACCAACGCCCTCATCGACAAGGACGGCTGGCTGCACAGCGGCGAC
ATCGCCTACTGGGACGAGGACGAGCACTTCTTCATCGTCGACCGGCTGAAGTCGCTGATC
AAGTACAAGGGCTACCAGGTGGCGCCGGCCGAGCTGGAGAGCATCCTGCTCCAGCACCCC
AACATCTTCGACGCCGGCGTGGCCGGGCTGCCGGACGACGACGCCGGCGAGCTGCCGGCC
GCGGTGGTGGTGCTGGAGCACGGCAAGACCATGACGGAGAAGGAGATCGTCGACTACGTG
GCCAGCCAGGTGACCACCGCCAAGAAGCTGCGGGGCGGCGTGGTGTTCGTGGACGAGGTC
CCGAAGGGCCTGACCGGGAAGCTCGACGCCCGGAAGATCCGCGAGATCCTGATCAAGGCC
AAGAAGGGCGGCAAGATCGCCGTGTAAGACTAGTGCATCACATTTAAAAGCATCTCAGCC
TACCATGAGAATAAGAGAAAGAAAATGAAGATCAATAGCTTATTCATCTCTTTTTCTTTT
TCGTTGGTGTAAAGCCAACACCCTGTCTAAAAAACATAAATTTCTTTAATCATTTTGCCT
CTTTTCTCTGTGCTTCAATTAATAAAAAATGGAAAGAACCTAGATCTAAAAAAAAAAAAA
AAAAAAAAAAAAAAAAAAAAAAAAAAAAAAAAAAAAAAAAAAAAAAAATGCATCCCC
CCCCCCCCCCCCCCCCCCCCCCCCAAAGGCTCTTTTCAGAGCCACCAGAATT

RPL35-PpLuc(GC)-ag-A64                                           (SEQ ID NO: 1466)

GGGGAGCGGGCGGCGGCGTTGGCGGCTTGTGCAGCAAAGCTTGAGGATGGAGGACGCCAA
GAACATCAAGAAGGGCCCGGCGCCCTTCTACCCGCTGGAGGACGGGACCGCCGGCGAGCA
GCTCCACAAGGCCATGAAGCGGTACGCCCTGGTGCCGGGCACGATCGCCTTCACCGACGC
CCACATCGAGGTCGACATCACCTACGCGGAGTACTTCGAGATGAGCGTGCGCCTGGCCGA
GGCCATGAAGCGGTACGGCCTGAACACCAACCACCGGATCGTGGTGTGCTCGGAGAACAG
CCTGCAGTTCTTCATGCCGGTGCTGGGCGCCCTCTTCATCGGCGTGGCCGTCGCCCCGGC
GAACGACATCTACAACGAGCGGGAGCTGCTGAACAGCATGGGGATCAGCCAGCCGACCGT
GGTGTTCGTGAGCAAGAAGGGCCTGCAGAAGATCCTGAACGTGCAGAAGAAGCTGCCCAT
CATCCAGAAGATCATCATCATGGACAGCAAGACCGACTACCAGGGCTTCCAGTCGATGTA
CACGTTCGTGACCAGCCACCTCCCGCCGGGCTTCAACGAGTACGACTTCGTCCCGGAGAG
CTTCGACCGGGACAAGACCATCGCCCTGATCATGAACAGCAGCGGCAGCACCGGCCTGCC
GAAGGGGGTGGCCCTGCCGCACCGGACCGCCTGCGTGCGCTTCTCGCACGCCCGGGACCC
CATCTTCGGCAACCAGATCATCCCGGACACCGCCATCCTGAGCGTGGTGCCGTTCCACCA
CGGCTTCGGCATGTTCACGACCCTGGGCTACCTCATCTGCGGCTTCCGGGTGGTCCTGAT
GTACCGGTTCGAGGAGGAGCTGTTCCTGCGGAGCCTGCAGGACTACAAGATCCAGAGCGC
GCTGCTCGTGCCGACCCTGTTCAGCTTCTTCGCCAAGAGCACCCTGATCGACAAGTACGA
CCTGTCGAACCTGCACGAGATCGCCAGCGGGGCGCCCCGCTGAGCAAGGAGGTGGGCGA
GGCCGTGGCCAAGCGGTTCCACCTCCCGGGCATCCGCCAGGGCTACGGCCTGACCGAGAC
CACGAGCGCGATCCTGATCACCCCCGAGGGGGACGACAAGCCGGGCGCCGTGGGCAAGGT
GGTCCCGTTCTTCGAGGCCAAGGTGGTGGACCTGGACACCGGCAAGACCCTGGGCGTGAA
CCAGCGGGGCGAGCTGTGCGTGCGGGGGCCGATGATCATGAGCGGCTACGTGAACAACCC
GGAGGCCACCAACGCCCTCATCGACAAGGACGGCTGGCTGCACAGCGGCGACATCGCCTA
CTGGGACGAGGACGAGCACTTCTTCATCGTCGACCGGCTGAAGTCGCTGATCAAGTACAA
GGGCTACCAGGTGGCGCCGGCCGAGCTGGAGAGCATCCTGCTCCAGCACCCCAACATCTT
CGACGCCGGCGTGGCCGGGCTGCCGGACGACGACGCCGGCGAGCTGCCGGCCGCGGTGGT
GGTGCTGGAGCACGGCAAGACCATGACGGAGAAGGAGATCGTCGACTACGTGGCCAGCCA
GGTGACCACCGCCAAGAAGCTGCGGGGCGGCGTGGTGTTCGTGGACGAGGTCCCGAAGGG
CCTGACCGGGAAGCTCGACGCCCGGAAGATCCGCGAGATCCTGATCAAGGCCAAGAAGGG
CGGCAAGATCGCCGTGTAAGACTAGTTATAAGACTGACTAGCCCGATGGGCCTCCCAACG
GGCCCTCCTCCCCTCCTTGCACCGAGATTAATAAAAAAAAAAAAAAAAAAAAAAAAAAAA
AAAAAAAAAAAAAAAAAAAAAAAAAAAA

RPL21-PpLuc(GC)-ag-A64 (SEQ ID NO: 1467)

GGGGCCGGAACCGCCATCTTCCAGTAATTCGCCAAAAAGCTTGAGGATGGAGGACGCCAA
GAACATCAAGAAGGGCCCGGCGCCCTTCTACCCGCTGGAGGACGGGACCGCCGGCGAGCA
GCTCCACAAGGCCATGAAGCGGTACGCCCTGGTGCCGGGCACGATCGCCTTCACCGACGC
CCACATCGAGGTCGACATCACCTACGCGGAGTACTTCGAGATGAGCGTGCGCCTGGCCGA
GGCCATGAAGCGGTACGGCCTGAACACCAACCACCGGATCGTGGTGTGCTCGGAGAACAG
CCTGCAGTTCTTCATGCCGGTGCTGGGCGCCCTCTTCATCGGCGTGGCCGTCGCCCCGGC
GAACGACATCTACAACGAGCGGGAGCTGCTGAACAGCATGGGGATCAGCCAGCCGACCGT
GGTGTTCGTGAGCAAGAAGGGCCTGCAGAAGATCCTGAACGTGCAGAAGAAGCTGCCCAT
CATCCAGAAGATCATCATCATGGACAGCAAGACCGACTACCAGGGCTTCCAGTCGATGTA
CACGTTCGTGACCAGCCACCTCCCGCCGGGCTTCAACGAGTACGACTTCGTCCCGGAGAG
CTTCGACCGGGACAAGACCATCGCCCTGATCATGAACAGCAGCGGCAGCACCGGCCTGCC
GAAGGGGGTGGCCCTGCCGCACCGGACCGCCTGCGTGCGCTTCTCGCACGCCCGGGACCC
CATCTTCGGCAACCAGATCATCCCGGACACCGCCATCCTGAGCGTGGTGCCGTTCCACCA
CGGCTTCGGCATGTTCACGACCCTGGGCTACCTCATCTGCGGCTTCCGGGTGGTCCTGAT
GTACCGGTTCGAGGAGGAGCTGTTCCTGCGGAGCCTGCAGGACTACAAGATCCAGAGCGC
GCTGCTCGTGCCGACCCTGTTCAGCTTCTTCGCCAAGAGCACCCTGATCGACAAGTACGA
CCTGTCGAACCTGCACGAGATCGCCAGCGGGGGCGCCCCGCTGAGCAAGGAGGTGGGCGA
GGCCGTGGCCAAGCGGTTCCACCTCCCGGGCATCCGCCAGGGCTACGGCCTGACCGAGAC
CACGAGCGCGATCCTGATCACCCCCGAGGGGGACGACAAGCCGGGCGCCGTGGGCAAGGT
GGTCCCGTTCTTCGAGGCCAAGGTGGTGGACCTGGACACCGGCAAGACGCTGGGCGTGAA
CCAGCGGGGCGAGCTGTGCGTGCGGGGGCCGATGATCATGAGCGGCTACGTGAACAACCC
GGAGGCCACCAACGCCCTCATCGACAAGGACGGCTGGCTGCACAGCGGCGACATCGCCTA
CTGGGACGAGGACGAGCACTTCTTCATCGTCGACCGGCTGAAGTCGCTGATCAAGTACAA
GGGCTACCAGGTGGCGCCGGCCGAGCTGGAGAGCATCCTGCTCCAGCACCCCAACATCTT
CGACGCCGGCGTGGCCGGGCTGCCGGACGACGACGCCGGCGAGCTGCCGGCCGCGGTGGT
GGTGCTGGAGCACGGCAAGACCATGACGGAGAAGGAGATCGTCGACTACGTGGCCAGCCA
GGTGACCACCGCCAAGAAGCTGCGGGGCGGCGTGGTGTTCGTGGACGAGGTCCCGAAGGG
CCTGACCGGGAAGCTCGACGCCCGGAAGATCCGCGAGATCCTGATCAAGGCCAAGAAGGG
CGGCAAGATCGCCGTGTAAGACTAGTTATAAGACTGACTAGCCCGATGGGCCTCCCAACG
GGCCCTCCTCCCCTCCTTGCACCGAGATTAATAAAAAAAAAAAAAAAAAAAAAAAAAAAA
AAAAAAAAAAAAAAAAAAAAAAAAAAAAAAAAAA atp5a1-PpLuc(GC)-ag-A64 (SEQ ID NO: 1468)

GGGCGGCTCGGCCATTTTGTCCCAGTCAGTCCGGAGGCTGCGGCTGCAGAAGTACCGCCT
GCGGAGTAACTGCAAAGAAGCTTGAGGATGGAGGACGCCAAGAACATCAAGAAGGGCCCG
GCGCCCTTCTACCCGCTGGAGGACGGGACCGCCGGCGAGCAGCTCCACAAGGCCATGAAG
CGGTACGCCCTGGTGCCGGGCACGATCGCCTTCACCGACGCCCACATCGAGGTCGACATC
ACCTACGCGGAGTACTTCGAGATGAGCGTGCGCCTGGCCGAGGCCATGAAGCGGTACGGC
CTGAACACCAACCACCGGATCGTGGTGTGCTCGGAGAACAGCCTGCAGTTCTTCATGCCG
GTGCTGGGCGCCCTCTTCATCGGCGTGGCCGTCGCCCCGGCGAACGACATCTACAACGAG
CGGGAGCTGCTGAACAGCATGGGGATCAGCCAGCCGACCGTGGTGTTCGTGAGCAAGAAG
GGCCTGCAGAAGATCCTGAACGTGCAGAAGAAGCTGCCCATCATCCAGAAGATCATCATC
ATGGACAGCAAGACCGACTACCAGGGCTTCCAGTCGATGTACACGTTCGTGACCAGCCAC
CTCCCGCCGGGCTTCAACGAGTACGACTTCGTCCCGGAGAGCTTCGACCGGGACAAGACC
ATCGCCCTGATCATGAACAGCAGCGGCAGCACCGGCCTGCCGAAGGGGGTGGCCCTGCCG
CACCGGACCGCCTGCGTGCGCTTCTCGCACGCCCGGGACCCCATCTTCGGCAACCAGATC
ATCCCGGACACCGCCATCCTGAGCGTGGTGCCGTTCCACCACGGCTTCGGCATGTTCACG
ACCCTGGGCTACCTCATCTGCGGCTTCCGGGTGGTCCTGATGTACCGGTTCGAGGAGGAG
CTGTTCCTGCGGAGCCTGCAGGACTACAAGATCCAGAGCGCGCTGCTCGTGCCGACCCTG
TTCAGCTTCTTCGCCAAGAGCACCCTGATCGACAAGTACGACCTGTCGAACCTGCACGAG
ATCGCCAGCGGGGGCGCCCCGCTGAGCAAGGAGGTGGGCGAGGCCGTGGCCAAGCGGTTC
CACCTCCCGGGCATCCGCCAGGGCTACGGCCTGACCGAGACCACGAGCGCGATCCTGATC
ACCCCCGAGGGGGACGACAAGCCGGGCGCCGTGGGCAAGGTGGTCCCGTTCTTCGAGGCC
AAGGTGGTGGACCTGGACACCGGCAAGACCCTGGGCGTGAACCAGCGGGGCGAGCTGTGC
GTGCGGGGGCCGATGATCATGAGCGGCTACGTGAACAACCCGGAGGCCACCAACGCCCTC
ATCGACAAGGACGGCTGGCTGCACAGCGGCGACATCGCCTACTGGGACGAGGACGAGCAC
TTCTTCATCGTCGACCGGCTGAAGTCGCTGATCAAGTACAAGGGCTACCAGGTGGCGCCG
GCCGAGCTGGAGAGCATCCTGCTCCAGCACCCCAACATCTTCGACGCCGGCGTGGCCGGG
CTGCCGGACGACGACGCCGGCGAGCTGCCGGCCGCGGTGGTGGTGCTGGAGCACGGCAAG
ACCATGACGGAGAAGGAGATCGTCGACTACGTGGCCAGCCAGGTGACCACCGCCAAGAAG
CTGCGGGGCGGCGTGGTGTTCGTGGACGAGGTCCCGAAGGGCCTGACCGGGAAGCTCGAC
GCCCGGAAGATCCGCGAGATCCTGATCAAGGCCAAGAAGGGCGGCAAGATCGCCGTGTAA
GACTAGTTATAAGACTGACTAGCCCGATGGGCCTCCCAACGGGCCCTCCTCCCCTCCTTG
CACCGAGATTAATAAAAAAAAAAAAAAAAAAAAAAAAAAAAAAAAAAAAAAAAAAAAAAA
AAAAAAAAAAAAAAAA

HSD17B4-PpLuc(GC)-ag-A64 (SEQ ID NO: 1469)

GGGTCCCGCAGTCGGCGTCCAGCGGCTCTGCTTGTTCGTGTGTGTGTCGTTGCAGGCCTT
ATTCAAGCTTGAGGATGGAGGACGCCAAGAACATCAAGAAGGGCCCGGCGCCCTTCTACC
CGCTGGAGGACGGGACCGCCGGCGAGCAGCTCCACAAGGCCATGAAGCGGTACGCCCTGG
TGCCGGGCACGATCGCCTTCACCGACGCCCACATCGAGGTCGACATCACCTACGCGGAGT
ACTTCGAGATGAGCGTGCGCCTGGCCGAGGCCATGAAGCGGTACGGCCTGAACACCAACC
ACCGGATCGTGGTGTGCTCGGAGAACAGCCTGCAGTTCTTCATGCCGGTGCTGGGCGCCC
TCTTCATCGGCGTGGCCGTCGCCCCGGCGAACGACATCTACAACGAGCGGGAGCTGCTGA
ACAGCATGGGGATCAGCCAGCCGACCGTGGTGTTCGTGAGCAAGAAGGGCCTGCAGAAGA
TCCTGAACGTGCAGAAGAAGCTGCCCATCATCCAGAAGATCATCATCATGGACAGCAAGA
CCGACTACCAGGGCTTCCAGTCGATGTACACGTTCGTGACCAGCCACCTCCCGCCGGGCT

-continued
```
TCAACGAGTACGACTTCGTCCCGGAGAGCTTCGACCGGGACAAGACCATCGCCCTGATCA
TGAACAGCAGCGGCAGCACCGGCCTGCCGAAGGGGGTGGCCCTGCCGCACCGGACCGCCT
GCGTGCGCTTCTCGCACGCCCGGGACCCCATCTTCGGCAACCAGATCATCCCGGACACCG
CCATCCTGAGCGTGGTGCCGTTCCACCACGGCTTCGGCATGTTCACGACCCTGGGCTACC
TCATCTGCGGCTTCCGGGTGGTCCTGATGTACCGGTTCGAGGAGGAGCTGTTCCTGCGGA
GCCTGCAGGACTACAAGATCCAGAGCGCGCTGCTCGTGCCGACCCTGTTCAGCTTCTTCG
CCAAGAGCACCCTGATCGACAAGTACGACCTGTCGAACCTGCACGAGATCGCCAGCGGGG
GCGCCCCGCTGAGCAAGGAGGTGGGCGAGGCCGTGGCCAAGCGGTTCCACCTCCCGGGCA
TCCGCCAGGGCTACGGCCTGACCGAGACCACGAGCGCGATCCTGATCACCCCCGAGGGGG
ACGACAAGCCGGGCGCCGTGGGCAAGGTGGTCCCGTTCTTCGAGGCCAAGGTGGTGGACC
TGGACACCGGCAAGACCCTGGGCGTGAACCAGCGGGGCGAGCTGTGCGTGCGGGGGCCGA
TGATCATGAGCGGCTACGTGAACAACCCGGAGGCCACCAACGCCCTCATCGACAAGGACG
GCTGGCTGCACAGCGGCGACATCGCCTACTGGGACGAGGACGAGCACTTCTTCATCGTCG
ACCGGCTGAAGTCGCTGATCAAGTACAAGGGCTACCAGGTGGCGCCGGCCGAGCTGGAGA
GCATCCTGCTCCAGCACCCCAACATCTTCGACGCCGGCGTGGCCGGGCTGCCGGACGACG
ACGCCGGCGAGCTGCCGGCCGCGGTGGTGGTGCTGGAGCACGGCAAGACCATGACGGAGA
AGGAGATCGTCGACTACGTGGCCAGCCAGGTGACCACCGCCAAGAAGCTGCGGGGCGGCG
TGGTGTTCGTGGACGAGGTCCCGAAGGGCCTGACCGGGAAGCTCGACGCCCGGAAGATCC
GCGAGATCCTGATCAAGGCCAAGAAGGGCGGCAAGATCGCCGTGTAAGACTAGTTATAAG
ACTGACTAGCCCGATGGGCCTCCCAACGGGCCCTCCTCCCCTCCTTGCACCGAGATTAAT
AAAAAAAAAAAAAAAAAAAAAAAAAAAAAAAAAAAAAAAAAAAAAAAAAAAAAAAAAAAA
AAAA
```

AIG1-PpLuc(GC)-ag-A64     (SEQ ID NO: 1470)

```
GGGCCGCCCAGCCGGTCCAGGCCTCTGGCGAACAAGCTTGAGGATGGAGGACGCCAAGAA
CATCAAGAAGGGCCCGGCGCCCTTCTACCCGCTGGAGGACGGGACCGCCGGCGAGCAGCT
CCACAAGGCCATGAAGCGGTACGCCCTGGTGCCGGGCACGATCGCCTTCACCGACGCCCA
CATCGAGGTCGACATCACCTACGCGGAGTACTTCGAGATGAGCGTGCGCCTGGCCGAGGC
CATGAAGCGGTACGGCCTGAACACCAACCACCGGATCGTGGTGTGCTCGGAGAACAGCCT
GCAGTTCTTCATGCCGGTGCTGGGCGCCCTCTTCATCGGCGTGGCCGTCGCCCCGGCGAA
CGACATCTACAACGAGCGGGAGCTGCTGAACAGCATGGGGATCAGCCAGCCGACCGTGGT
GTTCGTGAGCAAGAAGGGCCTGCAGAAGATCCTGAACGTGCAGAAGAAGCTGCCCATCAT
CCAGAAGATCATCATCATGGACAGCAAGACCGACTACCAGGGCTTCCAGTCGATGTACAC
GTTCGTGACCAGCCACCTCCCGCCGGGCTTCAACGAGTACGACTTCGTCCCGGAGAGCTT
CGACCGGGACAAGACCATCGCCCTGATCATGAACAGCAGCGGCAGCACCGGCCTGCCGAA
GGGGGTGGCCCTGCCGCACCGGACCGCCTGCGTGCGCTTCTCGCACGCCCGGGACCCCAT
CTTCGGCAACCAGATCATCCCGGACACCGCCATCCTGAGCGTGGTGCCGTTCCACCACGG
CTTCGGCATGTTCACGACCCTGGGCTACCTCATCTGCGGCTTCCGGGTGGTCCTGATGTA
CCGGTTCGAGGAGGAGCTGTTCCTGCGGAGCCTGCAGGACTACAAGATCCAGAGCGCGCT
GCTCGTGCCGACCCTGTTCAGCTTCTTCGCCAAGAGCACCCTGATCGACAAGTACGACCT
GTCGAACCTGCACGAGATCGCCAGCGGGGCGCCCCGCTGAGCAAGGAGGTGGGCGAGGC
CGTGGCCAAGCGGTTCCACCTCCCGGGCATCCGCCAGGGCTACGGCCTGACCGAGACCAC
GAGCGCGATCCTGATCACCCCCGAGGGGGACGACAAGCCGGGCGCCGTGGGCAAGGTGGT
CCCGTTCTTCGAGGCCAAGGTGGTGGACCTGGACACCGGCAAGACCCTGGGCGTGAACCA
GCGGGGCGAGCTGTGCGTGCGGGGGCCGATGATCATGAGCGGCTACGTGAACAACCCGGA
GGCCACCAACGCCCTCATCGACAAGGACGGCTGGCTGCACAGCGGCGACATCGCCTACTG
GGACGAGGACGAGCACTTCTTCATCGTCGACCGGCTGAAGTCGCTGATCAAGTACAAGGG
CTACCAGGTGGCGCCGGCCGAGCTGGAGAGCATCCTGCTCCAGCACCCCAACATCTTCGA
CGCCGGCGTGGCCGGGCTGCCGGACGACGACGCCGGCGAGCTGCCGGCCGCGGTGGTGGT
GCTGGAGCACGGCAAGACCATGACGGAGAAGGAGATCGTCGACTACGTGGCCAGCCAGGT
GACCACCGCCAAGAAGCTGCGGGGCGGCGTGGTGTTCGTGGACGAGGTCCCGAAGGGCCT
GACCGGGAAGCTCGACGCCCGGAAGATCCGCGAGATCCTGATCAAGGCCAAGAAGGGCGG
CAAGATCGCCGTGTAAGACTAGTTATAAGACTGACTAGCCCGATGGGCCTCCCAACGGGC
CCTCCTCCCCTCCTTGCACCGAGATTAATAAAAAAAAAAAAAAAAAAAAAAAAAAAAAAA
AAAAAAAAAAAAAAAAAAAAAAAAAAAAAA
```

COX6C-PpLuc(GC)-ag-A64     (SEQ ID NO: 1471)

```
GGAGTCAGGAAGGACGTTGGTGTTGAGGTTAGCATACGTATCAAGGACAGTAACTACCAA
GCTTGAGGATGGAGGACGCCAAGAACATCAAGAAGGGCCCGGCGCCCTTCTACCCGCTGG
AGGACGGGACCGCCGGCGAGCAGCTCCACAAGGCCATGAAGCGGTACGCCCTGGTGCCGG
GCACGATCGCCTTCACCGACGCCCACATCGAGGTCGACATCACCTACGCGGAGTACTTCG
AGATGAGCGTGCGCCTGGCCGAGGCCATGAAGCGGTACGGCCTGAACACCAACCACCGGA
TCGTGGTGTGCTCGGAGAACAGCCTGCAGTTCTTCATGCCGGTGCTGGGCGCCCTCTTCA
TCGGCGTGGCCGTCGCCCCGGCGAACGACATCTACAACGAGCGGGAGCTGCTGAACAGCA
TGGGGATCAGCCAGCCGACCGTGGTGTTCGTGAGCAAGAAGGGCCTGCAGAAGATCCTGA
ACGTGCAGAAGAAGCTGCCCATCATCCAGAAGATCATCATCATGGACAGCAAGACCGACT
ACCAGGGCTTCCAGTCGATGTACACGTTCGTGACCAGCCACCTCCCGCCGGGCTTCAACG
AGTACGACTTCGTCCCGGAGAGCTTCGACCGGGACAAGACCATCGCCCTGATCATGAACA
GCAGCGGCAGCACCGGCCTGCCGAAGGGGGTGGCCCTGCCGCACCGGACCGCCTGCGTGC
GCTTCTCGCACGCCCGGGACCCCATCTTCGGCAACCAGATCATCCCGGACACCGCCATCC
TGAGCGTGGTGCCGTTCCACCACGGCTTCGGCATGTTCACGACCCTGGGCTACCTCATCT
GCGGCTTCCGGGTGGTCCTGATGTACCGGTTCGAGGAGGAGCTGTTCCTGCGGAGCCTGC
AGGACTACAAGATCCAGAGCGCGCTGCTCGTGCCGACCCTGTTCAGCTTCTTCGCCAAGA
GCACCCTGATCGACAAGTACGACCTGTCGAACCTGCACGAGATCGCCAGCGGGGCGCCCC
CGCTGAGCAAGGAGGTGGGCGAGGCCGTGGCCAAGCGGTTCCACCTCCCGGGCATCCGCC
AGGGCTACGGCCTGACCGAGACCACGAGCGCGATCCTGATCACCCCCGAGGGGGACGACA
AGCCGGGCGCCGTGGGCAAGGTGGTCCCGTTCTTCGAGGCCAAGGTGGTGGACCTGGACA
CCGGCAAGACCCTGGGCGTGAACCAGCGGGGCGAGCTGTGCGTGCGGGGGCCGATGATCA
TGAGCGGCTACGTGAACAACCCGGAGGCCACCAACGCCCTCATCGACAAGGACGGCTGGC
```

-continued

TGCACAGCGGCGACATCGCCTACTGGGACGAGGACGAGCACTTCTTCATCGTCGACCGGC
TGAAGTCGCTGATCAAGTACAAGGGCTACCAGGTGGCGCCGGCCGAGCTGGAGAGCATCC
TGCTCCAGCACCCCAACATCTTCGACGCCGGCGTGGCCGGGCTGCCGGACGACGACGCCG
GCGAGCTGCCGGCCGCGGTGGTGGTGCTGGAGCACGGCAAGACCATGACGGAGAAGGAGA
TCGTCGACTACGTGGCCAGCCAGGTGACCACCGCCAAGAAGCTGCGGGGCGGCGTGGTGT
TCGTGGACGAGGTCCCGAAGGGCCTGACCGGGAAGCTCGACGCCCGGAAGATCCGCGAGA
TCCTGATCAAGGCCAAGAAGGGCGGCAAGATCGCCGTGTAAGACTAGTTATAAGACTGAC
TAGCCCGATGGGCCTCCCAACGGGCCCTCCTCCCCTCCTTGCACCGAGATTAATAAAAAA
AAAAAAAAAAAAAAAAAAAAAAAAAAAAAAAAAAAAAAAAAAAAAAAAAAAAAA

ASAH1-PpLuc(GC)-ag-A64            (SEQ ID NO: 1472)

GGGCCTCTGCTGGAGTCCGGGGAGTGGCGTTGGCTGCTAGAGCGAAGCTTGAGGATGGGA
GACGCCAAGAACATCAAGAAGGGCCCGGCGCCCTTCTACCCGCTGGAGGACGGGACCGCC
GGCGAGCAGCTCCACAAGGCCATGAAGCGGTACGCCCTGGTGCCGGGCACGATCGCCTTC
ACCGACGCCCACATCGAGGTCGACATCACCTACGCGGAGTACTTCGAGATGAGCGTGCGC
CTGGCCGAGGCCATGAAGCGGTACGGCCTGAACACCAACCACCGGATCGTGGTGTGCTCG
GAGAACAGCCTGCAGTTCTTCATGCCGGTGCTGGGCGCCCTCTTCATCGGCGTGGCCGTC
GCCCCGGCGAACGACATCTACAACGAGCGGGAGCTGCTGAACAGCATGGGGATCAGCCAG
CCGACCGTGGTGTTCGTGAGCAAGAAGGGCCTGCAGAAGATCCTGAACGTGCAGAAGAAG
CTGCCCATCATCCAGAAGATCATCATCATGGACAGCAAGACCGACTACCAGGGCTTCCAG
TCGATGTACACGTTCGTGACCAGCCACCTCCCGCCGGGCTTCAACGAGTACGACTTCGTC
CCGGAGAGCTTCGACCGGGACAAGACCATCGCCCTGATCATGAACAGCAGCGGCAGCACC
GGCCTGCCGAAGGGGGTGGCCCTGCCGCACCGGACCGCCTGCGTGCGCTTCTCGCACGCC
CGGGACCCCATCTTCGGCAACCAGATCATCCCGGACACCGCCATCCTGAGCGTGGTGCCG
TTCCACCACGGCTTCGGCATGTTCACGACCCTGGGCTACCTCATCTGCGGCTTCCGGGTG
GTCCTGATGTACCGGTTCGAGGAGGAGCTGTTCCTGCGGAGCCTGCAGGACTACAAGATC
CAGAGCGCGCTGCTCGTGCCGACCCTGTTCAGCTTCTTCGCCAAGAGCACCCTGATCGAC
AAGTACGACCTGTCGAACCTGCACGAGATCGCCAGCGGGGCGCCCCGCTGAGCAAGGAG
GTGGGCGAGGCCGTGGCCAAGCGGTTCCACCTCCCGGGCATCCGCCAGGGCTACGGCCTG
ACCGAGACCACGAGCGCGATCCTGATCACCCCCGAGGGGGACGACAAGCCGGGCGCCGTG
GGCAAGGTGGTCCCGTTCTTCGAGGCCAAGGTGGTGGACCTGGACACCGGCAAGACCCTG
GGCGTGAACCAGCGGGGCGAGCTGTGCGTGCGGGGGCCGATGATCATGAGCGGCTACGTG
AACAACCCGGAGGCCACCAACGCCCTCATCGACAAGGACGGCTGGCTGCACAGCGGCGAC
ATCGCCTACTGGGACGAGGACGAGCACTTCTTCATCGTCGACCGGCTGAAGTCGCTGATC
AAGTACAAGGGCTACCAGGTGGCGCCGGCCGAGCTGGAGAGCATCCTGCTCCAGCACCCC
AACATCTTCGACGCCGGCGTGGCCGGGCTGCCGGACGACGACGCCGGCGAGCTGCCGGCC
GCGGTGGTGGTGCTGGAGCACGGCAAGACCATGACGGAGAAGGAGATCGTCGACTACGTG
GCCAGCCAGGTGACCACCGCCAAGAAGCTGCGGGGCGGCGTGGTGTTCGTGGACGAGGTC
CCGAAGGGCCTGACCGGGAAGCTCGACGCCCGGAAGATCCGCGAGATCCTGATCAAGGCC
AAGAAGGGCGGCAAGATCGCCGTGTAAGACTAGTTATAAGACTGACTAGCCCGATGGGCC
TCCCAACGGGCCCTCCTCCCCTCCTTGCACCGAGATTAATAAAAAAAAAAAAAAAAAAAA
AAAAAAAAAAAAAAAAAAAAAAAAAAAAAAAAAAAAAAAAA

RPL35-PpLuc(GC)-ag-A64-histoneSL            (SEQ ID NO: 1473)

GGGGAGCGGGCGGCGGCGTTGGCGGCTTGTGCAGCAAAGCTTGAGGATGGAGGACGCCAA
GAACATCAAGAAGGGCCCGGCGCCCTTCTACCCGCTGGAGGACGGGACCGCCGGCGAGCA
GCTCCACAAGGCCATGAAGCGGTACGCCCTGGTGCCGGGCACGATCGCCTTCACCGACGC
CCACATCGAGGTCGACATCACCTACGCGGAGTACTTCGAGATGAGCGTGCGCCTGGCCGA
GGCCATGAAGCGGTACGGCCTGAACACCAACCACCGGATCGTGGTGTGCTCGGAGAACAG
CCTGCAGTTCTTCATGCCGGTGCTGGGCGCCCTCTTCATCGGCGTGGCCGTCGCCCCGGC
GAACGACATCTACAACGAGCGGGAGCTGCTGAACAGCATGGGGATCAGCCAGCCGACCGT
GGTGTTCGTGAGCAAGAAGGGCCTGCAGAAGATCCTGAACGTGCAGAAGAAGCTGCCCAT
CATCCAGAAGATCATCATCATGGACAGCAAGACCGACTACCAGGGCTTCCAGTCGATGTA
CACGTTCGTGACCAGCCACCTCCCGCCGGGCTTCAACGAGTACGACTTCGTCCCGGAGAG
CTTCGACCGGGACAAGACCATCGCCCTGATCATGAACAGCAGCGGCAGCACCGGCCTGCC
GAAGGGGGTGGCCCTGCCGCACCGGACCGCCTGCGTGCGCTTCTCGCACGCCCGGGACCC
CATCTTCGGCAACCAGATCATCCCGGACACCGCCATCCTGAGCGTGGTGCCGTTCCACCA
CGGCTTCGGCATGTTCACGACCCTGGGCTACCTCATCTGCGGCTTCCGGGTGGTCCTGAT
GTACCGGTTCGAGGAGGAGCTGTTCCTGCGGAGCCTGCAGGACTACAAGATCCAGAGCGC
GCTGCTCGTGCCGACCCTGTTCAGCTTCTTCGCCAAGAGCACCCTGATCGACAAGTACGA
CCTGTCGAACCTGCACGAGATCGCCAGCGGGGCGCCCCGCTGAGCAAGGAGGTGGGCGA
GGCCGTGGCCAAGCGGTTCCACCTCCCGGGCATCCGCCAGGGCTACGGCCTGACCGAGAC
CACGAGCGCGATCCTGATCACCCCCGAGGGGGACGACAAGCCGGGCGCCGTGGGCAAGGT
GGTCCCGTTCTTCGAGGCCAAGGTGGTGGACCTGGACACCGGCAAGACCCTGGGCGTGAA
CCAGCGGGGCGAGCTGTGCGTGCGGGGGCCGATGATCATGAGCGGCTACGTGAACAACCC
GGAGGCCACCAACGCCCTCATCGACAAGGACGGCTGGCTGCACAGCGGCGACATCGCCTA
CTGGGACGAGGACGAGCACTTCTTCATCGTCGACCGGCTGAAGTCGCTGATCAAGTACAA
GGGCTACCAGGTGGCGCCGGCCGAGCTGGAGAGCATCCTGCTCCAGCACCCCAACATCTT
CGACGCCGGCGTGGCCGGGCTGCCGGACGACGACGCCGGCGAGCTGCCGGCCGCGGTGGT
GGTGCTGGAGCACGGCAAGACCATGACGGAGAAGGAGATCGTCGACTACGTGGCCAGCCA
GGTGACCACCGCCAAGAAGCTGCGGGGCGGCGTGGTGTTCGTGGACGAGGTCCCGAAGGG
CCTGACCGGGAAGCTCGACGCCCGGAAGATCCGCGAGATCCTGATCAAGGCCAAGAAGGG
CGGCAAGATCGCCGTGTAAGACTAGTTATAAGACTGACTAGCCCGATGGGCCTCCCAACG
GGCCCTCCTCCCCTCCTTGCACCGAGATTAATAAAAAAAAAAAAAAAAAAAAAAAAAAAA
AAAAAAAAAAAAAAAAAAAAAAAAAAAAAAAAATGCATCAAAGGCTCTTTTCAGAGC
CACCA

RPL21-PpLuc(GC)-ag-A64-histoneSL            (SEQ ID NO: 1474)

-continued

GGGGCCGGAACCGCCATCTTCCAGTAATTCGCCAAAAAGCTTGAGGATGGAGGACGCCAA
GAACATCAAGAAGGGCCCGGCGCCCTTCTACCCGCTGGAGGACGGGACCGCCGGCGAGCA
GCTCCACAAGGCCATGAAGCGGTACGCCCTGGTGCCGGGCACGATCGCCTTCACCGACGC
CCACATCGAGGTCGACATCACCTACGCGGAGTACTTCGAGATGAGCGTGCGCCTGGCCGA
GGCCATGAAGCGGTACGGCCTGAACACCAACCACCGGATCGTGGTGTGCTCGGAGAACAG
CCTGCAGTTCTTCATGCCGGTGCTGGGCGCCCTCTTCATCGGCGTGGCCGTCGCCCCGGC
GAACGACATCTACAACGAGCGGGAGCTGCTGAACAGCATGGGGATCAGCCAGCCGACCGT
GGTGTTCGTGAGCAAGAAGGGCCTGCAGAAGATCCTGAACGTGCAGAAGAAGCTGCCCAT
CATCCAGAAGATCATCATCATGGACAGCAAGACCGACTACCAGGGCTTCCAGTCGATGTA
CACGTTCGTGACCAGCCACCTCCCGCCGGGCTTCAACGAGTACGACTTCGTCCCGGAGAG
CTTCGACCGGGACAAGACCATCGCCCTGATCATGAACAGCAGCGGCAGCACCGGCCTGCC
GAAGGGGGTGGCCCTGCCGCACCGGACCGCCTGCGTGCGCTTCTCGCACGCCCGGGACCC
CATCTTCGGCAACCAGATCATCCCGGACACCGCCATCCTGAGCGTGGTGCCGTTCCACCA
CGGCTTCGGCATGTTCACGACCCTGGGCTACCTCATCTGCGGCTTCCGGGTGGTCCTGAT
GTACCGGTTCGAGGAGGAGCTGTTCCTGCGGAGCCTGCAGGACTACAAGATCCAGAGCGC
GCTGCTCGTGCCGACCCTGTTCAGCTTCTTCGCCAAGAGCACCCTGATCGACAAGTACGA
CCTGTCGAACCTGCACGAGATCGCCAGCGGGGGCGCCCCGCTGAGCAAGGAGGTGGGCGA
GGCCGTGGCCAAGCGGTTCCACCTCCCGGGCATCCGCCAGGGCTACGGCCTGACCGAGAC
CACGAGCGCGATCCTGATCACCCCCGAGGGGGACGACAAGCCGGGCGCCGTGGGCAAGGT
GGTCCCGTTCTTCGAGGCCAAGGTGGTGGACCTGGACACCGGCAAGACCCTGGGCGTGAA
CCAGCGGGGCGAGCTGTGCGTGCGGGGGCCGATGATCATGAGCGGCTACGTGAACAACCC
GGAGGCCACCAACGCCCTCATCGACAAGGACGGCTGGCTGCACAGCGGCGACATCGCCTA
CTGGGACGAGGACGAGCACTTCTTCATCGTCGACCGGCTGAAGTCGCTGATCAAGTACAA
GGGCTACCAGGTGGCGCCGGCCGAGCTGGAGAGCATCCTGCTCCAGCACCCCAACATCTT
CGACGCCGGCGTGGCCGGGCTGCCGGACGACGACGCCGGCGAGCTGCCGGCCGCGGTGGT
GGTGCTGGAGCACGGCAAGACCATGACGGAGAAGGAGATCGTCGACTACGTGGCCAGCCA
GGTGACCACCGCCAAGAAGCTGCGGGGCGGCGTGGTGTTCGTGGACGAGGTCCCGAAGGG
CCTGACCGGGAAGCTCGACGCCCCGGAAGATCCGCGAGATCCTGATCAAGGCCAAGAAGGG
CGGCAAGATCGCCGTGTAAGACTAGTTATAAGACTGACTAGCCCGATGGGCCTCCCAACG
GGCCCTCCTCCCCTCCTTGCACCGAGATTAATAAAAAAAAAAAAAAAAAAAAAAAAAAA
AAAAAAAAAAAAAAAAAAAAAAAAAAAAAAAAAAAATGCATCAAAGGCTCTTTTCAGAGC
CACCA atp5a1-PpLuc(GC)-ag-A64-histoneSL                                    (SEQ ID NO: 1475)

GGGCGGCTCGGCCATTTTGTCCCAGTCAGTCCGGAGGCTGCGGCTGCAGAAGTACCGCT
GCGGAGTAACTGCAAAGAAGCTTGAGGATGGAGGACGCCAAGAACATCAAGAAGGGCCCG
GCGCCCTTCTACCCGCTGGAGGACGGGACCGCCGGCGAGCAGCTCCACAAGGCCATGAAG
CGGTACGCCCTGGTGCCGGGCACGATCGCCTTCACCGACGCCCACATCGAGGTCGACATC
ACCTACGCGGAGTACTTCGAGATGAGCGTGCGCCTGGCCGAGGCCATGAAGCGGTACGGC
CTGAACACCAACCACCGGATCGTGGTGTGCTCGGAGAACAGCCTGCAGTTCTTCATGCCG
GTGCTGGGCGCCCTCTTCATCGGCGTGGCCGTCGCCCCGGCGAACGACATCTACAACGAG
CGGGAGCTGCTGAACAGCATGGGGATCAGCCAGCCGACCGTGGTGTTCGTGAGCAAGAAG
GGCCTGCAGAAGATCCTGAACGTGCAGAAGAAGCTGCCCATCATCCAGAAGATCATCATC
ATGGACAGCAAGACCGACTACCAGGGCTTCCAGTCGATGTACACGTTCGTGACCAGCCAC
CTCCCGCCGGGCTTCAACGAGTACGACTTCGTCCCGGAGAGCTTCGACCGGGACAAGACC
ATCGCCCTGATCATGAACAGCAGCGGCAGCACCGGCCTGCCGAAGGGGGTGGCCCTGCCG
CACCGGACCGCCTGCGTGCGCTTCTCGCACGCCCGGGACCCCATCTTCGGCAACCAGATC
ATCCCGGACACCGCCATCCTGAGCGTGGTGCCGTTCCACCACGGCTTCGGCATGTTCACG
ACCCTGGGCTACCTCATCTGCGGCTTCCGGGTGGTCCTGATGTACCGGTTCGAGGAGGAG
CTGTTCCTGCGGAGCCTGCAGGACTACAAGATCCAGAGCGCGCTGCTCGTGCCGACCCTG
TTCAGCTTCTTCGCCAAGAGCACCCTGATCGACAAGTACGACCTGTCGAACCTGCACGAG
ATCGCCAGCGGGGGCGCCCCGCTGAGCAAGGAGGTGGGCGAGGCCGTGGCCAAGCGGTTC
CACCTCCCGGGCATCCGCCAGGGCTACGGCCTGACCGAGACCACGAGCGCGATCCTGATC
ACCCCCGAGGGGGACGACAAGCCGGGCGCCGTGGGCAAGGTGGTCCCGTTCTTCGAGGCC
AAGGTGGTGGACCTGGACACCGGCAAGACCCTGGGCGTGAACCAGCGGGGCGAGCTGTGC
GTGCGGGGGCCGATGATCATGAGCGGCTACGTGAACAACCCGGAGGCCACCAACGCCCTC
ATCGACAAGGACGGCTGGCTGCACAGCGGCGACATCGCCTACTGGGACGAGGACGAGCAC
TTCTTCATCGTCGACCGGCTGAAGTCGCTGATCAAGTACAAGGGCTACCAGGTGGCGCCG
GCCGAGCTGGAGAGCATCCTGCTCCAGCACCCCAACATCTTCGACGCCGGCGTGGCCGGG
CTGCCGGACGACGACGCCGGCGAGCTGCCGGCCGCGGTGGTGGTGCTGGAGCACGGCAAG
ACCATGACGGAGAAGGAGATCGTCGACTACGTGGCCAGCCAGGTGACCACCGCCAAGAAG
CTGCGGGGCGGCGTGGTGTTCGTGGACGAGGTCCCGAAGGGCCTGACCGGGAAGCTCGAC
GCCCGGAAGATCCGCGAGATCCTGATCAAGGCCAAGAAGGGCGGCAAGATCGCCGTGTAA
GACTAGTTATAAGACTGACTAGCCCGATGGGCCTCCCAACGGGCCCTCCTCCCCTCCTTG
CACCGAGATTAATAAAAAAAAAAAAAAAAAAAAAAAAAAAAAAAAAAAAAAAAAAAAAA
AAAAAAAAAAAAAAAATGCATCAAAGGCTCTTTTCAGAGCCACCA

HSD17B4-PpLuc(GC)-ag-A64-histoneSL                                   (SEQ ID NO: 1476)

GGGTCCCGCAGTCGGCGTCCAGCGGCTCTGCTTGTTCGTGTGTGTGTCGTTGCAGGCCTT
ATTCAAGCTTGAGGATGGAGGACGCCAAGAACATCAAGAAGGGCCCGGCGCCCTTCTACC
CGCTGGAGGACGGGACCGCCGGCGAGCAGCTCCACAAGGCCATGAAGCGGTACGCCCTGG
TGCCGGGCACGATCGCCTTCACCGACGCCCACATCGAGGTCGACATCACCTACGCGGAGT
ACTTCGAGATGAGCGTGCGCCTGGCCGAGGCCATGAAGCGGTACGGCCTGAACACCAACC
ACCGGATCGTGGTGTGCTCGGAGAACAGCCTGCAGTTCTTCATGCCGGTGCTGGGCGCCC
TCTTCATCGGCGTGGCCGTCGCCCCGGCGAACGACATCTACAACGAGCGGGAGCTGCTGA
ACAGCATGGGGATCAGCCAGCCGACCGTGGTGTTCGTGAGCAAGAAGGGCCTGCAGAAGA
TCCTGAACGTGCAGAAGAAGCTGCCCATCATCCAGAAGATCATCATCATGGACAGCAAGA
CCGACTACCAGGGCTTCCAGTCGATGTACACGTTCGTGACCAGCCACCTCCCGCCGGGCT
TCAACGAGTACGACTTCGTCCCGGAGAGCTTCGACCGGGACAAGACCATCGCCCTGATCA

-continued

```
TGAACAGCAGCGGCAGCACCGGCCTGCCGAAGGGGGTGGCCCTGCCGCACCGGACCGCCT
GCGTGCGCTTCTCGCACGCCCGGGACCCCATCTTCGGCAACCAGATCATCCCGGACACCG
CCATCCTGAGCGTGGTGCCGTTCCACCACGGCTTCGGCATGTTCACGACCCTGGGCTACC
TCATCTGCGGCTTCCGGGTGGTCCTGATGTACCGGTTCGAGGAGGAGCTGTTCCTGCGGA
GCCTGCAGGACTACAAGATCCAGAGCGCGCTGCTCGTGCCGACCCTGTTCAGCTTCTCG
CCAAGAGCACCCTGATCGACAAGTACGACCTGTCGAACCTGCACGAGATCGCCAGCGGGG
GCGCCCGCTGAGCAAGGAGGTGGGCGAGGCCGTGGCCAAGCGGTTCCACCTCCCGGGCA
TCCGCCAGGGCTACGGCCTGACCGAGACCACGAGCGCGATCCTGATCACCCCCGAGGGGG
ACGACAAGCCGGGCGCCGTGGGCAAGGTGGTCCCGTTCTTCGAGGCCAAGGTGGTGGACC
TGGACACCGGCAAGACCCTGGGCGTGAACCAGCGGGGCGAGCTGTGCGTGCGGGGGCCGA
TGATCATGAGCGGCTACGTGAACAACCCGGAGGCCACCAACGCCCTCATCGACAAGGACG
GCTGGCTGCACAGCGGCGACATCGCCTACTGGGACGAGGACGAGCACTTCTTCATCGTCG
ACCGGCTGAAGTCGCTGATCAAGTACAAGGGCTACCAGGTGGCGCCGGCCGAGCTGGAGA
GCATCCTGCTCCAGCACCCCAACATCTTCGACGCCGGCGTGGCCGGGCTGCCGGACGACG
ACGCCGGCGAGCTGCCGGCCGCGGTGGTGGTGCTGGAGCACGGCAAGACCATGACGGAGA
AGGAGATCGTCGACTACGTGGCCAGCCAGGTGACCACCGCCAAGAAGCTGCGGGGCGGCG
TGGTGTTCGTGGACGAGGTCCCGAAGGGCCTGACCGGGAAGCTCGACGCCCGGAAGATCC
GCGAGATCCTGATCAAGGCCAAGAAGGGCGGCAAGATCGCCGTGTAAGACTAGTTATAAG
ACTGACTAGCCCGATGGGCCTCCCAACGGGCCCTCCTCCCCTCCTTGCACCGAGATTAAT
AAAAAAAAAAAAAAAAAAAAAAAAAAAAAAAAAAAAAAAAAAAAAAAAAAAAAAAAAAAA
AAAATGCATCAAAGGCTCTTTTCAGAGCCACCA
```

AIG1-PpLuc(GC)-ag-A64-histoneSL (SEQ ID NO: 1477)

```
GGGCCGCCCAGCCGGTCCAGGCCTCTGGCGAACAAGCTTGAGGATGGAGGACGCCAAGAA
CATCAAGAAGGGCCCGGCGCCCTTCTACCCGCTGGAGGACGGGACCGCCGGCGAGCAGCT
CCACAAGGCCATGAAGCGGTACGCCCTGGTGCCGGGCACGATCGCCTTCACCGACGCCCA
CATCGAGGTCGACATCACCTACGCGGAGTACTTCGAGATGAGCGTGCGCCTGGCCGAGGC
CATGAAGCGGTACGGCCTGAACACCAACCACCGGATCGTGGTGTGCTCGGAGAACAGCCT
GCAGTTCTTCATGCCGGTGCTGGGCGCCCTCTTCATCGGCGTGGCCGTCGCCCCGGCGAA
CGACATCTACAACGAGCGGGAGCTGCTGAACAGCATGGGGATCAGCCAGCCGACCGTGGT
GTTCGTGAGCAAGAAGGGCCTGCAGAAGATCCTGAACGTGCAGAAGAAGCTGCCCATCAT
CCAGAAGATCATCATCATGGACAGCAAGACCGACTACCAGGGCTTCCAGTCGATGTACAC
GTTCGTGACCAGCCACCTCCCGCCGGGCTTCAACGAGTACGACTTCGTCCCGGAGAGCTT
CGACCGGGACAAGACCATCGCCCTGATCATGAACAGCAGCGGCAGCACCGGCCTGCCGAA
GGGGGTGGCCCTGCCGCACCGGACCGCCTGCGTGCGCTTCTCGCACGCCCGGGACCCCAT
CTTCGGCAACCAGATCATCCCGGACACCGCCATCCTGAGCGTGGTGCCGTTCCACCACGG
CTTCGGCATGTTCACGACCCTGGGCTACCTCATCTGCGGCTTCCGGGTGGTCCTGATGTA
CCGGTTCGAGGAGGAGCTGTTCCTGCGGAGCCTGCAGGACTACAAGATCCAGAGCGCGCT
GCTCGTGCCGACCCTGTTCAGCTTCTTCGCCAAGAGCACCCTGATCGACAAGTACGACCT
GTCGAACCTGCACGAGATCGCCAGCGGGGCGCCCCGCTGAGCAAGGAGGTGGGCGAGGC
CGTGGCCAAGCGGTTCCACCTCCCGGGCATCCGCCAGGGCTACGGCCTGACCGAGACCAC
GAGCGCGATCCTGATCACCCCCGAGGGGGACGACAAGCCGGGCGCCGTGGGCAAGGTGGT
CCCGTTCTTCGAGGCCAAGGTGGTGGACCTGGACACCGGCAAGACCCTGGGCGTGAACCA
GCGGGGCGAGCTGTGCGTGCGGGGGCCGATGATCATGAGCGGCTACGTGAACAACCCGGA
GGCCACCAACGCCCTCATCGACAAGGACGGCTGGCTGCACAGCGGCGACATCGCCTACTG
GGACGAGGACGAGCACTTCTTCATCGTCGACCGGCTGAAGTCGCTGATCAAGTACAAGGG
CTACCAGGTGGCGCCGGCCGAGCTGGAGAGCATCCTGCTCCAGCACCCCAACATCTTCGA
CGCCGGCGTGGCCGGGCTGCCGGACGACGACGCCGGCGAGCTGCCGGCCGCGGTGGTGGT
GCTGGAGCACGGCAAGACCATGACGGAGAAGGAGATCGTCGACTACGTGGCCAGCCAGGT
GACCACCGCCAAGAAGCTGCGGGGCGGCGTGGTGTTCGTGGACGAGGTCCCGAAGGGCCT
GACCGGGAAGCTCGACGCCCGGAAGATCCGCGAGATCCTGATCAAGGCCAAGAAGGGCGG
CAAGATCGCCGTGTAAGACTAGTTATAAGACTGACTAGCCCGATGGGCCTCCCAACGGGC
CCTCCTCCCCTCCTTGCACCGAGATTAATAAAAAAAAAAAAAAAAAAAAAAAAAAAAAAA
AAAAAAAAAAAAAAAAAAAAAAAAAAAAAAAATGCATCAAAGGCTCTTTTCAGAGCCAC
CA
```

COX6C-PpLuc(GC)-ag-A64-histoneSL (SEQ ID NO: 1478)

```
GGAGTCAGGAAGGACGTTGGTGTTGAGGTTAGCATACGTATCAAGGACAGTAACTACCAA
GCTTGAGGATGGAGGACGCCAAGAACATCAAGAAGGGCCCGGCGCCCTTCTACCCGCTGG
AGGACGGGACCGCCGGCGAGCAGCTCCACAAGGCCATGAAGCGGTACGCCCTGGTGCCGG
GCACGATCGCCTTCACCGACGCCCACATCGAGGTCGACATCACCTACGCGGAGTACTTCG
AGATGAGCGTGCGCCTGGCCGAGGCCATGAAGCGGTACGGCCTGAACACCAACCACCGGA
TCGTGGTGTGCTCGGAGAACAGCCTGCAGTTCTTCATGCCGGTGCTGGGCGCCCTCTTCA
TCGGCGTGGCCGTCGCCCCGGCGAACGACATCTACAACGAGCGGGAGCTGCTGAACAGCA
TGGGGATCAGCCAGCCGACCGTGGTGTTCGTGAGCAAGAAGGGCCTGCAGAAGATCCTGA
ACGTGCAGAAGAAGCTGCCCATCATCCAGAAGATCATCATCATGGACAGCAAGACCGACT
ACCAGGGCTTCCAGTCGATGTACACGTTCGTGACCAGCCACCTCCCGCCGGGCTTCAACG
AGTACGACTTCGTCCCGGAGAGCTTCGACCGGGACAAGACCATCGCCCTGATCATGAACA
GCAGCGGCAGCACCGGCCTGCCGAAGGGGGTGGCCCTGCCGCACCGGACCGCCTGCGTGC
GCTTCTCGCACGCCCGGGACCCCATCTTCGGCAACCAGATCATCCCGGACACCGCCATCC
TGAGCGTGGTGCCGTTCCACCACGGCTTCGGCATGTTCACGACCCTGGGCTACCTCATCT
GCGGCTTCCGGGTGGTCCTGATGTACCGGTTCGAGGAGGAGCTGTTCCTGCGGAGCCTGC
AGGACTACAAGATCCAGAGCGCGCTGCTCGTGCCGACCCTGTTCAGCTTCTTCGCCAAGA
GCACCCTGATCGACAAGTACGACCTGTCGAACCTGCACGAGATCGCCAGCGGGGCGCCCC
GCTGAGCAAGGAGGTGGGCGAGGCCGTGGCCAAGCGGTTCCACCTCCCGGGCATCCGCC
AGGGCTACGGCCTGACCGAGACCACGAGCGCGATCCTGATCACCCCCGAGGGGGACGACA
AGCCGGGCGCCGTGGGCAAGGTGGTCCCGTTCTTCGAGGCCAAGGTGGTGGACCTGGACA
CCGGCAAGACCCTGGGCGTGAACCAGCGGGGCGAGCTGTGCGTGCGGGGGCCGATGATCA
TGAGCGGCTACGTGAACAACCCGGAGGCCACCAACGCCCTCATCGACAAGGACGGCTGGC
```

-continued

TGCACAGCGGCGACATCGCCTACTGGGACGAGGACGAGCACTTCTTCATCGTCGACCGGC
TGAAGTCGCTGATCAAGTACAAGGGCTACCAGGTGGCGCCGGCCGAGCTGGAGAGCATCC
TGCTCCAGCACCCCAACATCTTCGACGCCGGCGTGGCCGGGCTGCCGGACGACGACGCCG
GCGAGCTGCCGGCCGCGGTGGTGGTGCTGGAGCACGGCAAGACCATGACGGAGAAGGAGA
TCGTCGACTACGTGGCCAGCCAGGTGACCACCGCCAAGAAGCTGCGGGGCGGCGTGGTGT
TCGTGGACGAGGTCCCGAAGGGCCTGACCGGGAAGCTCGACGCCCGGAAGATCCGCGAGA
TCCTGATCAAGGCCAAGAAGGGCGGCAAGATCGCCGTGTAAGACTAGTTATAAGACTGAC
TAGCCCGATGGGCCTCCCAACGGGCCCTCCTCCCCTCCTTGCACCGAGATTAATAAAAAA
AAAAAAAAAAAAAAAAAAAAAAAAAAAAAAAAAAAAAAAAAAAAAAAAAAAAAAAAAAAA
TGCATCAAAGGCTCTTTTCAGAGCCACCA

ASAH1-PpLuc(GC)-ag-A64-histoneSL
(SEQ ID NO: 1479)

GGGCCTCTGCTGGAGTCCGGGGAGTGGCGTTGGCTGCTAGAGCGAAGCTTGAGGATGGAG
GACGCCAAGAACATCAAGAAGGGCCCGGCGCCCTTCTACCCGCTGGAGGACGGGACCGCC
GGCGAGCAGCTCCACAAGGCCATGAAGCGGTACGCCCTGGTGCCGGGCACGATCGCCTTC
ACCGACGCCCACATCGAGGTCGACATCACCTACGCGGAGTACTTCGAGATGAGCGTGCGC
CTGGCCGAGGCCATGAAGCGGTACGGCCTGAACACCAACCACCGGATCGTGGTGTGCTCG
GAGAACAGCCTGCAGTTCTTCATGCCGGTGCTGGGCGCCCTCTTCATCGGCGTGGCCGTC
GCCCCGGCGAACGACATCTACAACGAGCGGGAGCTGCTGAACAGCATGGGGATCAGCCAG
CCGACCGTGGTGTTCGTGAGCAAGAAGGGCCTGCAGAAGATCCTGAACGTGCAGAAGAAG
CTGCCCATCATCCAGAAGATCATCATCATGGACAGCAAGACCGACTACCAGGGCTTCCAG
TCGATGTACACGTTCGTGACCAGCCACCTCCCGCCGGGCTTCAACGAGTACGACTTCGTC
CCGGAGAGCTTCGACCGGGACAAGACCATCGCCCTGATCATGAACAGCAGCGGCAGCACC
GGCCTGCCGAAGGGGGTGGCCCTGCCGCACCGGACCGCCTGCGTGCGCTTCTCGCACGCC
CGGGACCCCATCTTCGGCAACCAGATCATCCCGGACACCGCCATCCTGAGCGTGGTGCCG
TTCCACCACGGCTTCGGCATGTTCACGACCCTGGGCTACCTCATCTGCGGCTTCCGGGTG
GTCCTGATGTACCGGTTCGAGGAGGAGCTGTTCCTGCGGAGCCTGCAGGACTACAAGATC
CAGAGCGCGCTGCTCGTGCCGACCCTGTTCAGCTTCTTCGCCAAGAGCACCCTGATCGAC
AAGTACGACCTGTCGAACCTGCACGAGATCGCCAGCGGGGGCGCCCCGCTGAGCAAGGAG
GTGGGCGAGGCCGTGGCCAAGCGGTTCCACCTCCCGGGCATCCGCCAGGGCTACGGCCTG
ACCGAGACCACGAGCGCGATCCTGATCACCCCCGAGGGGGACGACAAGCCGGGCGCCGTG
GGCAAGGTGGTCCCGTTCTTCGAGGCCAAGGTGGTGGACCTGGACACCGGCAAGACCCTG
GGCGTGAACAGCGGGGCGAGCTGTGCGTGCGGGGGCCGATGATCATGAGCGGCTACGTG
AACAACCCGGAGGCCACCAACGCCCTCATCGACAAGGACGGCTGGCTGCACAGCGGCGAC
ATCGCCTACTGGGACGAGGACGAGCACTTCTTCATCGTCGACCGGCTGAAGTCGCTGATC
AAGTACAAGGGCTACCAGGTGGCGCCGGCCGAGCTGGAGAGCATCCTGCTCCAGCACCCC
AACATCTTCGACGCCGGCGTGGCCGGGCTGCCGGACGACGACGCCGGCGAGCTGCCGGCC
GCGGTGGTGGTGCTGGAGCACGGCAAGACCATGACGGAGAAGGAGATCGTCGACTACGTG
GCCAGCCAGGTGACCACCGCCAAGAAGCTGCGGGGCGGCGTGGTGTTCGTGGACGAGGTC
CCGAAGGGCCTGACCGGGAAGCTCGACGCCCGGAAGATCCGCGAGATCCTGATCAAGGCC
AAGAAGGGCGGCAAGATCGCCGTGTAAGACTAGTTATAAGACTGACTAGCCCGATGGGCC
TCCCAACGGGCCCTCCTCCCCTCCTTGCACCGAGATTAATAAAAAAAAAAAAAAAAAAAA
AAAAAAAAAAAAAAAAAAAAAAAAAAAAAAAAAAAAAAAAAAATGCATCAAAGGCTCTT
TTCAGAGCCACCA

RPL32-PpLuc(GC)-ag-A64-histoneSL
(SEQ ID NO: 1480)

GGGGCGCTGCCTACGGAGGTGGCAGCCATCTCCTTCTCGGCATCAAGCTTGAGGATGGAG
GACGCCAAGAACATCAAGAAGGGCCCGGCGCCCTTCTACCCGCTGGAGGACGGGACCGCC
GGCGAGCAGCTCCACAAGGCCATGAAGCGGTACGCCCTGGTGCCGGGCACGATCGCCTTC
ACCGACGCCCACATCGAGGTCGACATCACCTACGCGGAGTACTTCGAGATGAGCGTGCGC
CTGGCCGAGGCCATGAAGCGGTACGGCCTGAACACCAACCACCGGATCGTGGTGTGCTCG
GAGAACAGCCTGCAGTTCTTCATGCCGGTGCTGGGCGCCCTCTTCATCGGCGTGGCCGTC
GCCCCGGCGAACGACATCTACAACGAGCGGGAGCTGCTGAACAGCATGGGGATCAGCCAG
CCGACCGTGGTGTTCGTGAGCAAGAAGGGCCTGCAGAAGATCCTGAACGTGCAGAAGAAG
CTGCCCATCATCCAGAAGATCATCATCATGGACAGCAAGACCGACTACCAGGGCTTCCAG
TCGATGTACACGTTCGTGACCAGCCACCTCCCGCCGGGCTTCAACGAGTACGACTTCGTC
CCGGAGAGCTTCGACCGGGACAAGACCATCGCCCTGATCATGAACAGCAGCGGCAGCACC
GGCCTGCCGAAGGGGGTGGCCCTGCCGCACCGGACCGCCTGCGTGCGCTTCTCGCACGCC
CGGGACCCCATCTTCGGCAACCAGATCATCCCGGACACCGCCATCCTGAGCGTGGTGCCG
TTCCACCACGGCTTCGGCATGTTCACGACCCTGGGCTACCTCATCTGCGGCTTCCGGGTG
GTCCTGATGTACCGGTTCGAGGAGGAGCTGTTCCTGCGGAGCCTGCAGGACTACAAGATC
CAGAGCGCGCTGCTCGTGCCGACCCTGTTCAGCTTCTTCGCCAAGAGCACCCTGATCGAC
AAGTACGACCTGTCGAACCTGCACGAGATCGCCAGCGGGGGCGCCCCGCTGAGCAAGGAG
GTGGGCGAGGCCGTGGCCAAGCGGTTCCACCTCCCGGGCATCCGCCAGGGCTACGGCCTG
ACCGAGACCACGAGCGCGATCCTGATCACCCCCGAGGGGGACGACAAGCCGGGCGCCGTG
GGCAAGGTGGTCCCGTTCTTCGAGGCCAAGGTGGTGGACCTGGACACCGGCAAGACCCTG
GGCGTGAACAGCGGGGCGAGCTGTGCGTGCGGGGGCCGATGATCATGAGCGGCTACGTG
AACAACCCGGAGGCCACCAACGCCCTCATCGACAAGGACGGCTGGCTGCACAGCGGCGAC
ATCGCCTACTGGGACGAGGACGAGCACTTCTTCATCGTCGACCGGCTGAAGTCGCTGATC
AAGTACAAGGGCTACCAGGTGGCGCCGGCCGAGCTGGAGAGCATCCTGCTCCAGCACCCC
AACATCTTCGACGCCGGCGTGGCCGGGCTGCCGGACGACGACGCCGGCGAGCTGCCGGCC
GCGGTGGTGGTGCTGGAGCACGGCAAGACCATGACGGAGAAGGAGATCGTCGACTACGTG
GCCAGCCAGGTGACCACCGCCAAGAAGCTGCGGGGCGGCGTGGTGTTCGTGGACGAGGTC
CCGAAGGGCCTGACCGGGAAGCTCGACGCCCGGAAGATCCGCGAGATCCTGATCAAGGCC
AAGAAGGGCGGCAAGATCGCCGTGTAAGACTAGTTATAAGACTGACTAGCCCGATGGGCC
TCCCAACGGGCCCTCCTCCCCTCCTTGCACCGAGATTAATAAAAAAAAAAAAAAAAAAAA
AAAAAAAAAAAAAAAAAAAAAAAAAAAAAAAAAAAAAAAAAAATGCATCAAAGGCTCTT
TTCAGAGCCACCA

-continued

RPL32-PpLuc(GC)-albumin7-A64-C30-histoneSL (SEQ ID NO: 1481)

```
GGGGCGCTGCCTACGGAGGTGGCAGCCATCTCCTTCTCGGCATCAAGCTTGAGGATGGAG
GACGCCAAGAACATCAAGAAGGGCCCGGCGCCCTTCTACCCGCTGGAGGACGGGACCGCC
GGCGAGCAGCTCCACAAGGCCATGAAGCGGTACGCCCTGGTGCCGGGCACGATCGCCTTC
ACCGACGCCCACATCGAGGTCGACATCACCTACGCGGAGTACTTCGAGATGAGCGTGCGC
CTGGCCGAGGCCATGAAGCGGTACGGCCTGAACACCAACCACCGGATCGTGGTGTGCTCG
GAGAACAGCCTGCAGTTCTTCATGCCGGTGCTGGGCGCCCTCTTCATCGGCGTGGCCGTC
GCCCCGGCGAACGACATCTACAACGAGCGGGAGCTGCTGAACAGCATGGGGATCAGCCAG
CCGACCGTGGTGTTCGTGAGCAAGAAGGGCCTGCAGAAGATCCTGAACGTGCAGAAGAAG
CTGCCCATCATCCAGAAGATCATCATCATGGACAGCAAGACCGACTACCAGGGCTTCCAG
TCGATGTACACGTTCGTGACCAGCCACCTCCCGCCGGGCTTCAACGAGTACGACTTCGTC
CCGGAGAGCTTCGACCGGGACAAGACCATCGCCCTGATCATGAACAGCAGCGGCAGCACC
GGCCTGCCGAAGGGGGTGGCCCTGCCGCACCGGACCGCCTGCGTGCGCTTCTCGCACGCC
CGGGACCCCATCTTCGGCAACCAGATCATCCCGGACACCGCCATCCTGAGCGTGGTGCCG
TTCCACCACGGCTTCGGCATGTTCACGACCCTGGGCTACCTCATCTGCGGCTTCCGGGTG
GTCCTGATGTACCGGTTCGAGGAGGAGCTGTTCCTGCGGAGCCTGCAGGACTACAAGATC
CAGAGCGCGCTGCTCGTGCCGACCCTGTTCAGCTTCTTCGCCAAGAGCACCCTGATCGAC
AAGTACGACCTGTCGAACCTGCACGAGATCGCCAGCGGGGCGCCCCGCTGAGCAAGGAG
GTGGGCGAGGCCGTGGCCAAGCGGTTCCACCTCCCGGGCATCCGCCAGGGCTACGGCCTG
ACCGAGACCACGAGCGCGATCCTGATCACCCCCGAGGGGGACGACAAGCCGGGCGCCGTG
GGCAAGGTGGTCCCGTTCTTCGAGGCCAAGGTGGTGGACCTGGACACCGGCAAGACCCTG
GGCGTGAACCAGCGGGGCGAGCTGTGCGTGCGGGGGCCGATGATCATGAGCGGCTACGTG
AACAACCCGGAGGCCACCAACGCCCTCATCGACAAGGACGGCTGGCTGCACAGCGGCGAC
ATCGCCTACTGGGACGAGGACGAGCACTTCTTCATCGTCGACCGGCTGAAGTCGCTGATC
AAGTACAAGGGCTACCAGGTGGCGCCGGCCGAGCTGGAGAGCATCCTGCTCCAGCACCCC
AACATCTTCGACGCCGGCGTGGCCGGGCTGCCGGACGACGACGCCGGCGAGCTGCCGGCC
GCGGTGGTGGTGCTGGAGCACGGCAAGACCATGACGGAGAAGGAGATCGTCGACTACGTG
GCCAGCCAGGTGACCACCGCCAAGAAGCTGCGGGGCGGCGTGGTGTTCGTGGACGAGGTC
CCGAAGGGCCTGACCGGGAAGCTCGACGCCCGGAAGATCCGCGAGATCCTGATCAAGGCC
AAGAAGGGCGGCAAGATCGCCGTGTAAGACTAGTGCATCACATTTAAAAGCATCTCAGCC
TACCATGAGAATAAGAGAAAGAAAATGAAGATCAATAGCTTATTCATCTCTTTTTCTTTT
TCGTTGGTGTAAAGCCAACACCCTGTCTAAAAAACATAAATTTCTTTAATCATTTTGCCT
CTTTTCTCTGTGCTTCAATTAATAAAAAATGGAAAGAACCTAGATCTAAAAAAAAAAAAA
AAAAAAAAAAAAAAAAAAAAAAAAAAAAAAAAAAAAAAAAAAAAAAAAAATGCATCCCC
CCCCCCCCCCCCCCCCCCCCCCCCCCCAAAGGCTCTTTTCAGAGCCACCAGAATT
```

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US10738306B2). An electronic copy of the "Sequence Listing" will also be available from the USPTO upon request and payment of the fee set forth in 37 CFR 1.19(b)(3).

The invention claimed is:

1. An artificial nucleic acid molecule comprising, from 5' to 3':
   a) at least one 5'-untranslated region element (5'UTR element) which comprises a nucleic acid sequence having an identity of at least 95% to a nucleic acid sequence according to any of SEQ ID NOs: 1368 and 1452-1458, or a corresponding RNA sequence, wherein the 5'UTR element lacks a 5'TOP motif; and
   b) at least one open reading frame (ORF), wherein the ORF is heterologous relative to the 5'UTR element.

2. The artificial nucleic acid molecule according to claim 1, further comprising:
   c) at least one histone stem-loop.

3. The artificial nucleic acid molecule according to claim 1, further comprising at least one 3' UTR element of a mammalian gene positioned 3' relative to the ORF.

4. The artificial nucleic acid molecule according to claim 3, wherein the 3' UTR element comprises a 3' UTR element of a gene selected from the group consisting of an albumin gene, an α-globin gene, a β-globin gene, a tyrosine hydroxylase gene, a lipoxygenase gene, and a collagen alpha gene.

5. The artificial nucleic acid molecule according to claim 4, wherein the 3' UTR element comprises a 3' UTR element of a human albumin gene.

6. The artificial nucleic acid molecule according to claim 3, further comprising a poly(A) sequence and/or polyadenylation signal wherein the poly(A) sequence and/or polyadenylation signal is located within the 3' UTR element.

7. The artificial nucleic acid molecule according to claim 6, wherein the poly(A) sequence has a length of about 20 to about 300 adenine nucleotides.

8. The artificial nucleic acid molecule according to claim 3, wherein the at least one 3' UTR element comprises an mRNA-stabilizing element.

9. The artificial nucleic acid molecule according to claim 1, further comprising a poly(A) sequence and/or a polyadenylation signal.

10. The artificial nucleic acid molecule according to claim 1, further comprising a poly(C) sequence positioned 3' relative to the ORF.

11. The artificial nucleic acid molecule according to claim 1, wherein the molecule is a DNA and further comprises a promoter containing-sequence operably linked to the ORF.

12. The artificial nucleic acid molecule according to claim 1, wherein the molecule is a RNA.

13. The artificial nucleic acid molecule according to claim 12, wherein the RNA is a mRNA and comprises a 5' cap.

14. The artificial nucleic acid molecule according to claim 12, wherein the RNA comprises at least one nucleotide position that is substituted with an analogue of the nucleotide selected from the group consisting of 2-amino-6-chloropurineriboside-5'triphosphate, 2-aminoadenosine-5'-triphosphate, 2-thiocytidine-5'-triphosphate, 2-thiouridine-5'-triphosphate, 4-thiouridine-5'-triphosphate, 5-aminoallylcytidine-5'triphosphate, 5-aminoallyluridine-5'-triphosphate, 5-bromocytidine-5'-triphosphate, 5-bromouridine-5'-triphosphate, 5-iodocytidine-5'-triphosphate, 5-iodouridine-5'triphosphate, 5-methylcytidine-5'-triphosphate, 5-methyluridine-5'-triphosphate, 6-azacytidine-5'-triphosphate, 6-azauridine-5'-triphosphate, 6-chloropurineriboside-5'-triphosphate, 7-deazaadenosine-5'-triphosphate, 7-deazaguanosine-5'-triphosphate, 8-azaadenosine-5'-triphosphate, 8-azidoadenosine-5'-triphosphate, benzimidazoleriboside-5'-triphosphate, N1-methyladenosine-5'-triphosphate, N1-methylguanosine-5'-triphosphate,triphosphate, N6-methyladenosine-5'-triphosphate, 06-methylguanosine-5'-pseudouridine-5'-triphosphate, puromycin-5'-triphosphate andxanthosine-5'-triphosphate.

15. The artificial nucleic acid molecule according to claim 1, wherein one or more codon of the open reading frame is modified to a codon encoding the same amino acid but having an increased G/C content compared to the wild-type codon, thereby increasing the G/C content of the open reading frame compared to the wild type version of the open reading frame.

16. The artificial nucleic acid molecule according to claim 1, wherein the ORF encodes a reporter polypeptide, a human polypeptide, a tumour antigen or an infectious disease antigen.

17. The artificial nucleic acid molecule according to claim 1, wherein the ORF encodes an antibody or a portion thereof.

18. A pharmaceutical composition comprising a RNA molecule in accordance with claim 12 in a pharmaceutically acceptable carrier.

19. A method of treatment comprising administering to a subject a pharmaceutically effective dose of the pharmaceutical composition of claim 18.

20. A method of expressing a polypeptide in a subject comprising administering an artificial nucleic acid molecule according to claim 1 to the subject, wherein the polypeptide is encoded by the ORF of said artificial nucleic acid molecule.

* * * * *